(12) United States Patent
Cha et al.

(10) Patent No.: US 10,651,411 B2
(45) Date of Patent: May 12, 2020

(54) COMPOUND AND ORGANIC LIGHT EMITTING DEVICE CONTAINING SAME

(71) Applicant: LG Chem, Ltd., Seoul (KR)

(72) Inventors: Yongbum Cha, Daejeon (KR); Jin Joo Kim, Daejeon (KR); Seong So Kim, Daejeon (KR); Jemin Ryu, Daejeon (KR)

(73) Assignee: LG Chem, Ltd. (KR)

( * ) Notice: Subject to any disclaimer, the term of this patent is extended or adjusted under 35 U.S.C. 154(b) by 216 days.

(21) Appl. No.: 15/568,116

(22) PCT Filed: Sep. 9, 2016

(86) PCT No.: PCT/KR2016/010163
§ 371 (c)(1),
(2) Date: Oct. 20, 2017

(87) PCT Pub. No.: WO2017/047993
PCT Pub. Date: Mar. 23, 2017

(65) Prior Publication Data
US 2018/0145272 A1    May 24, 2018

(30) Foreign Application Priority Data

Sep. 16, 2015 (KR) .......... 10-2015-0131230
Aug. 23, 2016 (KR) .......... 10-2016-0107194

(51) Int. Cl.
*H01L 51/50*   (2006.01)
*C09K 11/06*   (2006.01)
(Continued)

(52) U.S. Cl.
CPC .......... *H01L 51/508* (2013.01); *C07C 13/567* (2013.01); *C07C 13/72* (2013.01); *C07C 25/22* (2013.01); *C07C 211/54* (2013.01); *C07C 211/61* (2013.01); *C07C 255/58* (2013.01); *C07D 209/86* (2013.01); *C07D 213/16* (2013.01); *C07D 235/18* (2013.01); *C07D 239/26* (2013.01); *C07D 239/74* (2013.01);
(Continued)

(58) Field of Classification Search
None
See application file for complete search history.

(56) References Cited

U.S. PATENT DOCUMENTS

2004/0251816 A1   12/2004   Leo et al.
2006/0141287 A1   6/2006    Klubek et al.
(Continued)

FOREIGN PATENT DOCUMENTS

JP   2011162525 A   8/2011
JP   2012044011 A   3/2012
(Continued)

OTHER PUBLICATIONS

Search report from International Application No. PCT/KR2016/010163, dated Dec. 19, 2016.
(Continued)

*Primary Examiner* — Gregory D Clark
(74) *Attorney, Agent, or Firm* — Lerner, David, Littenberg, Krumholz & Mentlik, LLP

(57) ABSTRACT

The present specification relates to a novel compound and an organic light emitting device including the same.

17 Claims, 1 Drawing Sheet

(51) Int. Cl.
| | |
|---|---|
| *C07C 13/72* | (2006.01) |
| *C07C 13/567* | (2006.01) |
| *C07F 7/08* | (2006.01) |
| *C07F 9/53* | (2006.01) |
| *C07C 25/22* | (2006.01) |
| *C07C 211/61* | (2006.01) |
| *C07F 5/02* | (2006.01) |
| *C07D 251/24* | (2006.01) |
| *C07D 235/18* | (2006.01) |
| *C07D 333/76* | (2006.01) |
| *C07D 307/91* | (2006.01) |
| *C07D 209/86* | (2006.01) |
| *C07D 213/16* | (2006.01) |
| *C07D 239/74* | (2006.01) |
| *C07C 255/58* | (2006.01) |
| *C07C 211/54* | (2006.01) |
| *C07D 239/26* | (2006.01) |

(52) U.S. Cl.
CPC .......... *C07D 251/24* (2013.01); *C07D 307/91* (2013.01); *C07D 333/76* (2013.01); *C07F 5/025* (2013.01); *C07F 7/0812* (2013.01); *C07F 9/5325* (2013.01); *C09K 11/06* (2013.01); *H01L 51/50* (2013.01); *H01L 51/5064* (2013.01); *C07C 2603/18* (2017.05); *C07C 2603/94* (2017.05)

(56) References Cited

U.S. PATENT DOCUMENTS

| | | | |
|---|---|---|---|
| 2010/0207110 A1* | 8/2010 | Nishimura | C09K 11/06 257/40 |
| 2011/0198989 A1* | 8/2011 | Nishide | C07C 13/72 313/504 |
| 2013/0015403 A1 | 1/2013 | Becker et al. | |
| 2013/0049581 A1 | 2/2013 | Nishide et al. | |
| 2016/0211456 A1* | 7/2016 | Yen | H01L 51/0056 |
| 2018/0033966 A1 | 2/2018 | Park et al. | |
| 2019/0006597 A1 | 1/2019 | Lee et al. | |

FOREIGN PATENT DOCUMENTS

| | | | |
|---|---|---|---|
| KR | 20110070251 A | 6/2011 | |
| KR | 20130135516 A | 12/2013 | |
| KR | 20150010016 A | 1/2015 | |
| KR | 101493482 B1 | 2/2015 | |
| KR | 101520955 B1 | 6/2015 | |
| KR | 2015105534 * | 9/2015 | ............ C07C 15/20 |
| KR | 20150105534 A | 9/2015 | |
| WO | 2003012890 A2 | 2/2003 | |
| WO | 2013100464 A1 | 7/2013 | |
| WO | 2014057873 A1 | 4/2014 | |
| WO | 2015009076 A1 | 1/2015 | |

OTHER PUBLICATIONS

Extended European Search Report including Written Opinion for Application No. EP16846814.8 dated Mar. 6, 2019.

* cited by examiner

[Figure 1]
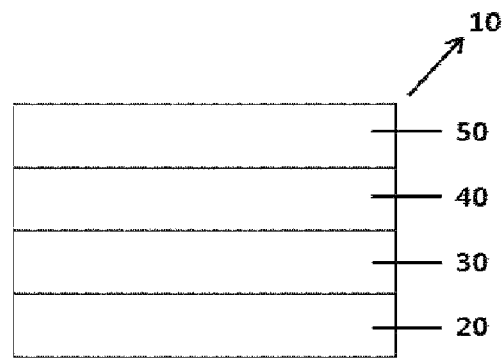
[Figure 2]
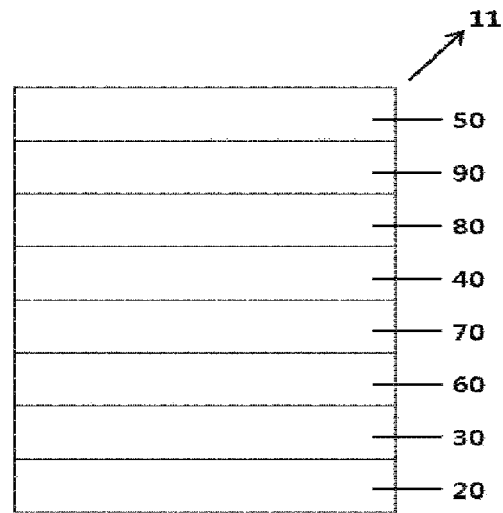

COMPOUND AND ORGANIC LIGHT EMITTING DEVICE CONTAINING SAME

CROSS-REFERENCE TO RELATED APPLICATIONS

The present application is a national phase entry under 35 U.S.C. § 371 of International Application No. PCT/KR2016/010163, filed Sep. 9, 2016, which claims priority to and the benefit of Korean Patent Application Nos. 10-2015-0131230 and 10-2016-0107194, filed in the Korean Intellectual Property Office on Sep. 16, 2015 and Aug. 23, 2016, respectively, the entire contents of which are incorporated herein by reference.

TECHNICAL FIELD

The present specification relates to a novel compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

International Publication No. 2003-012890

DISCLOSURE

Technical Problem

The present specification provides a novel compound and an organic light emitting device including the same.

Technical Solution

An exemplary embodiment of the present specification provides a compound represented by the following Chemical Formula 1.

[Chemical Formula 1]

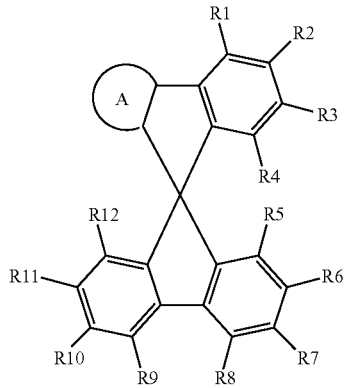

In Chemical Formula 1,

A is a substituted or unsubstituted tetracyclic aromatic ring,

R1 to R12 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups may combine with each other to form a substituted or unsubstituted ring, and at least one of R1 to R12 has a substituent other than hydrogen.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include a compound represented by the following Chemical Formula 1.

Advantageous Effects

An organic light emitting device including the compound according to an exemplary embodiment of the present specification has excellent thermal stability and may improve efficiency, low driving voltage and/or lifetime characteristics.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

MODE FOR INVENTION

Hereinafter, the present specification will be described in more detail.

The present specification provides the compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with the another member, but also a case where still another member is present between the two members.

In the present specification, examples of the substituents will be described below, but the present specification is not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

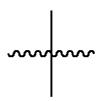

means a moiety bonded to another substituent or a binding portion. In the present specification, the halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

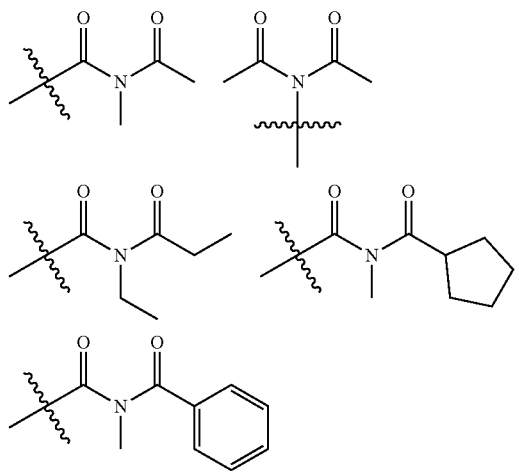

In the present specification, for an amide group, the nitrogen of the amide group may be substituted with hydrogen, a straight-chained, branch-chained, or cyclic alkyl group having 1 to 30 carbon atoms. Specifically, the amide group may be a compound having the following structural formulae, but is not limited thereto.

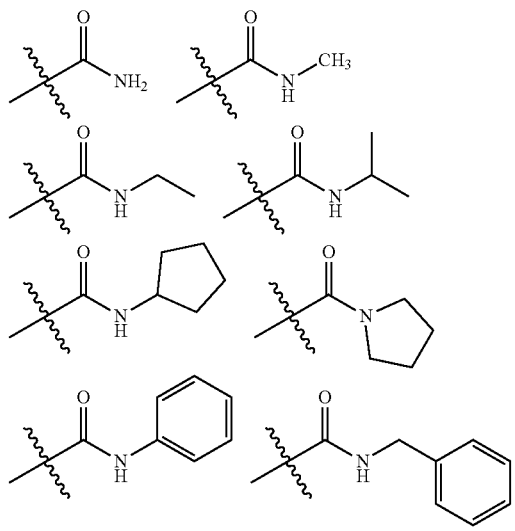

In the present specification, the number of carbon atoms of a carbonyl group is not particularly limited, but is preferably 1 to 30. Specifically, the carbonyl group may be a compound having the following structures, but is not limited thereto.

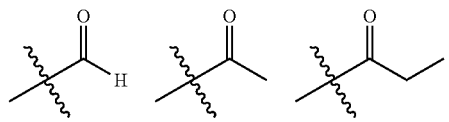

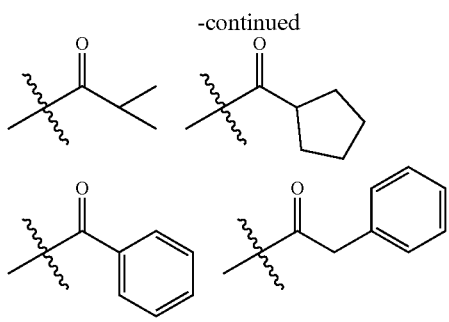

In the present specification, for an ester group, the oxygen of the ester group may be substituted with a straight-chained, branch-chained, or cyclic alkyl group having 1 to 25 carbon atoms, or an aryl group having 6 to 30 carbon atoms. Specifically, the ester group may be a compound having the following structural formulae, but is not limited thereto.

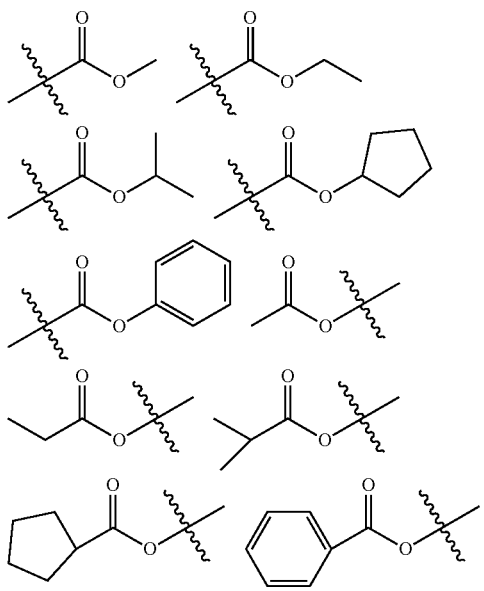

In the present specification, the alkyl group may be straight-chained or branch-chained, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the cycloalkyl group is not particularly limited, but a cycloalkyl group having 3 to 30 carbon atoms is preferred, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branch-chained, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the amine group may be selected from the group consisting of —$NH_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, and the like, but are not limited thereto.

In the present specification, the N-alkylarylamine group means an amine group in which an alkyl group and an aryl group are substituted with N of the amine group. In the present specification, the N-arylheteroarylamine group means an amine group in which an aryl group and a heteroaryl group are substituted with N of the amine group.

In the present specification, the N-alkylheteroarylamine group means an amine group in which an alkyl group and a heteroarylamine group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but are not limited thereto.

In the present specification, the alkenyl group may be straight-chained or branch-chained, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group may be —$BR_{100}R_{101}$, and $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight-chained or branch-chained alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of the phosphine oxide group include a diphenylphosphine oxide group, dinaphthylphosphine oxide, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a perylenyl group, a chrysenyl group, a fluorenyl group, and the like, but are not limited thereto. In the present specification, the fluorenyl group may be substituted, and adjacent substituents may combine with each other to form a ring.

When the fluorenyl group is substituted, the fluorenyl group may be

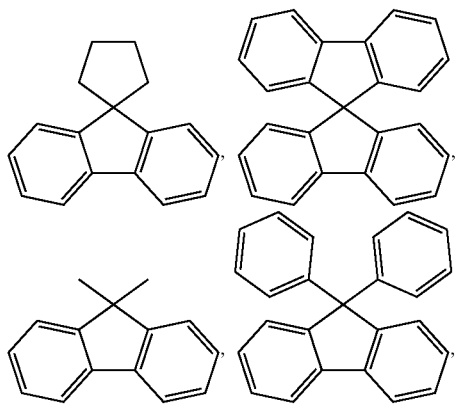

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, the heteroaryl group includes one or more of an atom other than carbon, that is, a heteroatom, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of the heterocyclic group include a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the N-arylheteroarylamine group and the N-alkylheteroarylamine group are the same as the above-described examples of the heteroaryl group.

In the present specification, the arylene group means that there are two bonding positions in an aryl group, that is, a divalent group. The above-described description on the aryl group may be applied, except that the arylene groups are each a divalent group.

In the present specification, the heteroarylene group means that there are two bonding positions in a heteroaryl group, that is, a divalent group. The above-described description on the heteroaryl group may be applied, except that these are each a divalent group.

In the present specification, in a substituted or unsubstituted ring formed by combining adjacent groups, the "ring" means a substituted or unsubstituted hydrocarbon ring; or a substituted or unsubstituted hetero ring.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a hetero ring includes one or more of an atom other than carbon, that is, a heteroatom, and specifically, the heteroatom may include one or more atoms selected from the group consisting of O, N, Se, and S, and the like. The hetero ring may be monocyclic or polycyclic, may be an aromatic ring, an aliphatic ring, or a fused ring of the aromatic ring and the aliphatic ring, and may be selected from the examples of the heteroaryl group, except for the hetero ring which is not monovalent.

According to an exemplary embodiment of the present specification, in Chemical Formula 1, Ar4 is a substituted or unsubstituted fluoranthene ring; or a substituted or unsubstituted triphenylene ring.

According to an exemplary embodiment of the present specification, in Chemical Formula 1, A is represented by the following Chemical Formula A-1 or A-2.

[Chemical Formula A-1]

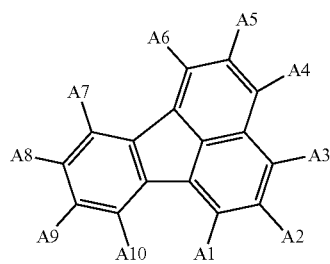

[Chemical Formula A-2]

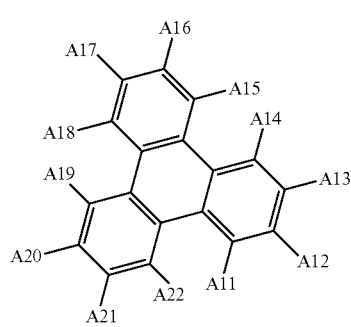

In Chemical Formulae A-1 and A-2,
A1 and A2; A2 and A3; A4 and A5; A5 and A6; A7 and A8; A8 and A9; A9 and A10; A11 and A12; A12 and A13; A13 and A14; A15 and A16; A16 and A17; A17 and A18; A19 and A20; A20 and A21; or A21 and A22 in A1 to A22 are moieties directly bonded to Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to an exemplary embodiment of the present specification, Chemical Formula 1 is represented by the following Chemical Formula 1-1 or 1-2.

[Chemical Formula 1-1]

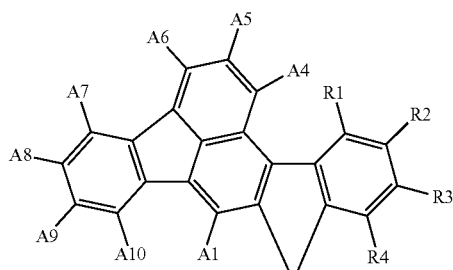

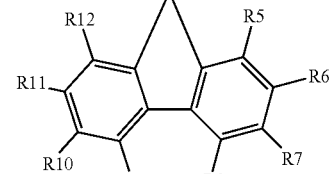

[Chemical Formula 1-2]

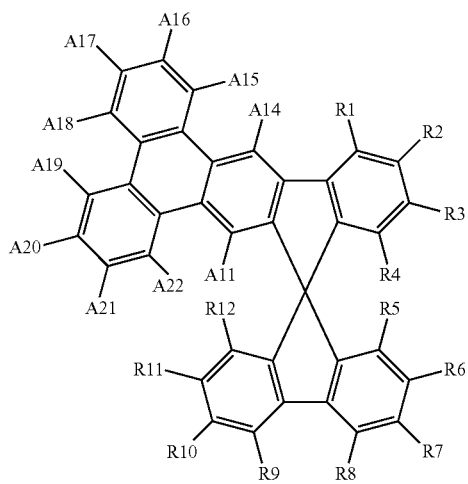

In Chemical Formulae 1-1 and 1-2, the definitions of R1 to R12 are the same as those in Chemical Formula 1, and A1, A4 to A11, and A14 to A22 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to an exemplary embodiment of the present specification, Chemical Formula 1 is represented by the following Chemical Formula 1-3 or 1-4.

[Chemical Formula 1-3]

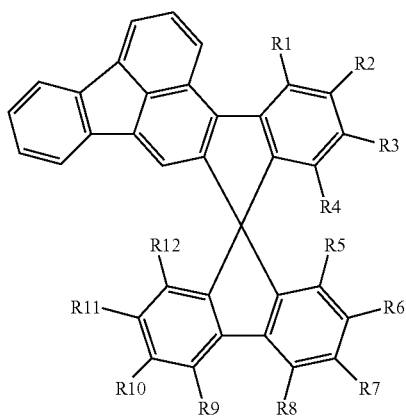

[Chemical Formula 1-4]

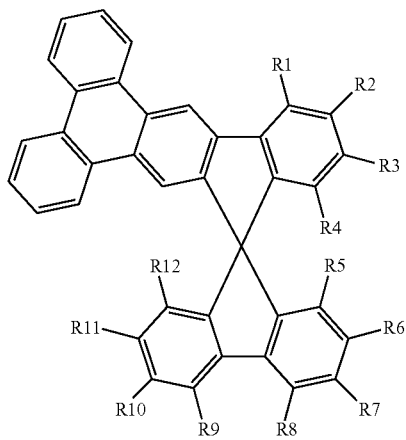

In Chemical Formulae 1-3 and 1-4, the definitions of R1 to R12 are the same as those in Chemical Formula 1.

According to an exemplary embodiment of the present specification, in Chemical Formula 1, R1 to R12 are the same as or different from each other, and are each independently selected from the group consisting of hydrogen; a substituted or unsubstituted diarylamine group; a substituted or unsubstituted diheteroaryl amine group; a substituted or unsubstituted silyl group; a substituted or unsubstituted phosphine oxide group; a substituted or unsubstituted monocyclic or polycyclic aryl group having 6 to 30 carbon atoms; and a substituted or unsubstituted monocyclic or polycyclic heteroaryl group having 2 to 30 carbon atoms.

According to an exemplary embodiment of the present specification, in Chemical Formula 1, R1 to R12 are the same as or different from each other, and are each independently selected from the group consisting of a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted chrysenyl group; a substituted or unsubstituted quarterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; a substituted or unsubstituted pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted dimethylphosphine oxide group; a substituted or unsubstituted diphenylphosphine oxide group; a substituted or unsubstituted dinaphthylphosphine oxide group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted diphenylamine group; a substituted or unsubstituted N-phenylnaphthylamine group; a substituted or unsubstituted N-phenylbiphenylamine group; a substituted or unsubstituted N-phenylphenanthrenylamine group; a substituted or unsubstituted N-biphenylnaphthylamine group; a substituted or unsubstituted dibiphenylamine group; a substituted or unsubstituted N-biphenylphenanthrenylamine group; a substituted or unsubstituted dinaphthylamine group; a substituted or unsubstituted N-quarterphenylfluorenylamine group; a substituted or unsubstituted N-terphenylfluorenylamine group; a substituted or unsubstituted N-biphenyl terphenylamine group; a substituted or unsubstituted N-biphenylfluorenylamine group; a substituted or unsubstituted N-phenylfluorenylamine group; a substituted or unsubstituted N-naphthylfluorenylamine group; a substituted or unsubstituted N-phenanthrenylfluorenylamine group; a substituted or unsubstituted difluorenylamine group; a substituted or unsubstituted N-phenyl terphenylamine group; a substituted or unsubstituted N-phenylcarbazolylamine group; a substituted or unsubstituted N-biphenylcarbazolylamine group; a substituted or unsubstituted N-phenylbenzocarbazolylamine group; a substituted or unsubstituted N-biphenylbenzocarbazolylamine group; a substituted or unsubstituted N-phenyldibenzofuranylamine group; a substituted or unsubstituted N-phenyldibenzothiopheneamine group; a substituted or unsubstituted N-fluorenylcarbazolylamine group; a substituted or unsubstituted benzocarbazolyl group; a substituted or unsubstituted dibenzocarbazolyl group; a substituted or unsubstituted carbazolyl group; substituted or unsubstituted

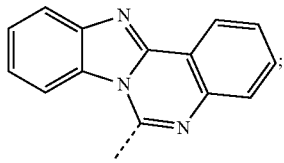

substituted or unsubstituted

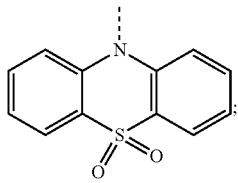

and a structure represented by the following Chemical Formula a, at least one of R1 to R12 has a substituent other than hydrogen, and means a moiety bonded to Chemical Formula 1.

[Chemical Formula a]

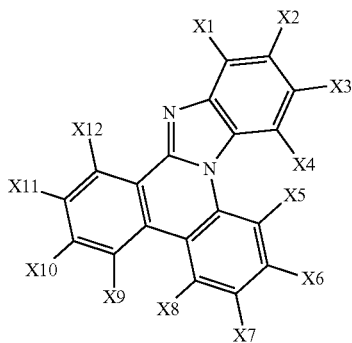

In Chemical Formula a, at least one of X1 to X12 is a moiety bonded to Chemical Formula 1, and the others are the same as or different from each other, and are each independently hydrogen; a substituted or unsubstituted alkyl group; a substituted or unsubstituted aryl group; or a substituted or unsubstituted heteroaryl group, or adjacent groups are linked to each other to form a substituted or unsubstituted ring.

According to an exemplary embodiment of the present specification, in Chemical Formula a, one of X1 to X12 is a moiety bonded to Chemical Formula 1, and the others are hydrogen.

According to an exemplary embodiment of the present specification, in Chemical Formula a, X11 and X12 are linked to each other to form a substituted or unsubstituted monocyclic or polycyclic hydrocarbon ring having 6 to 20 carbon atoms.

According to an exemplary embodiment of the present specification, in Chemical Formula a, X11 and X12 are linked to each other to form a substituted or unsubstituted monocyclic or polycyclic hydrocarbon ring having 6 to 10 carbon atoms.

According to an exemplary embodiment of the present specification, in Chemical Formula a, X11 and X12 are linked to each other to form a substituted or unsubstituted benzene ring.

According to an exemplary embodiment of the present specification, in Chemical Formula a, X11 and X12 are linked to each other to form a benzene ring.

According to an exemplary embodiment of the present specification, in Chemical Formula 1, R1 to R12 are the same as or different from each other, and are each independently selected from the group consisting of hydrogen; a phenyl group; a biphenyl group; a phenanthrenyl group; a naphthyl group; a terphenyl group; a fluorenyl group; an anthracenyl group; a chrysenyl group; a quarterphenyl group; a spirobifluorenyl group; a pyrenyl group; a triphenylenyl group; a perylenyl group; a triazinyl group; a pyrimidyl group; a pyridyl group; a quinolinyl group; a quinazolinyl group; a benzoquinolinyl group; a phenanthrolinyl group; a quinoxalinyl group; a dibenzofuranyl group; a dibenzothiophene group; benzonaphthofuranyl group; a benzonaphthothiophene group; a dimethylphosphine oxide group; diphenylphosphine oxide group; dinaphthylphosphine oxide group; a benzoxazolyl group; a benzothiazolyl group; a benzimidazolyl group; a triphenylsilyl group; a phenothiazinyl group; a phenoxazinyl group; a thiophene group; a diphenylamine group; an N-phenylnaphthylamine group; an N-phenylbiphenylamine group; an N-phenylphenanthrenylamine group; an N-biphenylnaphthylamine group; a dibiphenylamine group; an N-biphenylphenanthrenylamine group; a dinaphthylamine group; N-a quarterphenylfluorenylamine group; an N-terphenylfluorenylamine group; an N-biphenyl terphenylamine group; an N-biphenylfluorenylamine group; a substituted or unsubstituted N-phenylfluorenylamine group; an N-naphthylfluorenylamine group; an N-phenanthrenylfluorenylamine group; a difluorenylamine group; an N-phenyl terphenylamine group; an N-phenylcarbazolylamine group; an N-biphenylcarbazolylamine group; an N-phenylbenzocarbazolylamine group; an N-biphenylbenzocarbazolylamine group; an N-phenyldibenzofuranylamine group; an N-phenyldibenzothipheneamine group; an N-fluorenylcarbazolylamine group; a benzocarbazolyl group; a dibenzocarbazolyl group; a carbazolyl group;

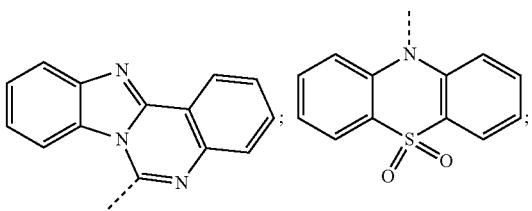

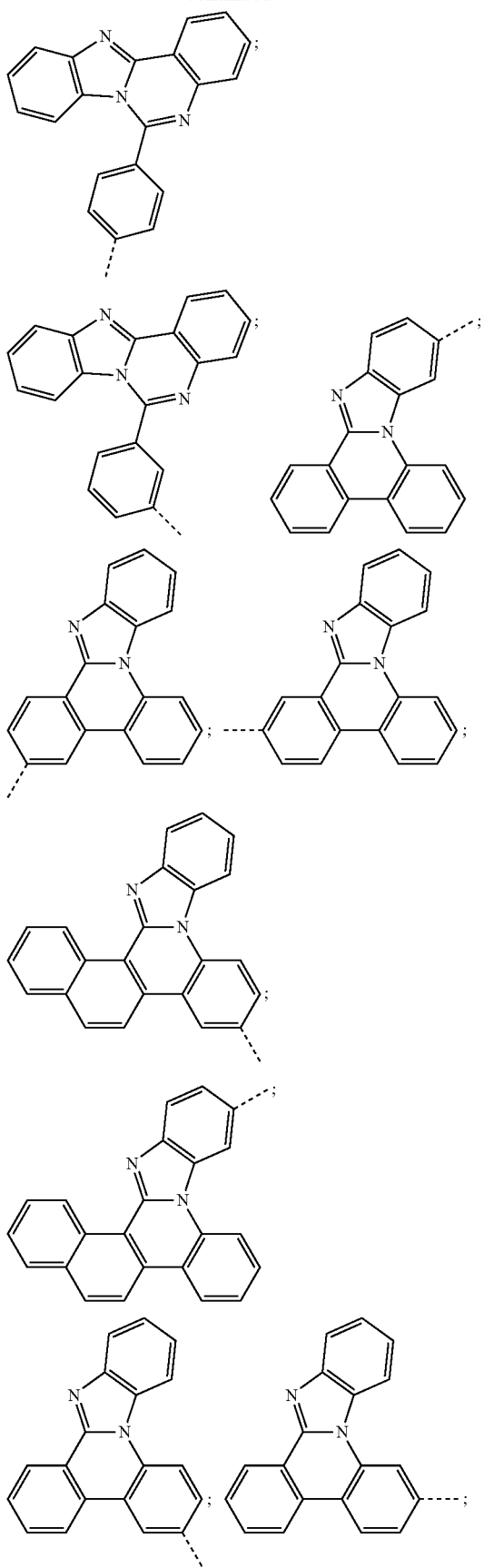

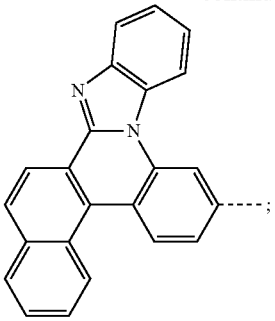

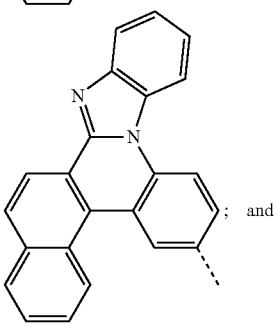

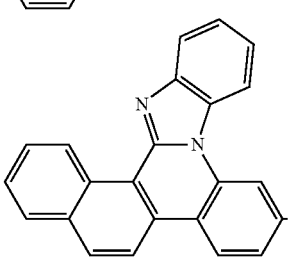

at least one of R1 to R12 has a substituent other than hydrogen, and

R1 to R12 may be unsubstituted or substituted with one or more selected from the group consisting of deuterium; a fluorine group; a nitrile group; a methyl group; an ethyl group; an n-propyl group; an isopropyl group; a t-butyl group; a trimethylsilyl group; a trifluoromethyl group; a trifluoromethoxy group; a pentafluoroethyl group; a cyclohexyl group; a phenyl group; a biphenyl group; a naphthyl group; a fluorenyl group; a phenanthrenyl group; a carbazolyl group; a benzocarbazolyl group; a pyridyl group; a triazinyl group; a triphenylenyl group; a pyrimidyl group; a quinolinyl group; a dibenzofuranyl group; a dibenzothiophene group; a benzimidazolyl group; a benzothiazolyl group; a benzoxazolyl group; a thiophene group; a dimethylphosphine oxide group; a diphenylphosphine oxide group; a dinaphthylphosphine oxide group; a trimethylsilyl group; a triphenylsilyl group; a diphenylamine group; a dibiphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenathrenylfluorenylamine group; an N-biphenylfluorenylamine group; and

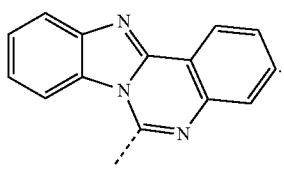
means a moiety bonded to Chemical Formula 1.
According to an exemplary embodiment of the present specification, in Chemical Formula 1, R1 to R12 are the same as or different from each other, and are each independently represented by hydrogen; or any one of the following structural formulae [R-1] to [R-5], and at least one of R1 to R12 has a substituent other than hydrogen.
[R-1]
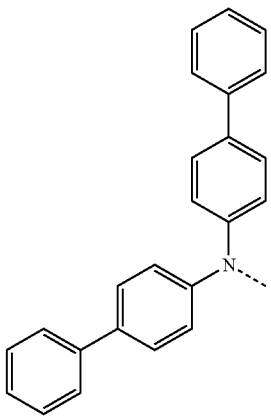
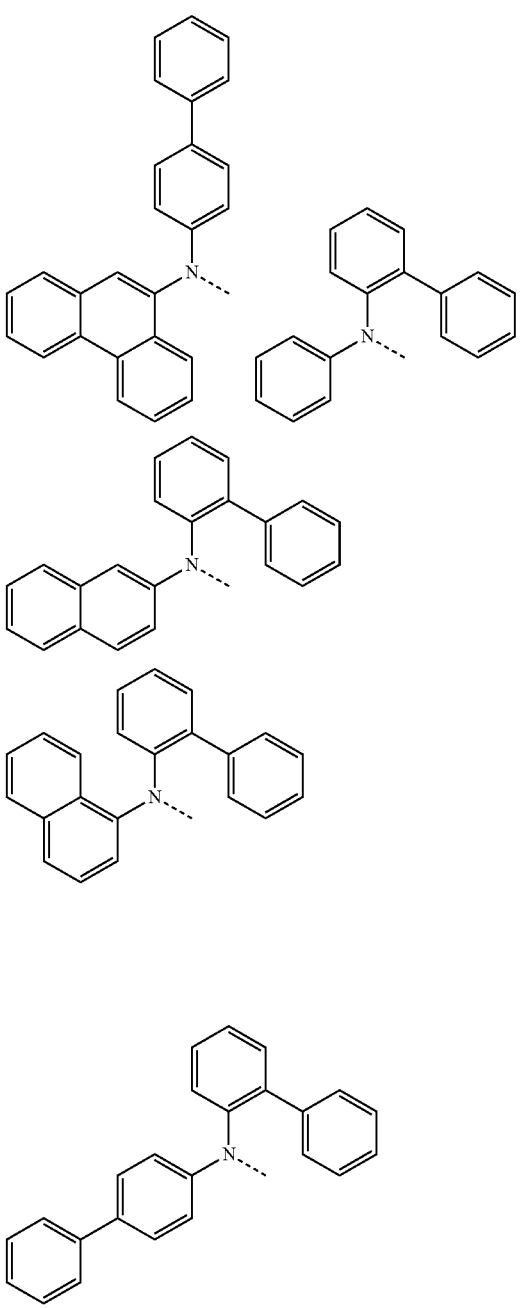

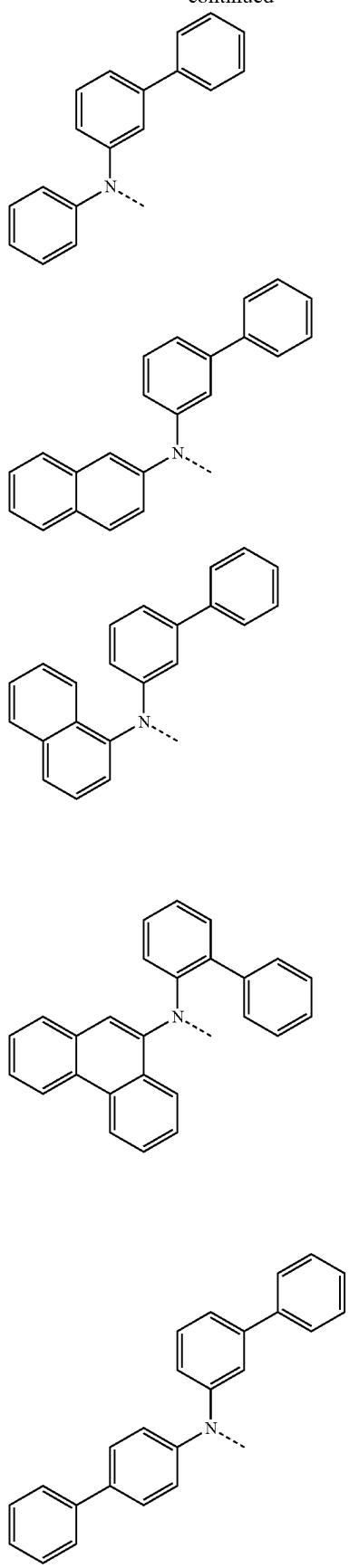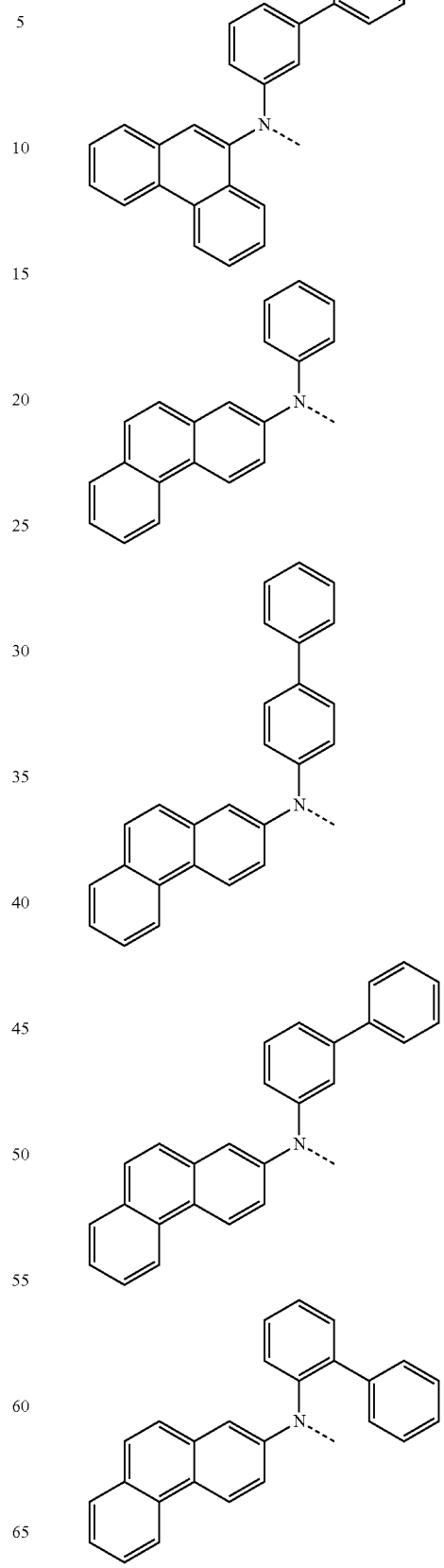

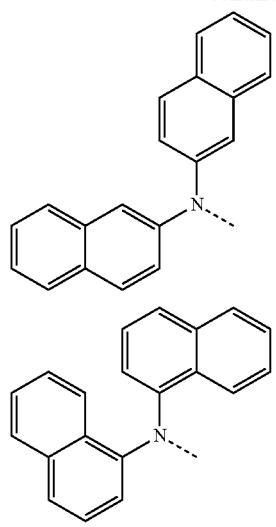
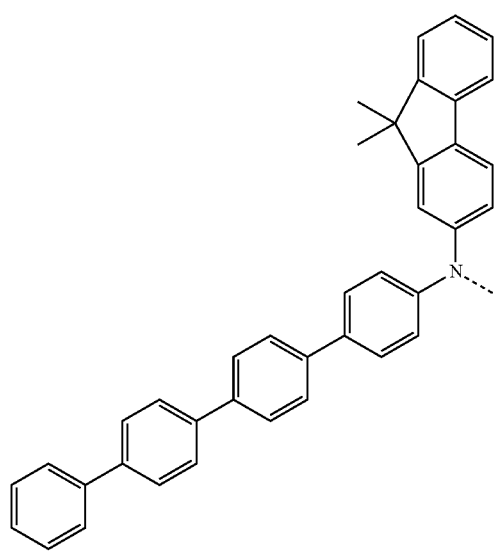
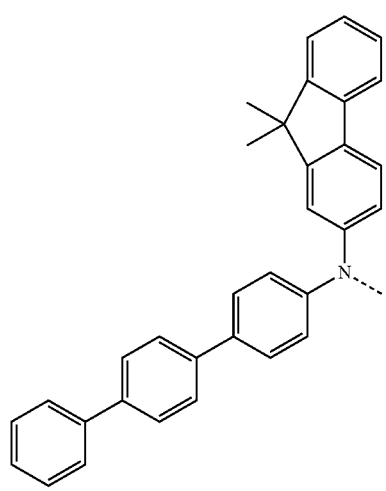
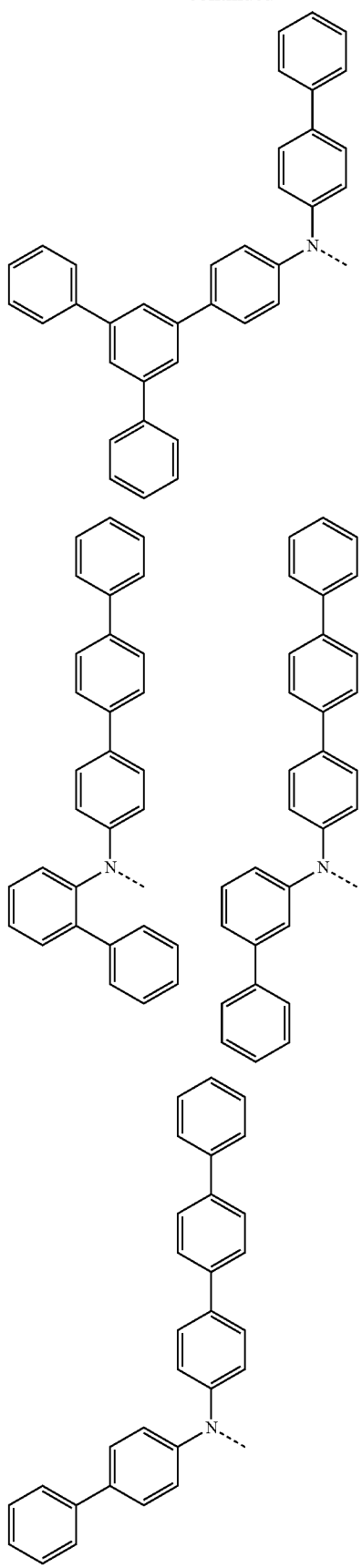

-continued
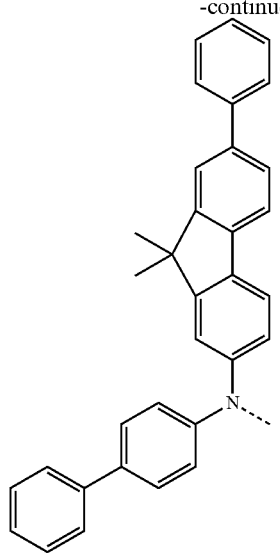
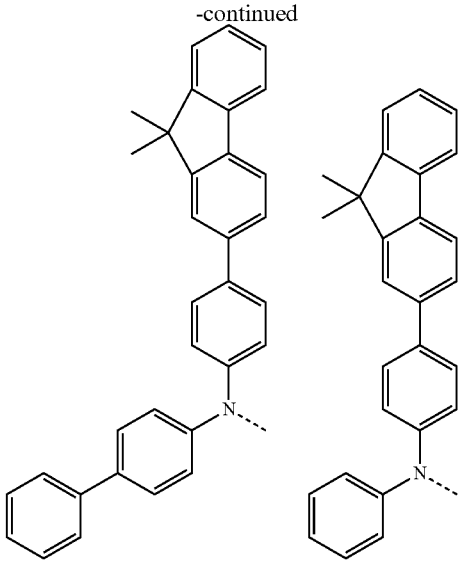
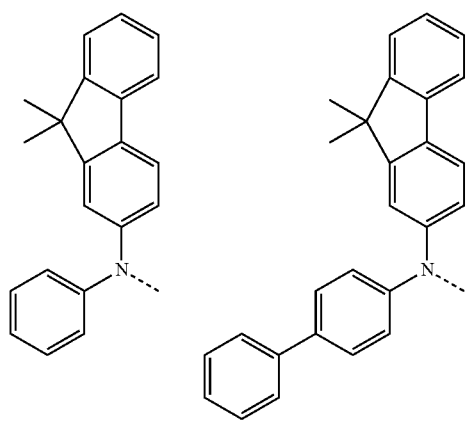
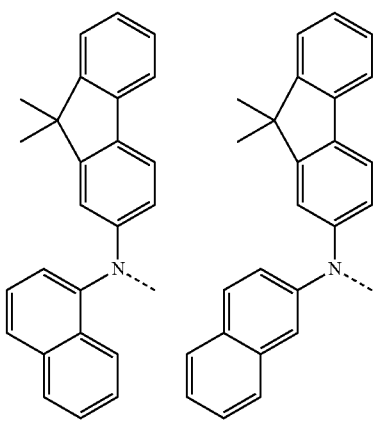
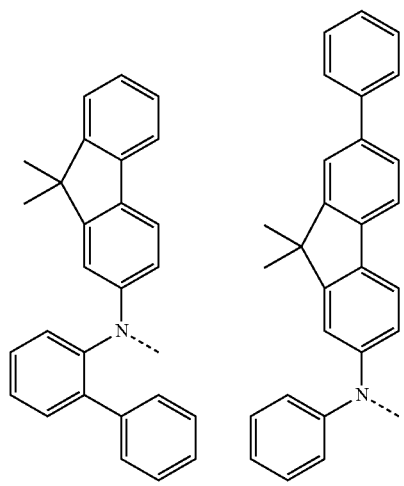
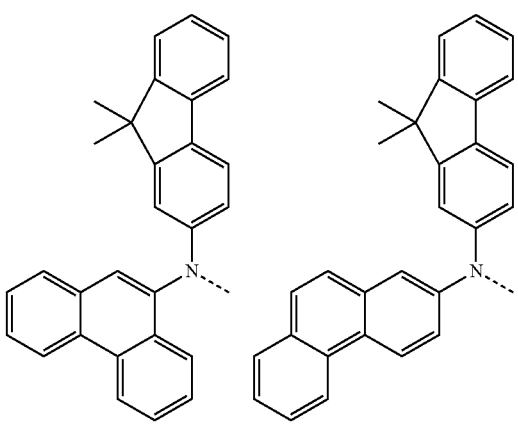

25
-continued
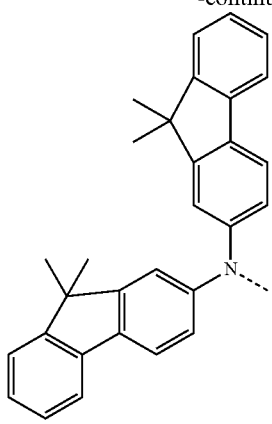
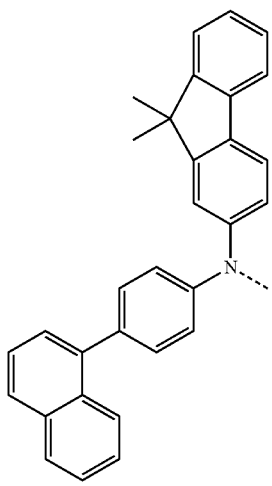
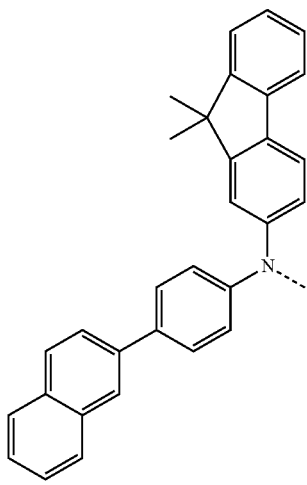
26
-continued
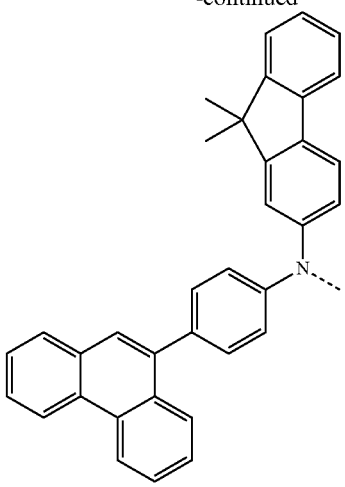
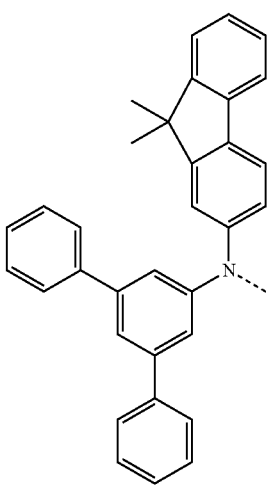
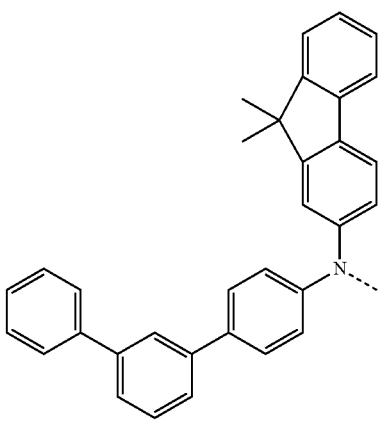

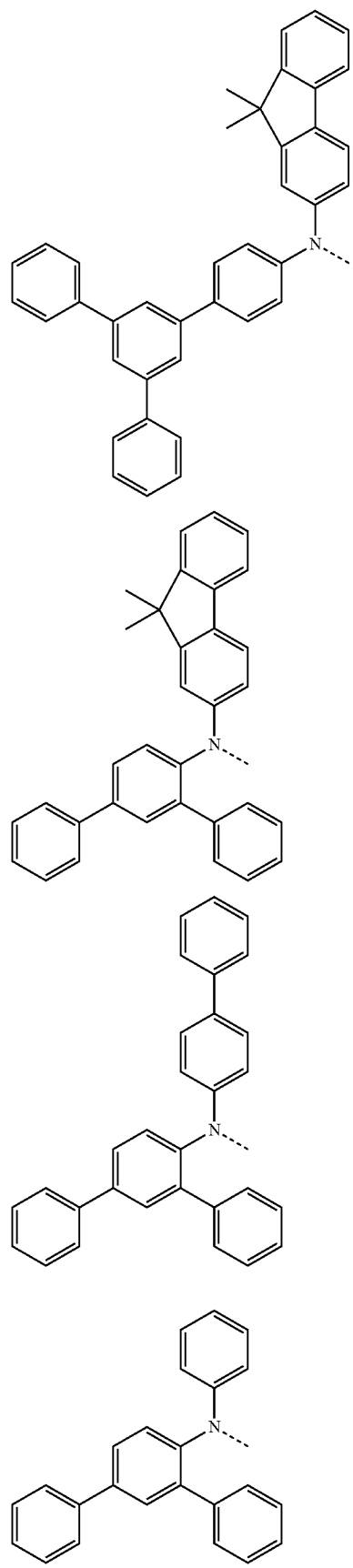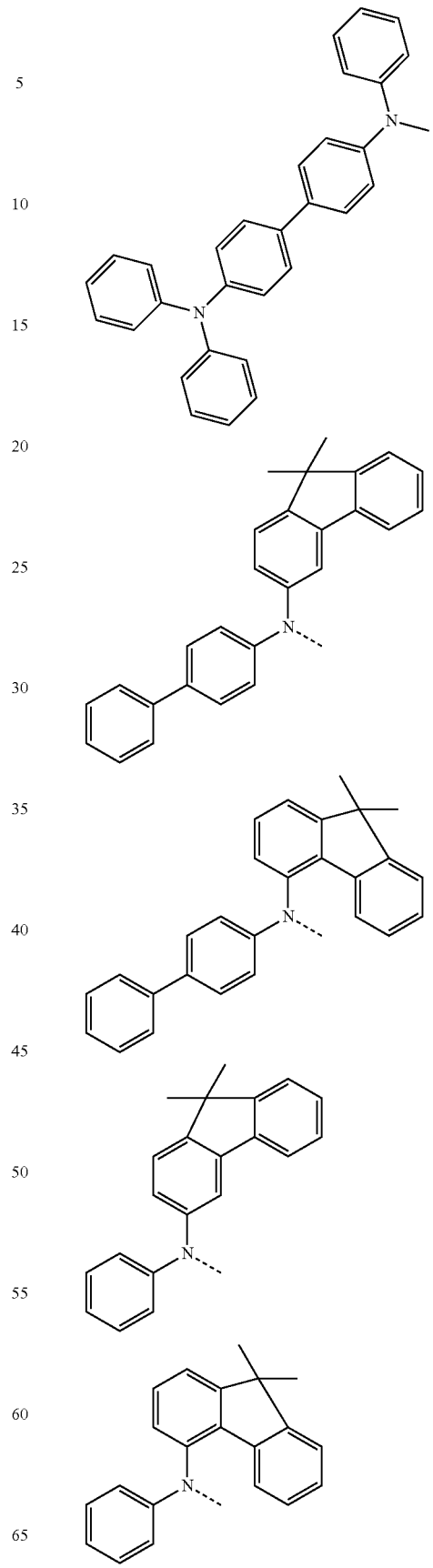

29
-continued
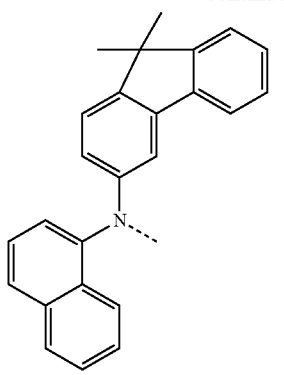
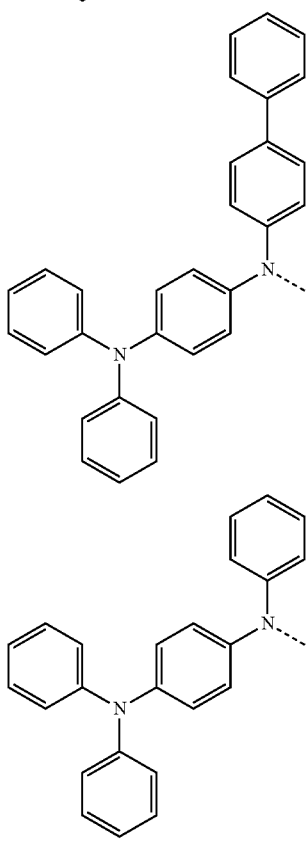
30
-continued
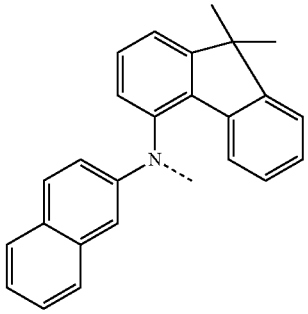
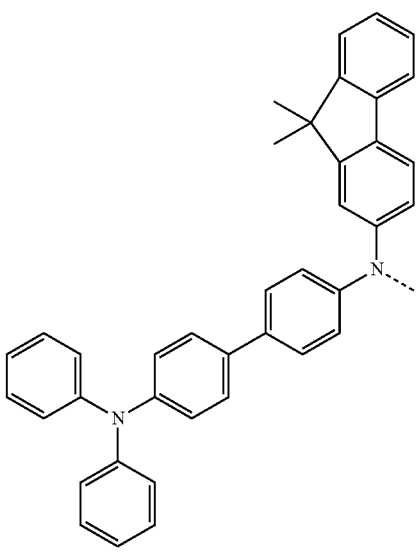
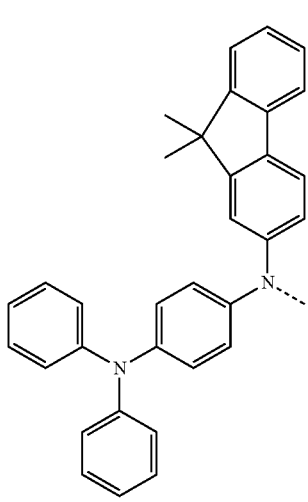
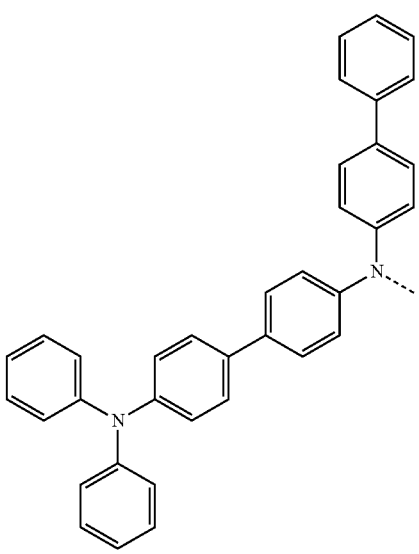

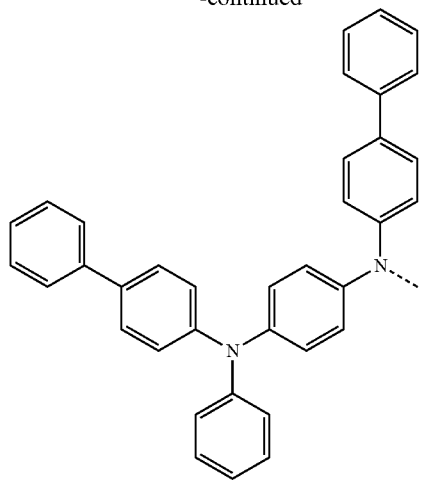
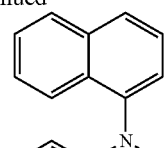
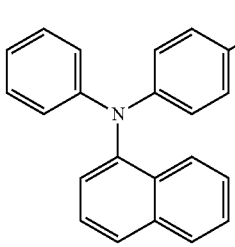
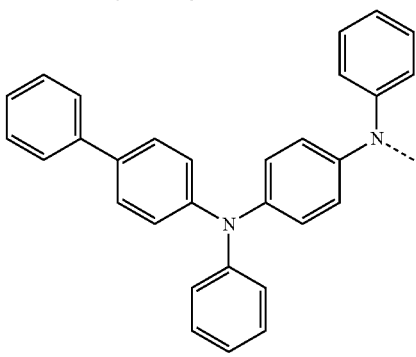
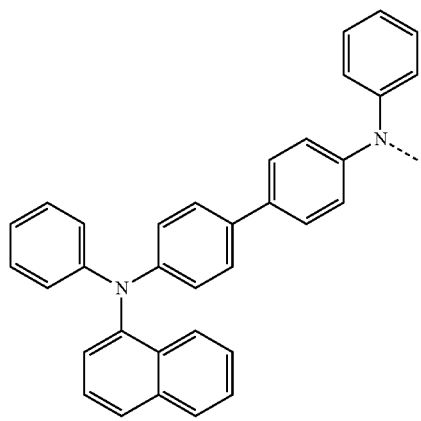
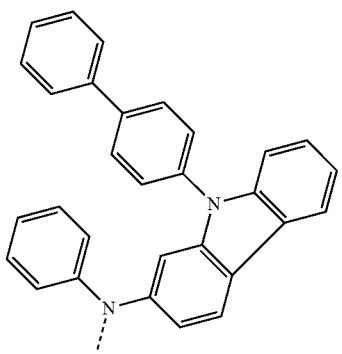
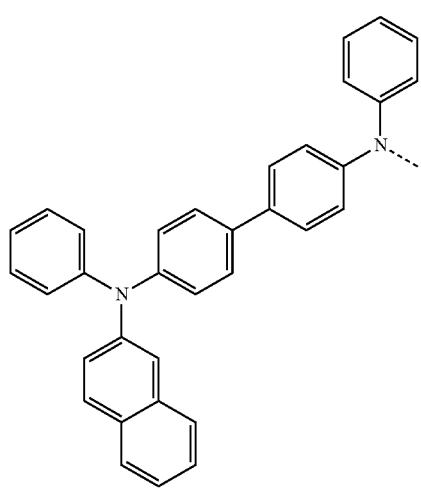
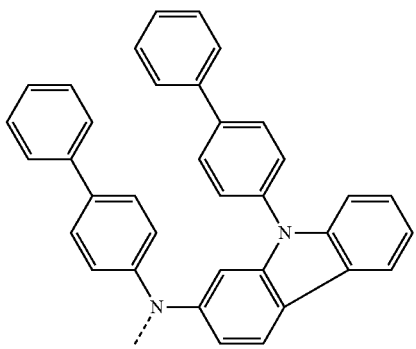

33
-continued
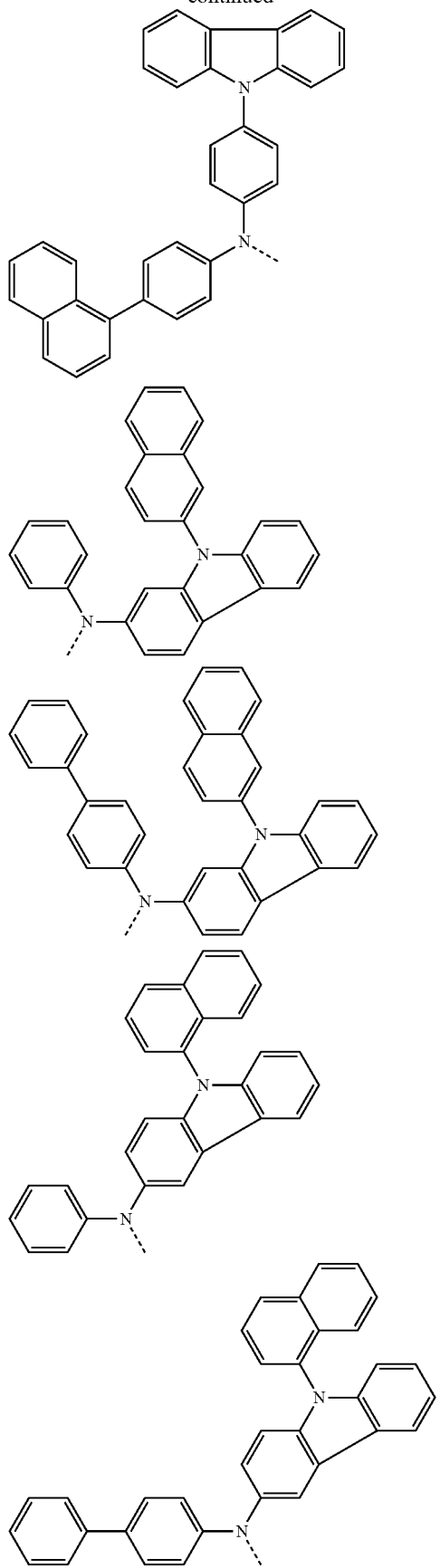
34
-continued
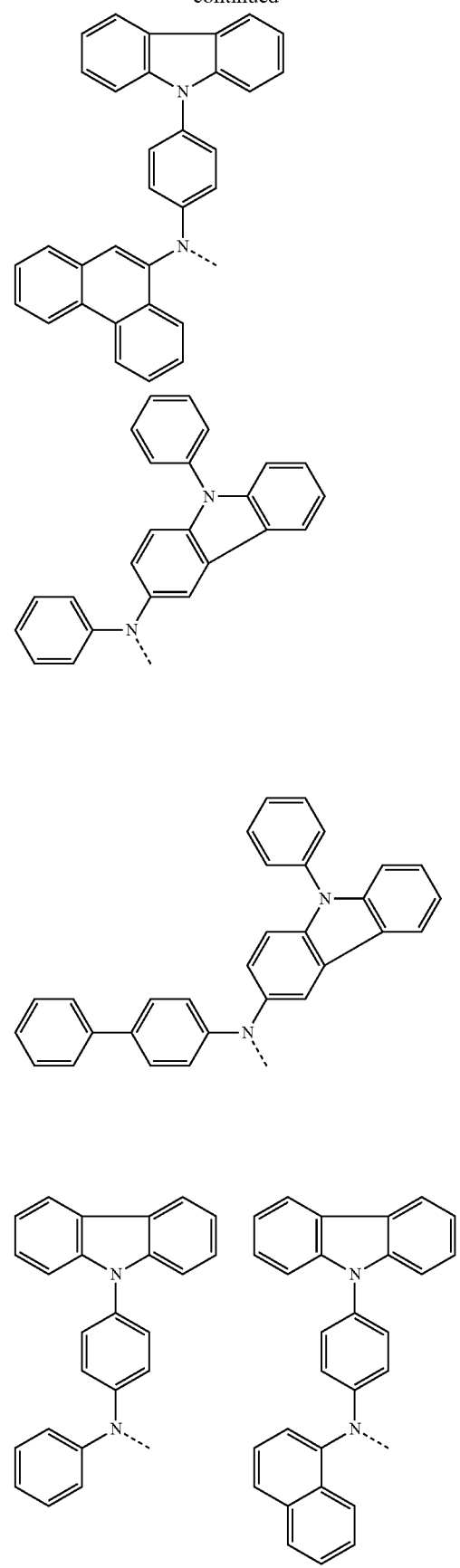

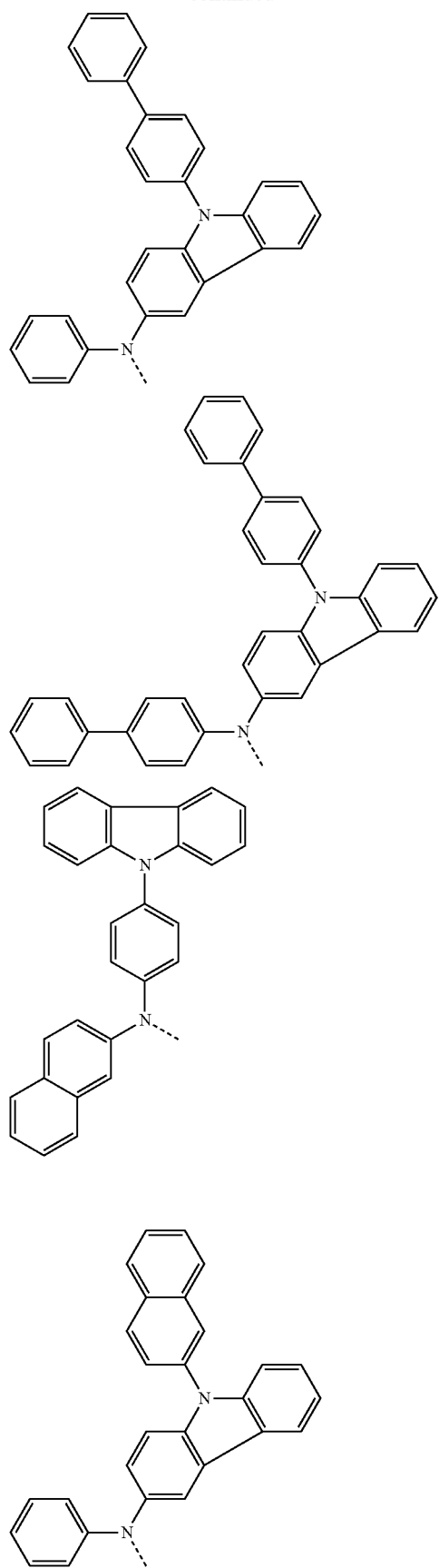
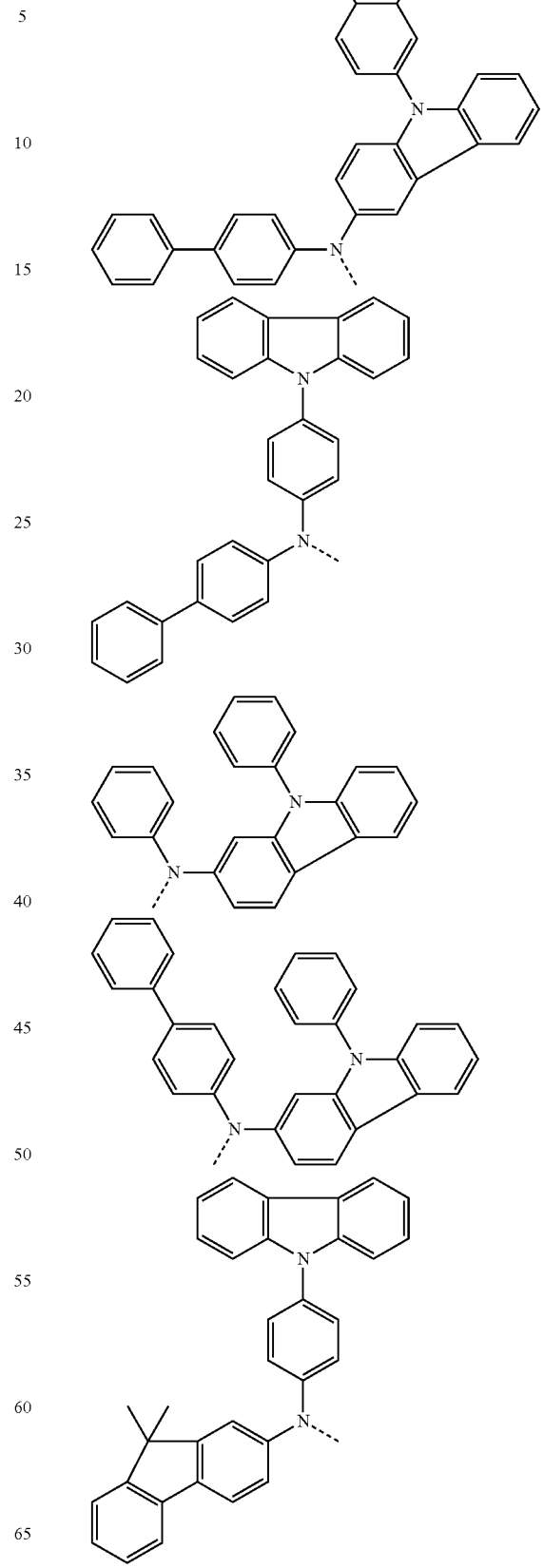

37
-continued
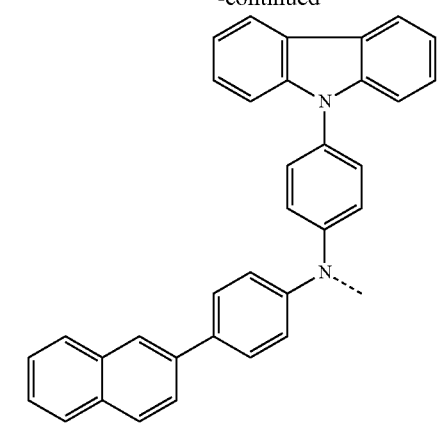
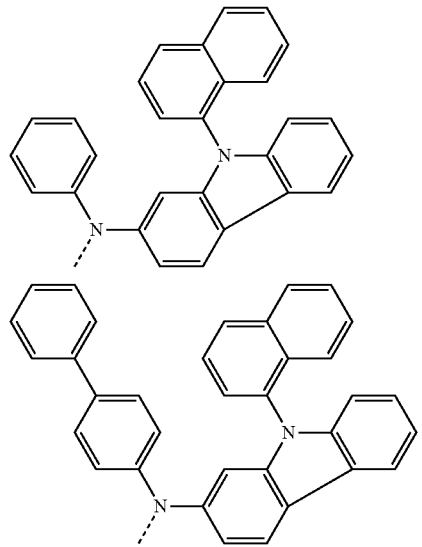
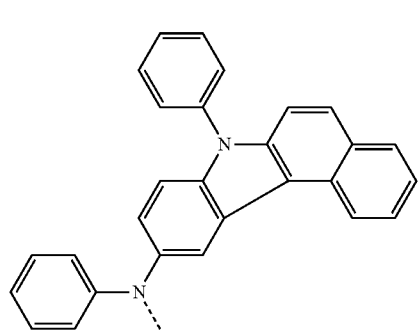
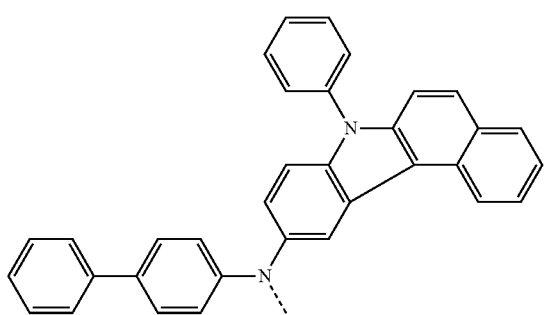
38
-continued
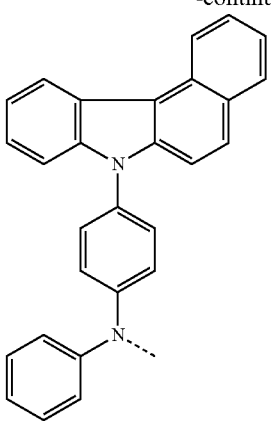
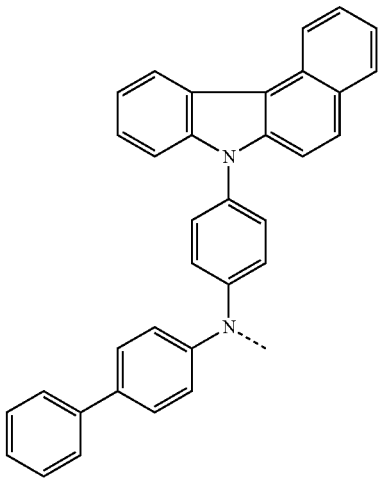
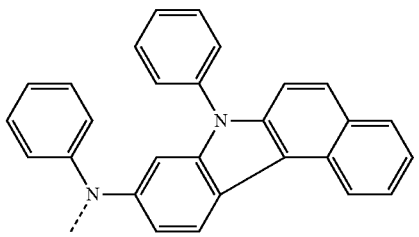
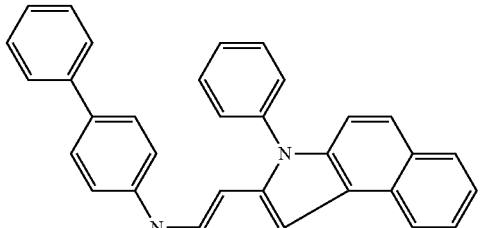

-continued
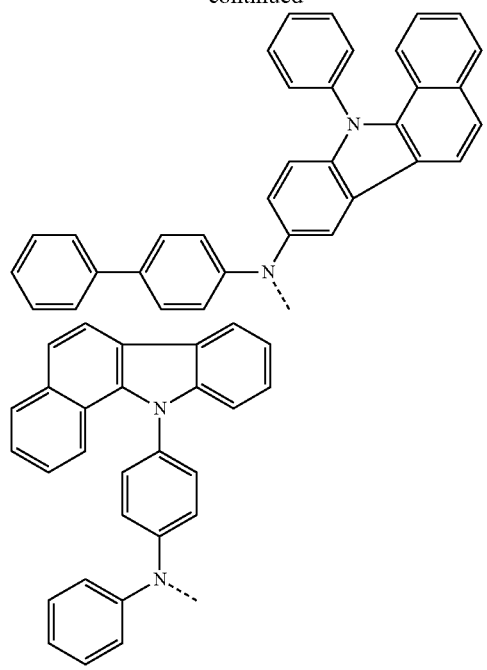
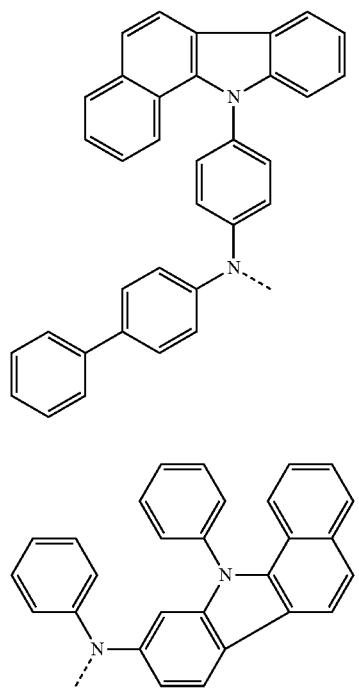
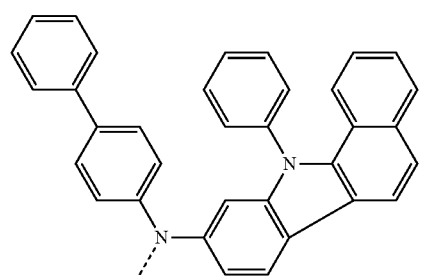
-continued
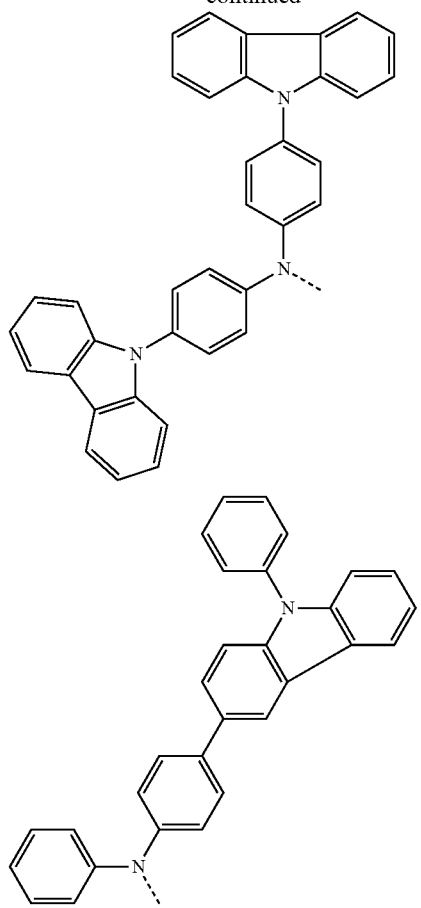
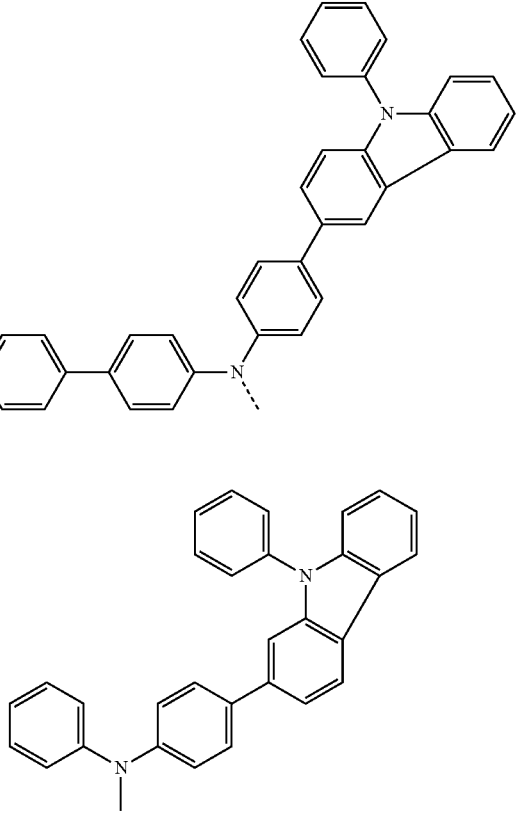

41
-continued
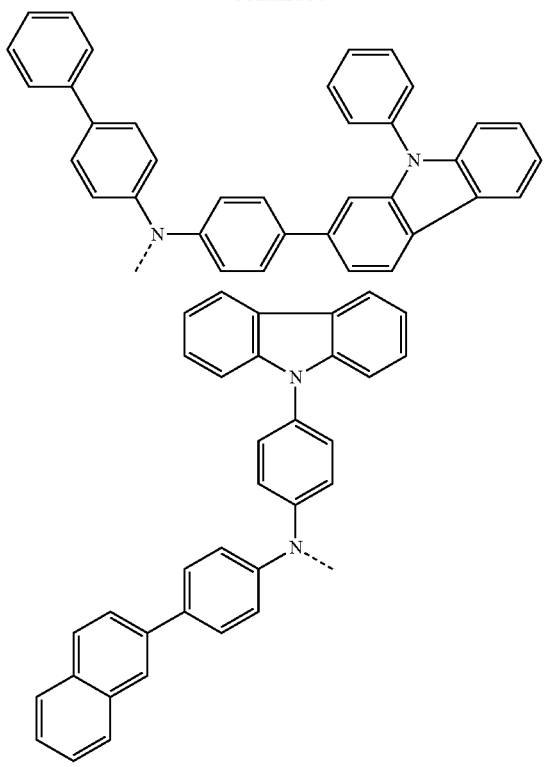
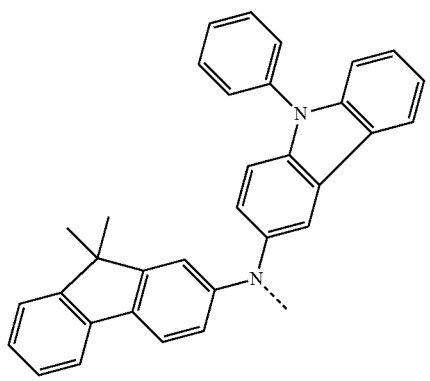
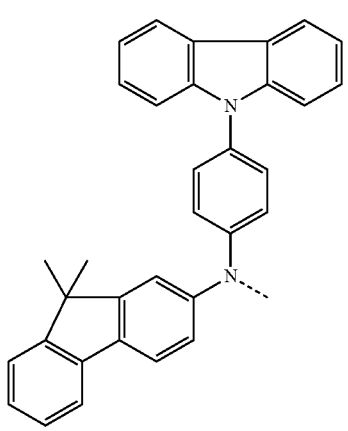
42
-continued
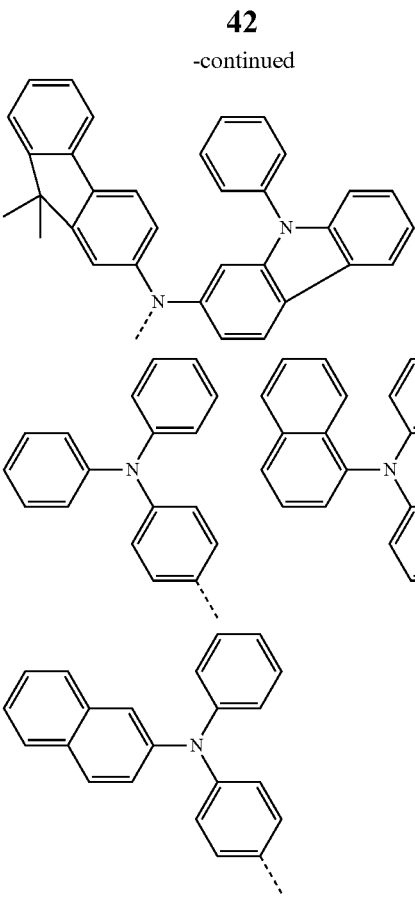
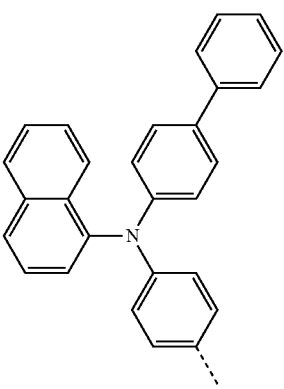
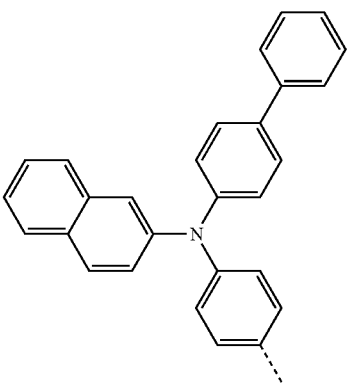

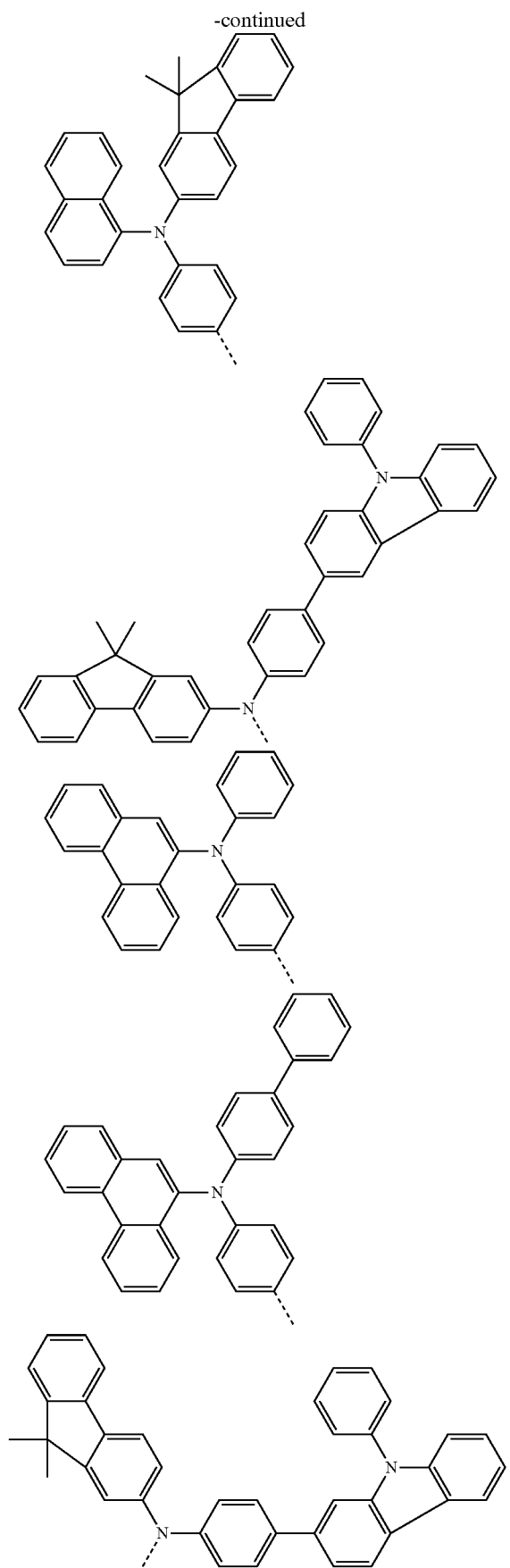
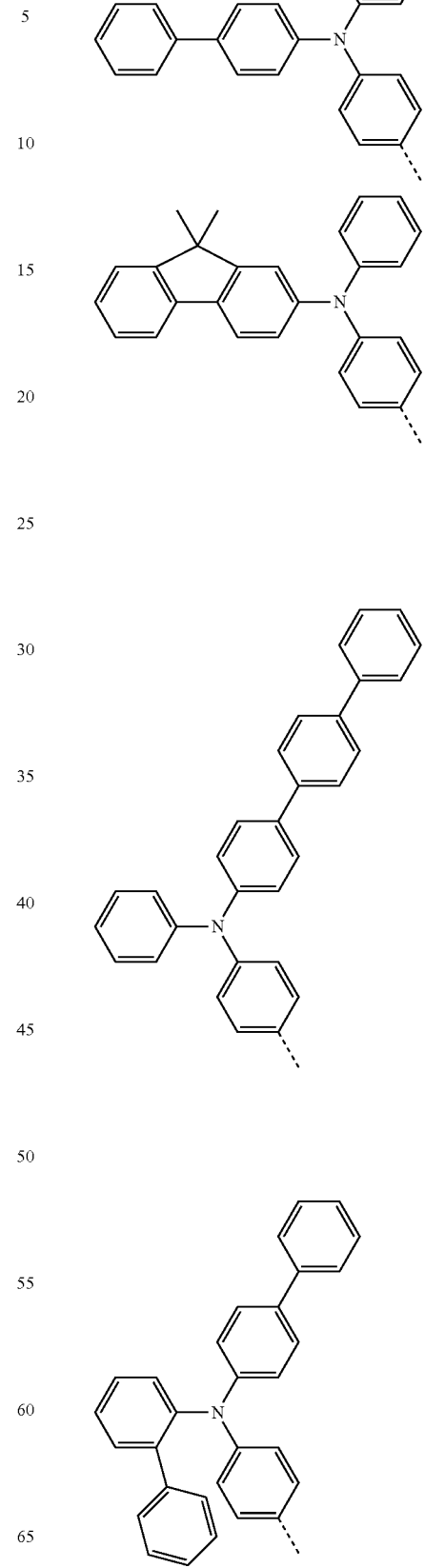

-continued
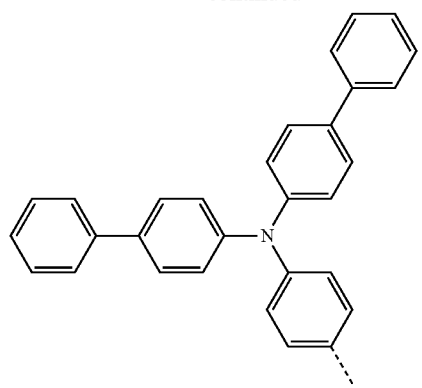
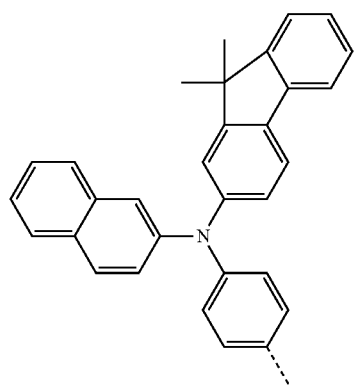
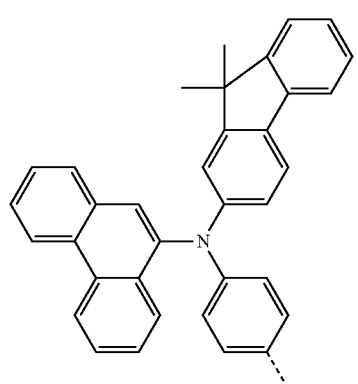
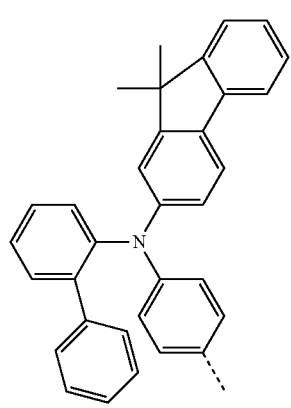
-continued
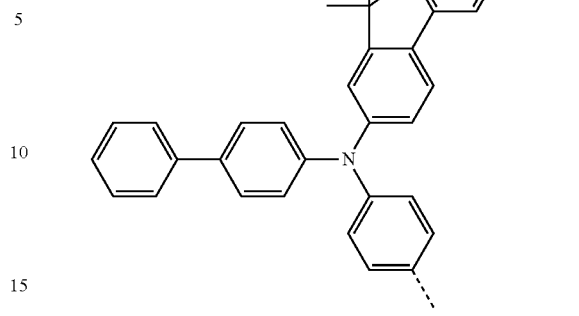
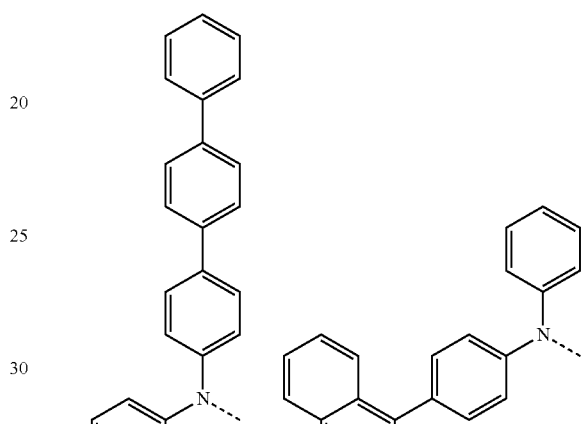
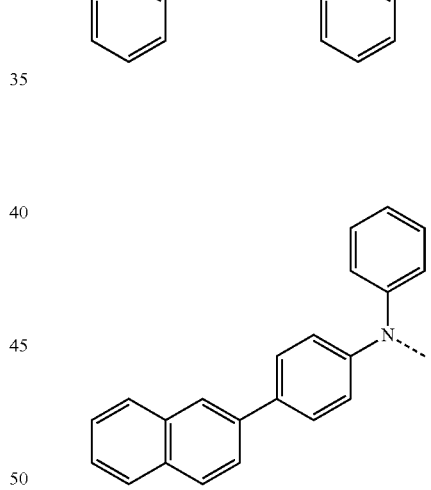
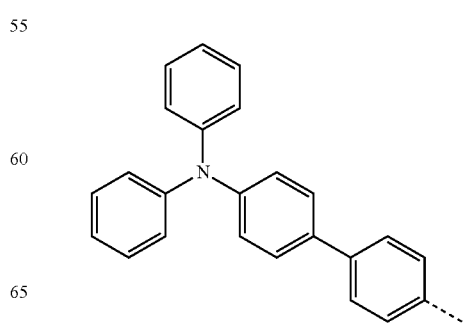

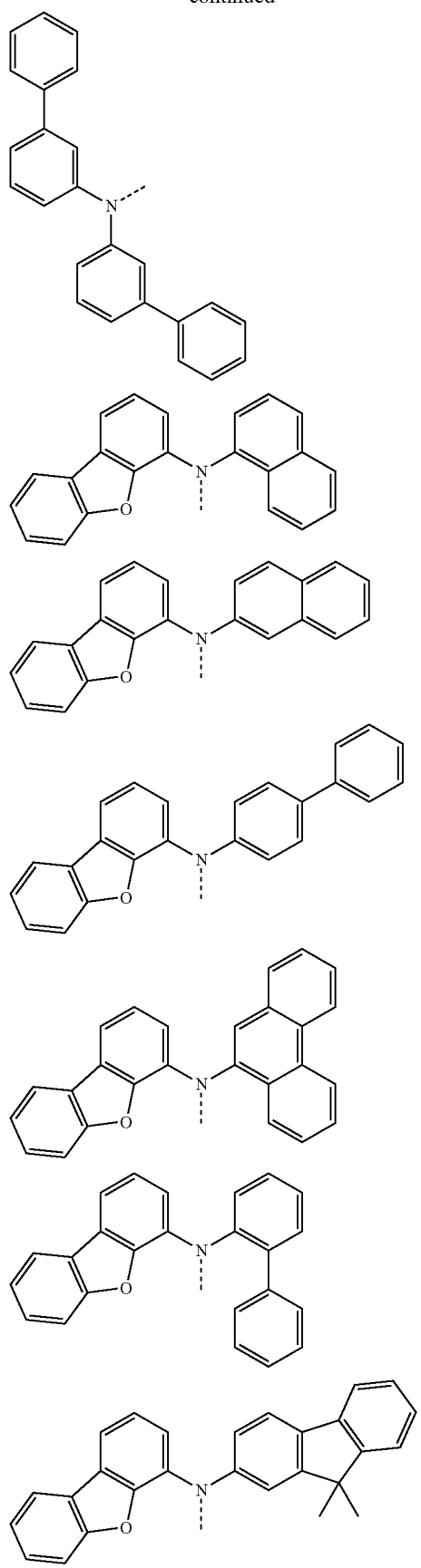
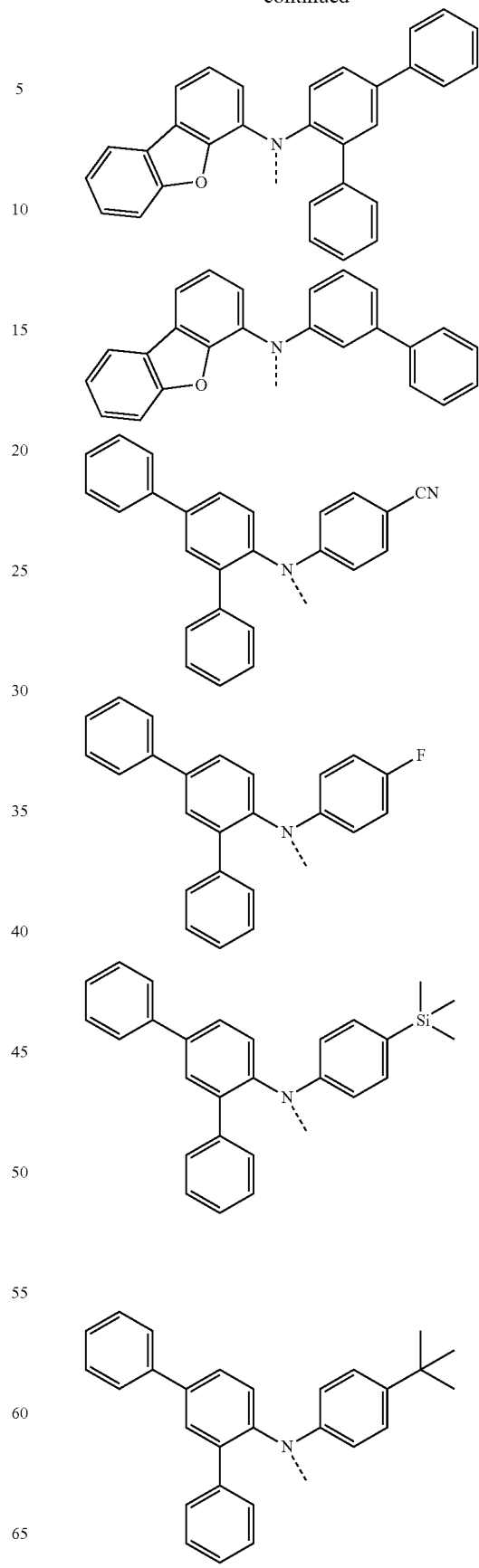

49
-continued
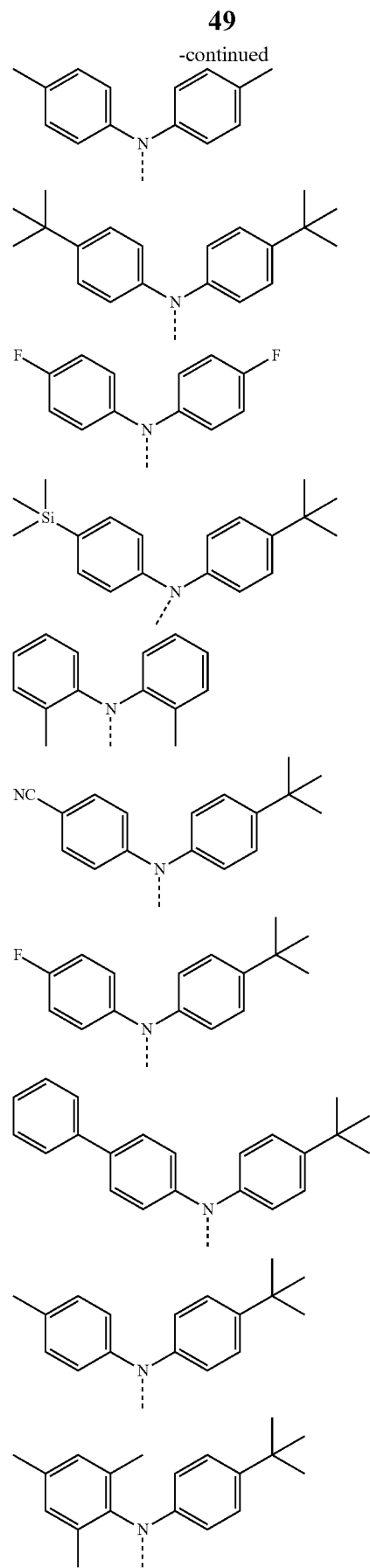
50
-continued
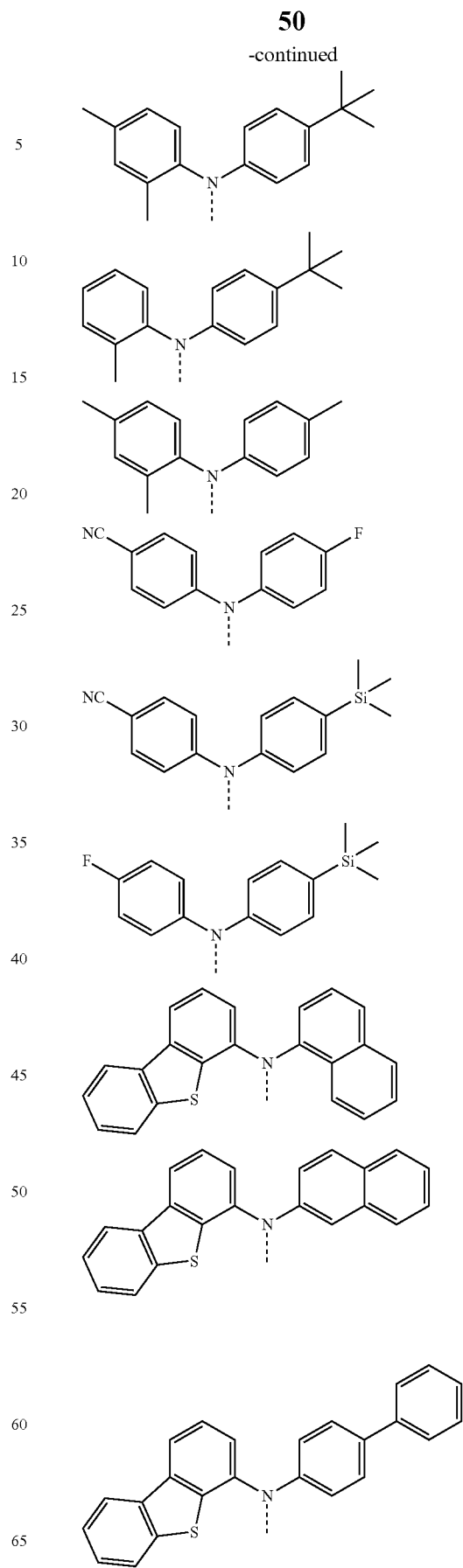

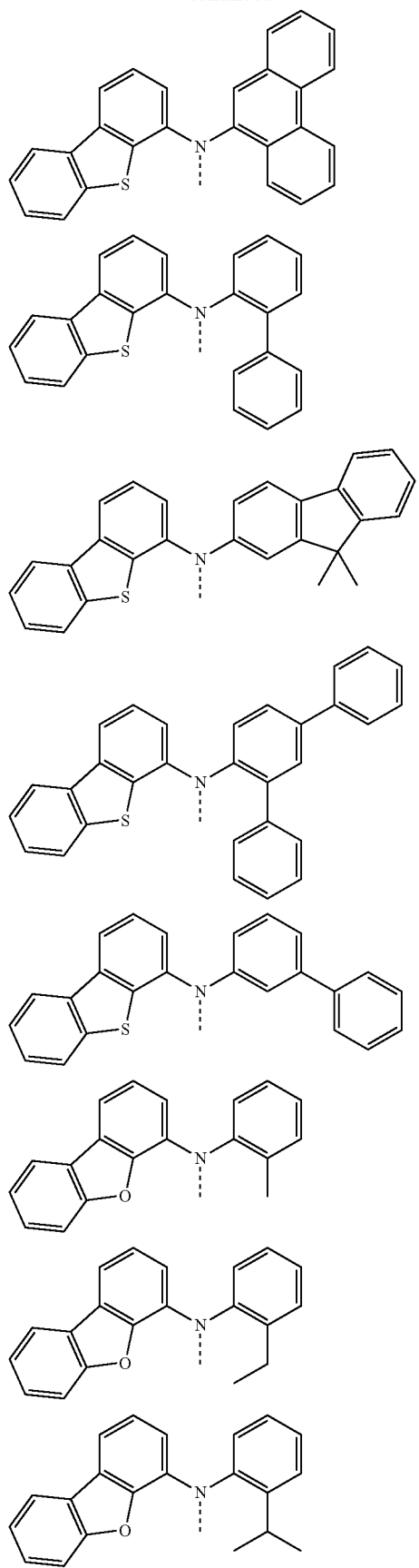
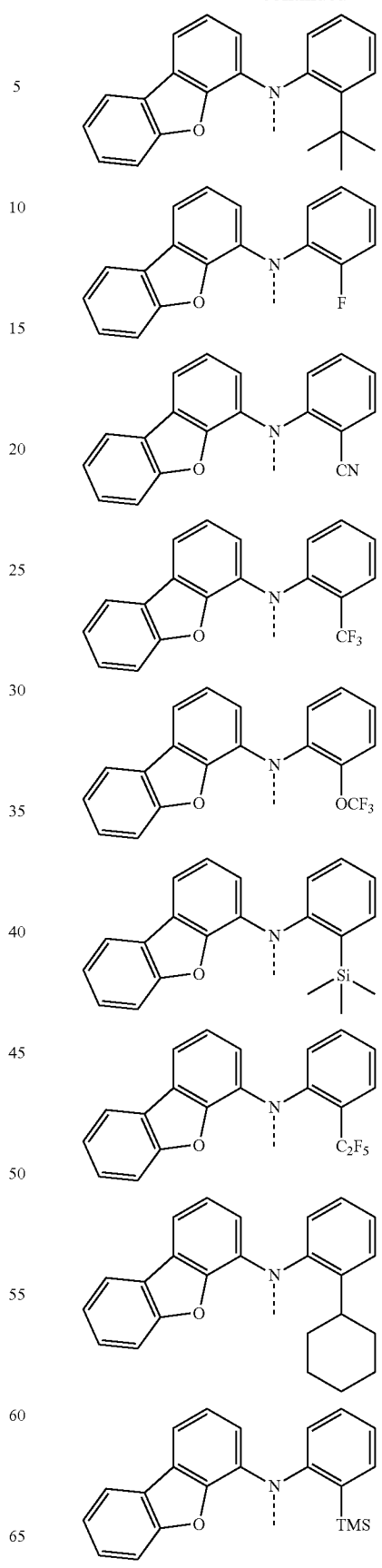

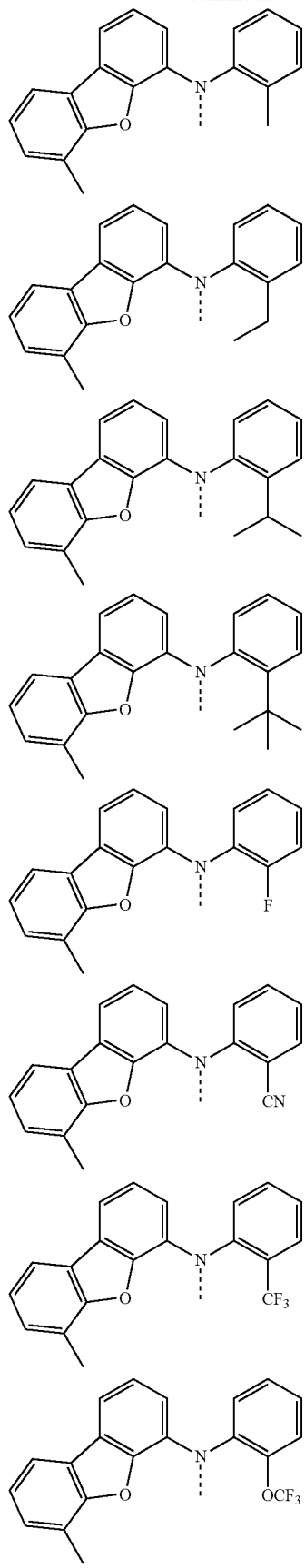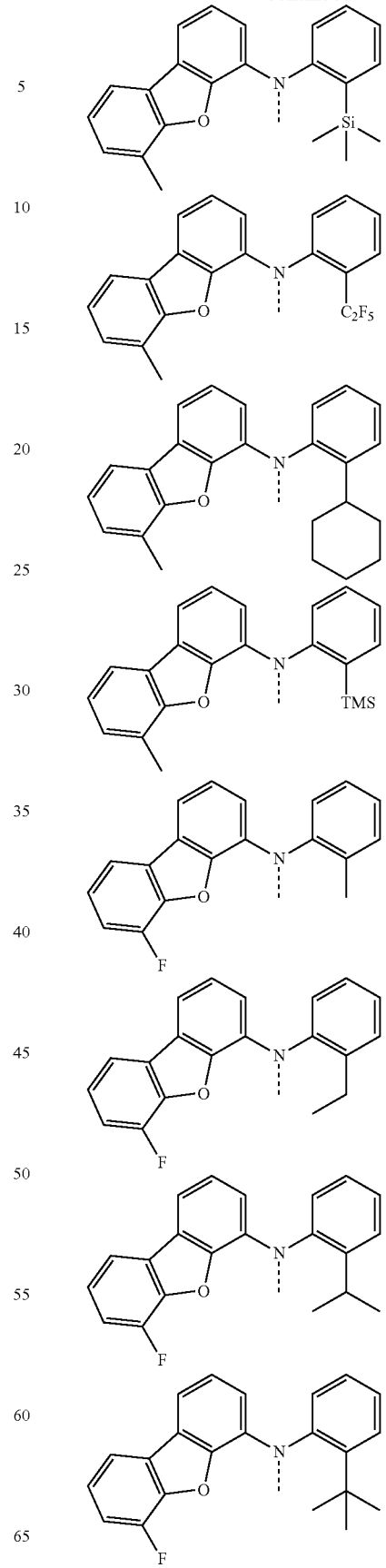

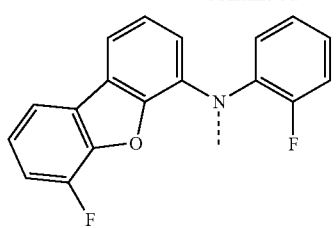
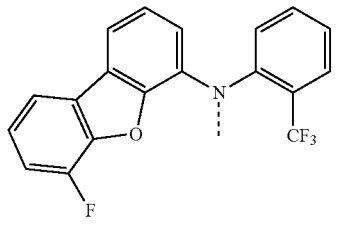
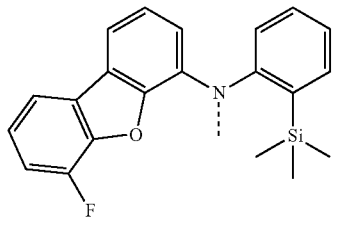
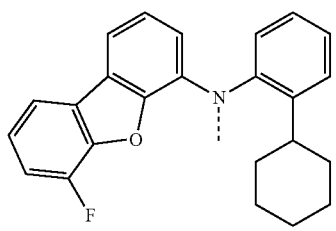
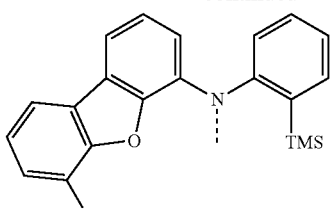

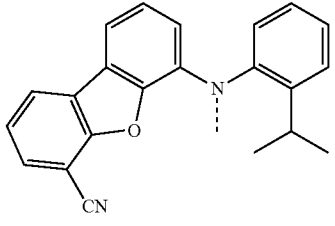
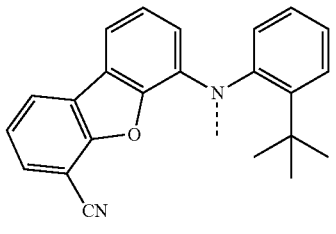
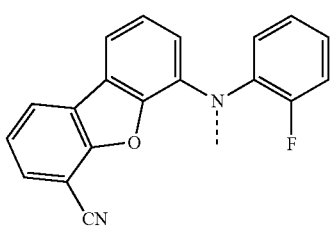
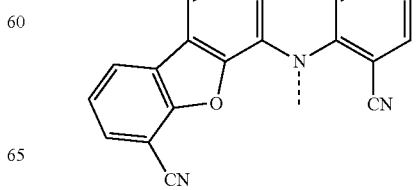

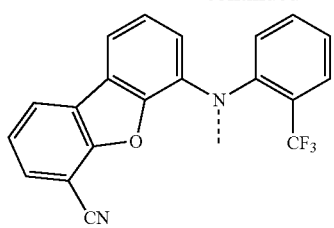
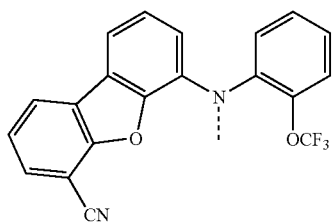
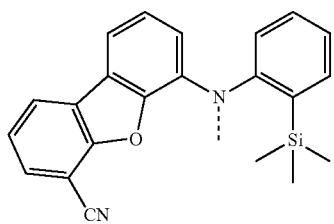

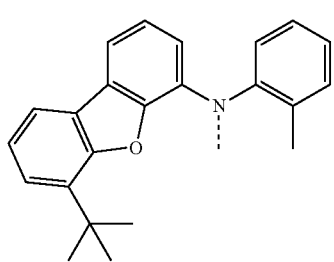
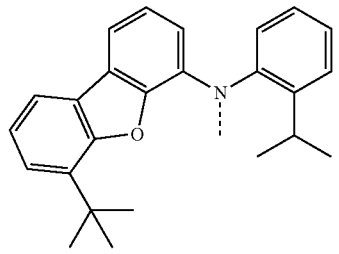
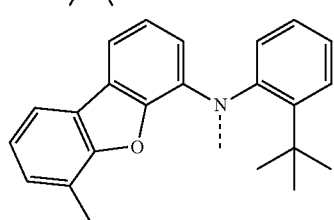
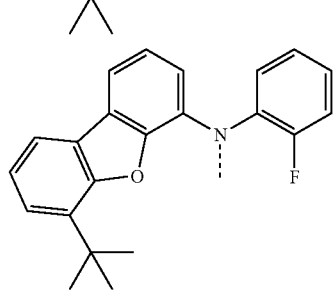
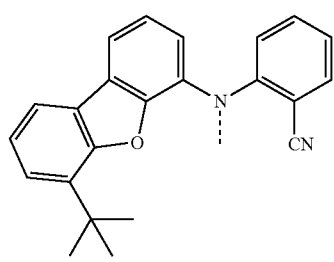
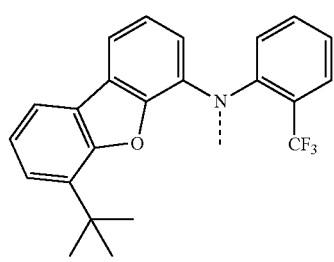

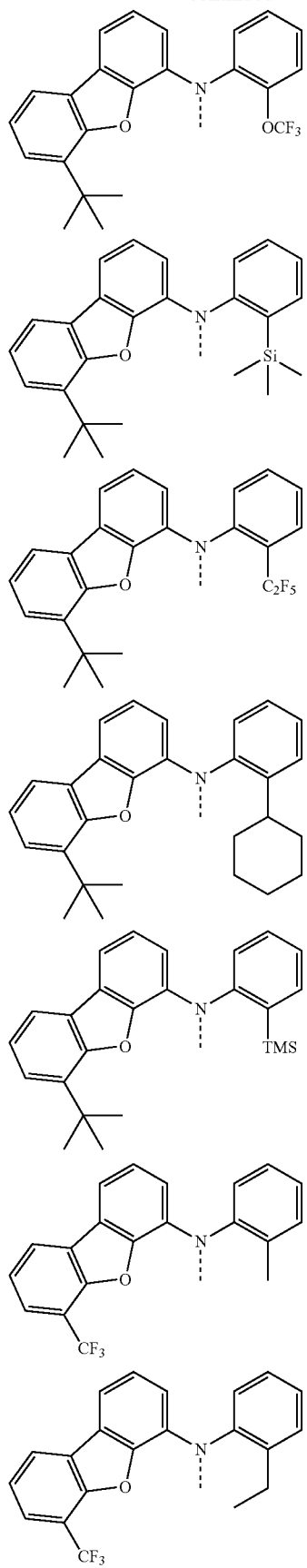
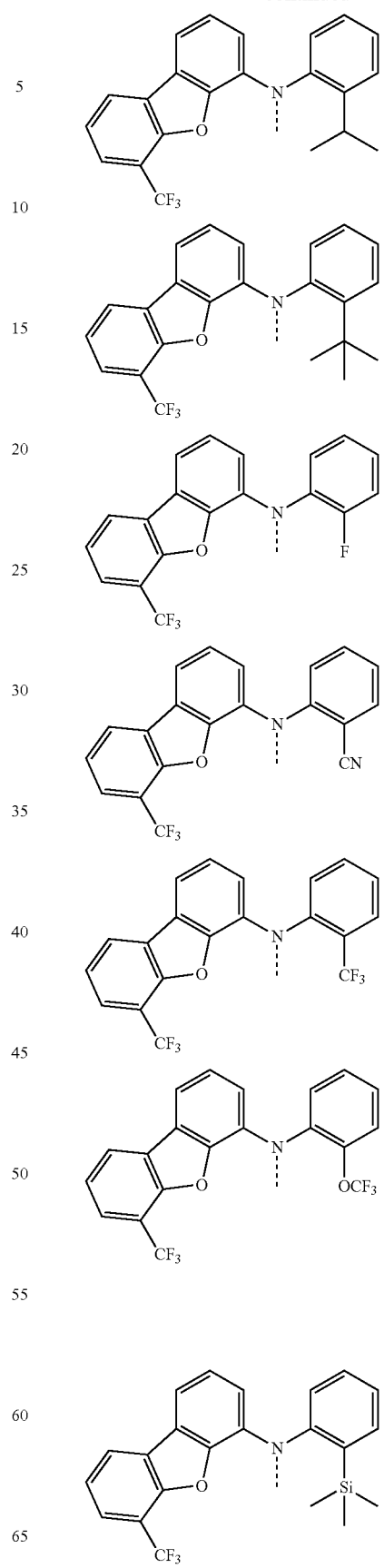

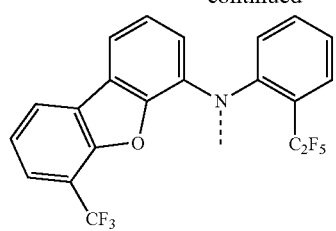
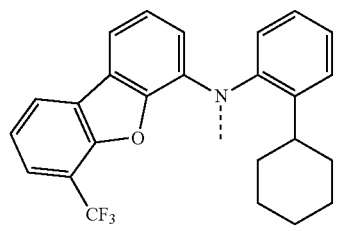
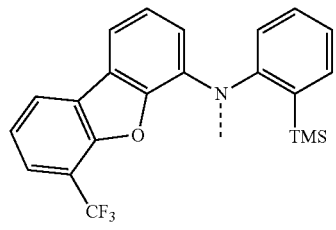
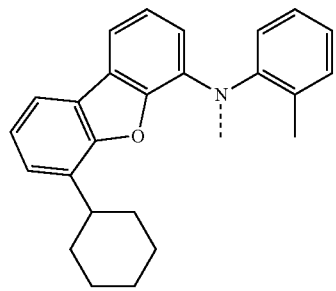
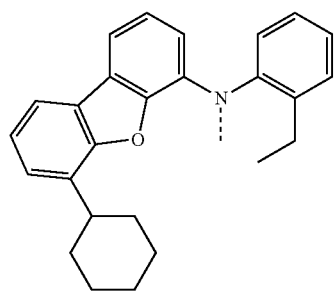
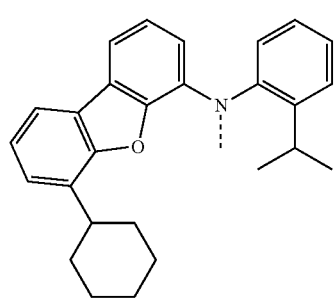
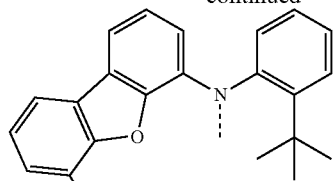
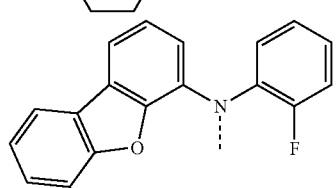
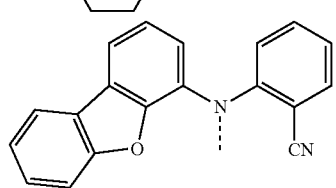
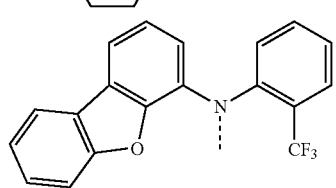
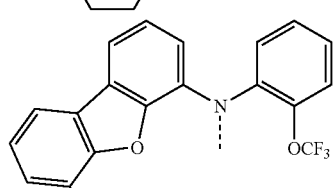
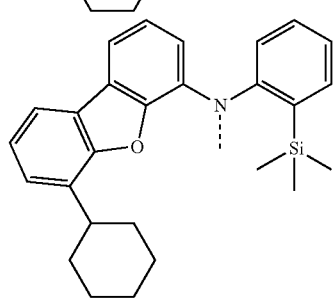

-continued
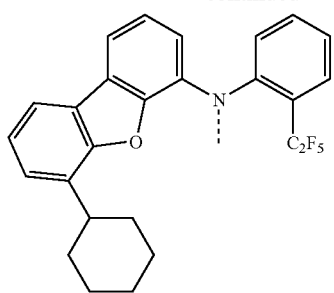
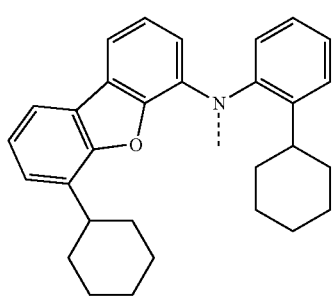
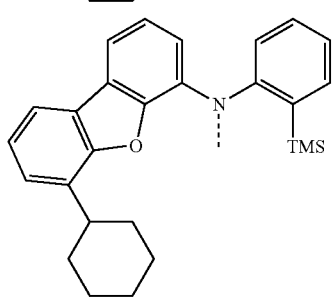
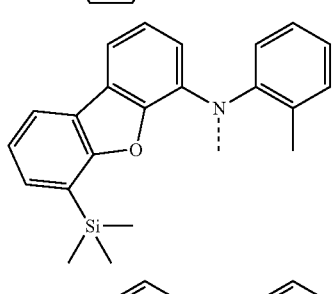
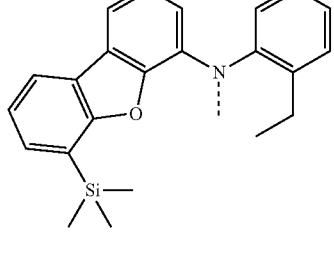
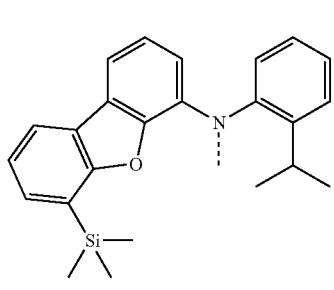
-continued
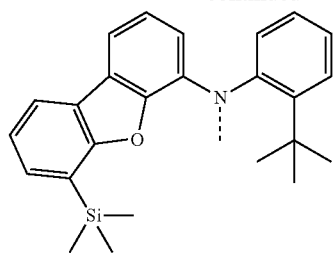
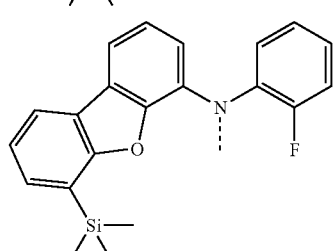
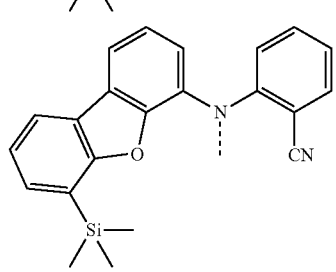
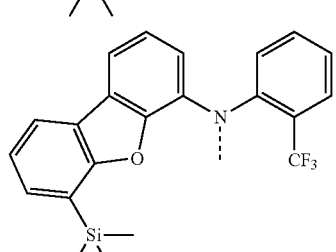
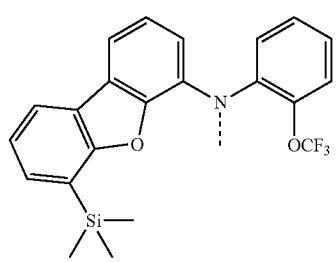
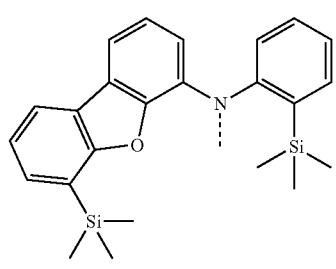

-continued
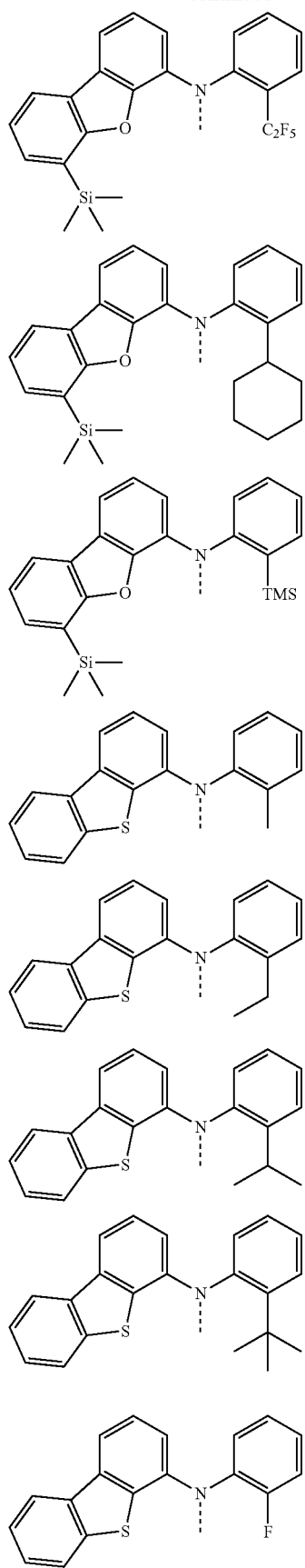
-continued
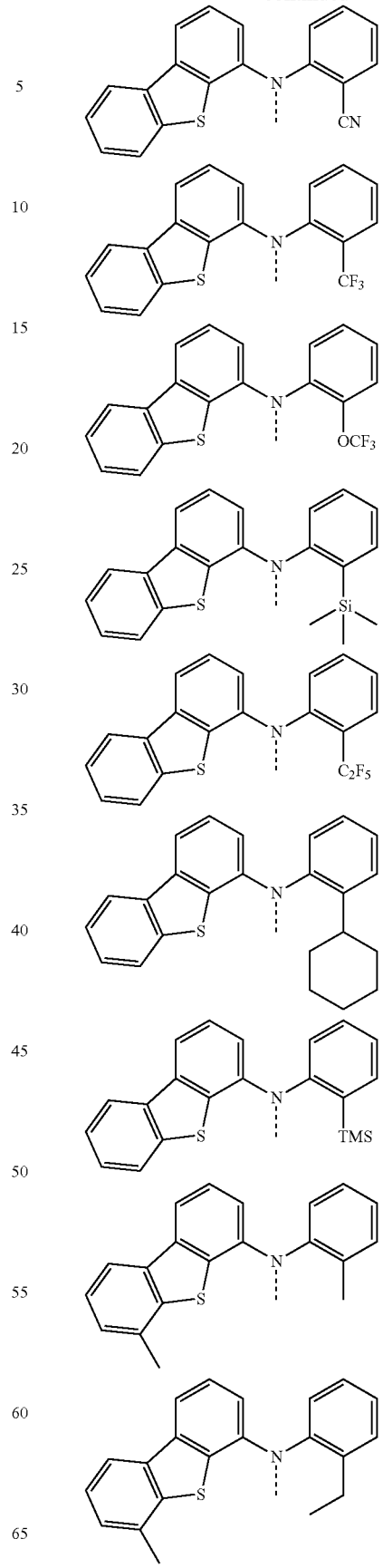

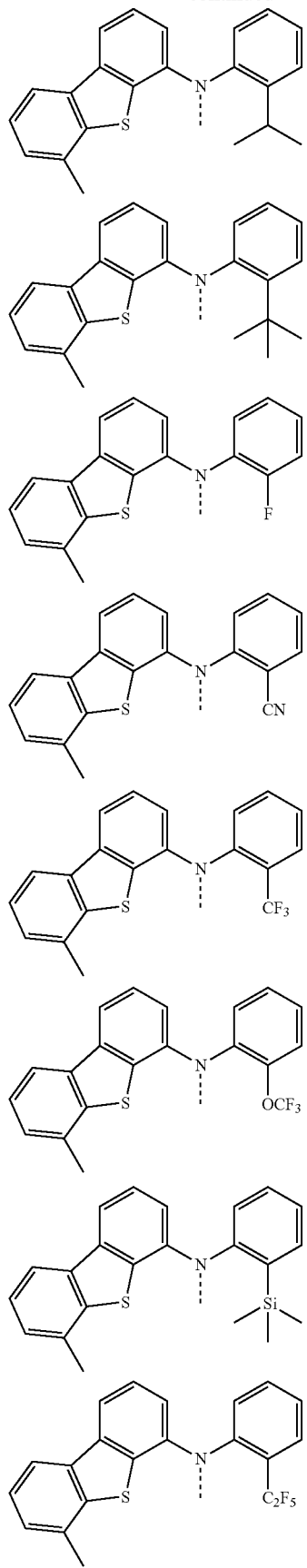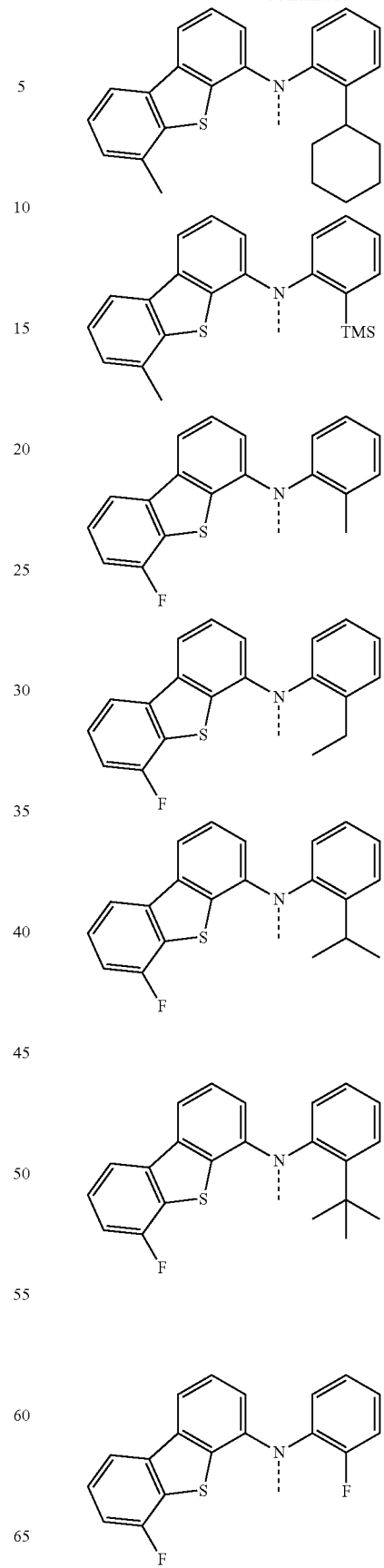

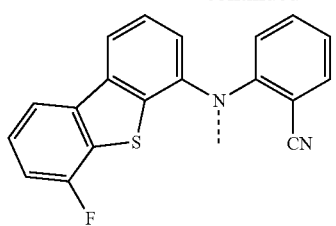
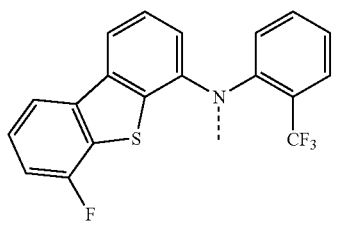
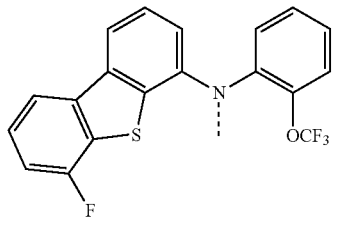
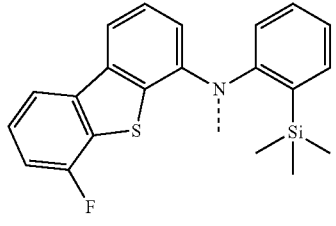

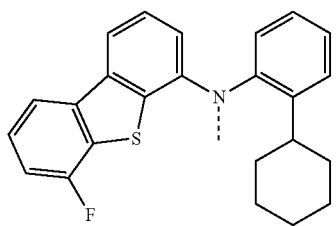
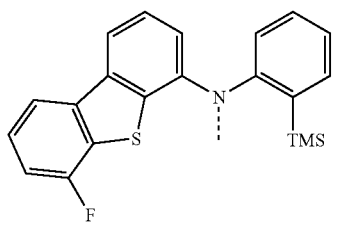
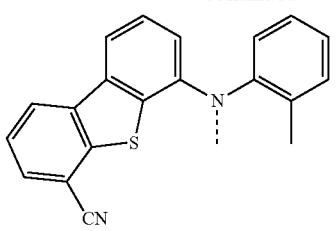
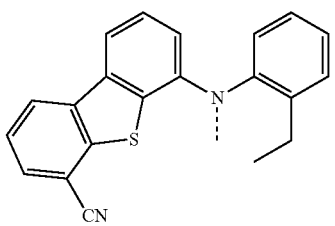
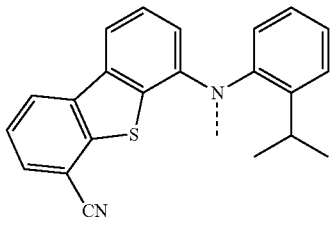
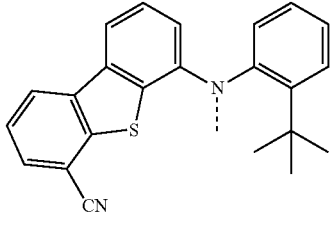
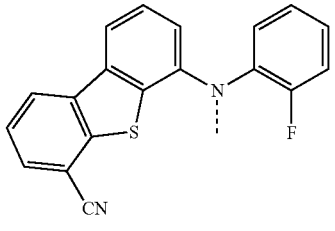
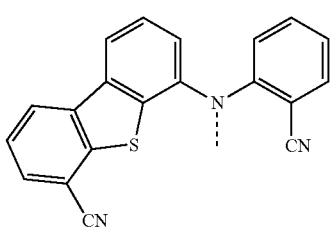
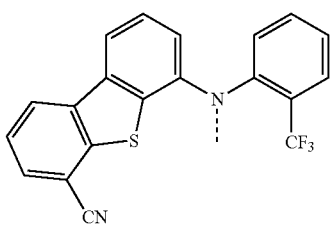

71
-continued
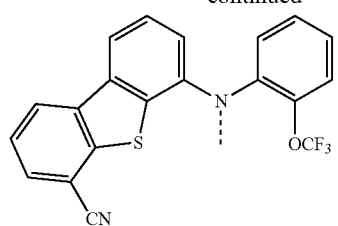
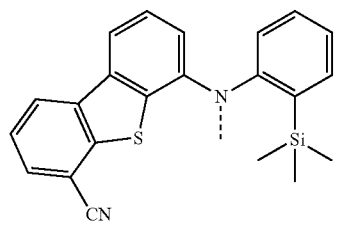
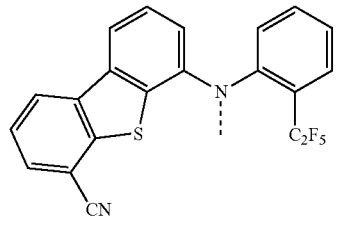
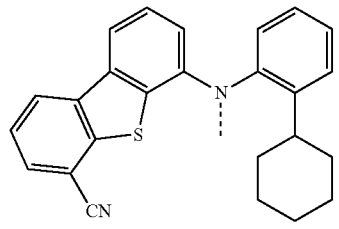
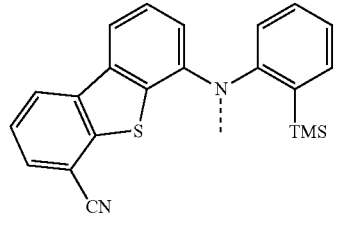
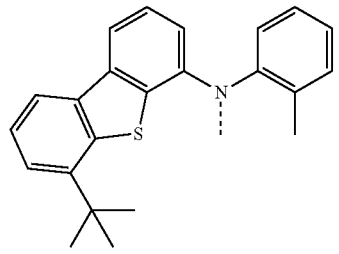
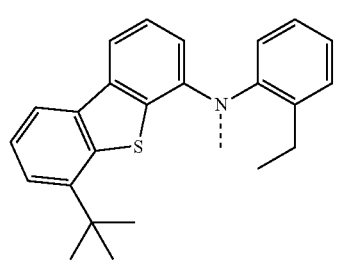
72
-continued
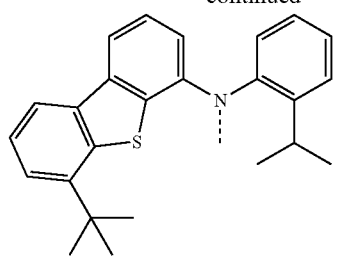
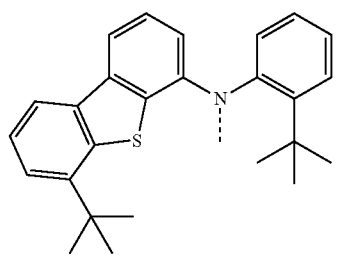
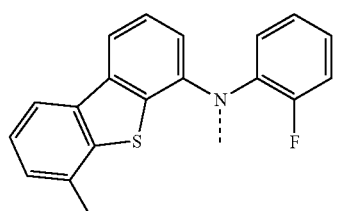
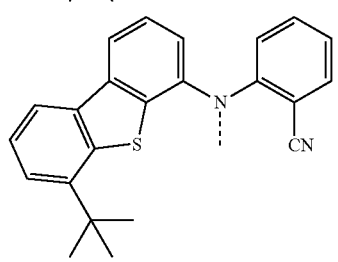
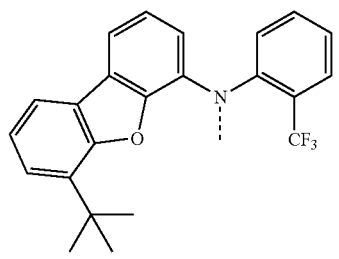
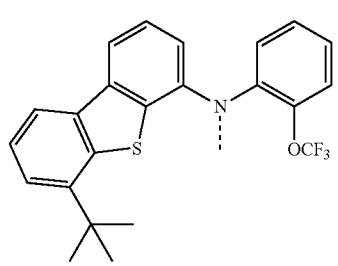

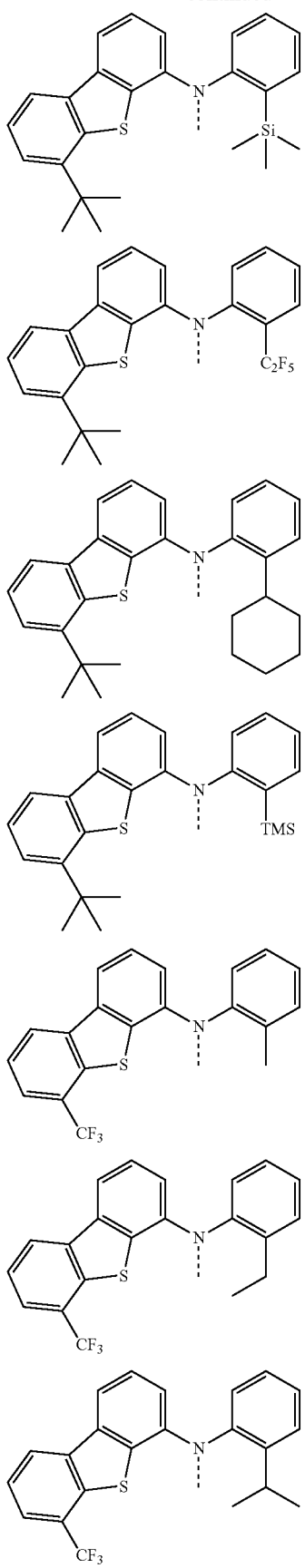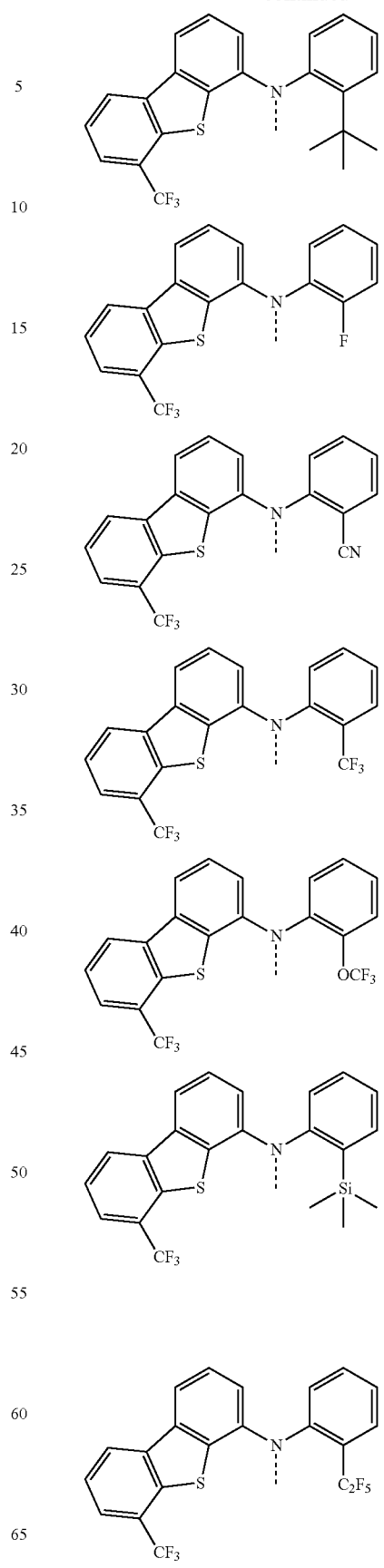

75
-continued
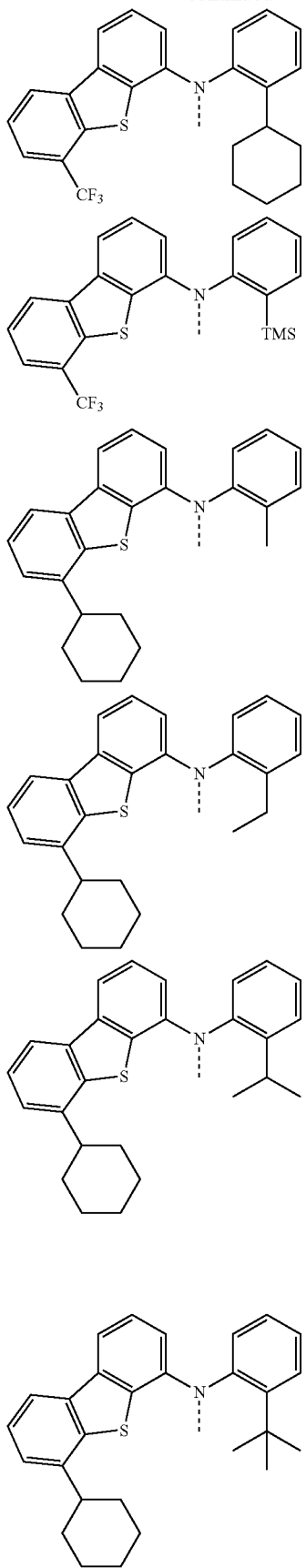
76
-continued
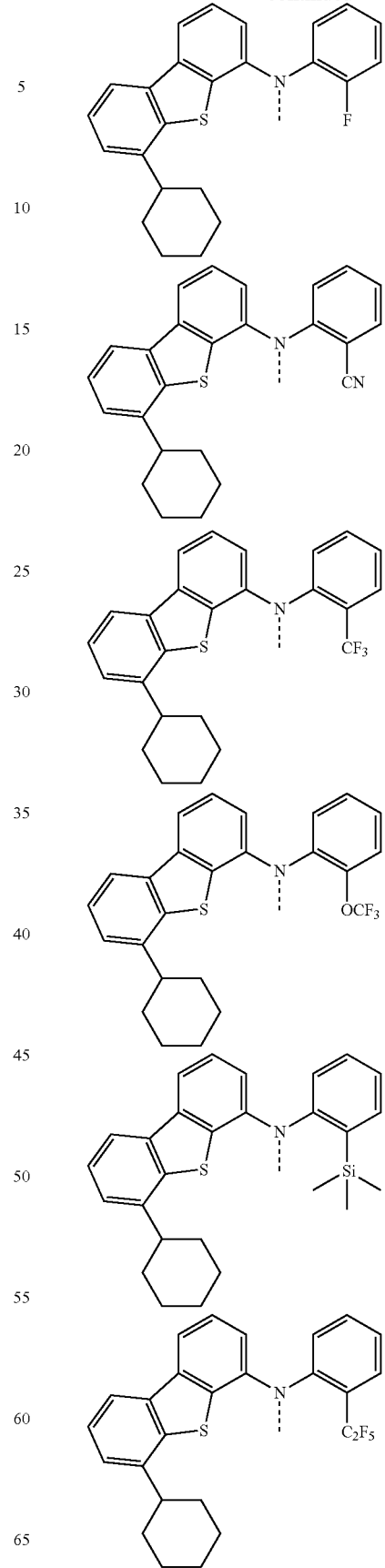

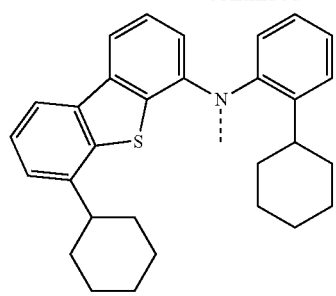
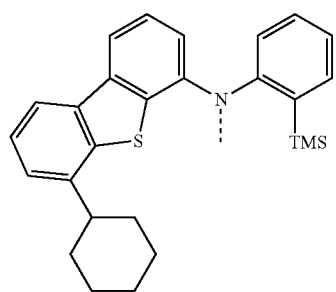
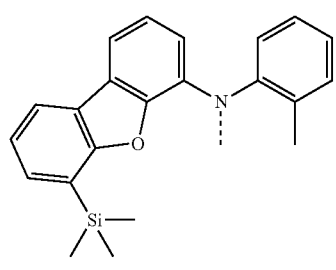
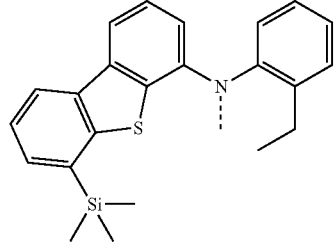
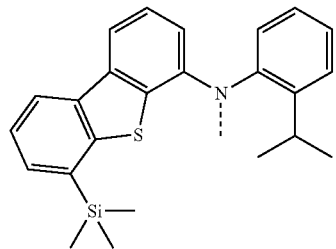
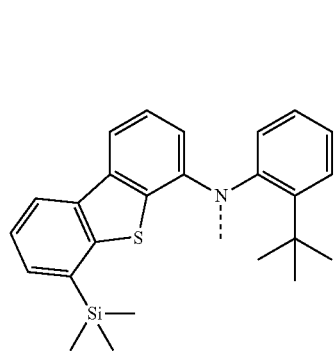
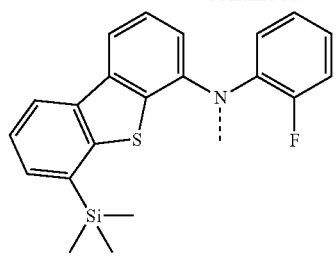
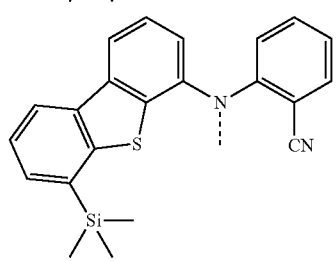
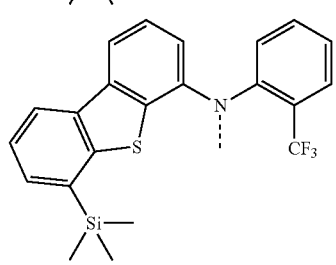
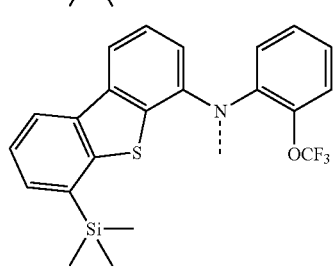
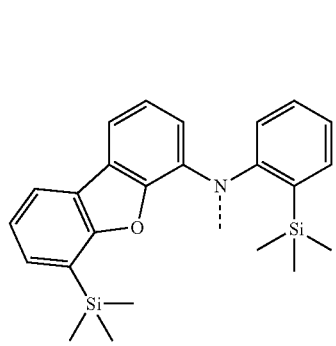
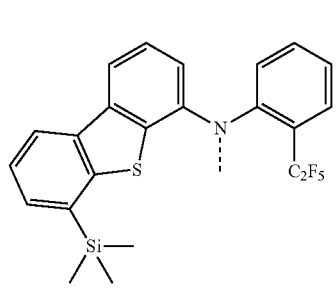

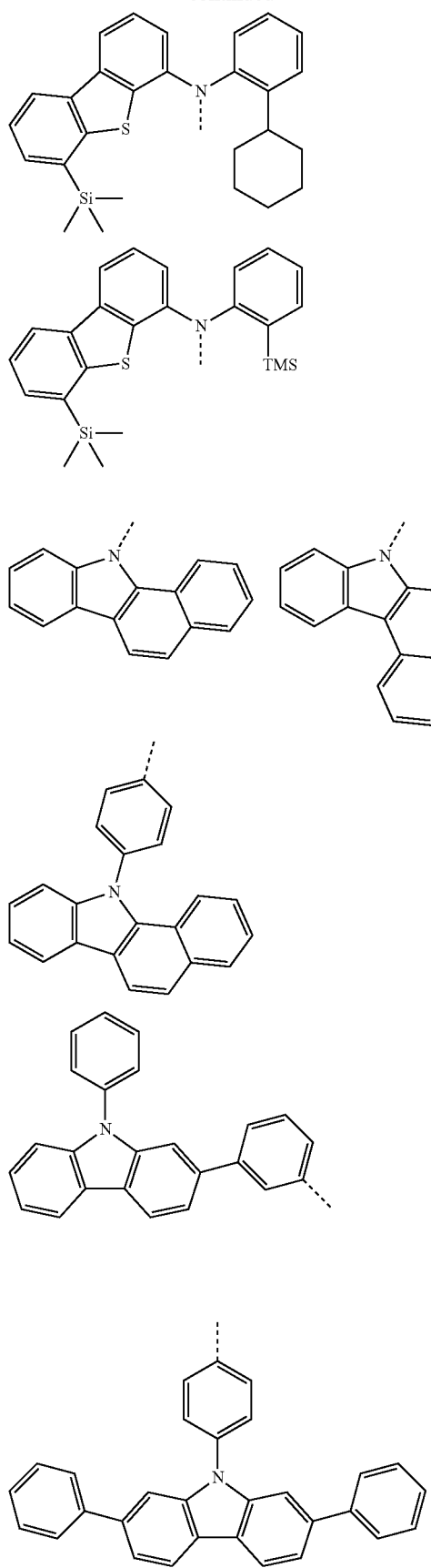
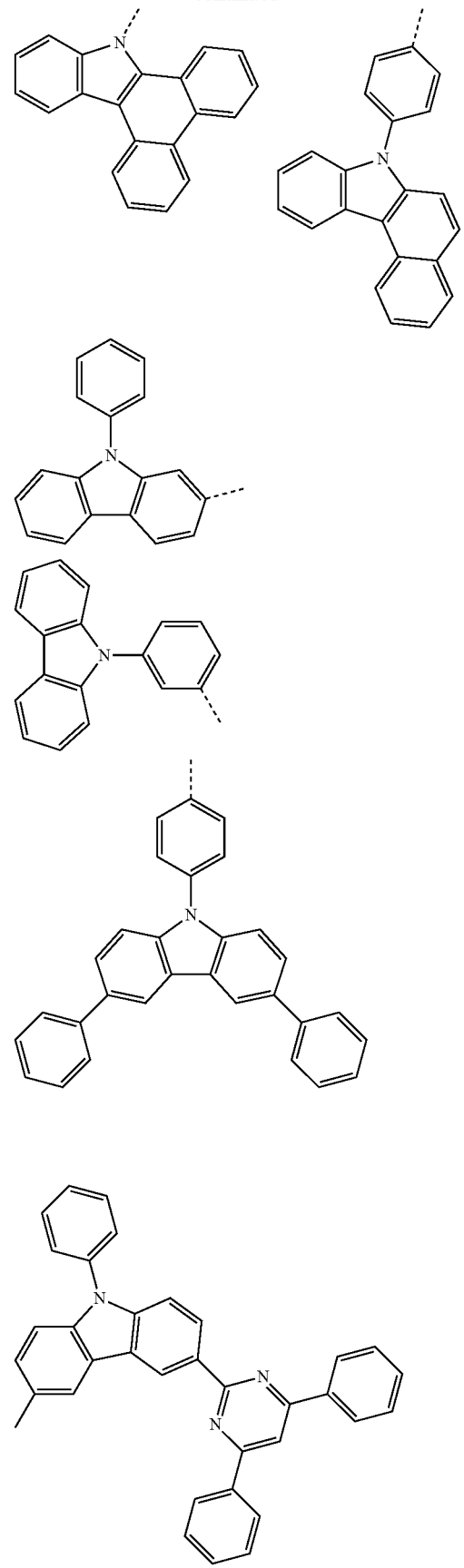
[R-2]

-continued
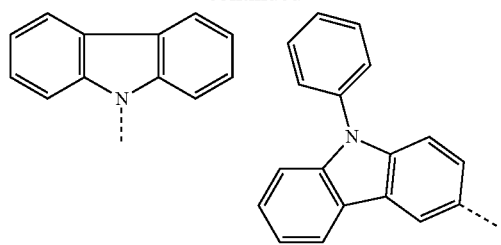
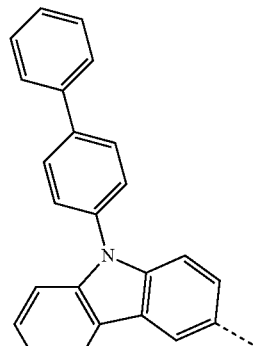
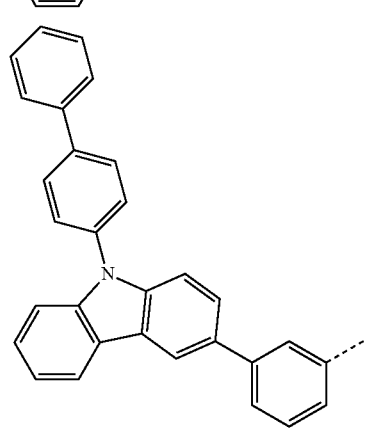
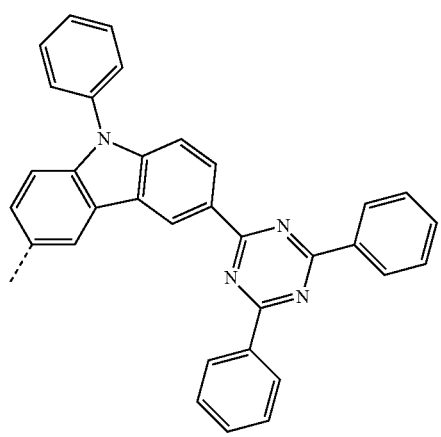
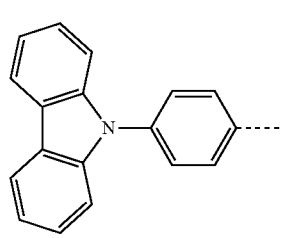
-continued
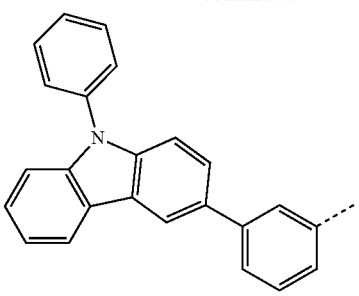
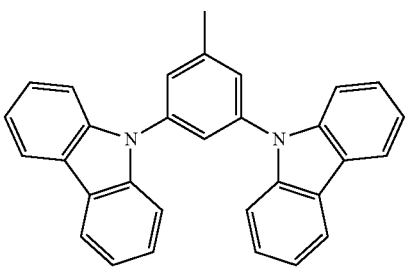
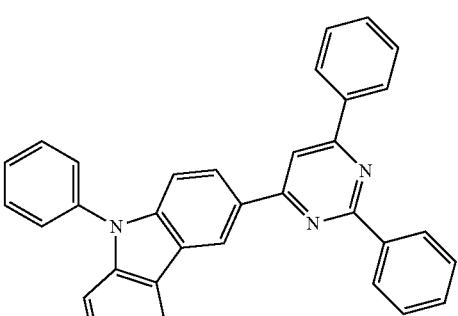
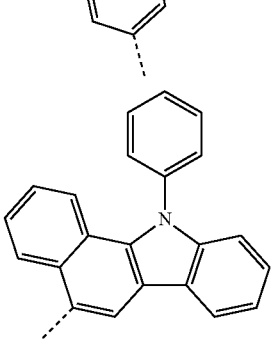
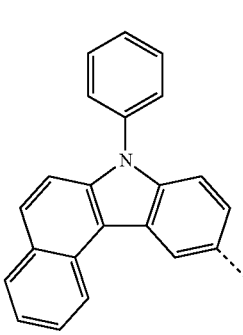
[R-3]
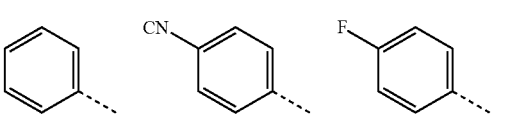

-continued
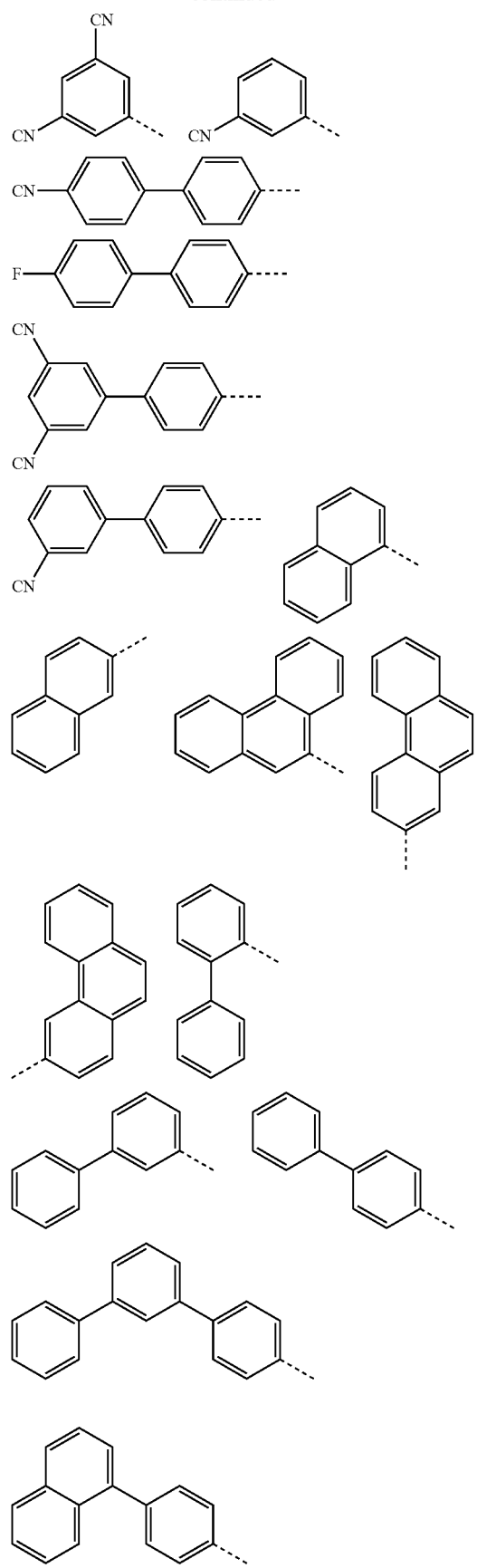
-continued
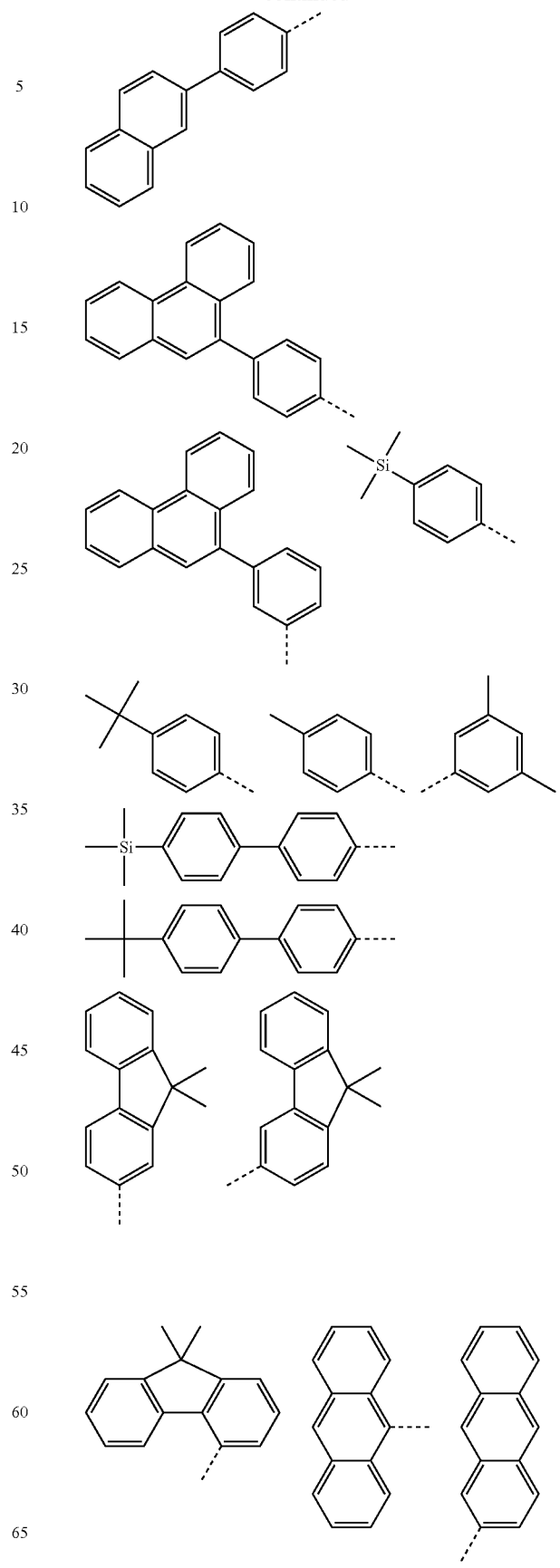

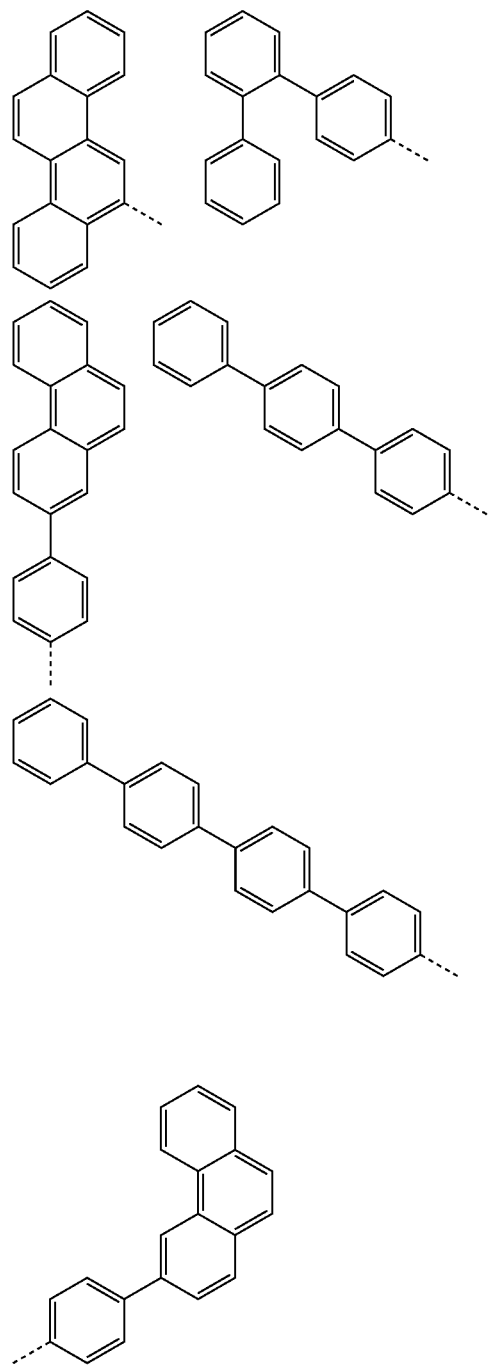
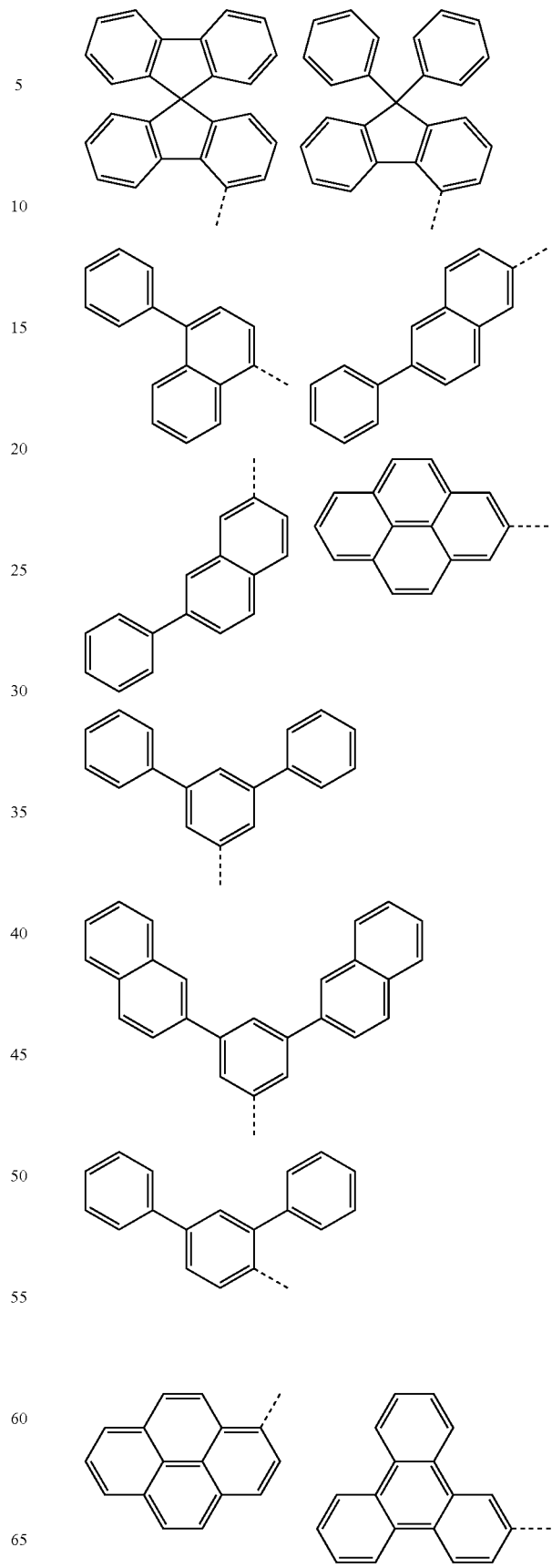

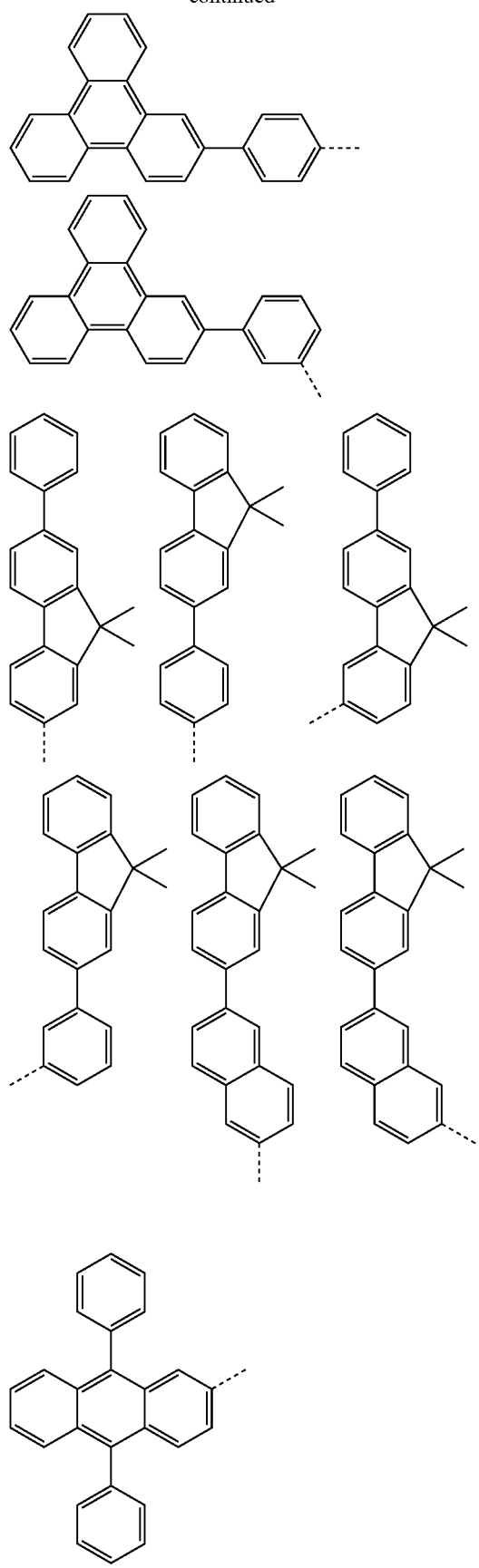
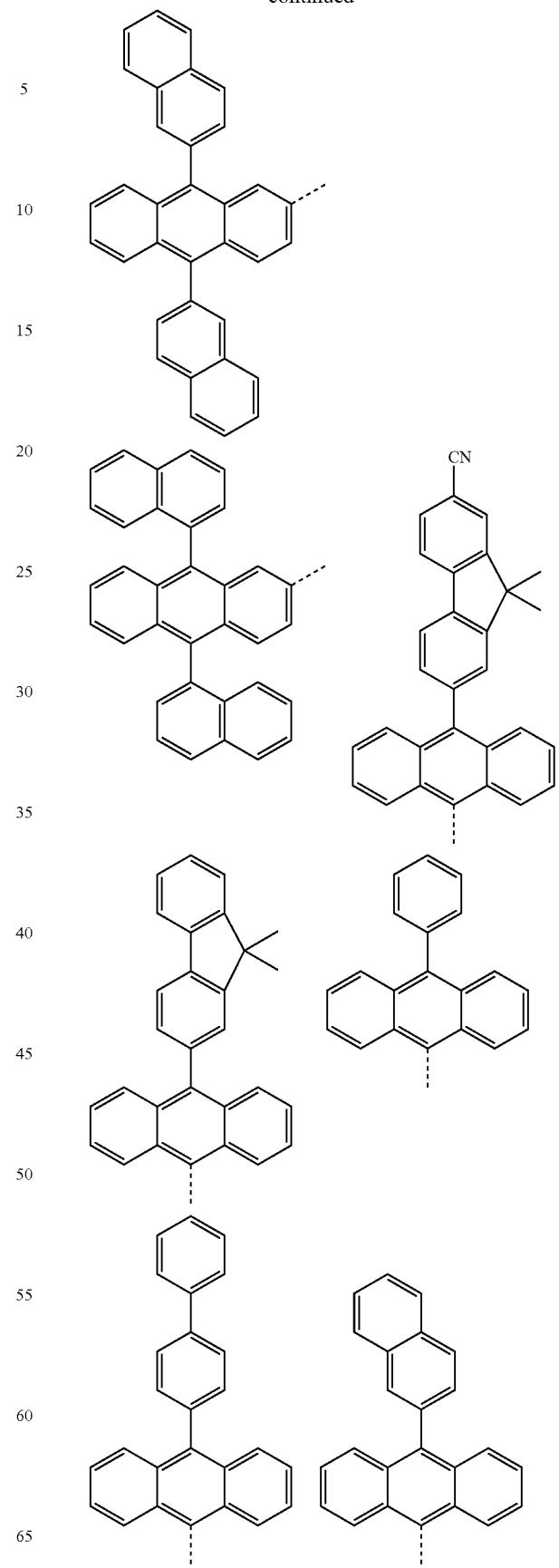

-continued
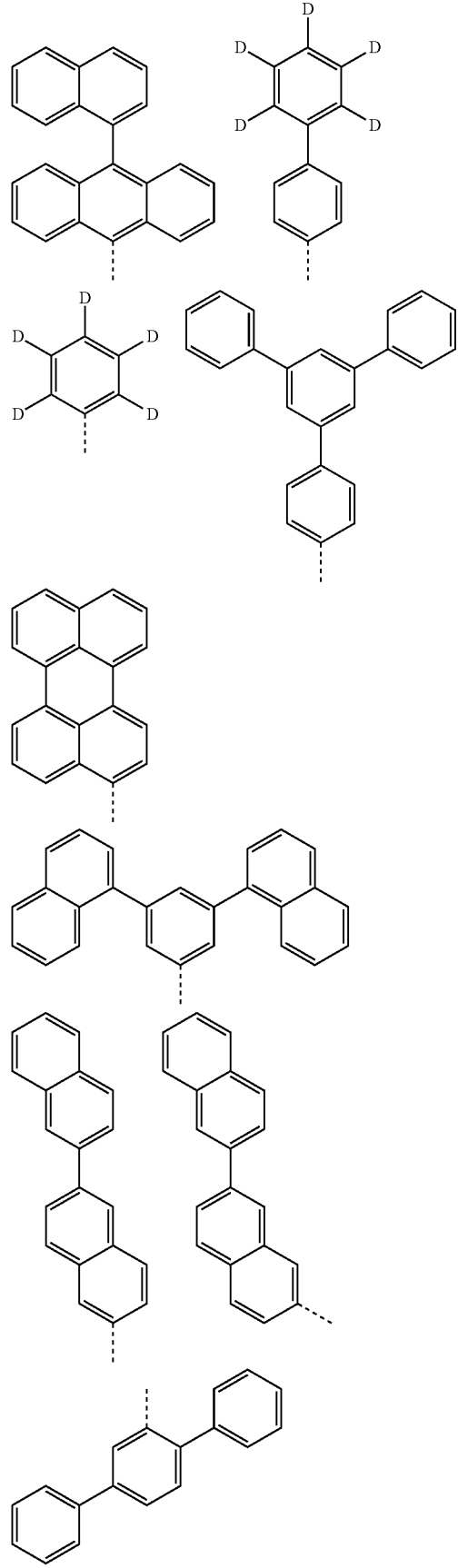
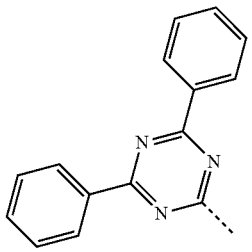
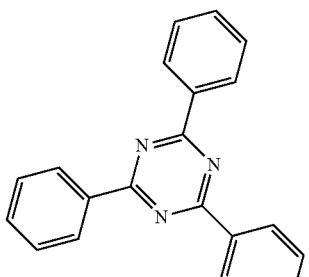
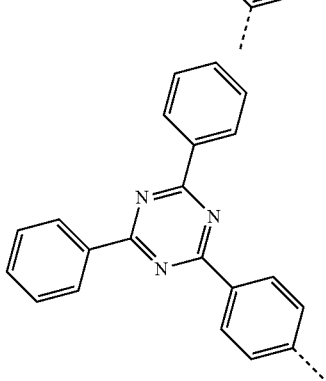
[R-4]
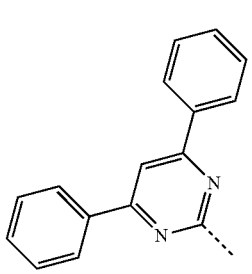
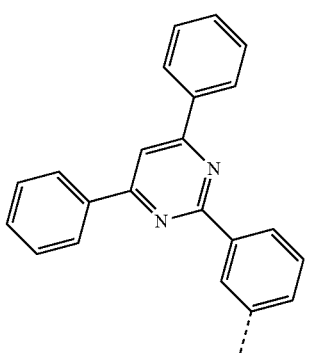

-continued
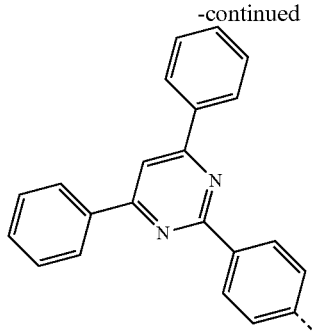
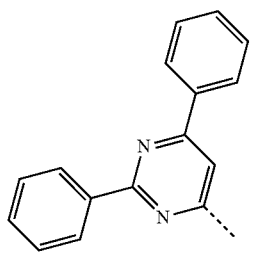
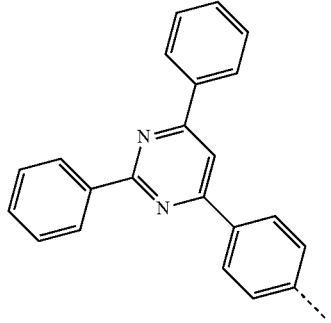
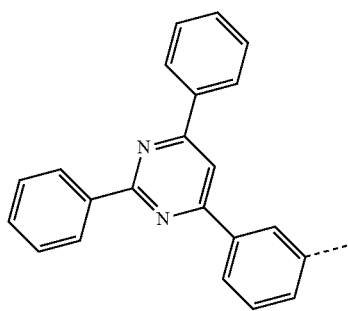
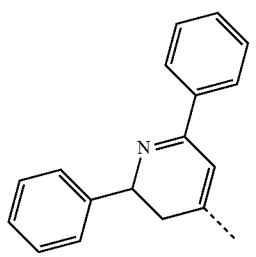
-continued
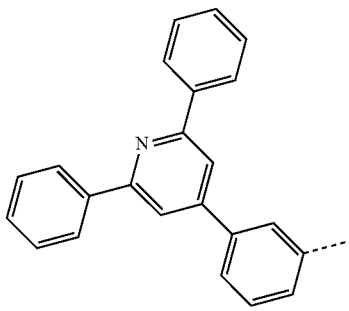
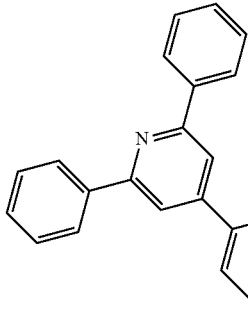
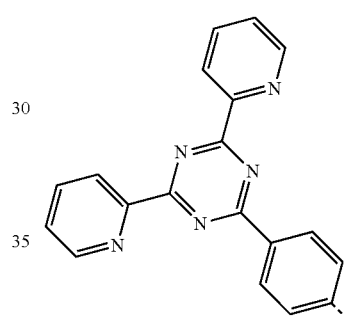
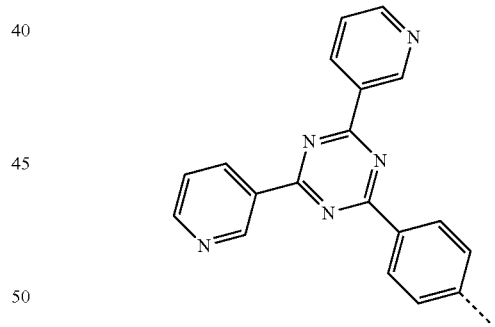
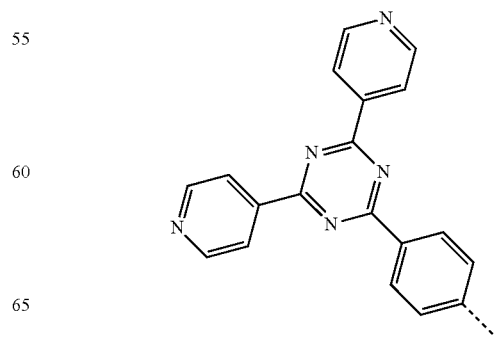

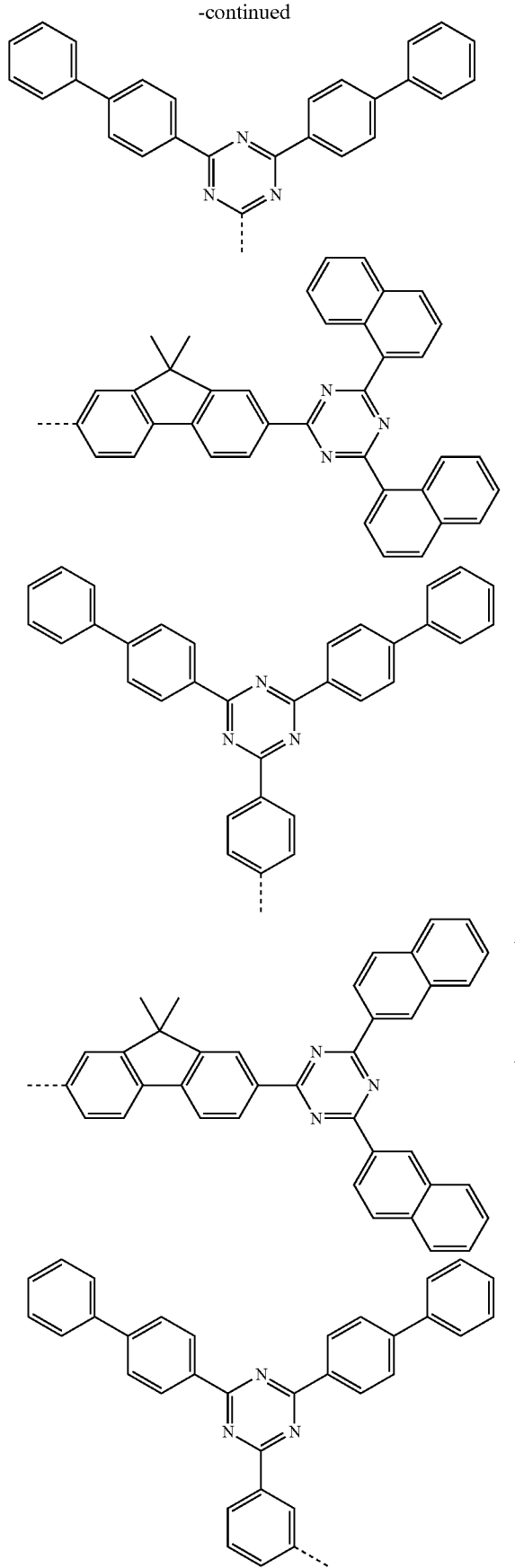
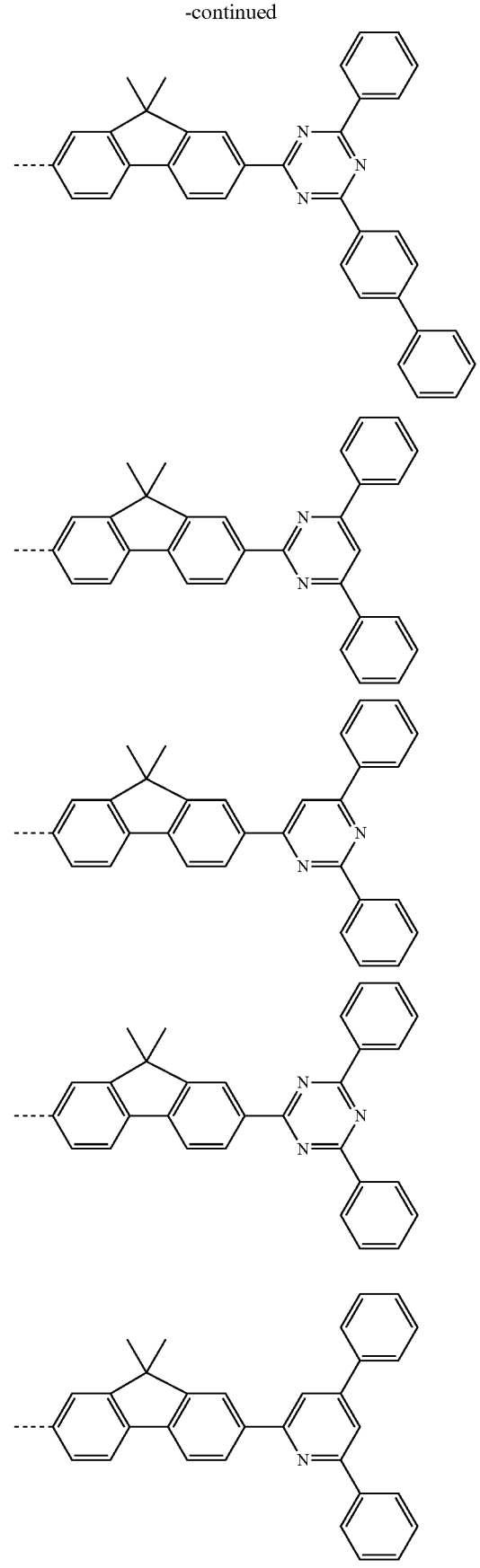

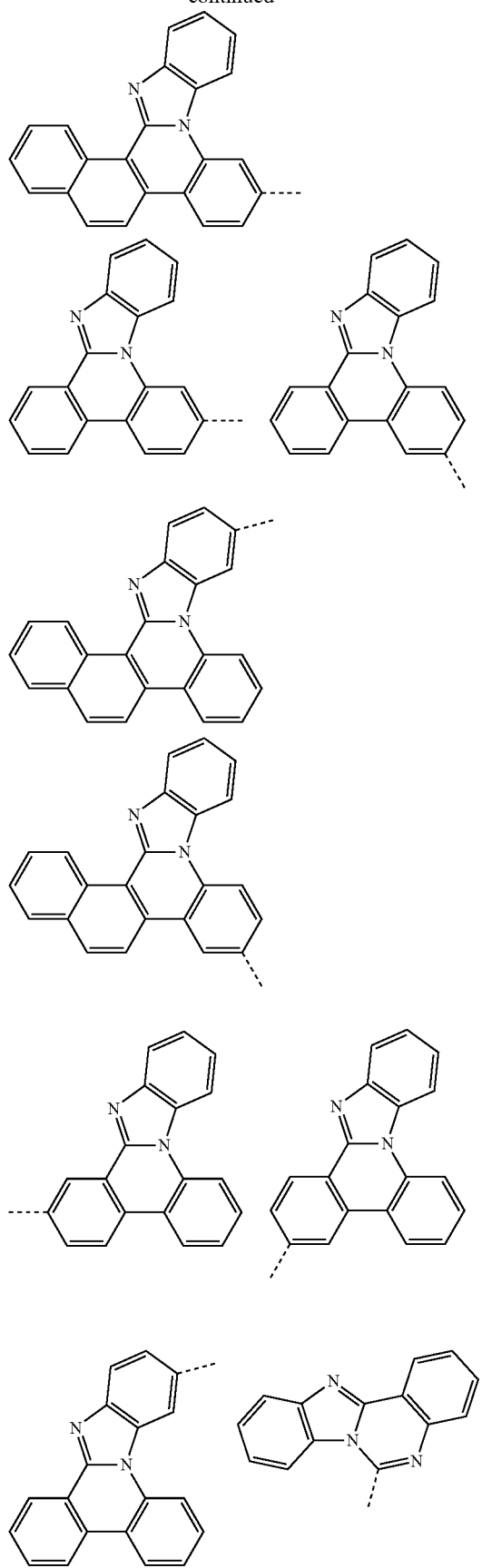
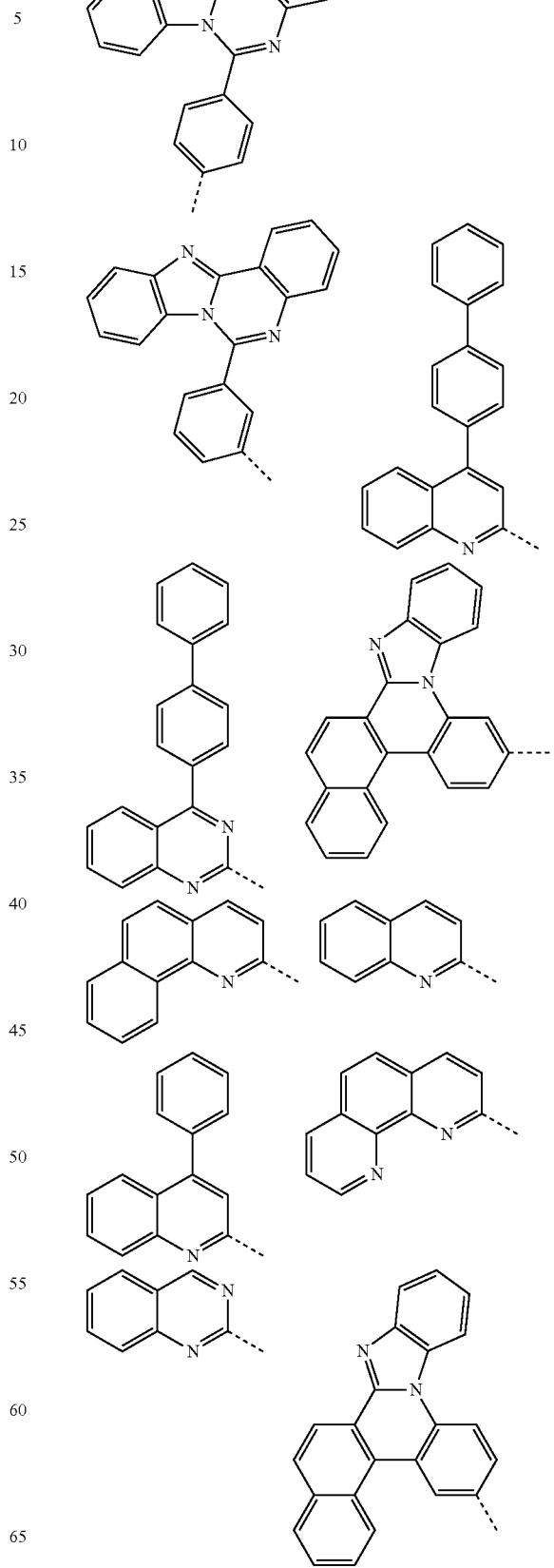

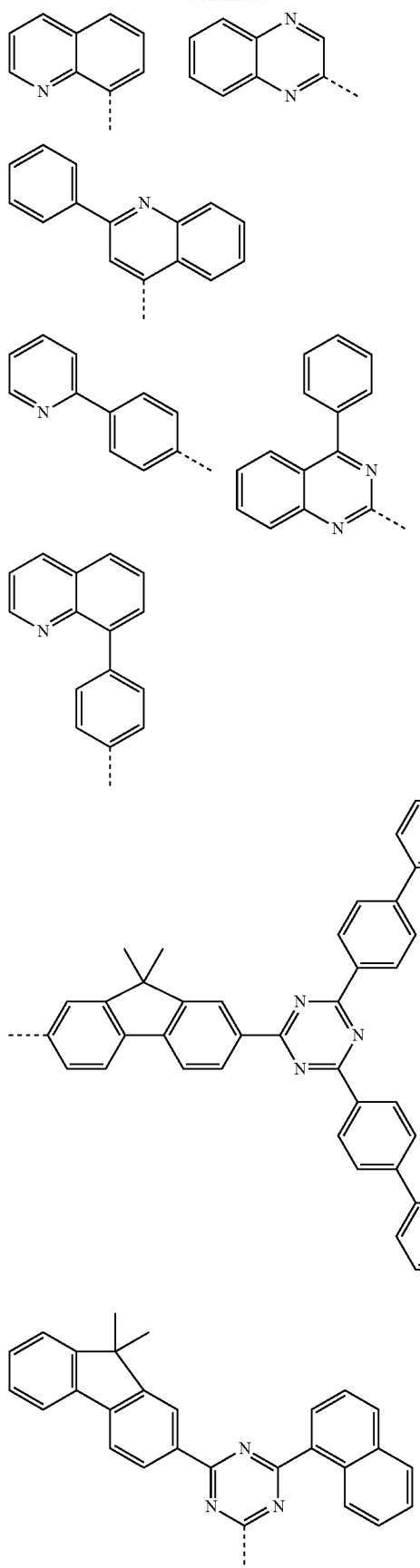
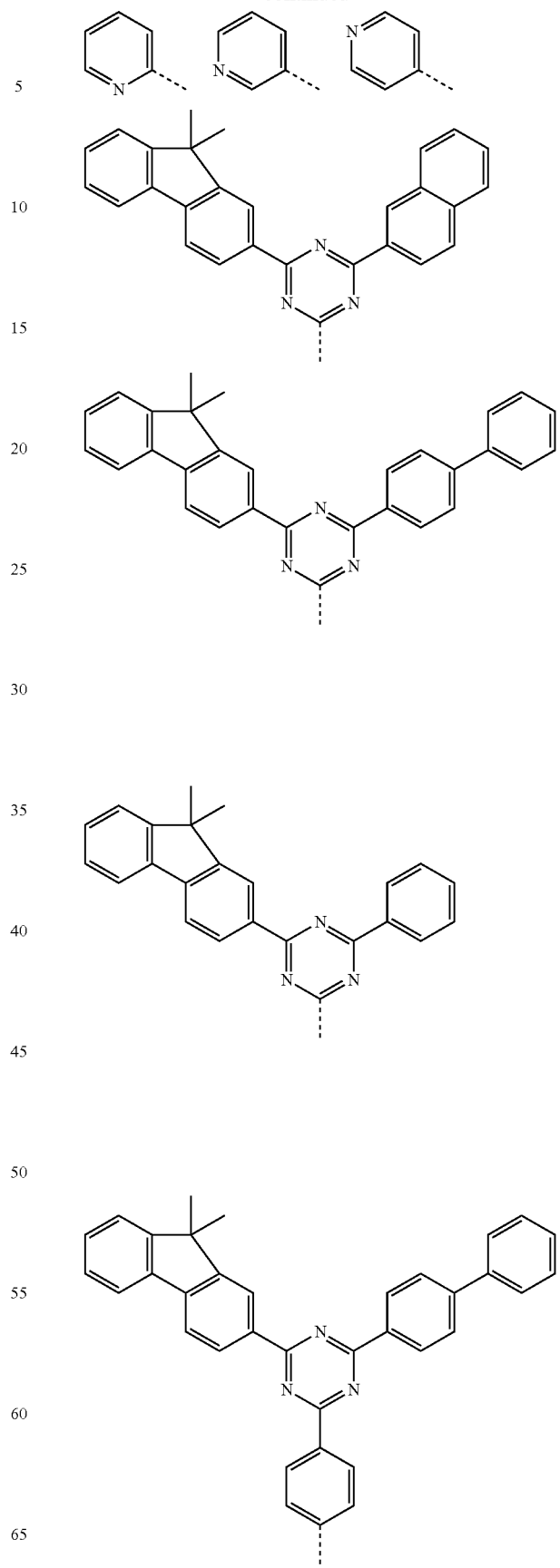

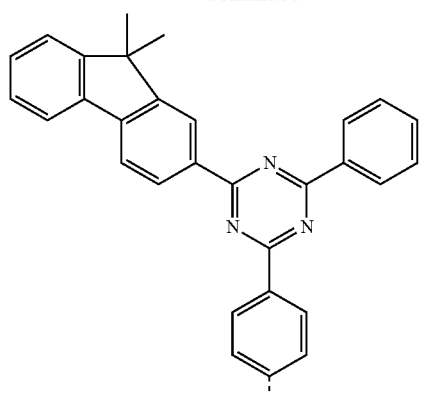
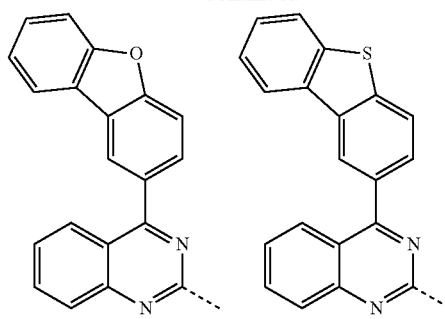
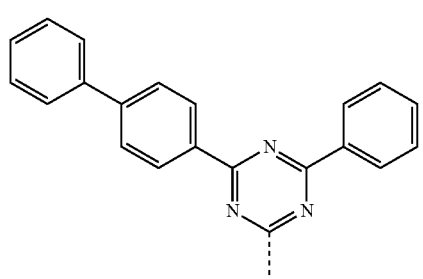
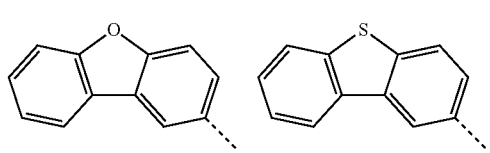
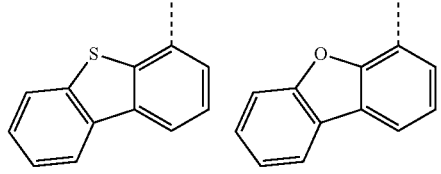
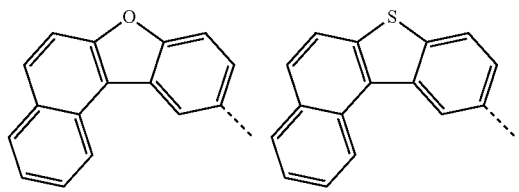
[R-5]
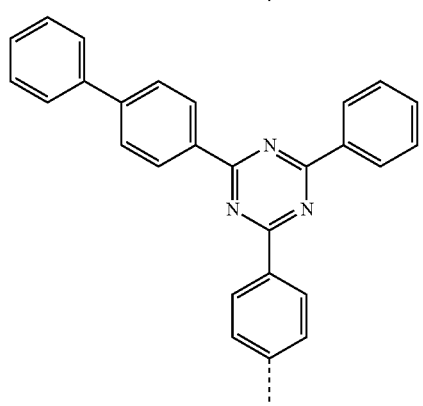
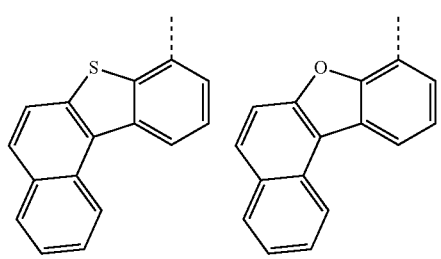
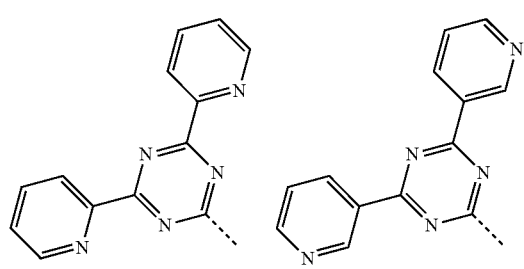
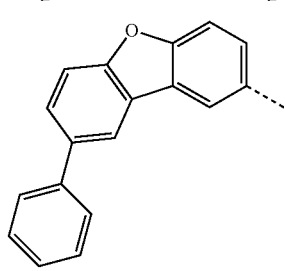
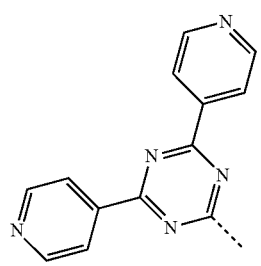
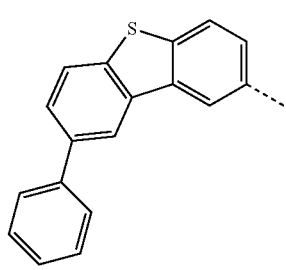

101
-continued
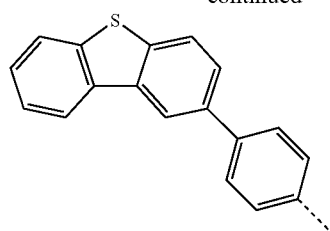
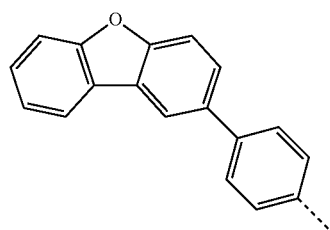
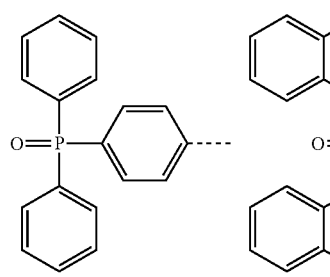 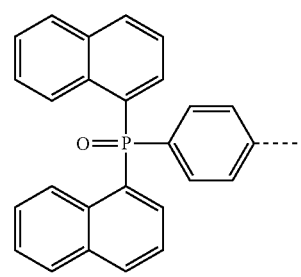
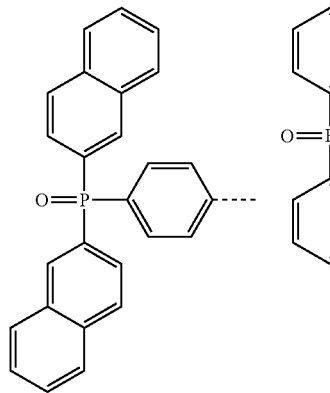 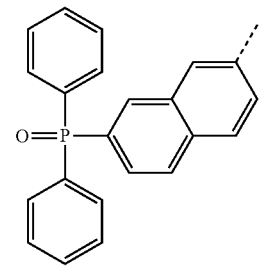
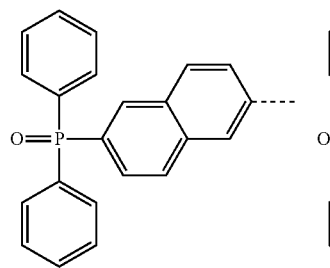 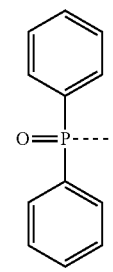
102
-continued
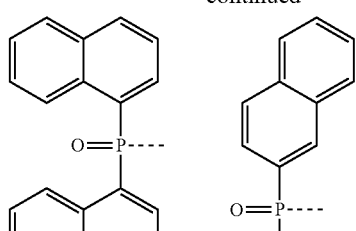
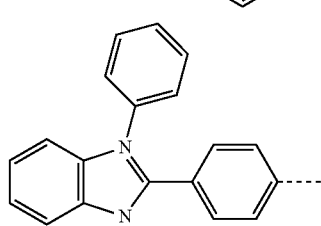
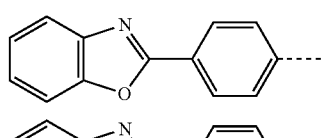
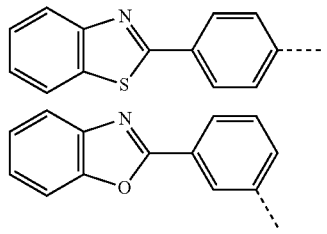
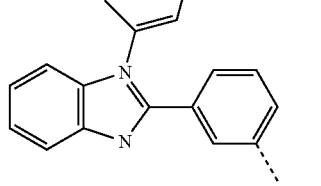
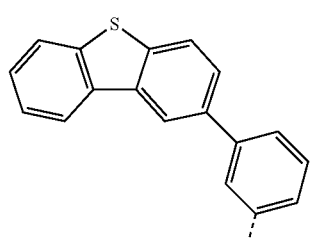
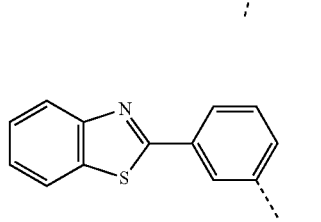

103
-continued
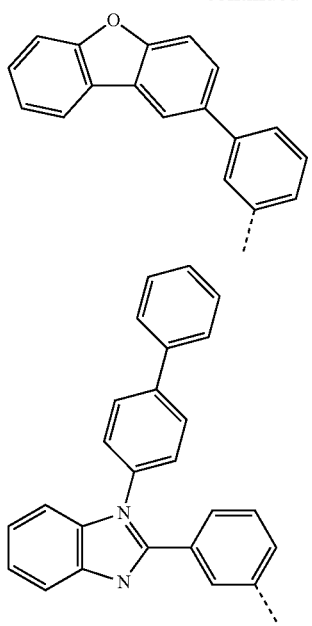
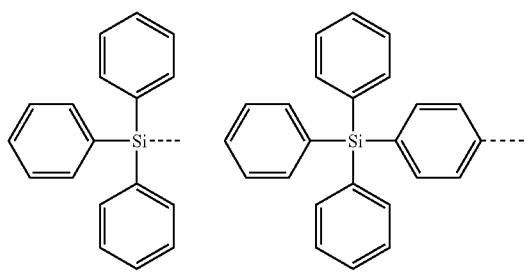
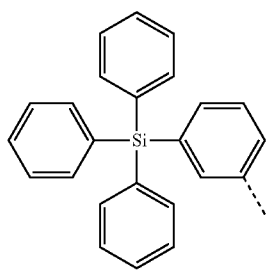
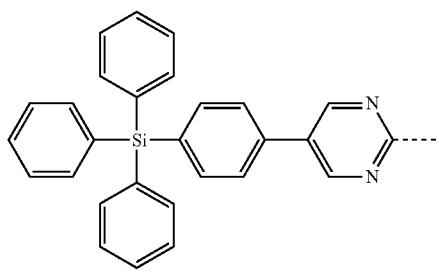
104
-continued
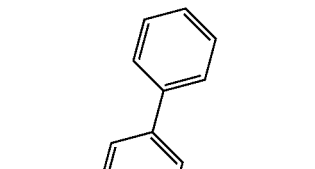
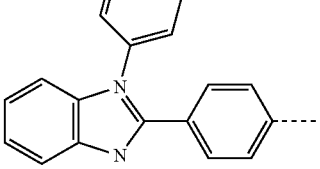
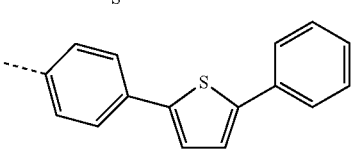
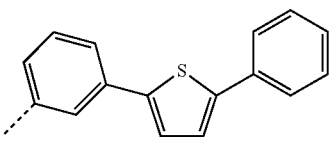
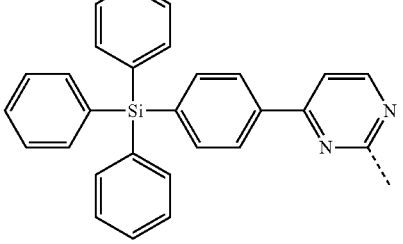
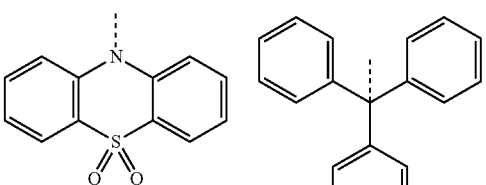
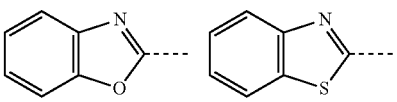
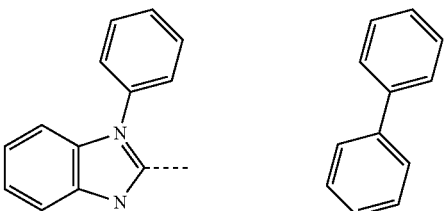
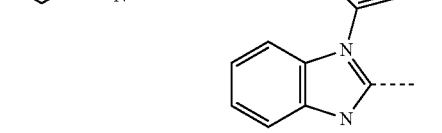

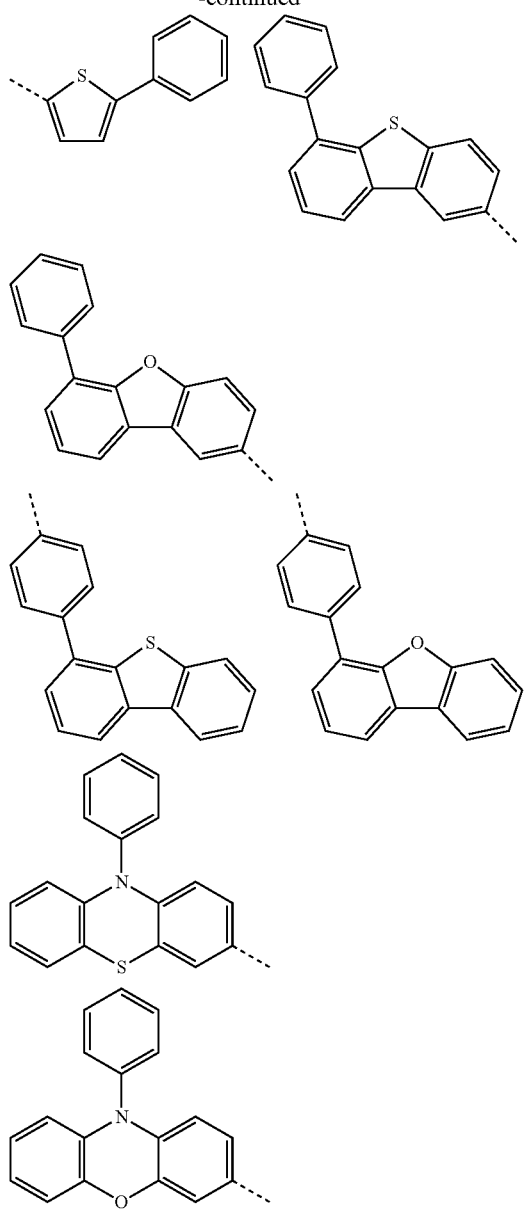
In the structural formulae, - - - means a moiety bonded to Chemical Formula 1.
According to an exemplary embodiment of the present specification, Chemical Formula 1 is represented by any one of the following compounds.
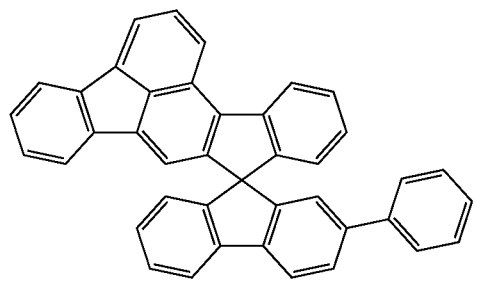
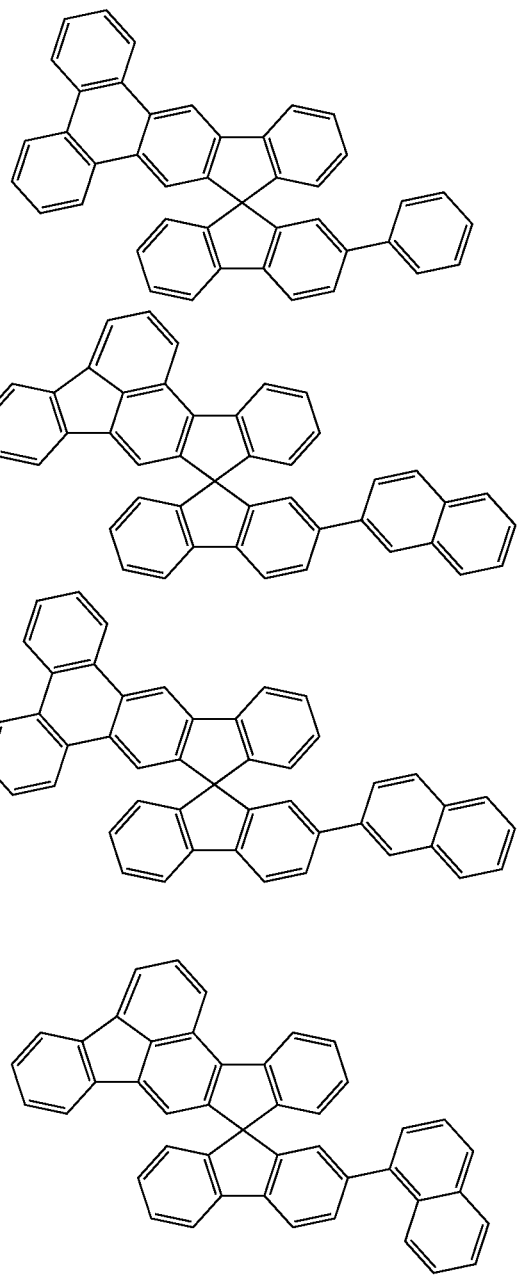
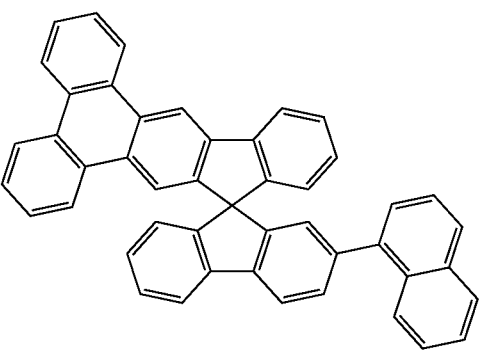

107
-continued
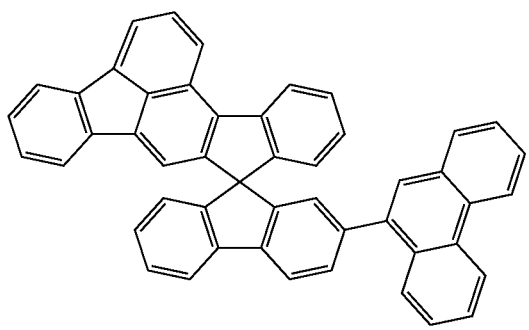
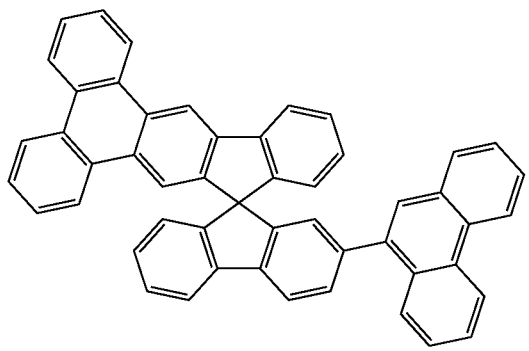
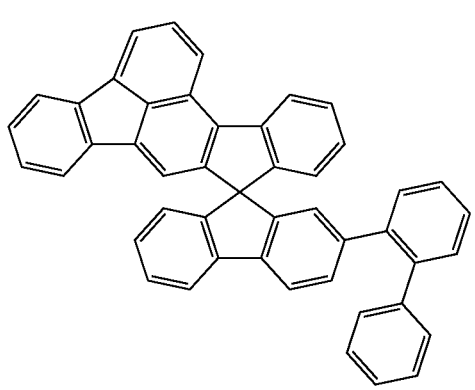
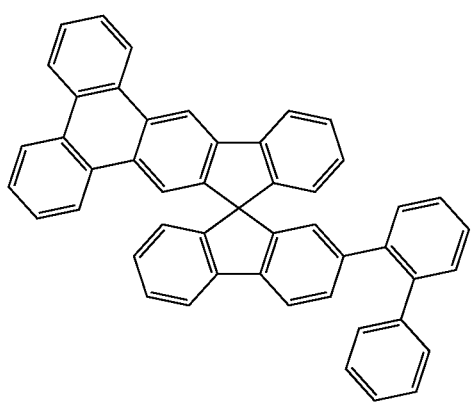
108
-continued
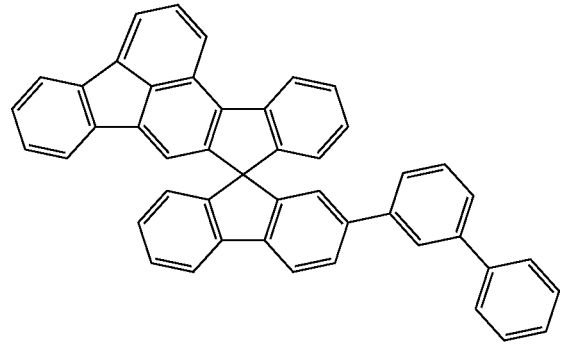
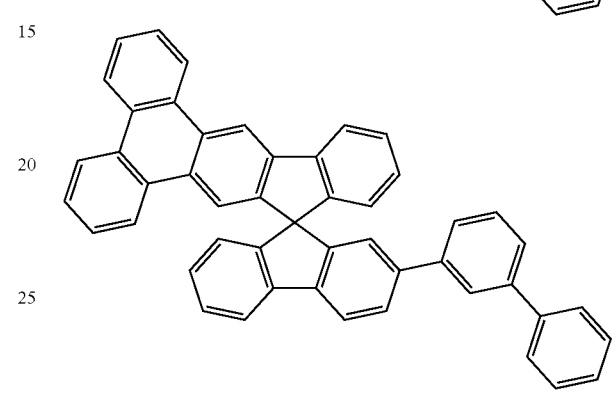
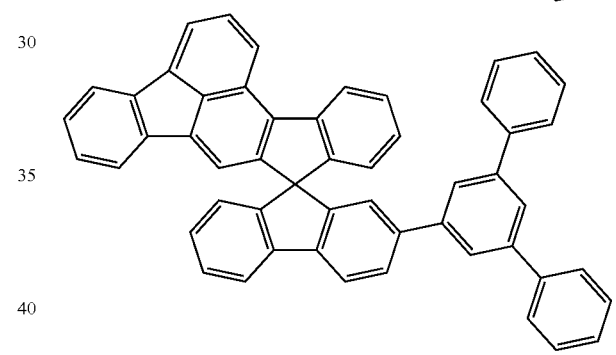
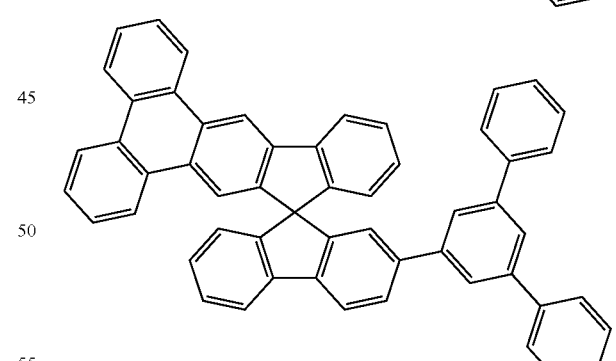
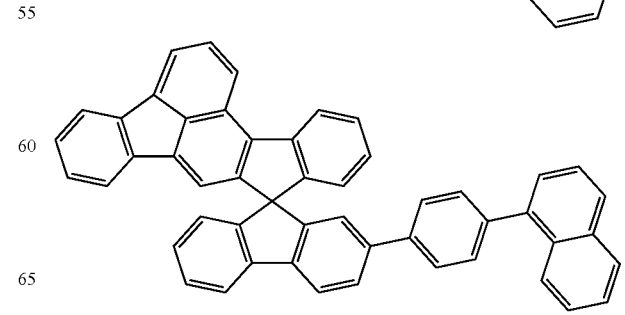

109
-continued
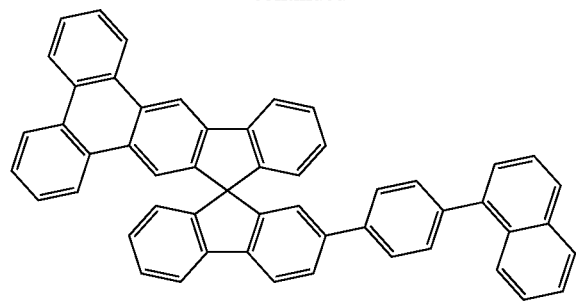
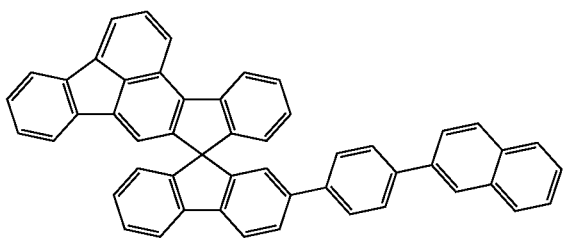
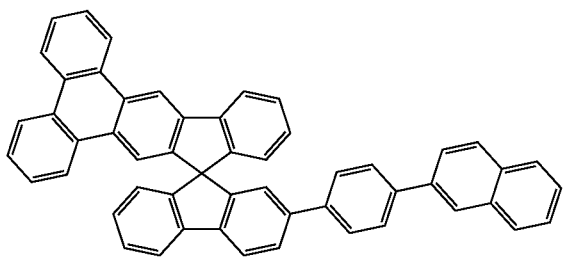
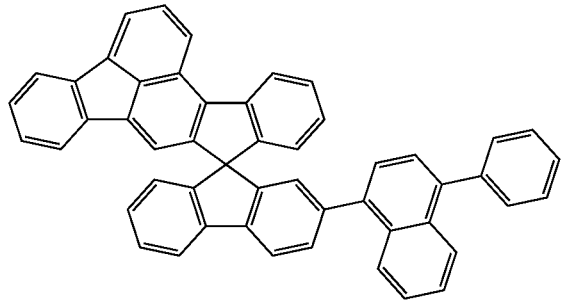
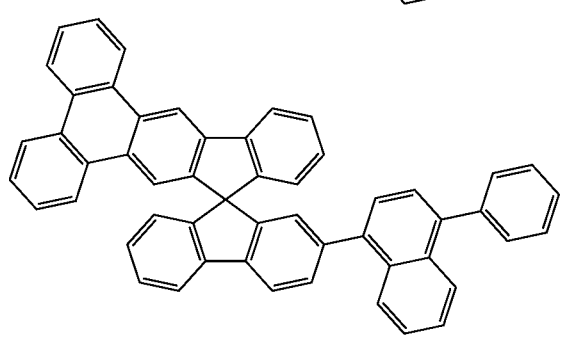
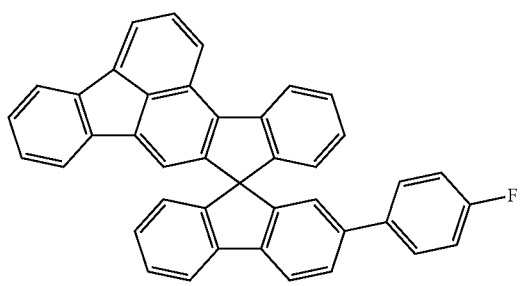
110
-continued
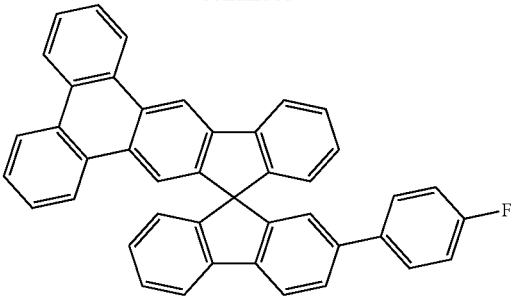
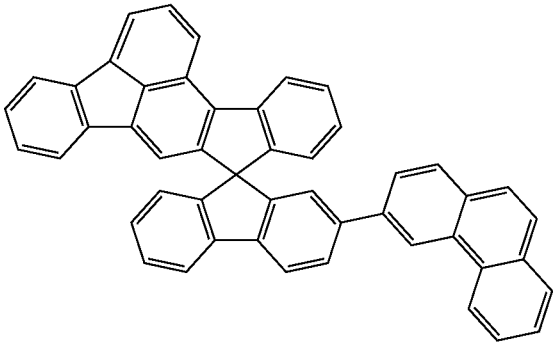
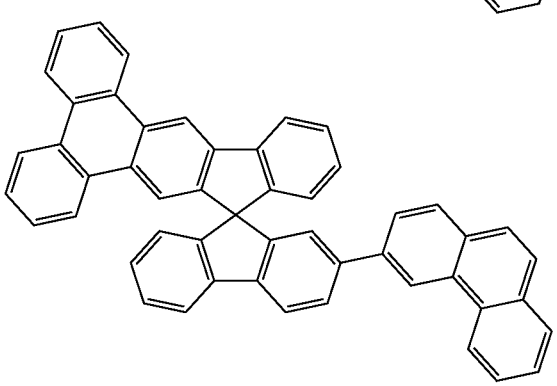
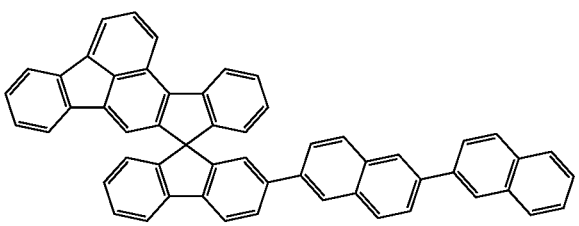

111
-continued
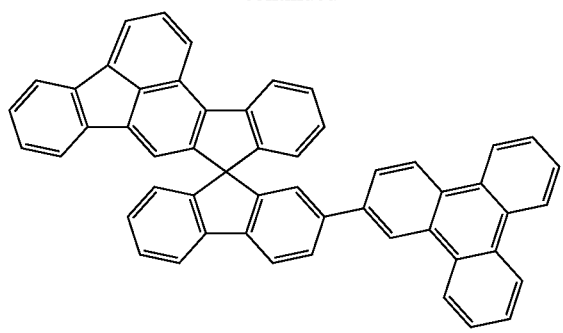
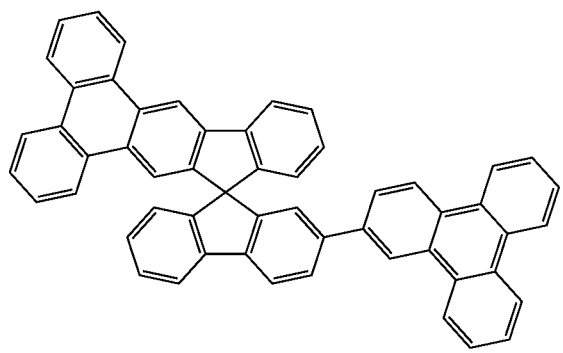
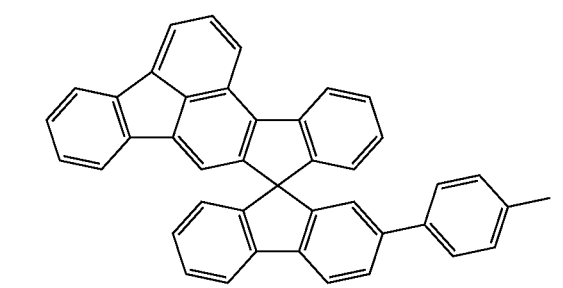
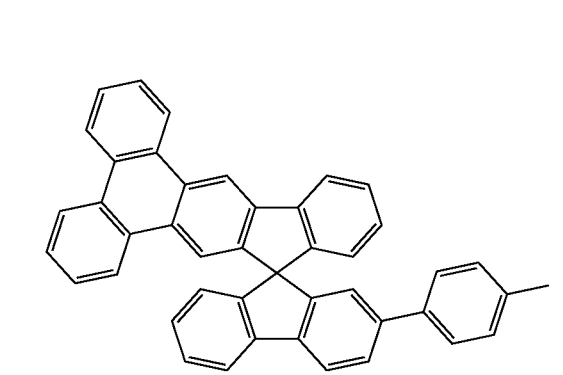
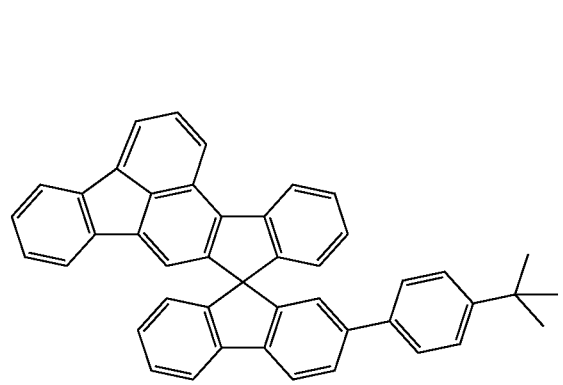
112
-continued
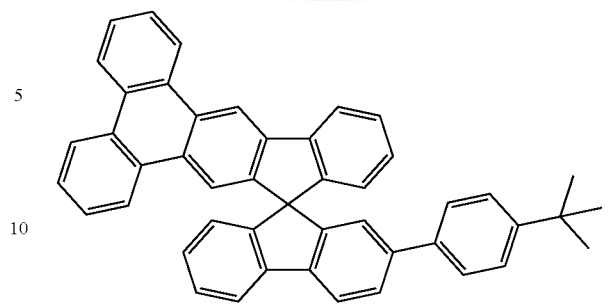
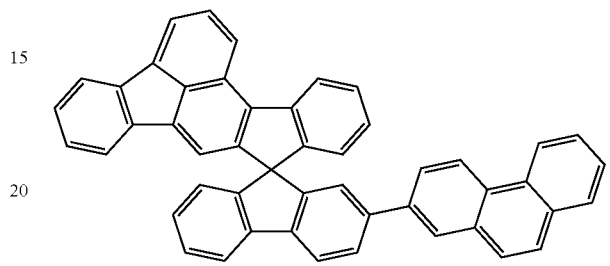
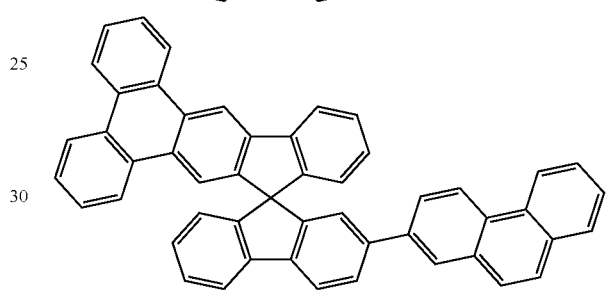
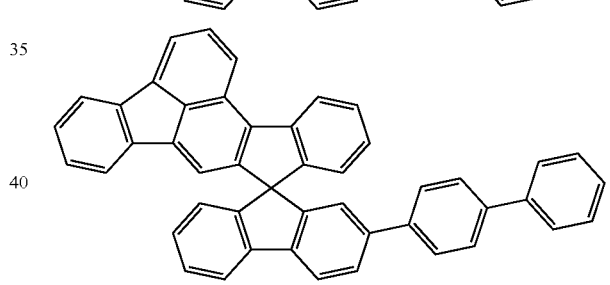
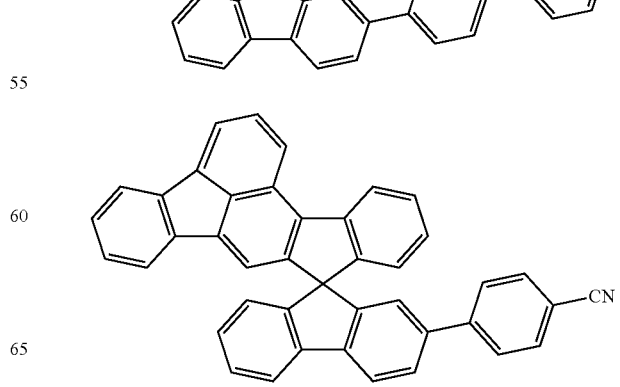

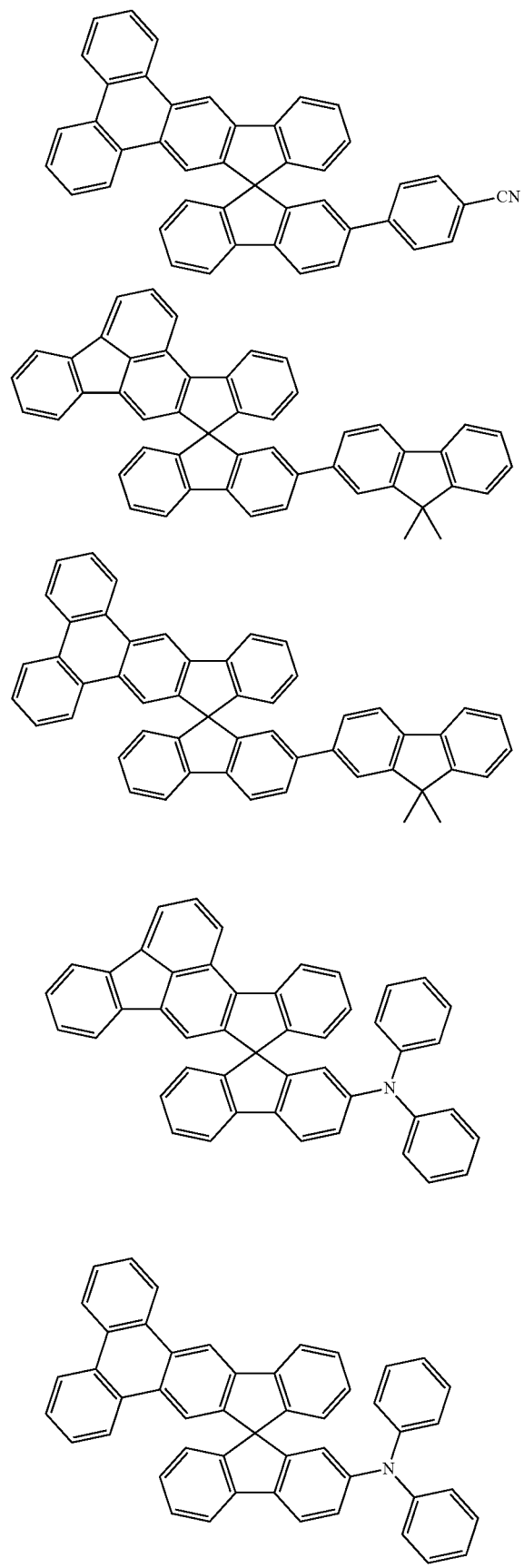

115
-continued
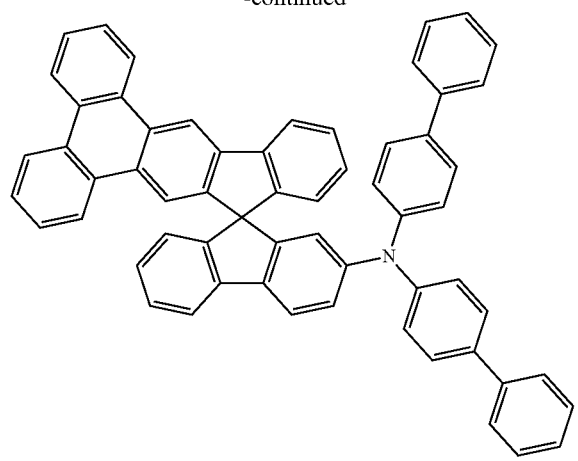
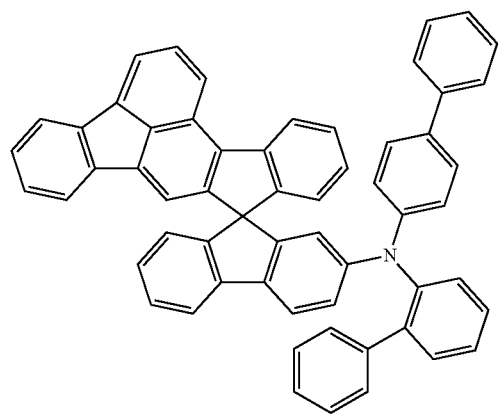
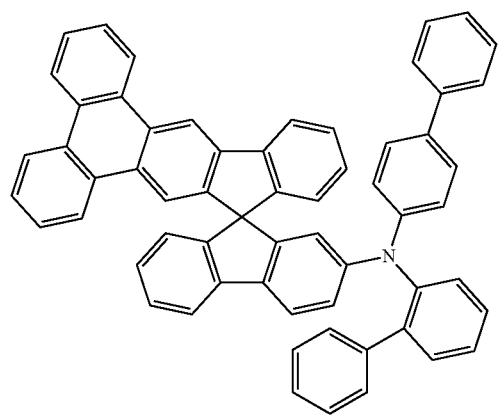
116
-continued
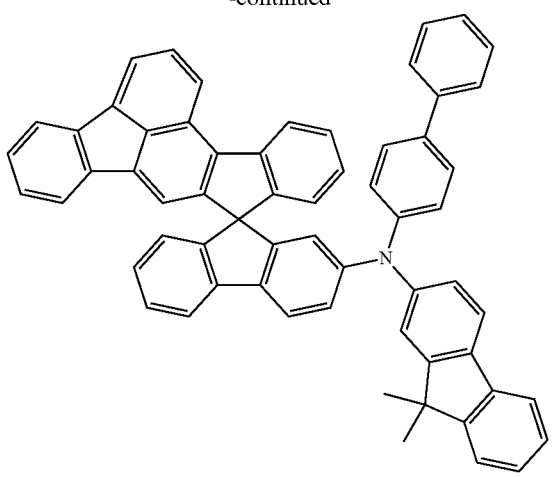
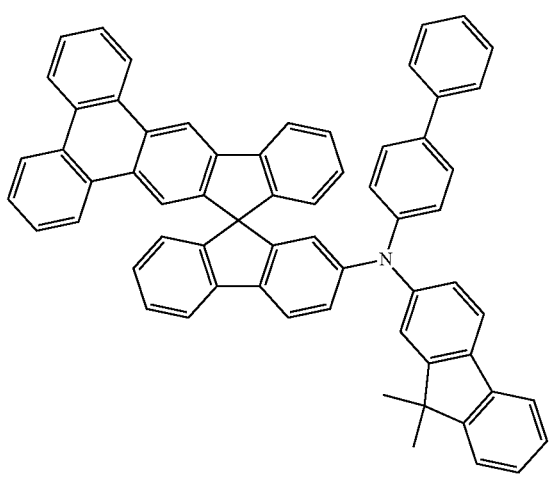
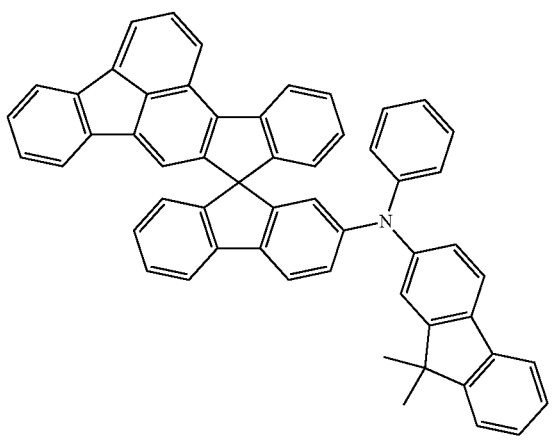

117
-continued
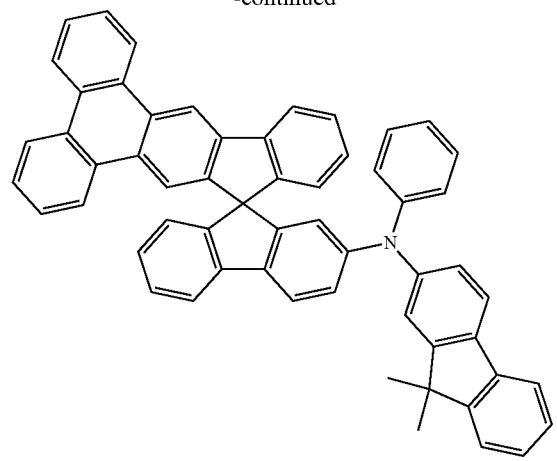
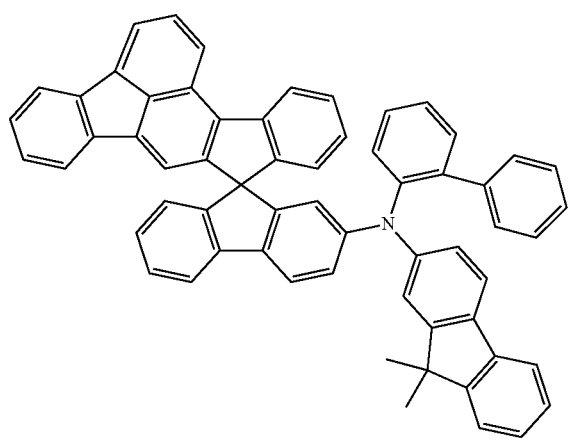
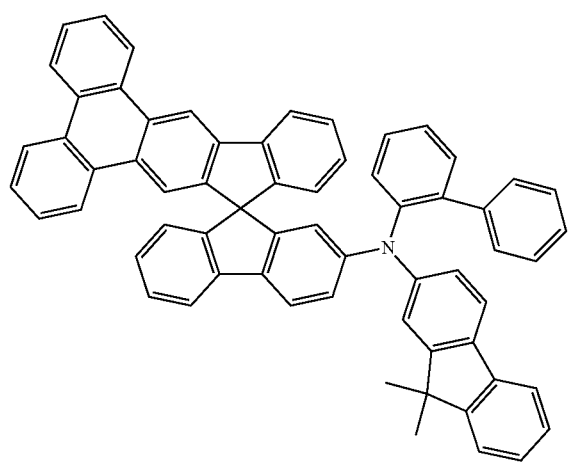
118
-continued
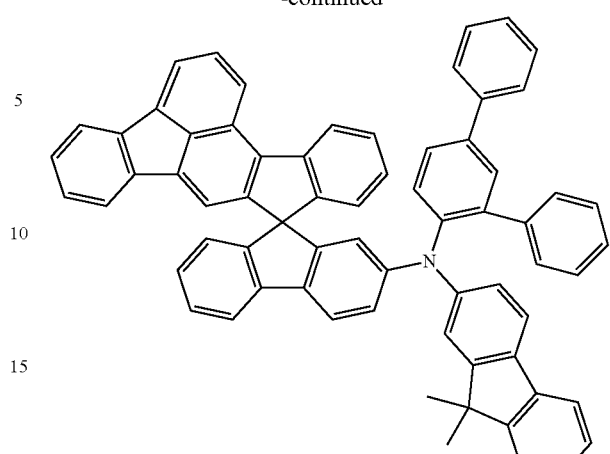
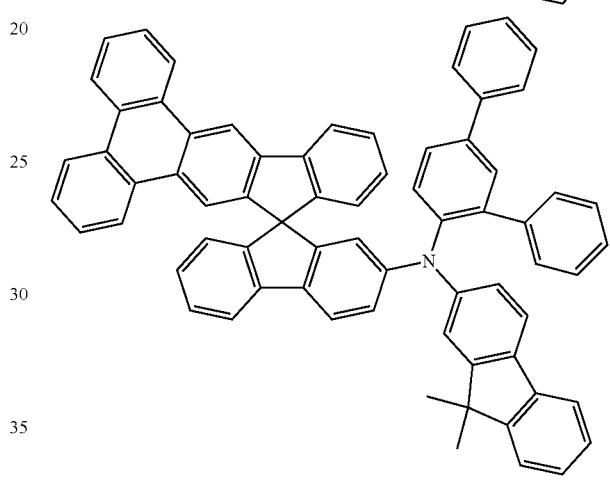
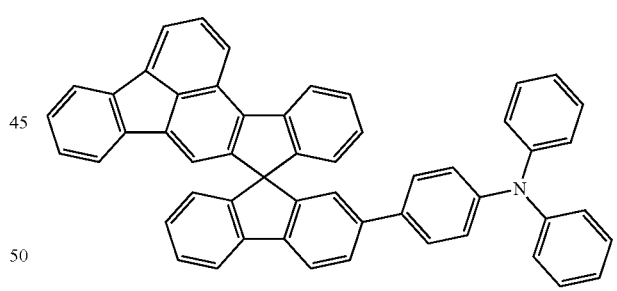
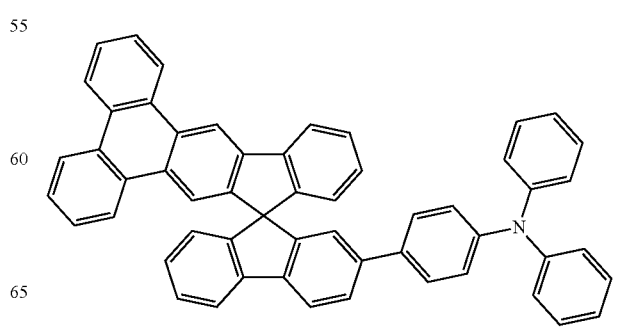

119
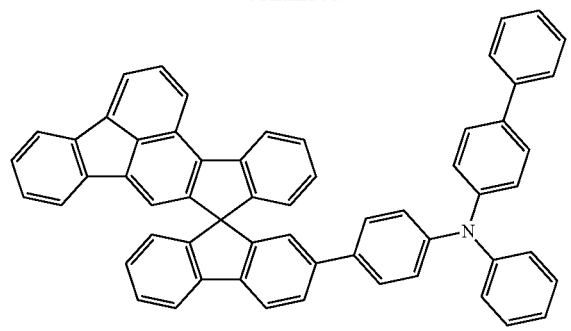
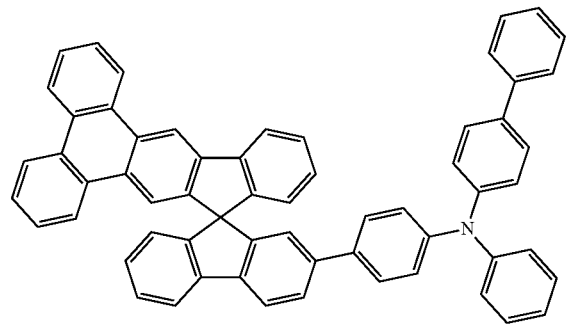
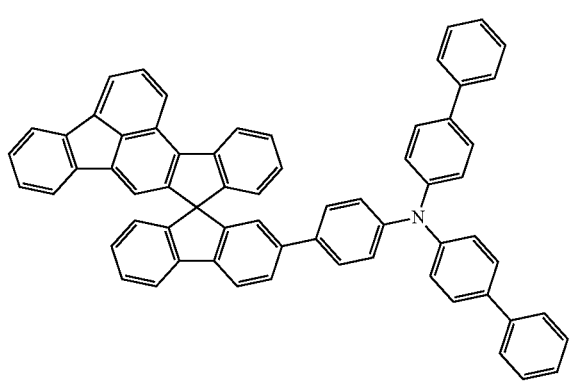
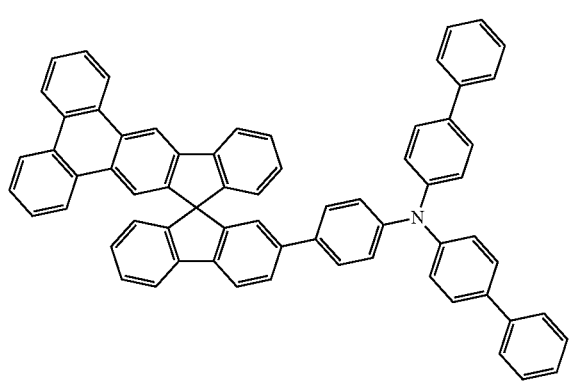
120
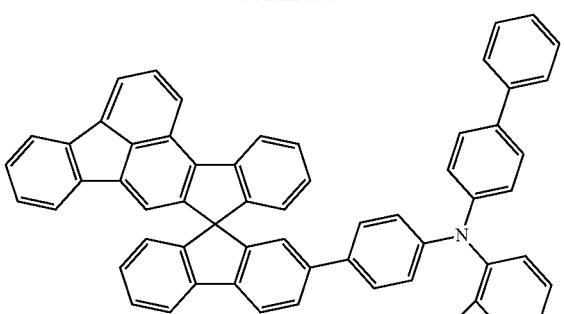
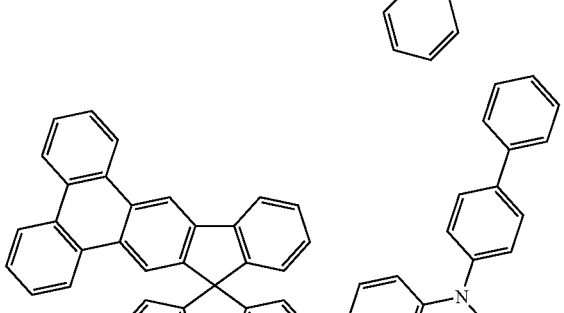
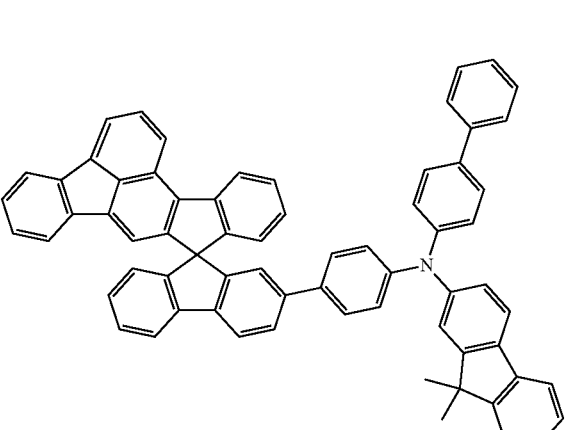
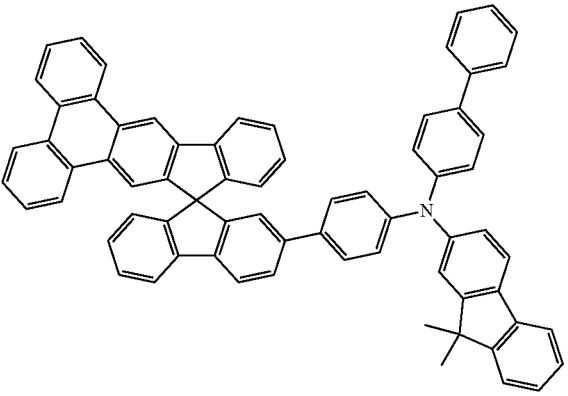

121
-continued
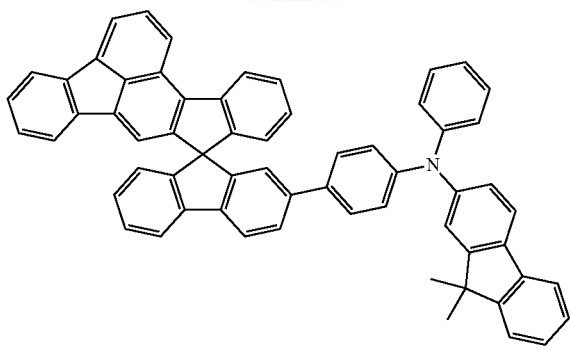
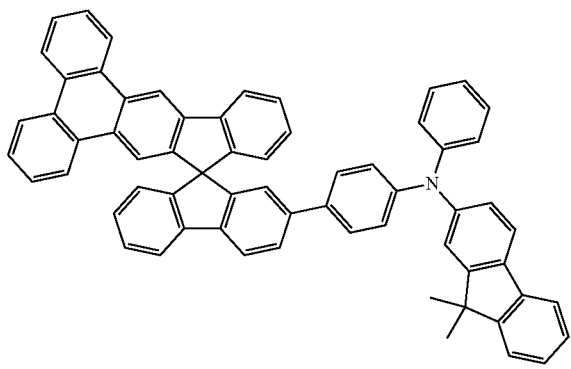
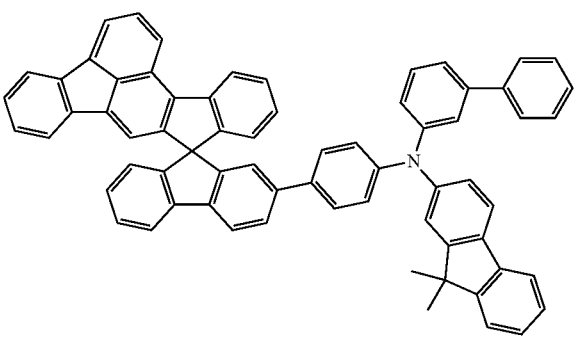
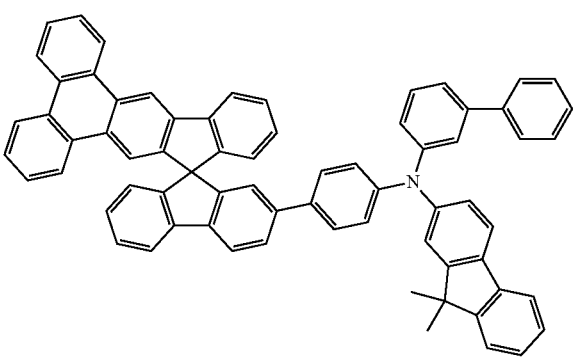
122
-continued
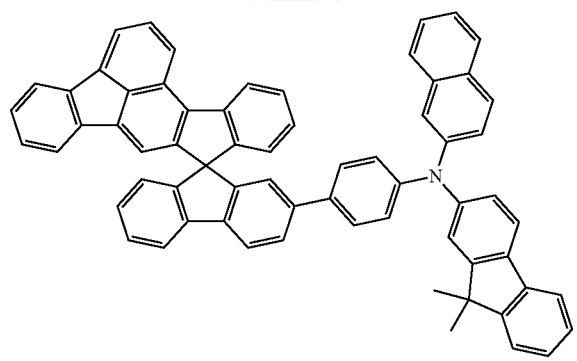
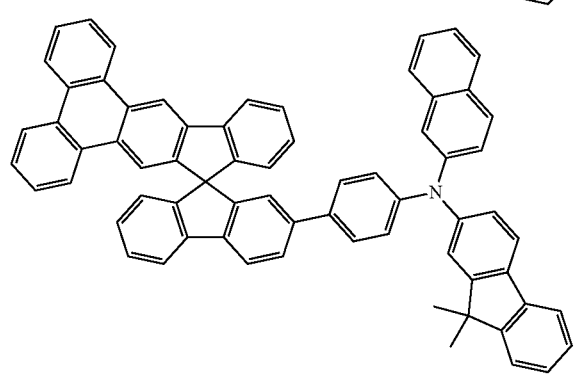
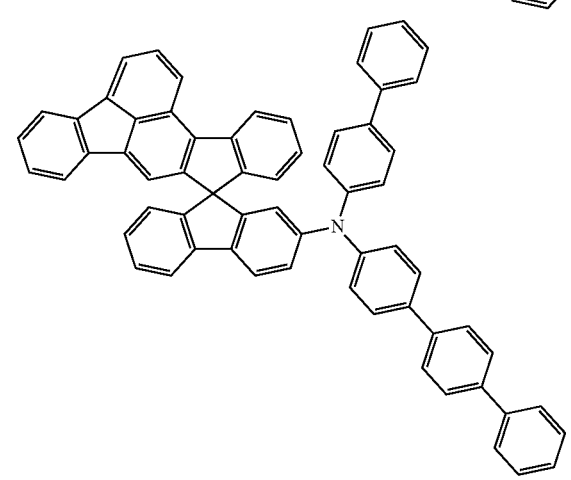
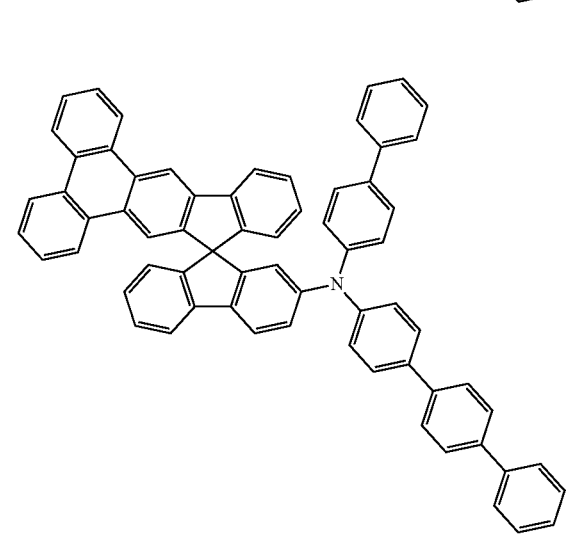

123
-continued
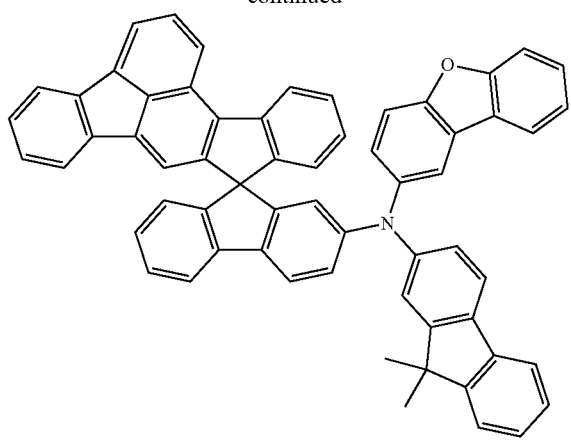
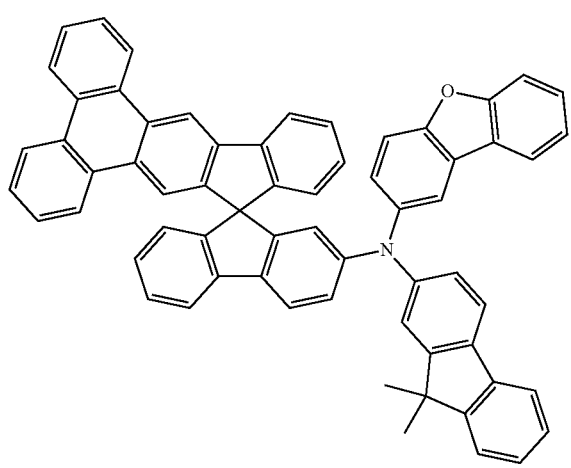
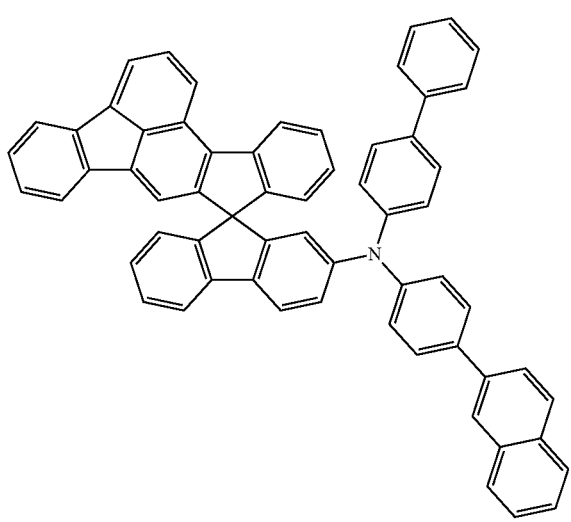
124
-continued
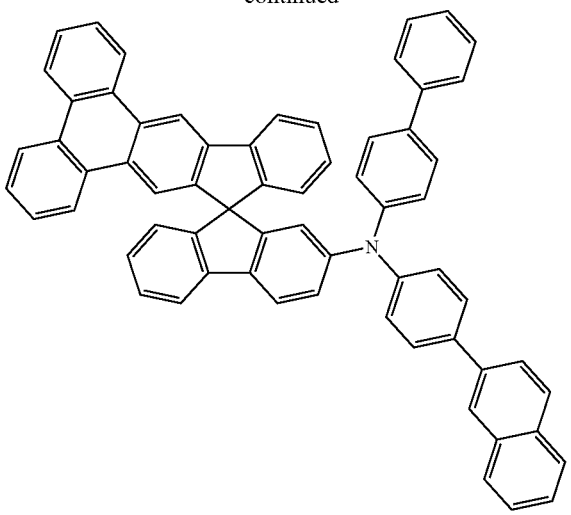
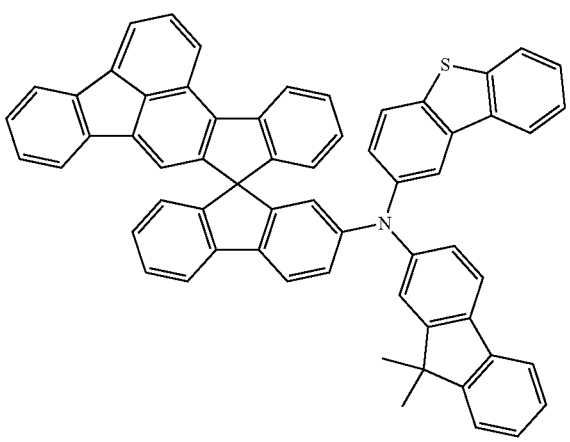
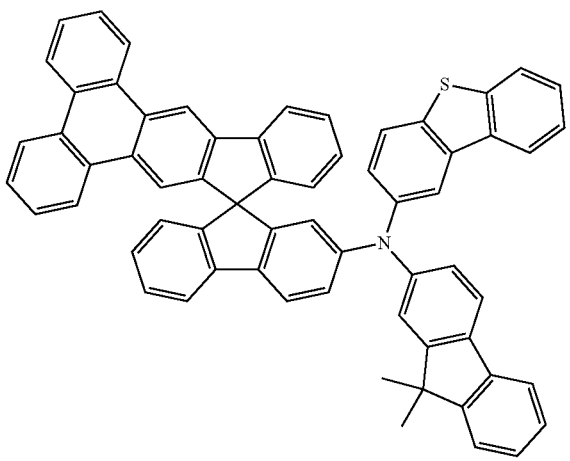

125
-continued
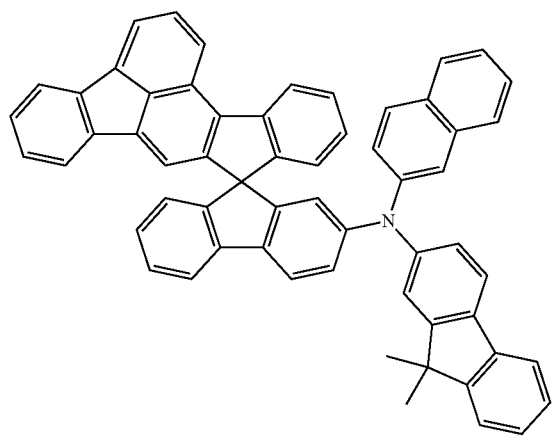
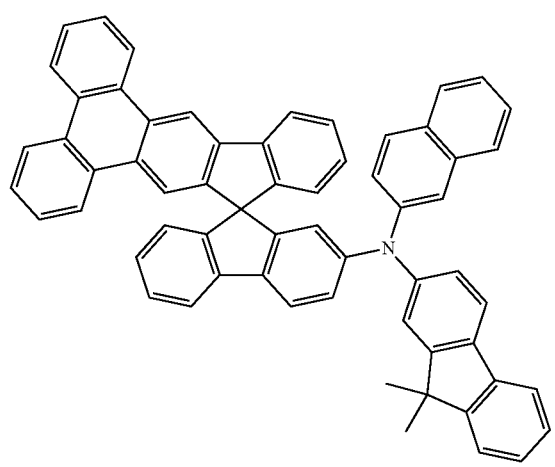
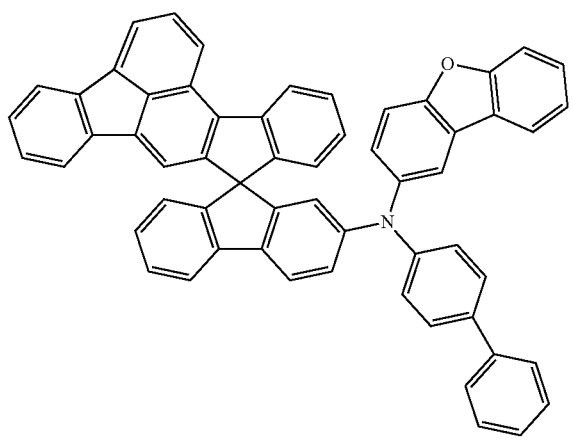
126
-continued
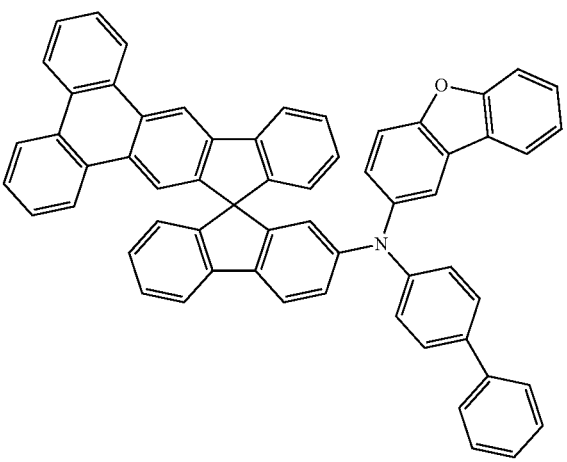
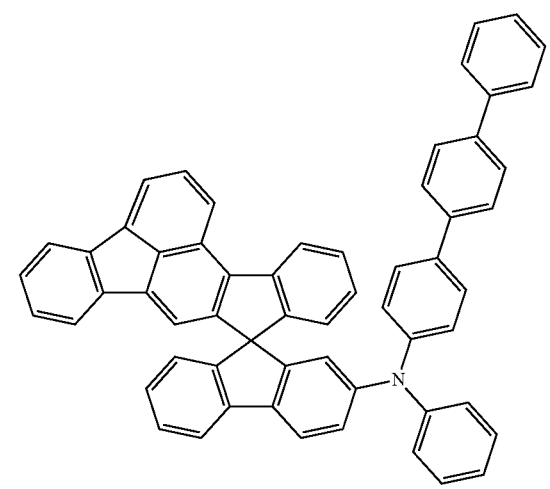
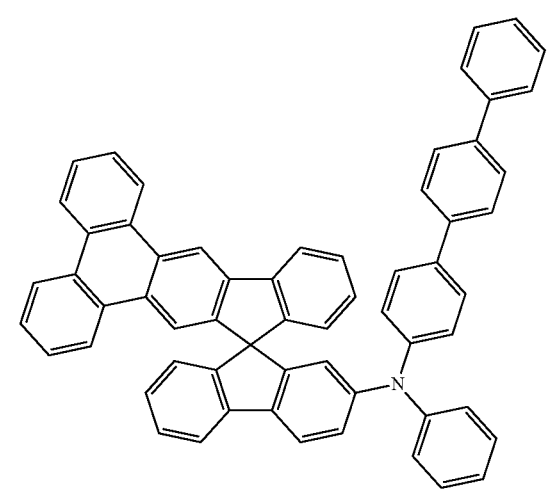

127
-continued
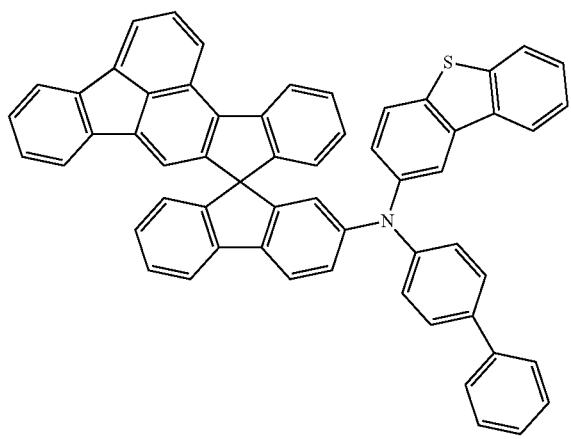
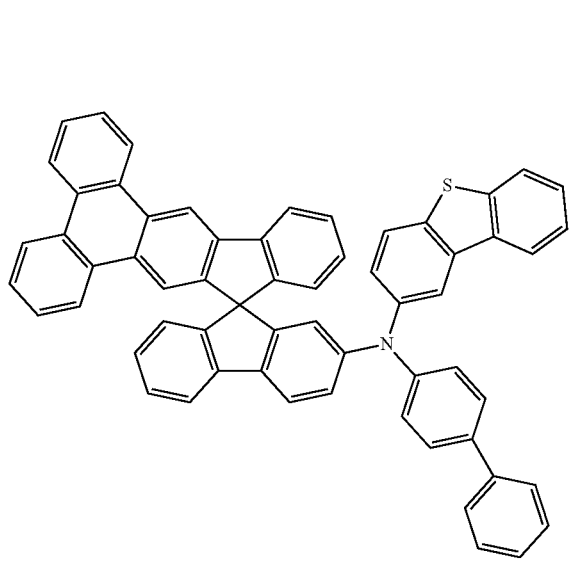
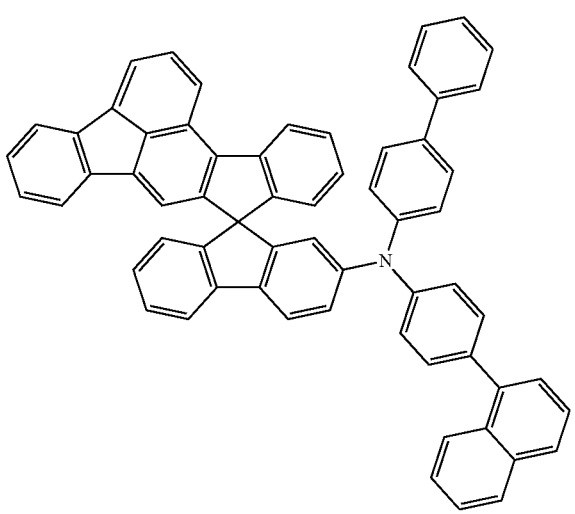
128
-continued
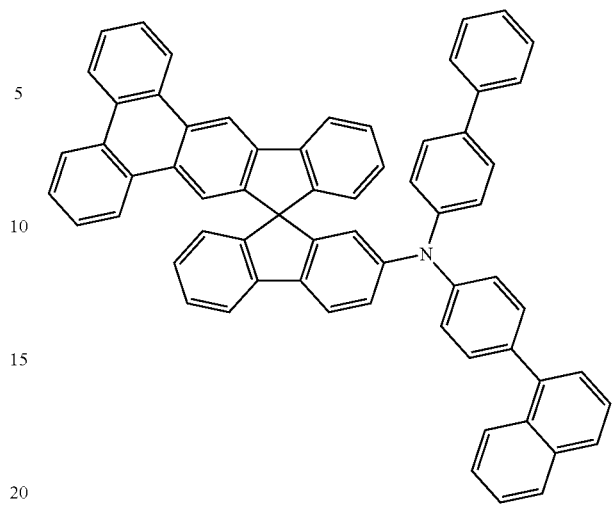
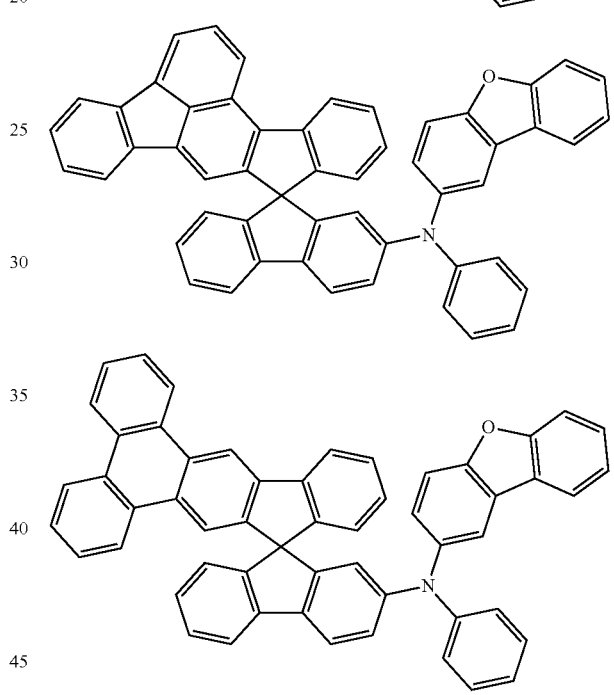
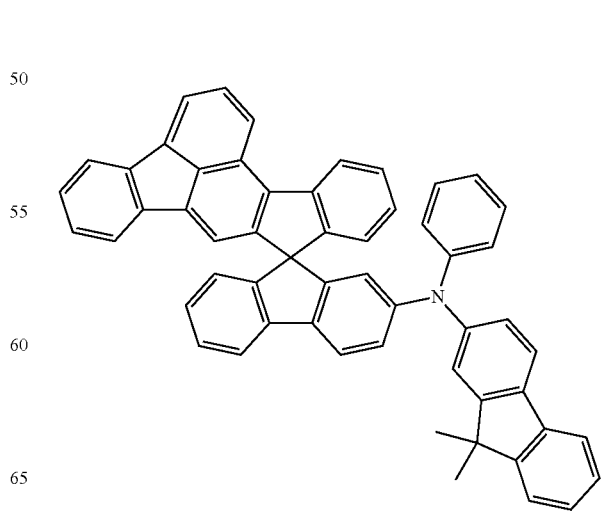

129
-continued
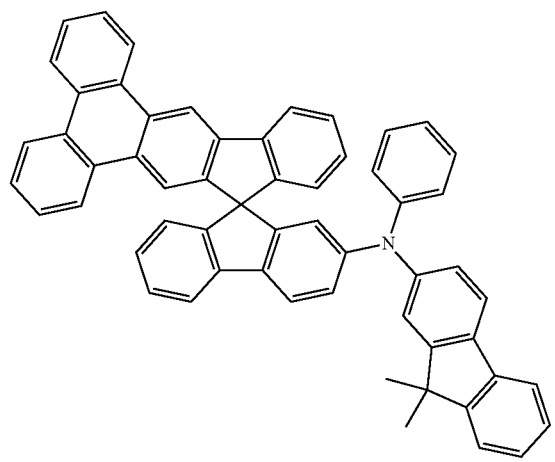
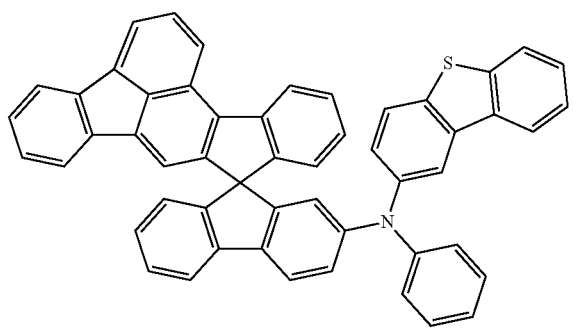
130
-continued
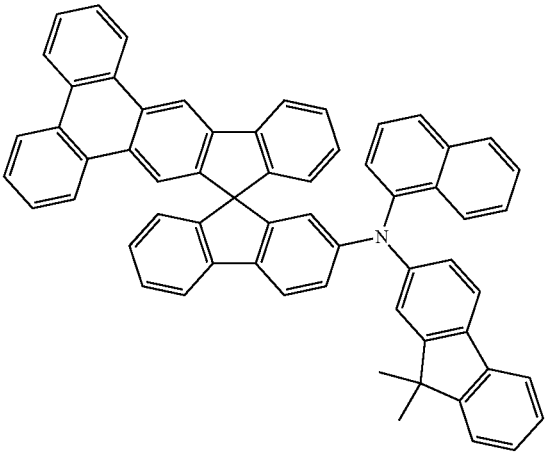
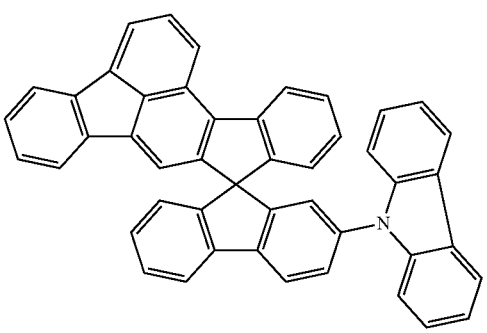
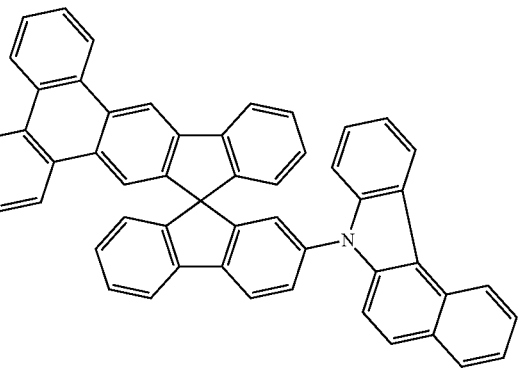
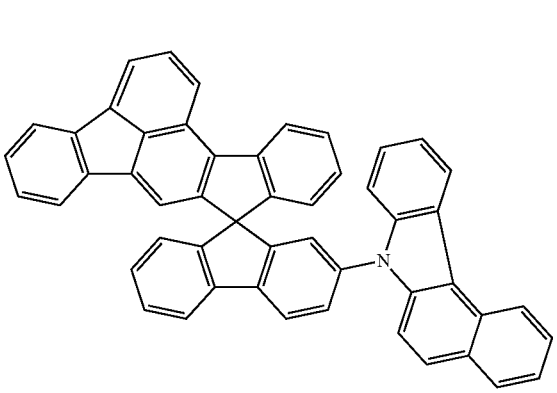

131
-continued
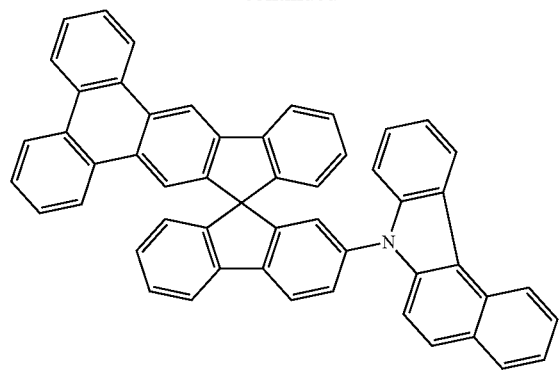
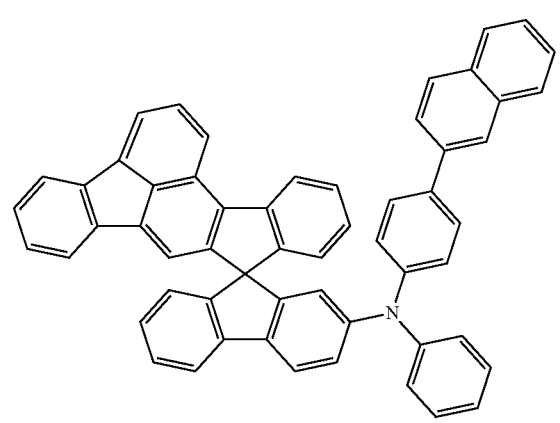
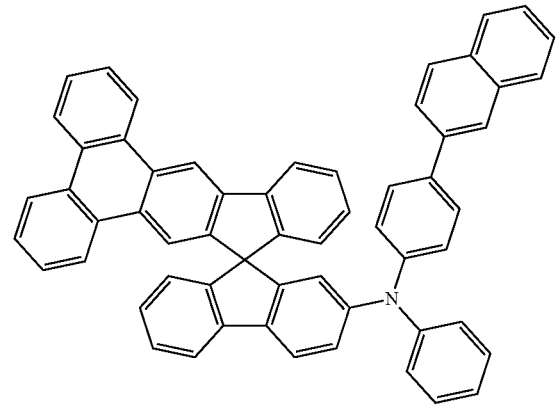
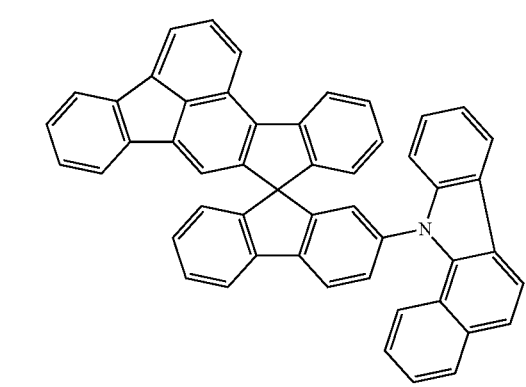
132
-continued
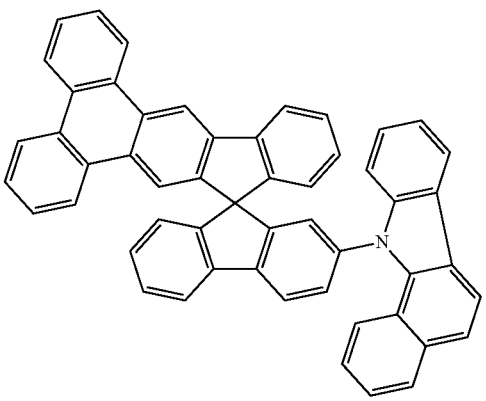
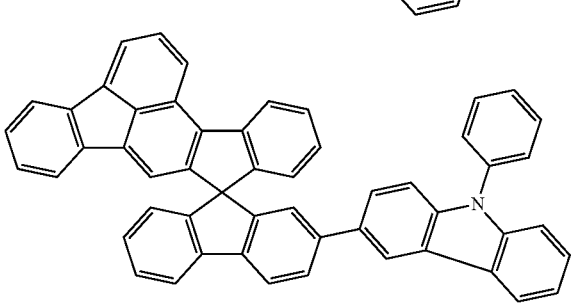
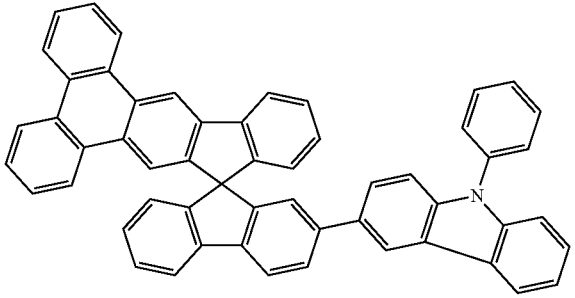
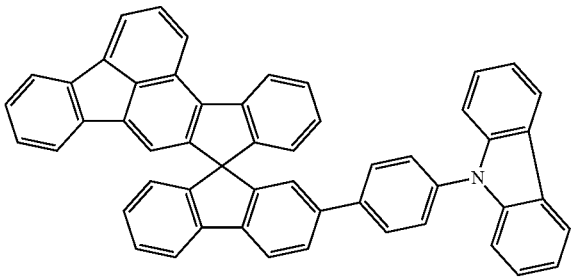
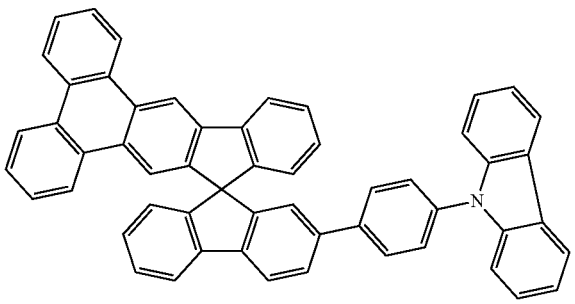

133
-continued
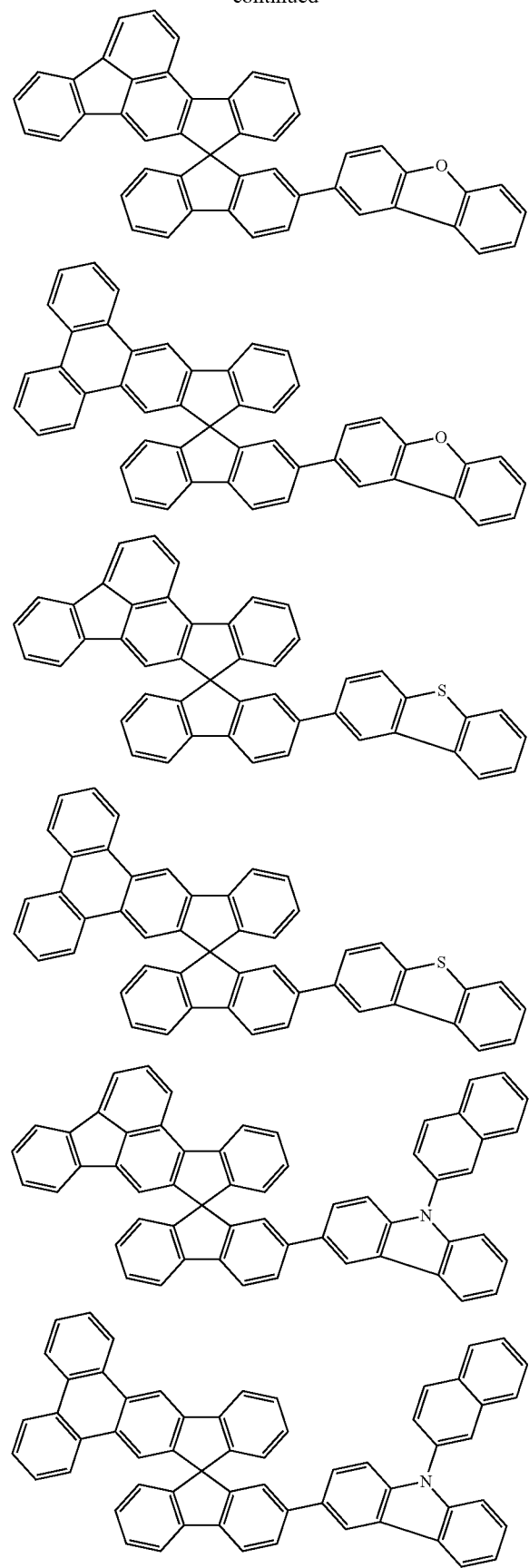
134
-continued
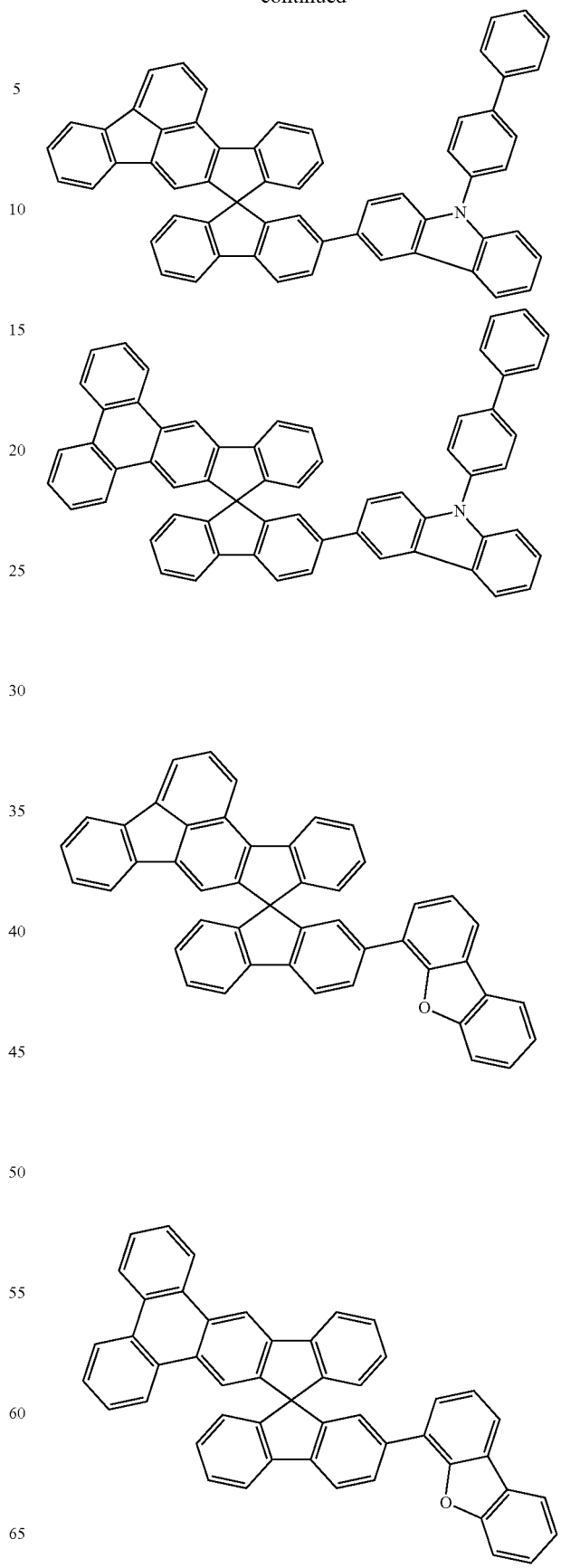

135
-continued
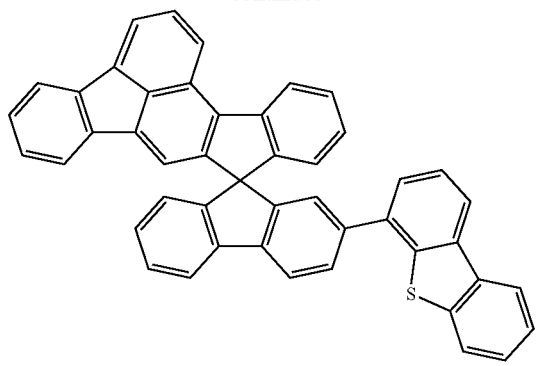
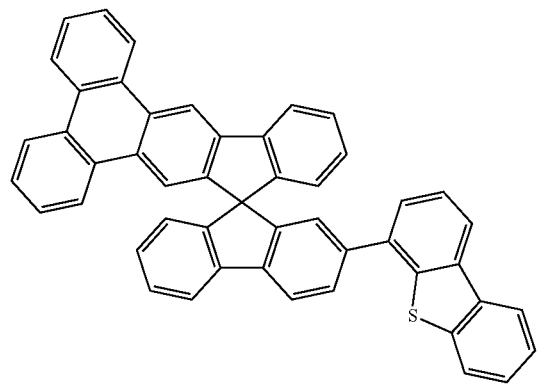
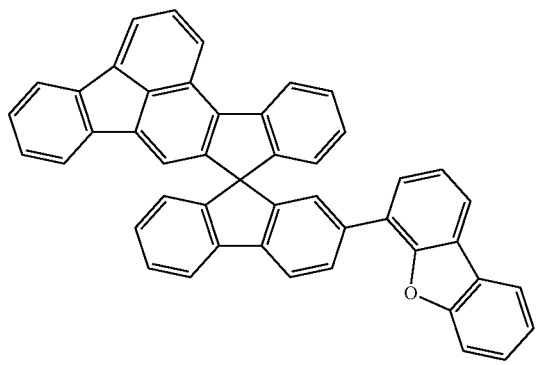
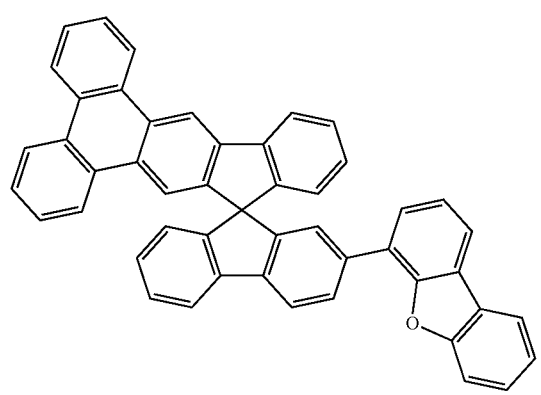
136
-continued
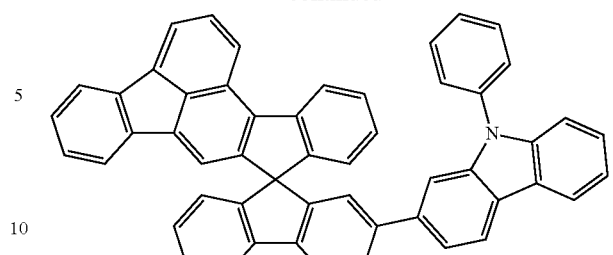
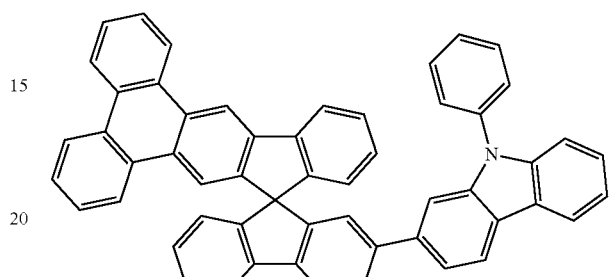
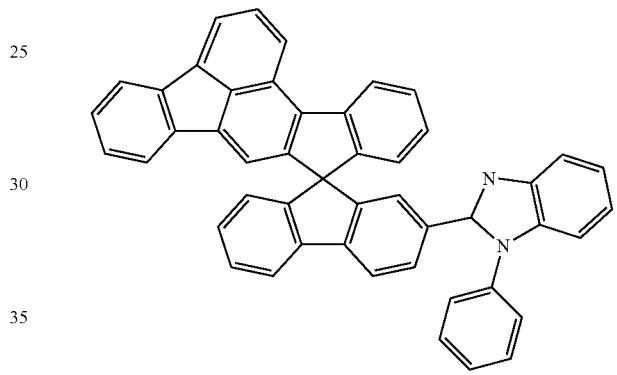
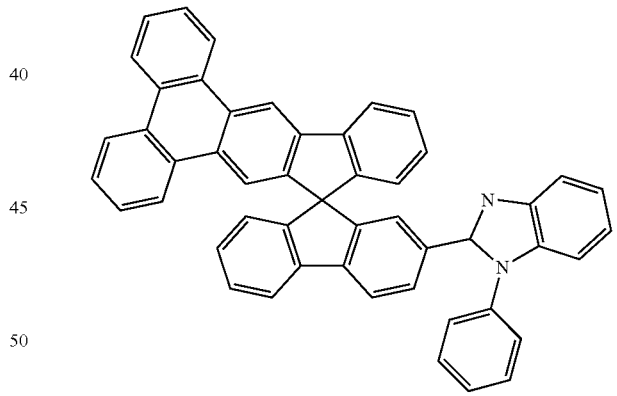
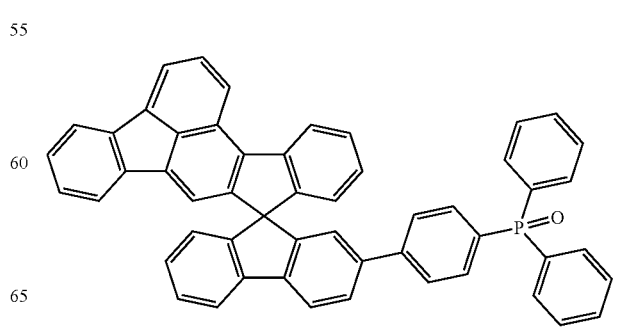

137
-continued
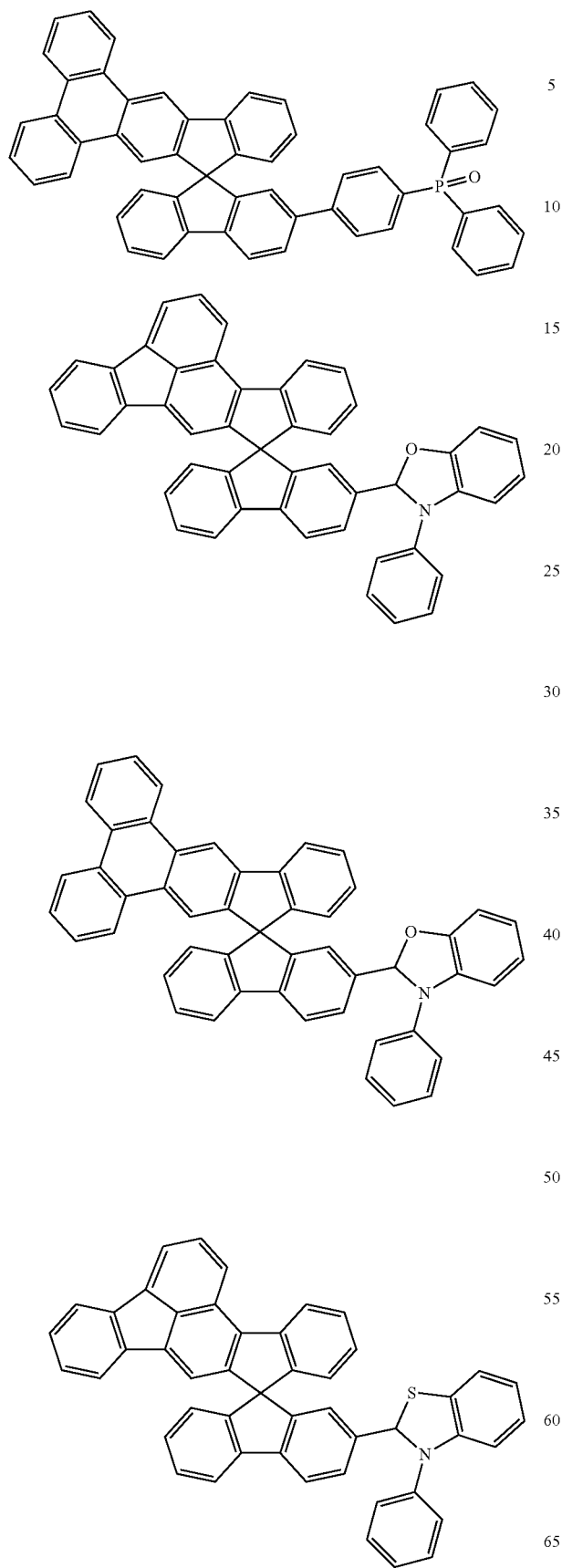
138
-continued
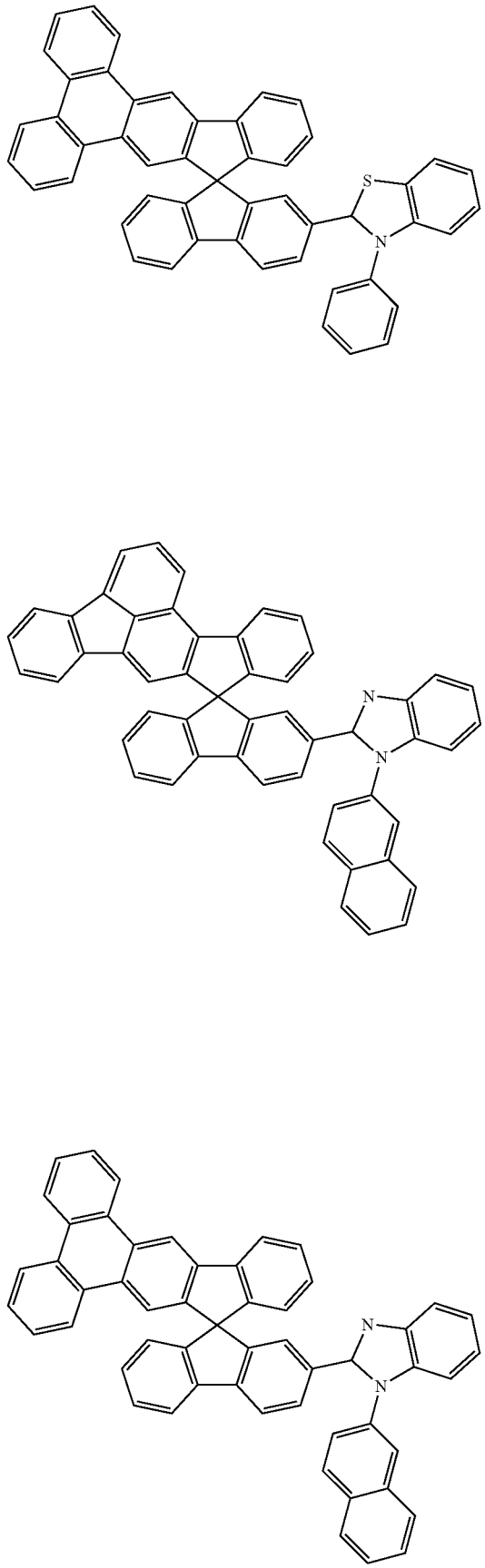

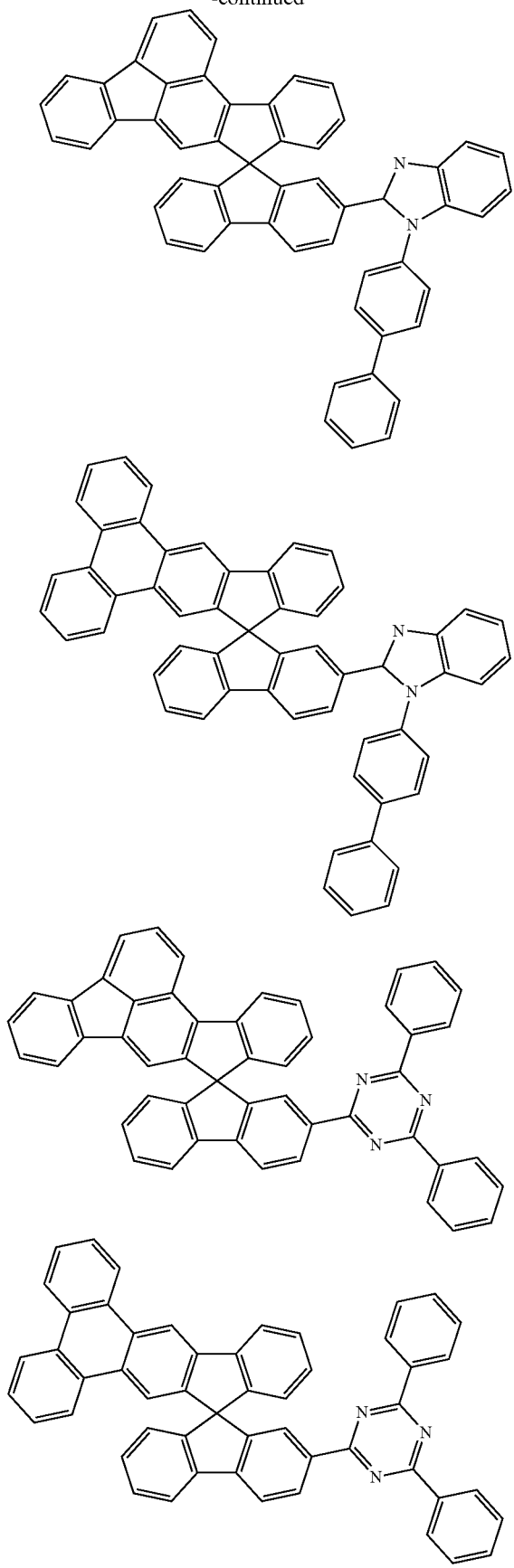

141
-continued
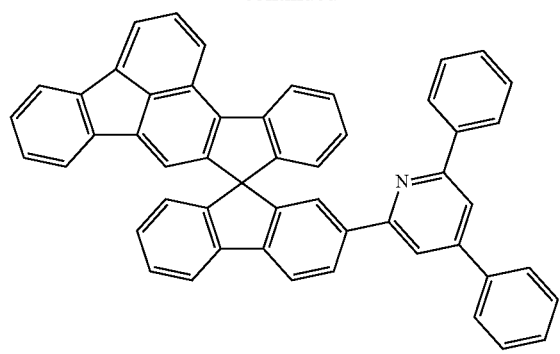
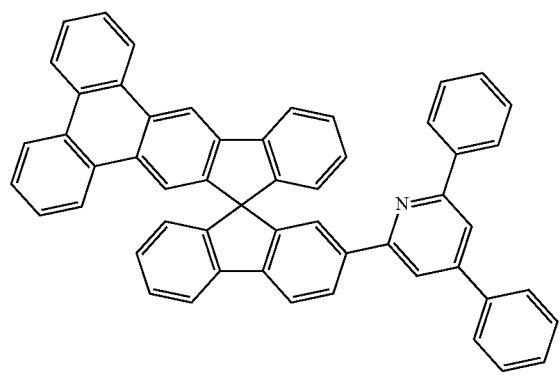
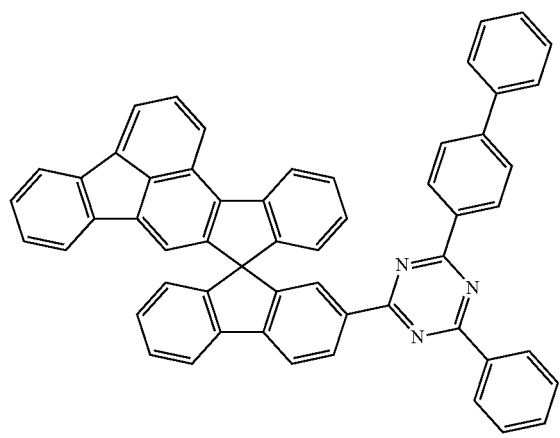
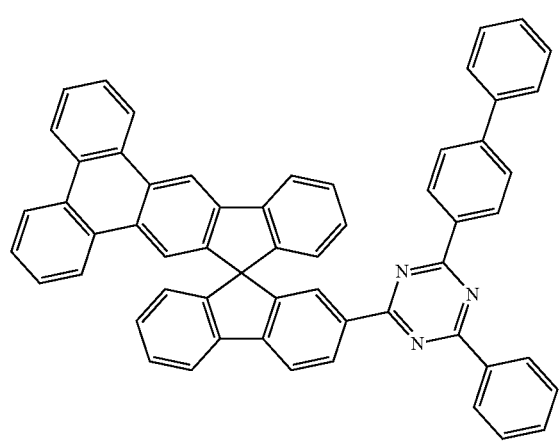
142
-continued
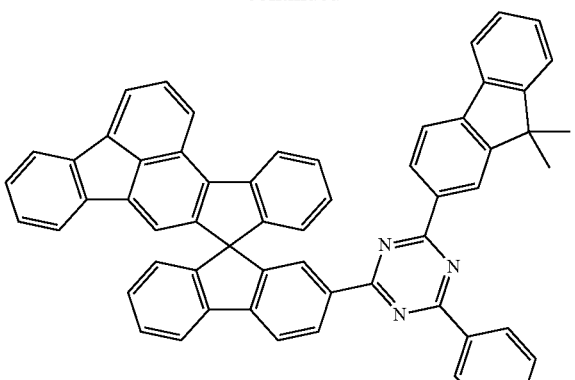
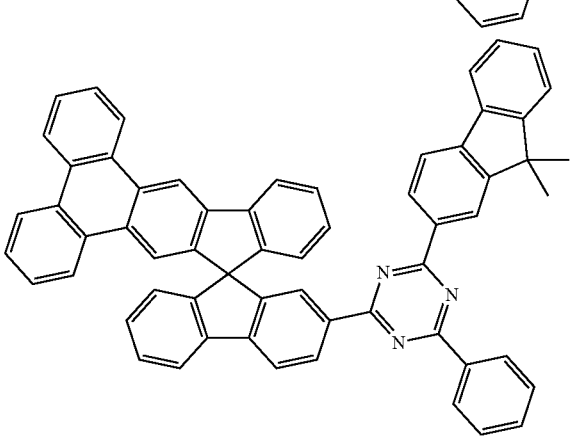
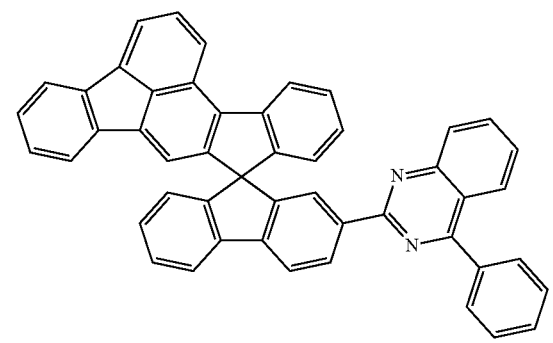
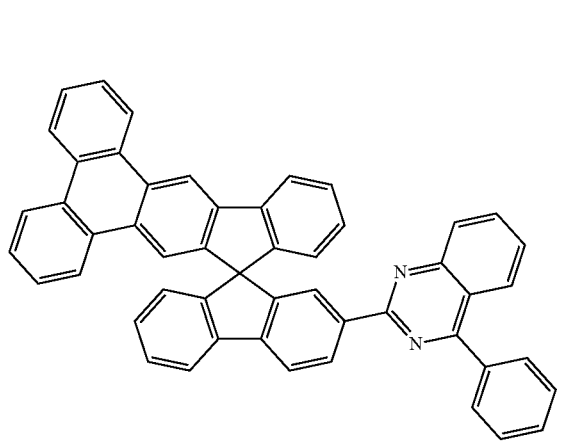

143
-continued
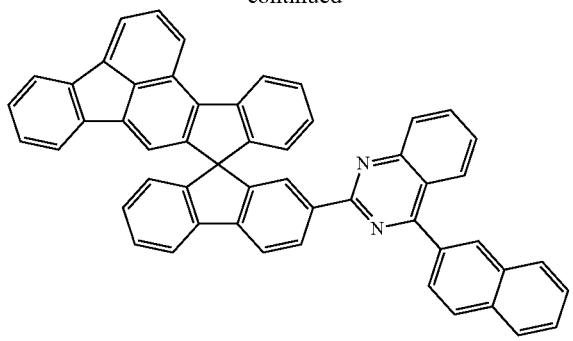
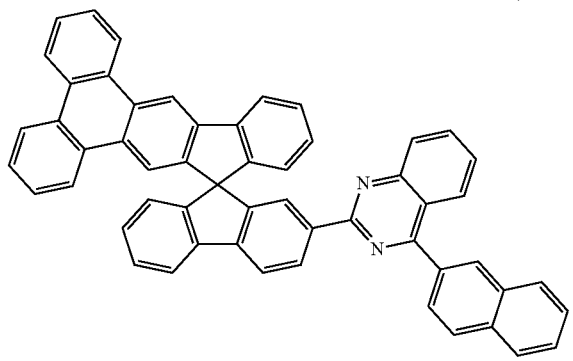
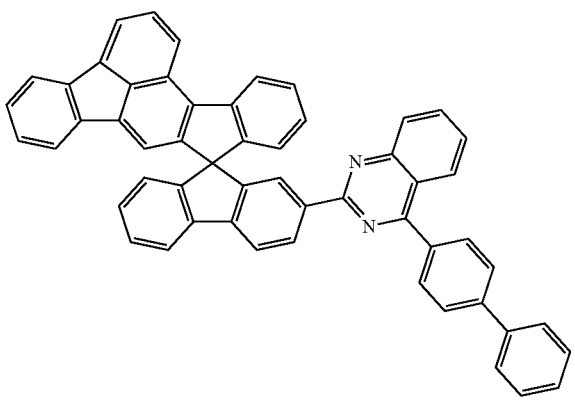
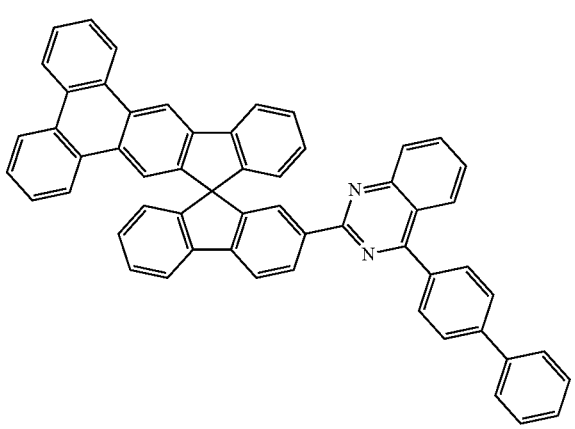
144
-continued
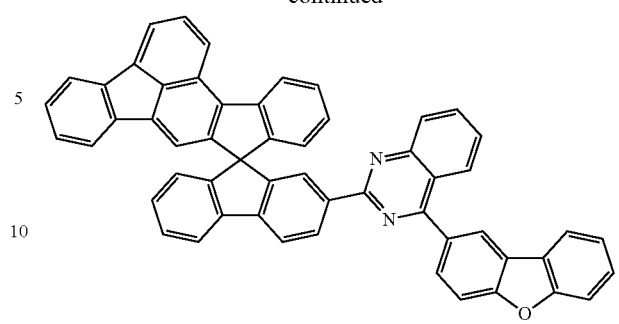
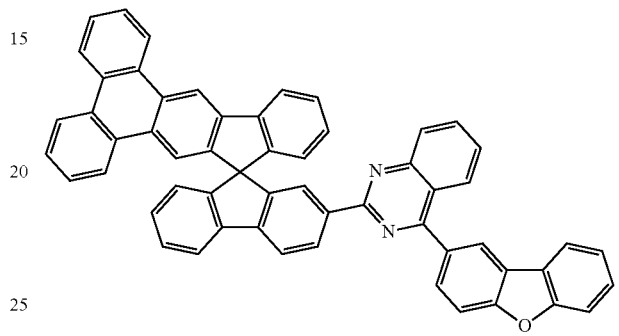
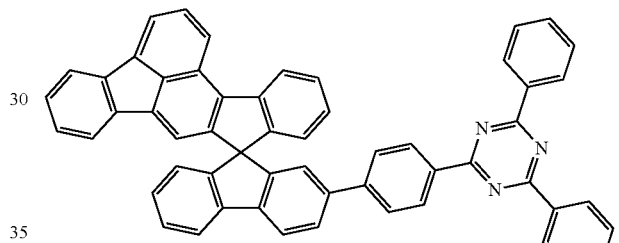
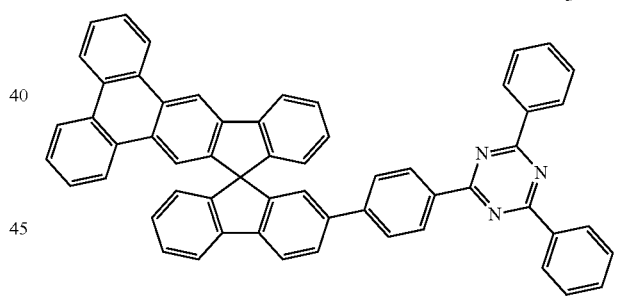
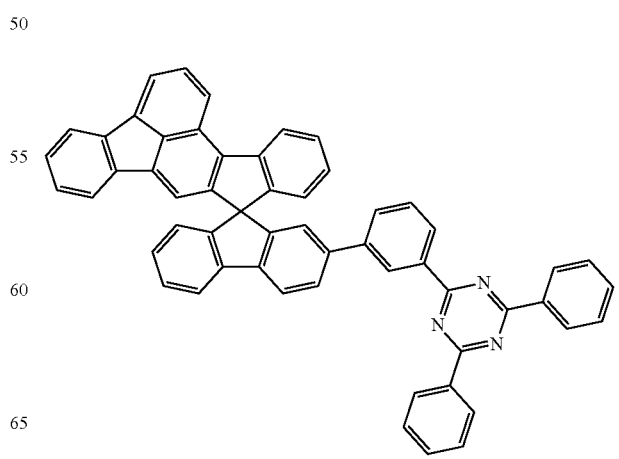

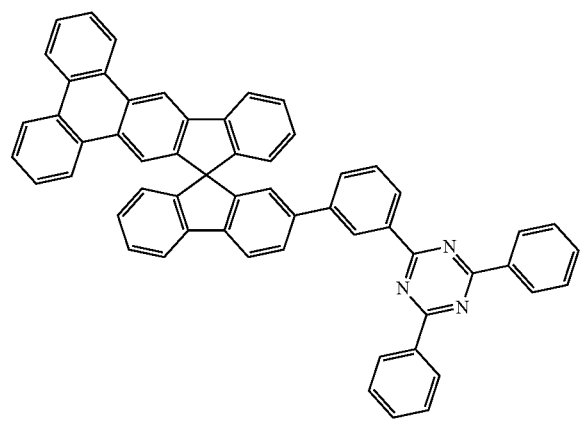
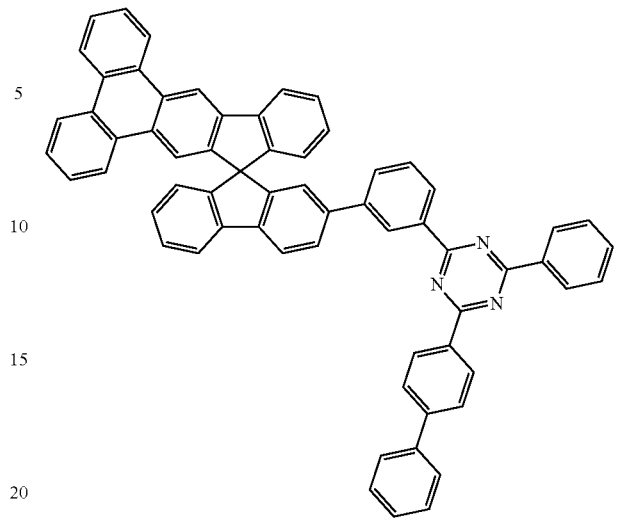
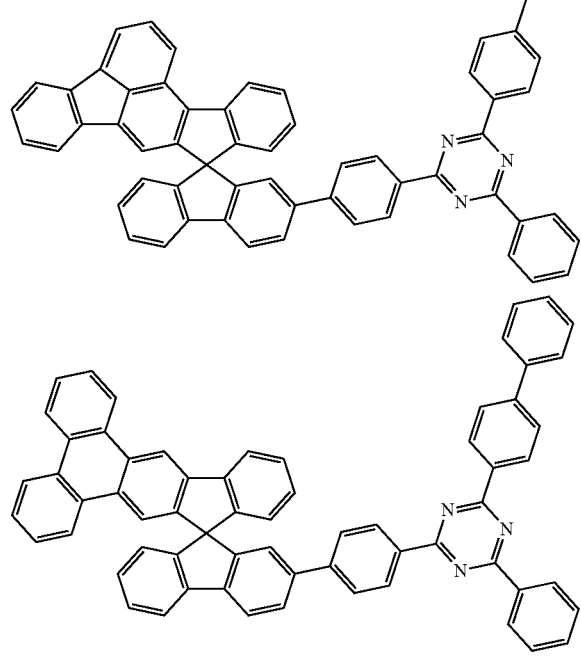
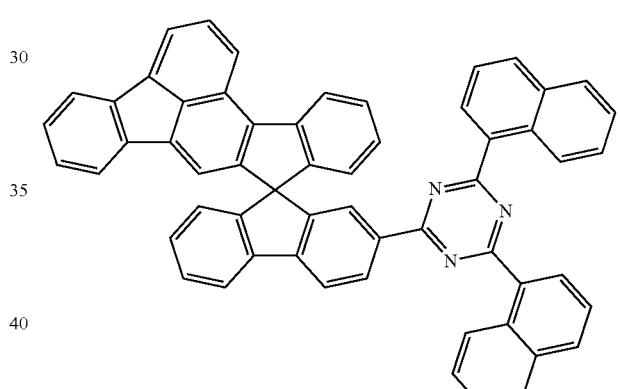
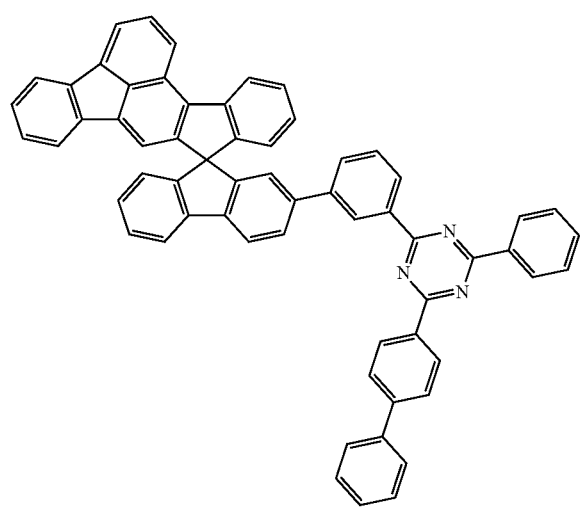
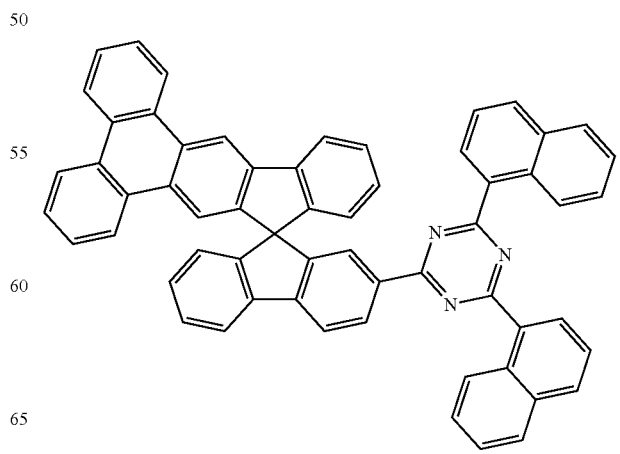

147
-continued
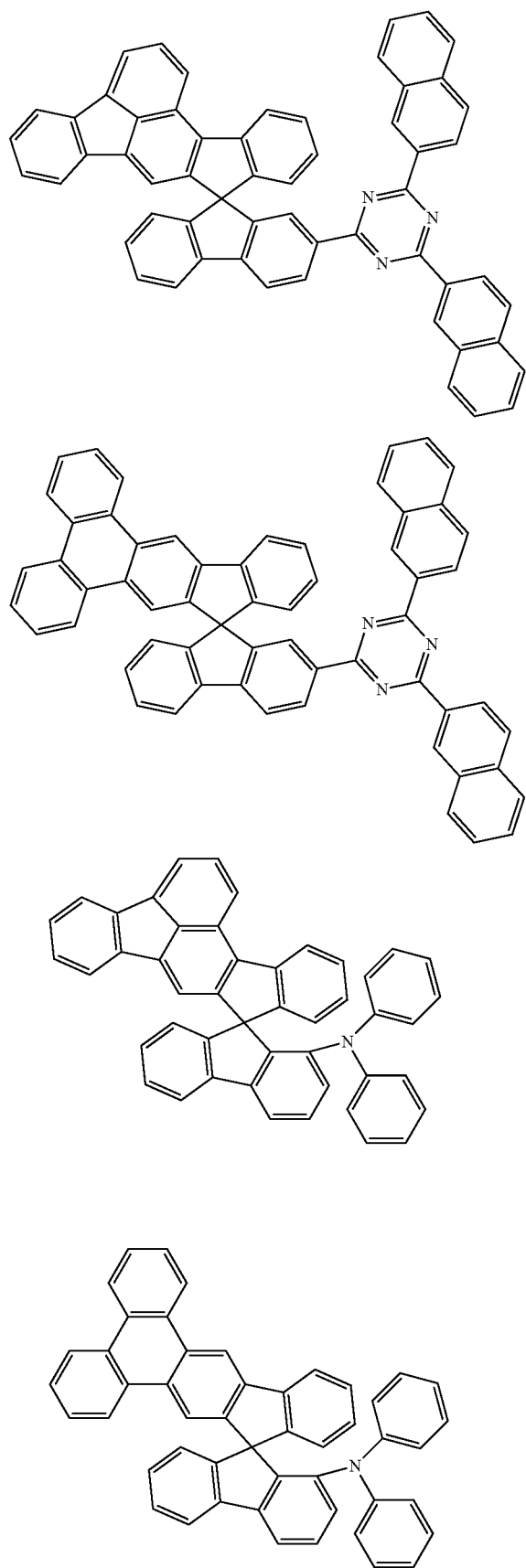
148
-continued
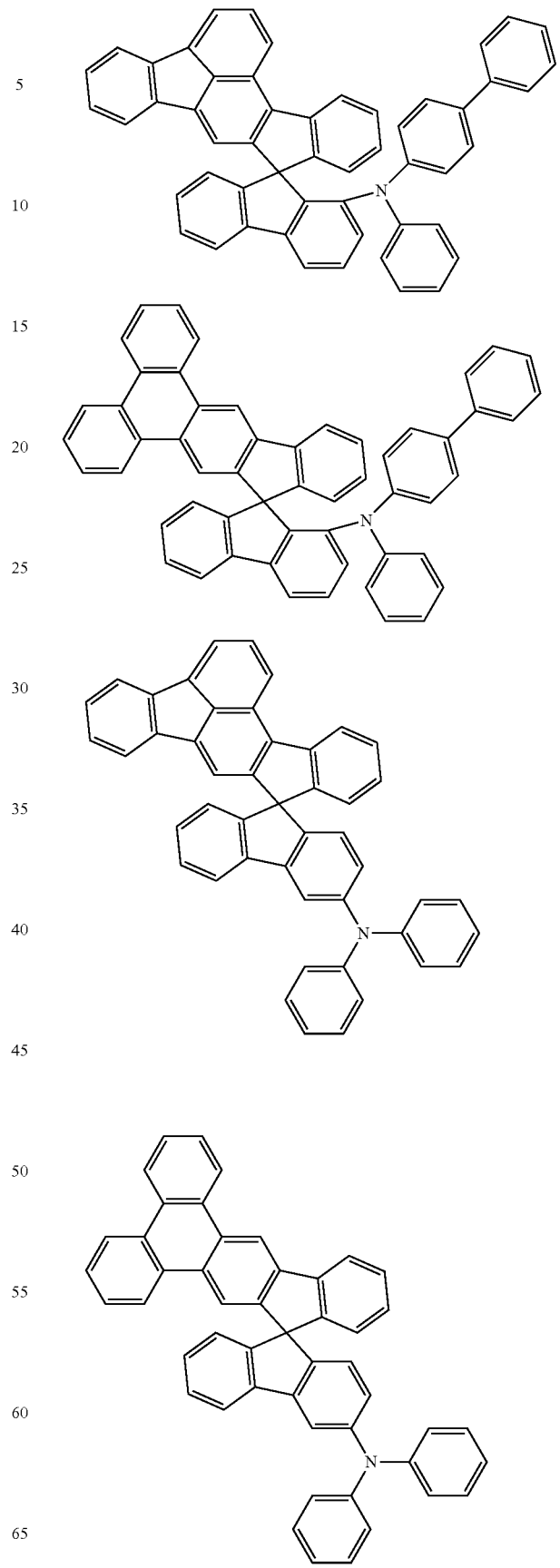

149
-continued
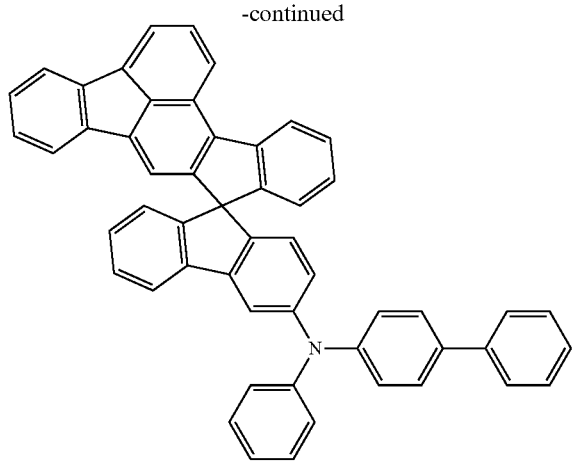
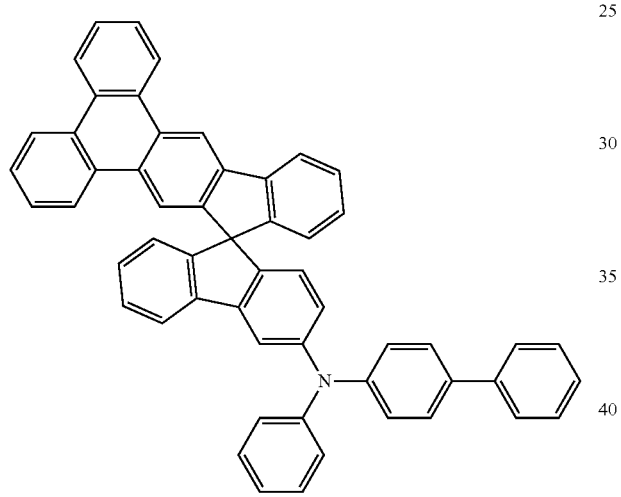
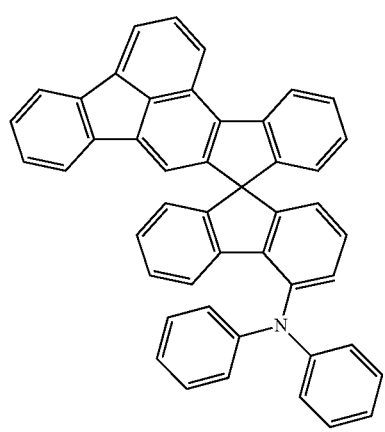
150
-continued
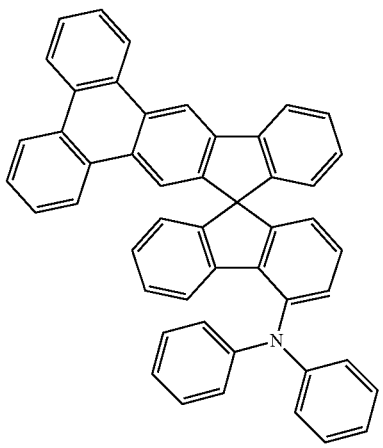
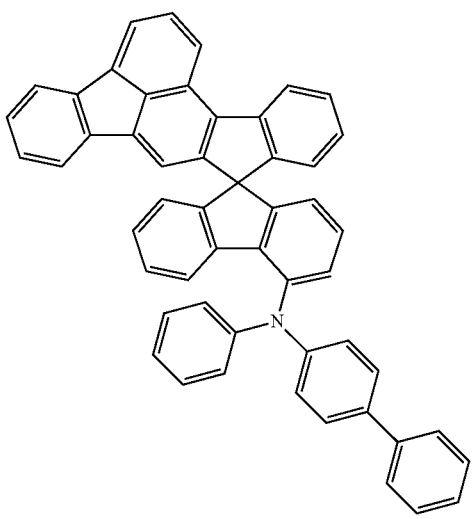
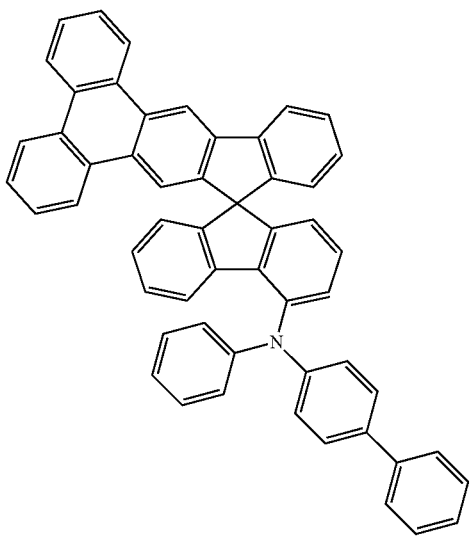

151
-continued
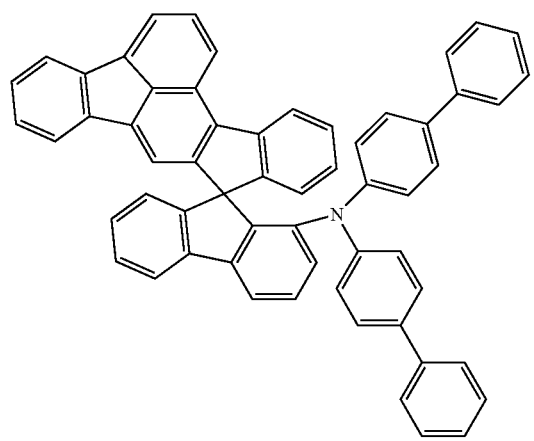
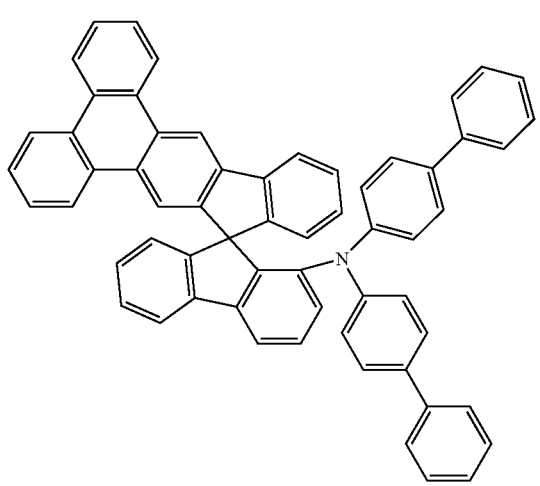
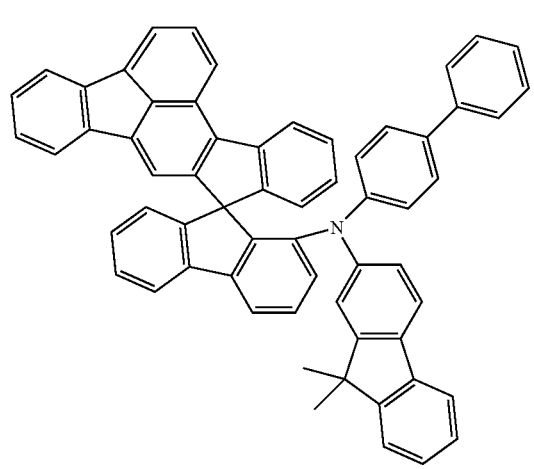
152
-continued
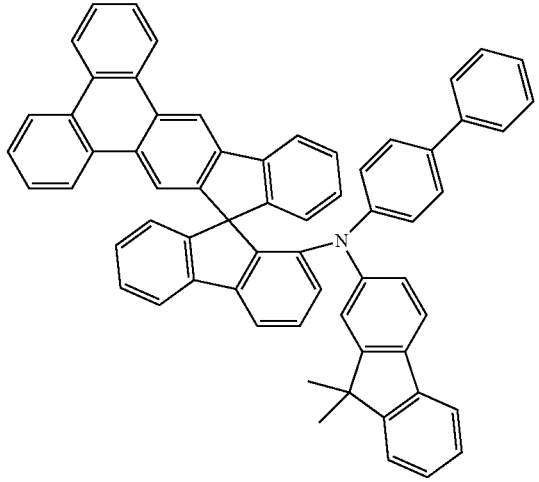
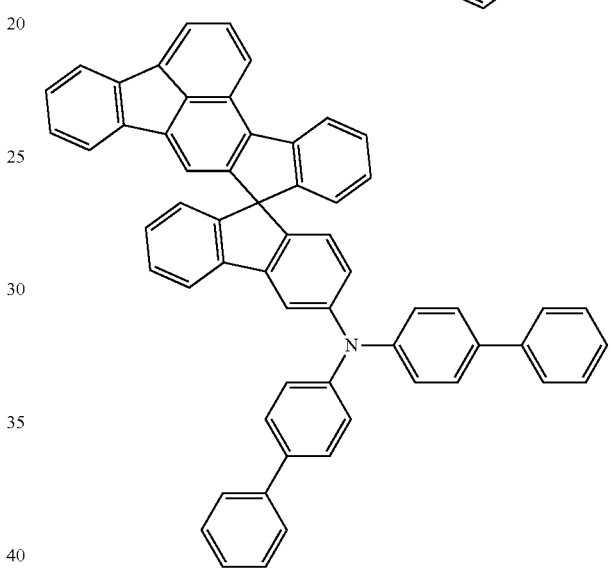
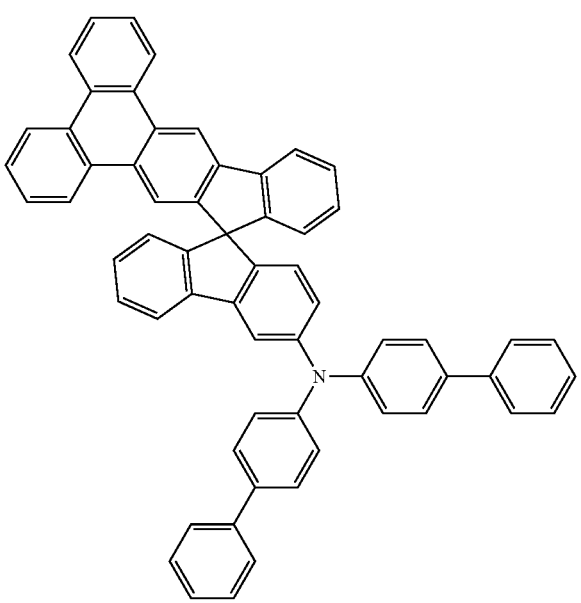

153
-continued
154
-continued
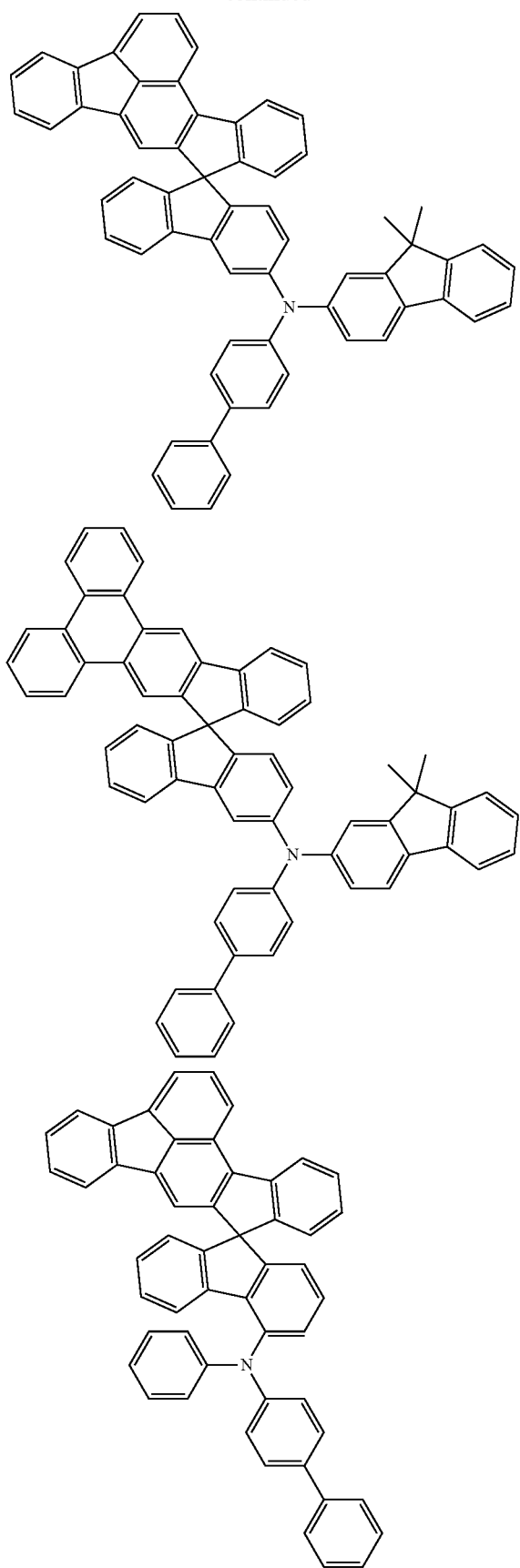
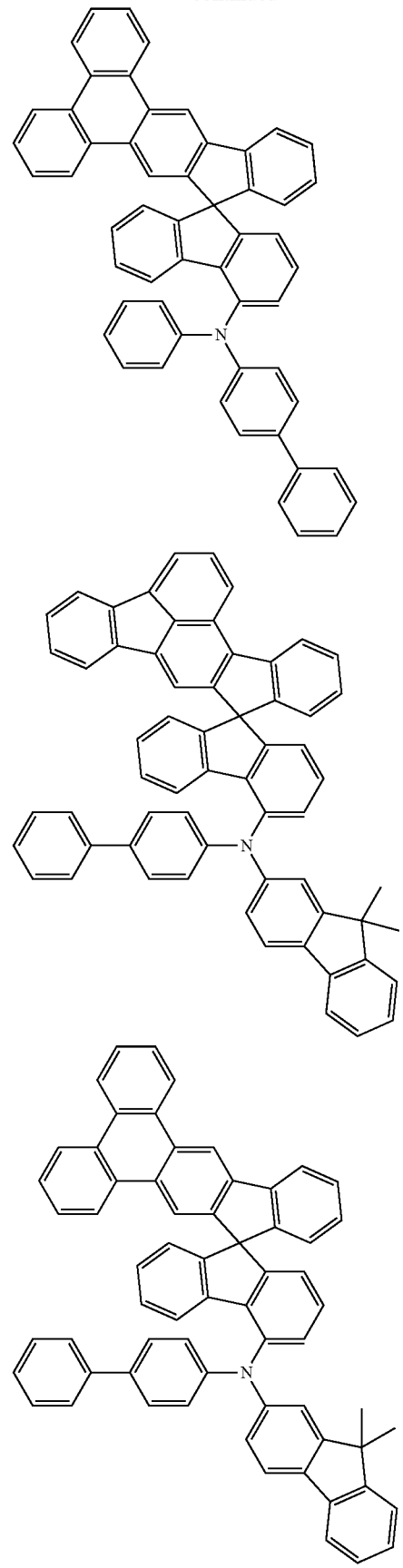

155
-continued
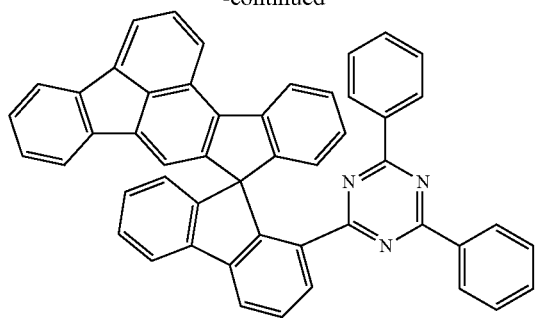
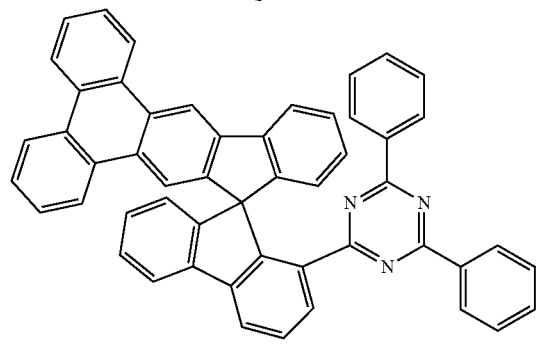
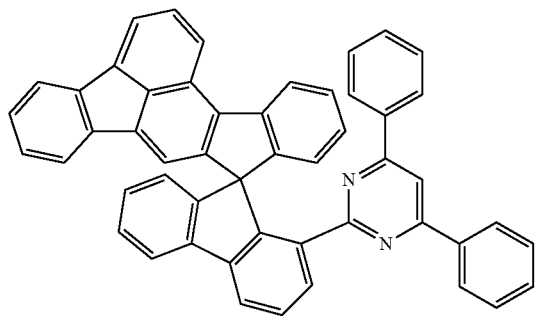
156
-continued
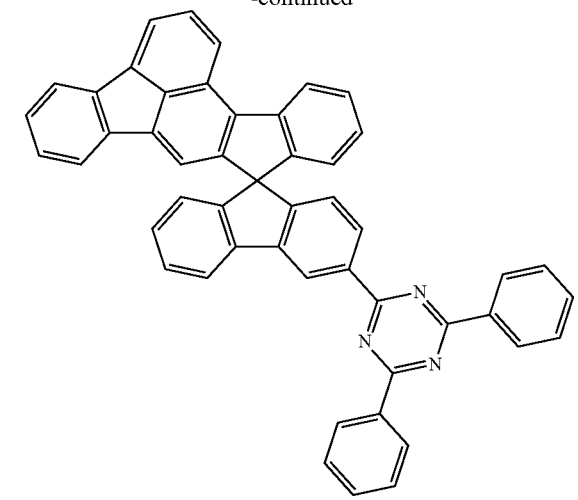
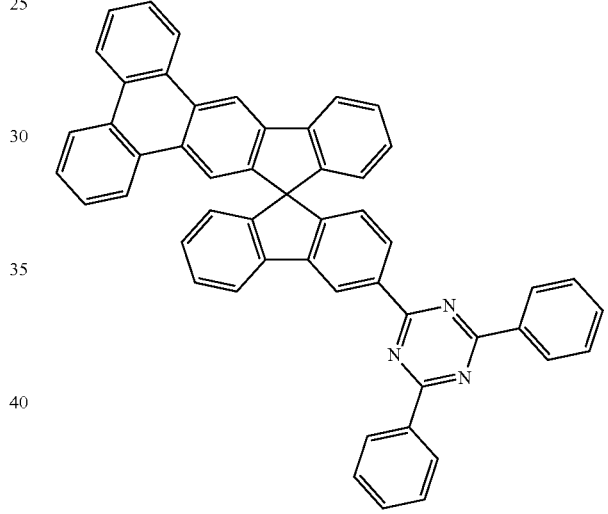
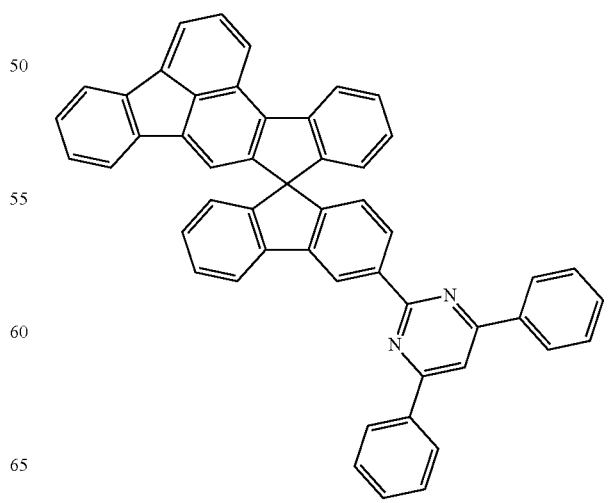

157
-continued
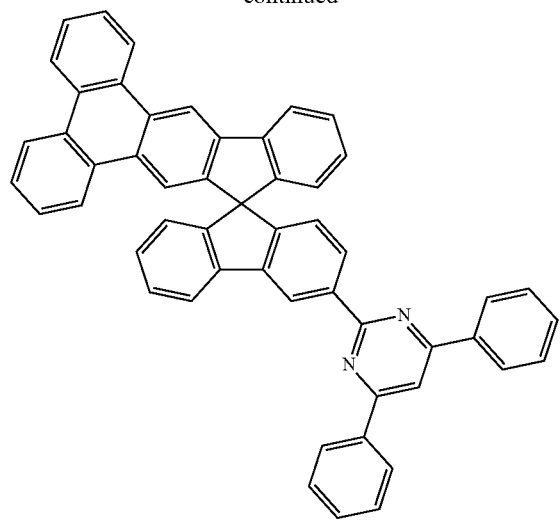
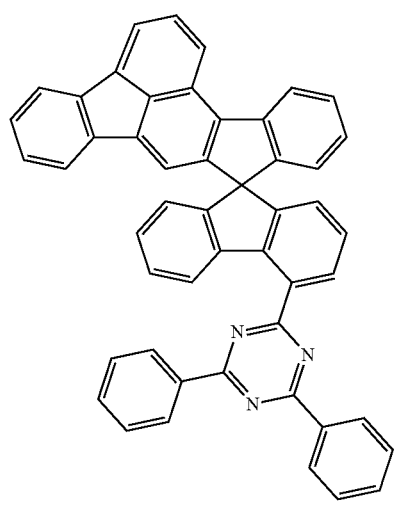
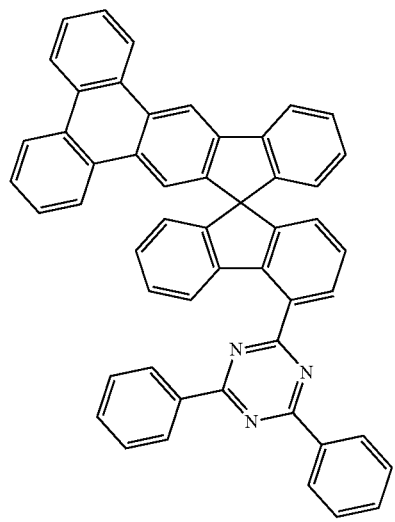
158
-continued
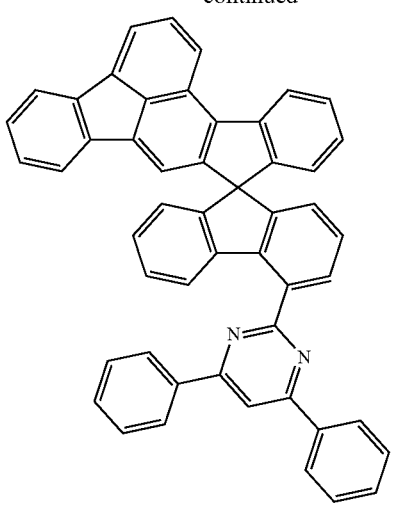
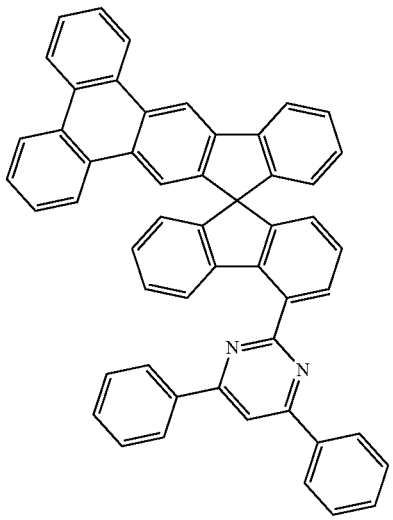
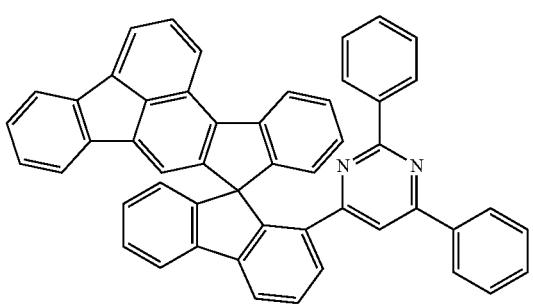
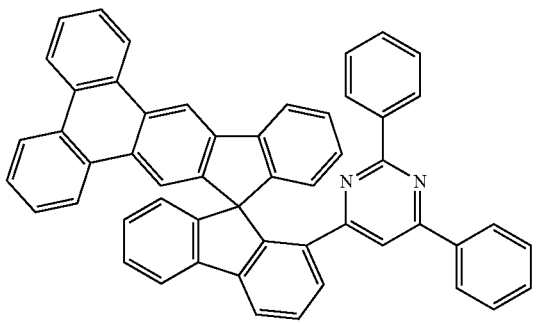

159
-continued
160
-continued
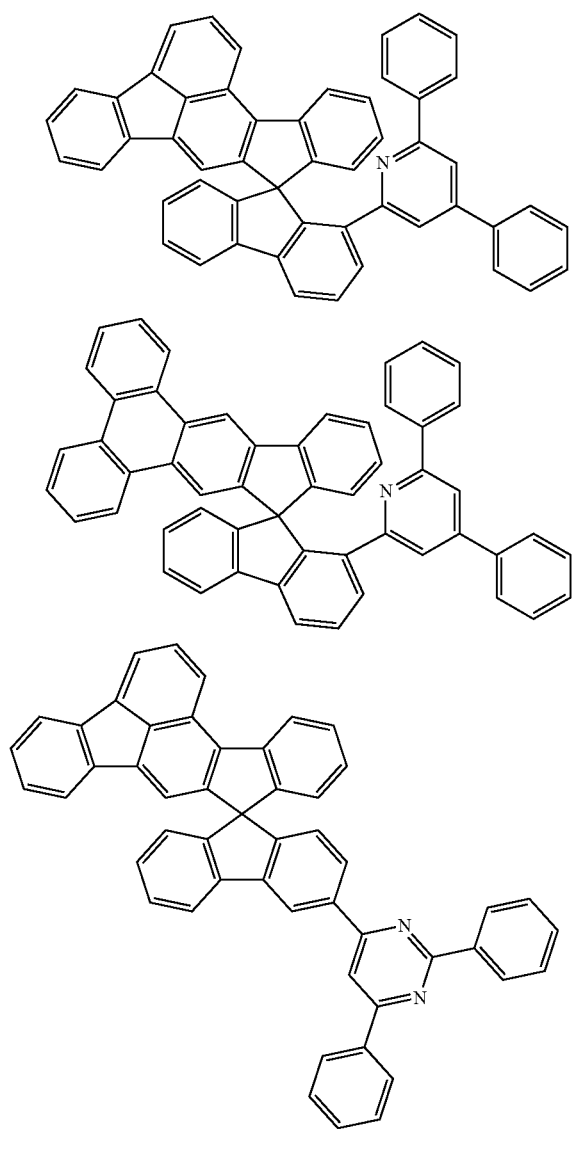
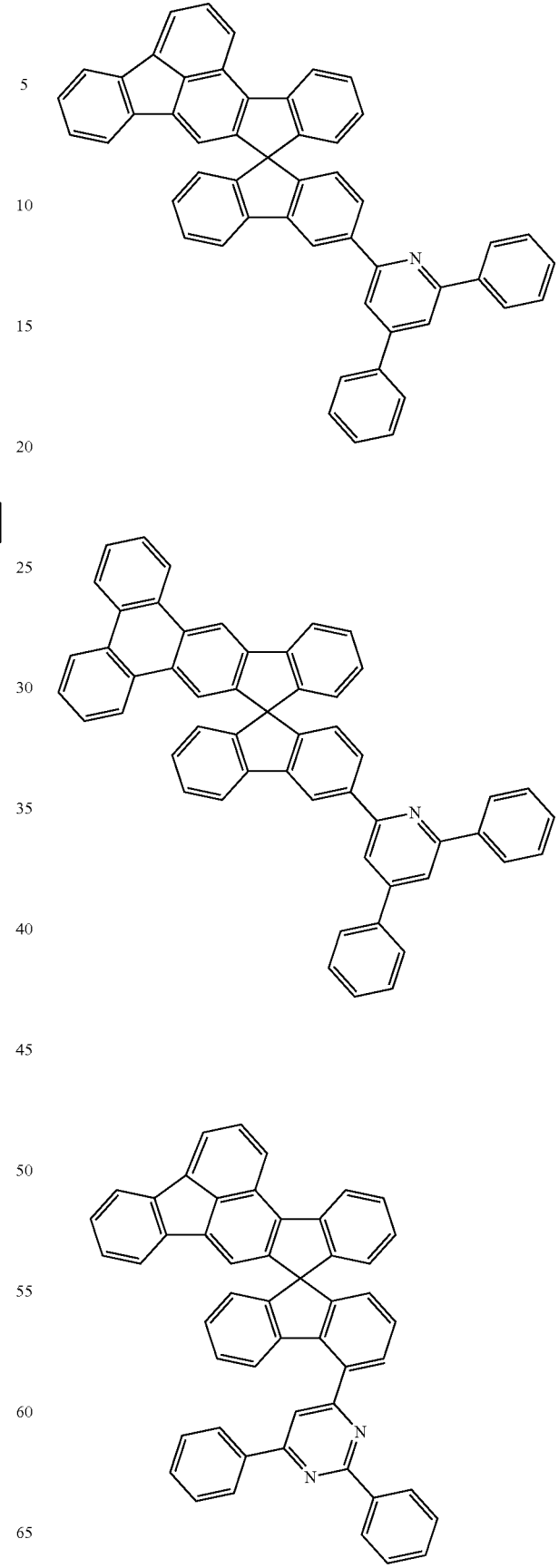

161
-continued
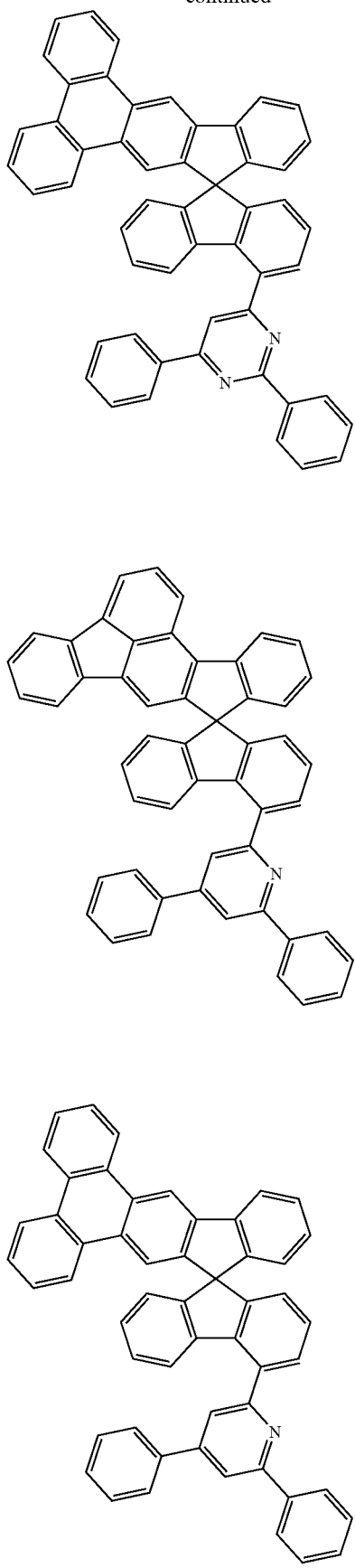
162
-continued
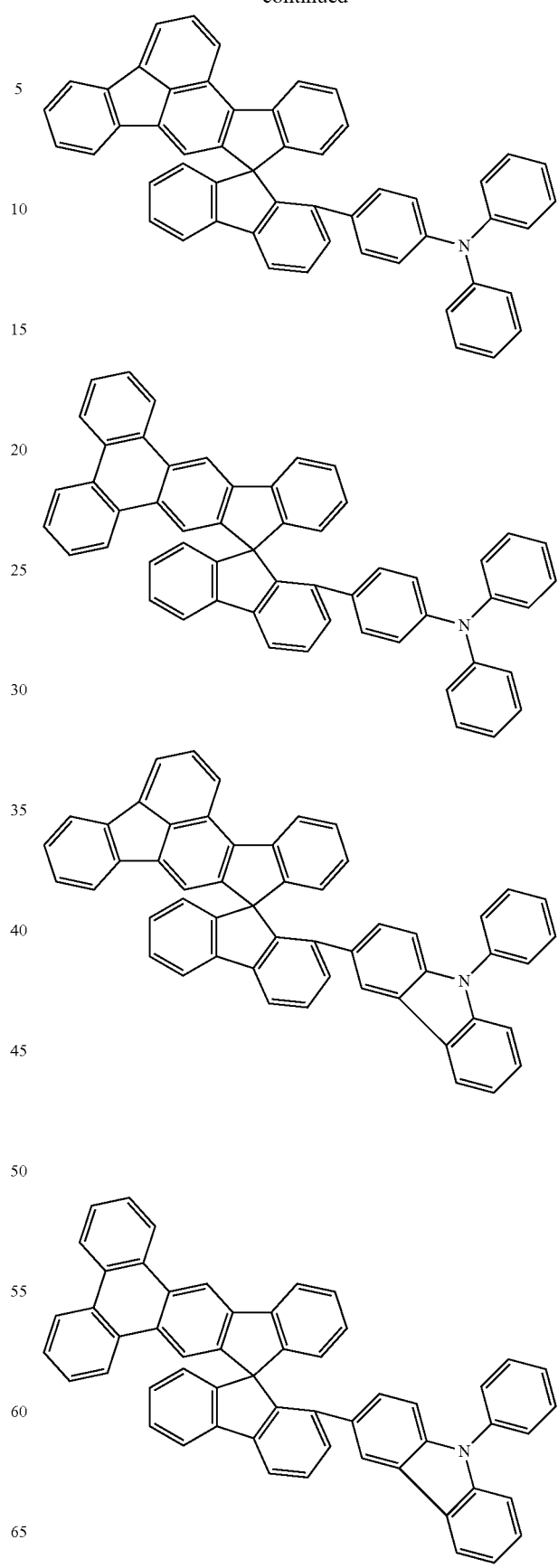

163
-continued
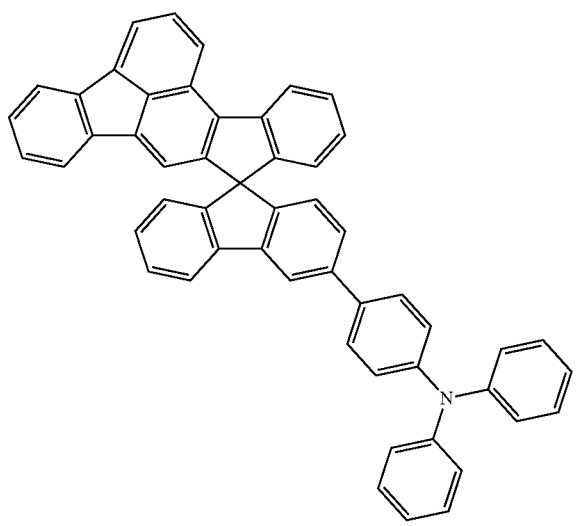
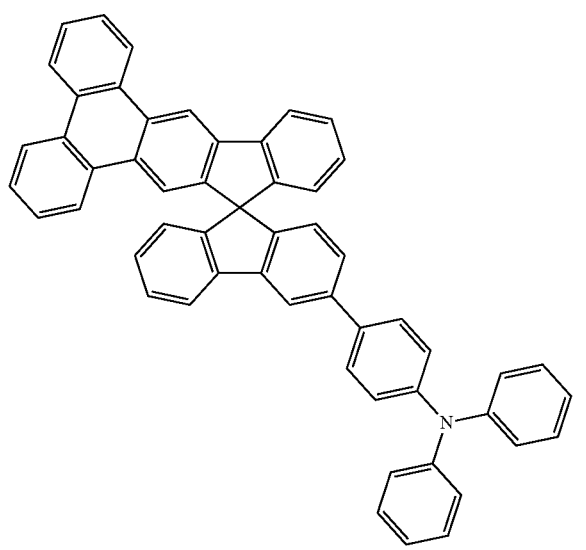
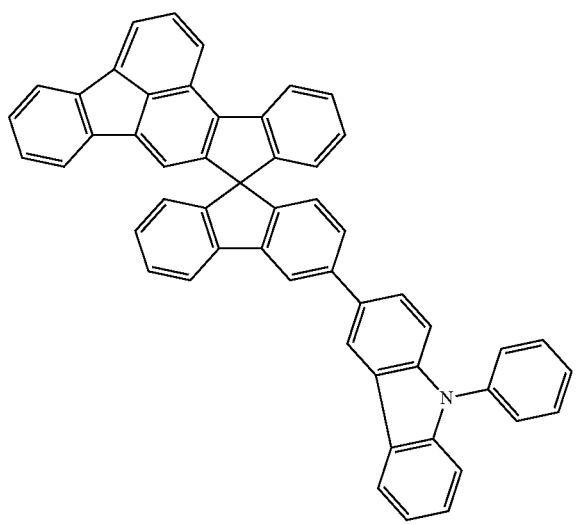
164
-continued
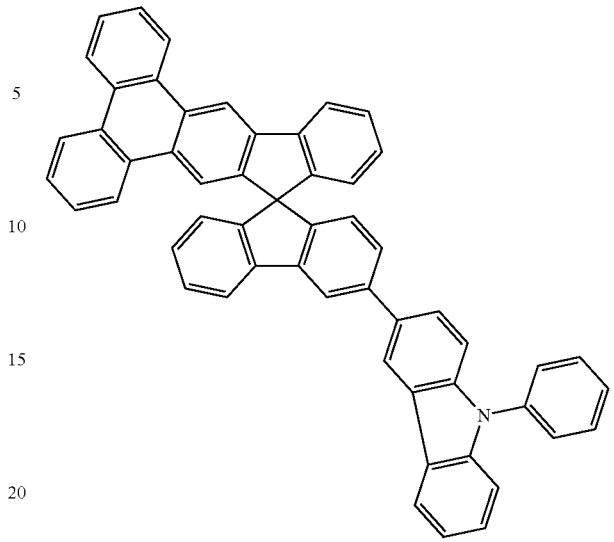
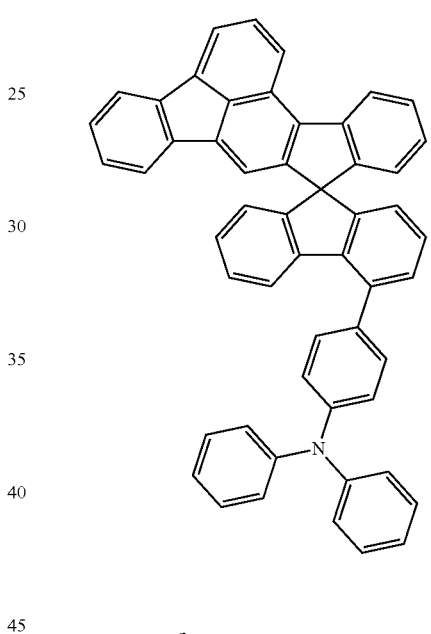
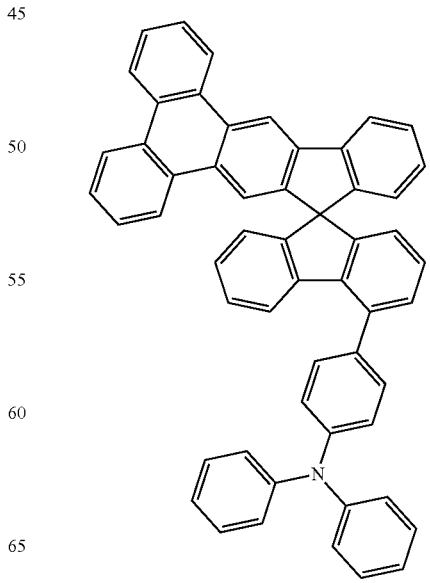

165
-continued
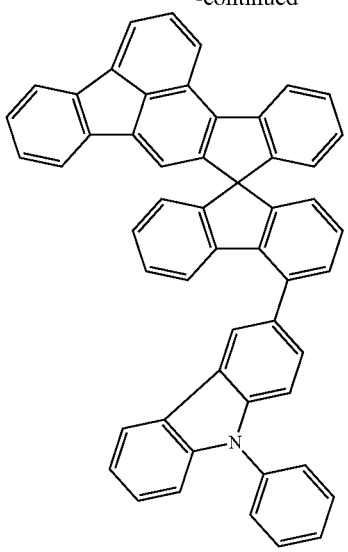
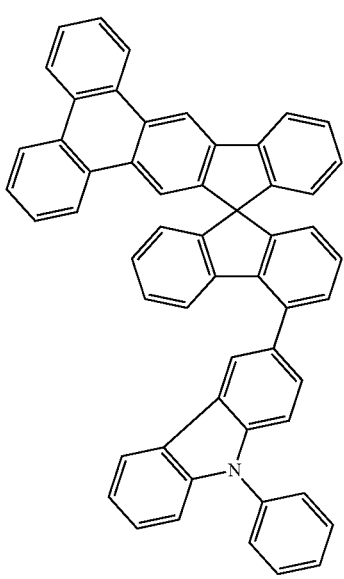
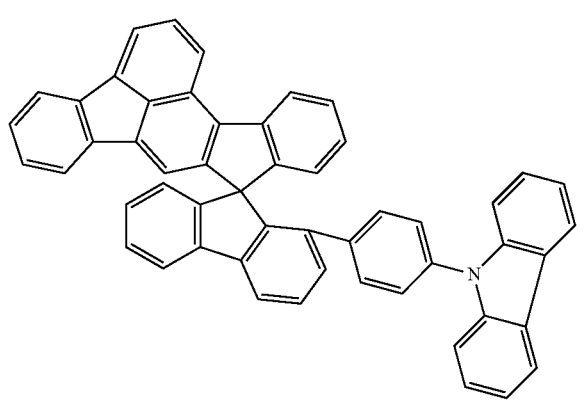
166
-continued
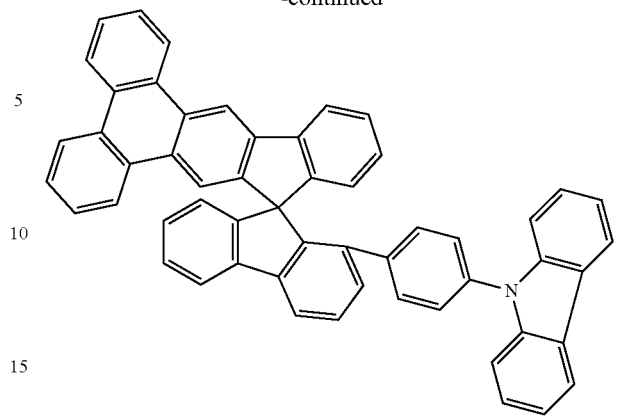
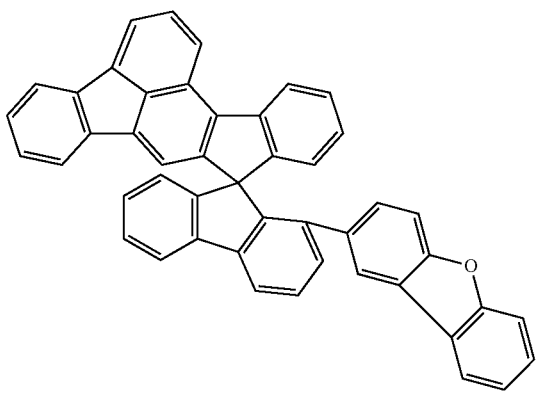
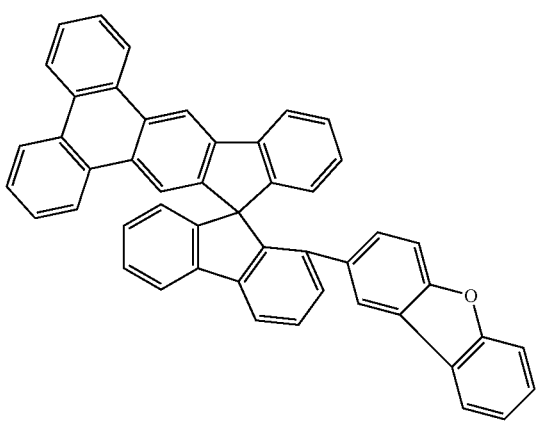

167
-continued
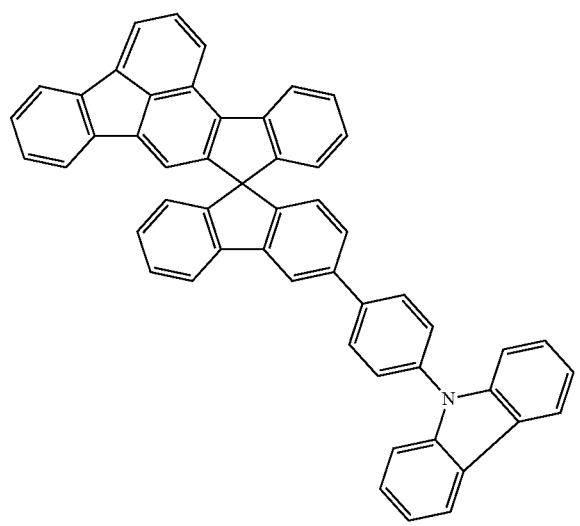
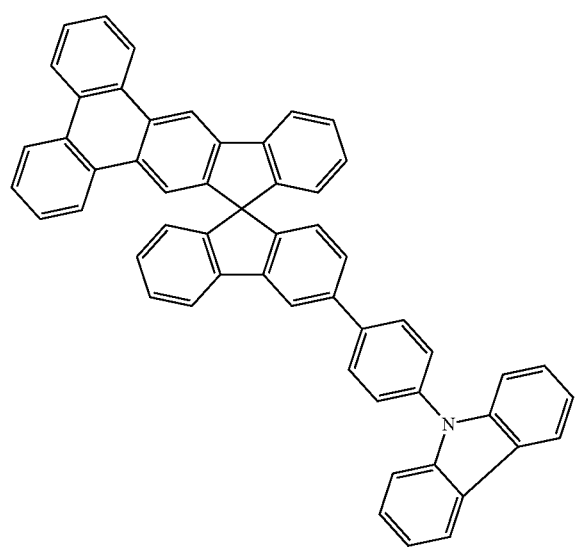
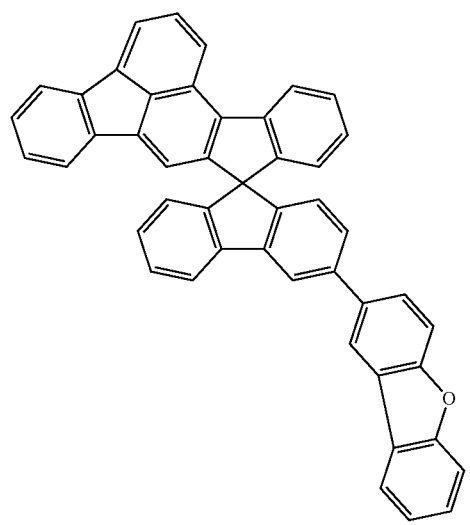
168
-continued
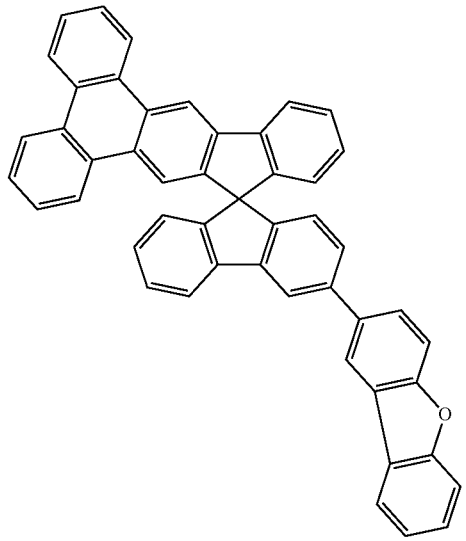
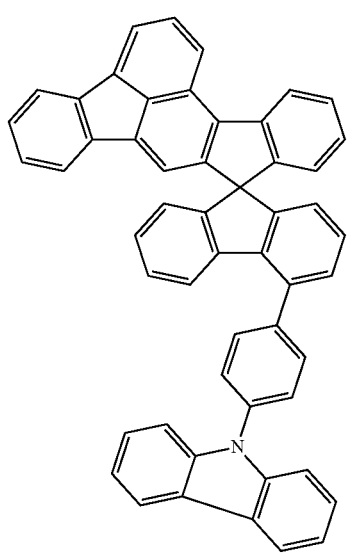
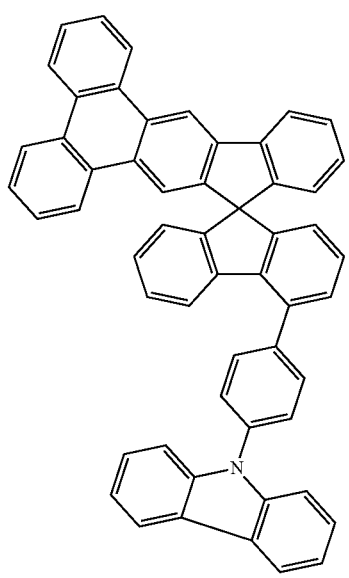

169
-continued
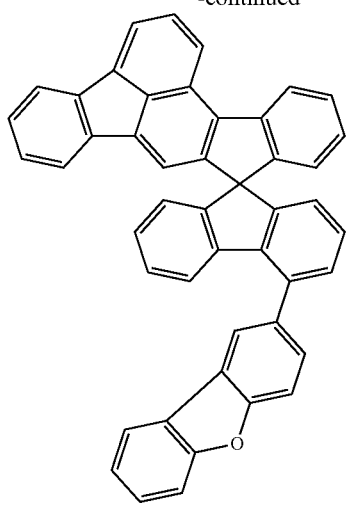
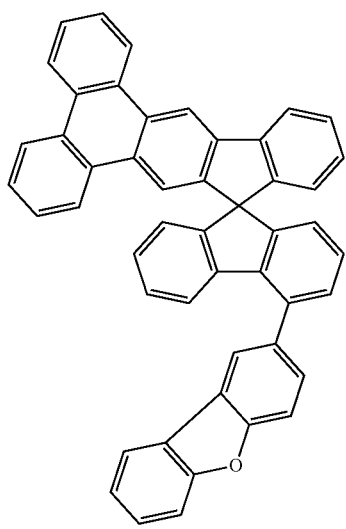
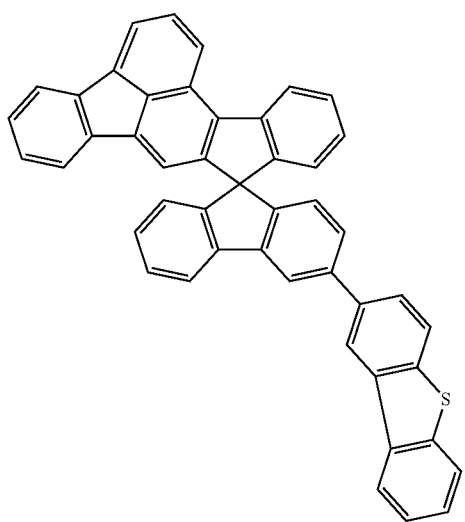
170
-continued
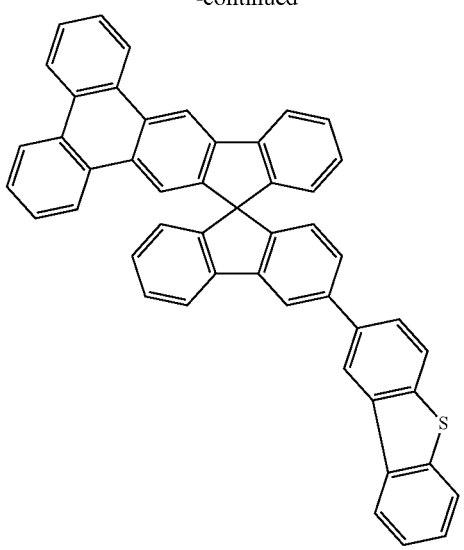
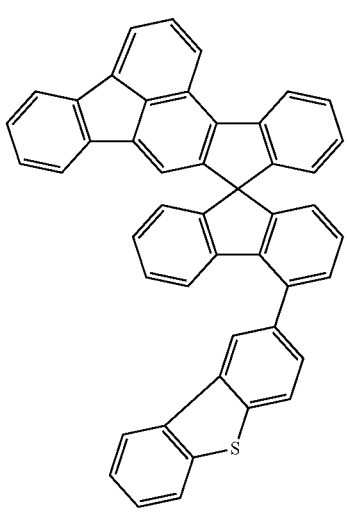
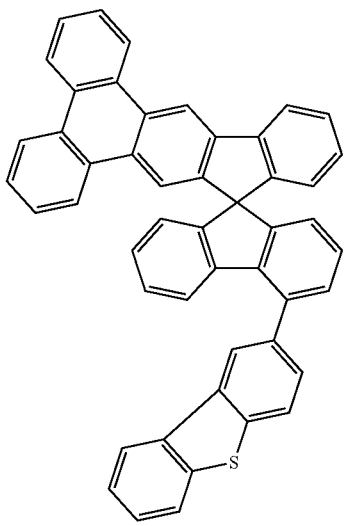

171
-continued
172
-continued
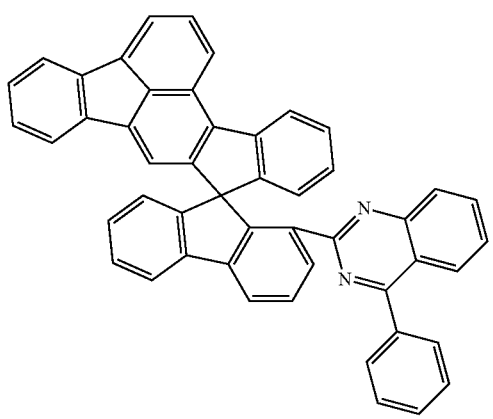
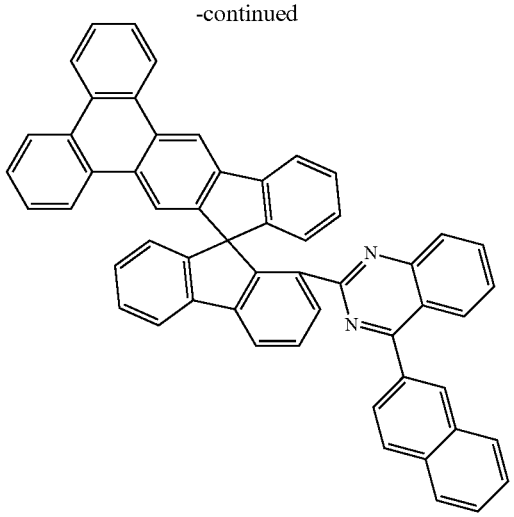
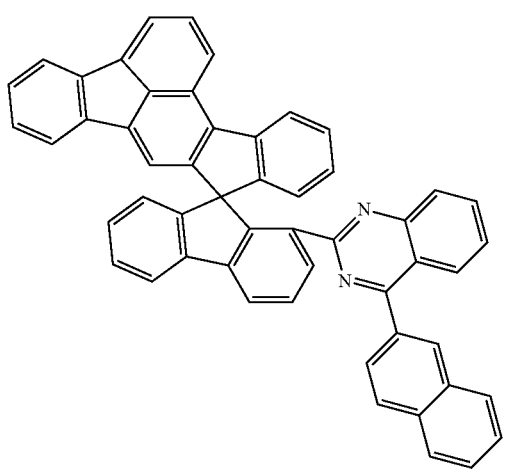

173
-continued
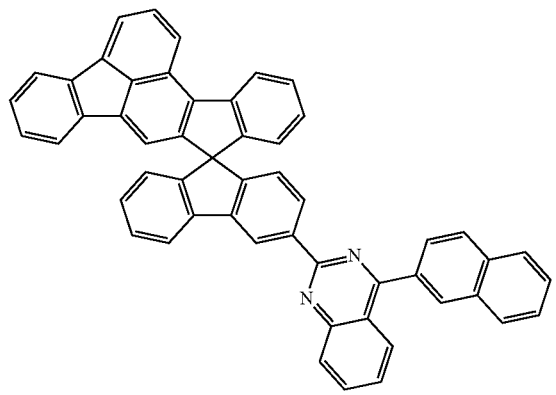
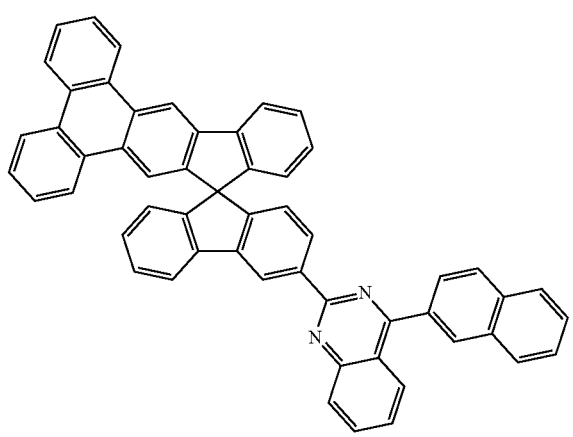
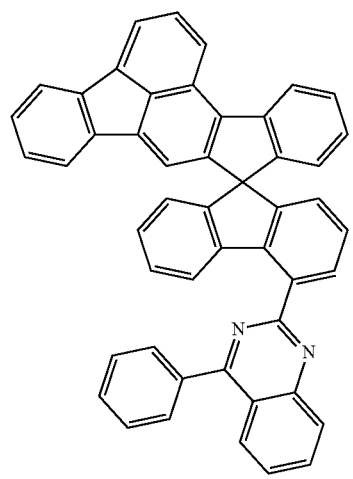
174
-continued
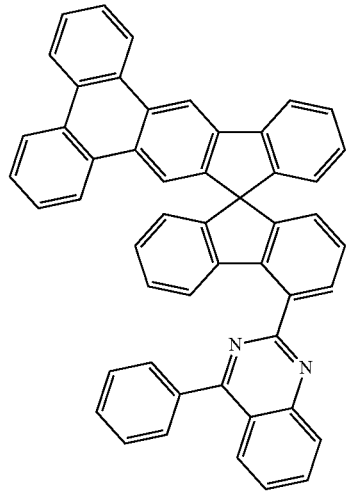
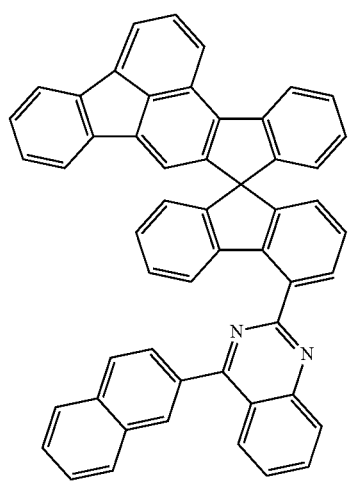
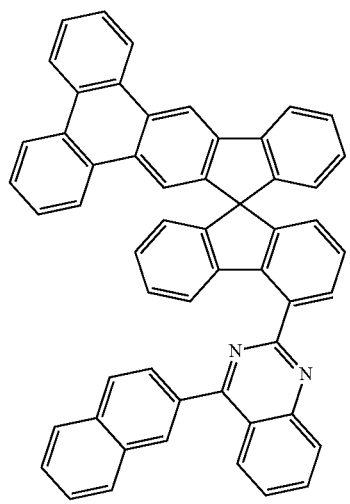

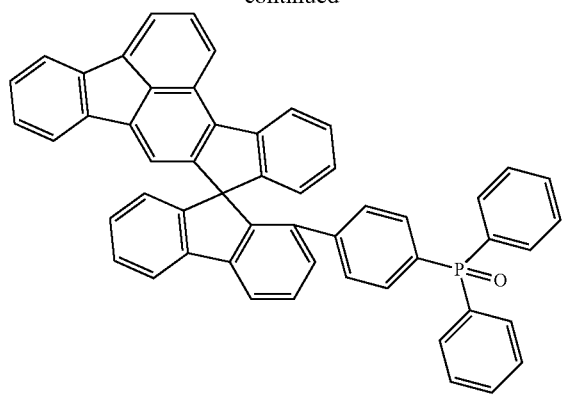
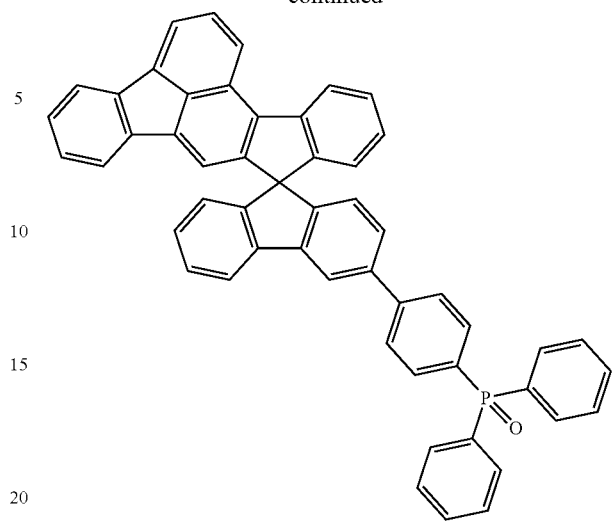
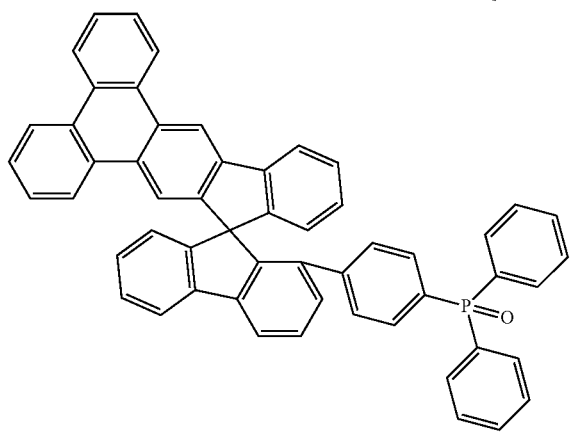
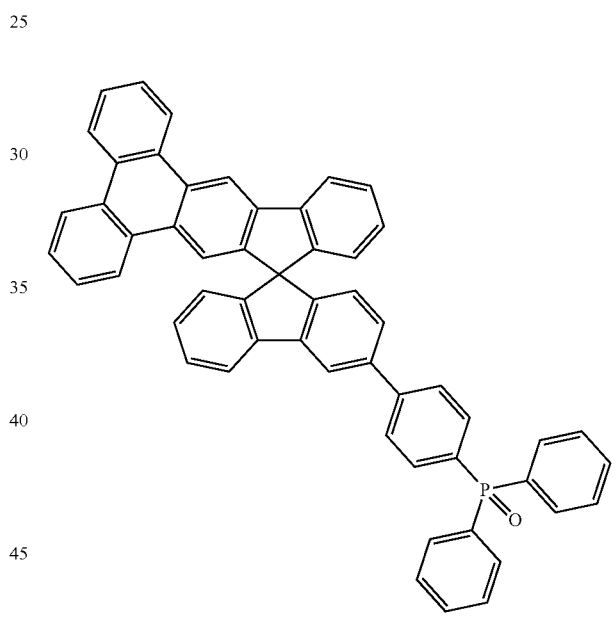
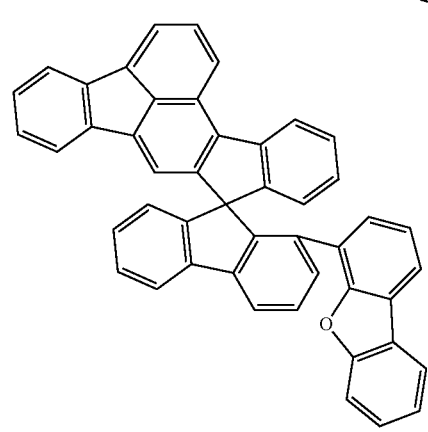
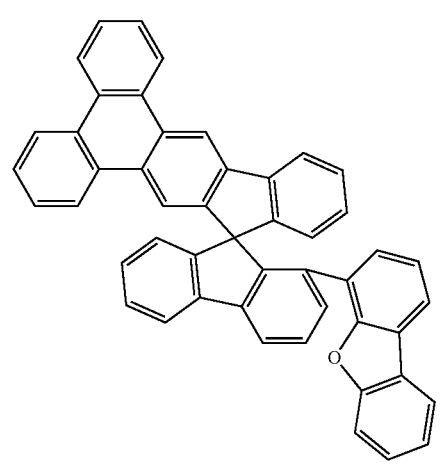
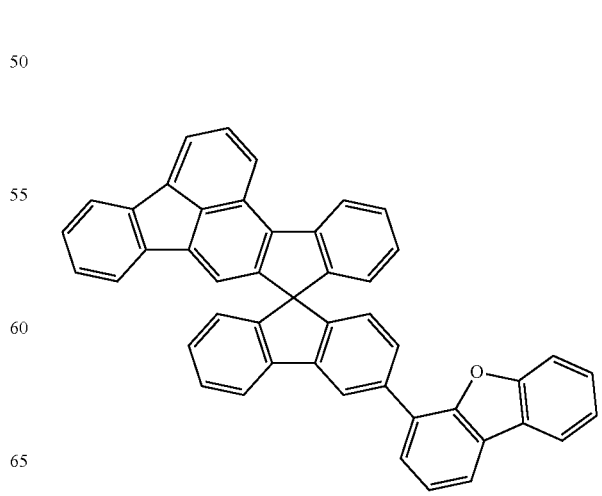

177
-continued
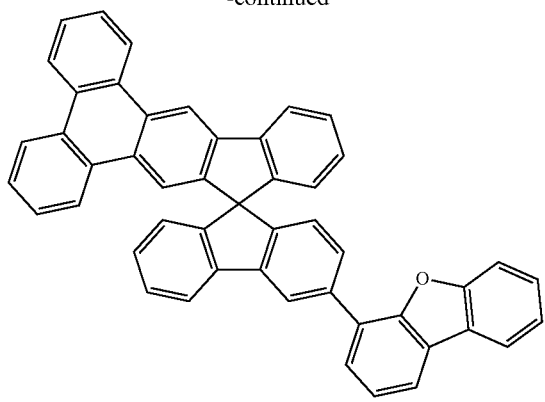
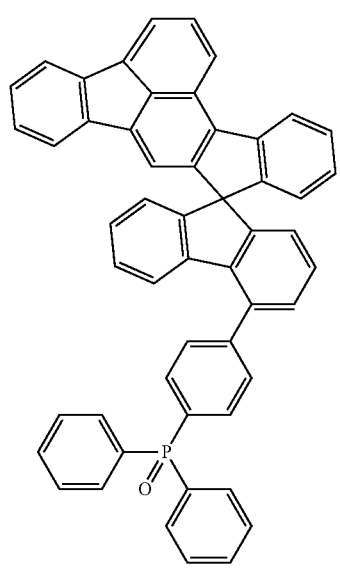
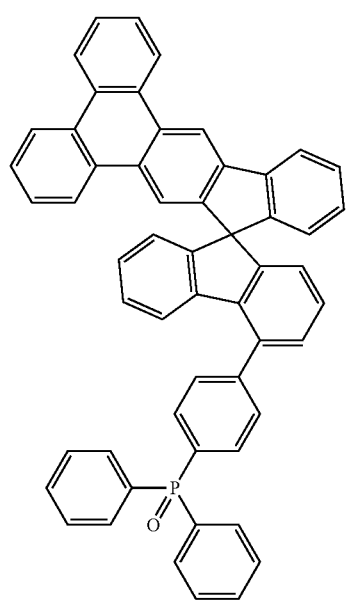
178
-continued
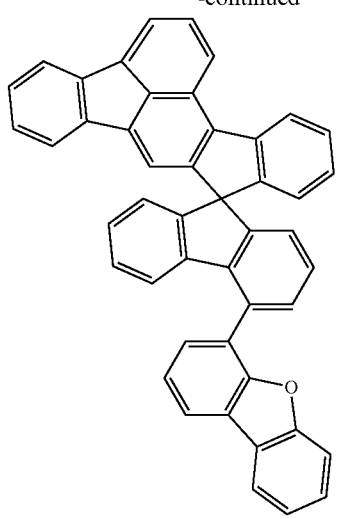
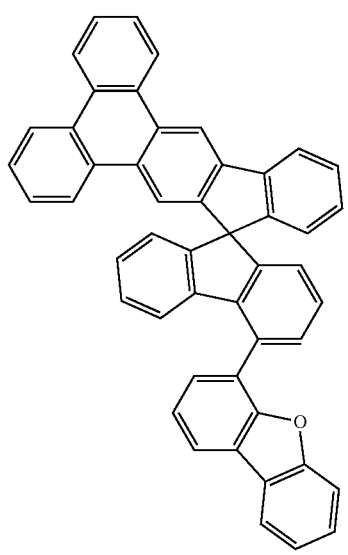
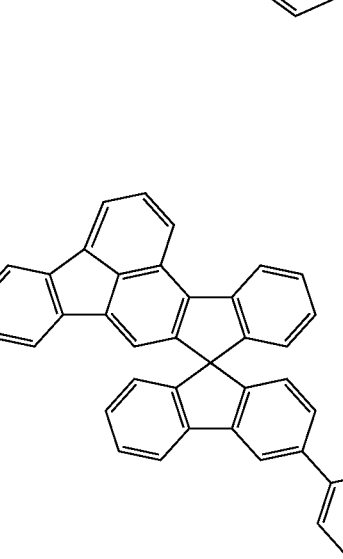

179
-continued
180
-continued
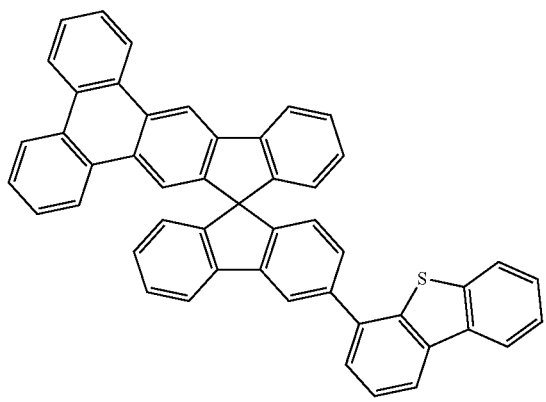
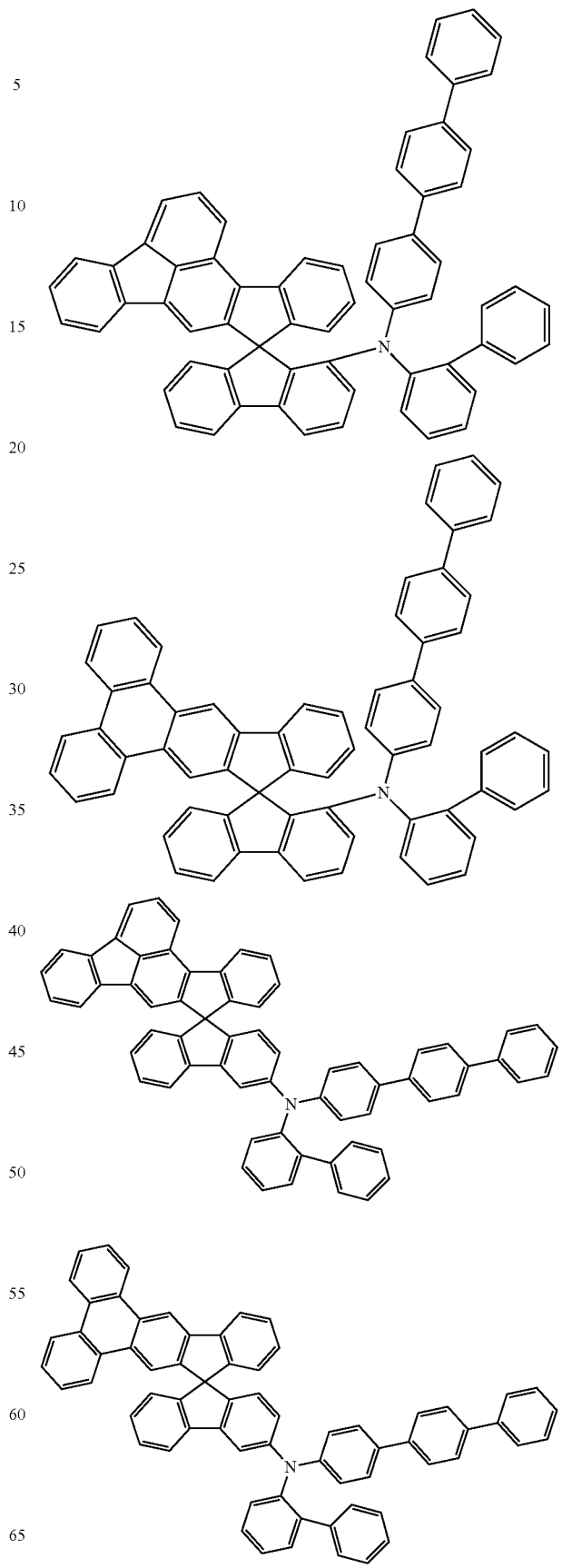

181
-continued
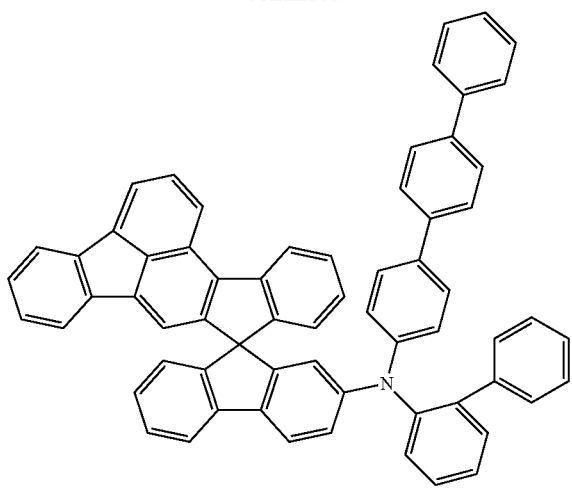
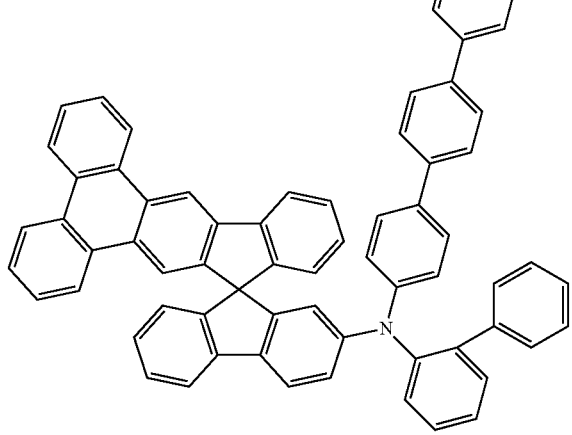
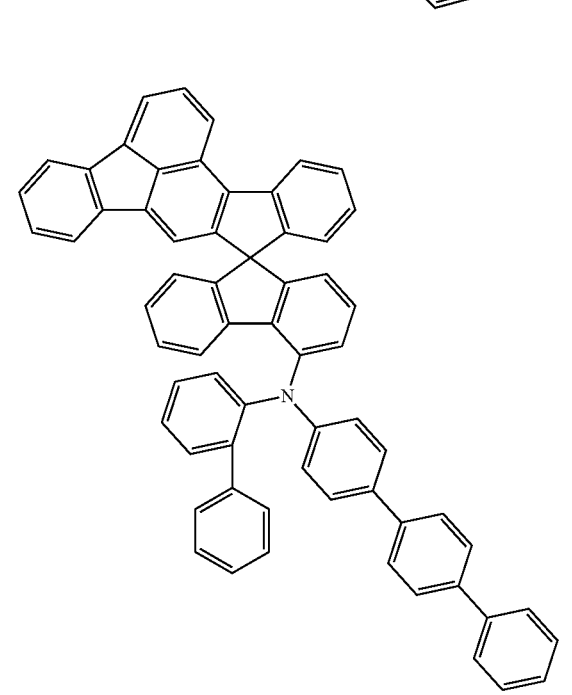
182
-continued
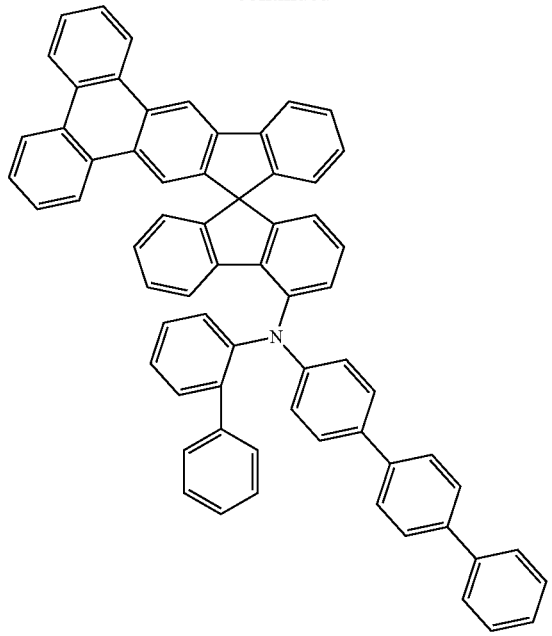
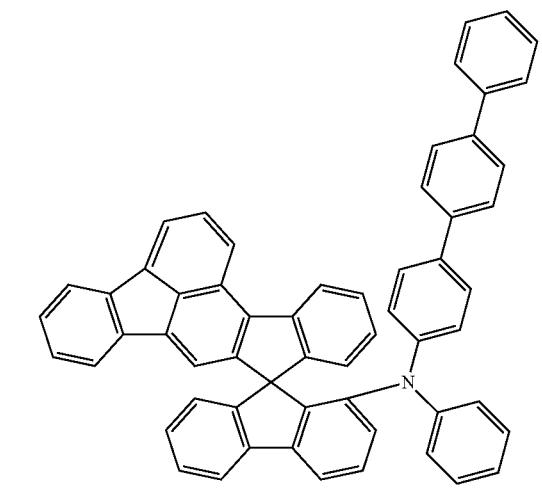
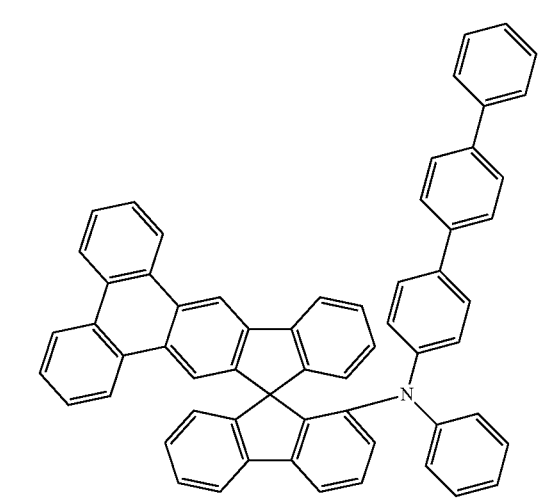

183
-continued
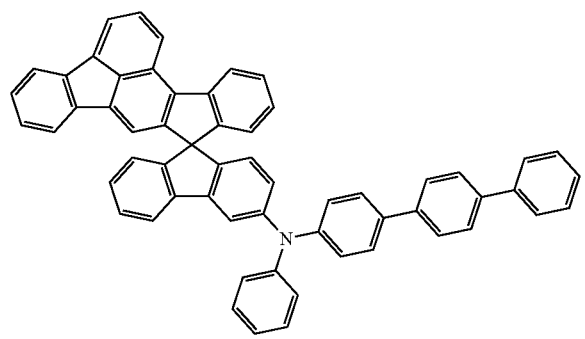
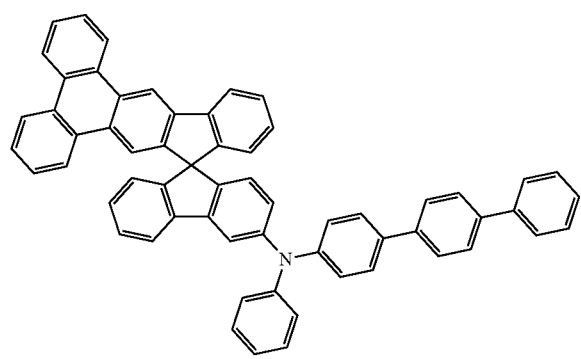
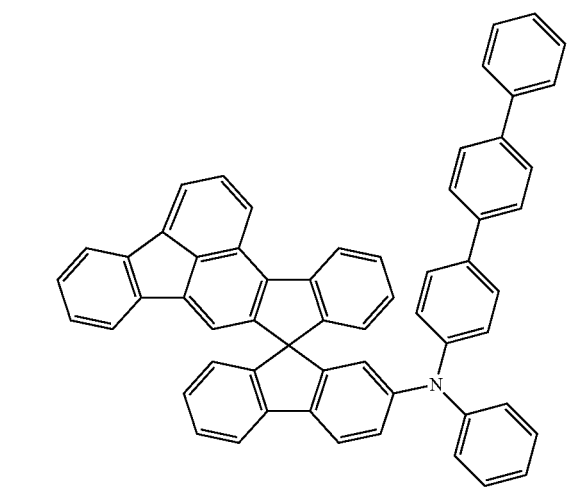
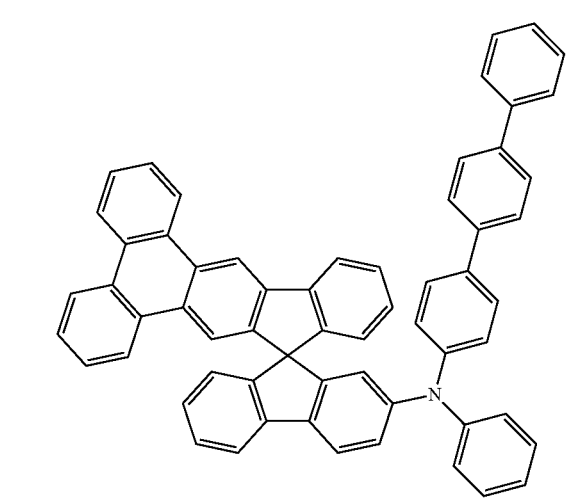
184
-continued
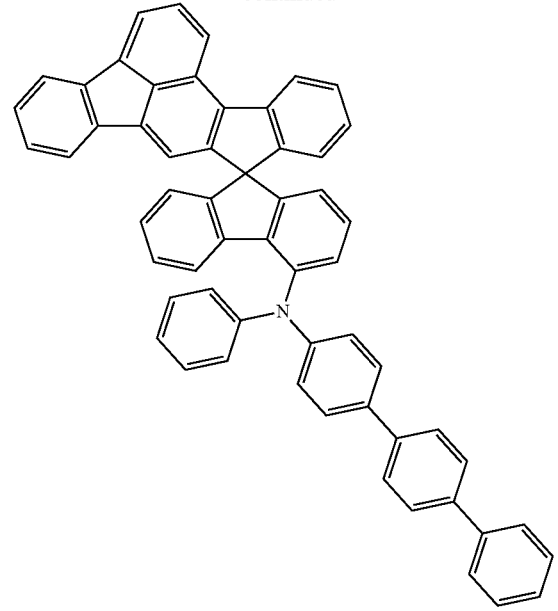
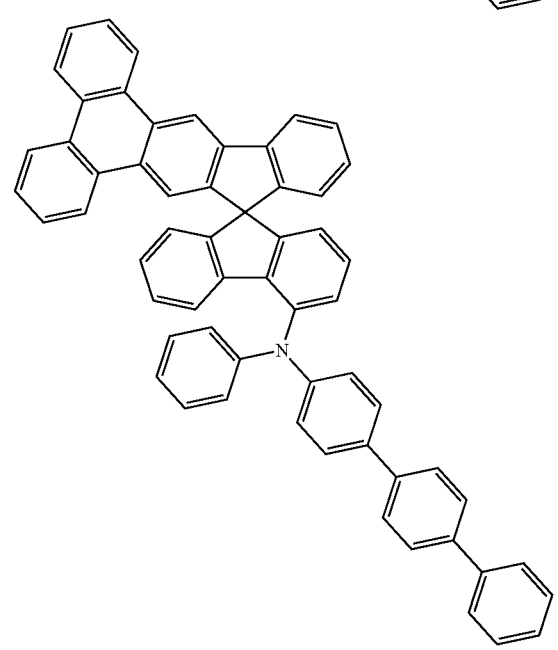
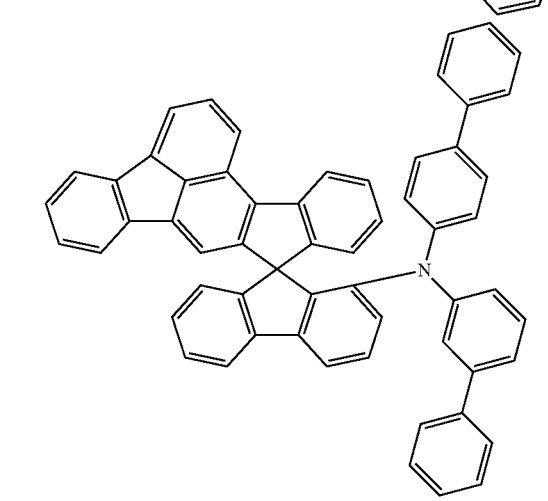

185
-continued
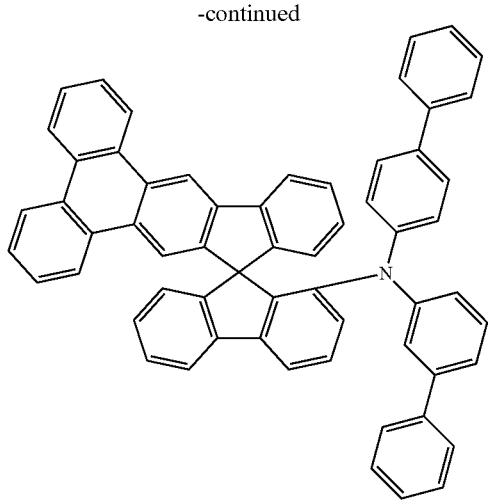
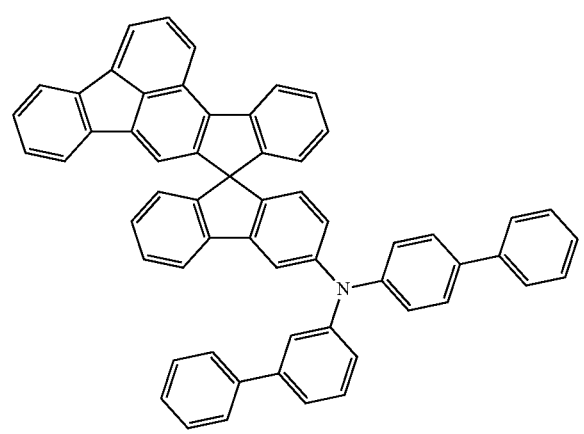
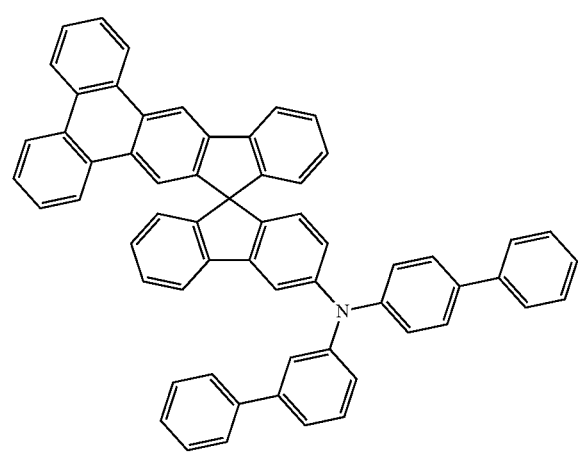
186
-continued
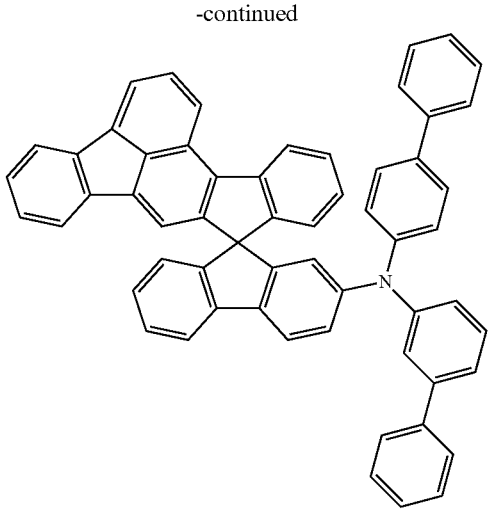
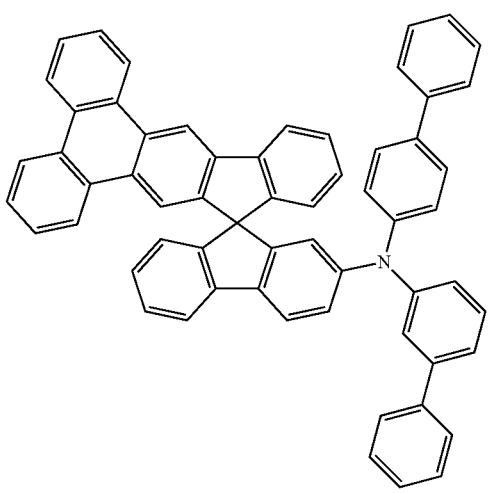
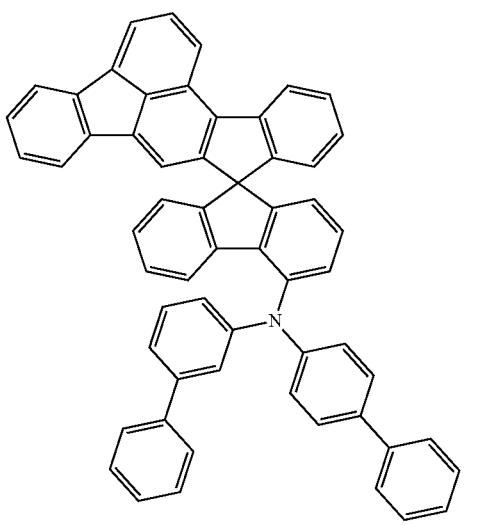

187
-continued
188
-continued
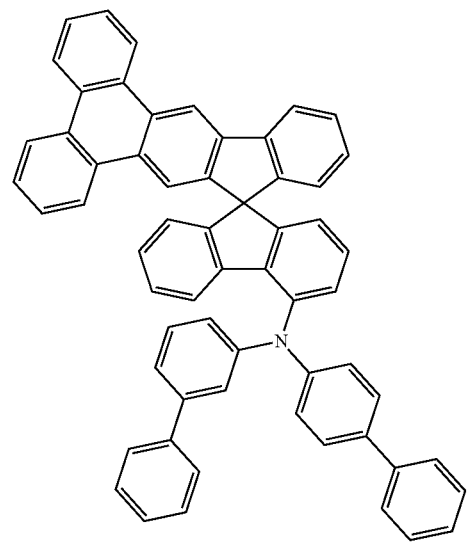
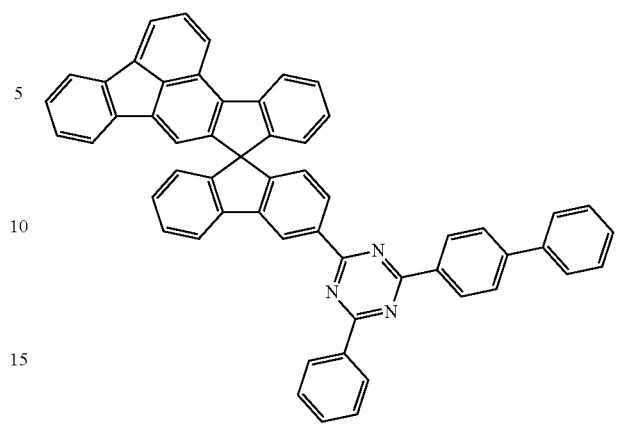
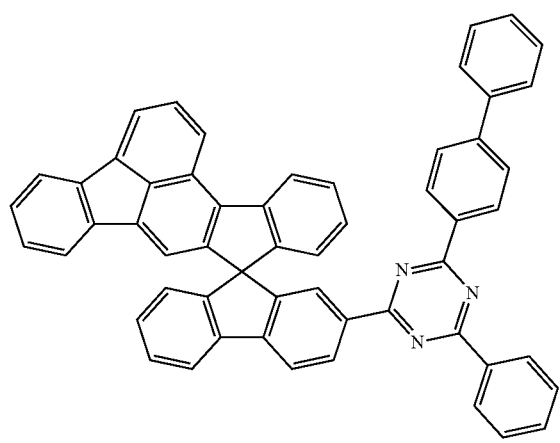
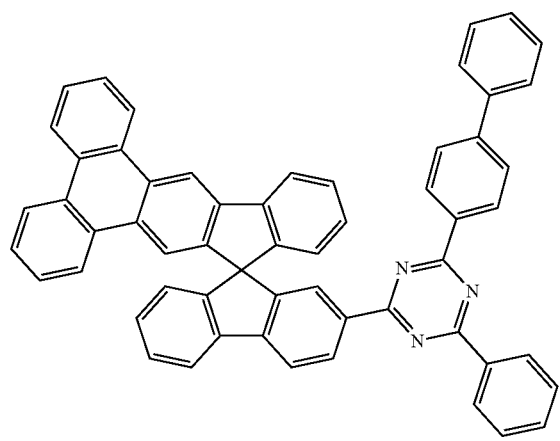
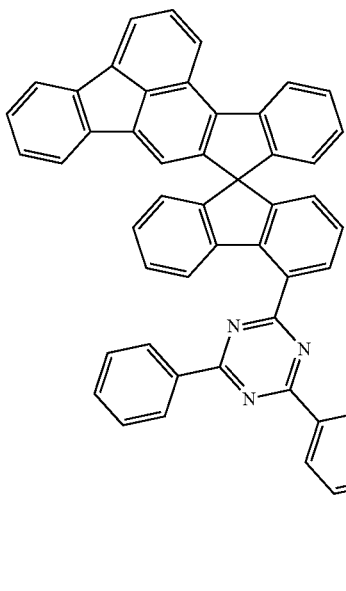

189
-continued
190
-continued
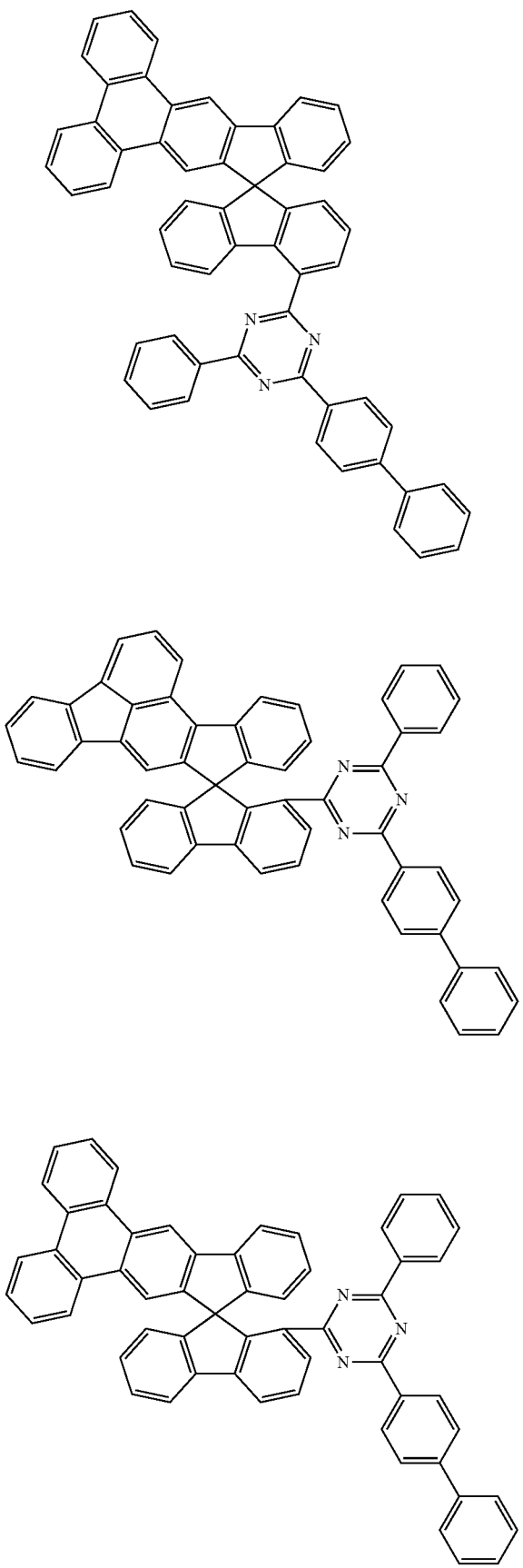
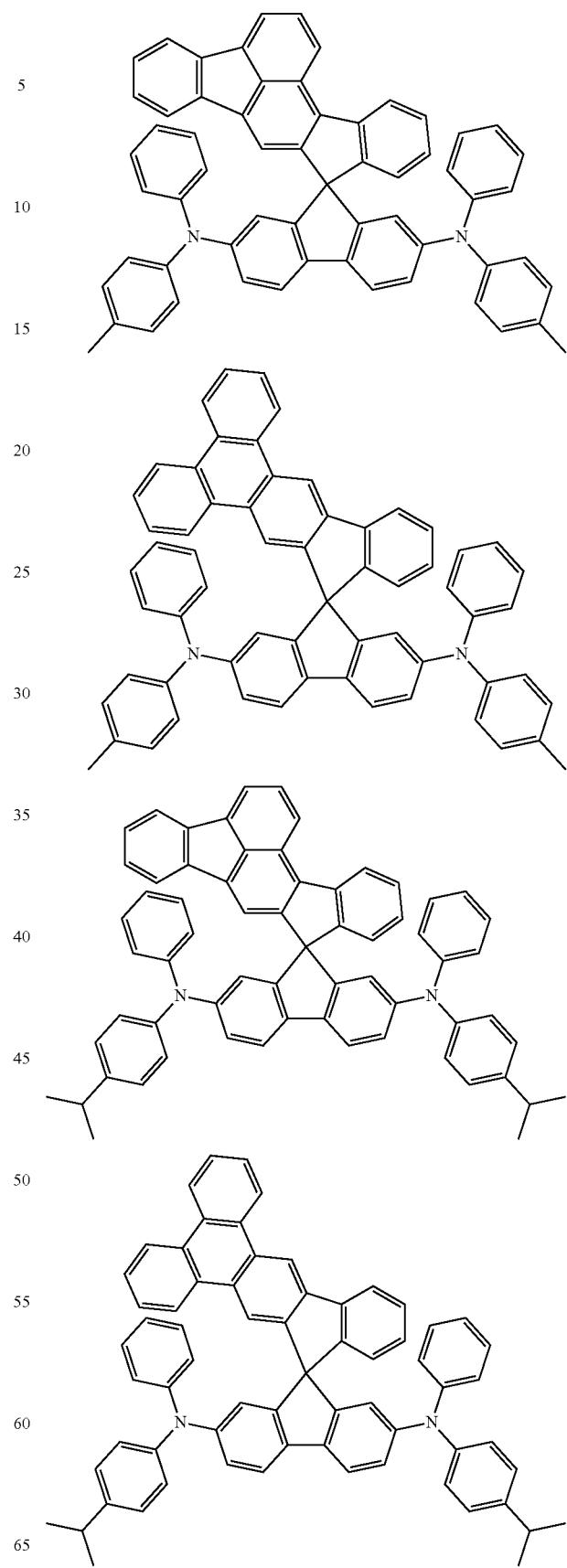

191
-continued
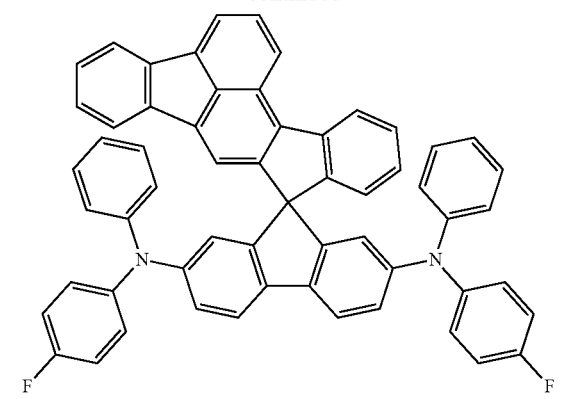
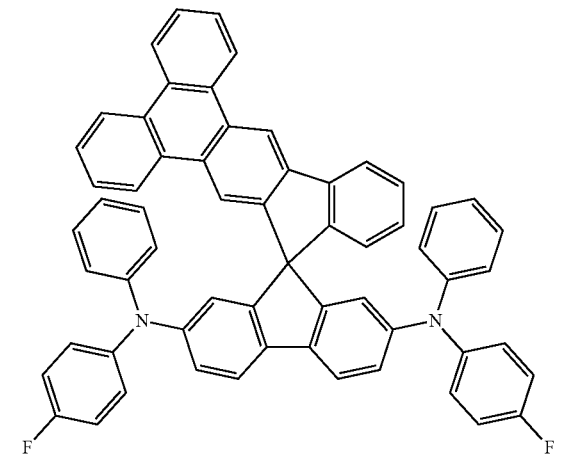
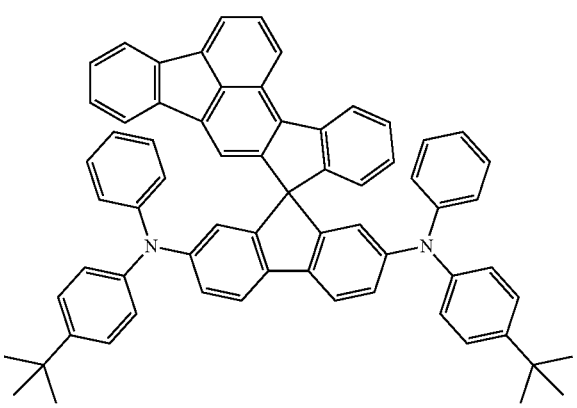
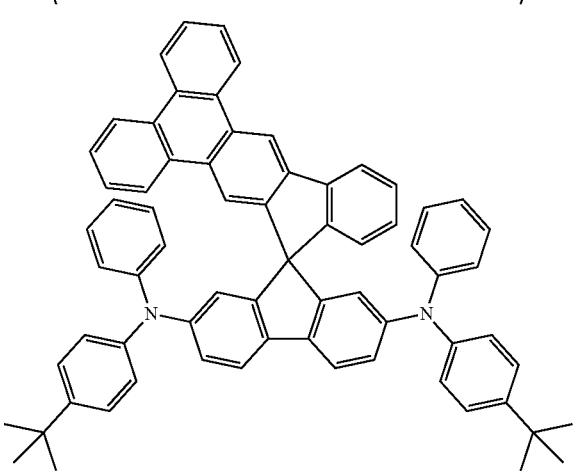
192
-continued
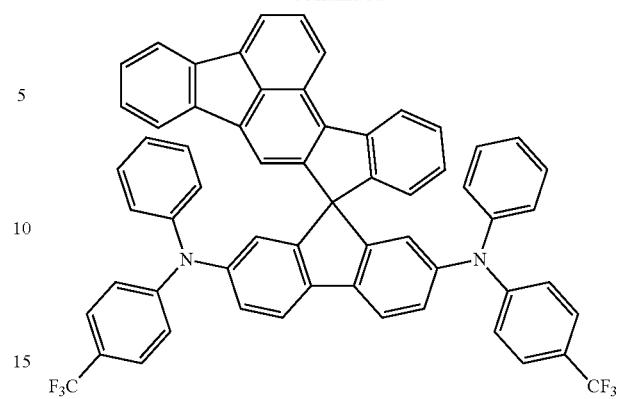
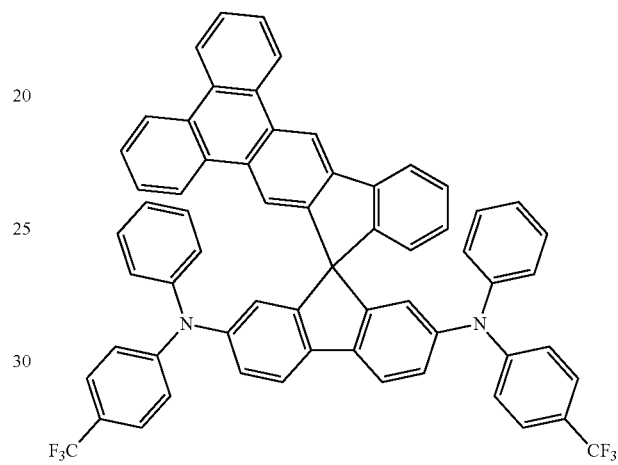
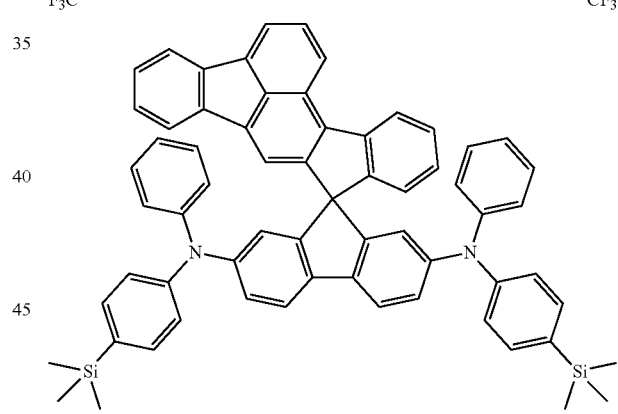
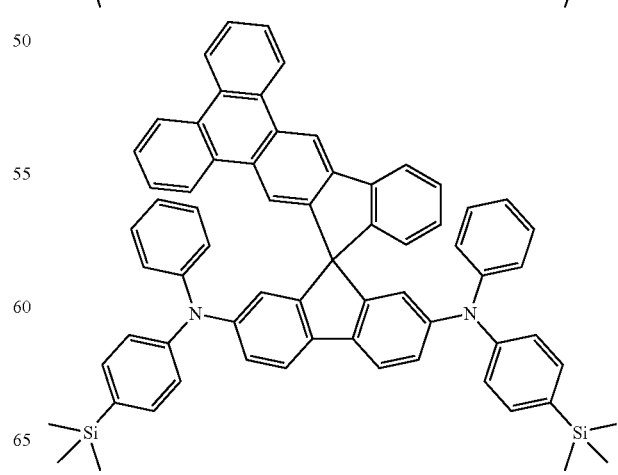

| 193 | 194 |
|---|---|
| -continued | -continued |
| 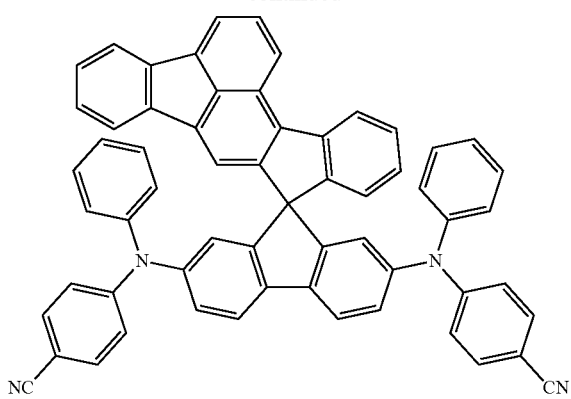 | 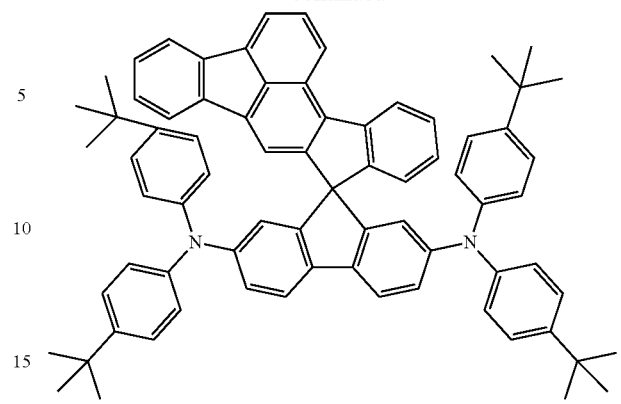 |
| 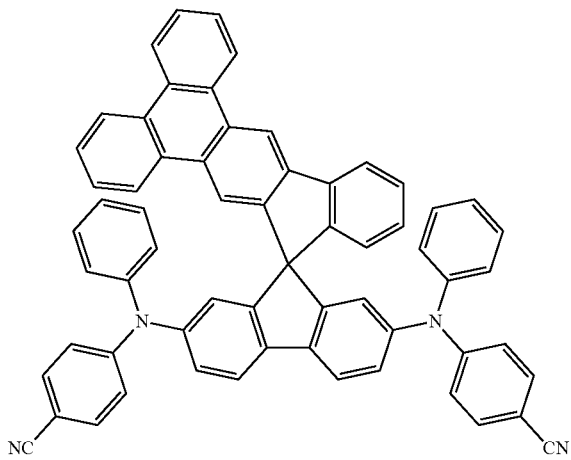 | 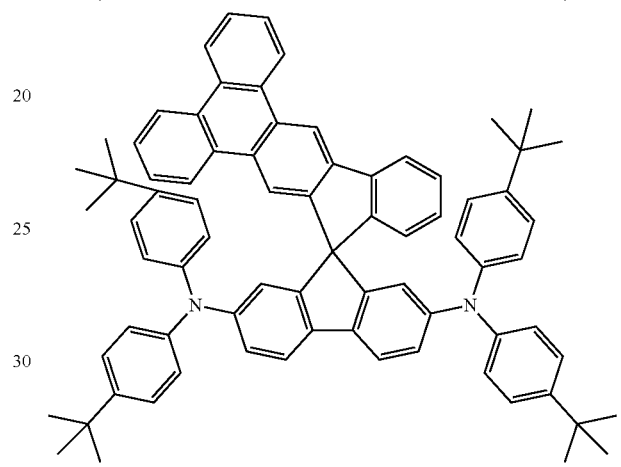 |
| 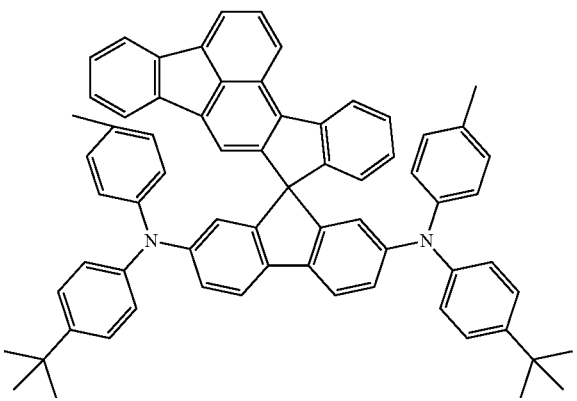 | 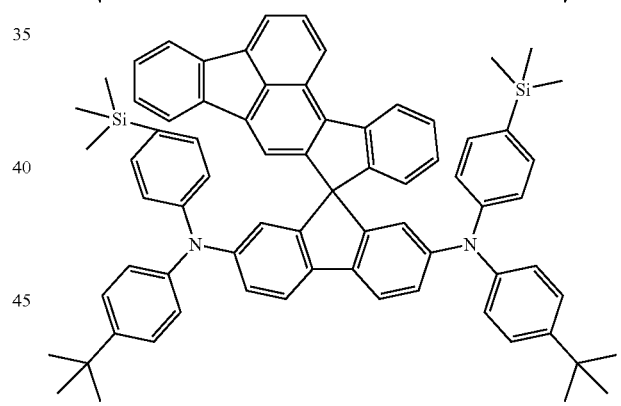 |
| 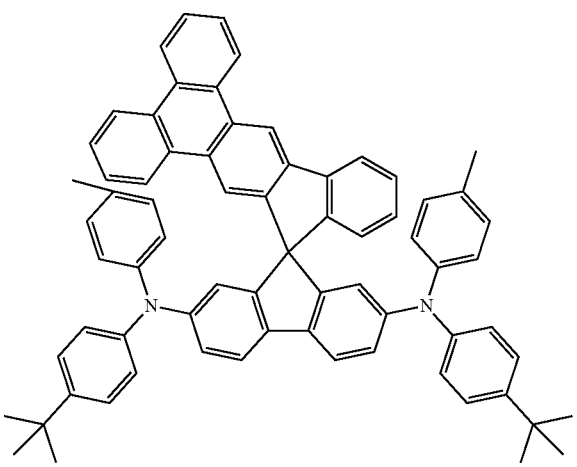 | 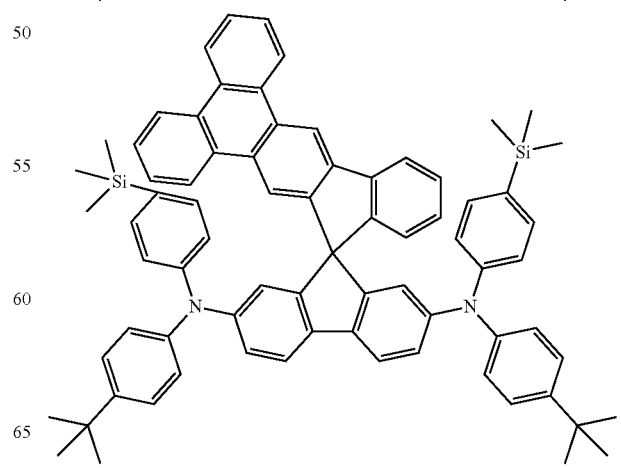 |

-continued
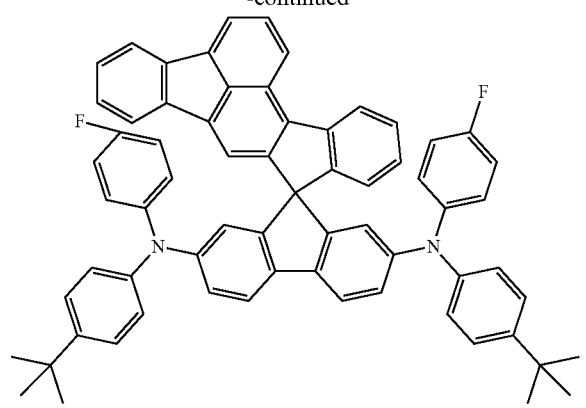
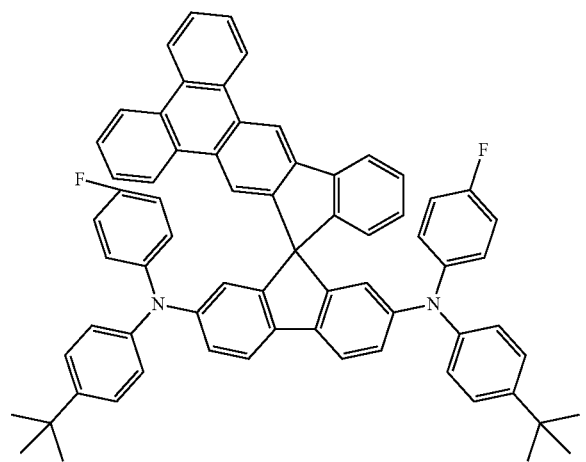
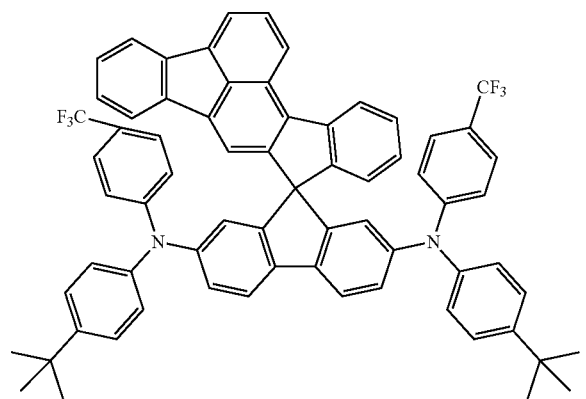
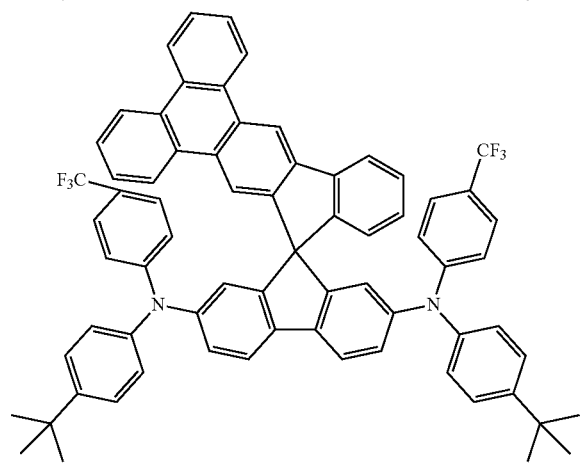
-continued
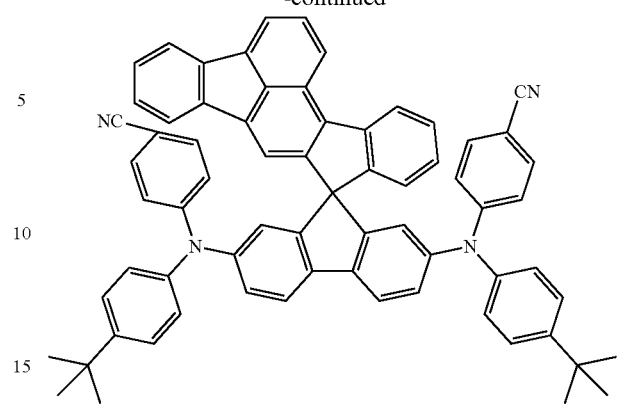
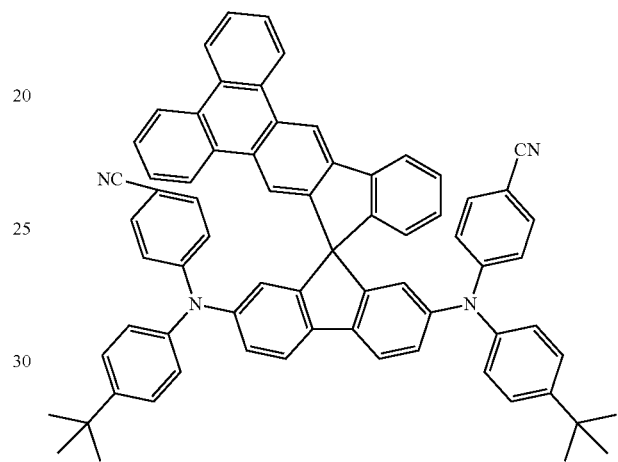
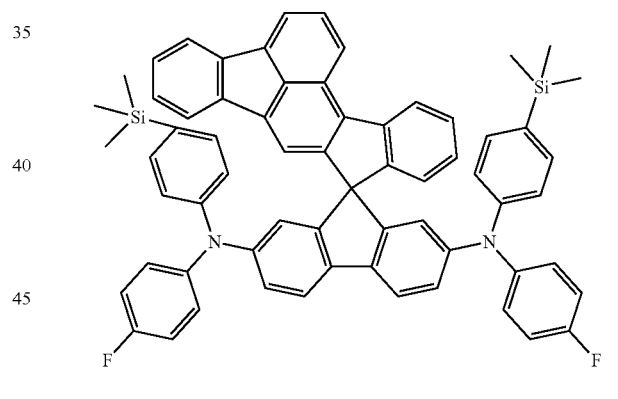
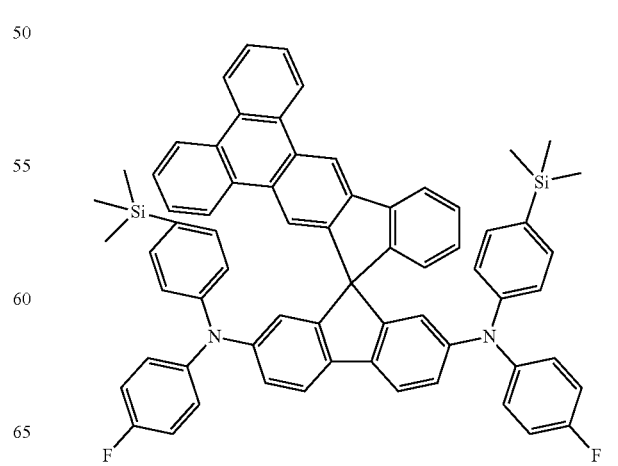

-continued
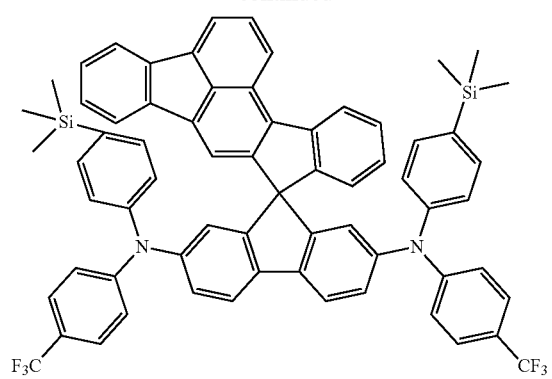
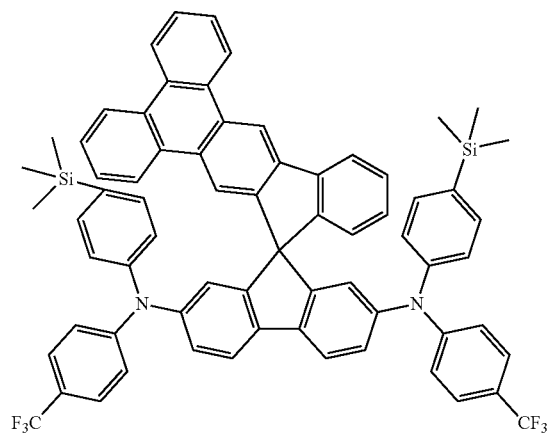
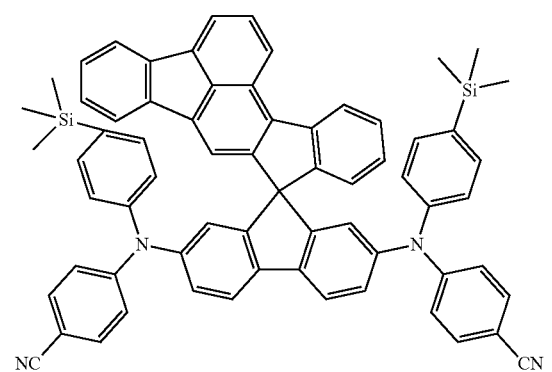
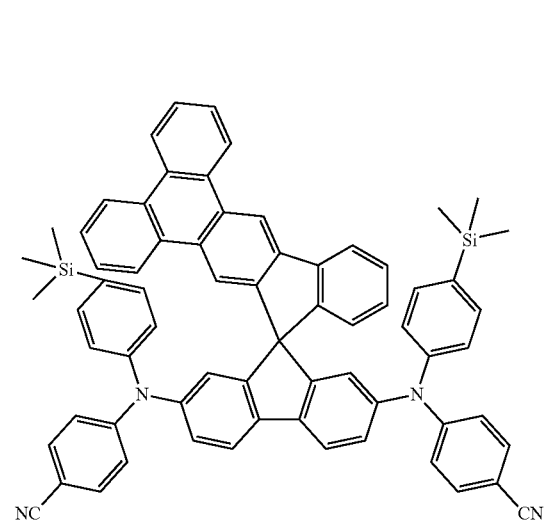
-continued
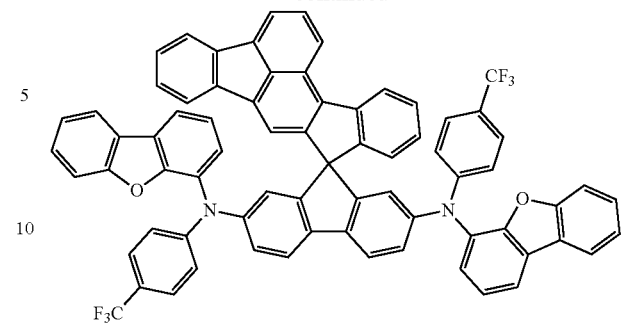
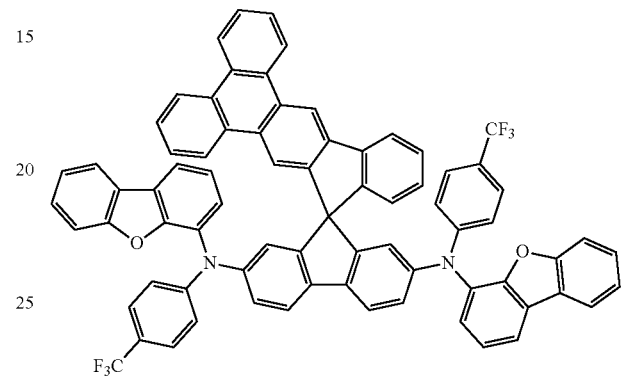
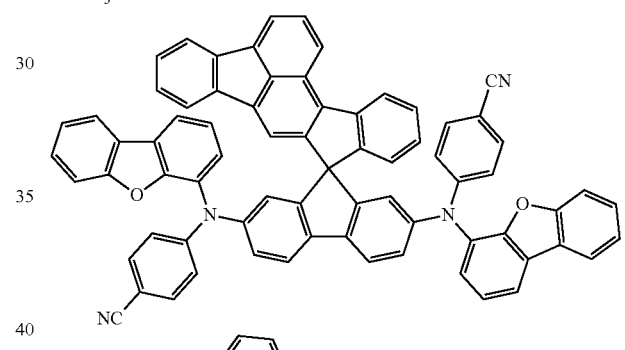
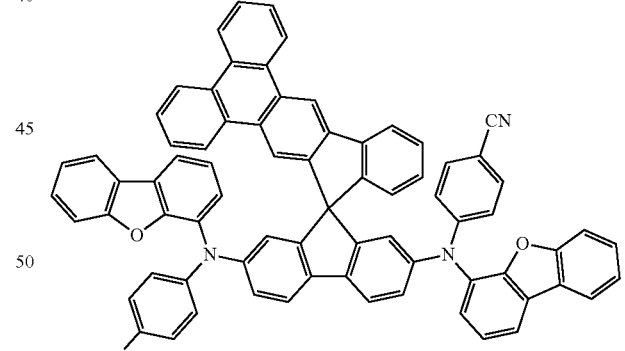
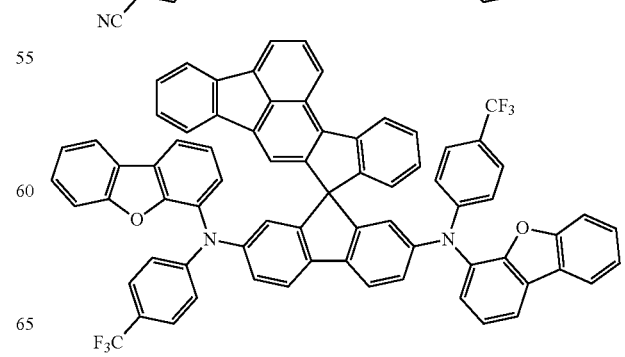

199
-continued
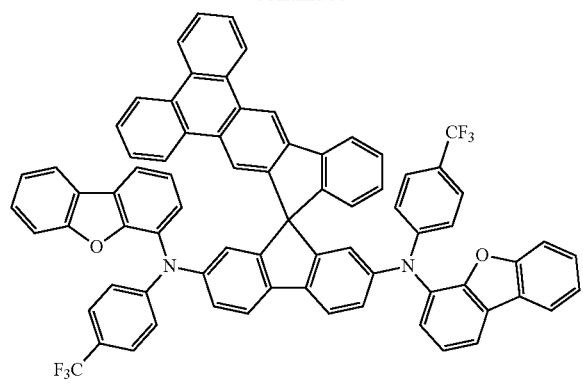
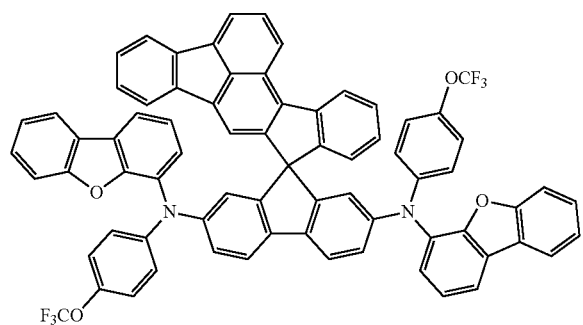
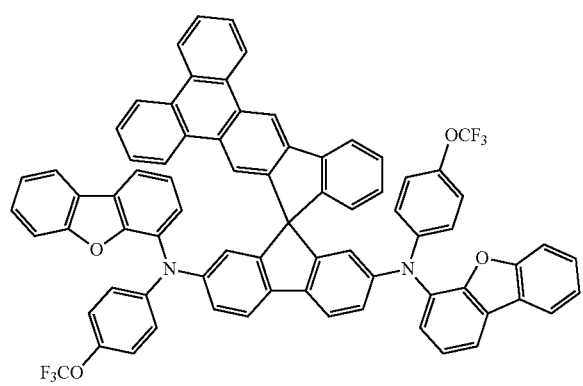
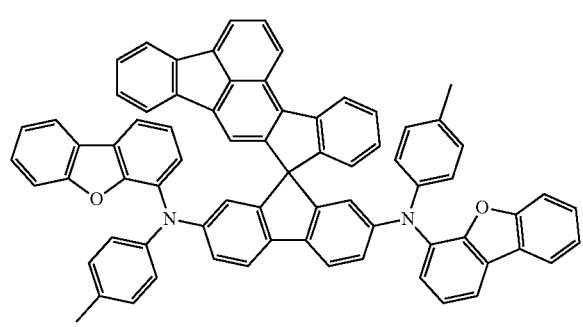
200
-continued
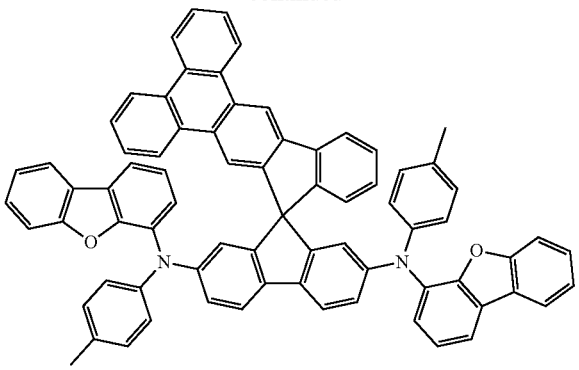
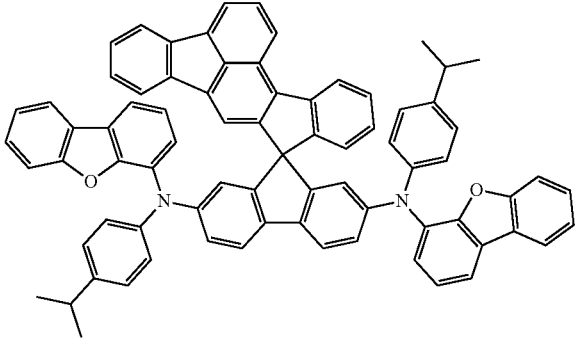
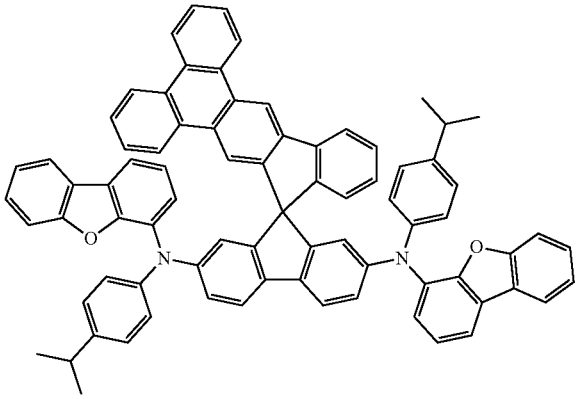
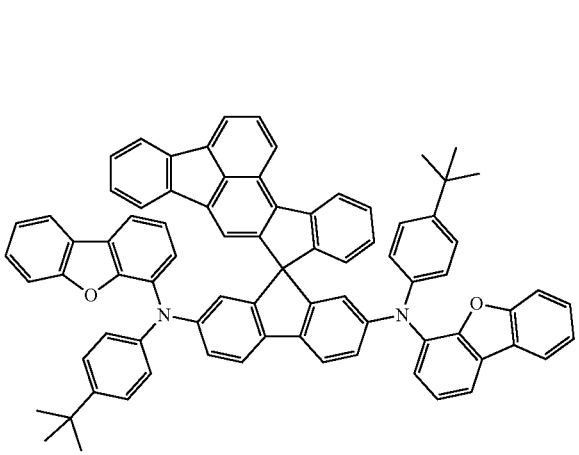

201
-continued
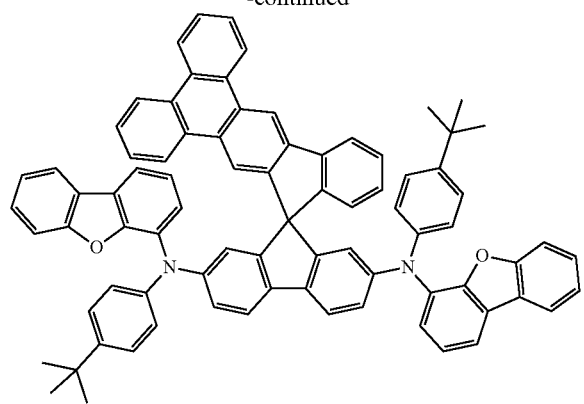
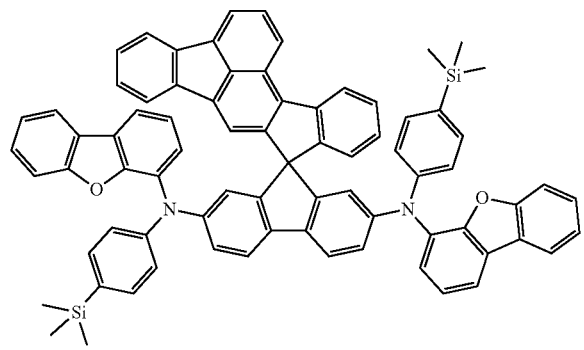
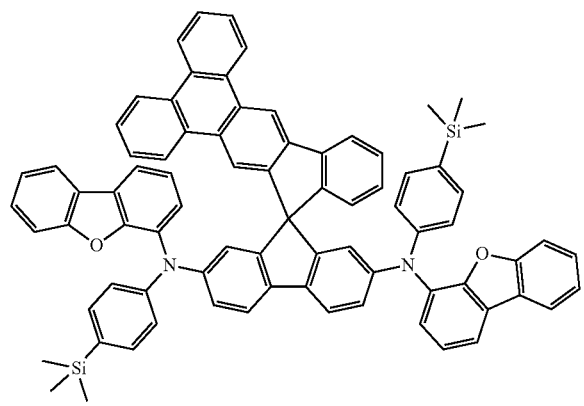
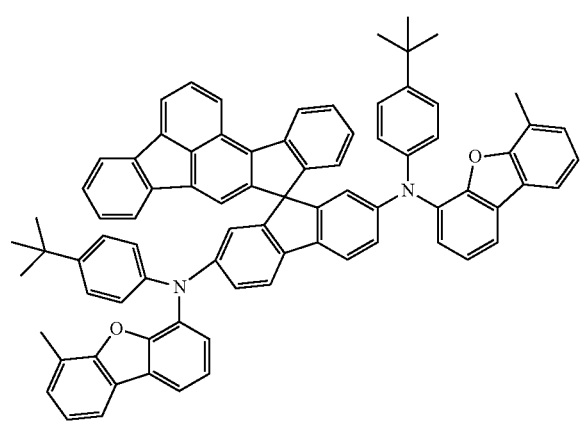
202
-continued
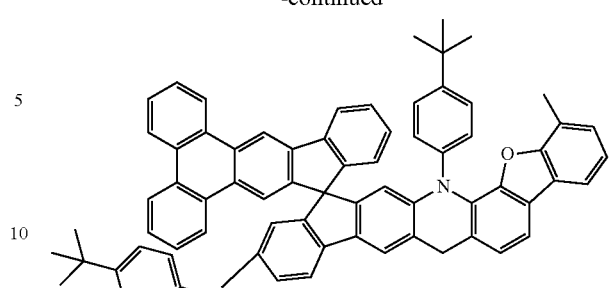
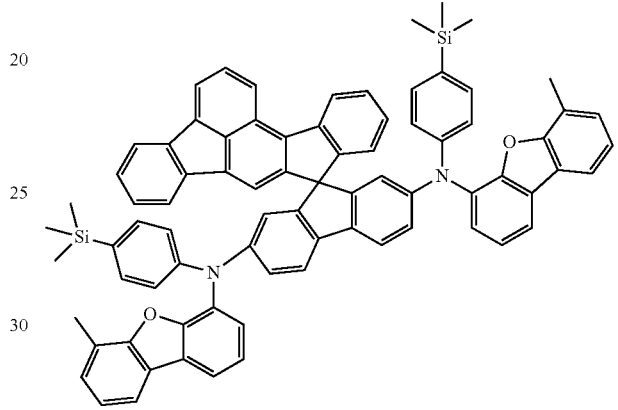
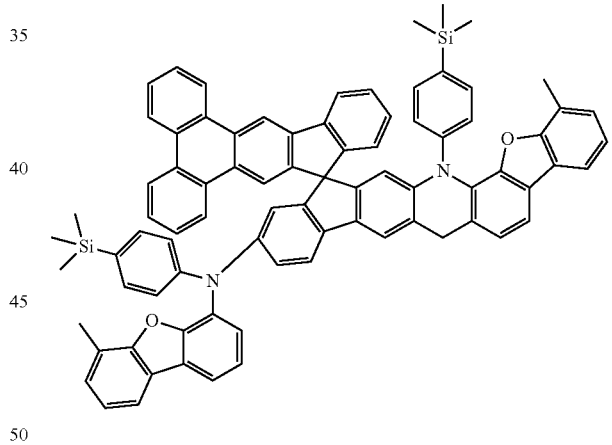
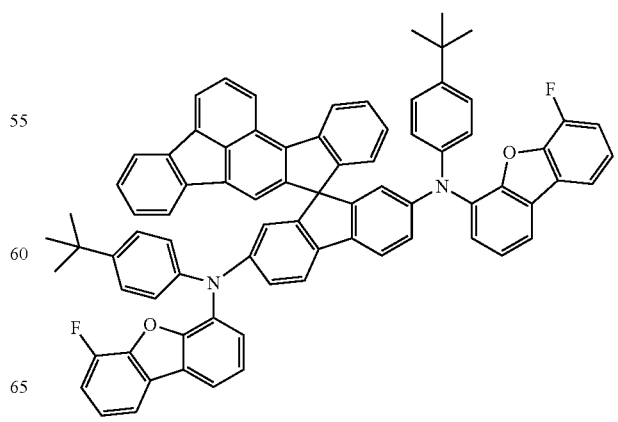

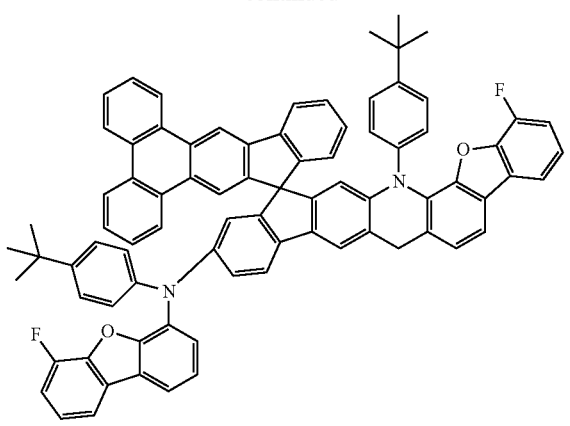
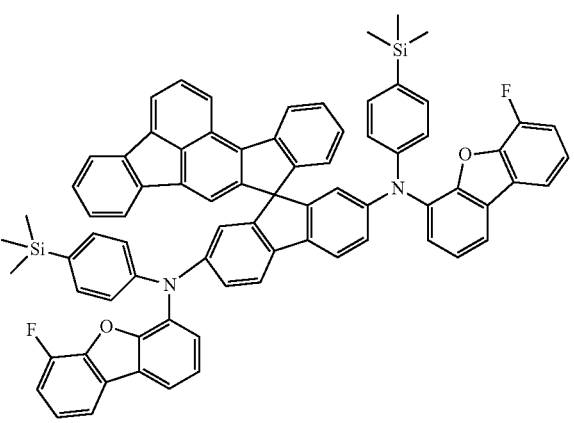
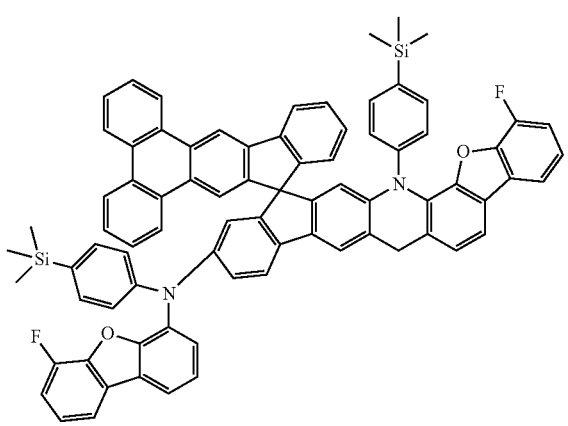
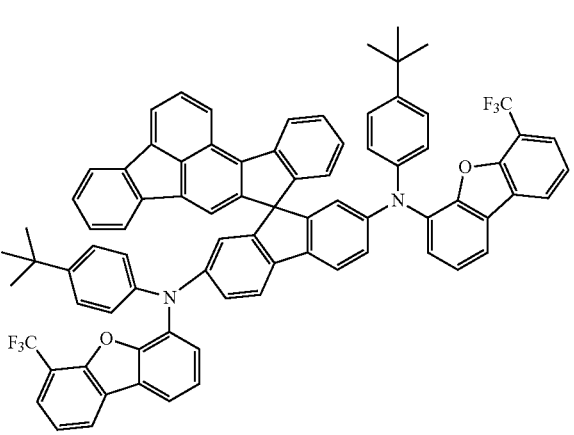
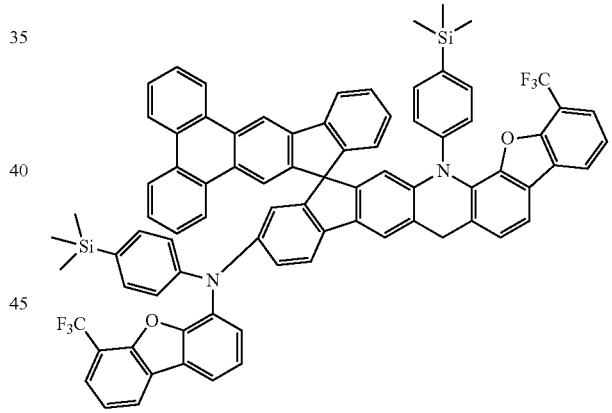
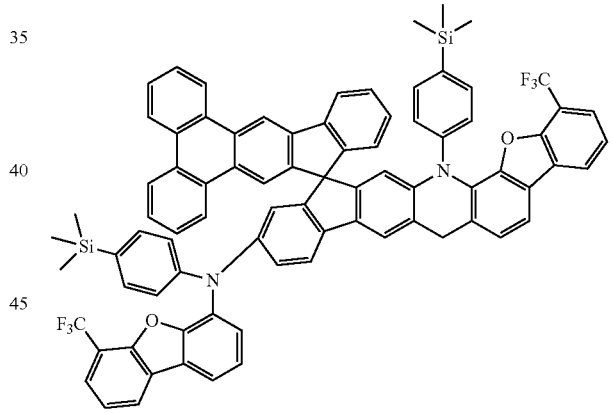
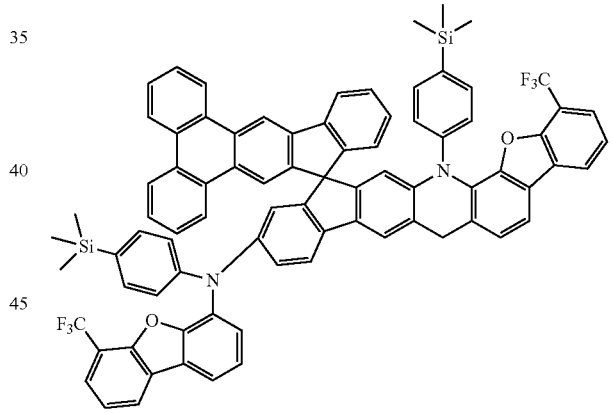
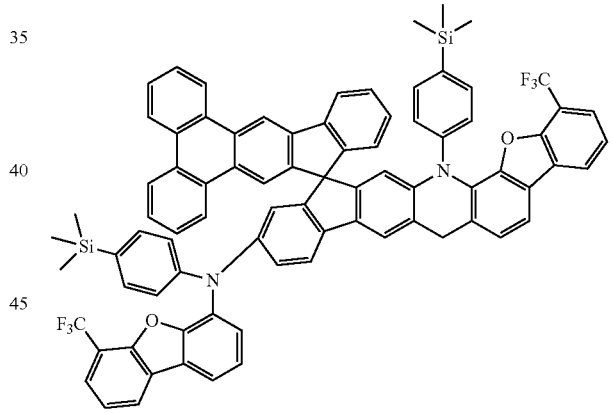

205
-continued
206
-continued
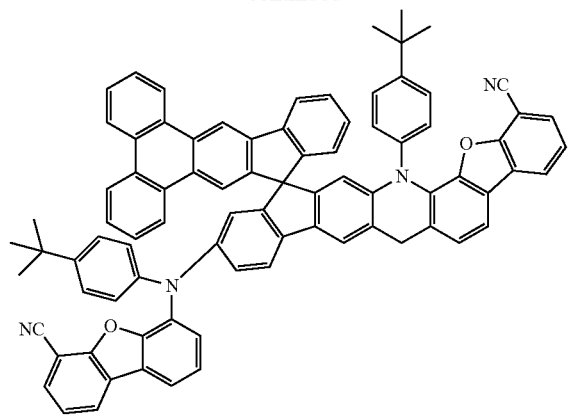
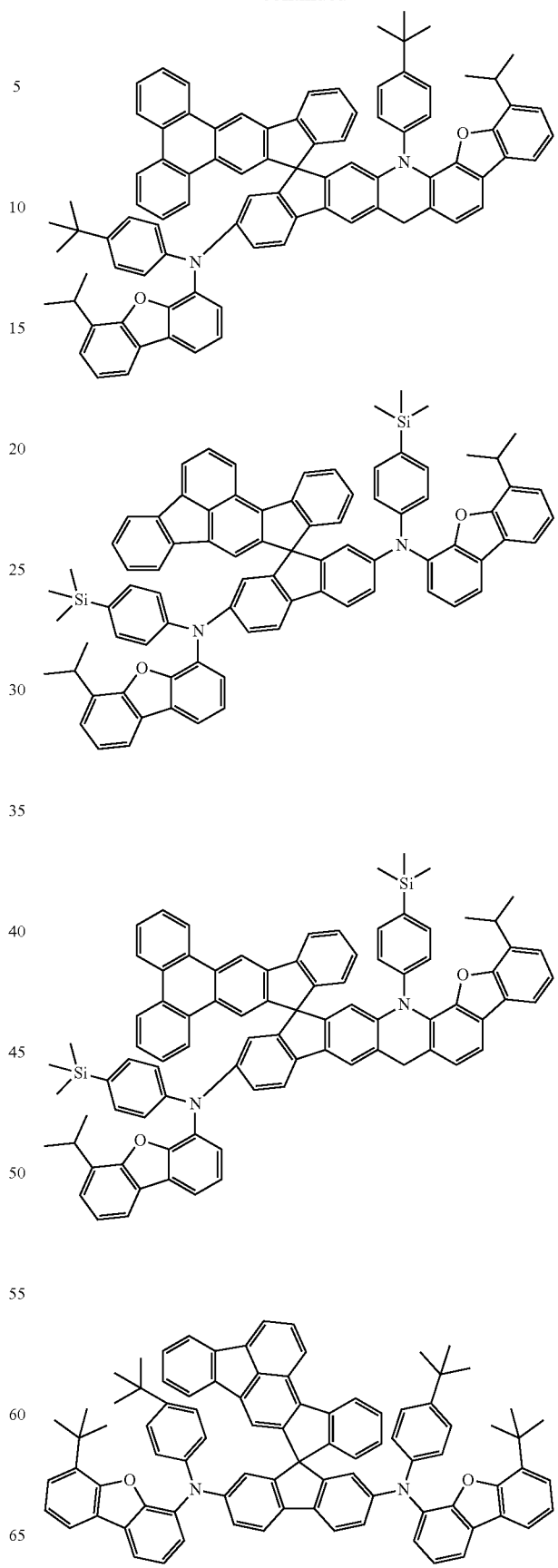

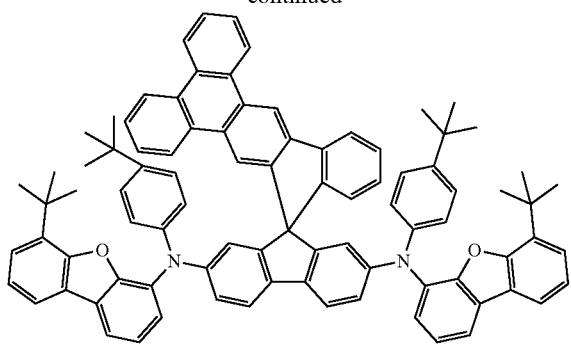
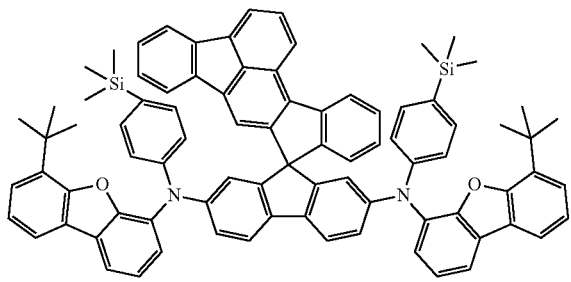
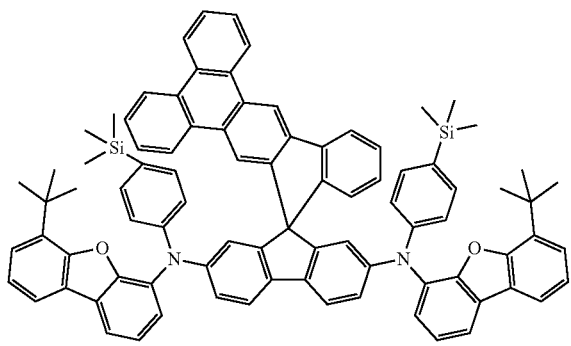
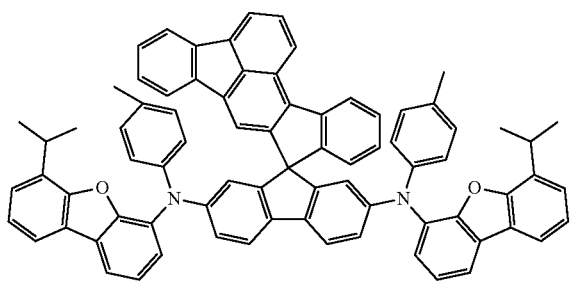
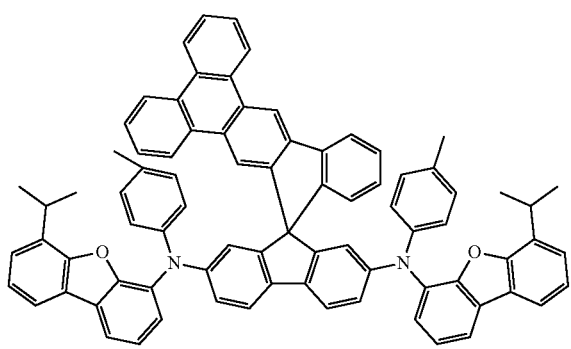

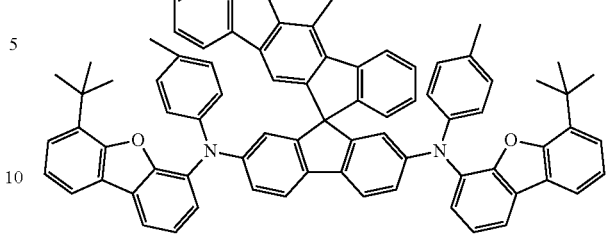
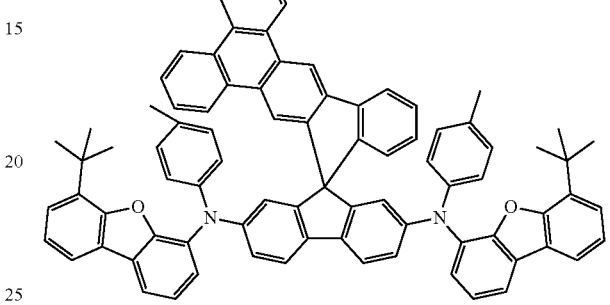

According to an exemplary embodiment of the present specification, the compound represented by Chemical Formula 1 may be prepared by the following General Formulae 1 to 4, but is not limited thereto.

The following General Formulae 1 and 3 represent general preparation methods of the core of Chemical Formula 1-1, and the following General Formulae 2 and 4 represent general preparation methods of the core of Chemical Formula 1-2.

[General Formula 1]

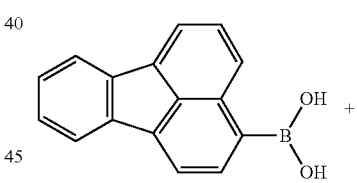

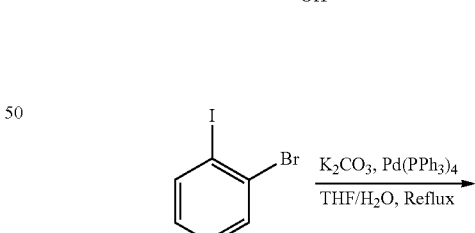

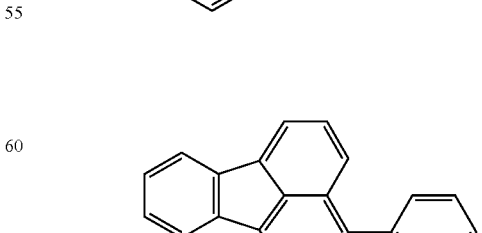

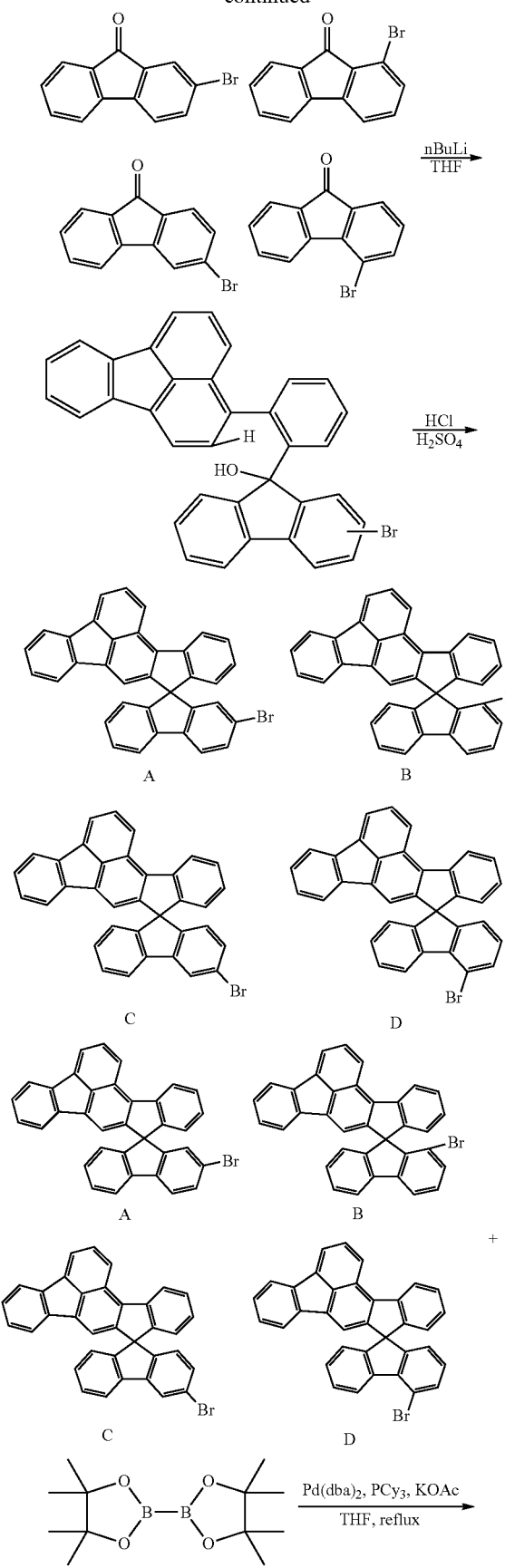

211
-continued
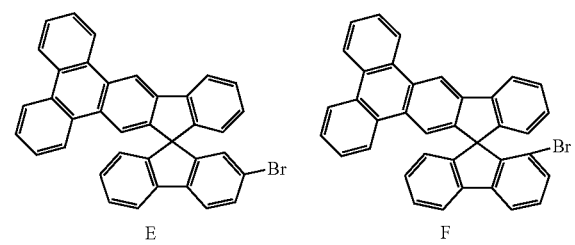
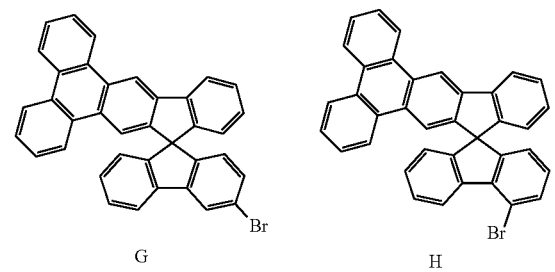
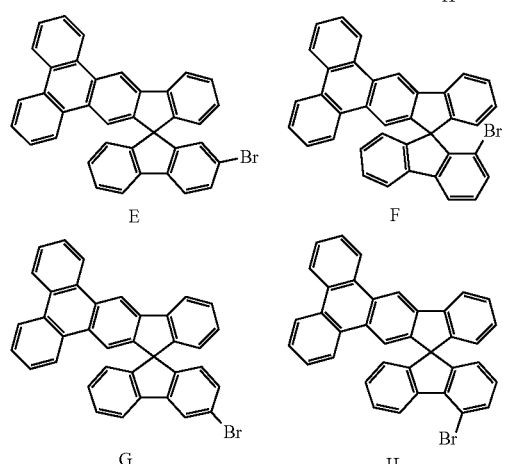
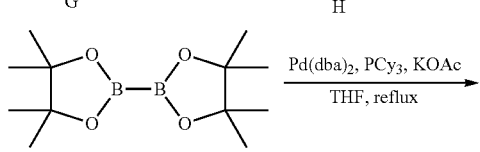
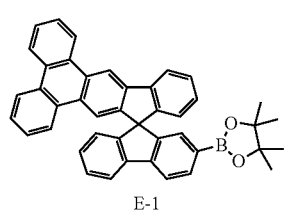
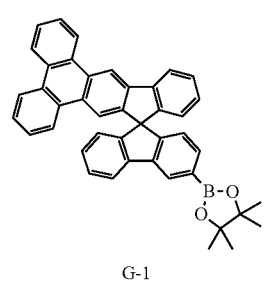
212
-continued
[General Formula 3]
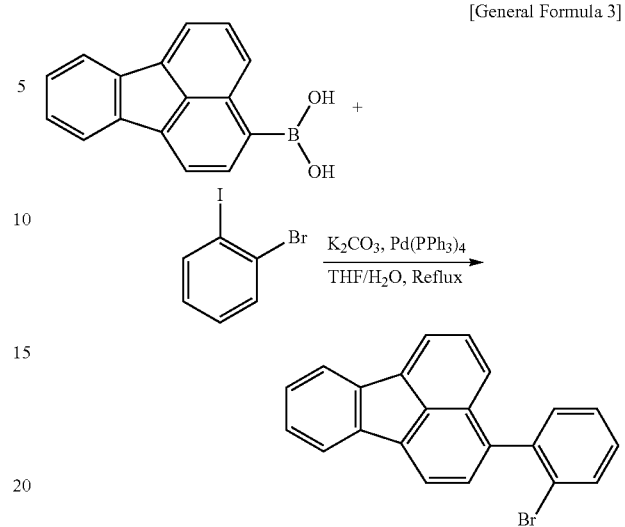
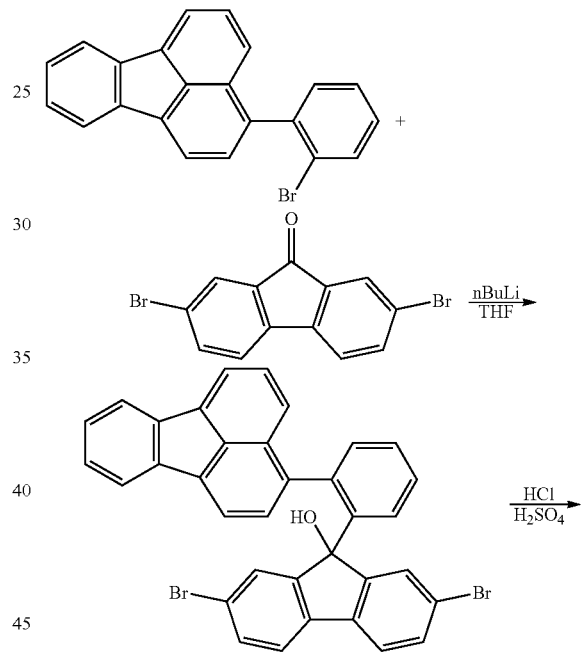
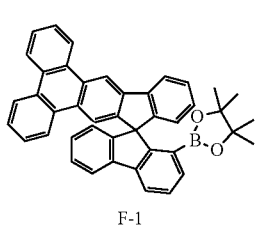
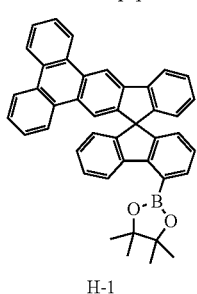
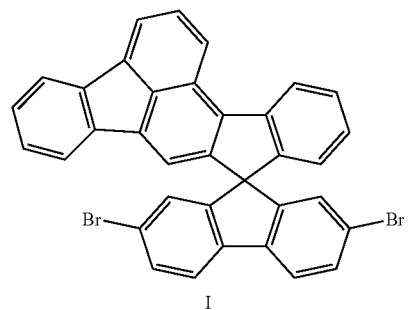
[General Formula 4]
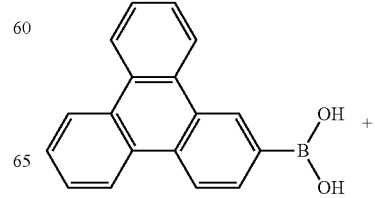

-continued

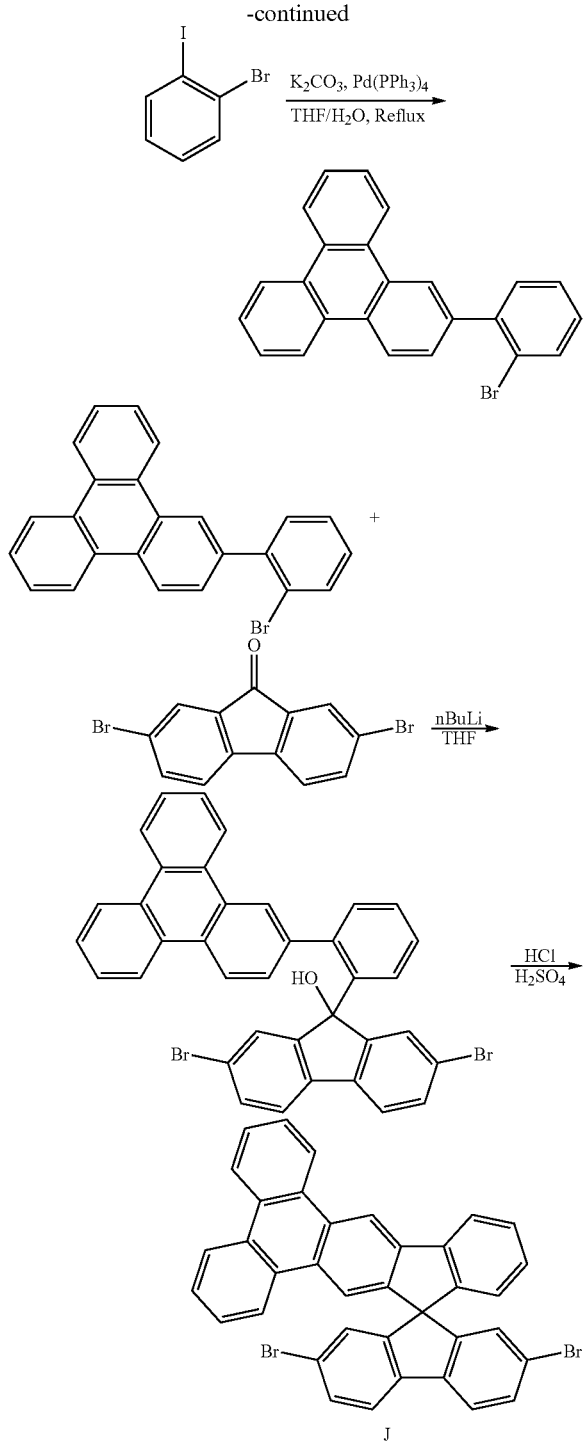

An exemplary embodiment of the present specification provides an organic light emitting device including: a first electrode; a second electrode provided to face the first electrode; and one or more organic material layers provided between the first electrode and the second electrode, in which one or more layers of the organic material layers include the compound represented by Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transport layer, an electron blocking layer, a light emitting layer, a hole blocking layer, an electron transport layer, an electron injection layer, and the like as organic material layers. However, the structure of the organic light emitting device is not limited thereto, and may include a fewer number of organic layers.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transport layer 70, a light emitting layer 40, an electron transport layer 80, an electron injection layer 90, and a second electrode 50 are sequentially stacked on a substrate 20. FIG. 2 is an exemplified structure according to exemplary embodiments of the present specification, and may further include other organic material layers.

According to an exemplary embodiment of the present specification, the organic material layer includes a hole injection layer or a hole transport layer, and the hole injection layer or the hole transport layer includes the compound represented by Chemical Formula 1.

According to an exemplary embodiment of the present specification, the organic material layer includes an electron blocking layer, and the electron blocking layer includes the compound represented by Chemical Formula 1.

According to an exemplary embodiment of the present specification, the organic material layer includes a light emitting layer, and the light emitting layer includes the compound represented by Chemical Formula 1.

According to an exemplary embodiment of the present specification, the organic material layer includes a light emitting layer, and the light emitting layer includes the compound represented by Chemical Formula 1 as a host of the light emitting layer.

According to an exemplary embodiment of the present specification, the organic material layer includes a light emitting layer, and the light emitting layer includes the compound represented by Chemical Formula 1 as a phosphorescent host or a fluorescent host of the light emitting layer.

According an exemplary embodiment of the present specification, the organic material layer includes the compound represented by Chemical Formula 1 as a host of the light emitting layer, and includes another organic compound, a metal or a metal compound as a dopant.

According to an exemplary embodiment of the present specification, the organic material layer includes a light emitting layer, and the light emitting layer includes the compound represented by Chemical Formula 1 as a dopant of the light emitting layer.

According to an exemplary embodiment of the present specification, the organic material layer includes an electron transport layer, an electron injection layer, or a layer which transports and injects electrons simultaneously, and the electron transport layer, the electron injection layer, or the layer which transports and injects electrons simultaneously includes the compound.

According to an exemplary embodiment of the present specification, the organic material layer further includes a hole injection layer or a hole transport layer, which includes a compound including an arylamino group, a carbazole group, or a benzocarbazole group, in addition to the organic material layer including the compound represented by Chemical Formula 1.

According to an exemplary embodiment of the present specification, the organic material layer includes a light emitting layer, and the light emitting layer includes a compound represented by the following Chemical Formula 1-A.

[Chemical Formula 1-A]

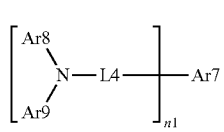

In Chemical Formula 1-A,
n1 is an integer of 1 or more,
Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L4 is a direct bond; a substituted or unsubstituted arylene group; or a substituted or unsubstituted heteroarylene group,
Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and
when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L4 is a direct bond.

According to an exemplary embodiment of the present specification, n1 is 2.

In an exemplary embodiment of the present specification, Ar7 is a divalent pyrene group which is unsubstituted or substituted with deuterium, a methyl group, an ethyl group, or a tert-butyl group.

According to an exemplary embodiment of the present specification, Ar8 and Ar9 are the same as or different from each other, and are each independently a substituted or unsubstituted aryl group having 6 to 30 carbon atoms.

According to an exemplary embodiment of the present specification, Ar8 and Ar9 are the same as or different from each other, and are each independently an aryl group which is unsubstituted or substituted with a germanium group substituted with an alkyl group.

According to an exemplary embodiment of the present specification, Ar8 and Ar9 are the same as or different from each other, and are each independently an aryl group which is unsubstituted or substituted with a trimethylgermanium group.

According to an exemplary embodiment of the present specification, Ar8 and Ar9 are the same as or different from each other, and are each independently a substituted or unsubstituted phenyl group.

According to an exemplary embodiment of the present specification, Ar8 and Ar9 are a phenyl group which is unsubstituted or substituted with a trimethylgermanium group.

According to an exemplary embodiment of the present specification, Chemical Formula 1-A is represented by the following compound.

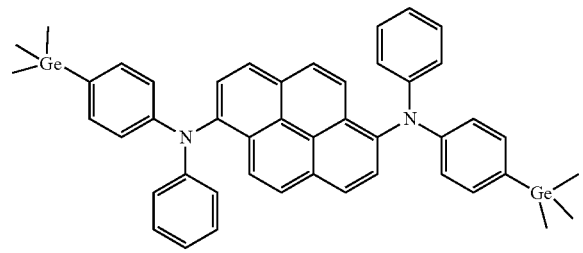

According to an exemplary embodiment of the present specification, the organic material layer includes a light emitting layer, and the light emitting layer includes a compound represented by the following Chemical Formula 2-A.

[Chemical Formula 2-A]

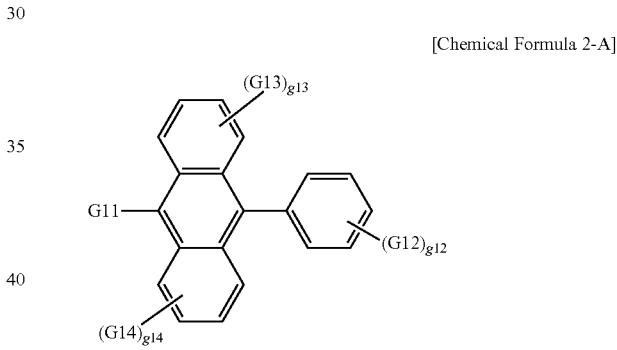

In Chemical Formula 2-A,
G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

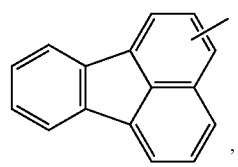

G12 is a phenyl group, a 1-naphtyl group, a 2-naphtyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, G11 is a 1-naphthyl group.

According to an exemplary embodiment of the present specification, G12 is a 2-naphthyl group.

According to an exemplary embodiment of the present specification, G13 and G14 are hydrogen.

According to an exemplary embodiment of the present specification, Chemical Formula 2-A is represented by the following compound.

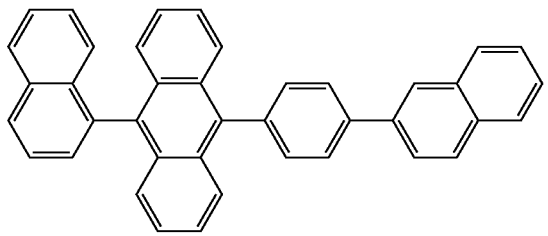 [SMILES: c1ccc2cc(-c3ccc(-c4c5ccccc5c(-c5cccc6ccccc56)c5ccccc45)cc3)ccc2c1]

The organic light emitting device of the present specification may be manufactured by the materials and methods known in the art, except that one or more layers of the organic material layers include the compound of the present specification, that is, the compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which may be used as a second electrode, thereon, by using a physical vapor deposition (PVD) method such as sputtering or e-beam evaporation. In addition to the method as described above, an organic light emitting device may be made by sequentially depositing a negative electrode material, an organic material layer, and a first electrode material on a substrate. Further, the compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO$_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or LiO$_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes into a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and the hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The electron blocking layer is a layer which may improve the lifetime and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

The light emitting material for the light emitting layer is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxyquinoline aluminum complex (Alq3); a carbazole-based compound; a dimerized styryl compound; BAlq; a 10-hydroxybenzoquinoline-metal compound; a benzoxazole, benzothiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material for the electron transport layer is suitably a material which may inject electrons well from a negative electrode and transfer the electrons to a light emitting layer, and has large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a positive electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the material to be used.

According to an exemplary embodiment of the present specification, the compound represented by Chemical Formula 1 may be included in an organic solar cell or an organic transistor in addition to the organic light emitting device. Hereinafter, the present specification will be described in detail with reference to Examples in order to specifically explain the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

Preparation Example 1

Preparation of Compound 1-1

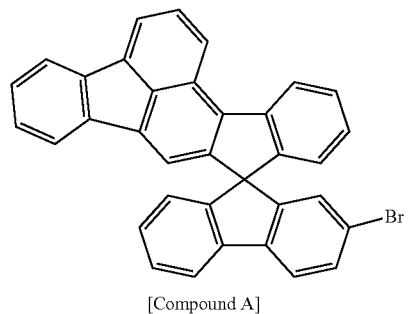

[Compound A]

+

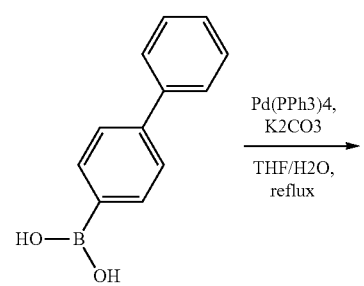

Pd(PPh3)4, K2CO3
THF/H2O, reflux
→

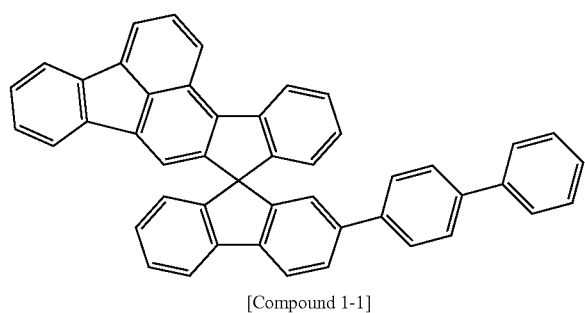

[Compound 1-1]

Compound A (15.0 g, 28.96 mmol) and [1,1'-biphenyl]-4-ylboronic acid (6.59 g, 33.3 mmol) were completely dissolved in 300 ml of tetrahydrofuran in a 500-ml round bottom flask under a nitrogen atmosphere, and then an aqueous 2 M potassium carbonate solution (150 ml) was added thereto, tetrakis-(triphenylphosphine)palladium (1.01 g, 0.87 mmol) were put thereinto, and then the resulting mixture was heated and stirred for 2 hours. The temperature was lowered to normal temperature, the aqueous layer was removed, and the resulting product was dried over anhydrous magnesium sulfate, and then concentrated under reduced pressure, and recrystallized with 250 ml of ethyl acetate to prepare Compound 1-1 (14.98 g, yield: 87%).

MS[M+H]$^+$=593

Preparation Example 2

Preparation of Compound 1-2

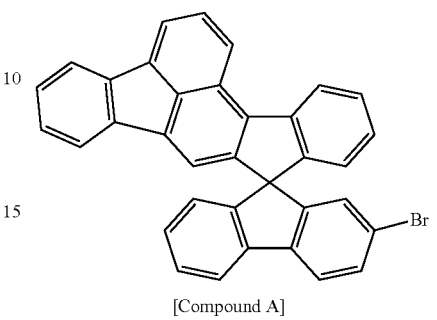

[Compound A]

+

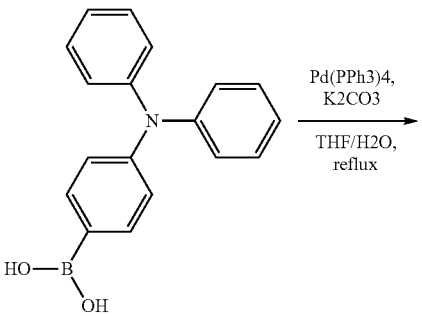

Pd(PPh3)4, K2CO3
THF/H2O, reflux
→

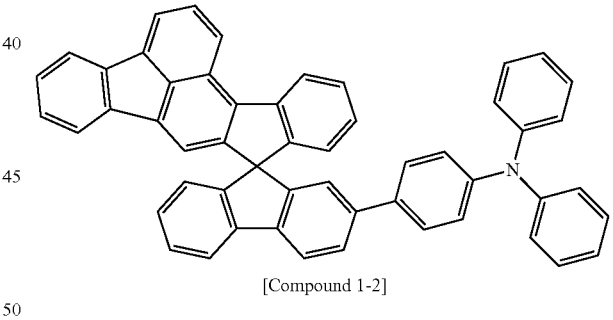

[Compound 1-2]

Compound A (15.0 g, 28.96 mmol) and (4-(diphenylamino)phenyl)boronic acid (9.62 g, 33.3 mmol) were completely dissolved in 260 ml of tetrahydrofuran in a 500-ml round bottom flask under a nitrogen atmosphere, and then an aqueous 2 M potassium carbonate solution (130 ml) was added thereto, tetrakis-(triphenylphosphine)palladium (1.01 g, 0.87 mmol) were put thereinto, and then the resulting mixture was heated and stirred for 3 hours. The temperature was lowered to normal temperature, the aqueous layer was removed, and the resulting product was dried over anhydrous magnesium sulfate, and then concentrated under reduced pressure, and recrystallized with 200 ml of ethyl acetate to prepare Compound 1-2 (16.25 g, yield: 82%).

MS[M+H]$^+$=684

Preparation Example 3

Preparation of Compound 1-3

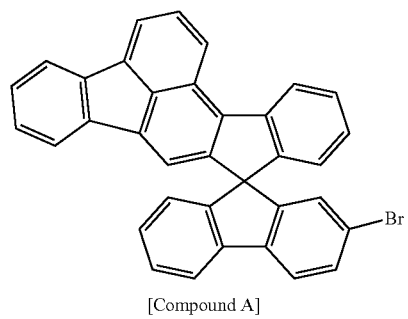

[Compound A]

+

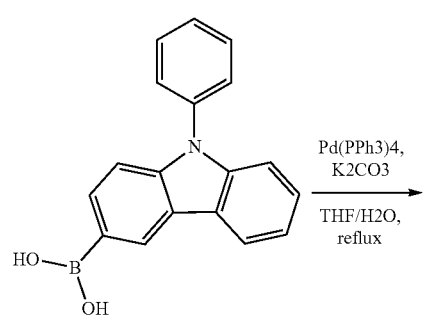

Compound A (15.0 g, 28.96 mmol) and 9-phenyl-9H-carbazol-3-ylboronic acid (9.62 g, 33.3 mmol) were completely dissolved in 260 ml of tetrahydrofuran in a 500-ml round bottom flask under a nitrogen atmosphere, and then an aqueous 2 M potassium carbonate solution (130 ml) was added thereto, tetrakis-(triphenylphosphine)palladium (1.01 g, 0.87 mmol) were put thereinto, and then the resulting mixture was heated and stirred for 4 hours. The temperature was lowered to normal temperature, the aqueous layer was removed, and the resulting product was dried over anhydrous magnesium sulfate, and then concentrated under reduced pressure, and recrystallized with 200 ml of ethyl acetate to prepare Compound 1-3 (14.63 g, yield: 74%).

MS[M+H]$^+$=682

Preparation Example 4

Preparation of Compound 1-4

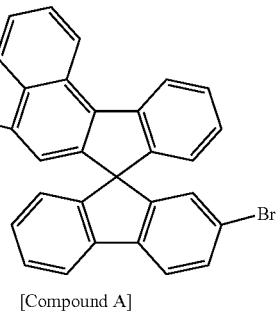

[Compound A]

+

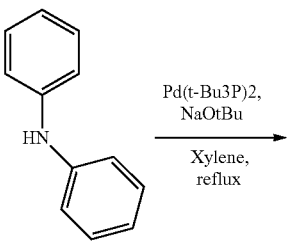

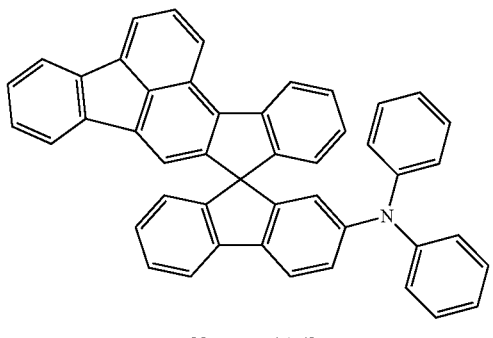

[Compound 1-4]

Compound A (15.0 g, 28.96 mmol) and diphenylamine (5.63 g, 33.3 mmol) were completely dissolved in 180 ml of xylene in a 500-ml round bottom flask under a nitrogen atmosphere, and then sodium tert-butoxide (3.62 g, 37.65 mol) was added thereto, bis(tri-tert-butylphosphine) palladium(0) (0.15 g, 0.29 mmol) were put thereinto, and then the resulting mixture was heated and stirred for 2 hours. The temperature was lowered to normal temperature, the mixture was filtered to remove the base, and then xylene was concentrated under reduced pressure, and the residue was purified by column chromatography at a ratio of tetrahydrofuran:hexane=1:20 to prepare Compound 1-4 (14.25 g, yield: 81%).

MS[M+H]$^+$=608

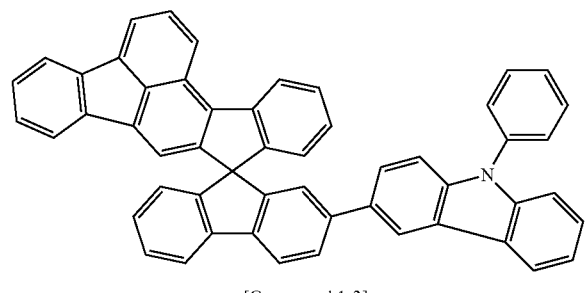

[Compound 1-3]

Preparation Example 5

Preparation of Compound 1-5

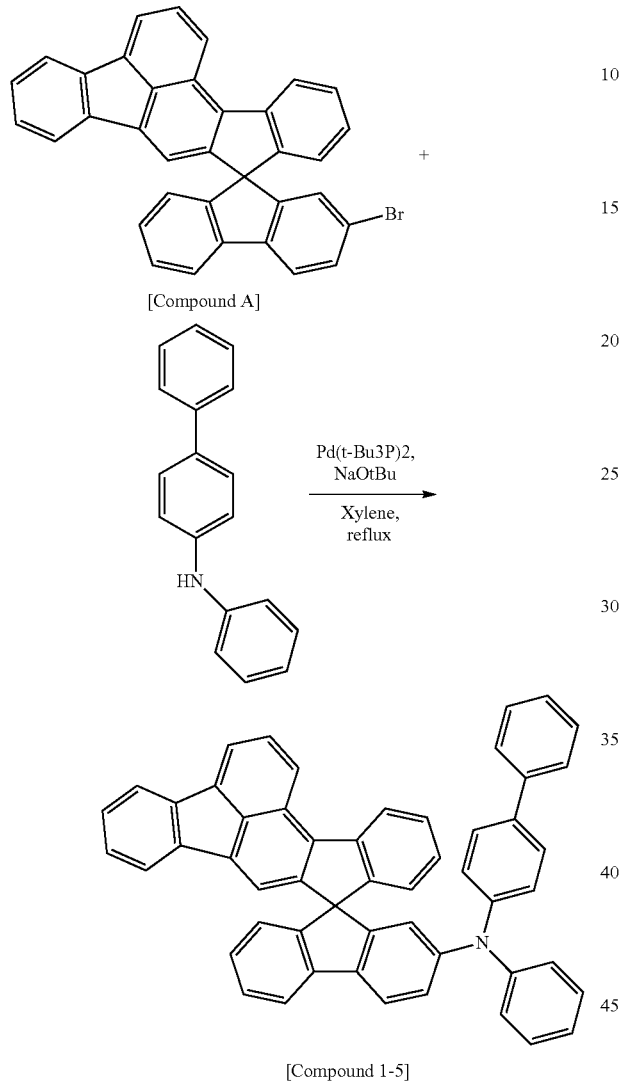

Compound A (15.0 g, 28.96 mmol) and N-phenyl-[1,1'-biphenyl]-4-amine (8.16 g, 33.3 mmol) were completely dissolved in 280 ml of xylene in a 500-ml round bottom flask under a nitrogen atmosphere, and then sodium tert-butoxide (3.62 g, 37.65 mol) was added thereto, bis(tri-tert-butylphosphine) palladium(0) (0.15 g, 0.29 mmol) were put thereinto, and then the resulting mixture was heated and stirred for 3 hours. The temperature was lowered to normal temperature, the mixture was filtered to remove the base, and then xylene was concentrated under reduced pressure, and the residue was purified by column chromatography at a ratio of tetrahydrofuran:hexane=1:15 to prepare Compound 1-5 (16.11 g, yield: 80%).

MS[M+H]$^+$=684

Preparation Example 6

Preparation of Compound 1-6

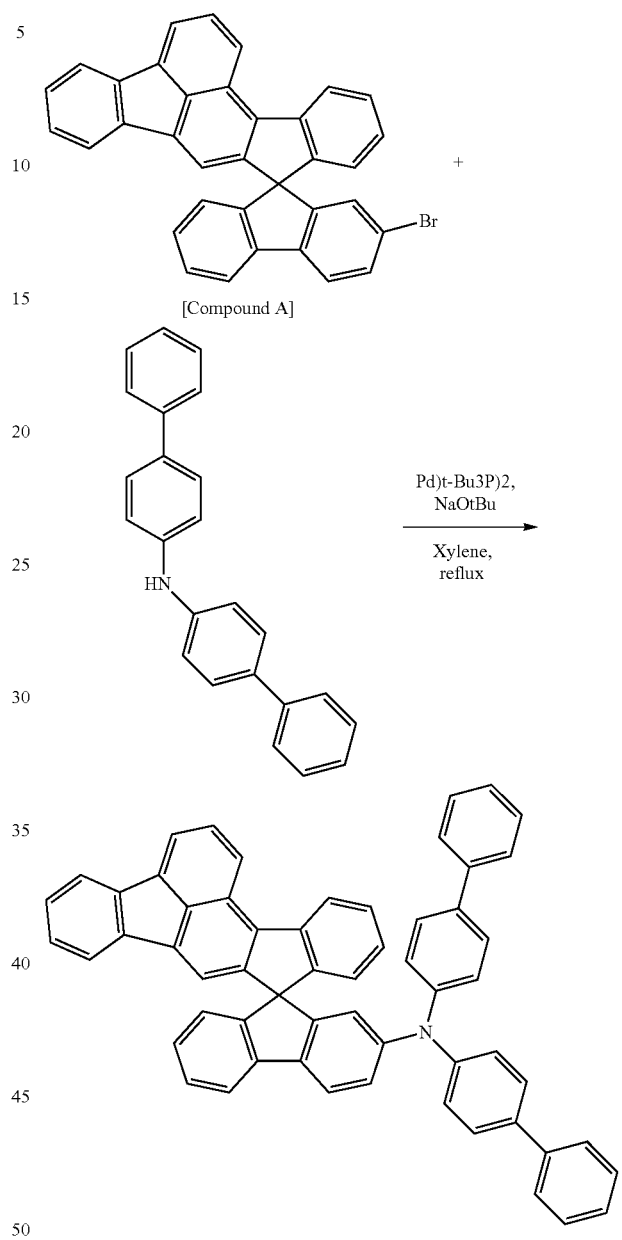

Compound A (15.0 g, 28.96 mmol) and di([1,1'-biphenyl]-4-yl)amine (10.69 g, 33.3 mmol) were completely dissolved in 320 ml of xylene in a 500-ml round bottom flask under a nitrogen atmosphere, and then sodium tert-butoxide (3.62 g, 37.65 mol) was added thereto, bis(tri-tert-butylphosphine) palladium(0) (0.15 g, 0.29 mmol) were put thereinto, and then the resulting mixture was heated and stirred for 5 hours. The temperature was lowered to normal temperature, the mixture was filtered to remove the base, and then xylene was concentrated under reduced pressure, and the residue was purified by column chromatography at a ratio of tetrahydrofuran:hexane=1:9 to prepare Compound 1-6 (19.44 g, yield: 93%).

MS[M+H]$^+$=760

Preparation Example 7

Preparation of Compound 1-7

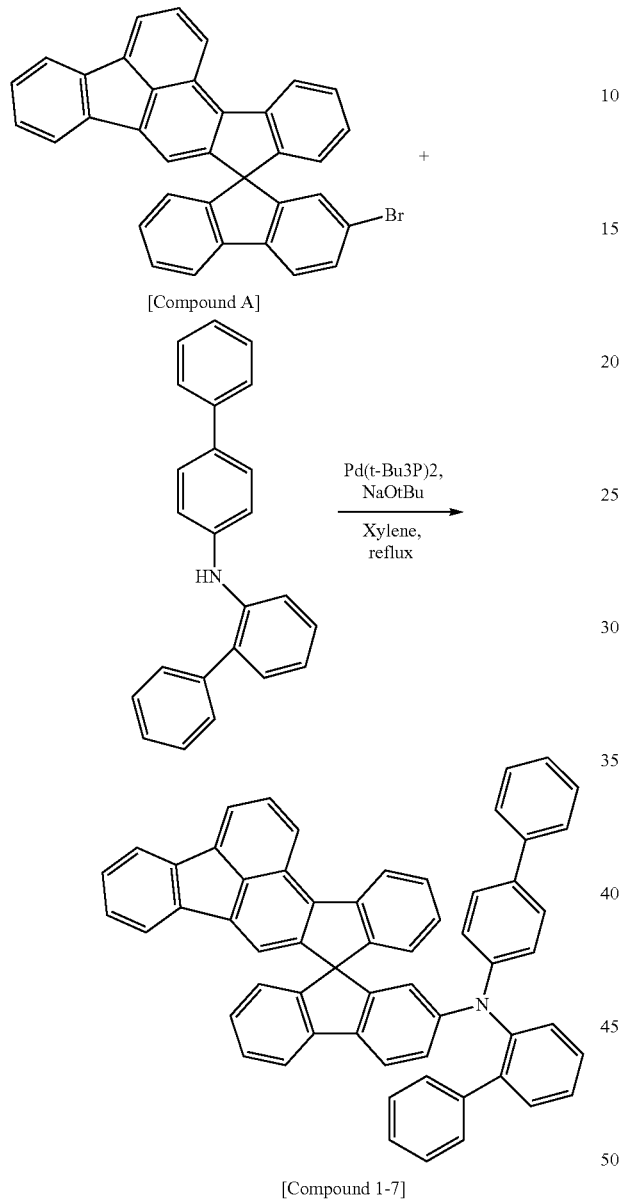

Preparation Example 8

Preparation of Compound 1-8

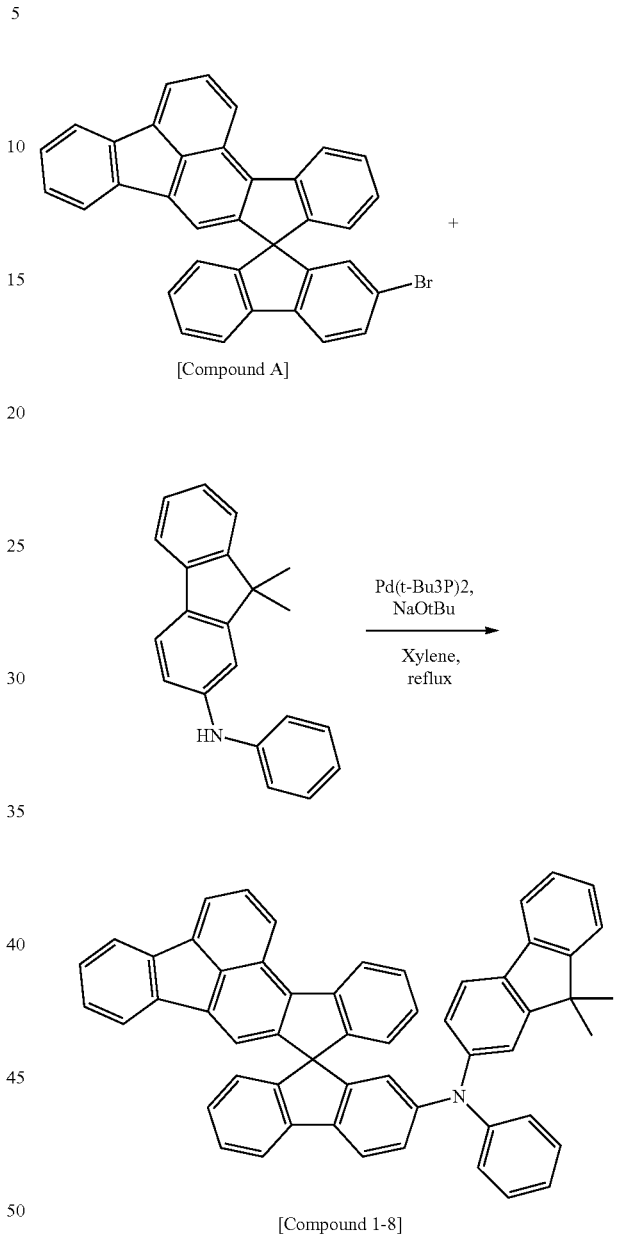

Compound A (15.0 g, 28.96 mmol) and N-([1,1'-biphenyl]-4-yl)-[1,1'-biphenyl]-2-amine (10.69 g, 33.3 mmol) were completely dissolved in 320 ml of xylene in a 500-ml round bottom flask under a nitrogen atmosphere, and then sodium tert-butoxide (3.62 g, 37.65 mol) was added thereto, bis(tri-tert-butylphosphine) palladium(0) (0.15 g, 0.29 mmol) were put thereinto, and then the resulting mixture was heated and stirred for 5 hours. The temperature was lowered to normal temperature, the mixture was filtered to remove the base, and then xylene was concentrated under reduced pressure, and the residue was purified by column chromatography at a ratio of tetrahydrofuran:hexane=1:12 to prepare Compound 1-7 (15.89 g, yield: 75%).

MS[M+H]$^+$=760

Compound A (15.0 g, 28.96 mmol) and 9,9-dimethyl-N-phenyl-9H-fluoren-2-amine (9.52 g, 33.3 mmol) were completely dissolved in 320 ml of xylene in a 500-ml round bottom flask under a nitrogen atmosphere, and then sodium tert-butoxide (3.62 g, 37.65 mol) was added thereto, bis(tri-tert-butylphosphine) palladium(0) (0.15 g, 0.29 mmol) were put thereinto, and then the resulting mixture was heated and stirred for 3 hours. The temperature was lowered to normal temperature, the mixture was filtered to remove the base, and then xylene was concentrated under reduced pressure, and the residue was purified by column chromatography at a ratio of tetrahydrofuran:hexane=1:18 to prepare Compound 1-8 (14.77 g, yield: 70%).

MS[M+H]$^+$=724

Preparation Example 9

Preparation of Compound 1-9

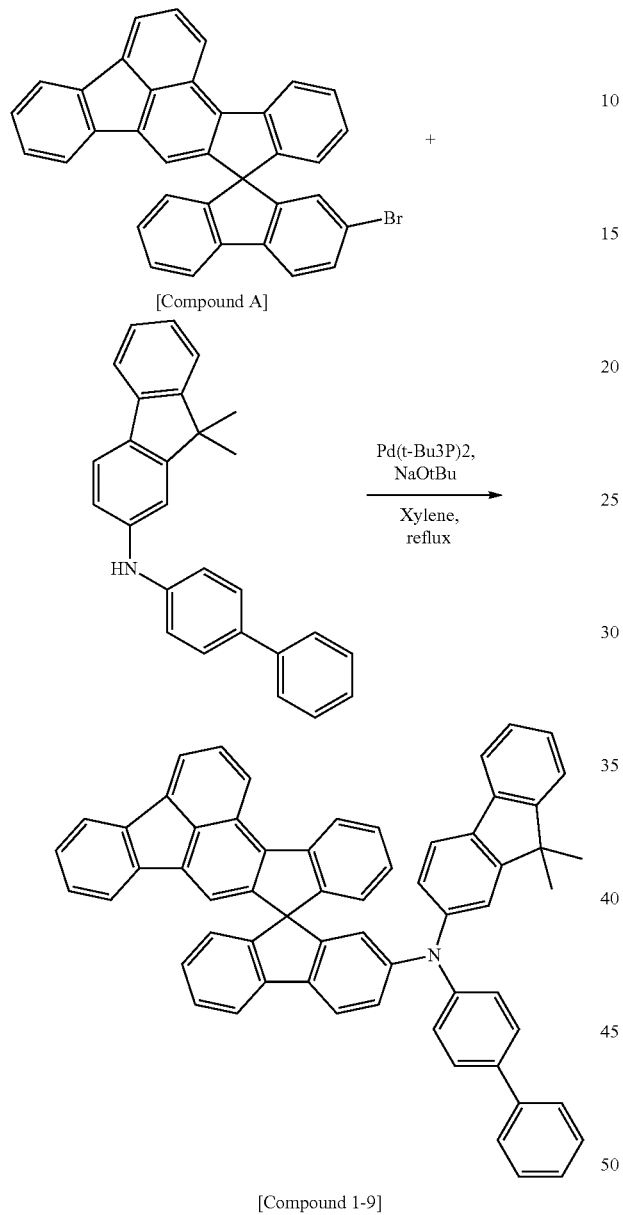

[Compound 1-9]

Compound A (15.0 g, 28.96 mmol) and N-([1,1'-biphenyl]-4-yl)-9,9-dimethyl-9H-fluoren-2-amine (12.02 g, 33.3 mmol) were completely dissolved in 320 ml of xylene in a 500-ml round bottom flask under a nitrogen atmosphere, and then sodium tert-butoxide (3.62 g, 37.65 mol) was added thereto, bis(tri-tert-butylphosphine) palladium(0) (0.15 g, 0.29 mmol) were put thereinto, and then the resulting mixture was heated and stirred for 3 hours. The temperature was lowered to normal temperature, the mixture was filtered to remove the base, and then xylene was concentrated under reduced pressure, and the residue was purified by column chromatography at a ratio of tetrahydrofuran:hexane=1:18 to prepare Compound 1-9 (18.50 g, yield: 81%).

MS[M+H]$^+$=800

Preparation Example 10

Preparation of Compound 1-10

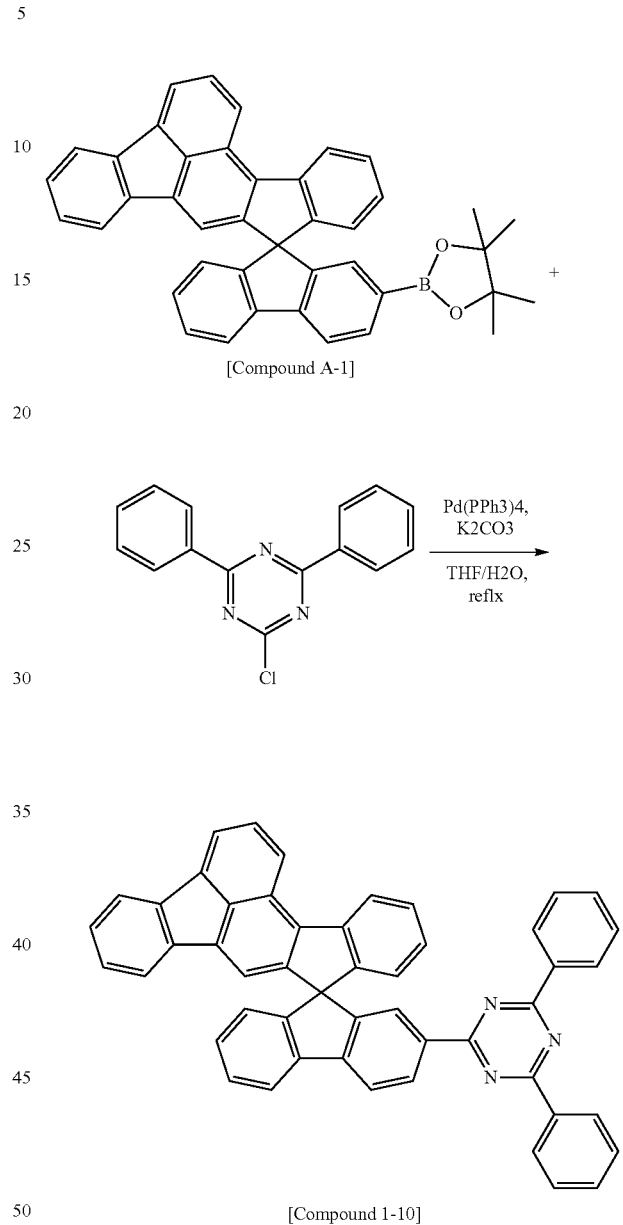

[Compound 1-10]

Compound A-1 (15.0 g, 26.74 mmol) and 2-chloro-4,6-diphenyl-1,3,5-triazine (6.49 g, 33.3 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) were put thereinto, and then the resulting mixture was heated and stirred for 6 hours. The temperature was lowered to normal temperature, the aqueous layer was removed, and the resulting product was dried over anhydrous magnesium sulfate, and then concentrated under reduced pressure, and recrystallized with 300 ml of ethyl acetate to prepare Compound 1-10 (16.12 g, yield: 83%).

MS[M+H]$^+$=672

231
Preparation Example 11
Preparation of Compound 1-11

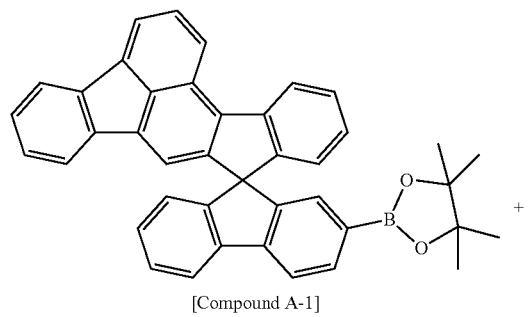
[Compound A-1]

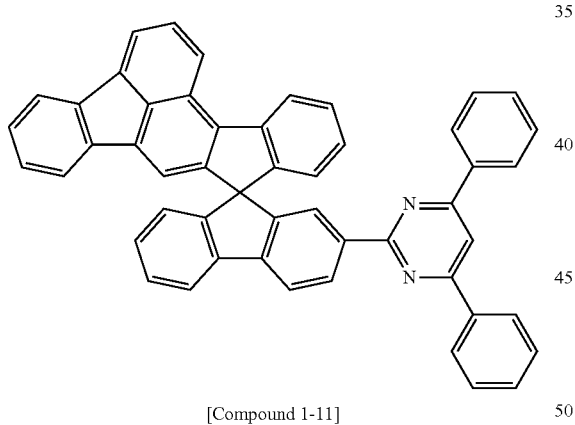
[Compound 1-11]

Compound A-1 (15.0 g, 26.74 mmol) and 2-chloro-4,6-diphenylpyrimidine (6.49 g, 33.3 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) were put thereinto, and then the resulting mixture was heated and stirred for 3 hours. The temperature was lowered to normal temperature, the aqueous layer was removed, and the resulting product was dried over anhydrous magnesium sulfate, and then concentrated under reduced pressure, and recrystallized with 280 ml of ethyl acetate to prepare Compound 1-11 (14.81 g, yield: 76%).

MS[M+H]$^+$=671

232
Preparation Example 12
Preparation of Compound 1-12

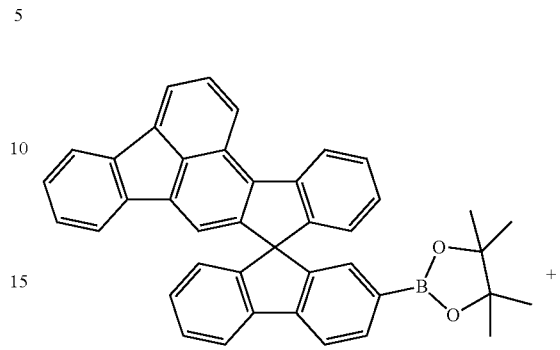
[Compound A-1]

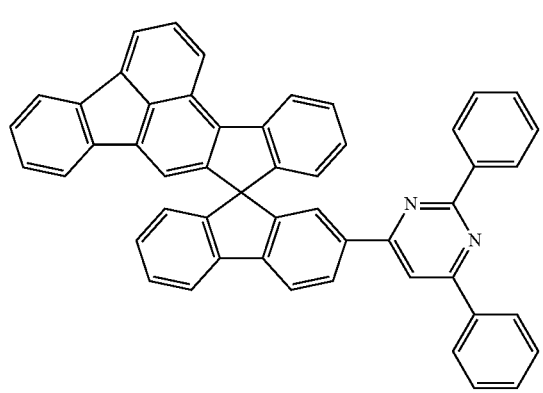
[Compound 1-12]

Compound A-1 (15.0 g, 26.74 mmol) and 4-chloro-2,6-diphenylpyrimidine (6.49 g, 33.3 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) were put thereinto, and then the resulting mixture was heated and stirred for 4 hours. The temperature was lowered to normal temperature, the aqueous layer was removed, and the resulting product was dried over anhydrous magnesium sulfate, and then concentrated under reduced pressure, and recrystallized with 330 ml of ethyl acetate to prepare Compound 1-12 (13.52 g, yield: 71%).

MS[M+H]$^+$=671

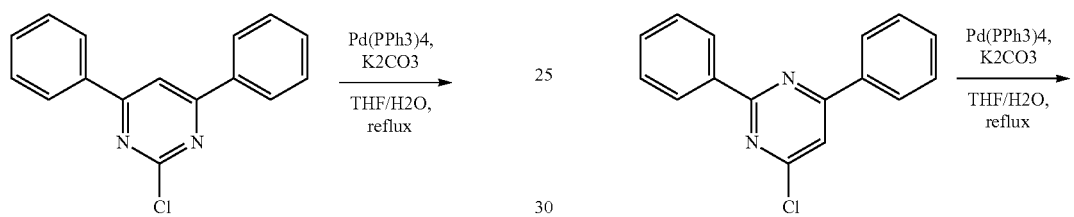

Preparation Example 13

Preparation of Compound 1-13

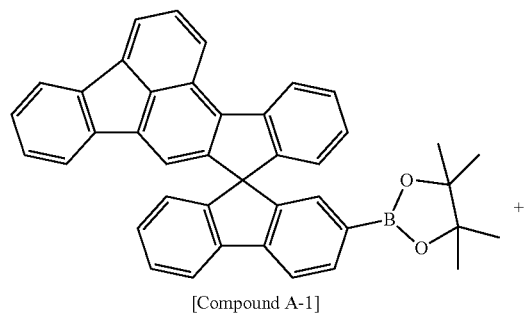

[Compound A-1]

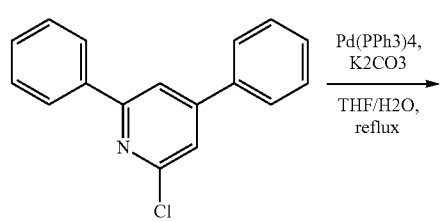

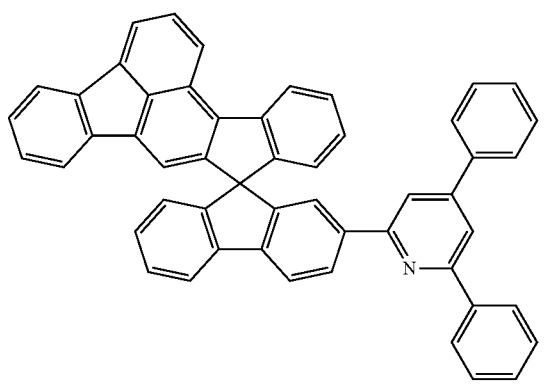

[Compound 1-13]

Compound A-1 (15.0 g, 26.74 mmol) and 2-chloro-4,6-diphenylpyridine (6.49 g, 33.3 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) were put thereinto, and then the resulting mixture was heated and stirred for 6 hours. The temperature was lowered to normal temperature, the aqueous layer was removed, and the resulting product was dried over anhydrous magnesium sulfate, and then concentrated under reduced pressure, and recrystallized with 350 ml of ethyl acetate to prepare Compound 1-13 (11.19 g, yield: 62%).

$MS[M+H]^+=670$

Preparation Example 14

Preparation of Compound 1-14

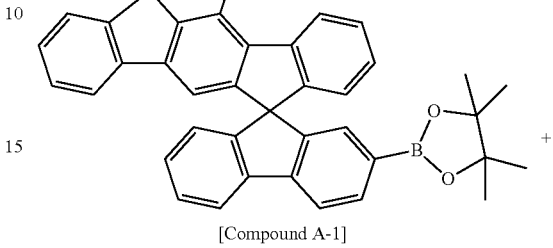

[Compound A-1]

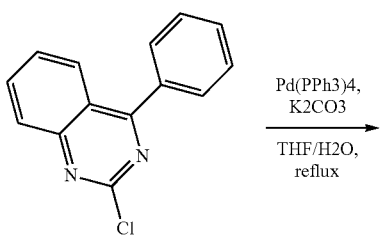

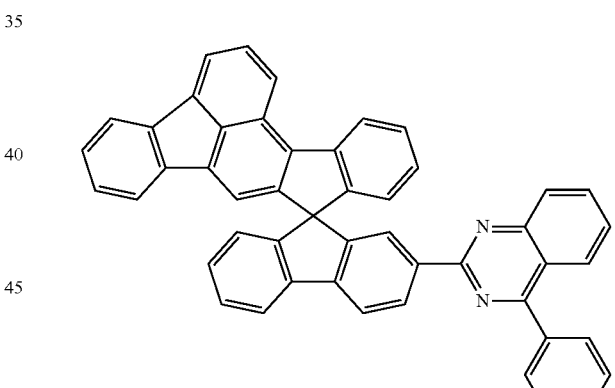

[Compound 1-14]

Compound A-1 (15.0 g, 26.74 mmol) and 2-chloro-4-phenylquinazoline (6.49 g, 33.3 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) were put thereinto, and then the resulting mixture was heated and stirred for 7 hours. The temperature was lowered to normal temperature, the aqueous layer was removed, and the resulting product was dried over anhydrous magnesium sulfate, and then concentrated under reduced pressure, and recrystallized with 350 ml of ethyl acetate to prepare Compound 1-14 (14.86 g, yield: 80%).

$MS[M+H]^+=645$

Preparation Example 15

Preparation of Compound 1-15

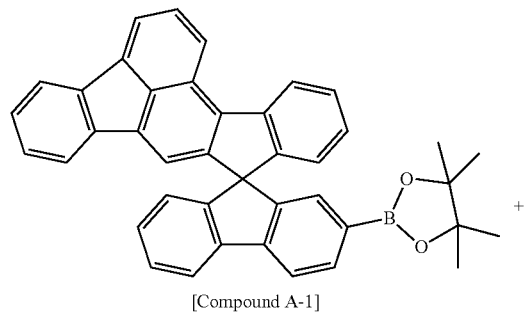
[Compound A-1]

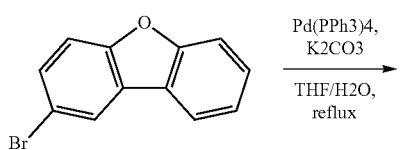

Pd(PPh3)4, K2CO3

THF/H2O, reflux

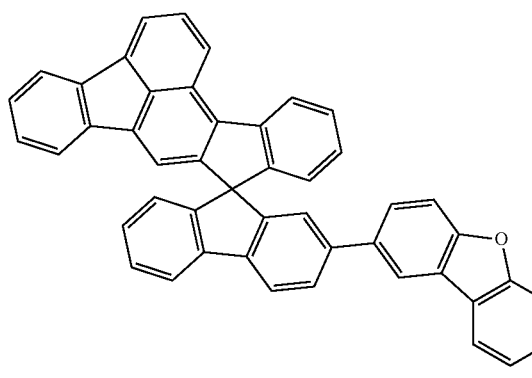
[Compound 1-15]

Compound A-1 (15.0 g, 26.74 mmol) and 2-bromodibenzo[b,d]furan (8.19 g, 33.3 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) were put thereinto, and then the resulting mixture was heated and stirred for 7 hours. The temperature was lowered to normal temperature, the aqueous layer was removed, and the resulting product was dried over anhydrous magnesium sulfate, and then concentrated under reduced pressure, and recrystallized with 350 ml of ethyl acetate to prepare Compound 1-15 (14.67 g, yield: 84%).

MS[M+H]$^+$=607

Preparation Example 16

Preparation of Compound 1-16

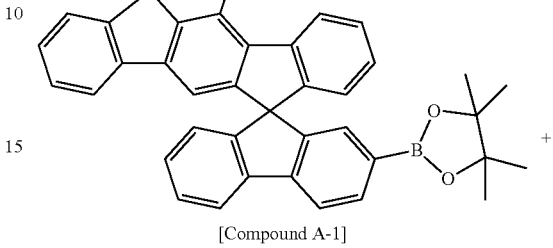
[Compound A-1]

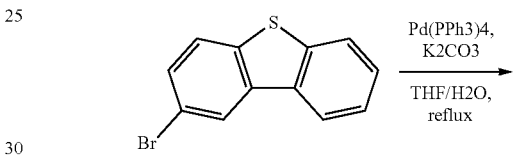

Pd(PPh3)4, K2CO3

THF/H2O, reflux

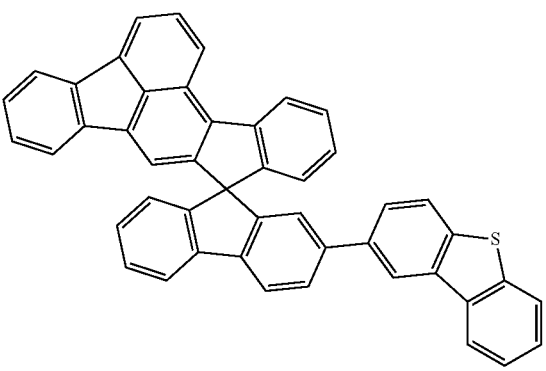
[Compound 1-16]

Compound A-1 (15.0 g, 26.74 mmol) and 2-bromodibenzo[b,d]thiophene (8.19 g, 33.3 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) were put thereinto, and then the resulting mixture was heated and stirred for 5 hours. The temperature was lowered to normal temperature, the aqueous layer was removed, and the resulting product was dried over anhydrous magnesium sulfate, and then concentrated under reduced pressure, and recrystallized with 350 ml of ethyl acetate to prepare Compound 1-16 (13.21 g, yield: 74%).

MS[M+H]$^+$=623

Preparation Example 17

Preparation of Compound 1-17

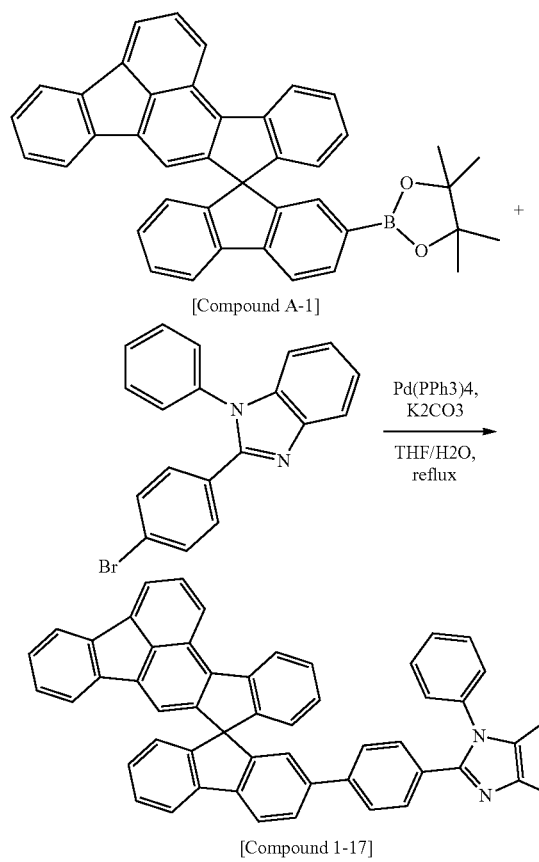

Compound A-1 (15.0 g, 26.74 mmol) and 2-2-(4-bromophenyl)-1-phenyl-1H-benzo[d]imidazole (11.59 g, 33.3 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) were put thereinto, and then the resulting mixture was heated and stirred for 5 hours. The temperature was lowered to normal temperature, the aqueous layer was removed, and the resulting product was dried over anhydrous magnesium sulfate, and then concentrated under reduced pressure, and recrystallized with 350 ml of ethyl acetate to prepare Compound 1-17 (13.21 g, yield: 74%).

MS[M+H]$^+$=709

Preparation Examples 18 to 26

Preparation of Compounds 1-18 to 1-26

The following Compounds 1-18 to 1-26 were prepared in the same manner as in Preparation Examples 1 to 9, except that Compound B of General Formula 1 was used instead of Compound A in Preparation Examples 1 to 9.

Preparation Examples 27 to 34

Preparation of Compounds 1-27 to 1-34

The following Compounds 1-27 to 1-34 were prepared in the same manner as in Preparation Examples 10 to 17, except that Compound B-1 of General Formula 1 was used instead of Compound A-1 in Preparation Examples 10 to 17.

Preparation Examples 35 to 43

Preparation of Compounds 1-35 to 1-43

The following Compounds 1-35 to 1-43 were prepared in the same manner as in Preparation Examples 1 to 9, except that Compound C of General Formula 1 was used instead of Compound A in Preparation Examples 1 to 9.

Preparation Examples 44 to 51

Preparation of Compounds 1-44 to 1-51

The following Compounds 1-44 to 1-51 were prepared in the same manner as in Preparation Examples 10 to 17, except that Compound C-1 of General Formula 1 was used instead of Compound A-1 in Preparation Examples 10 to 17.

Preparation Examples 52 to 60

Preparation of Compounds 1-52 to 1-60

The following Compounds 1-52 to 1-60 were prepared in the same manner as in Preparation Examples 1 to 9, except that Compound D of General Formula 1 was used instead of Compound A in Preparation Examples 1 to 9.

Preparation Examples 61 to 68

Preparation of Compounds 1-61 to 1-68

The following Compounds 1-61 to 1-68 were prepared in the same manner as in Preparation Examples 10 to 17, except that Compound D-1 of General Formula 1 was used instead of Compound A-1 in Preparation Examples 10 to 17.

Preparation Examples 69 to 77

Preparation of Compounds 2-1 to 2-9

The following Compounds 2-1 to 2-9 were prepared in the same manner as in Preparation Examples 1 to 9, except that Compound E of General Formula 2 was used instead of Compound A in Preparation Examples 1 to 9.

Preparation Examples 78 to 85

Preparation of Compounds 2-10 to 2-17

The following Compounds 2-10 to 2-17 were prepared in the same manner as in Preparation Examples 10 to 17, except that Compound E-1 of General Formula 2 was used instead of Compound A-1 in Preparation Examples 10 to 17.

Preparation Examples 86 to 94

Preparation of Compounds 2-18 to 2-26

The following Compounds 2-18 to 2-26 were prepared in the same manner as in Preparation Examples 1 to 9, except that Compound F of General Formula 2 was used instead of Compound A in Preparation Examples 1 to 9.

Preparation Examples 95 to 102

Preparation of Compounds 2-27 to 2-34

The following Compounds 2-27 to 2-34 were prepared in the same manner as in Preparation Examples 10 to 17, except that Compound F-1 of General Formula 2 was used instead of Compound A-1 in Preparation Examples 10 to 17.

Preparation Examples 103 to 111

Preparation of Compounds 2-35 to 2-43

The following Compounds 2-35 to 2-43 were prepared in the same manner as in Preparation Examples 1 to 9, except that Compound G of General Formula 2 was used instead of Compound A in Preparation Examples 1 to 9.

Preparation Examples 112 to 119

Preparation of Compounds 2-44 to 2-51

The following Compounds 2-44 to 2-51 were prepared in the same manner as in Preparation Examples 10 to 17, except that Compound G-1 of General Formula 2 was used instead of Compound A-1 in Preparation Examples 10 to 17.

Preparation Examples 120 to 128

Preparation of Compounds 2-52 to 2-60

The following Compounds 2-52 to 2-60 were prepared in the same manner as in Preparation Examples 1 to 9, except that Compound H of General Formula 2 was used instead of Compound A in Preparation Examples 1 to 9.

Preparation Examples 129 to 136

Preparation of Compounds 2-61 to 2-68

The following Compounds 2-61 to 2-68 were prepared in the same manner as in Preparation Examples 10 to 17, except that Compound H-1 of General Formula 2 was used instead of Compound A-1 in Preparation Examples 10 to 17.

1-18

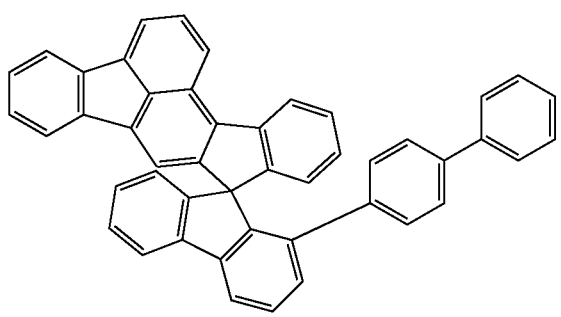

1-19

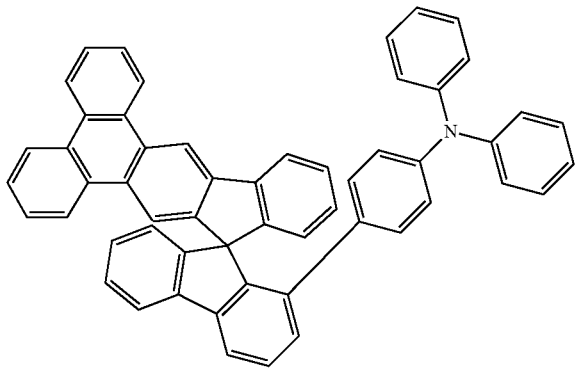

1-20

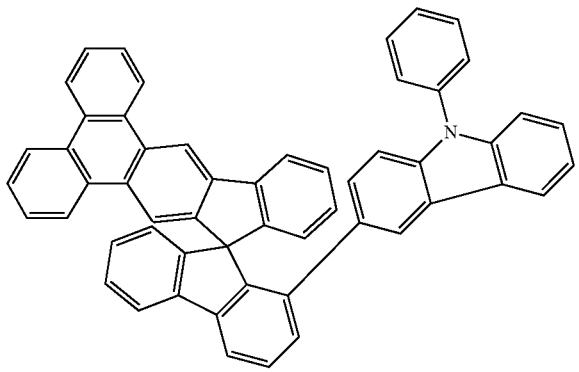

1-21

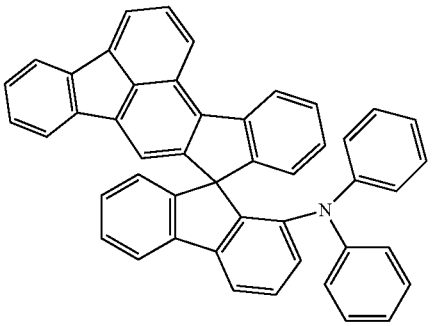

1-22

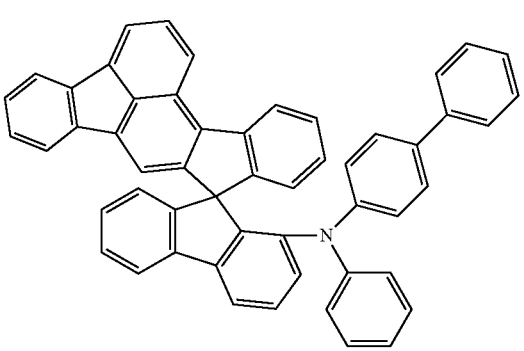

241
-continued
1-23
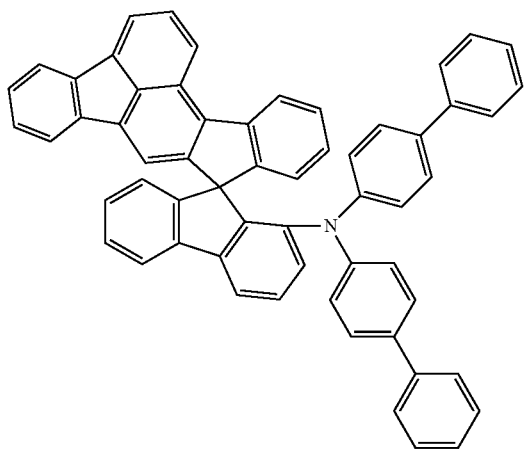
1-24
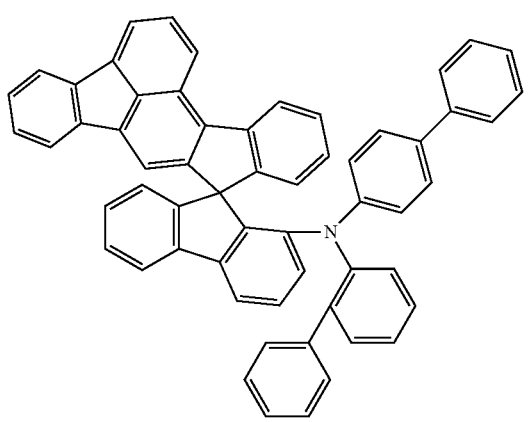
1-25
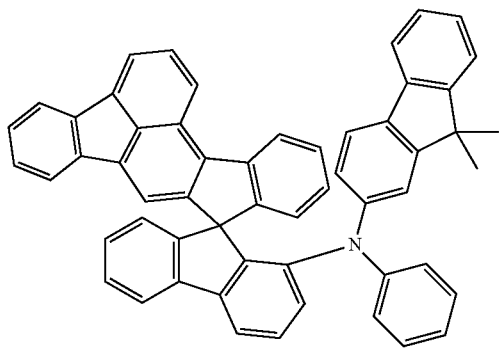
242
-continued
1-26
1-27
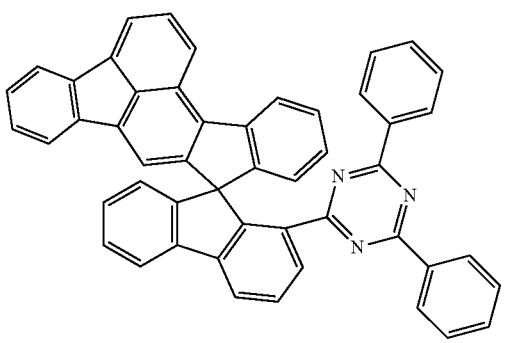
1-28
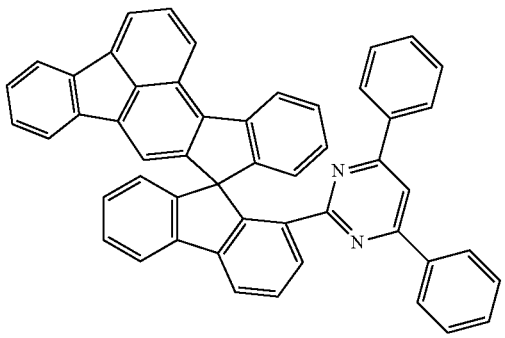
1-29
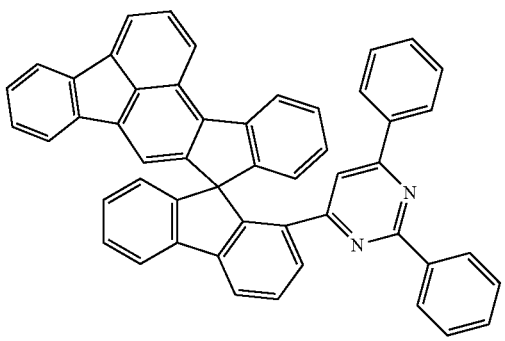

1-30
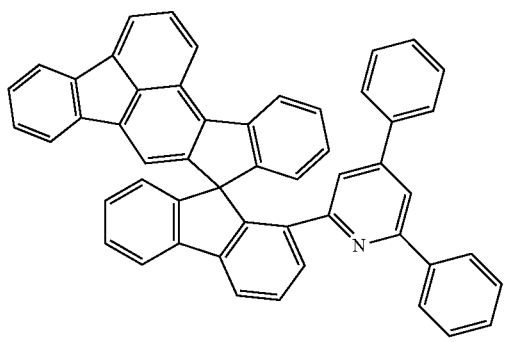
1-31
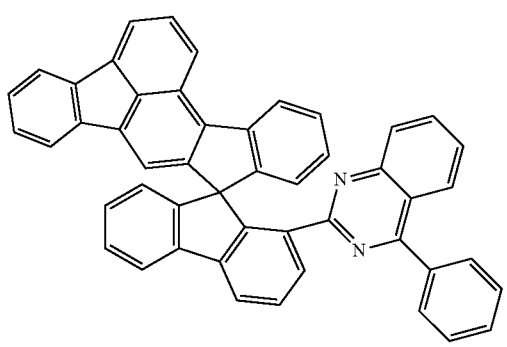
1-32
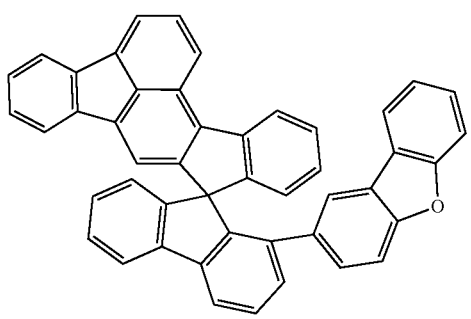
1-33
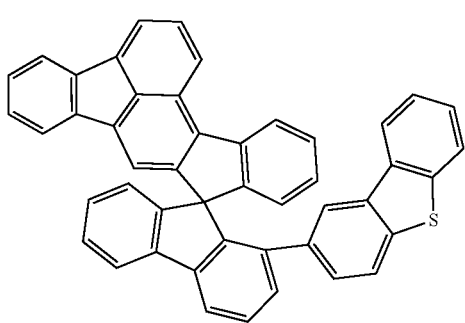
1-34
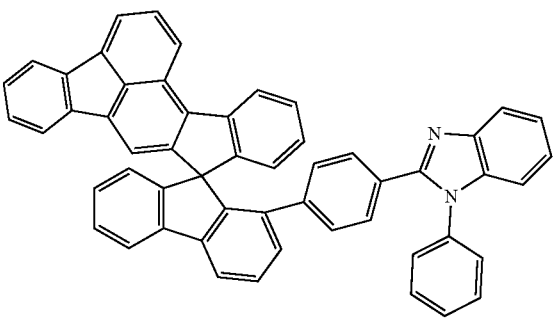
1-35
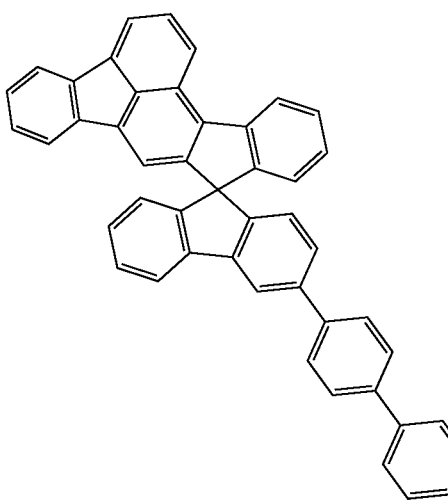
1-36
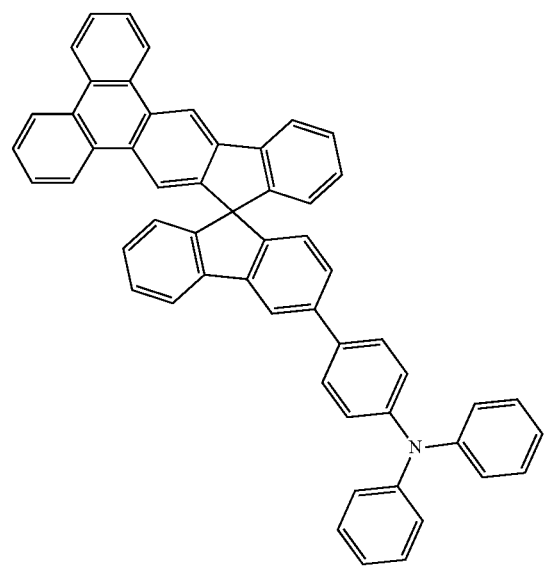

245
-continued
1-37
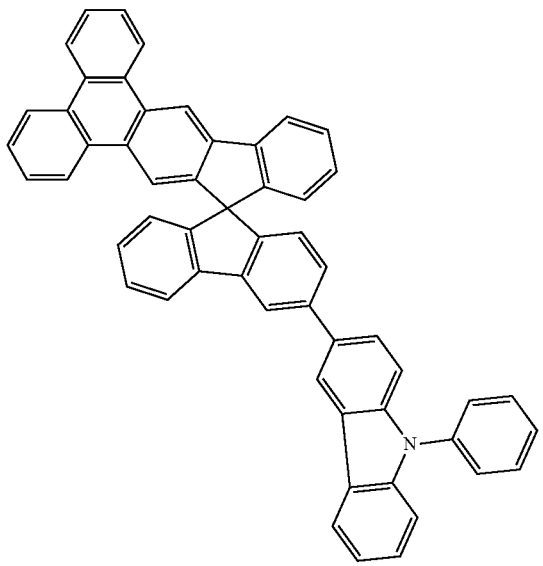
1-38
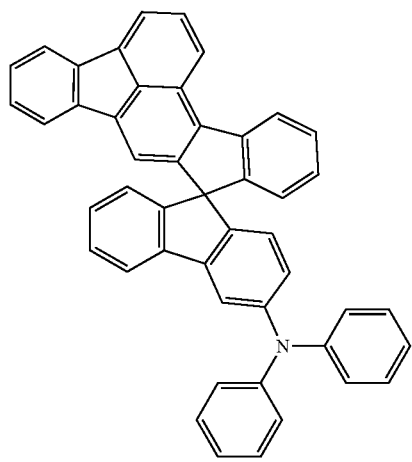
1-39
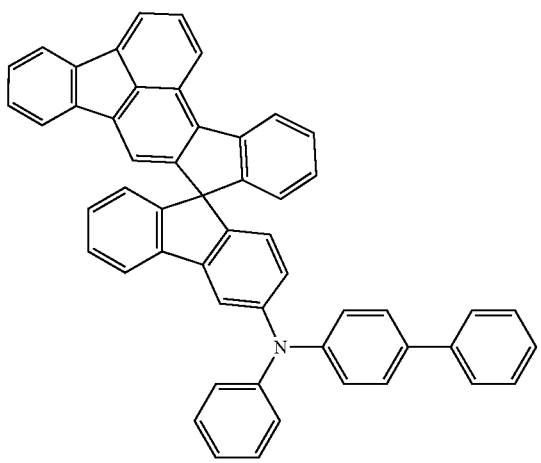
246
-continued
1-40
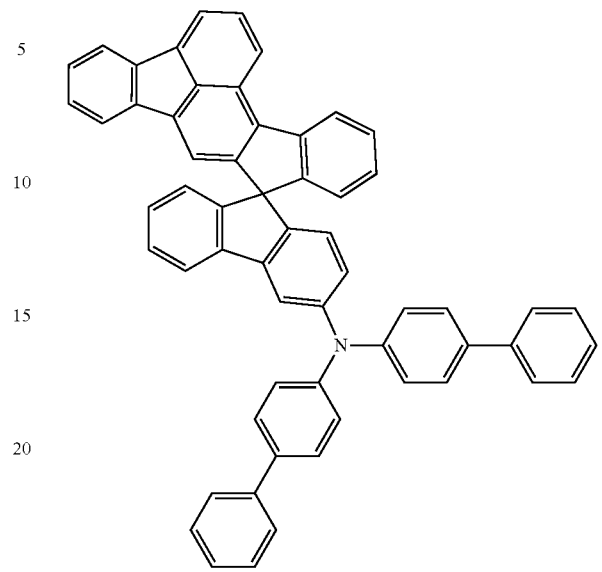
1-41
1-42
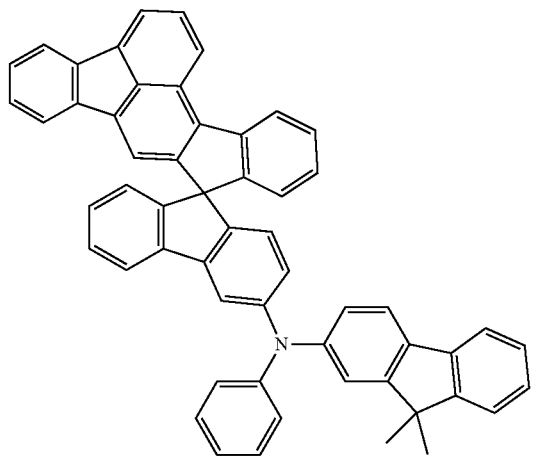

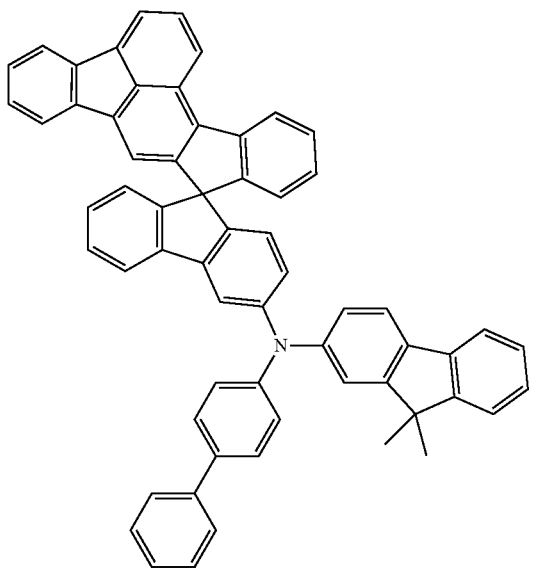
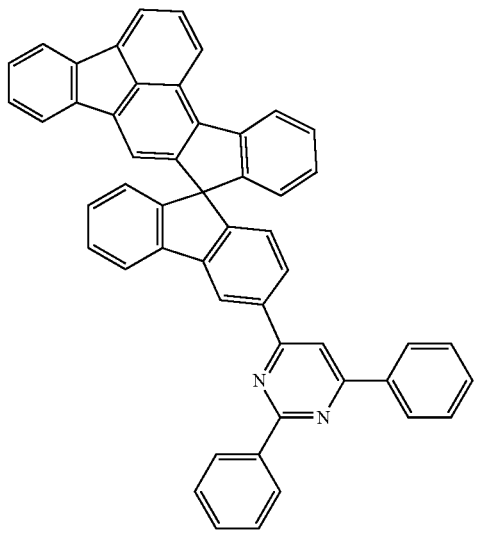
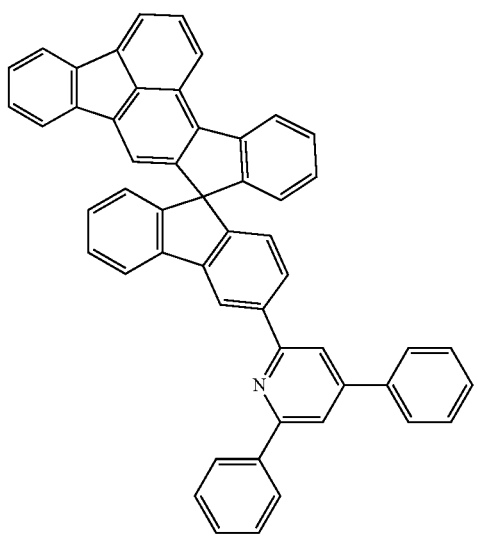

-continued
1-49
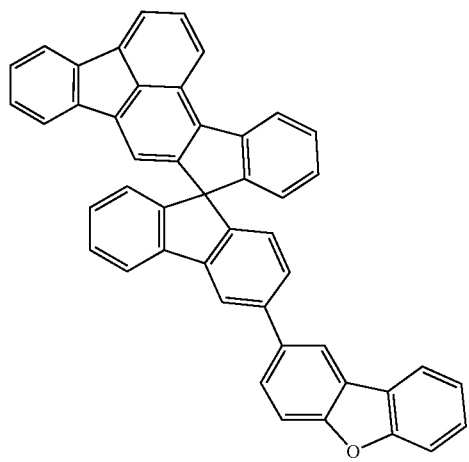
1-50
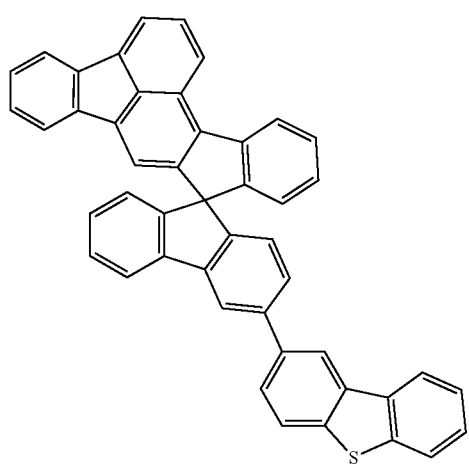
1-51
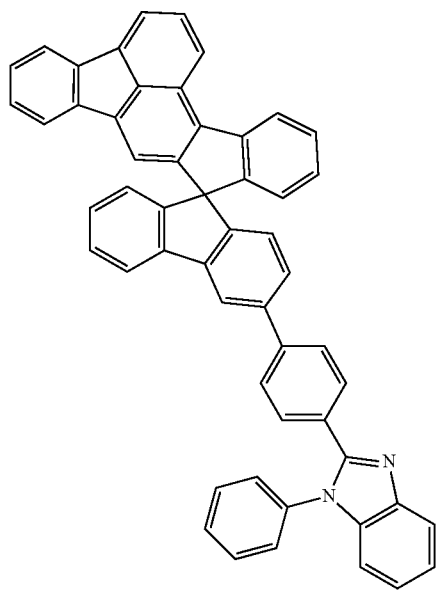
-continued
1-52
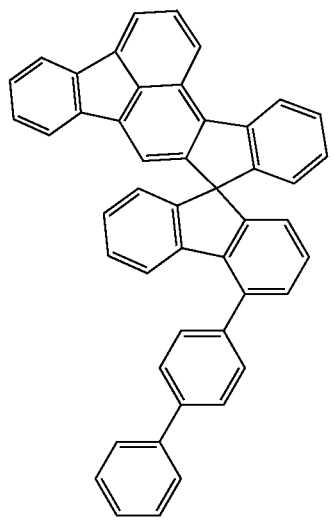
1-53
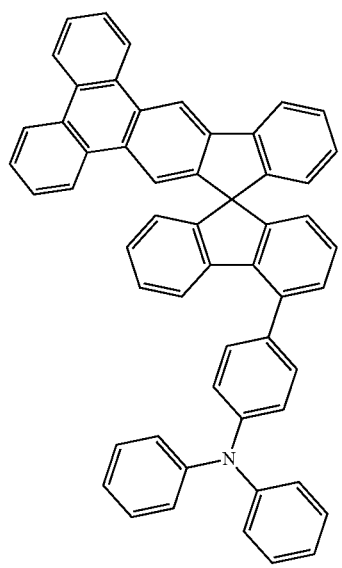
1-54
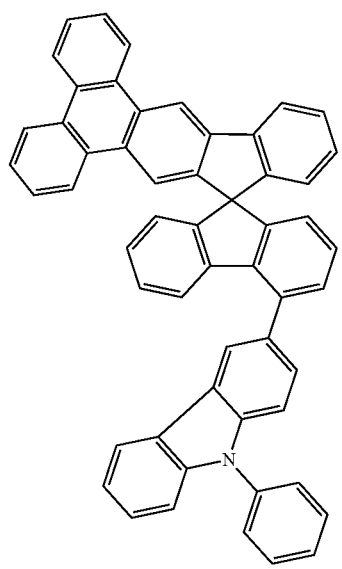

1-55
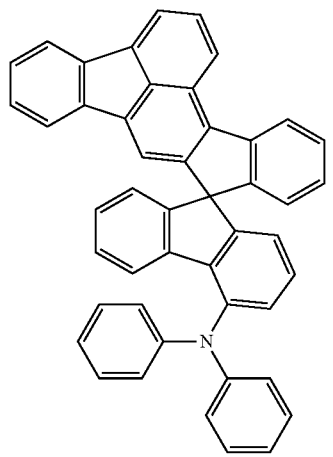
1-56
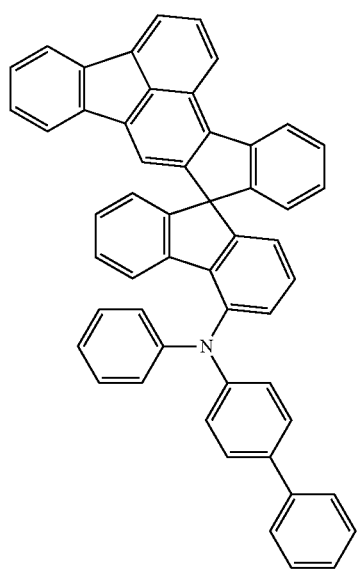
1-57
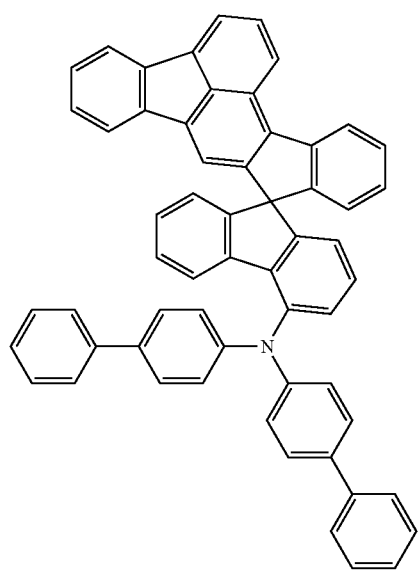
1-58
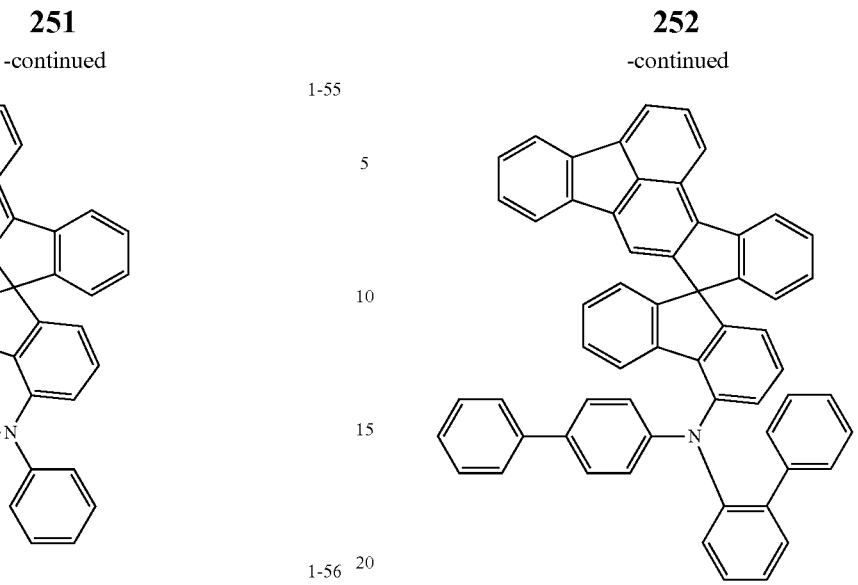
1-59
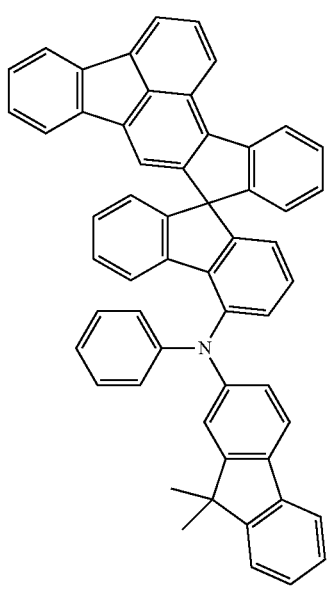
1-60
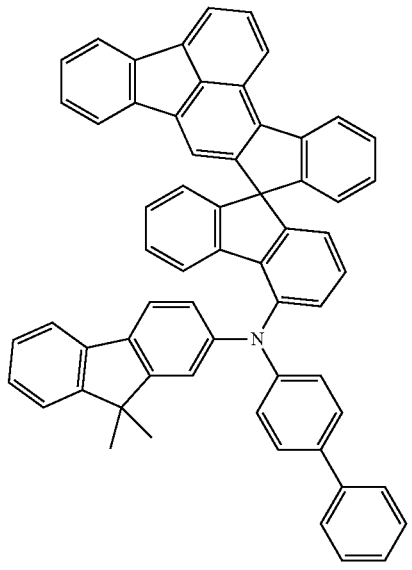

1-61
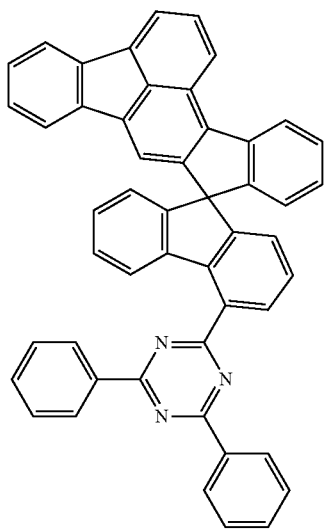
1-62
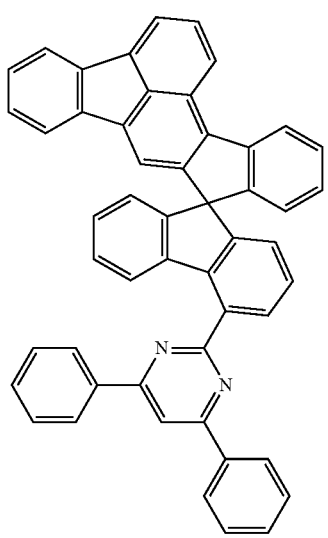
1-63
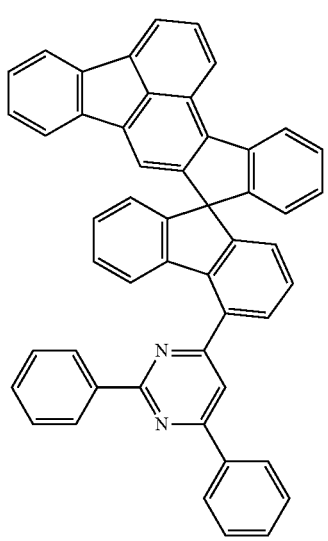
1-64
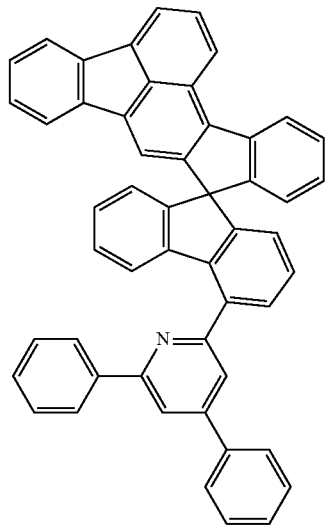
1-65
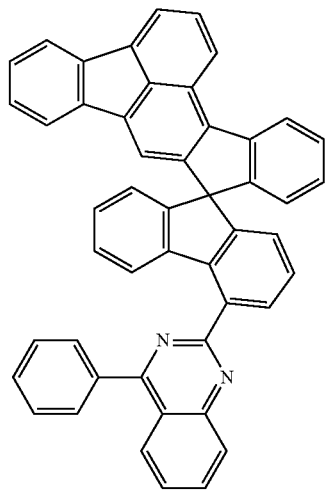
1-66
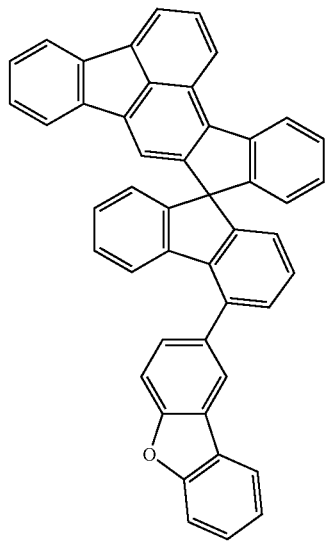

1-67
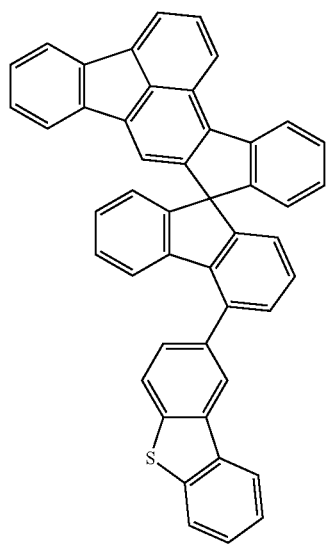
1-68
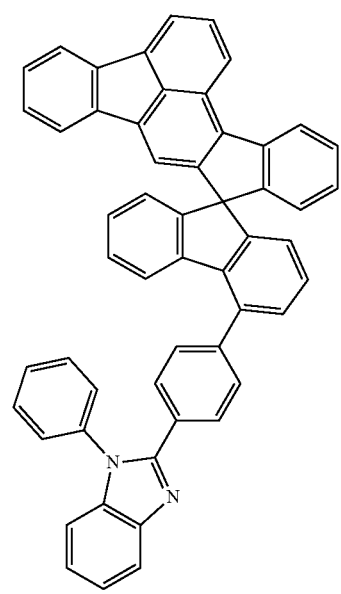
2-1
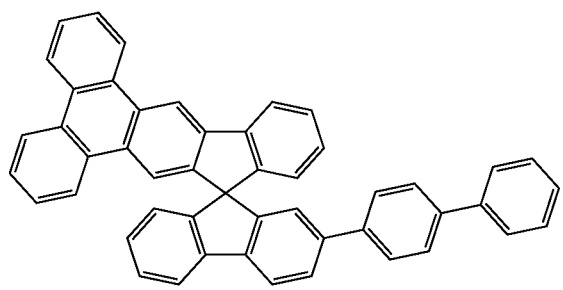
2-2
2-3
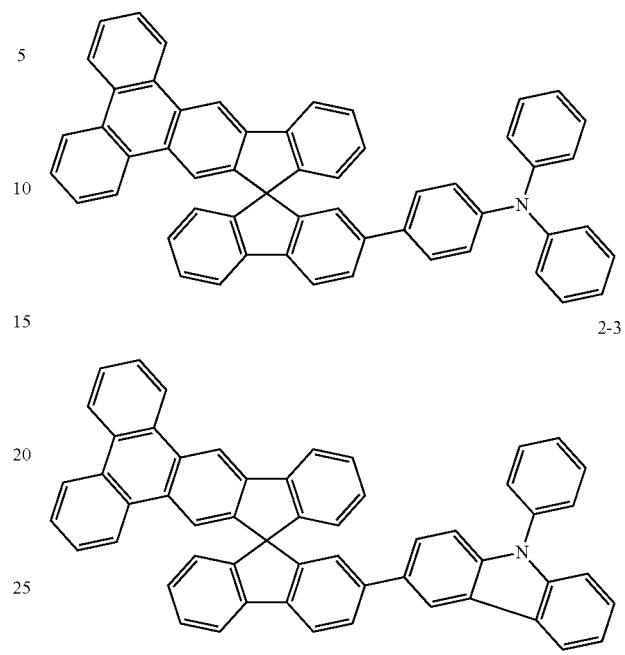
2-4
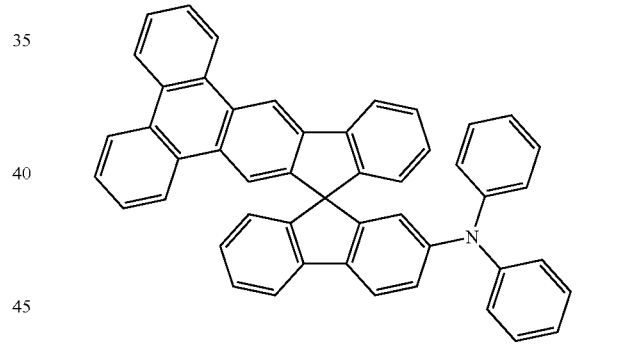
2-5
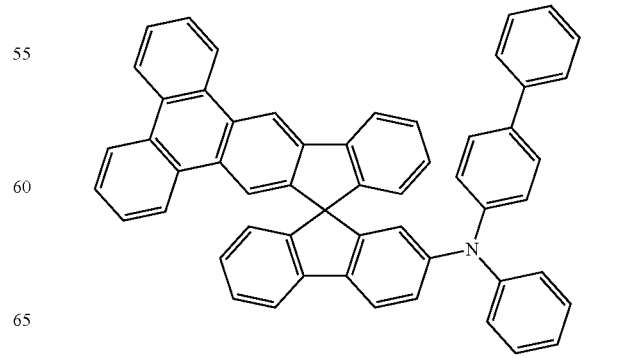

2-6
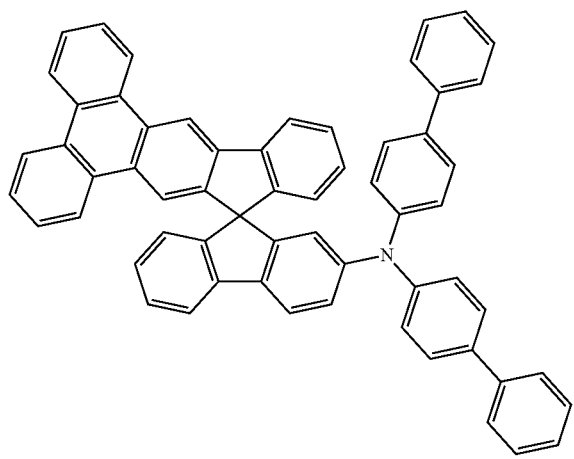
2-9
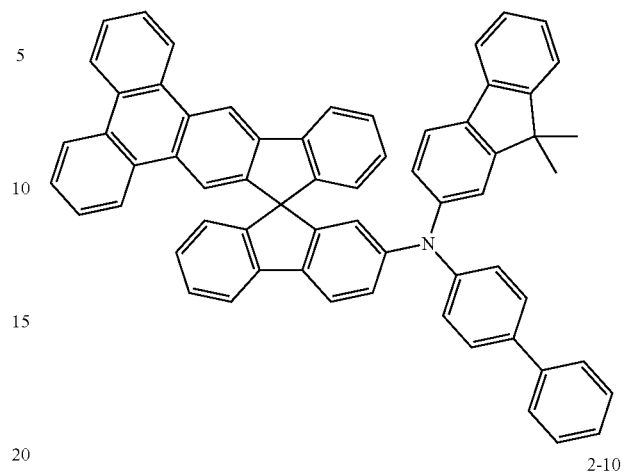
2-7
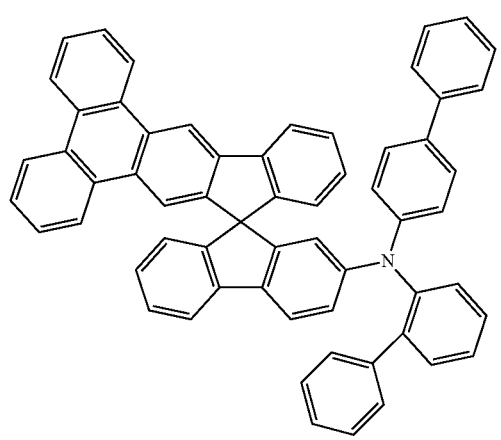
2-10
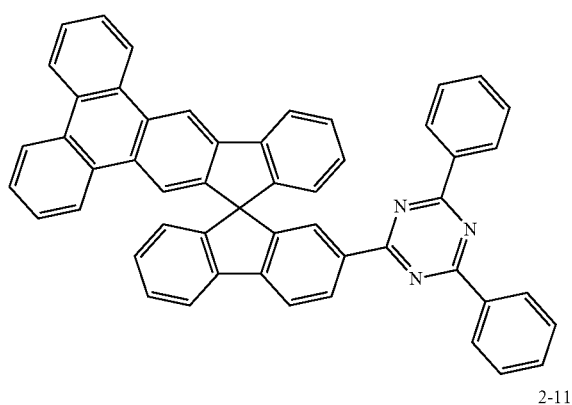
2-11
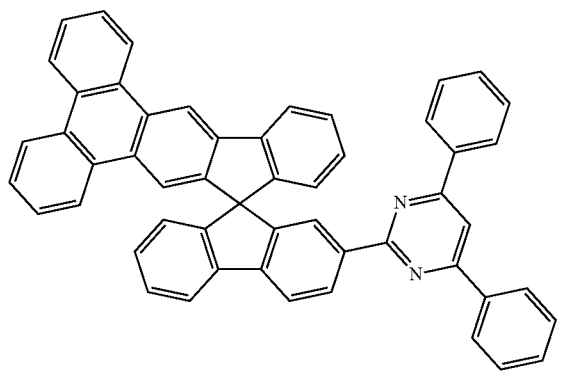
2-8
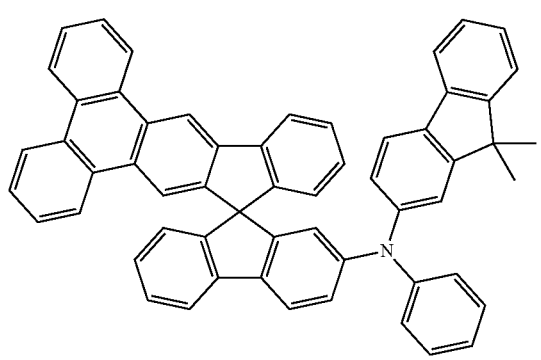
2-12
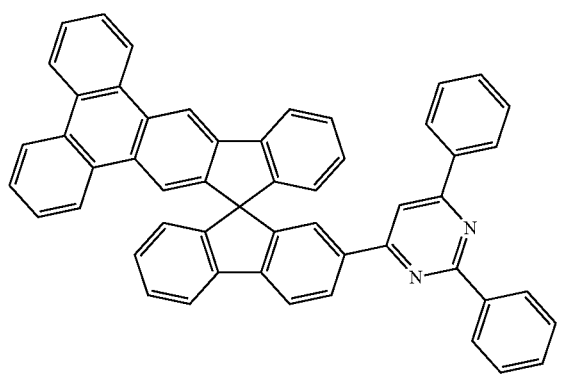

2-13
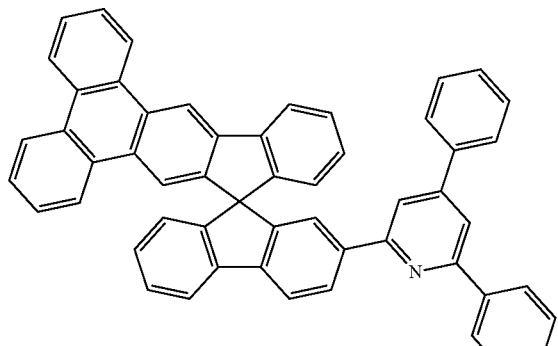
2-14
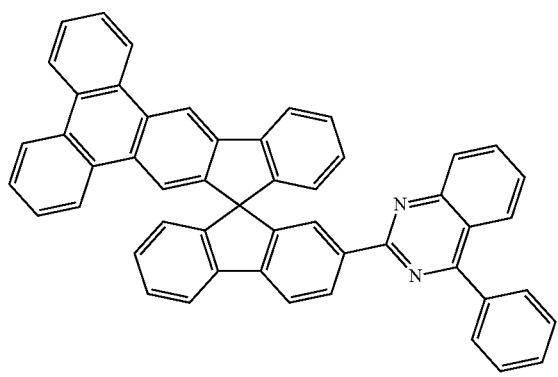
2-15
2-16
2-17
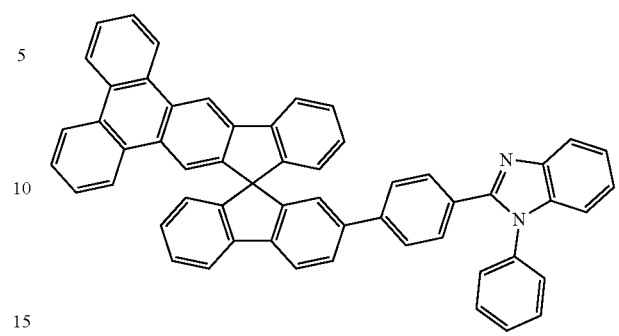
2-18
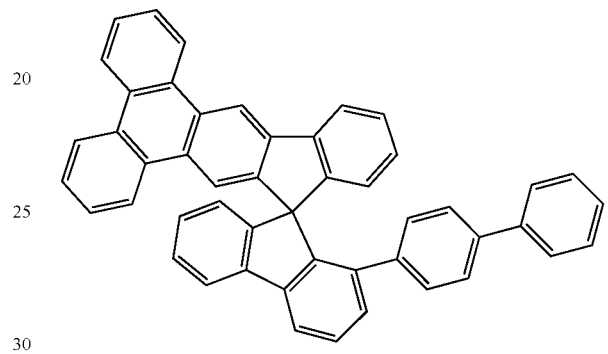
2-19
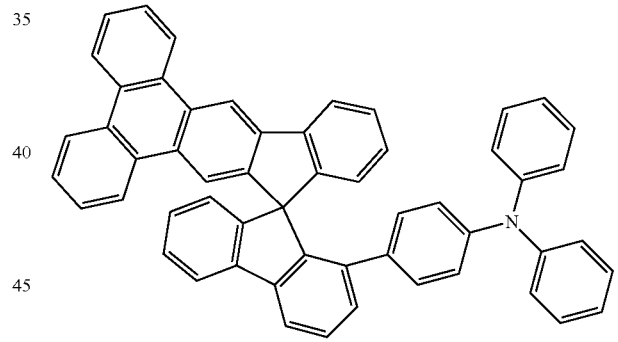
2-20
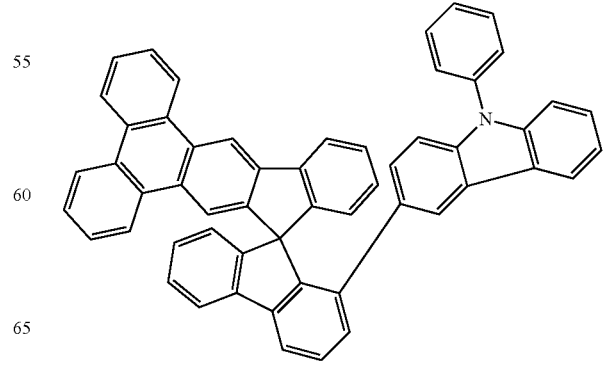

2-21
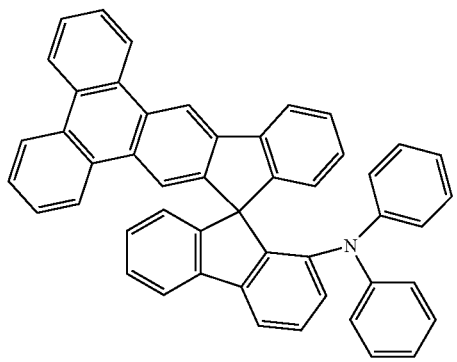
2-22
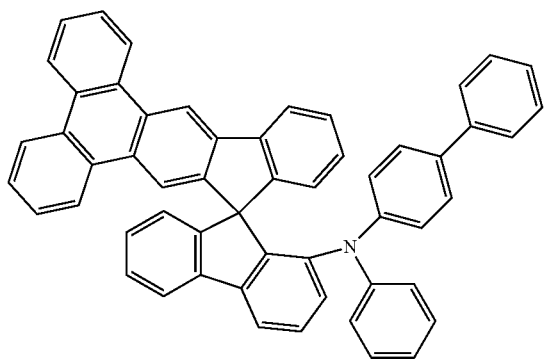
2-23
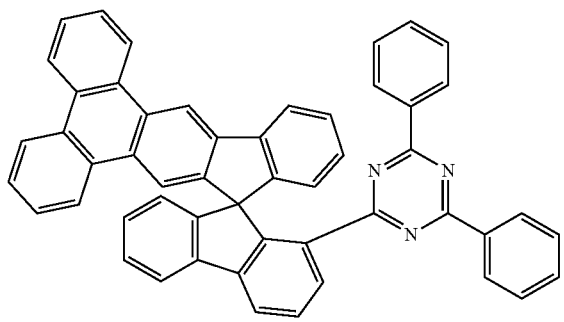
2-24
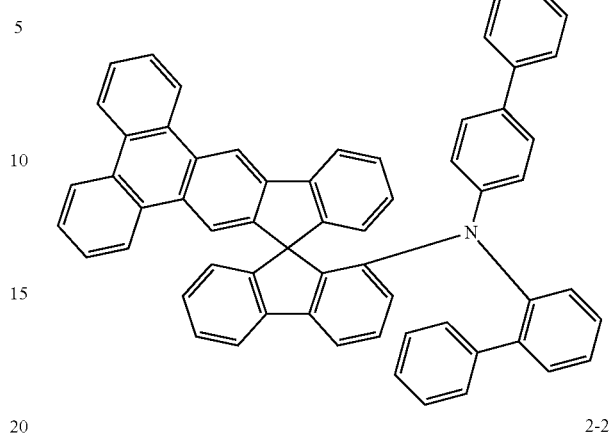
2-25
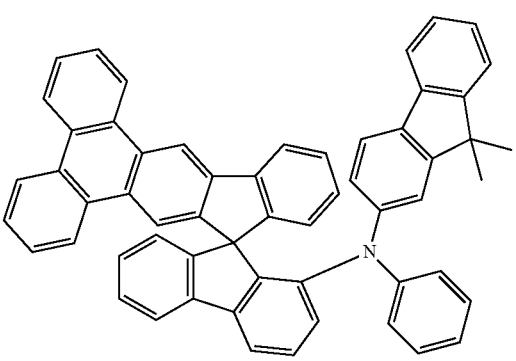
2-26
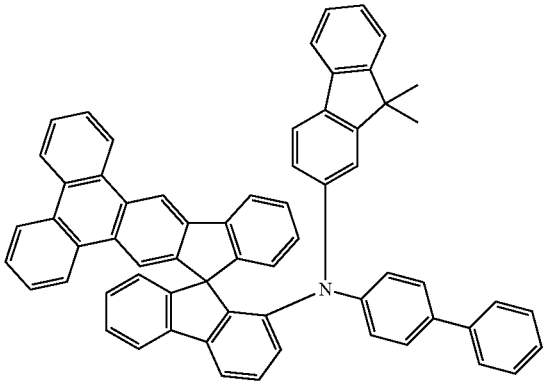
2-27
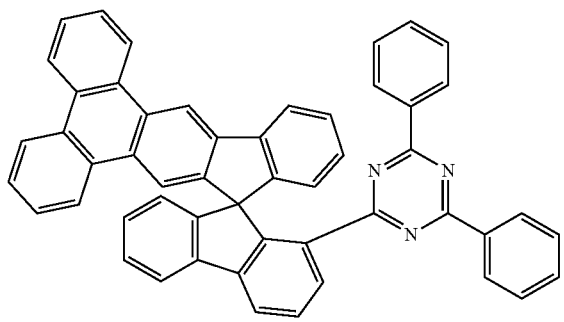

2-28
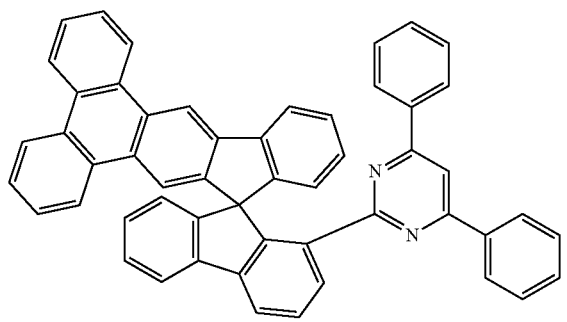
2-29
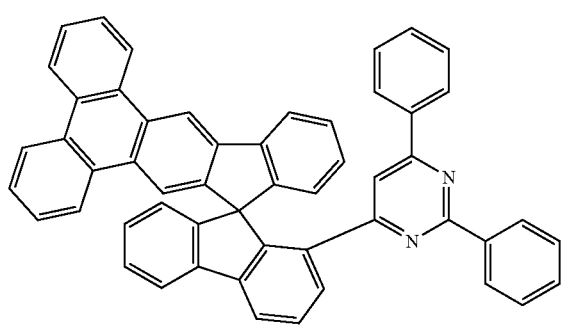
2-30
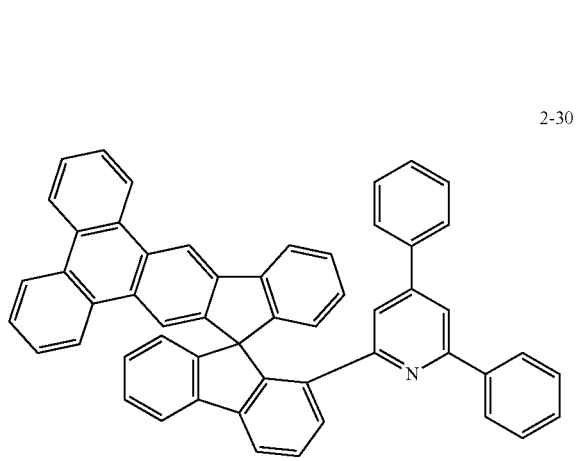
2-31
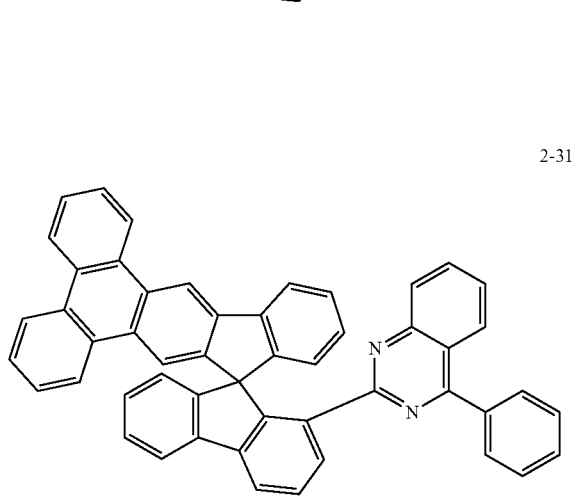
2-32
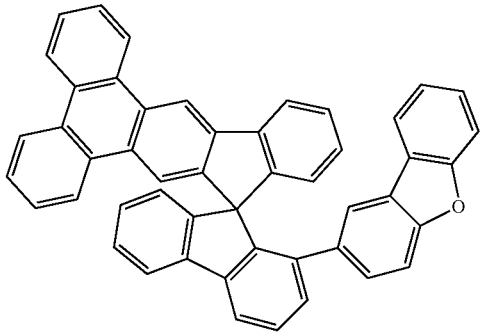
2-33
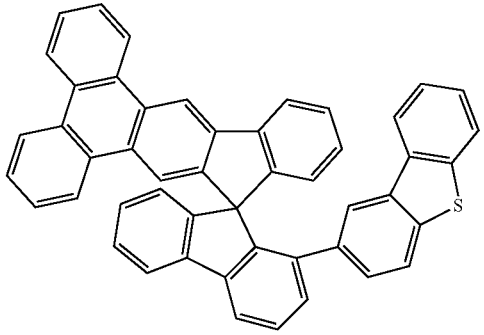
2-34
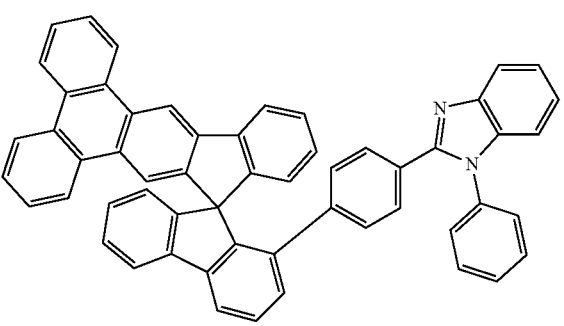
2-35
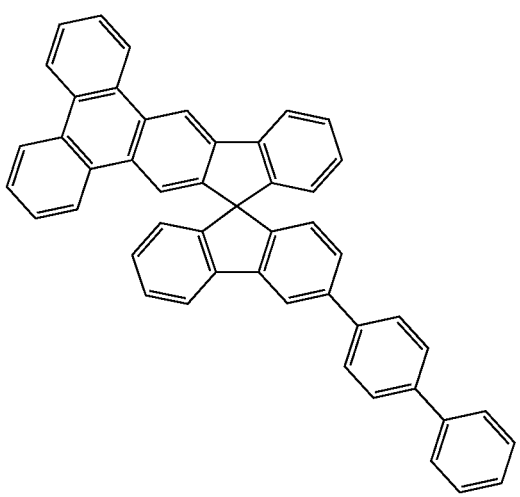

265
-continued
2-36
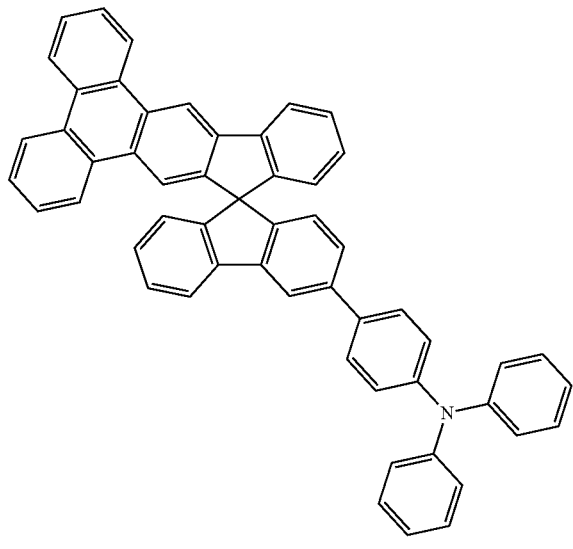
2-37
2-38
266
-continued
2-39
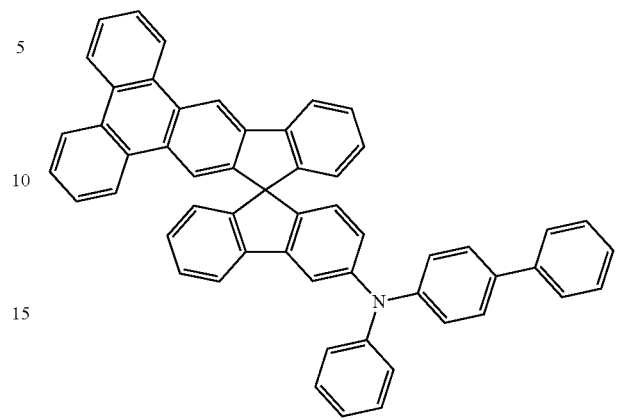
2-40
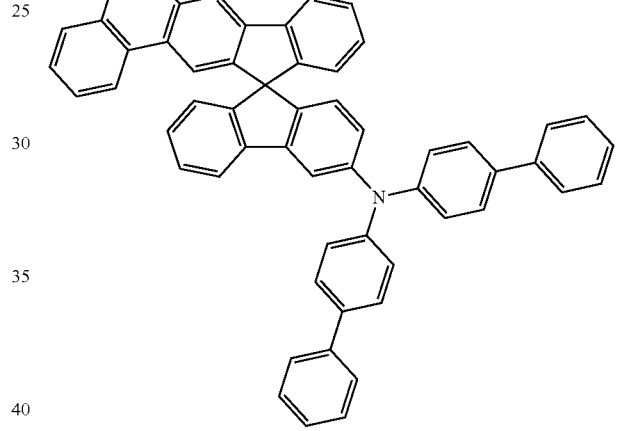
2-41
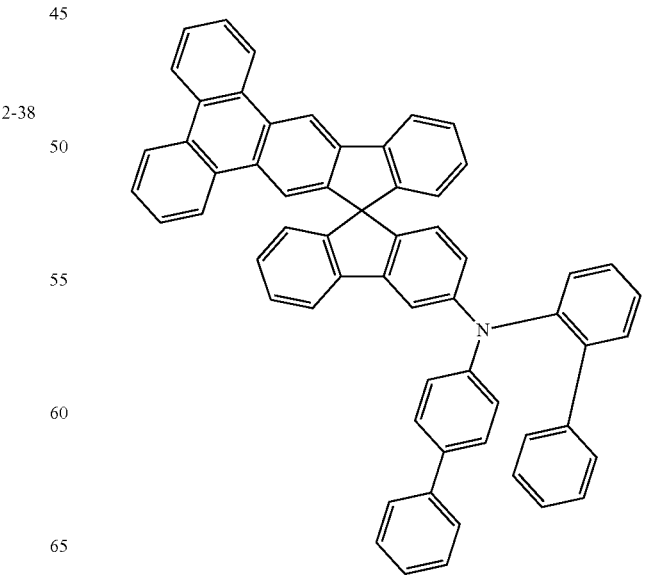

-continued
2-42
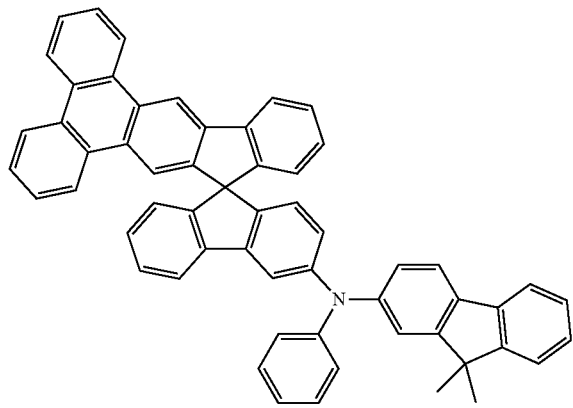
2-43
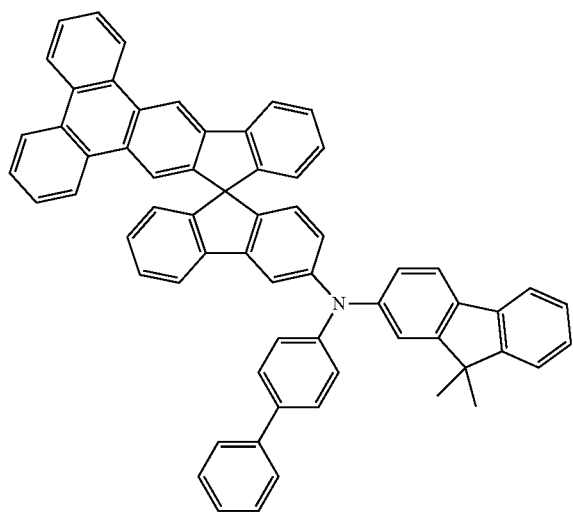
2-44
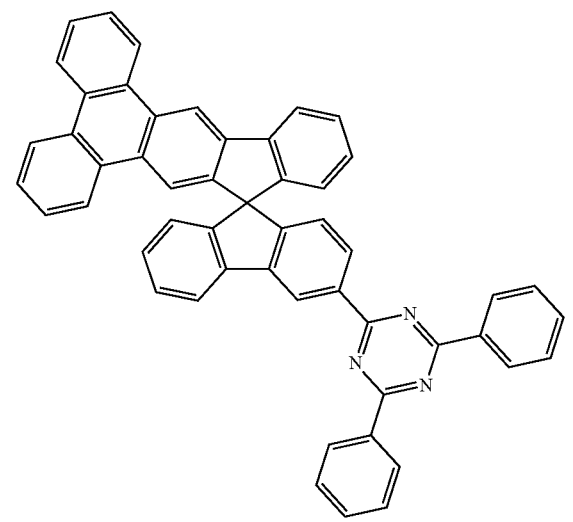
-continued
2-45
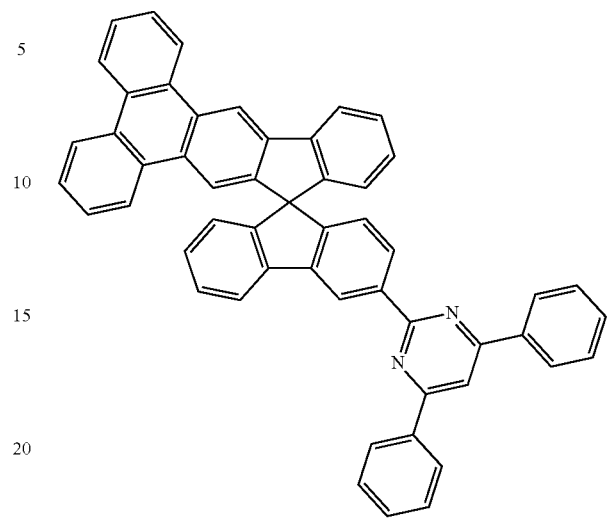
2-46
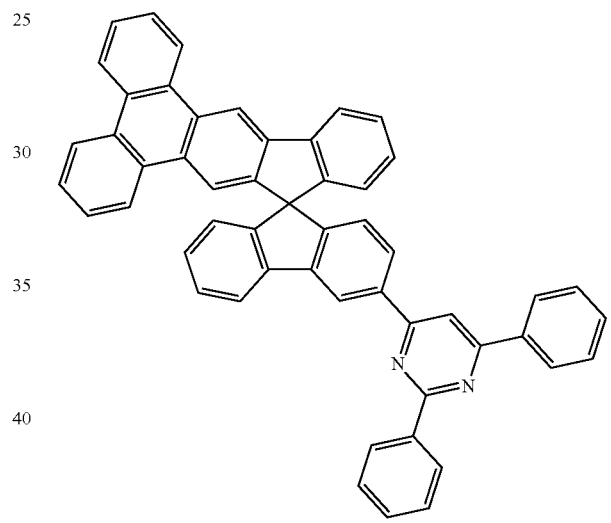
2-47
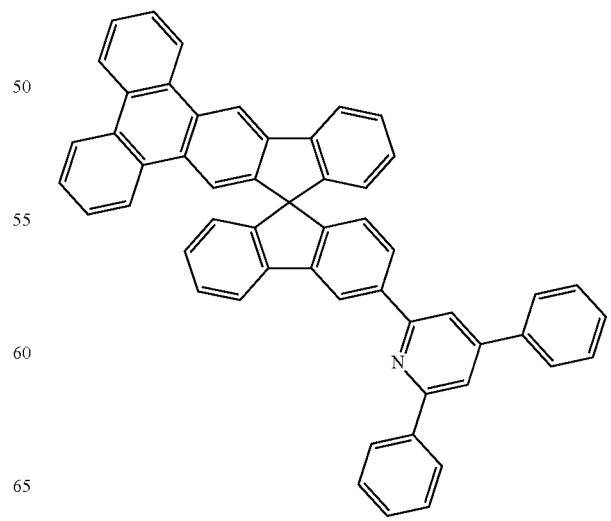

2-48
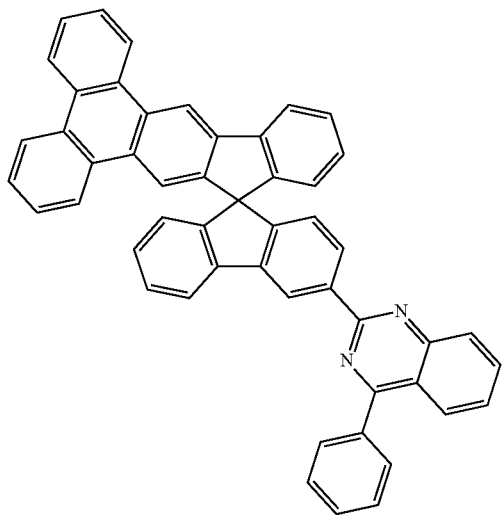
2-51
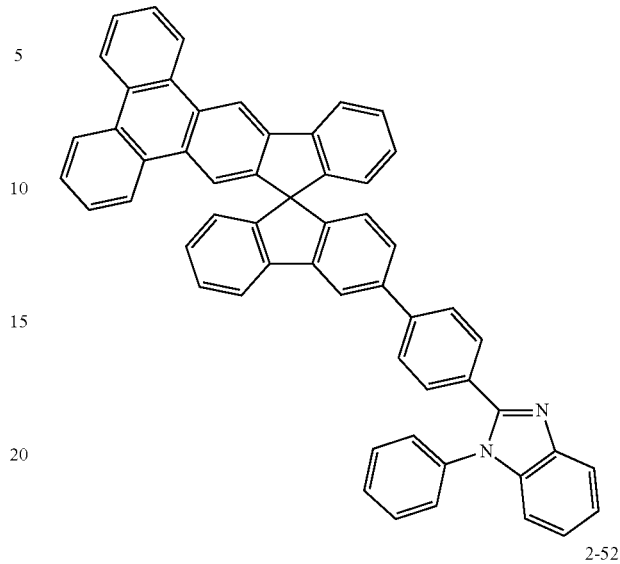
2-49
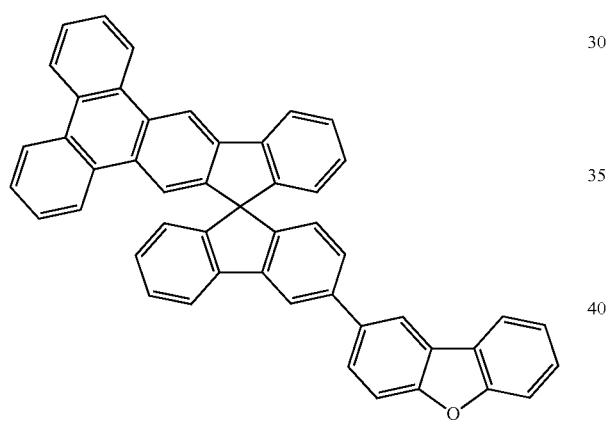
2-52
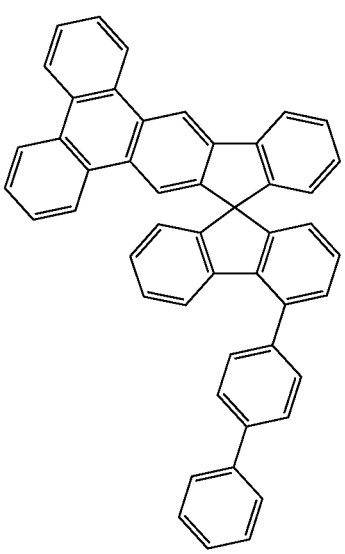
2-50
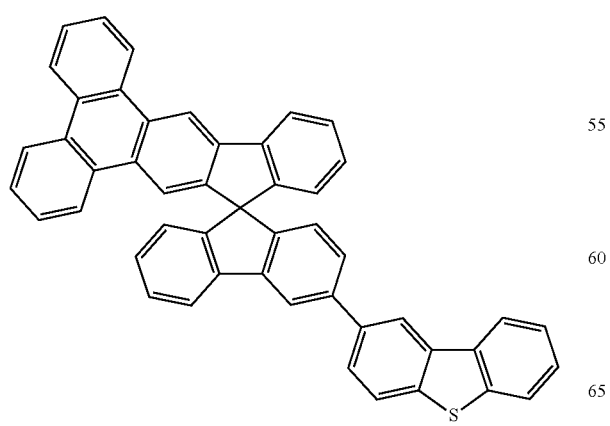
2-53
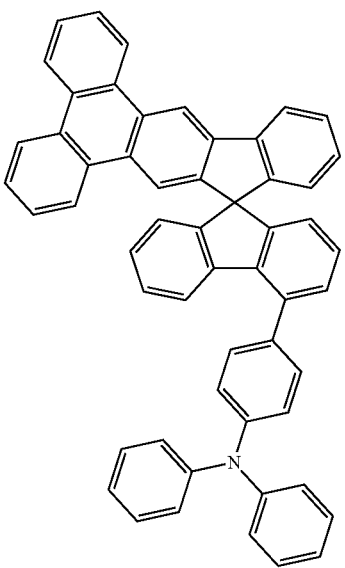

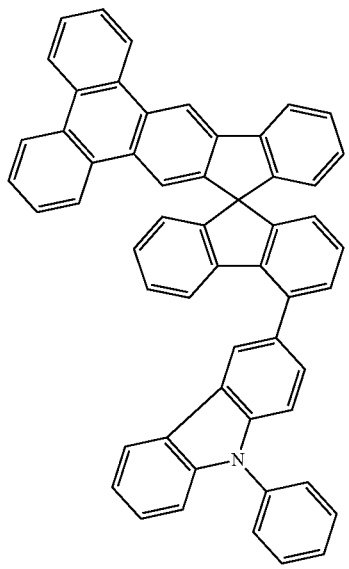
2-54
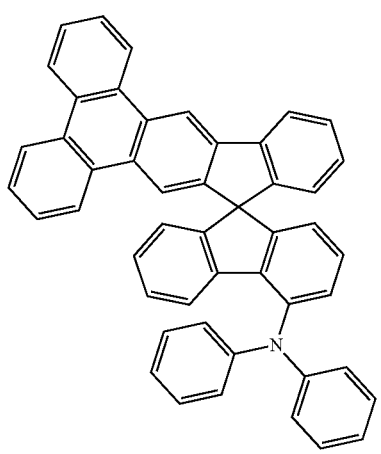
2-55
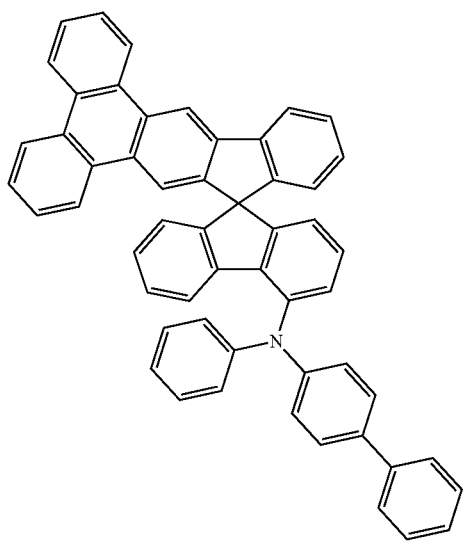
2-56
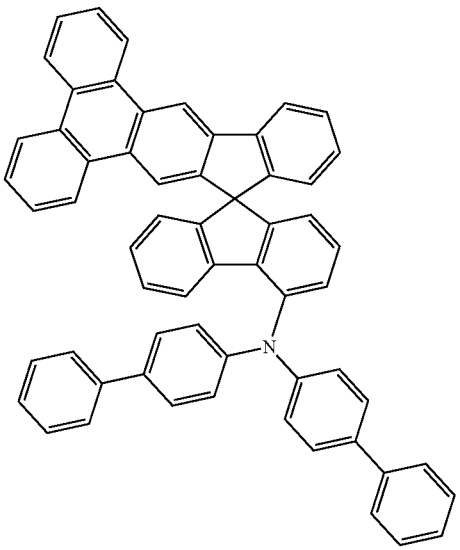
2-57
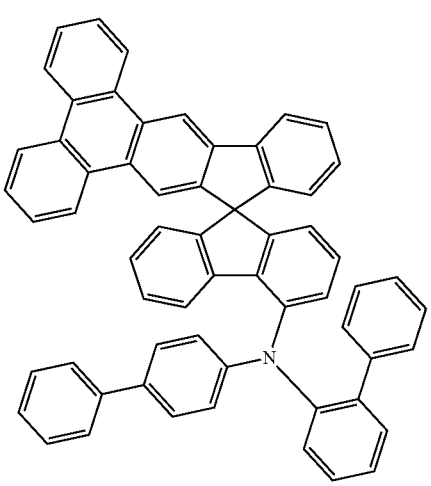
2-58
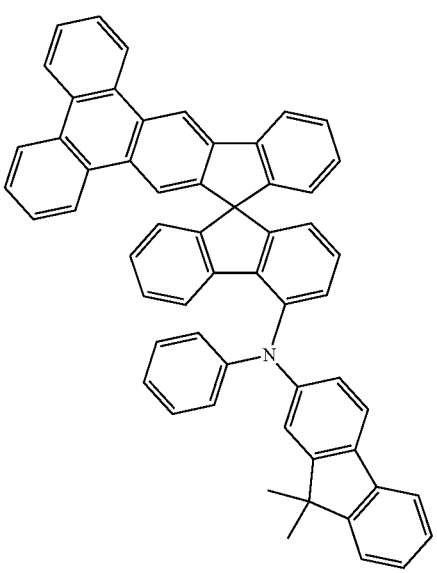
2-59

2-60
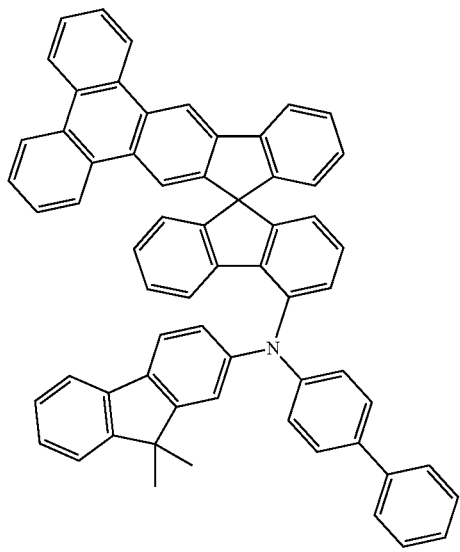
2-61
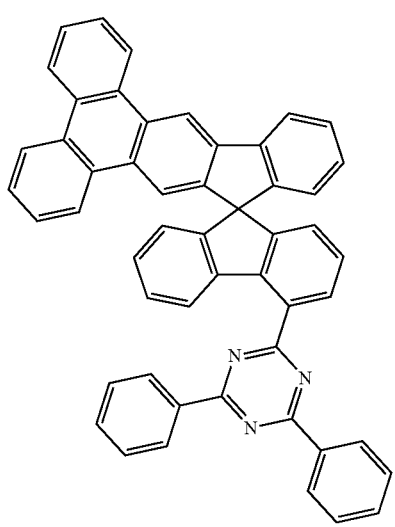
2-62
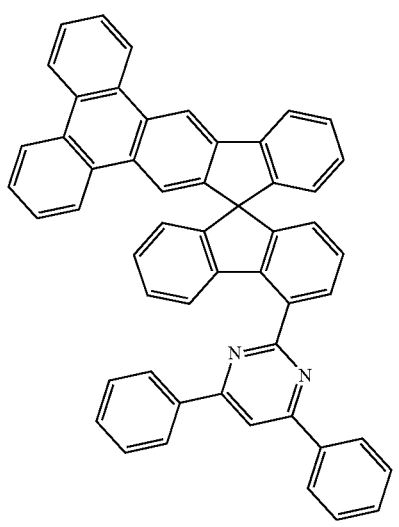
2-63
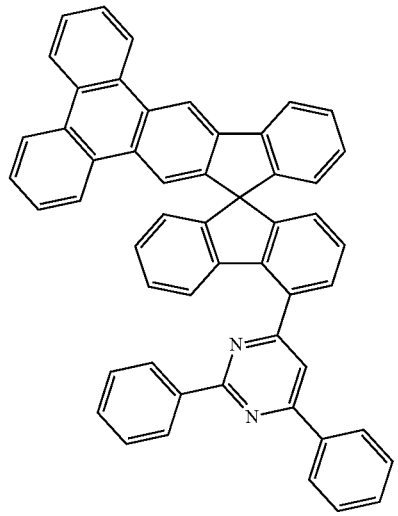
2-64
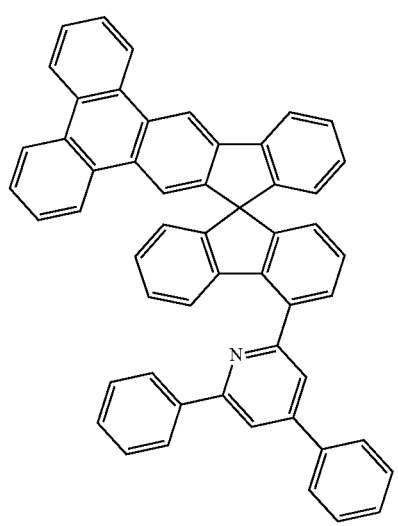
2-65

-continued

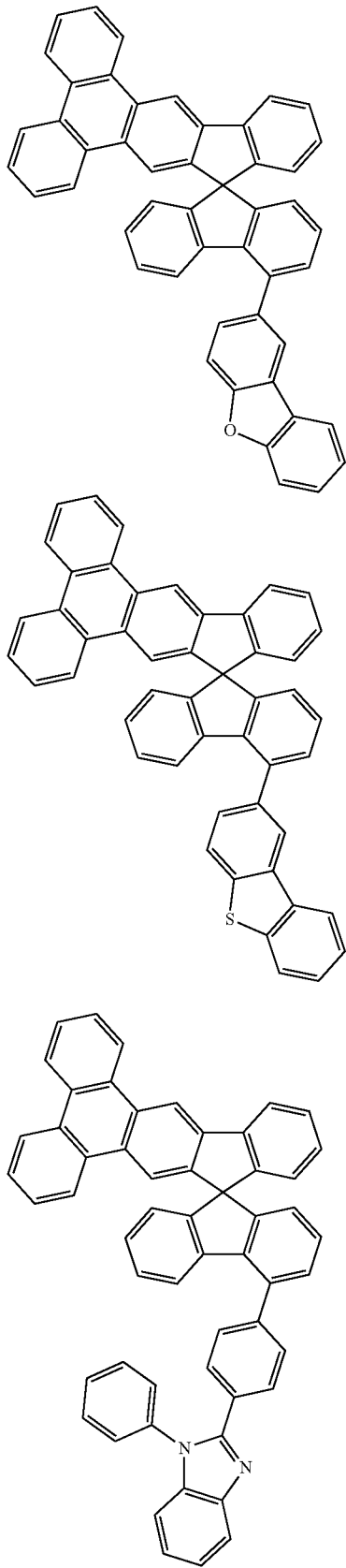

Preparation Example 137

Preparation of Compound 1-69

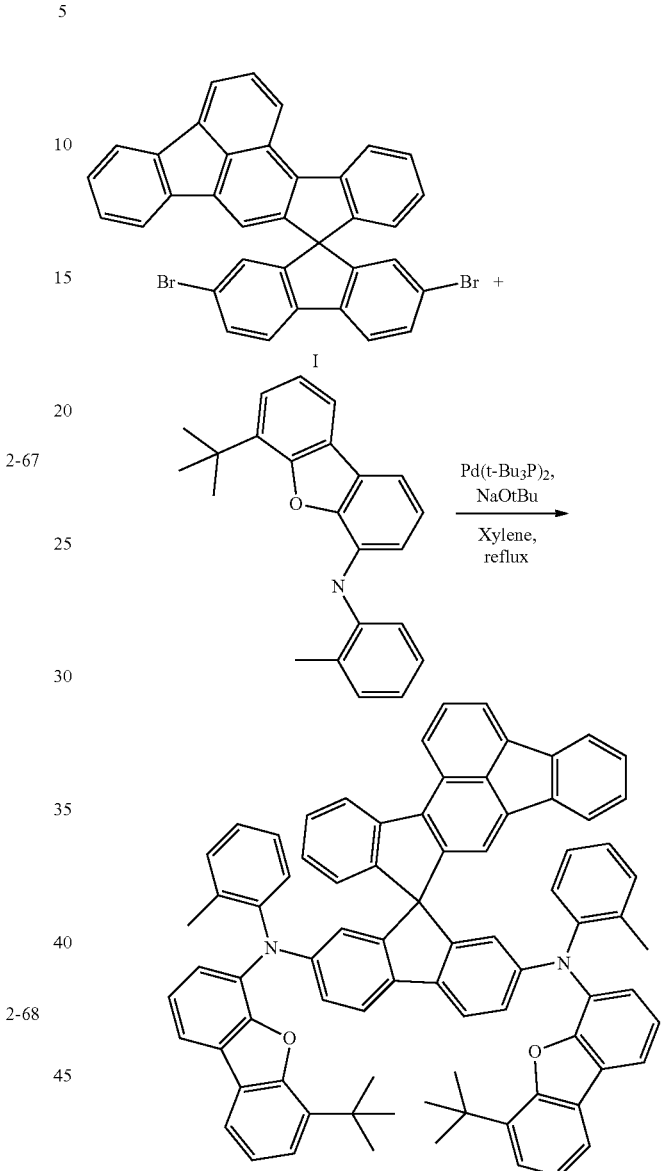

[Compound 1-69]

Compound I (5.21 g, 8.74 mmol) and 6-(tert-butyl)-N-(o-tolyl)dibenzo[b,d]furan-4-amine (6.04 g, 18.36 mmol) were completely dissolved in 160 ml of xylene in a 500-ml round bottom flask under a nitrogen atmosphere, and then sodium tert-butoxide (2.02 g, 20.98 mmol) was added thereto, bis(tri-tert-butylphosphine) palladium(0) (0.04 g, 0.09 mmol) were put thereinto, and then the resulting mixture was heated and stirred for 3 hours. The temperature was lowered to normal temperature, the mixture was filtered to remove the base, and then xylene was concentrated under reduced pressure, and the residue was purified by column chromatography at a ratio of tetrahydrofuran:hexane=1:25 to prepare Compound 1-69 (4.59 g, purity: 99.99%, yield: 64%).

MS[M+H]$^+$=1095

Preparation Example 138

Preparation of Compound 1-70

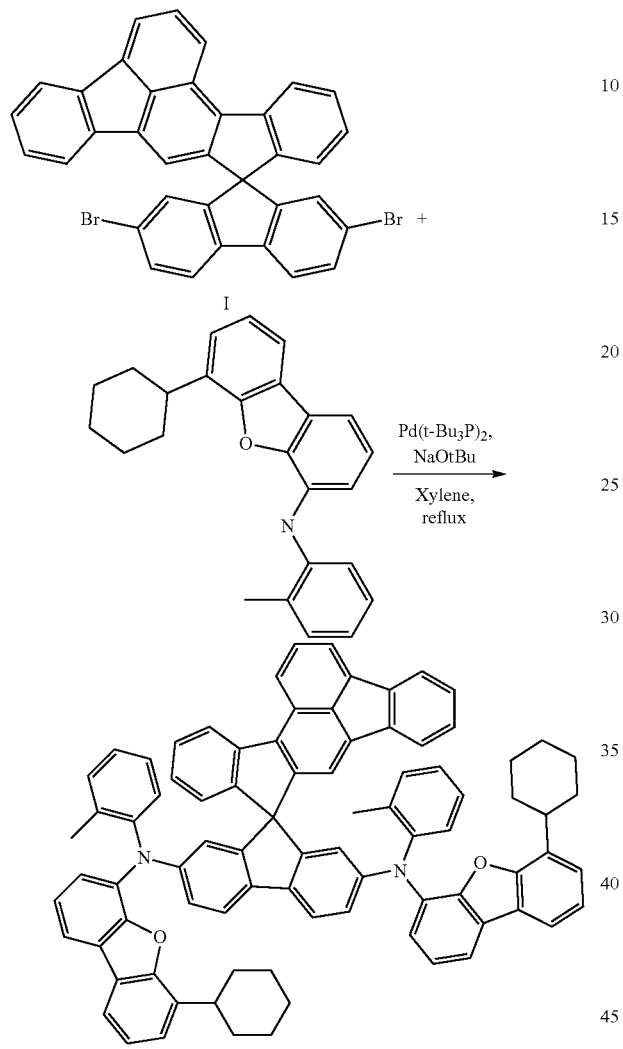

[Compound 1-70]

Preparation Example 139

Preparation of Compound 1-71

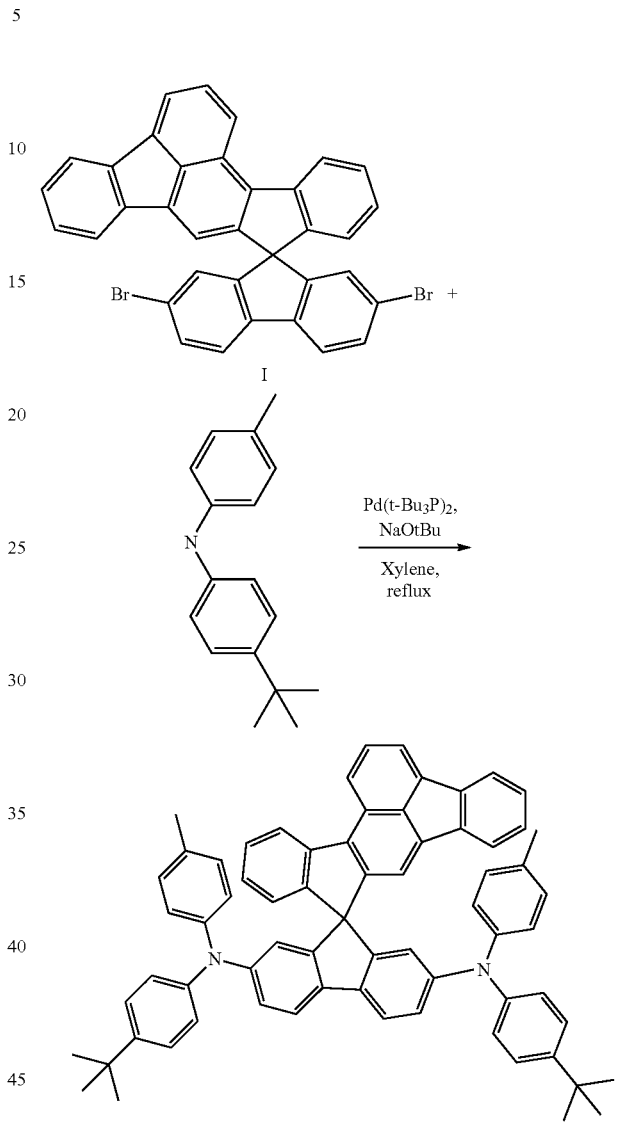

[Compound 1-71]

Compound I (4.35 g, 7.30 mmol) and 6-cyclohexyl-N-(o-tolyl)dibenzo[b,d]furan-4-amine (5.44 g, 15.33 mmol) were completely dissolved in 170 ml of xylene in a 500-ml round bottom flask under a nitrogen atmosphere, and then sodium tert-butoxide (1.68 g, 17.52 mmol) was added thereto, bis(tri-tert-butylphosphine) palladium(0) (0.04 g, 0.07 mmol) were put thereinto, and then the resulting mixture was heated and stirred for 4 hours. The temperature was lowered to normal temperature, the mixture was filtered to remove the base, and then xylene was concentrated under reduced pressure, and the residue was purified by column chromatography at a ratio of tetrahydrofuran:hexane=1:20 to prepare Compound 1-70 (3.32 g, purity: 99.98%, yield: 42%).

MS[M+H]$^+$=1147

Compound I (5.36 g, 8.99 mmol) and 4-(tert-butyl)-N-(p-tolyl)aniline (4.51 g, 18.89 mmol) were completely dissolved in 210 ml of xylene in a 500-ml round bottom flask under a nitrogen atmosphere, and then sodium tert-butoxide (2.07 g, 21.58 mmol) was added thereto, bis(tri-tert-butylphosphine) palladium(0) (0.05 g, 0.09 mmol) were put thereinto, and then the resulting mixture was heated and stirred for 3 hours. The temperature was lowered to normal temperature, the mixture was filtered to remove the base, and then xylene was concentrated under reduced pressure, and the residue was purified by column chromatography at a ratio of tetrahydrofuran:hexane=1:35 to prepare Compound 1-71 (2.67 g, purity: 99.99%, yield: 32%).

MS[M+H]$^+$=915

Preparation Example 140

Preparation of Compound 1-72

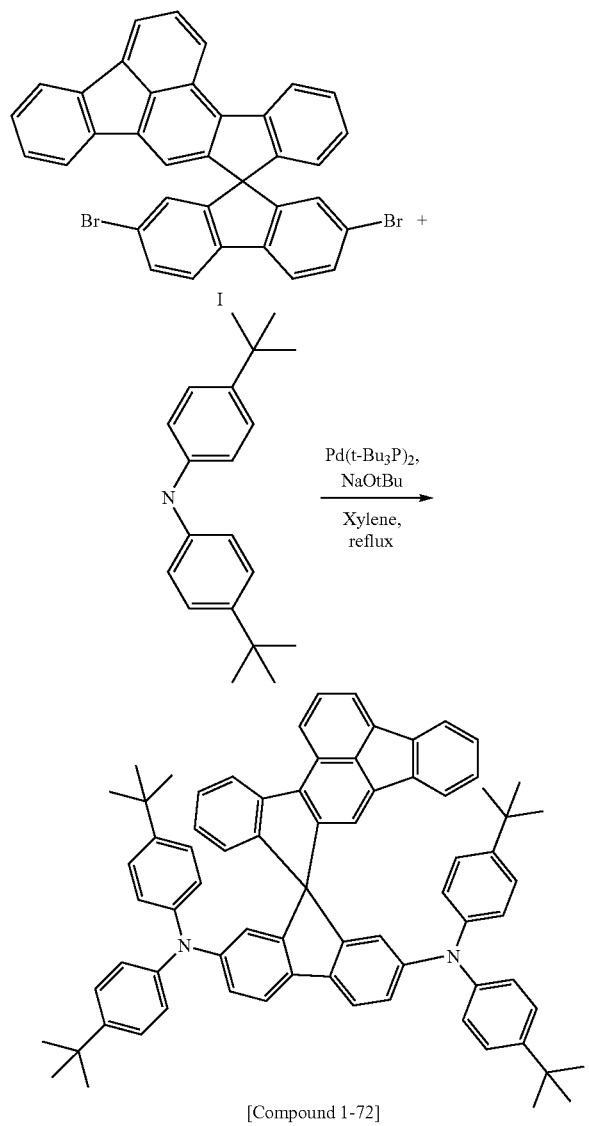

[Compound 1-72]

Compound I (4.81 g, 8.07 mmol) and bis(4-(tert-butyl)phenyl)amine (4.76 g, 16.95 mmol) were completely dissolved in 180 ml of xylene in a 500-ml round bottom flask under a nitrogen atmosphere, and then sodium tert-butoxide (1.86 g, 19.37 mmol) was added thereto, bis(tri-tert-butylphosphine) palladium(0) (0.04 g, 0.08 mmol) were put thereinto, and then the resulting mixture was heated and stirred for 5 hours. The temperature was lowered to normal temperature, the mixture was filtered to remove the base, and then xylene was concentrated under reduced pressure, and the residue was purified by column chromatography at a ratio of tetrahydrofuran:hexane=1:30 to prepare Compound 1-72 (3.47 g, purity: 99.99%, yield: 43%).

MS[M+H]$^+$=999

Preparation Example 141

Preparation of Compound 2-69

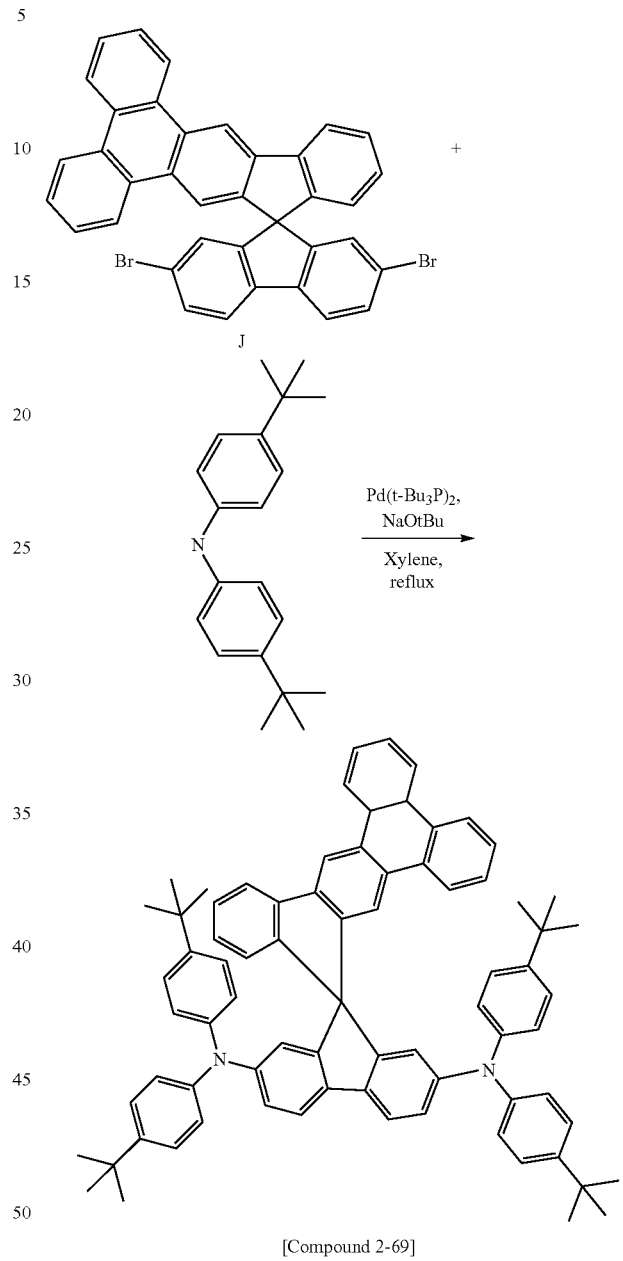

[Compound 2-69]

Compound J (3.57 g, 5.74 mmol) and bis(4-(tert-butyl)phenyl)amine (3.39 g, 12.05 mmol) were completely dissolved in 200 ml of xylene in a 500-ml round bottom flask under a nitrogen atmosphere, and then sodium tert-butoxide (1.32 g, 13.77 mmol) was added thereto, bis(tri-tert-butylphosphine) palladium(0) (0.03 g, 0.06 mmol) were put thereinto, and then the resulting mixture was heated and stirred for 4 hours. The temperature was lowered to normal temperature, the mixture was filtered to remove the base, and then xylene was concentrated under reduced pressure, and the residue was purified by column chromatography at a ratio of tetrahydrofuran:hexane=1:35 to prepare Compound 2-69 (3.47 g, purity: 99.99%, yield: 58%).

MS[M+H]$^+$=1025

Preparation Example 142

Compound 2-70

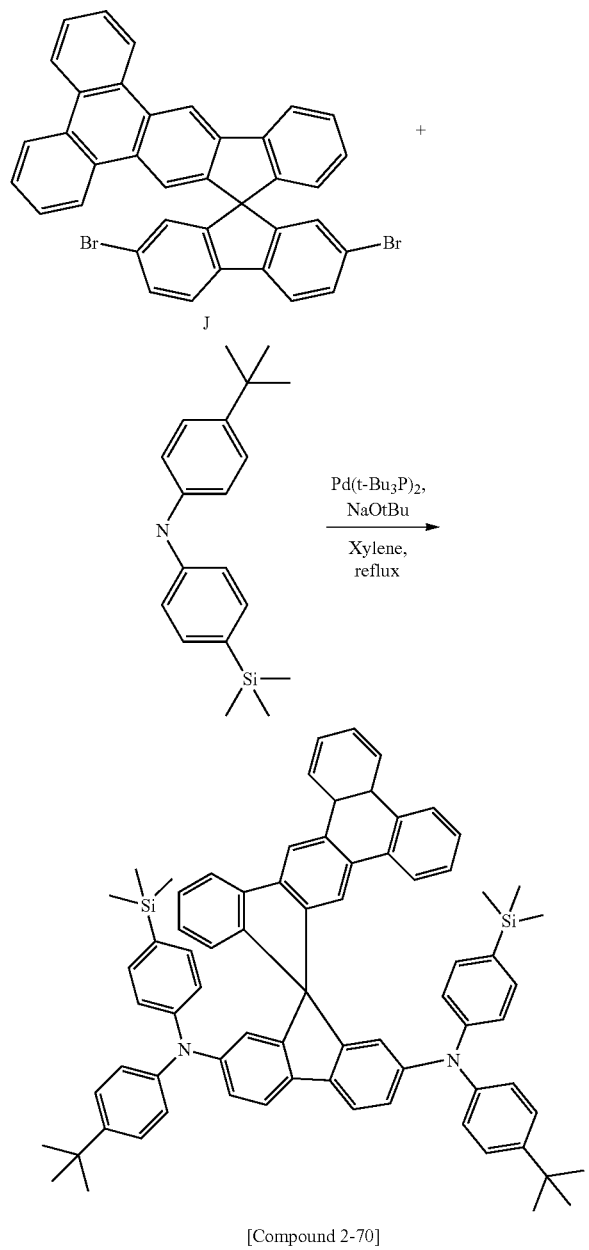

[Compound 2-70]

Compound J (3.64 g, 5.85 mmol) and 4-(tert-butyl)-N-(4-(trimethylsilyl)phenyl)aniline (3.65 g, 12.29 mmol) were completely dissolved in 230 ml of xylene in a 500-ml round bottom flask under a nitrogen atmosphere, and then sodium tert-butoxide (1.35 g, 14.05 mmol) was added thereto, bis(tri-tert-butylphosphine) palladium(0) (0.03 g, 0.06 mmol) were put thereinto, and then the resulting mixture was heated and stirred for 4 hours. The temperature was lowered to normal temperature, the mixture was filtered to remove the base, and then xylene was concentrated under reduced pressure, and the residue was purified by column chromatography at a ratio of tetrahydrofuran:hexane=1:25 to prepare Compound 2-70 (4.26 g, purity: 99.99%, yield: 69%).

Experimental Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

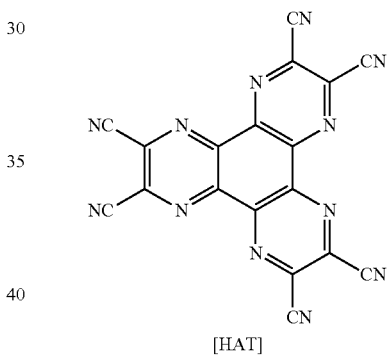

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transport layer.

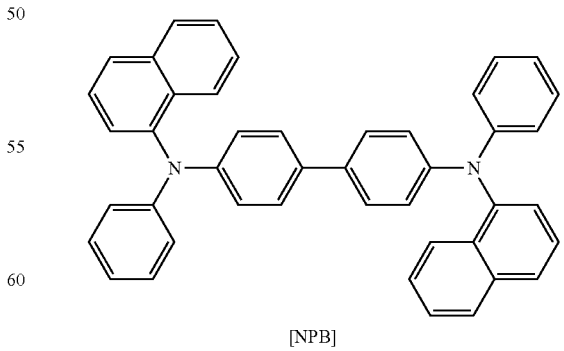

[NPB]

Subsequently, the following Compound 1-2 was vacuum deposited to have a film thickness of 100 Å on the hole transport layer, thereby forming an electron blocking layer.

[Compound 1-2]

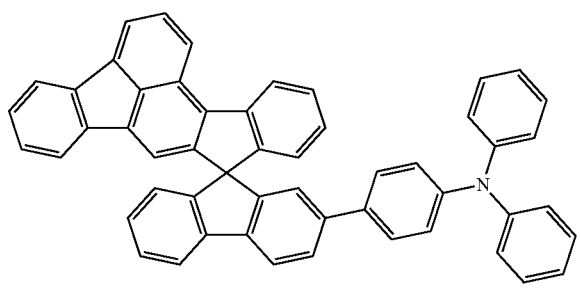

Subsequently, the following BH and BD were vacuum deposited at a weight ratio of 25:1 to have a film thickness of 300 Å on the electron blocking layer, thereby forming a light emitting layer.

[BH]

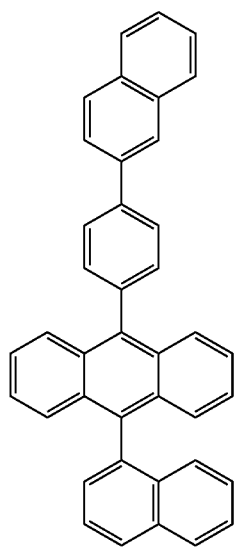

[BD]

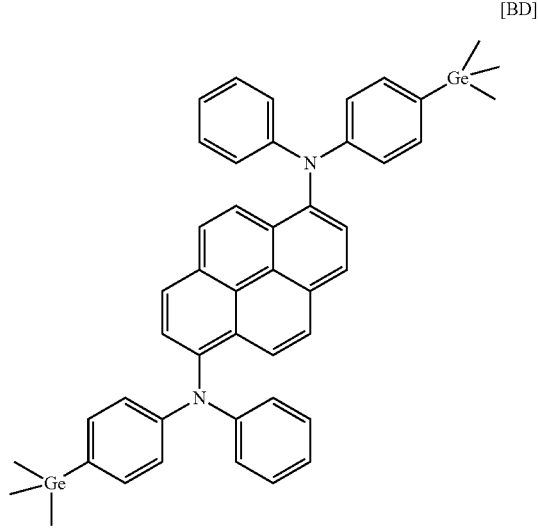

[ET1]

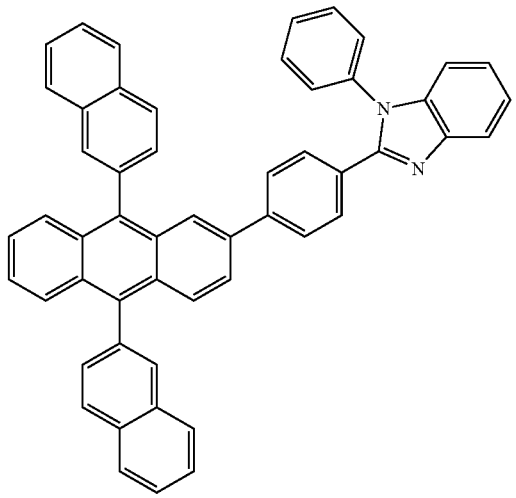

[LiQ]

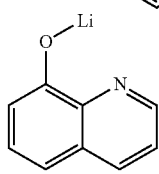

Compound ET1 and Compound LiQ (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

Experimental Example 1-2

An organic light emitting device was manufactured in the same manner as in Experimental Example 1-1, except that Compound 1-3 was used instead of Compound 1-2 in Experimental Example 1-1.

Experimental Example 1-3

An organic light emitting device was manufactured in the same manner as in Experimental Example 1-1, except that Compound 1-4 was used instead of Compound 1-2 in Experimental Example 1-1.

Experimental Example 1-4

An organic light emitting device was manufactured in the same manner as in Experimental Example 1-1, except that Compound 1-5 was used instead of Compound 1-2 in Experimental Example 1-1.

Experimental Example 1-5

An organic light emitting device was manufactured in the same manner as in Experimental Example 1-1, except that Compound 1-6 was used instead of Compound 1-2 in Experimental Example 1-1.

Experimental Example 1-6

An organic light emitting device was manufactured in the same manner as in Experimental Example 1-1, except that Compound 1-7 was used instead of Compound 1-2 in Experimental Example 1-1.

Experimental Example 1-7

An organic light emitting device was manufactured in the same manner as in Experimental Example 1-1, except that Compound 1-8 was used instead of Compound 1-2 in Experimental Example 1-1.

Experimental Example 1-8

An organic light emitting device was manufactured in the same manner as in Experimental Example 1-1, except that Compound 1-9 was used instead of Compound 1-2 in Experimental Example 1-1.

Experimental Example 1-9

An organic light emitting device was manufactured in the same manner as in Experimental Example 1-1, except that Compound 1-19 was used instead of Compound 1-2 in Experimental Example 1-1.

Experimental Example 1-10

An organic light emitting device was manufactured in the same manner as in Experimental Example 1-1, except that Compound 1-20 was used instead of Compound 1-2 in Experimental Example 1-1.

Experimental Example 1-11

An organic light emitting device was manufactured in the same manner as in Experimental Example 1-1, except that Compound 1-21 was used instead of Compound 1-2 in Experimental Example 1-1.

Experimental Example 1-12

An organic light emitting device was manufactured in the same manner as in Experimental Example 1-1, except that Compound 1-22 was used instead of Compound 1-2 in Experimental Example 1-1.

Experimental Example 1-13

An organic light emitting device was manufactured in the same manner as in Experimental Example 1-1, except that Compound 1-23 was used instead of Compound 1-2 in Experimental Example 1-1.

Experimental Example 1-14

An organic light emitting device was manufactured in the same manner as in Experimental Example 1-1, except that Compound 1-24 was used instead of Compound 1-2 in Experimental Example 1-1.

Experimental Example 1-15

An organic light emitting device was manufactured in the same manner as in Experimental Example 1-1, except that Compound 1-25 was used instead of Compound 1-2 in Experimental Example 1-1.

Experimental Example 1-16

An organic light emitting device was manufactured in the same manner as in Experimental Example 1-1, except that Compound 1-26 was used instead of Compound 1-2 in Experimental Example 1-1.

Experimental Example 1-17

An organic light emitting device was manufactured in the same manner as in Experimental Example 1-1, except that Compound 1-36 was used instead of Compound 1-2 in Experimental Example 1-1.

Experimental Example 1-18

An organic light emitting device was manufactured in the same manner as in Experimental Example 1-1, except that Compound 1-37 was used instead of Compound 1-2 in Experimental Example 1-1.

Experimental Example 1-19

An organic light emitting device was manufactured in the same manner as in Experimental Example 1-1, except that Compound 1-38 was used instead of Compound 1-2 in Experimental Example 1-1.

Experimental Example 1-20

An organic light emitting device was manufactured in the same manner as in Experimental Example 1-1, except that Compound 1-39 was used instead of Compound 1-2 in Experimental Example 1-1.

Experimental Example 1-21

An organic light emitting device was manufactured in the same manner as in Experimental Example 1-1, except that Compound 1-40 was used instead of Compound 1-2 in Experimental Example 1-1.

Experimental Example 1-22

An organic light emitting device was manufactured in the same manner as in Experimental Example 1-1, except that Compound 1-41 was used instead of Compound 1-2 in Experimental Example 1-1.

Experimental Example 1-23

An organic light emitting device was manufactured in the same manner as in Experimental Example 1-1, except that Compound 1-42 was used instead of Compound 1-2 in Experimental Example 1-1.

Experimental Example 1-24

An organic light emitting device was manufactured in the same manner as in Experimental Example 1-1, except that Compound 1-43 was used instead of Compound 1-2 in Experimental Example 1-1.

Experimental Example 1-25

An organic light emitting device was manufactured in the same manner as in Experimental Example 1-1, except that Compound 1-53 was used instead of Compound 1-2 in Experimental Example 1-1.

Experimental Example 1-26

An organic light emitting device was manufactured in the same manner as in Experimental Example 1-1, except that Compound 1-54 was used instead of Compound 1-2 in Experimental Example 1-1.

Experimental Example 1-27

An organic light emitting device was manufactured in the same manner as in Experimental Example 1-1, except that Compound 1-55 was used instead of Compound 1-2 in Experimental Example 1-1.

Experimental Example 1-28

An organic light emitting device was manufactured in the same manner as in Experimental Example 1-1, except that Compound 1-56 was used instead of Compound 1-2 in Experimental Example 1-1.

Experimental Example 1-29

An organic light emitting device was manufactured in the same manner as in Experimental Example 1-1, except that Compound 1-57 was used instead of Compound 1-2 in Experimental Example 1-1.

Experimental Example 1-30

An organic light emitting device was manufactured in the same manner as in Experimental Example 1-1, except that Compound 1-58 was used instead of Compound 1-2 in Experimental Example 1-1.

Experimental Example 1-31

An organic light emitting device was manufactured in the same manner as in Experimental Example 1-1, except that Compound 1-59 was used instead of Compound 1-2 in Experimental Example 1-1.

Experimental Example 1-32

An organic light emitting device was manufactured in the same manner as in Experimental Example 1-1, except that Compound 1-60 was used instead of Compound 1-2 in Experimental Example 1-1.

Experimental Example 1-33

An organic light emitting device was manufactured in the same manner as in Experimental Example 1-1, except that Compound 2-2 was used instead of Compound 1-2 in Experimental Example 1-1.

Experimental Example 1-34

An organic light emitting device was manufactured in the same manner as in Experimental Example 1-1, except that Compound 2-3 was used instead of Compound 1-2 in Experimental Example 1-1.

Experimental Example 1-35

An organic light emitting device was manufactured in the same manner as in Experimental Example 1-1, except that Compound 2-4 was used instead of Compound 1-2 in Experimental Example 1-1.

Experimental Example 1-36

An organic light emitting device was manufactured in the same manner as in Experimental Example 1-1, except that Compound 2-5 was used instead of Compound 1-2 in Experimental Example 1-1.

Experimental Example 1-37

An organic light emitting device was manufactured in the same manner as in Experimental Example 1-1, except that Compound 2-6 was used instead of Compound 1-2 in Experimental Example 1-1.

Experimental Example 1-38

An organic light emitting device was manufactured in the same manner as in Experimental Example 1-1, except that Compound 2-7 was used instead of Compound 1-2 in Experimental Example 1-1.

Experimental Example 1-39

An organic light emitting device was manufactured in the same manner as in Experimental Example 1-1, except that Compound 2-8 was used instead of Compound 1-2 in Experimental Example 1-1.

Experimental Example 1-40

An organic light emitting device was manufactured in the same manner as in Experimental Example 1-1, except that Compound 2-9 was used instead of Compound 1-2 in Experimental Example 1-1.

Experimental Example 1-41

An organic light emitting device was manufactured in the same manner as in Experimental Example 1-1, except that Compound 2-19 was used instead of Compound 1-2 in Experimental Example 1-1.

Experimental Example 1-42

An organic light emitting device was manufactured in the same manner as in Experimental Example 1-1, except that Compound 2-20 was used instead of Compound 1-2 in Experimental Example 1-1.

Experimental Example 1-43

An organic light emitting device was manufactured in the same manner as in Experimental Example 1-1, except that Compound 2-21 was used instead of Compound 1-2 in Experimental Example 1-1.

Experimental Example 1-44

An organic light emitting device was manufactured in the same manner as in Experimental Example 1-1, except that Compound 2-22 was used instead of Compound 1-2 in Experimental Example 1-1.

Experimental Example 1-45

An organic light emitting device was manufactured in the same manner as in Experimental Example 1-1, except that Compound 2-23 was used instead of Compound 1-2 in Experimental Example 1-1.

Experimental Example 1-46

An organic light emitting device was manufactured in the same manner as in Experimental Example 1-1, except that Compound 2-24 was used instead of Compound 1-2 in Experimental Example 1-1.

Experimental Example 1-47

An organic light emitting device was manufactured in the same manner as in Experimental Example 1-1, except that Compound 2-25 was used instead of Compound 1-2 in Experimental Example 1-1.

Experimental Example 1-48

An organic light emitting device was manufactured in the same manner as in Experimental Example 1-1, except that Compound 2-26 was used instead of Compound 1-2 in Experimental Example 1-1.

Experimental Example 1-49

An organic light emitting device was manufactured in the same manner as in Experimental Example 1-1, except that Compound 2-36 was used instead of Compound 1-2 in Experimental Example 1-1.

Experimental Example 1-50

An organic light emitting device was manufactured in the same manner as in Experimental Example 1-1, except that Compound 2-37 was used instead of Compound 1-2 in Experimental Example 1-1.

Experimental Example 1-51

An organic light emitting device was manufactured in the same manner as in Experimental Example 1-1, except that Compound 2-38 was used instead of Compound 1-2 in Experimental Example 1-1.

Experimental Example 1-52

An organic light emitting device was manufactured in the same manner as in Experimental Example 1-1, except that Compound 2-39 was used instead of Compound 1-2 in Experimental Example 1-1.

Experimental Example 1-53

An organic light emitting device was manufactured in the same manner as in Experimental Example 1-1, except that Compound 2-40 was used instead of Compound 1-2 in Experimental Example 1-1.

Experimental Example 1-54

An organic light emitting device was manufactured in the same manner as in Experimental Example 1-1, except that Compound 2-41 was used instead of Compound 1-2 in Experimental Example 1-1.

Experimental Example 1-55

An organic light emitting device was manufactured in the same manner as in Experimental Example 1-1, except that Compound 2-42 was used instead of Compound 1-2 in Experimental Example 1-1.

Experimental Example 1-56

An organic light emitting device was manufactured in the same manner as in Experimental Example 1-1, except that Compound 2-43 was used instead of Compound 1-2 in Experimental Example 1-1.

Experimental Example 1-57

An organic light emitting device was manufactured in the same manner as in Experimental Example 1-1, except that Compound 2-53 was used instead of Compound 1-2 in Experimental Example 1-1.

Experimental Example 1-58

An organic light emitting device was manufactured in the same manner as in Experimental Example 1-1, except that Compound 2-54 was used instead of Compound 1-2 in Experimental Example 1-1.

Experimental Example 1-59

An organic light emitting device was manufactured in the same manner as in Experimental Example 1-1, except that Compound 2-55 was used instead of Compound 1-2 in Experimental Example 1-1.

Experimental Example 1-60

An organic light emitting device was manufactured in the same manner as in Experimental Example 1-1, except that Compound 2-56 was used instead of Compound 1-2 in Experimental Example 1-1.

Experimental Example 1-61

An organic light emitting device was manufactured in the same manner as in Experimental Example 1-1, except that Compound 2-57 was used instead of Compound 1-2 in Experimental Example 1-1.

Experimental Example 1-62

An organic light emitting device was manufactured in the same manner as in Experimental Example 1-1, except that Compound 2-58 was used instead of Compound 1-2 in Experimental Example 1-1.

Experimental Example 1-63

An organic light emitting device was manufactured in the same manner as in Experimental Example 1-1, except that Compound 2-59 was used instead of Compound 1-2 in Experimental Example 1-1.

Experimental Example 1-64

An organic light emitting device was manufactured in the same manner as in Experimental Example 1-1, except that Compound 2-60 was used instead of Compound 1-2 in Experimental Example 1-1.

Comparative Example 1-1

An organic light emitting device was manufactured in the same manner as in Experimental Example 1-1, except that EB 1 (TCTA) was used instead of Compound 1-2 in Experimental Example 1-1.

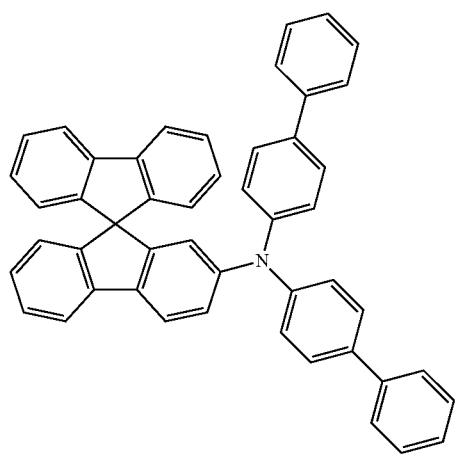

[EB 1]

Comparative Example 1-2

An organic light emitting device was manufactured in the same manner as in Experimental Example 1-1, except that EB 2 was used instead of Compound 1-2 in Experimental Example 1-1.

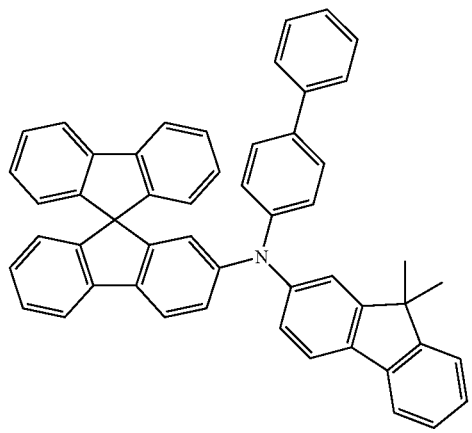

[EB 2]

Comparative Example 1-3

An organic light emitting device was manufactured in the same manner as in Experimental Example 1-1, except that EB 3 was used instead of Compound 1-2 in Experimental Example 1-1.

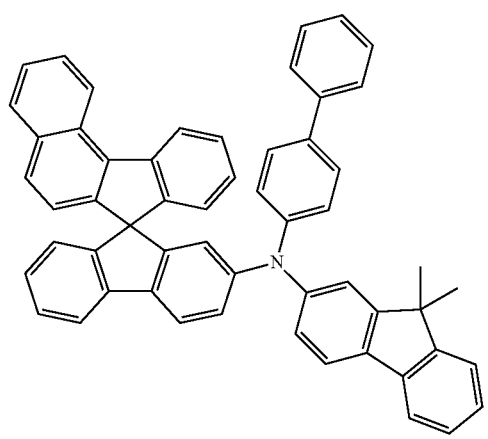

[EB 3]

Comparative Example 1-4

An organic light emitting device was manufactured in the same manner as in Experimental Example 1-1, except that EB 4 was used instead of Compound 1-2 in Experimental Example 1-1.

[EB 4]

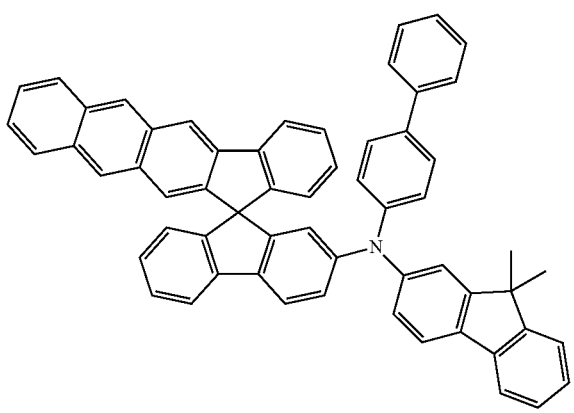

When current was applied to the organic light emitting devices manufactured in Experimental Examples 1-1 to 1-64 and Comparative Examples 1-1 to 1-4, the results of Table 1 were obtained.

TABLE 1

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1-2 | 3.95 | 5.25 | (0.139, 0.122) |
| Experimental Example 1-2 | Compound 1-3 | 3.82 | 5.38 | (0.138, 0.126) |
| Experimental Example 1-3 | Compound 1-4 | 3.67 | 5.71 | (0.138, 0.127) |
| Experimental Example 1-4 | Compound 1-5 | 3.68 | 5.62 | (0.137, 0.125) |
| Experimental Example 1-5 | Compound 1-6 | 3.69 | 5.73 | (0.136, 0.125) |
| Experimental Example 1-6 | Compound 1-7 | 3.64 | 5.67 | (0.136, 0.127) |
| Experimental Example 1-7 | Compound 1-8 | 3.63 | 5.78 | (0.136, 0.125) |
| Experimental Example 1-8 | Compound 1-9 | 3.64 | 5.61 | (0.137, 0.125) |
| Experimental Example 1-9 | Compound 1-19 | 3.73 | 5.58 | (0.138, 0.125) |
| Experimental Example 1-10 | Compound 1-20 | 3.78 | 5.42 | (0.136, 0.125) |
| Experimental Example 1-11 | Compound 1-21 | 3.73 | 5.57 | (0.137, 0.125) |
| Experimental Example 1-12 | Compound 1-22 | 3.75 | 5.45 | (0.136, 0.125) |
| Experimental Example 1-13 | Compound 1-23 | 3.82 | 5.58 | (0.138, 0.126) |
| Experimental Example 1-14 | Compound 1-24 | 3.87 | 5.51 | (0.137, 0.125) |
| Experimental Example 1-15 | Compound 1-25 | 3.80 | 5.42 | (0.136, 0.127) |
| Experimental Example 1-16 | Compound 1-26 | 3.81 | 5.53 | (0.135, 0.127) |
| Experimental Example 1-17 | Compound 1-36 | 3.64 | 5.67 | (0.138, 0.127) |
| Experimental Example 1-18 | Compound 1-37 | 3.73 | 5.58 | (0.137, 0.125) |
| Experimental Example 1-19 | Compound 1-38 | 3.64 | 5.61 | (0.137, 0.125) |
| Experimental Example 1-20 | Compound 1-39 | 3.73 | 5.58 | (0.136, 0.127) |
| Experimental Example 1-21 | Compound 1-40 | 3.64 | 5.62 | (0.135, 0.127) |
| Experimental Example 1-22 | Compound 1-41 | 3.73 | 5.57 | (0.138, 0.127) |
| Experimental Example 1-23 | Compound 1-42 | 3.69 | 5.65 | (0.137, 0.125) |
| Experimental Example 1-24 | Compound 1-43 | 3.78 | 5.68 | (0.137, 0.125) |
| Experimental Example 1-25 | Compound 1-53 | 3.57 | 5.81 | (0.136, 0.125) |
| Experimental Example 1-26 | Compound 1-54 | 3.61 | 5.85 | (0.139, 0.122) |
| Experimental Example 1-27 | Compound 1-55 | 3.63 | 5.98 | (0.138, 0.126) |
| Experimental Example 1-28 | Compound 1-56 | 3.62 | 5.81 | (0.138, 0.127) |
| Experimental Example 1-29 | Compound 1-57 | 3.64 | 5.82 | (0.137, 0.125) |
| Experimental Example 1-30 | Compound 1-58 | 3.60 | 5.83 | (0.136, 0.125) |
| Experimental Example 1-31 | Compound 1-59 | 3.61 | 5.97 | (0.136, 0.127) |
| Experimental Example 1-32 | Compound 1-60 | 3.60 | 5.88 | (0.136, 0.125) |
| Experimental Example 1-33 | Compound 2-2 | 4.05 | 5.15 | (0.137, 0.125) |
| Experimental Example 1-34 | Compound 2-3 | 3.92 | 5.28 | (0.138, 0.125) |
| Experimental Example 1-35 | Compound 2-4 | 3.77 | 5.61 | (0.136, 0.125) |
| Experimental Example 1-36 | Compound 2-5 | 3.78 | 5.52 | (0.137, 0.125) |
| Experimental Example 1-37 | Compound 2-6 | 3.79 | 5.63 | (0.136, 0.125) |
| Experimental Example 1-38 | Compound 2-7 | 3.74 | 5.57 | (0.138, 0.126) |
| Experimental Example 1-39 | Compound 2-8 | 3.73 | 5.68 | (0.137, 0.125) |
| Experimental Example 1-40 | Compound 2-9 | 3.74 | 5.51 | (0.136, 0.127) |
| Experimental Example 1-41 | Compound 2-19 | 3.83 | 5.48 | (0.135, 0.127) |
| Experimental Example 1-42 | Compound 2-20 | 3.88 | 5.32 | (0.138, 0.127) |
| Experimental Example 1-43 | Compound 2-21 | 3.83 | 5.47 | (0.137, 0.125) |
| Experimental Example 1-44 | Compound 2-22 | 3.85 | 5.35 | (0.137, 0.125) |
| Experimental Example 1-45 | Compound 2-23 | 3.92 | 5.48 | (0.136, 0.127) |
| Experimental Example 1-46 | Compound 2-24 | 3.97 | 5.41 | (0.135, 0.127) |
| Experimental Example 1-47 | Compound 2-25 | 3.90 | 5.32 | (0.138, 0.127) |
| Experimental Example 1-48 | Compound 2-26 | 3.91 | 5.43 | (0.137, 0.125) |
| Experimental Example 1-49 | Compound 2-36 | 3.74 | 5.57 | (0.137, 0.125) |
| Experimental Example 1-50 | Compound 2-37 | 3.83 | 5.48 | (0.136, 0.125) |
| Experimental Example 1-51 | Compound 2-38 | 3.74 | 5.51 | (0.136, 0.125) |
| Experimental Example 1-52 | Compound 2-39 | 3.83 | 5.48 | (0.136, 0.125) |
| Experimental Example 1-53 | Compound 2-40 | 3.74 | 5.52 | (0.136, 0.125) |
| Experimental Example 1-54 | Compound 2-41 | 3.83 | 5.47 | (0.136, 0.125) |
| Experimental Example 1-55 | Compound 2-42 | 3.79 | 5.55 | (0.136, 0.125) |
| Experimental Example 1-56 | Compound 2-43 | 3.88 | 5.58 | (0.136, 0.125) |
| Experimental Example 1-57 | Compound 2-53 | 3.67 | 5.71 | (0.136, 0.125) |
| Experimental Example 1-58 | Compound 2-54 | 3.71 | 5.75 | (0.136, 0.125) |
| Experimental Example 1-59 | Compound 2-55 | 3.73 | 5.88 | (0.136, 0.125) |

TABLE 1-continued

| | Compound (Electron blocking layer) | Voltage (V@10 mA/cm²) | Efficiency (cd/A@10 mA/cm²) | Color coordinate (x, y) |
|---|---|---|---|---|
| Experimental Example 1-60 | Compound 2-56 | 3.72 | 5.71 | (0.136, 0.125) |
| Experimental Example 1-61 | Compound 2-57 | 3.74 | 5.72 | (0.136, 0.125) |
| Experimental Example 1-62 | Compound 2-58 | 3.70 | 5.73 | (0.136, 0.125) |
| Experimental Example 1-63 | Compound 2-59 | 3.71 | 5.87 | (0.136, 0.125) |
| Experimental Example 1-64 | Compound 2-60 | 3.70 | 5.78 | (0.136, 0.125) |
| Comparative Example 1-1 | EB-1 | 4.36 | 4.63 | (0.138, 0.127) |
| Comparative Example 1-2 | EB-2 | 4.31 | 4.58 | (0.139, 0.125) |
| Comparative Example 1-3 | EB-3 | 4.49 | 4.42 | (0.139, 0.126) |
| Comparative Example 1-4 | EB-4 | 4.56 | 4.32 | (0.139, 0.127) |

As seen in Table 1, it can be known that the compounds of Experimental Examples 1-1 to 1-64 exhibited lower voltage and higher efficiency characteristics than EB 1 (TCTA) of Comparative 1-1, which is frequently used as an electron blocking layer in an organic light emitting device, and Comparative Examples 1-2 to 1-4 in which A of Chemical Formula 1 is formed of phenyl, naphthalene, or anthracene.

It could be confirmed that the compound of Chemical Formula 1 according to the present specification has excellent electron blocking capability, and thus exhibits low voltage and high efficiency characteristics, and may be applied to an organic light emitting device.

Experimental Examples 2-1 to 2-64

An experiment was performed in the same manner as in Experimental Example 1-1, except that EB 1 in Comparative Example 1-1 was used instead of Compound 1-2 in Experimental Example 1-1 as an electron blocking layer, and the Compounds in Experimental Examples 1-1 to 1-64, were used instead of NPB in Experimental Example 1-1 as a hole transport layer.

Comparative Example 2-1

An experiment was performed in the same manner as in Experimental Example 1-1, except that EB 1 in Comparative Example 1-1 was used instead of Compound 1-2 in Experimental Example 1-1 as an electron blocking layer, and NPB (HT 1) in Experimental Example 1-1 was used as a hole transport layer.

Comparative Example 2-2

An experiment was performed in the same manner as in Experimental Example 1-1, except that EB 1 in Comparative Example 1-1 was used instead of Compound 1-2 in Experimental Example 1-1 as an electron blocking layer, and HT 2 was used as a hole transport layer.

[HT 2]

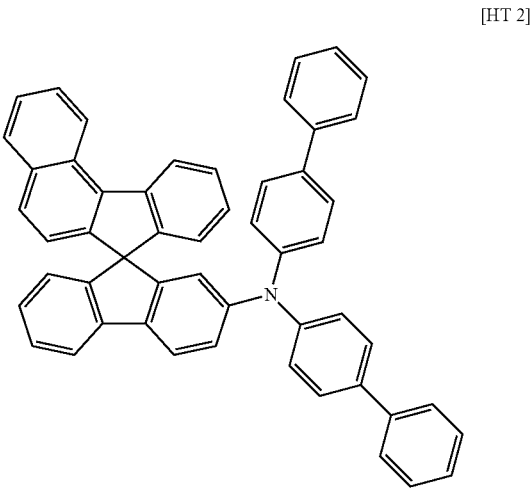 [SMILES: c1ccc(-c2ccc(N(c3ccc(-c4ccccc4)cc3)c3ccc4c(c3)C3(c5ccccc5-4)c4ccccc4-c4c3ccc3ccccc43)cc2)cc1]

Comparative Example 2-3

An experiment was performed in the same manner as in Experimental Example 1-1, except that EB 1 in Comparative Example 1-1 was used instead of Compound 1-2 in Experimental Example 1-1 as an electron blocking layer, and HT 3 was used as a hole transport layer.

[HT 3]

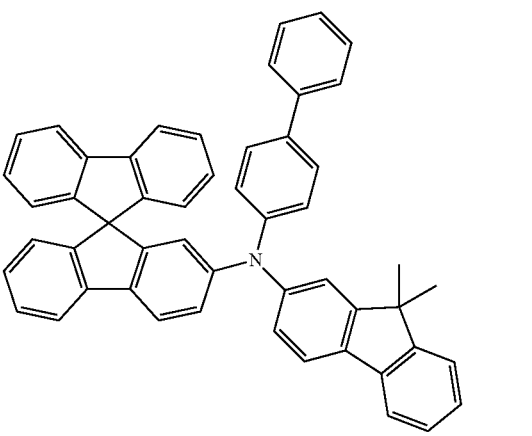

Comparative Example 2-4

An experiment was performed in the same manner as in Experimental Example 1-1, except that EB 1 in Comparative Example 1-1 was used instead of Compound 1-2 in Experimental Example 1-1 as an electron blocking layer, and HT 4 was used as a hole transport layer.

[HT 4]

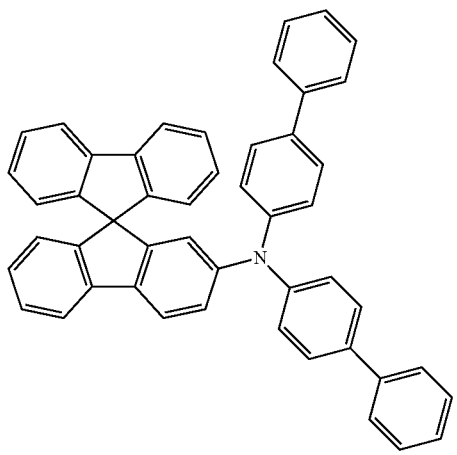

Comparative Example 2-5

An experiment was performed in the same manner as in Experimental Example 1-1, except that EB 1 in Comparative Example 1-1 was used instead of Compound 1-2 in Experimental Example 1-1 as an electron blocking layer, and HT 5 was used as a hole transport layer.

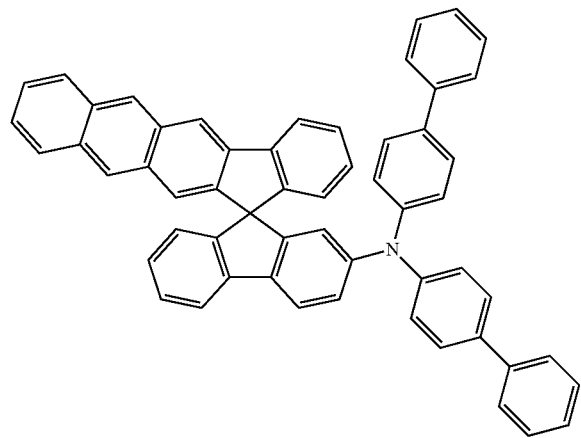 [SMILES: c1ccc(-c2ccc(N(c3ccc(-c4ccccc4)cc3)c3ccc4c(c3)C3(c5ccccc5-4)c4ccccc4-c4cc5cc6ccccc6cc5cc43)cc2)cc1]

When current was applied to the organic light emitting devices manufactured in Experimental Examples 2-1 to 2-64 and Comparative Examples 2-1 to 2-5, the results of Table 2 were obtained.

TABLE 2

| | Compound (hole transport layer) | Voltage (V@10 mA/cm$^2$) | Efficiency (cd/A@10 mA/cm$^2$) | Color coordinate (x, y) |
|---|---|---|---|---|
| Experimental Example 2-1 | Compound 1-2 | 4.15 | 5.75 | (0.139, 0.122) |
| Experimental Example 2-2 | Compound 1-3 | 4.02 | 5.88 | (0.138, 0.126) |
| Experimental Example 2-3 | Compound 1-4 | 3.87 | 6.25 | (0.138, 0.127) |
| Experimental Example 2-4 | Compound 1-5 | 3.88 | 6.24 | (0.137, 0.125) |

TABLE 2-continued

| | Compound (hole transport layer) | Voltage (V@10 mA/cm$^2$) | Efficiency (cd/A@10 mA/cm$^2$) | Color coordinate (x, y) |
|---|---|---|---|---|
| Experimental Example 2-5 | Compound 1-6 | 3.89 | 6.22 | (0.136, 0.125) |
| Experimental Example 2-6 | Compound 1-7 | 3.84 | 6.13 | (0.136, 0.127) |
| Experimental Example 2-7 | Compound 1-8 | 3.83 | 6.20 | (0.136, 0.125) |
| Experimental Example 2-8 | Compound 1-9 | 3.84 | 6.10 | (0.137, 0.125) |
| Experimental Example 2-9 | Compound 1-19 | 3.93 | 6.01 | (0.138, 0.125) |
| Experimental Example 2-10 | Compound 1-20 | 3.98 | 5.92 | (0.136, 0.125) |
| Experimental Example 2-11 | Compound 1-21 | 3.93 | 6.05 | (0.137, 0.125) |
| Experimental Example 2-12 | Compound 1-22 | 3.95 | 5.95 | (0.136, 0.125) |
| Experimental Example 2-13 | Compound 1-23 | 4.02 | 6.08 | (0.138, 0.126) |
| Experimental Example 2-14 | Compound 1-24 | 3.97 | 6.01 | (0.137, 0.125) |
| Experimental Example 2-15 | Compound 1-25 | 4.00 | 5.92 | (0.136, 0.127) |
| Experimental Example 2-16 | Compound 1-26 | 4.01 | 6.02 | (0.135, 0.127) |
| Experimental Example 2-17 | Compound 1-36 | 3.84 | 6.15 | (0.138, 0.127) |
| Experimental Example 2-18 | Compound 1-37 | 3.93 | 6.03 | (0.137, 0.125) |
| Experimental Example 2-19 | Compound 1-38 | 3.84 | 6.13 | (0.137, 0.125) |
| Experimental Example 2-20 | Compound 1-39 | 3.93 | 6.05 | (0.136, 0.127) |
| Experimental Example 2-21 | Compound 1-40 | 3.84 | 6.16 | (0.135, 0.127) |
| Experimental Example 2-22 | Compound 1-41 | 3.93 | 6.07 | (0.138, 0.127) |
| Experimental Example 2-23 | Compound 1-42 | 3.89 | 6.15 | (0.137, 0.125) |
| Experimental Example 2-24 | Compound 1-43 | 3.98 | 6.18 | (0.137, 0.125) |
| Experimental Example 2-25 | Compound 1-53 | 3.75 | 6.31 | (0.136, 0.125) |
| Experimental Example 2-26 | Compound 1-54 | 3.86 | 6.35 | (0.139, 0.122) |
| Experimental Example 2-27 | Compound 1-55 | 3.85 | 6.48 | (0.138, 0.126) |
| Experimental Example 2-28 | Compound 1-56 | 3.81 | 6.31 | (0.138, 0.127) |
| Experimental Example 2-29 | Compound 1-57 | 3.84 | 6.32 | (0.137, 0.125) |
| Experimental Example 2-30 | Compound 1-58 | 3.80 | 6.33 | (0.136, 0.125) |
| Experimental Example 2-31 | Compound 1-59 | 3.81 | 6.47 | (0.136, 0.127) |
| Experimental Example 2-32 | Compound 1-60 | 3.80 | 6.35 | (0.136, 0.125) |
| Experimental Example 2-33 | Compound 2-2 | 4.25 | 5.65 | (0.137, 0.125) |
| Experimental Example 2-34 | Compound 2-3 | 4.12 | 5.78 | (0.138, 0.125) |
| Experimental Example 2-35 | Compound 2-4 | 3.97 | 6.11 | (0.136, 0.125) |
| Experimental Example 2-36 | Compound 2-5 | 3.98 | 6.02 | (0.137, 0.125) |
| Experimental Example 2-37 | Compound 2-6 | 3.95 | 6.13 | (0.136, 0.125) |
| Experimental Example 2-38 | Compound 2-7 | 3.94 | 6.07 | (0.138, 0.126) |
| Experimental Example 2-39 | Compound 2-8 | 3.93 | 6.18 | (0.137, 0.125) |
| Experimental Example 2-40 | Compound 2-9 | 3.90 | 6.01 | (0.136, 0.127) |
| Experimental Example 2-41 | Compound 2-19 | 4.03 | 5.98 | (0.135, 0.127) |

TABLE 2-continued

| | Compound (hole transport layer) | Voltage (V@10 mA/cm²) | Efficiency (cd/A@10 mA/cm²) | Color coordinate (x, y) |
|---|---|---|---|---|
| Experimental Example 2-42 | Compound 2-20 | 4.08 | 5.82 | (0.138, 0.127) |
| Experimental Example 2-43 | Compound 2-21 | 4.03 | 5.97 | (0.137, 0.125) |
| Experimental Example 2-44 | Compound 2-22 | 4.05 | 5.85 | (0.137, 0.125) |
| Experimental Example 2-45 | Compound 2-23 | 4.12 | 5.94 | (0.136, 0.127) |
| Experimental Example 2-46 | Compound 2-24 | 4.14 | 5.92 | (0.135, 0.127) |
| Experimental Example 2-47 | Compound 2-25 | 4.12 | 5.83 | (0.138, 0.127) |
| Experimental Example 2-48 | Compound 2-26 | 4.18 | 5.98 | (0.137, 0.125) |
| Experimental Example 2-49 | Compound 2-36 | 3.94 | 6.07 | (0.137, 0.125) |
| Experimental Example 2-50 | Compound 2-37 | 4.01 | 5.99 | (0.136, 0.125) |
| Experimental Example 2-51 | Compound 2-38 | 3.94 | 6.015 | (0.136, 0.125) |
| Experimental Example 2-52 | Compound 2-39 | 4.03 | 5.96 | (0.136, 0.125) |
| Experimental Example 2-53 | Compound 2-40 | 3.94 | 6.02 | (0.136, 0.125) |
| Experimental Example 2-54 | Compound 2-41 | 4.03 | 5.92 | (0.136, 0.125) |
| Experimental Example 2-55 | Compound 2-42 | 3.98 | 6.05 | (0.136, 0.125) |
| Experimental Example 2-56 | Compound 2-43 | 4.05 | 6.01 | (0.136, 0.125) |
| Experimental Example 2-57 | Compound 2-53 | 3.84 | 6.21 | (0.136, 0.125) |
| Experimental Example 2-58 | Compound 2-54 | 3.93 | 6.25 | (0.136, 0.125) |
| Experimental Example 2-59 | Compound 2-55 | 3.92 | 6.38 | (0.136, 0.125) |
| Experimental Example 2-60 | Compound 2-56 | 3.97 | 6.21 | (0.136, 0.125) |
| Experimental Example 2-61 | Compound 2-57 | 3.99 | 6.22 | (0.136, 0.125) |
| Experimental Example 2-62 | Compound 2-58 | 3.98 | 6.23 | (0.136, 0.125) |
| Experimental Example 2-63 | Compound 2-59 | 3.91 | 6.37 | (0.136, 0.125) |
| Experimental Example 2-64 | Compound 2-60 | 3.90 | 6.28 | (0.136, 0.125) |
| Comparative Example 2-1 | NPB (HT 1) | 4.56 | 5.13 | (0.138, 0.127) |
| Comparative Example 2-2 | HT 2 | 4.51 | 5.08 | (0.139, 0.125) |
| Comparative Example 2-3 | HT 3 | 4.69 | 4.92 | (0.139, 0.126) |
| Comparative Example 2-4 | HT 4 | 4.76 | 4.82 | (0.139, 0.127) |
| Comparative Example 2-5 | HT 5 | 4.82 | 4.95 | (0.139, 0.127) |

As seen in Table 2, it can be known that the compounds of Experimental Examples 2-1 to 2-64 exhibited lower voltage and higher efficiency characteristics than NPB (Comparative Example 2-1), which is frequently used as a hole transport layer in an organic light emitting device, and Comparative Examples 2-2 to 2-5 in which A of Chemical Formula 1 is formed of phenyl, naphthalene, or anthracene.

It could be confirmed that the compound of Chemical Formula 1 according to the present specification has excellent electron transport capability, and thus exhibits low voltage and high efficiency characteristics, and may be applied to an organic light emitting device.

Experimental Example 3-1

The compounds prepared in the Preparation Examples were subjected to high-purity sublimation purification by a typically known method, and then green organic light emitting devices were manufactured by the following method.

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

An organic EL device was manufactured by configuring the light emitting device in the order of m-MTDATA (60 nm)/TCTA (80 nm)/Compound 1-10+10% Ir(ppy)$_3$(300 nm)/BCP (10 nm)/Alq$_3$ (30 nm)/LiF (1 nm)/Al (200 nm) on the thus prepared ITO transparent electrode by using Compound 1-10 as a host.

The structures of m-MTDATA, TCTA, Ir(ppy)$_3$, and BCP are as follows.

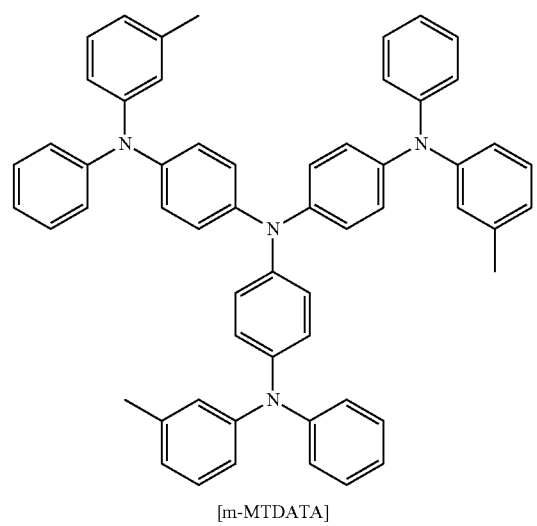

[m-MTDATA]

-continued

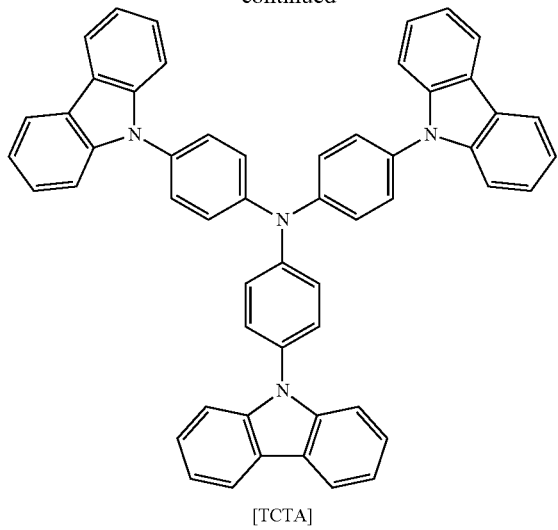

[TCTA]

[Ir(ppy)3]

[BCP]

Experimental Example 3-2

An organic light emitting device was manufactured in the same manner as in Experimental Example 3-1, except that Compound 1-11 was used instead of Compound 1-10 in Experimental Example 3-1.

Experimental Example 3-3

An organic light emitting device was manufactured in the same manner as in Experimental Example 3-1, except that Compound 1-12 was used instead of Compound 1-10 in Experimental Example 3-1.

Experimental Example 3-4

An organic light emitting device was manufactured in the same manner as in Experimental Example 3-1, except that Compound 1-13 was used instead of Compound 1-10 in Experimental Example 3-1.

Experimental Example 3-5

An organic light emitting device was manufactured in the same manner as in Experimental Example 3-1, except that Compound 1-14 was used instead of Compound 1-10 in Experimental Example 3-1.

Experimental Example 3-6

An organic light emitting device was manufactured in the same manner as in Experimental Example 3-1, except that Compound 1-27 was used instead of Compound 1-10 in Experimental Example 3-1.

Experimental Example 3-7

An organic light emitting device was manufactured in the same manner as in Experimental Example 3-1, except that Compound 1-28 was used instead of Compound 1-10 in Experimental Example 3-1.

Experimental Example 3-8

An organic light emitting device was manufactured in the same manner as in Experimental Example 3-1, except that Compound 1-29 was used instead of Compound 1-10 in Experimental Example 3-1.

Experimental Example 3-9

An organic light emitting device was manufactured in the same manner as in Experimental Example 3-1, except that Compound 1-30 was used instead of Compound 1-10 in Experimental Example 3-1.

Experimental Example 3-10

An organic light emitting device was manufactured in the same manner as in Experimental Example 3-1, except that Compound 1-31 was used instead of Compound 1-10 in Experimental Example 3-1.

Experimental Example 3-11

An organic light emitting device was manufactured in the same manner as in Experimental Example 3-1, except that Compound 1-44 was used instead of Compound 1-10 in Experimental Example 3-1.

Experimental Example 3-12

An organic light emitting device was manufactured in the same manner as in Experimental Example 3-1, except that Compound 1-45 was used instead of Compound 1-10 in Experimental Example 3-1.

Experimental Example 3-13

An organic light emitting device was manufactured in the same manner as in Experimental Example 3-1, except that Compound 1-46 was used instead of Compound 1-10 in Experimental Example 3-1.

Experimental Example 3-14

An organic light emitting device was manufactured in the same manner as in Experimental Example 3-1, except that Compound 1-47 was used instead of Compound 1-10 in Experimental Example 3-1.

Experimental Example 3-15

An organic light emitting device was manufactured in the same manner as in Experimental Example 3-1, except that Compound 1-48 was used instead of Compound 1-10 in Experimental Example 3-1.

Experimental Example 3-16

An organic light emitting device was manufactured in the same manner as in Experimental Example 3-1, except that Compound 1-61 was used instead of Compound 1-10 in Experimental Example 3-1.

Experimental Example 3-17

An organic light emitting device was manufactured in the same manner as in Experimental Example 3-1, except that Compound 1-62 was used instead of Compound 1-10 in Experimental Example 3-1.

Experimental Example 3-18

An organic light emitting device was manufactured in the same manner as in Experimental Example 3-1, except that Compound 1-63 was used instead of Compound 1-10 in Experimental Example 3-1.

Experimental Example 3-19

An organic light emitting device was manufactured in the same manner as in Experimental Example 3-1, except that Compound 1-64 was used instead of Compound 1-10 in Experimental Example 3-1.

Experimental Example 3-20

An organic light emitting device was manufactured in the same manner as in Experimental Example 3-1, except that Compound 1-65 was used instead of Compound 1-10 in Experimental Example 3-1.

Experimental Example 3-21

An organic light emitting device was manufactured in the same manner as in Experimental Example 3-1, except that Compound 2-10 was used instead of Compound 1-10 in Experimental Example 3-1.

Experimental Example 3-22

An organic light emitting device was manufactured in the same manner as in Experimental Example 3-1, except that Compound 2-11 was used instead of Compound 1-10 in Experimental Example 3-1.

Experimental Example 3-23

An organic light emitting device was manufactured in the same manner as in Experimental Example 3-1, except that Compound 2-12 was used instead of Compound 1-10 in Experimental Example 3-1.

Experimental Example 3-24

An organic light emitting device was manufactured in the same manner as in Experimental Example 3-1, except that Compound 2-13 was used instead of Compound 1-10 in Experimental Example 3-1.

Experimental Example 3-25

An organic light emitting device was manufactured in the same manner as in Experimental Example 3-1, except that Compound 2-14 was used instead of Compound 1-10 in Experimental Example 3-1.

Experimental Example 3-26

An organic light emitting device was manufactured in the same manner as in Experimental Example 3-1, except that Compound 2-27 was used instead of Compound 1-10 in Experimental Example 3-1.

Experimental Example 3-27

An organic light emitting device was manufactured in the same manner as in Experimental Example 3-1, except that Compound 2-28 was used instead of Compound 1-10 in Experimental Example 3-1.

Experimental Example 3-28

An organic light emitting device was manufactured in the same manner as in Experimental Example 3-1, except that Compound 2-29 was used instead of Compound 1-10 in Experimental Example 3-1.

Experimental Example 3-29

An organic light emitting device was manufactured in the same manner as in Experimental Example 3-1, except that Compound 2-30 was used instead of Compound 1-10 in Experimental Example 3-1.

Experimental Example 3-30

An organic light emitting device was manufactured in the same manner as in Experimental Example 3-1, except that Compound 2-31 was used instead of Compound 1-10 in Experimental Example 3-1.

Experimental Example 3-31

An organic light emitting device was manufactured in the same manner as in Experimental Example 3-1, except that Compound 2-44 was used instead of Compound 1-10 in Experimental Example 3-1.

Experimental Example 3-32

An organic light emitting device was manufactured in the same manner as in Experimental Example 3-1, except that Compound 2-45 was used instead of Compound 1-10 in Experimental Example 3-1.

Experimental Example 3-33

An organic light emitting device was manufactured in the same manner as in Experimental Example 3-1, except that Compound 2-46 was used instead of Compound 1-10 in Experimental Example 3-1.

Experimental Example 3-34

An organic light emitting device was manufactured in the same manner as in Experimental Example 3-1, except that Compound 2-47 was used instead of Compound 1-10 in Experimental Example 3-1.

Experimental Example 3-35

An organic light emitting device was manufactured in the same manner as in Experimental Example 3-1, except that Compound 2-48 was used instead of Compound 1-10 in Experimental Example 3-1.

Experimental Example 3-36

An organic light emitting device was manufactured in the same manner as in Experimental Example 3-1, except that Compound 2-61 was used instead of Compound 1-10 in Experimental Example 3-1.

Experimental Example 3-37

An organic light emitting device was manufactured in the same manner as in Experimental Example 3-1, except that Compound 2-62 was used instead of Compound 1-10 in Experimental Example 3-1.

Experimental Example 3-38

An organic light emitting device was manufactured in the same manner as in Experimental Example 3-1, except that Compound 2-63 was used instead of Compound 1-10 in Experimental Example 3-1.

Experimental Example 3-39

An organic light emitting device was manufactured in the same manner as in Experimental Example 3-1, except that Compound 2-64 was used instead of Compound 1-10 in Experimental Example 3-1.

Experimental Example 3-40

An organic light emitting device was manufactured in the same manner as in Experimental Example 3-1, except that Compound 2-65 was used instead of Compound 1-10 in Experimental Example 3-1.

Comparative Example 3-1

An organic light emitting device was manufactured in the same manner as in Experimental Example 3-1, except that GH 1 (CBP) was used instead of Compound 1-10 in Experimental Example 3-1.

[GH 1]

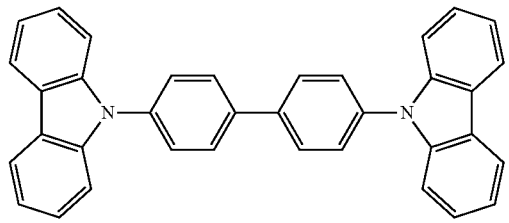

When current was applied to the organic light emitting devices manufactured in Experimental Examples 3-1 to 3-40 and Comparative Example 3-1, the results of Table 3 were obtained.

TABLE 3

| | Compound (Host) | Voltage (V@10 mA/cm$^2$) | Efficiency (cd/A@10 mA/cm$^2$) | EL peak (nm) |
|---|---|---|---|---|
| Experimental Example 3-1 | Compound 1-10 | 6.18 | 43.93 | 517 |
| Experimental Example 3-2 | Compound 1-11 | 6.26 | 45.24 | 516 |
| Experimental Example 3-3 | Compound 1-12 | 6.15 | 44.79 | 518 |
| Experimental Example 3-4 | Compound 1-13 | 6.29 | 46.15 | 517 |
| Experimental Example 3-5 | Compound 1-14 | 6.28 | 44.31 | 515 |
| Experimental Example 3-6 | Compound 1-27 | 6.13 | 45.63 | 516 |
| Experimental Example 3-7 | Compound 1-28 | 6.29 | 45.62 | 516 |
| Experimental Example 3-8 | Compound 1-29 | 6.27 | 46.64 | 517 |
| Experimental Example 3-9 | Compound 1-30 | 6.24 | 46.68 | 518 |
| Experimental Example 3-10 | Compound 1-31 | 6.18 | 43.83 | 517 |
| Experimental Example 3-11 | Compound 1-44 | 6.26 | 45.24 | 516 |
| Experimental Example 3-12 | Compound 1-45 | 6.15 | 44.52 | 518 |
| Experimental Example 3-13 | Compound 1-46 | 6.29 | 46.95 | 517 |
| Experimental Example 3-14 | Compound 1-47 | 6.28 | 44.31 | 515 |
| Experimental Example 3-15 | Compound 1-48 | 6.13 | 45.13 | 516 |
| Experimental Example 3-16 | Compound 1-61 | 6.29 | 45.42 | 516 |
| Experimental Example 3-17 | Compound 1-62 | 6.27 | 45.64 | 517 |
| Experimental Example 3-18 | Compound 1-63 | 6.24 | 46.08 | 518 |
| Experimental Example 3-19 | Compound 1-64 | 6.24 | 46.08 | 518 |
| Experimental Example 3-20 | Compound 1-65 | 6.24 | 46.08 | 518 |
| Experimental Example 3-21 | Compound 2-10 | 6.24 | 46.08 | 518 |
| Experimental Example 3-22 | Compound 2-11 | 6.24 | 46.08 | 518 |
| Experimental Example 3-23 | Compound 2-12 | 6.24 | 46.08 | 518 |
| Experimental Example 3-24 | Compound 2-13 | 6.24 | 46.08 | 518 |
| Experimental Example 3-25 | Compound 2-14 | 6.24 | 46.08 | 518 |
| Experimental Example 3-26 | Compound 2-27 | 6.24 | 46.08 | 518 |
| Experimental Example 3-27 | Compound 2-28 | 6.24 | 46.08 | 518 |

TABLE 3-continued

| | Compound (Host) | Voltage (V@10 mA/cm²) | Efficiency (cd/A@10 mA/cm²) | EL peak (nm) |
|---|---|---|---|---|
| Experimental Example 3-28 | Compound 2-29 | 6.24 | 46.08 | 518 |
| Experimental Example 3-29 | Compound 2-30 | 6.24 | 46.08 | 518 |
| Experimental Example 3-30 | Compound 2-31 | 6.24 | 46.08 | 518 |
| Experimental Example 3-31 | Compound 2-44 | 6.24 | 46.08 | 518 |
| Experimental Example 3-32 | Compound 2-45 | 6.24 | 46.08 | 518 |
| Experimental Example 3-33 | Compound 2-46 | 6.24 | 46.08 | 518 |
| Experimental Example 3-34 | Compound 2-47 | 6.24 | 46.08 | 518 |
| Experimental Example 3-35 | Compound 2-48 | 6.24 | 46.08 | 518 |
| Experimental Example 3-36 | Compound 2-61 | 6.24 | 46.08 | 518 |
| Experimental Example 3-37 | Compound 2-62 | 6.24 | 46.08 | 518 |
| Experimental Example 3-38 | Compound 2-63 | 6.24 | 46.08 | 518 |
| Experimental Example 3-39 | Compound 2-64 | 6.24 | 46.08 | 518 |
| Experimental Example 3-40 | Compound 2-65 | 6.24 | 46.08 | 518 |
| Comparative Example 3-1 | GH 1 (CBP) | 7.01 | 38.72 | 517 |

As a result of the experiment, it could be confirmed that the green organic light emitting devices of Experimental Examples 3-1 to 3-40 in which the compound represented by Chemical Formula 1 according to the present specification was used as a host material of the green light emitting layer exhibited better performances in terms of current efficiency and driving voltage than the green organic light emitting device of Comparative Example 3-1 in which CBP (GH 1) in the related art was used.

Experimental Example 4-1

The compounds prepared in the Preparation Examples were subjected to high-purity sublimation purification by a typically known method, and then red organic light emitting devices were manufactured by the following method.

An ITO glass was patterned and then washed, such that the light emitting area of the ITO glass became 2 mm×2 mm. The substrate was mounted on a vacuum chamber, and then the base pressure was allowed to be $1\times10^{-6}$ torr, and then for the organic material, DNTPD (700 Å), α-NPB (300 Å), and Compound 1-14 were used as hosts (90 wt %) on the ITO, the following (piq)$_2$Ir(acac) (10 wt %) was co-deposited as a dopant, films were formed in the order of Alq$_3$ (350 Å), LiF (5 Å), and Al (1,000 Å), and measurements were made at 0.4 mA.

The structures of DNTPD, α-NPB, (piq)$_2$Ir(acac), and Alq$_3$ are as follows.

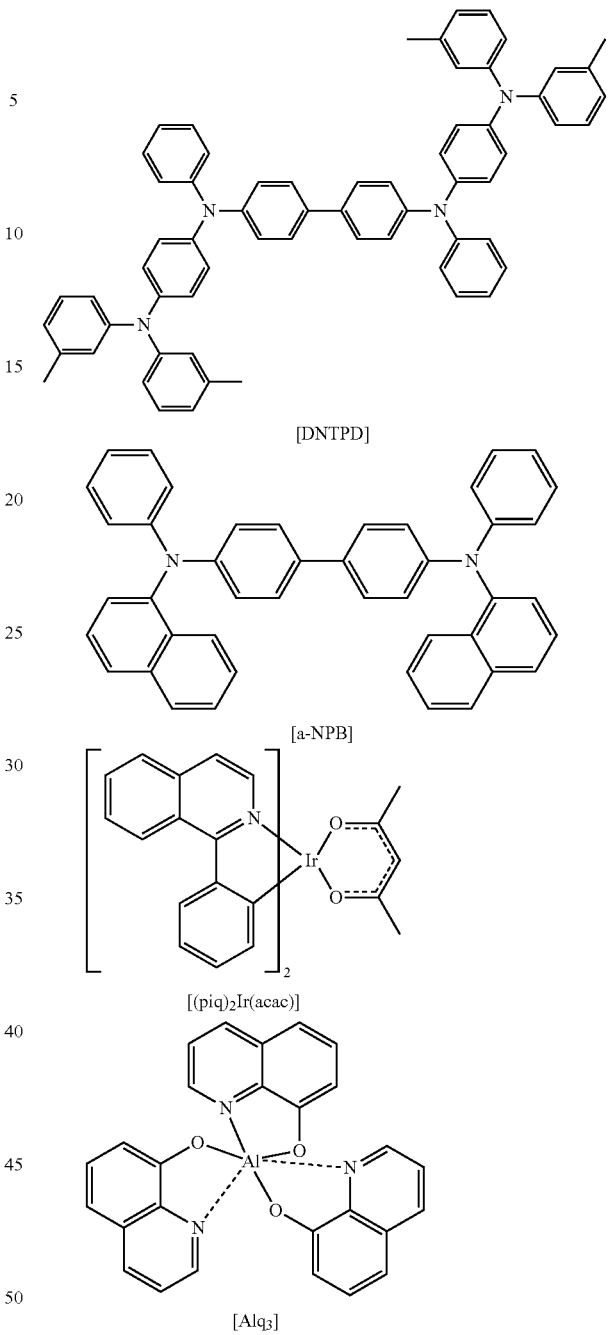

[DNTPD]

[a-NPB]

[(piq)$_2$Ir(acac)]

[Alq$_3$]

Experimental Example 4-2

An organic light emitting device was manufactured in the same manner as in Experimental Example 4-1, except that Compound 1-10 was used instead of Compound 1-14 in Experimental Example 4-1.

Experimental Example 4-3

An organic light emitting device was manufactured in the same manner as in Experimental Example 4-1, except that Compound 1-27 was used instead of Compound 1-14 in Experimental Example 4-1.

Experimental Example 4-4

An organic light emitting device was manufactured in the same manner as in Experimental Example 4-1, except that Compound 1-31 was used instead of Compound 1-14 in Experimental Example 4-1.

Experimental Example 4-5

An organic light emitting device was manufactured in the same manner as in Experimental Example 4-1, except that Compound 1-44 was used instead of Compound 1-14 in Experimental Example 4-1.

Experimental Example 4-6

An organic light emitting device was manufactured in the same manner as in Experimental Example 4-1, except that Compound 1-48 was used instead of Compound 1-14 in Experimental Example 4-1.

Experimental Example 4-7

An organic light emitting device was manufactured in the same manner as in Experimental Example 4-1, except that Compound 1-61 was used instead of Compound 1-14 in Experimental Example 4-1.

Experimental Example 4-8

An organic light emitting device was manufactured in the same manner as in Experimental Example 4-1, except that Compound 1-65 was used instead of Compound 1-14 in Experimental Example 4-1.

Comparative Example 1

An organic light emitting device was manufactured in the same manner as in Experimental Example 4-1, except that the following RH 1 (CBP) was used instead of Compound 1-14 in Experimental Example 4-1.

[RH 1]

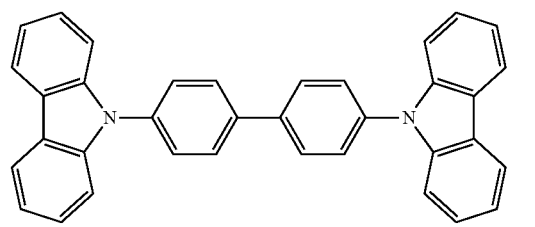

For the organic light emitting devices manufactured according to Experimental Examples 4-1 to 4-8 and Comparative Example 4-1, the voltages, current densities, luminances, color coordinates, and lifetimes were measured, and the results are shown in the following Table 4. T95 means the time taken for the luminance to be reduced to 95% of the initial luminance (5,000 nit).

TABLE 4

| Classification | Host | Dopant | Voltage (V) | Luminance (cd/m$^2$) | Color coordinate (x, y) | T95 (hr) |
|---|---|---|---|---|---|---|
| Experimental Example 4-1 | Compound 1-14 | (piq)$_2$Ir(acac) | 4.3 | 1860 | (0.670, 0.329) | 465 |
| Experimental Example 4-2 | Compound 1-10 | (piq)$_2$Ir(acac) | 4.2 | 1850 | (0.674, 0.325) | 415 |
| Experimental Example 4-3 | Compound 1-27 | (piq)$_2$Ir(acac) | 4.1 | 1900 | (0.672, 0.327) | 440 |
| Experimental Example 4-4 | Compound 1-31 | (piq)$_2$Ir(acac) | 4.3 | 1840 | (0.673, 0.335) | 435 |
| Experimental Example 4-5 | Compound 1-44 | (piq)$_2$Ir(acac) | 4.0 | 1790 | (0.675, 0.333) | 405 |
| Experimental Example 4-6 | Compound 1-48 | (piq)$_2$Ir(acac) | 4.2 | 1810 | (0.670, 0.339) | 420 |
| Experimental Example 4-7 | Compound 1-61 | (piq)$_2$Ir(acac) | 4.3 | 1970 | (0.671, 0.338) | 445 |
| Experimental Example 4-8 | Compound 1-65 | (piq)$_2$Ir(acac) | 4.3 | 1860 | (0.668, 0.329) | 465 |
| Comparative Example 4-1 | RH 1 | (piq)$_2$Ir(acac) | 6.1 | 1200 | (0.670, 0.327) | 235 |

As a result of the experiment, it could be confirmed that the red organic light emitting devices of Experimental Examples 4-1 to 4-8 in which the compound of Chemical Formula 1 according to the present specification was used as a host material of the light emitting layer exhibited better performances in terms of current efficiency, driving voltage, and lifetime than the red organic light emitting device of Comparative Example 4-1 in which CBP (RH 1) in the related art was used.

Experimental Example 5-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

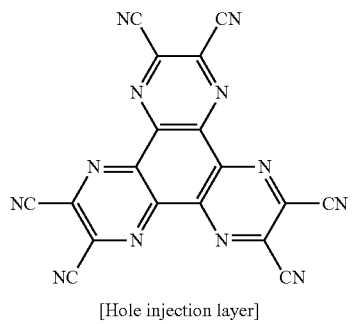

[Hole injection layer]
HAT

The following compound N4,N4,N4',N4'-tetra([1,1'-biphenyl]-4-yl)-[1,1'-biphenyl]-4,4'-diamine [HIL] (300 Å), which is a material for transporting holes, was vacuum deposited on the hole injection layer, thereby forming a hole transport layer.

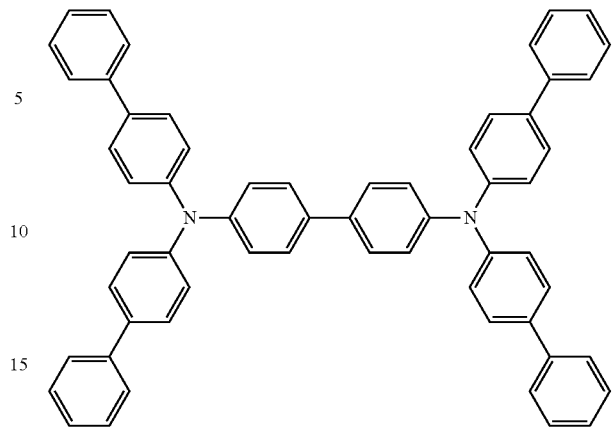

[Hole transport layer]

$N^4N^4,N^{4'},N^{4'}$-tetra([1,1'-biphenyl]-4-yl)-[1,1'-biphenyl]-4,4'-diamine

Subsequently, the following compound N,N-di([1,1'-biphenyl]-4-yl)-4'-(9H-carbazol-9-yl)-[1,1'-biphenyl]-4-amine was vacuum deposited to have a film thickness of 100 Å on the hole transport layer, thereby forming an electron blocking layer.

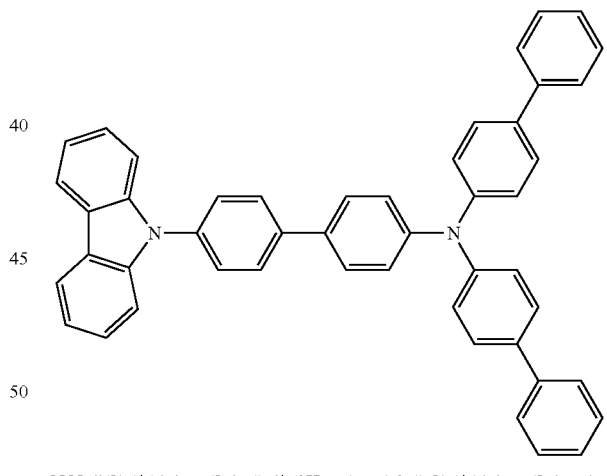

N,N-di([1,1'-biphenyl]-4-yl)-4'-(9H-carbazol-9yl)-[1,1'-biphenyl]-4-amine
[Electron blocking layer]

Subsequently, the following BH and the following Compound 1-69 as the BD (Blue dopant) were vacuum deposited at a weight ratio of 25:1 to have a film thickness of 300 Å on the electron blocking layer, thereby forming a light emitting layer.

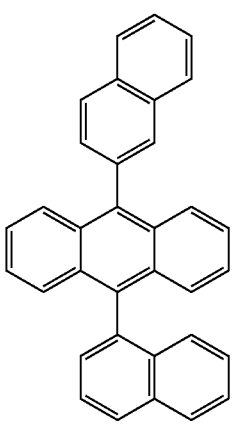

[9-(naphthalen-1-yl)-10-(napthalen-2-yl)anthracene]
BH

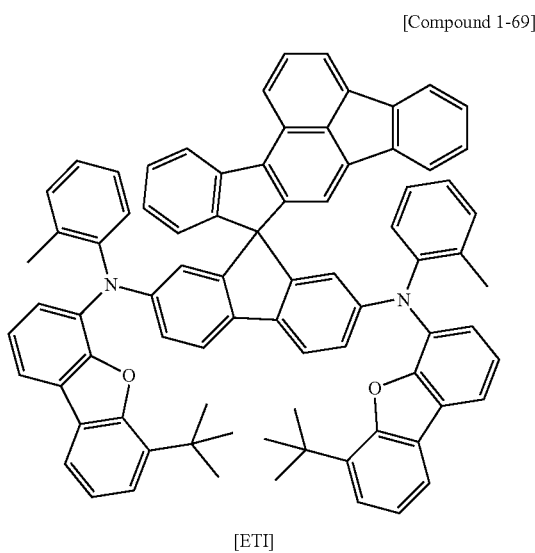

[ETI]

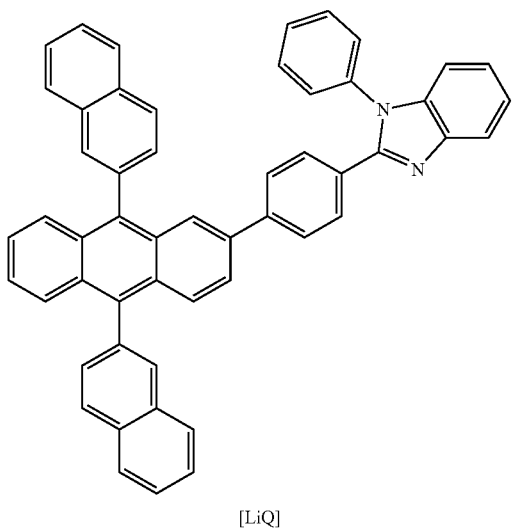

[LiQ]

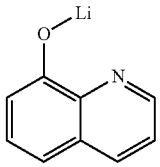

Compound ET1 and Compound LiQ (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Experimental Example 5-2

An organic light emitting device was manufactured in the same manner as in Experimental Example 5-1, except that Compound 1-70 was used instead of Compound 1-69 in Experimental Example 5-1.

Experimental Example 5-3

An organic light emitting device was manufactured in the same manner as in Experimental Example 5-1, except that Compound 1-71 was used instead of Compound 1-69 in Experimental Example 5-1.

Experimental Example 5-4

An organic light emitting device was manufactured in the same manner as in Experimental Example 5-1, except that Compound 1-72 was used instead of Compound 1-69 in Experimental Example 5-1.

Experimental Example 5-5

An organic light emitting device was manufactured in the same manner as in Experimental Example 5-1, except that Compound 2-69 was used instead of Compound 1-69 in Experimental Example 5-1.

Experimental Example 5-6

An organic light emitting device was manufactured in the same manner as in Experimental Example 5-1, except that Compound 2-70 was used instead of Compound 1-69 in Experimental Example 5-1.

Comparative Example 5-1

An organic light emitting device was manufactured in the same manner as in Experimental Example 5-1, except that the following compound BD 1 was used instead of Compound 1-69 in Experimental Example 5-1.

[BD 1]

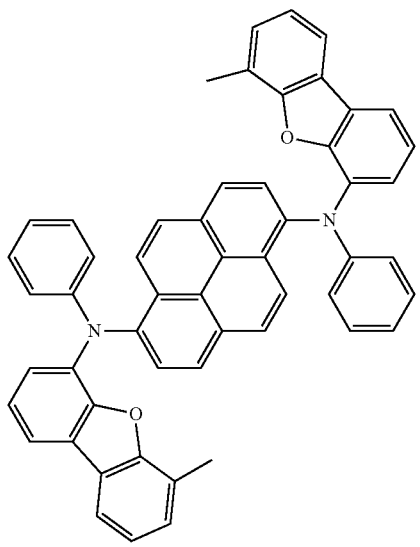

Comparative Example 5-2

An organic light emitting device was manufactured in the same manner as in Experimental Example 5-1, except that BD 2 was used instead of Compound 1-69 in Experimental Example 5-1.

[BD 2]

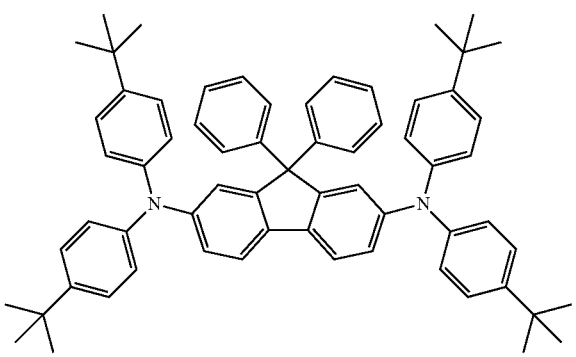

Comparative Example 5-3

An organic light emitting device was manufactured in the same manner as in Experimental Example 5-1, except that BD 3 was used instead of Compound 1-69 in Experimental Example 5-1.

[BD 3]

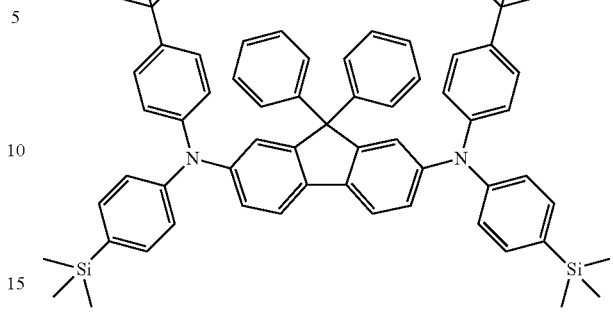

When current was applied to the organic light emitting devices manufactured in Experimental Examples 5-1 to 5-6 and Comparative Examples 5-1 to 5-3, the voltages, efficiencies, color coordinates, and lifetimes were measured, and the results are shown in the following Table 5. T90 means the time taken for the luminance to be reduced to 90% of the initial luminance (5,000 nit).

TABLE 5

| | Compound (Light emitting layer dopant) | Voltage (V@10 mA/cm$^2$) | Efficiency (cd/A@10 mA/cm$^2$) | Color coordinate (x, y) | T90 (hr) |
|---|---|---|---|---|---|
| Experimental Example 5-1 | Compound 1-69 | 4.36 | 6.72 | (0.141, 0.044) | 86 |
| Experimental Example 5-2 | Compound 1-70 | 4.53 | 6.51 | (0.142, 0.045) | 75 |
| Experimental Example 5-3 | Compound 1-71 | 4.45 | 6.48 | (0.141, 0.046) | 79 |
| Experimental Example 5-4 | Compound 1-72 | 4.40 | 6.50 | (0.141, 0.047) | 81 |
| Experimental Example 5-5 | Compound 2-69 | 4.39 | 6.58 | (0.141, 0.047) | 95 |
| Experimental Example 5-6 | Compound 2-70 | 4.29 | 6.45 | (0.141, 0.047) | 102 |
| Comparative Example 5-1 | BD 1 | 4.95 | 5.61 | (0.144, 0.046) | 51 |
| Comparative Example 5-2 | BD 2 | 4.77 | 5.87 | (0.145, 0.041) | 56 |
| Comparative Example 5-3 | BD 3 | 4.70 | 5.98 | (0.144, 0.040) | 54 |

As seen in Table 5, it could be confirmed that Experimental Examples 5-1 to 5-6 for the compound according to an exemplary embodiment of the present specification and the organic light emitting device using the same indicated various color coordinates with a compound including, as a substituent, an amine group substituted with a silyl group, a fluorine group, a heteroaryl group, an aryl group, and the like, as a dopant of the light emitting layer, exhibited low voltage and high efficiency characteristics in the organic light emitting device, and could be applied to the organic light emitting device. In particular, it can be seen that in Compound 2-69 and Compound 2-70, which had a core including triphenylene, the lifetimes were significantly increased.

Although the preferred exemplary embodiments (an electron blocking layer, a hole transport layer, a green light emitting layer, a red light emitting layer, and a blue light emitting layer) of the present invention have been described above, the present invention is not limited thereto, and various modifications can be made and carried out within the scope of the claims and the detailed description of the invention, and also fall within the scope of the invention.

EXPLANATION OF REFERENCE NUMERALS AND SYMBOLS

10, 11: Organic light emitting device
20: Substrate
30: First electrode
40: Light emitting layer
50: Second electrode
60: Hole injection layer
70: Hole transport layer
80: Electron transport layer
90: Electron injection layer

The invention claimed is:
1. A compound represented by the following Chemical Formula 1:

[Chemical Formula 1]

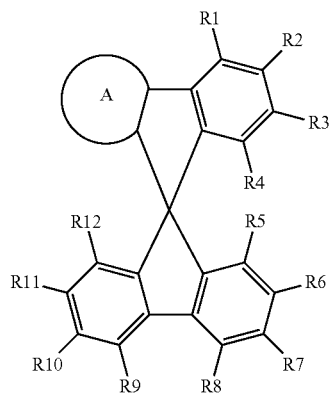

in Chemical Formula 1,
A is a substituted or unsubstituted fluoranthene ring, or an unsubstituted or deuterium substituted triphenylene ring,
R1 to R4 are each independently hydrogen or deuterium,
R5 to R12 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups optionally combine with each other to form a substituted or unsubstituted ring, and
at least one of R5 to R12 has a substituent other than hydrogen.

2. The compound of claim 1, wherein A is represented by the following Chemical Formula A-1 or A-2:

[Chemical Formula A-1]

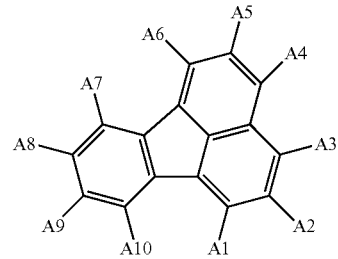

[Chemical Formula A-2]

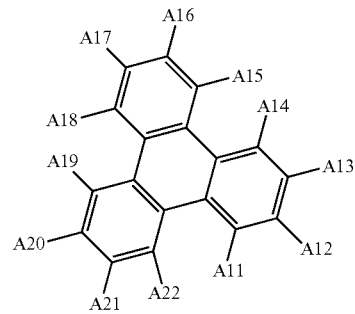

in Chemical Formulae A-1 and A-2,
A1 and A2; A2 and A3; A4 and A5; A5 and A6; A7 and A8; A8 and A9; A9 and A10; A11 and A12; A12 and A13; A13 and A14; A15 and A16; A16 and A17; A17 and A18; A19 and A20; A20 and A21; or A21 and A22 in A1 to A22 are moieties directly bonded to Chemical Formula 1, and the others of A1 to A10 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and
wherein the others of A11 to A22 are the same as or different from each other, and are each independently hydrogen or deuterium.

3. The compound of claim 1, wherein Chemical Formula 1 is represented by the following Chemical Formula 1-1 or 1-2:

[Chemical Formula 1-1]

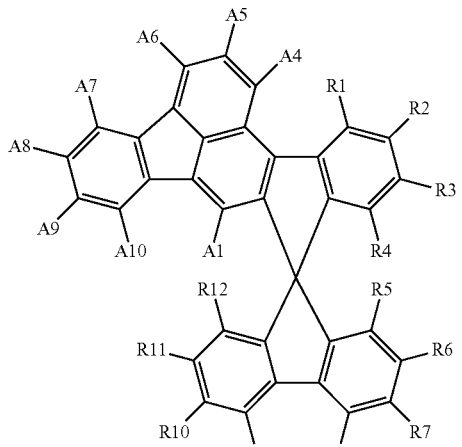

[Chemical Formula 1-2]

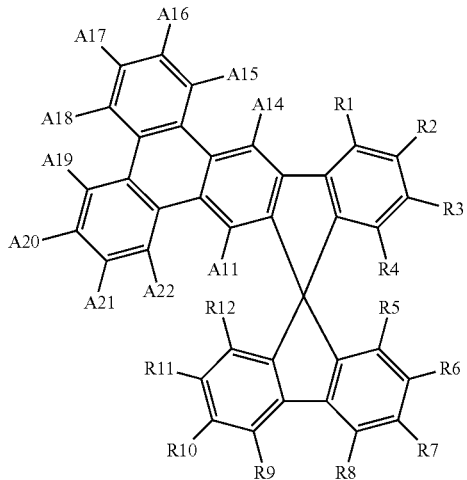

in Chemical Formulae 1-1 and 1-2,
the definitions of R1 to R12 are the same as those in Chemical Formula 1, and
A1, and A4 to A10 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and
wherein A11, and A14 to A22 are the same as or different from each other, and are each independently hydrogen or deuterium.

4. The compound of claim 1, wherein Chemical Formula 1 is represented by Chemical Formula 1-3 or 1-4:

[Chemical Formula 1-3]

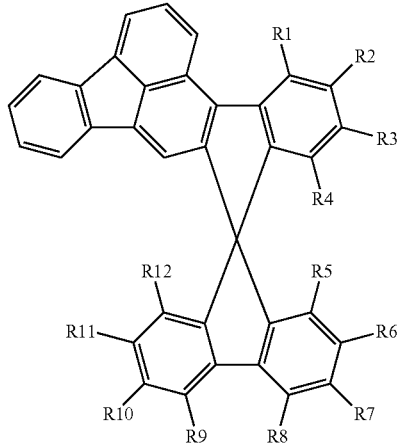

[Chemical Formula 1-4]

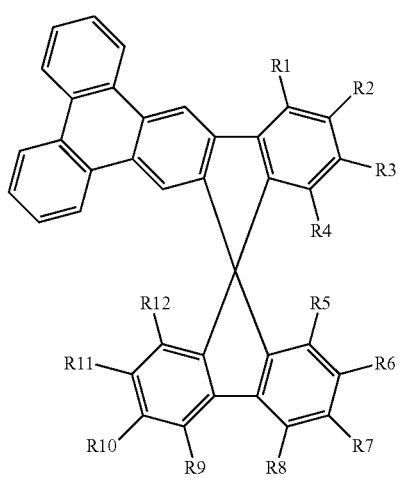

in Chemical Formulae 1-3 and 1-4,
the definitions of R1 to R12 are the same as those in Chemical Formula 1.

5. The compound of claim 1, wherein R5 to R12 are the same as or different from each other, and are each independently selected from the group consisting of hydrogen; a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted chrysenyl group; a substituted or unsubstituted quarterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; a substituted or unsubstituted pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted dimethylphosphine oxide group; a substituted or unsubstituted diphenylphosphine oxide group; a substituted or unsubstituted dinaphthylphosphine oxide group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted diphenylamine group; a substituted or unsubstituted N-phenylnaphthylamine group; a substituted or unsubstituted N-phenylbiphenylamine group; a substituted or unsubstituted N-phenylphenanthrenylamine group; a substituted or unsubstituted N-biphenylnaphthylamine group; a substituted or unsubstituted dibiphenylamine group; a substituted or unsubstituted N-biphenylphenanthrenylamine group; a substituted or unsubstituted dinaphthylamine group; a substituted or unsubstituted N-quarterphenylfluorenylamine group; a substituted or unsubstituted N-terphenylfluorenylamine group; a substituted or unsubstituted N-biphenyl terphenylamine group; a substituted or unsubstituted N-biphenylfluorenylamine group; a substituted or unsubstituted N-phenylfluorenylamine group; a substituted or unsubstituted N-naphthylfluorenylamine group; a substituted or unsubstituted N-phenanthrenylfluorenylamine group; a substituted or unsubstituted difluorenylamine group; a substituted or unsubstituted N-phenyl terphenylamine group; a substituted or unsubstituted N-phenylcarbazolylamine group; a substituted or unsubstituted N-biphenylcarbazolylamine group; a substituted or unsubstituted N-phenylbenzocarbazolylamine group; a substituted or unsubstituted N-biphenylbenzocarbazolylamine group; a substituted or unsubstituted N-phenyldibenzofuranylamine group; a substituted or unsubstituted N-phenyldibenzothiopheneamine group; a substituted or unsubstituted N-fluorenylcarbazolylamine group; a substituted or unsubstituted benzocarbazolyl group; a substituted or unsubstituted dibenzocarbazolyl group; a substituted or unsubstituted carbazolyl group; substituted or unsubstituted

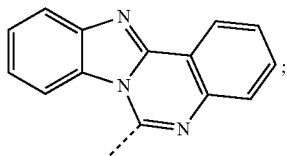

substituted or unsubstituted

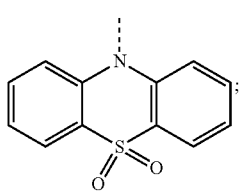

and a structure represented by the following Chemical Formula a, at least one of R5 to R12 has a substituent other than hydrogen, and ---- is a moiety bonded to Chemical Formula 1,

[Chemical Formula a]

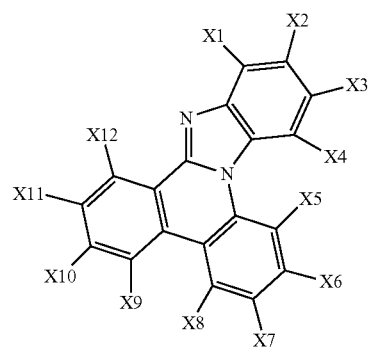

in Chemical Formula a, at least one of X1 to X12 is a moiety bonded to Chemical Formula 1, and the others are the same as or different from each other, and are each independently hydrogen; a substituted or unsubstituted alkyl group; a substituted or unsubstituted aryl group; or a substituted or unsubstituted heteroaryl group, or adjacent groups are linked to each other to form a substituted or unsubstituted ring.

6. The compound of claim 1, wherein R5 to R12 are the same as or different from each other, and are each independently represented by hydrogen; or any one of the following structural formulae [R-1] to [R-5], and at least one of R5 to R12 has a substituent other than hydrogen;

[R-1]

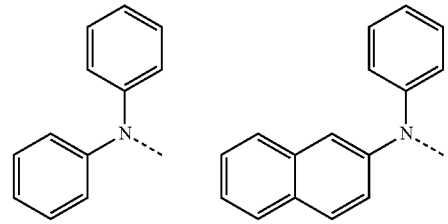

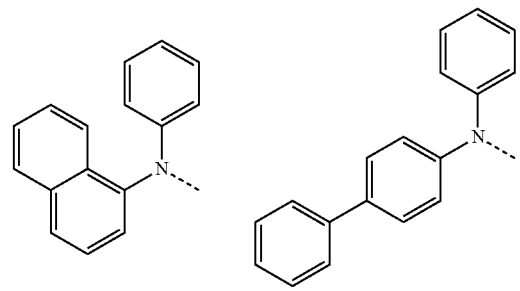

323
-continued
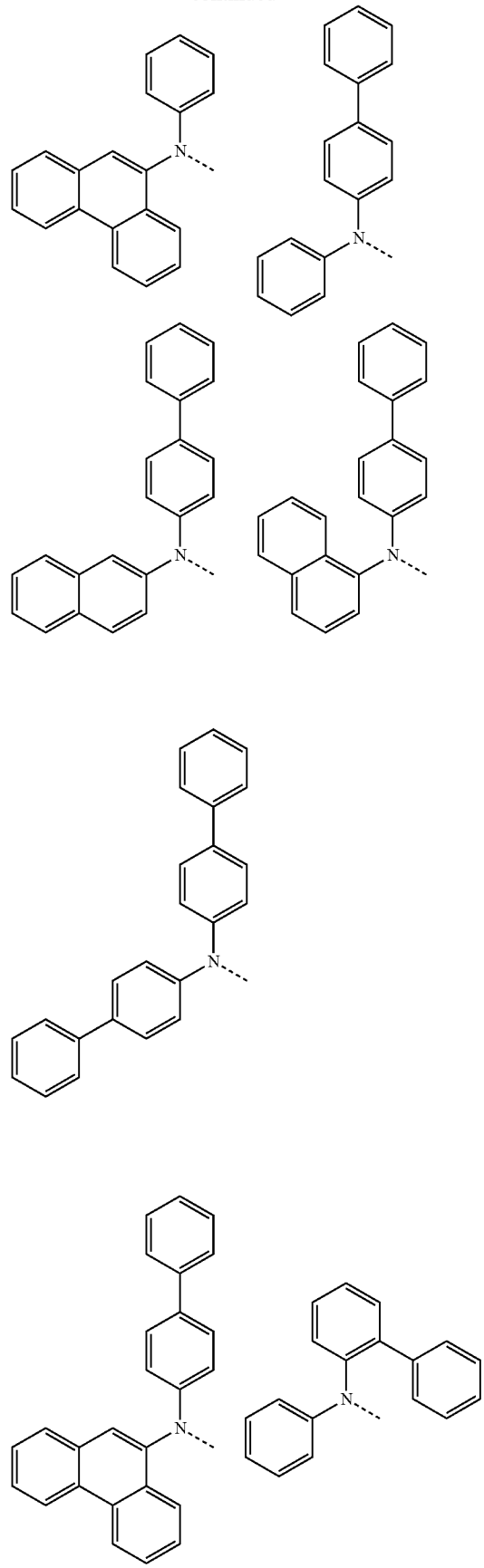
324
-continued
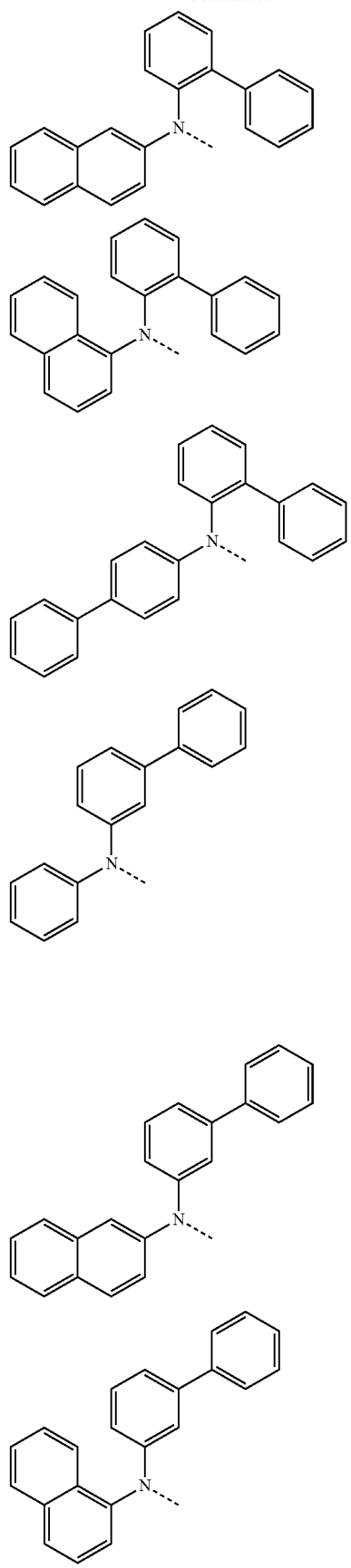

325
-continued
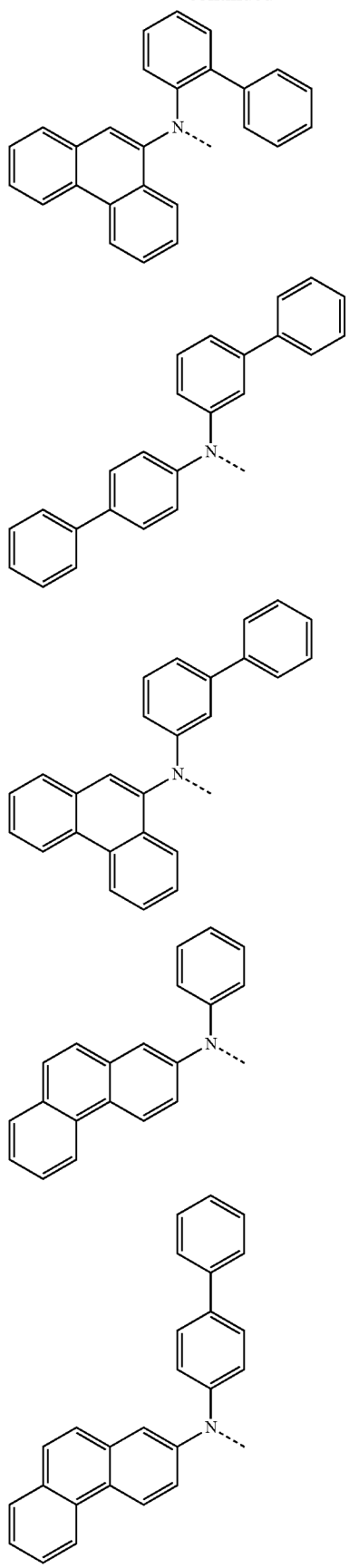
326
-continued
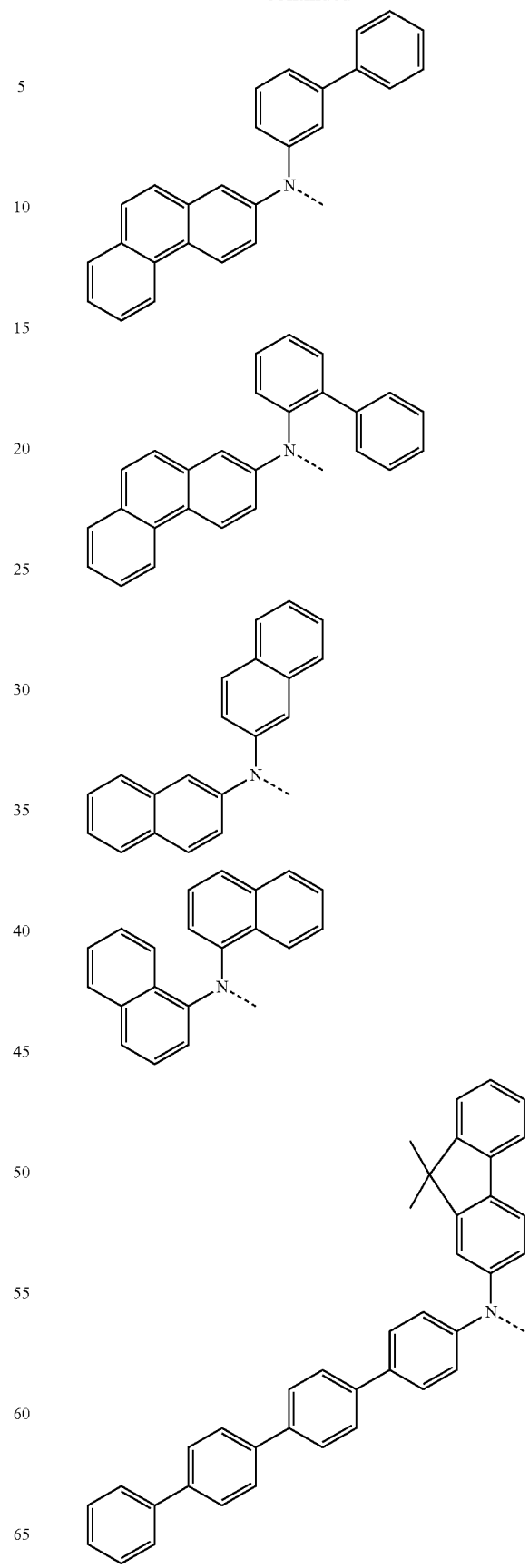

327
-continued
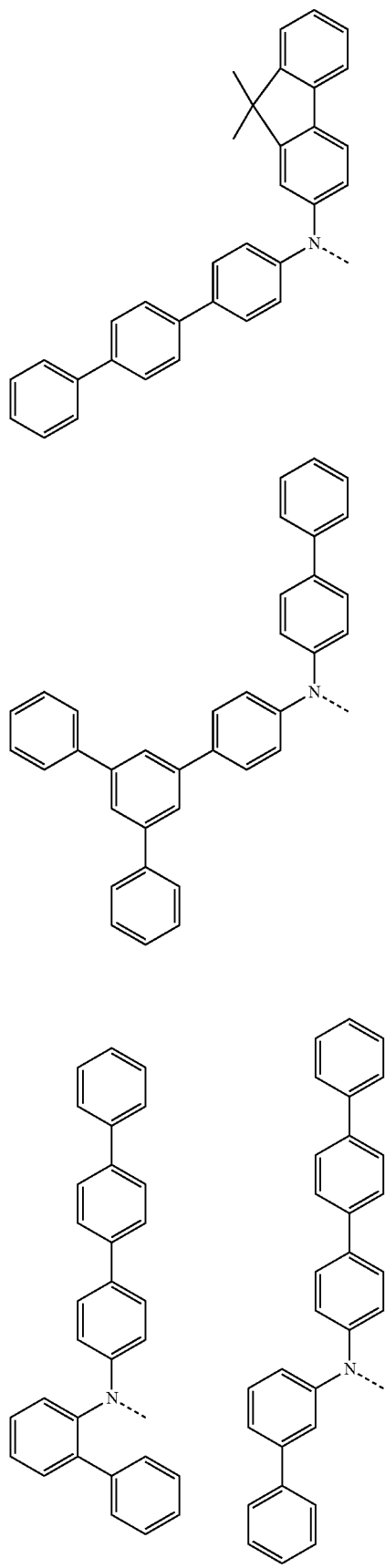
328
-continued
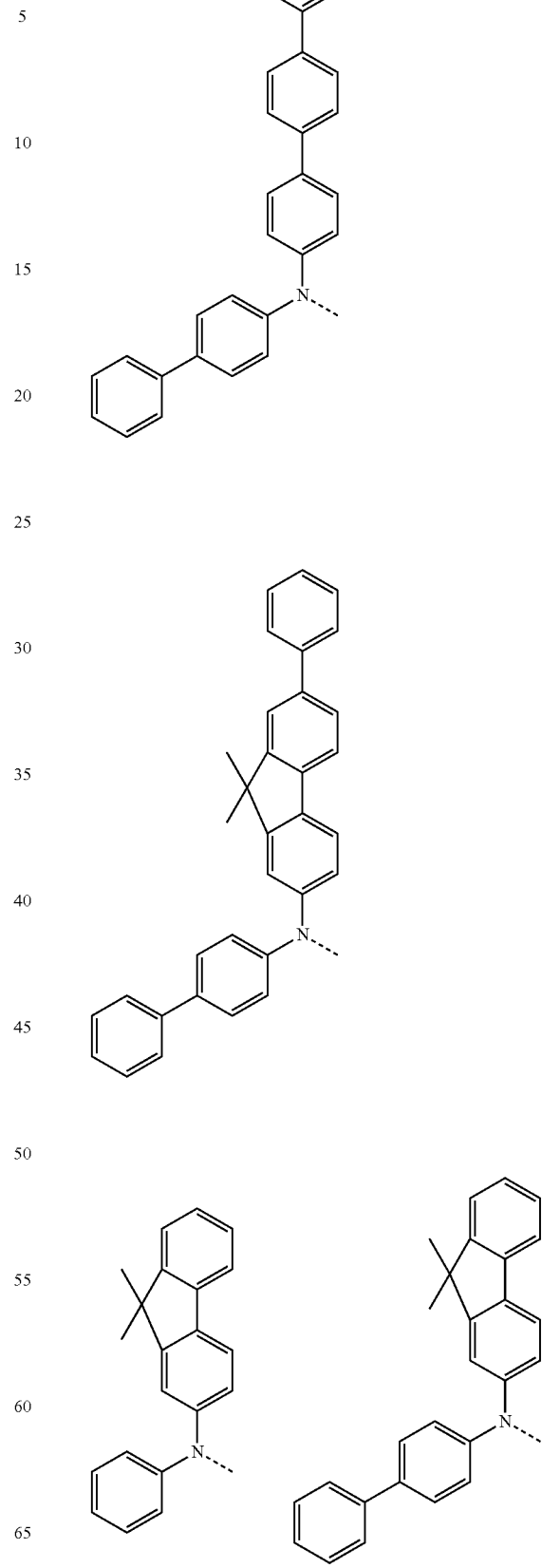

329
-continued
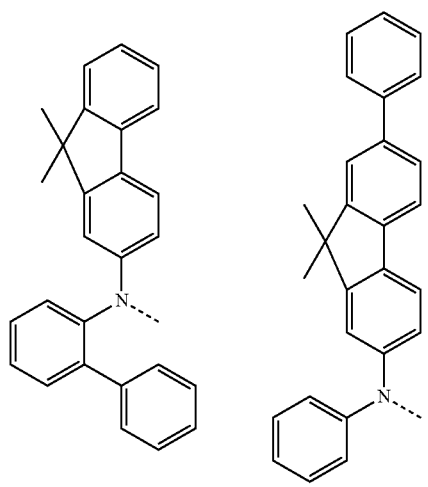
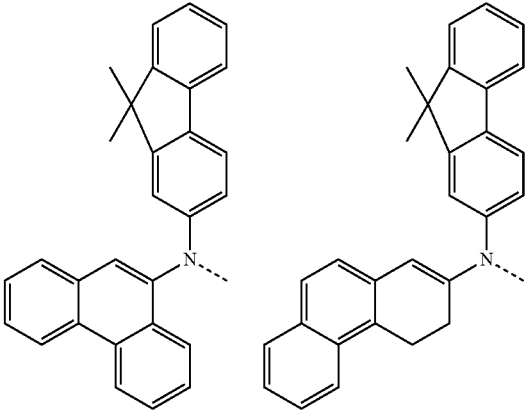
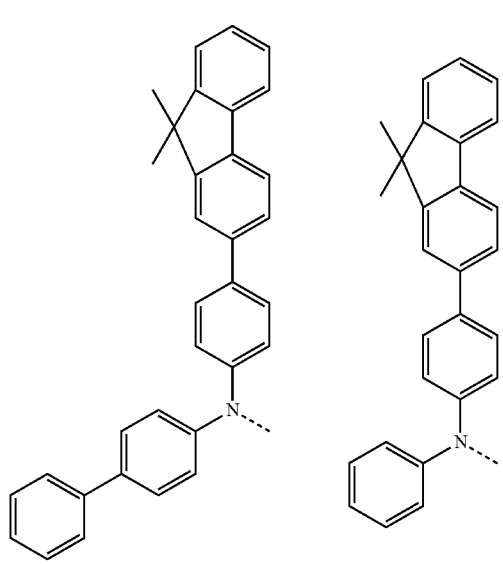
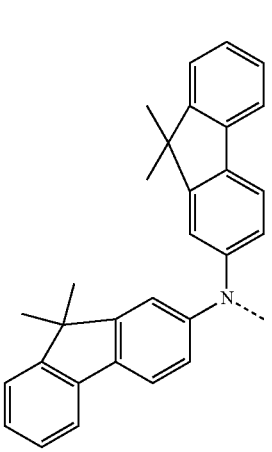
330
-continued
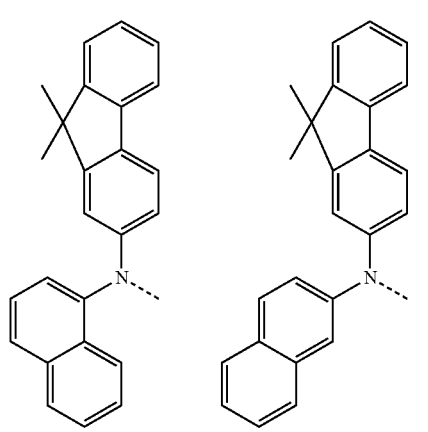
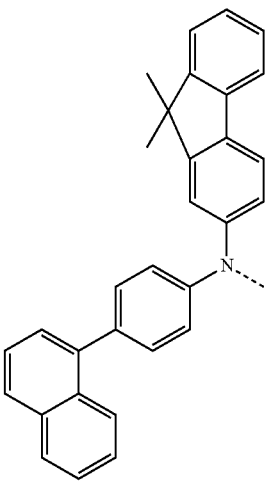

331
-continued
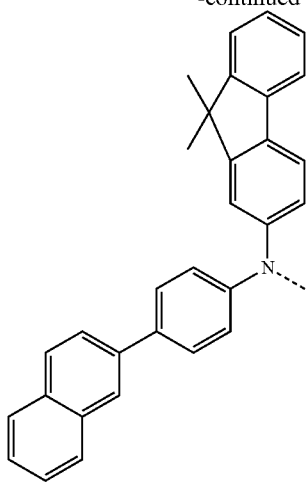
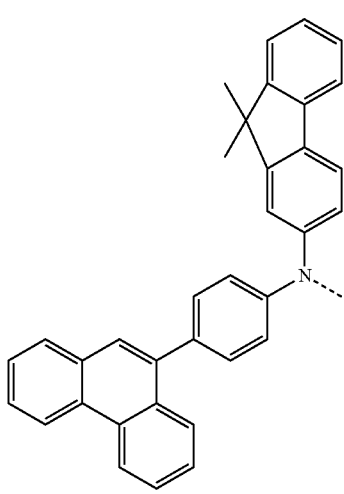
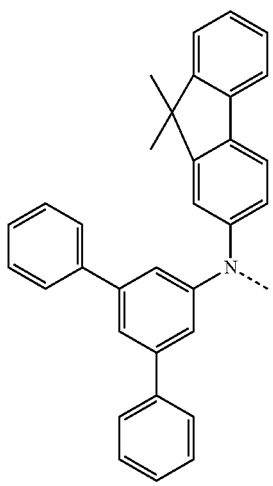
332
-continued
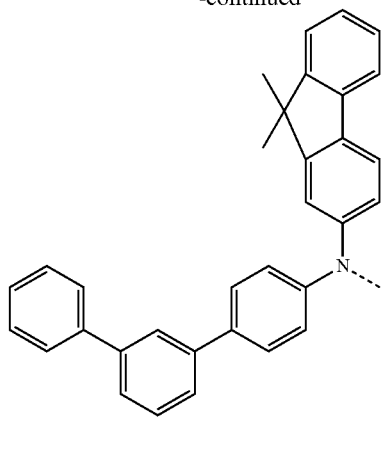
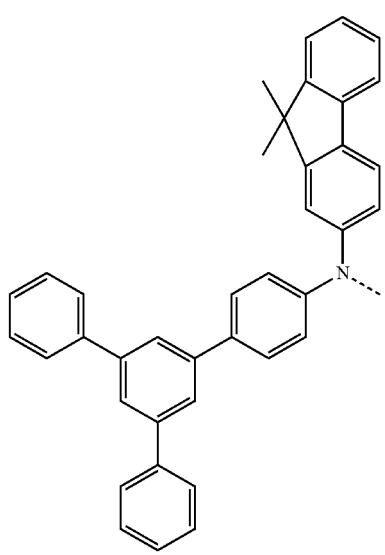
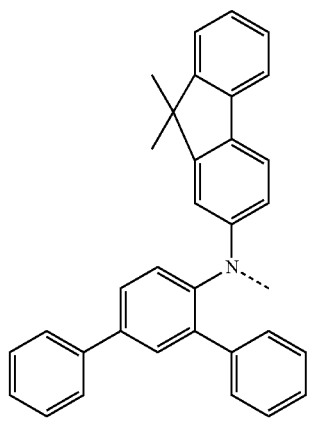

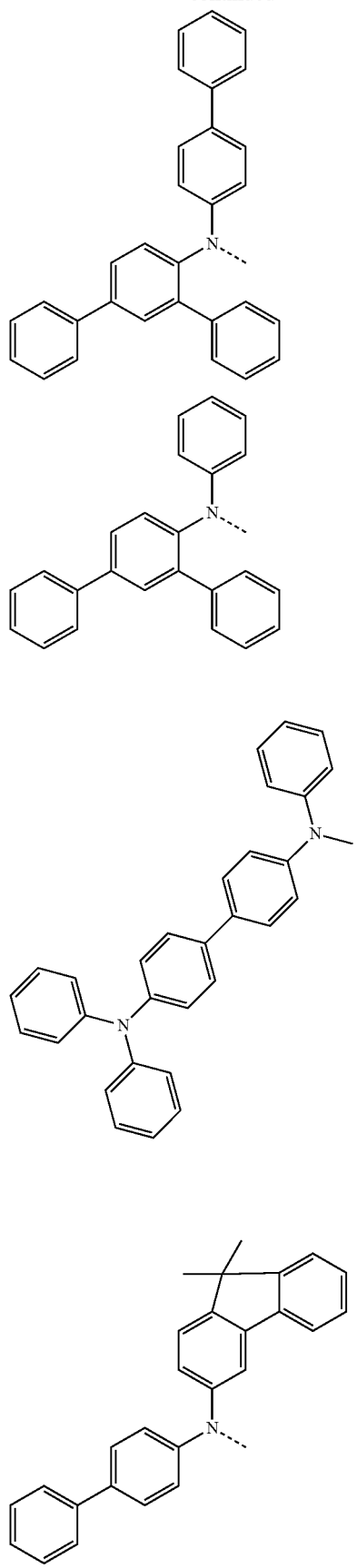

335
-continued
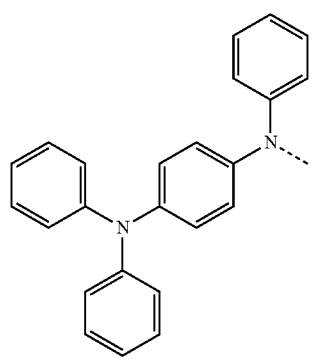
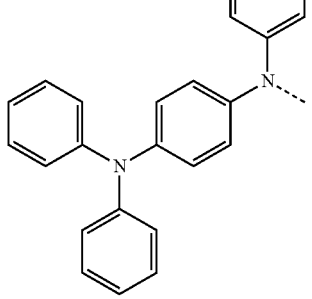
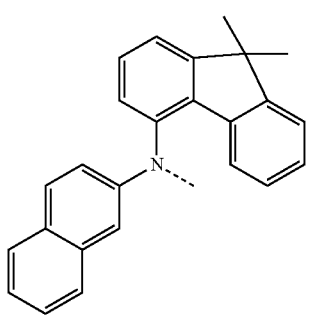
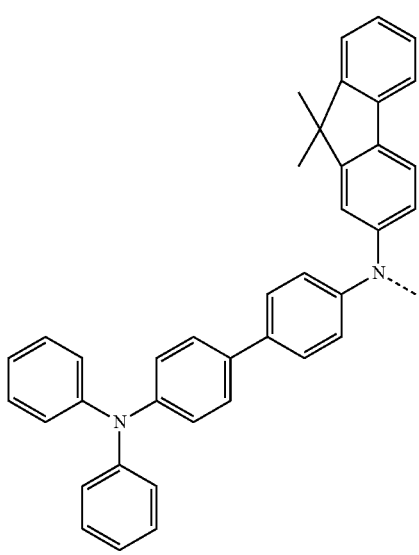
336
-continued
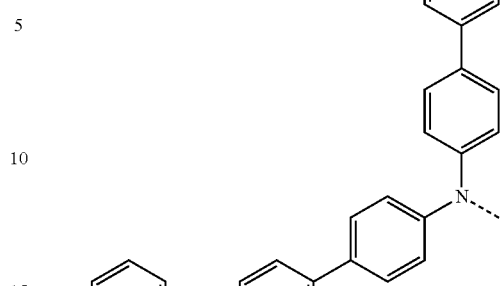
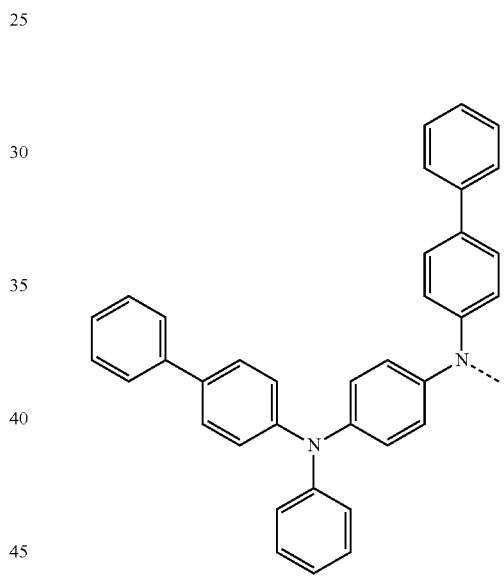
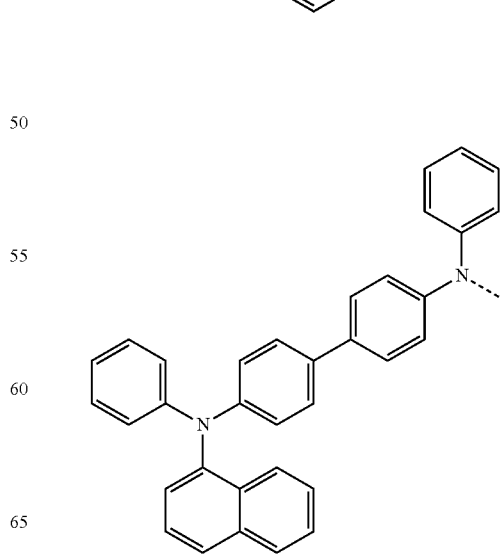

337
-continued
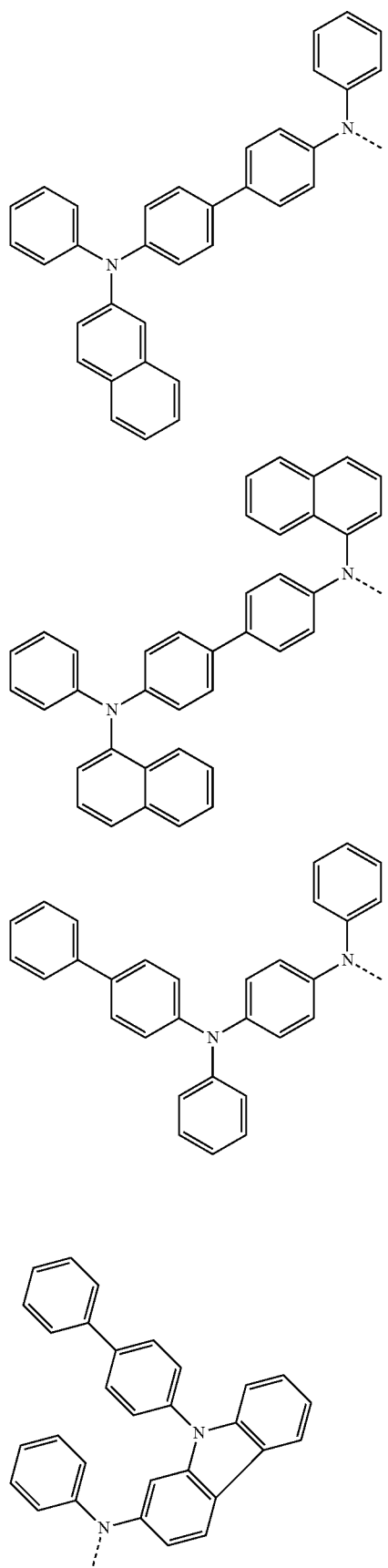
338
-continued
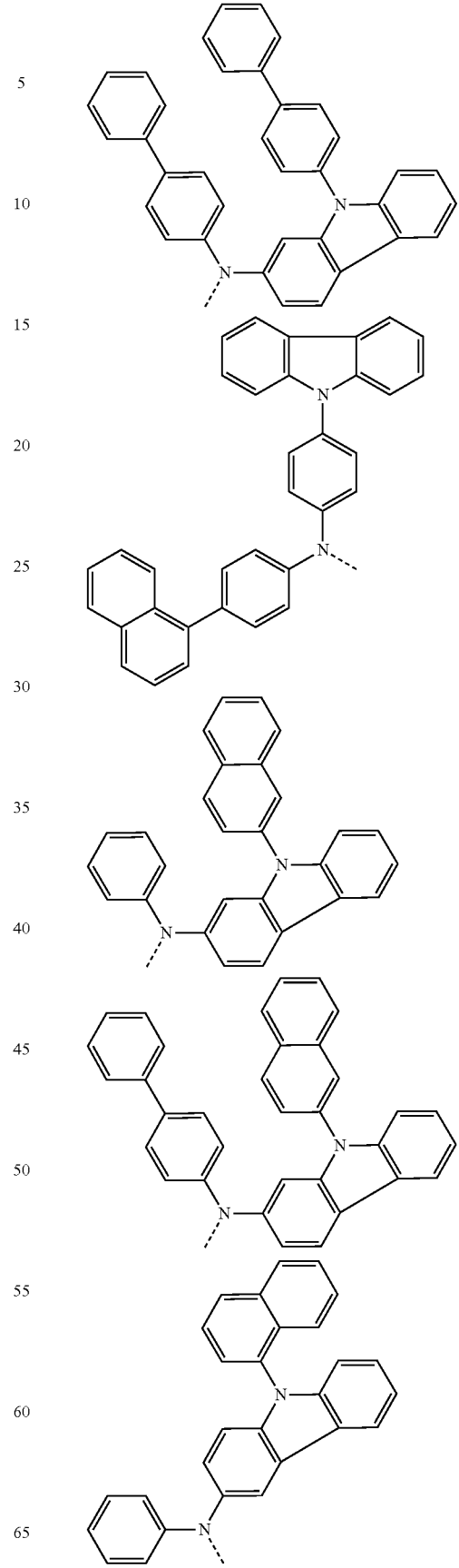

339
-continued
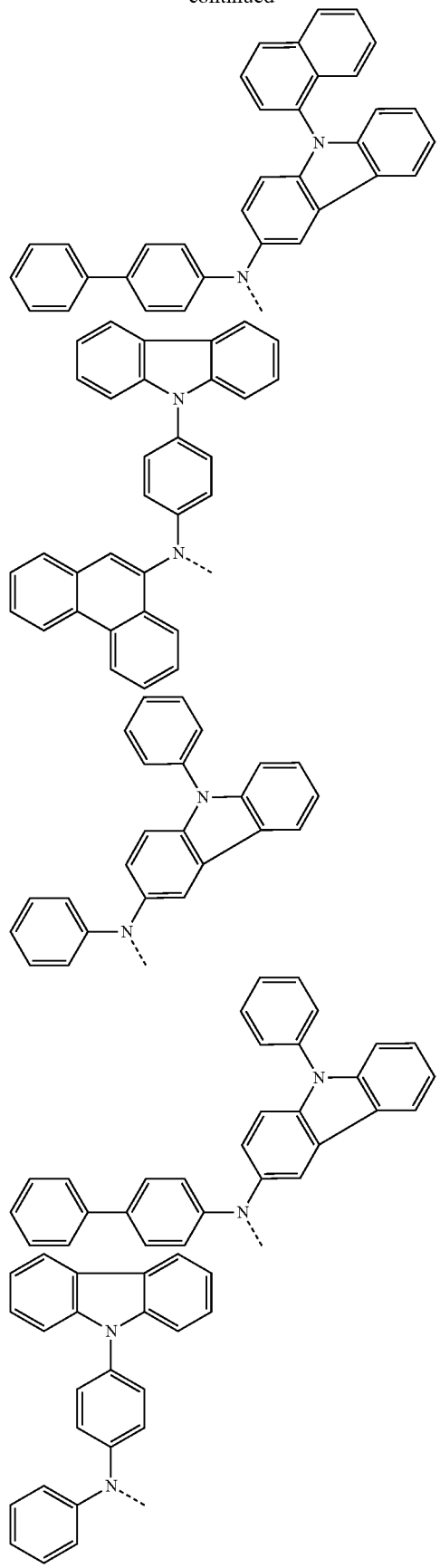
340
-continued
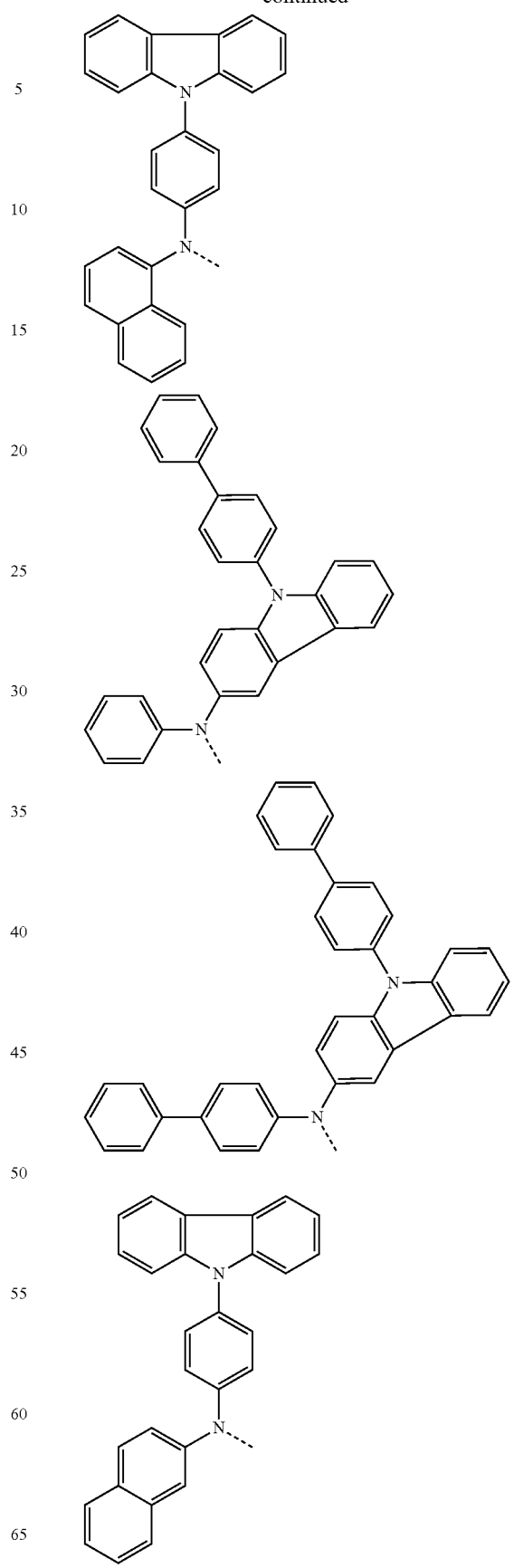

341
-continued
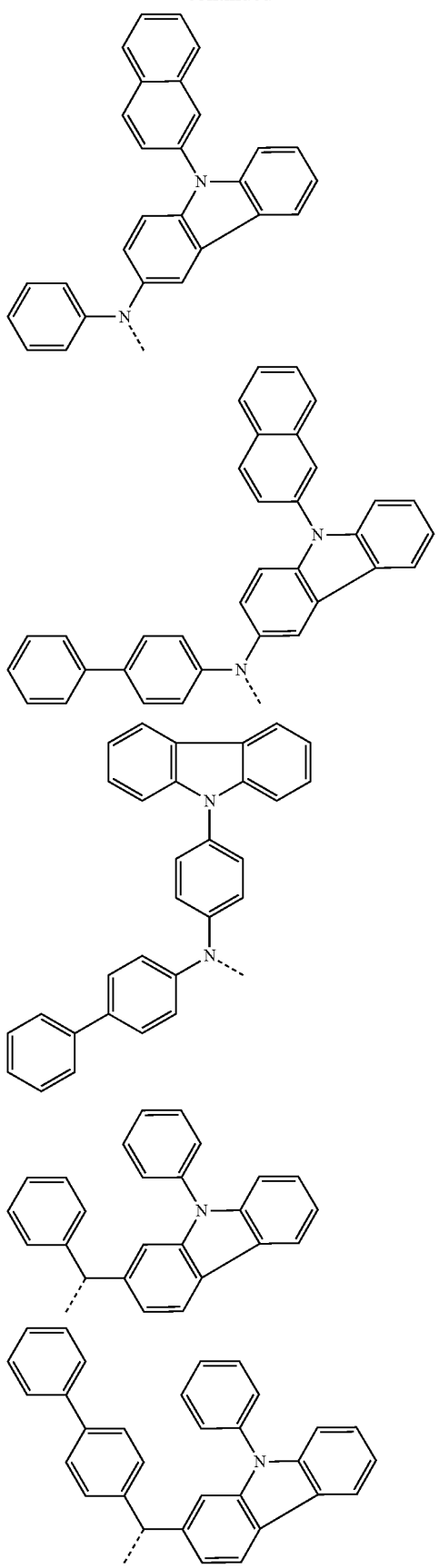
342
-continued
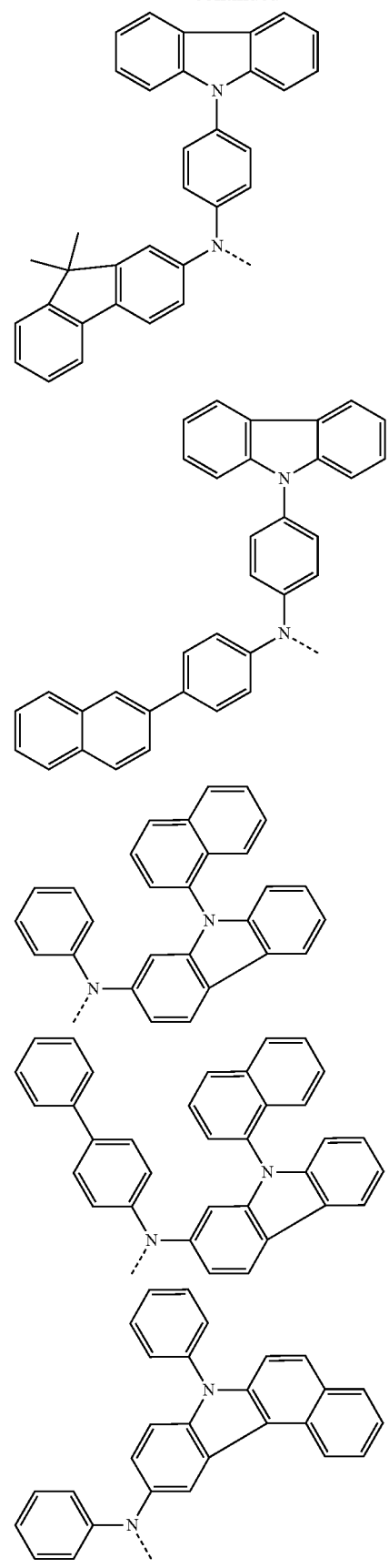

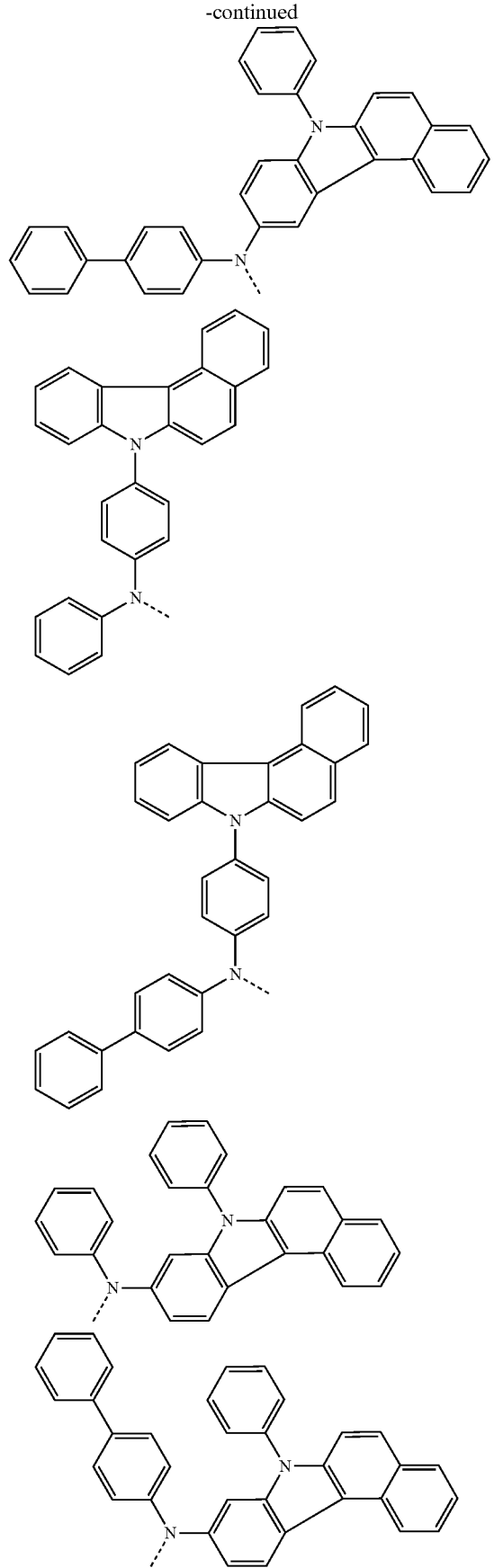
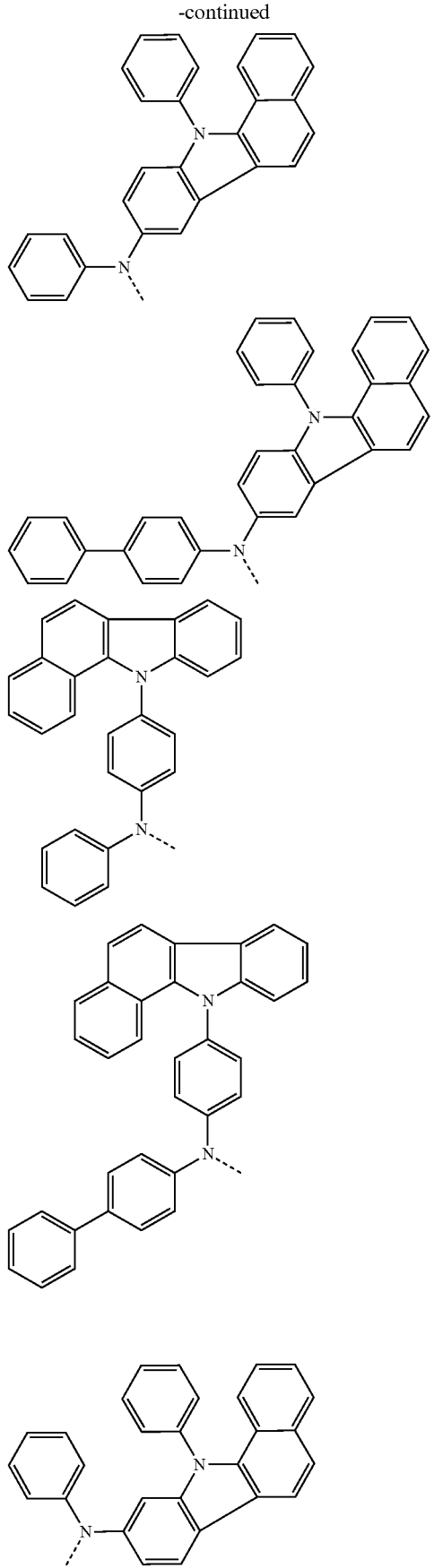

345
-continued
346
-continued
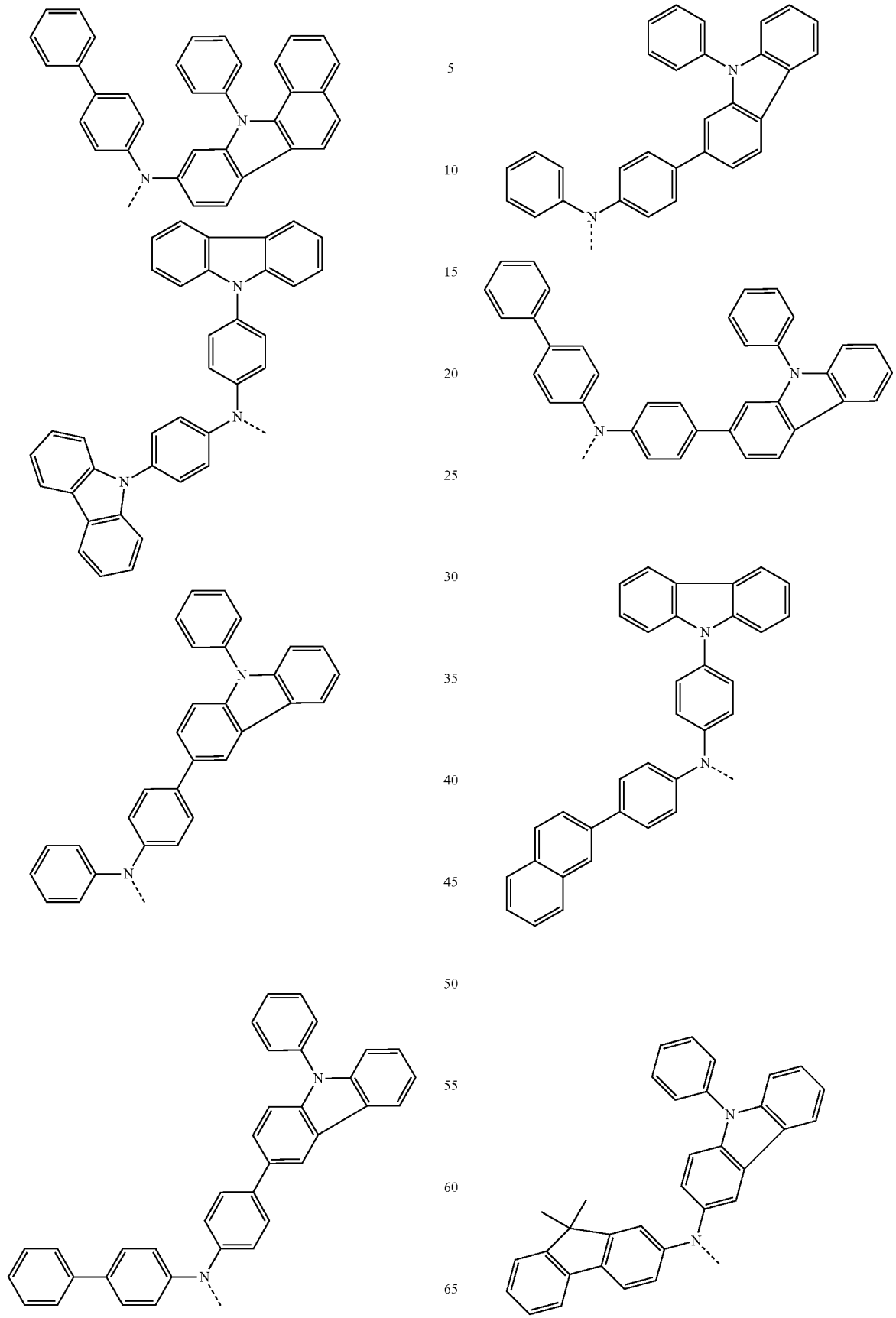

347
-continued
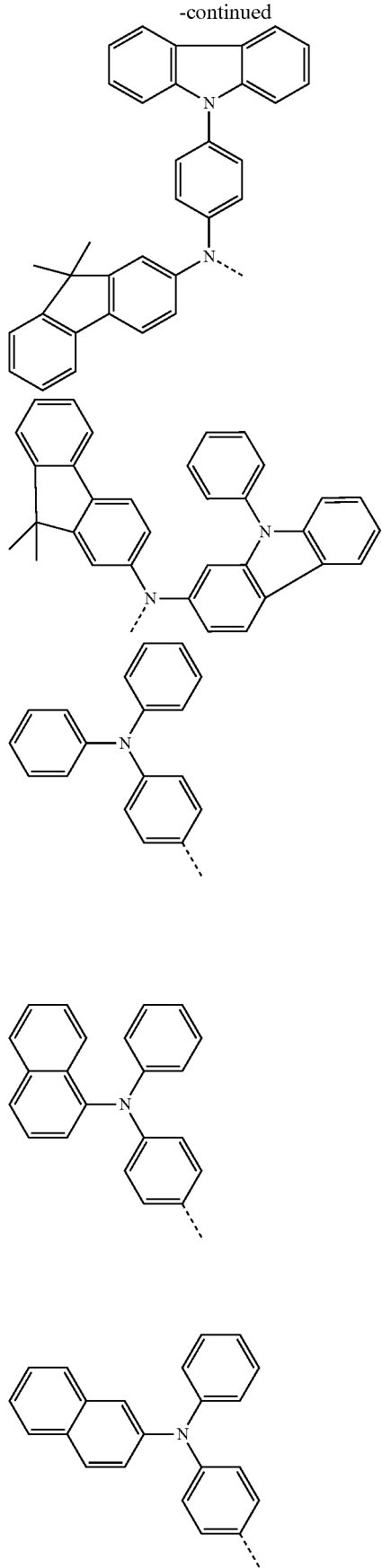
348
-continued
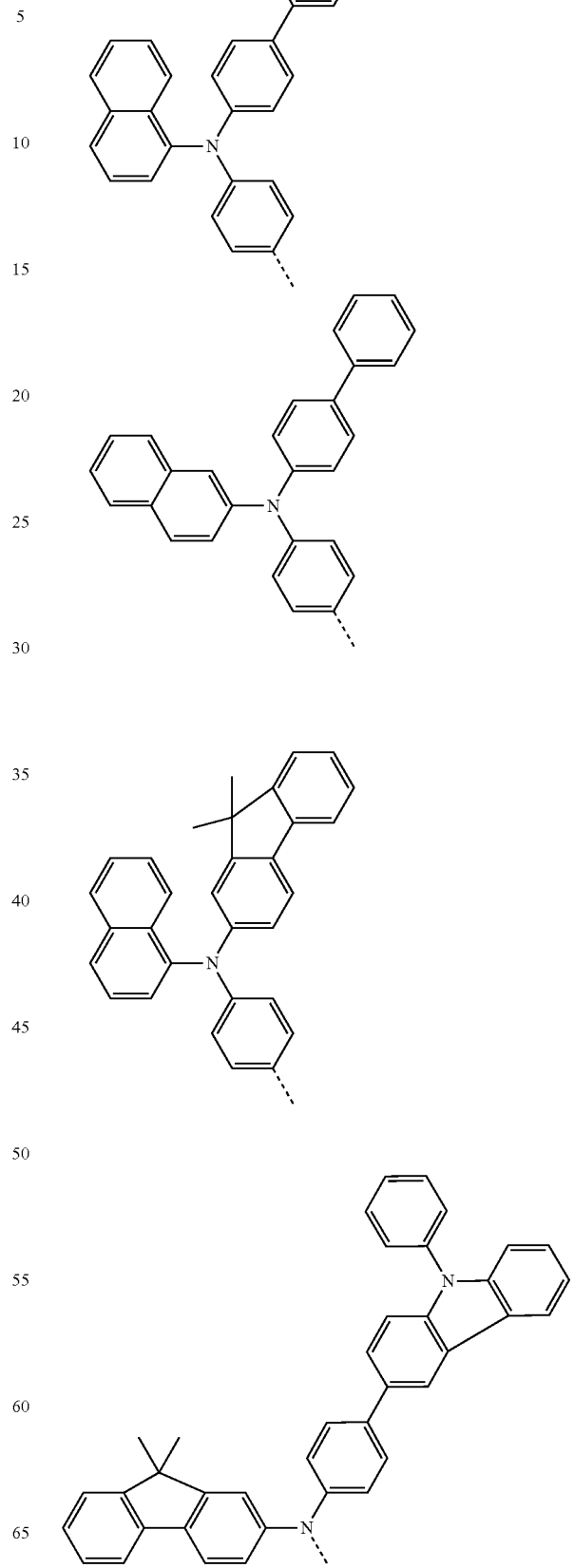

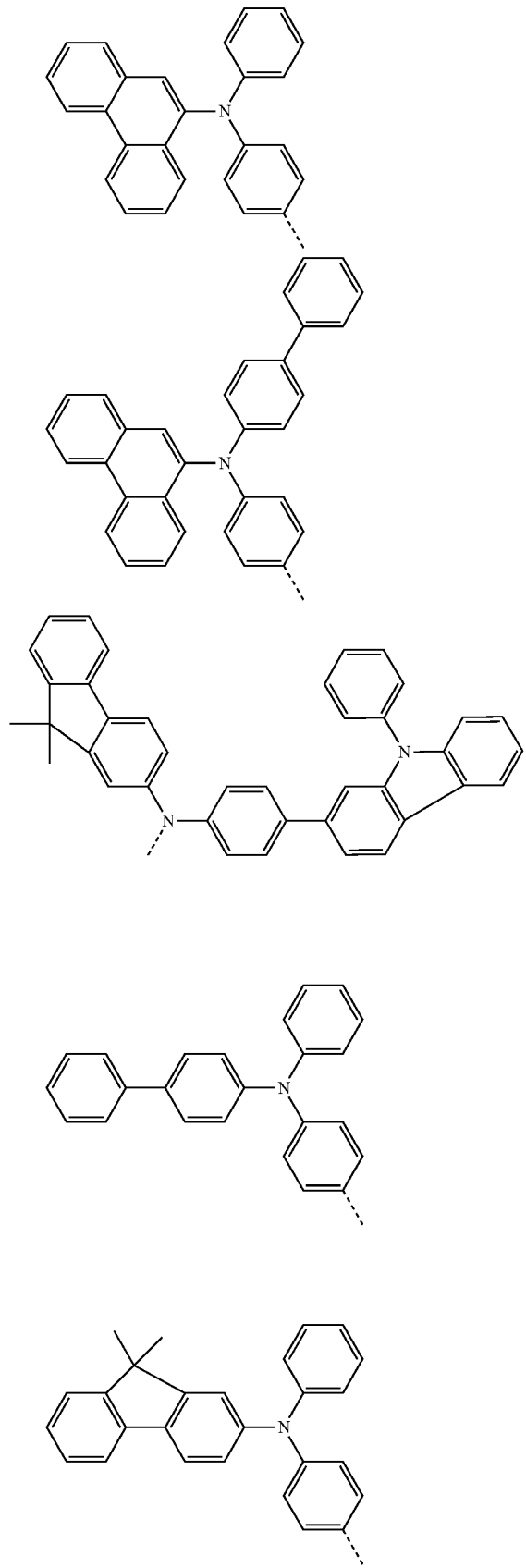
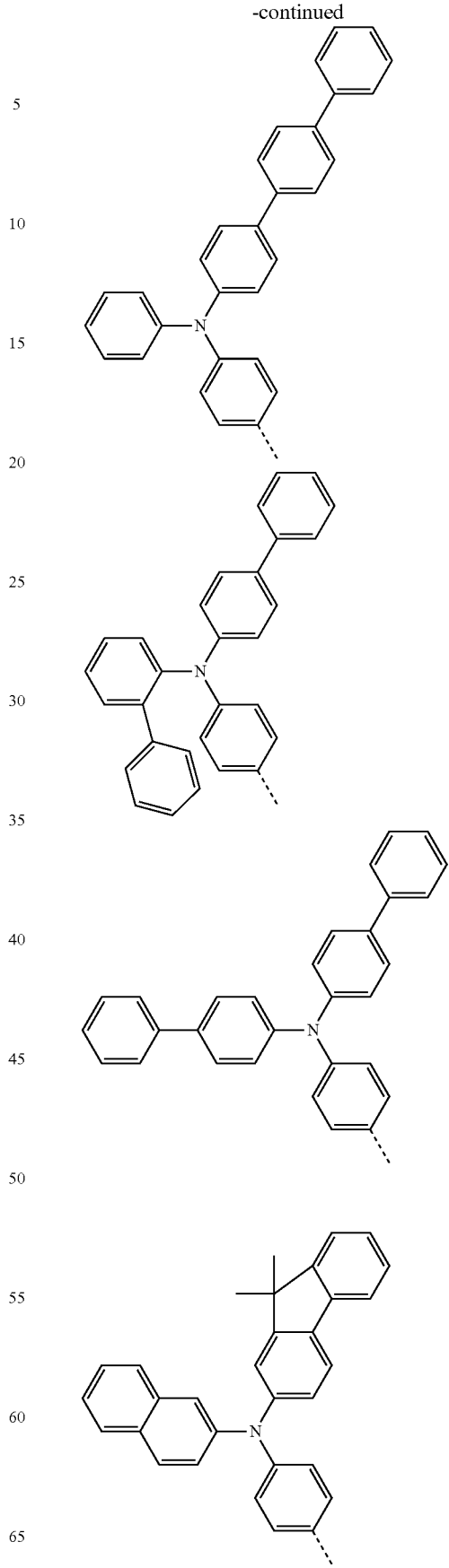

351
-continued
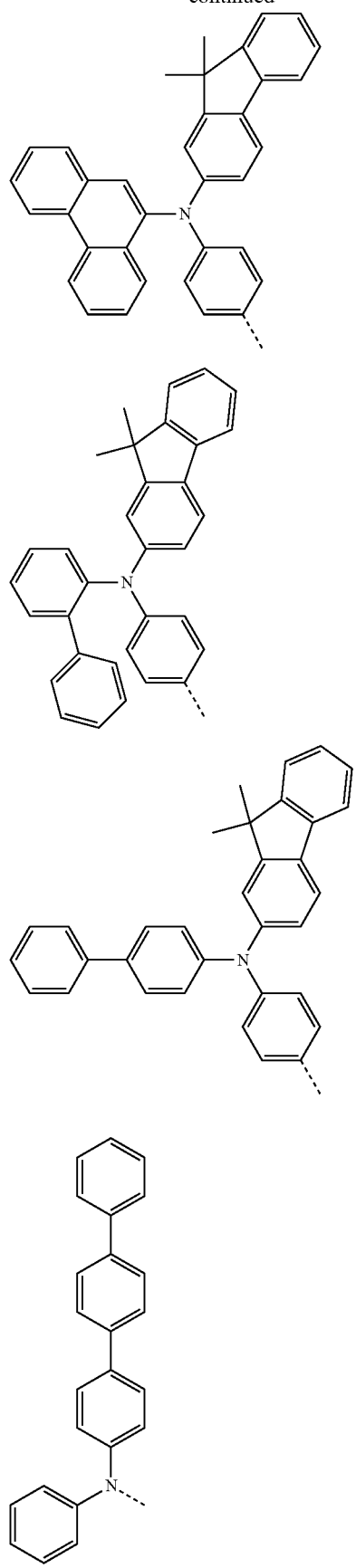
352
-continued
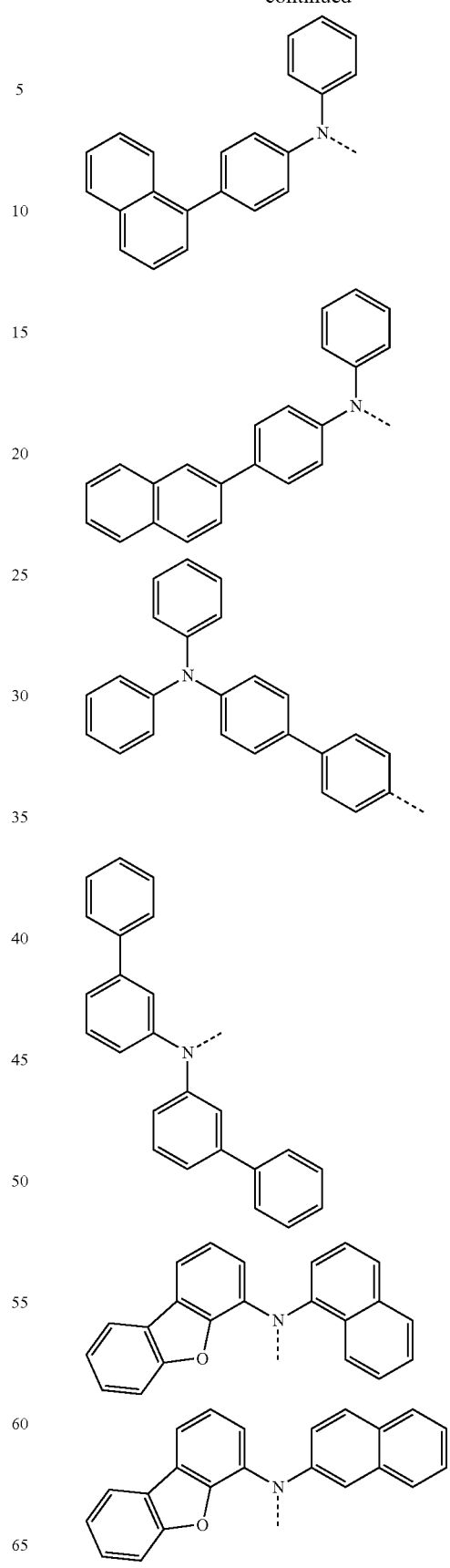

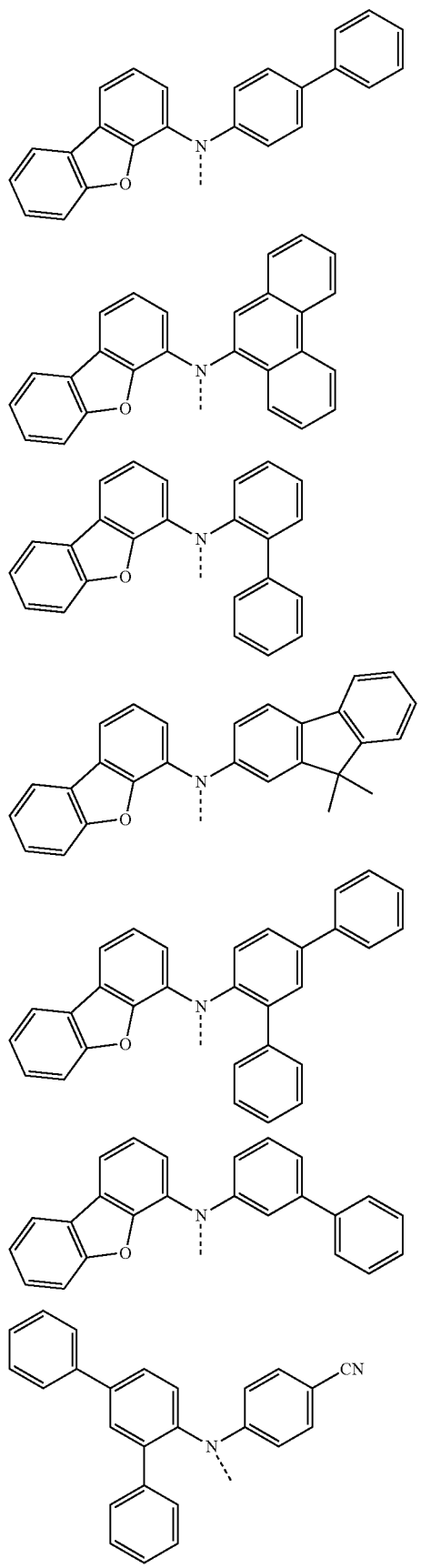
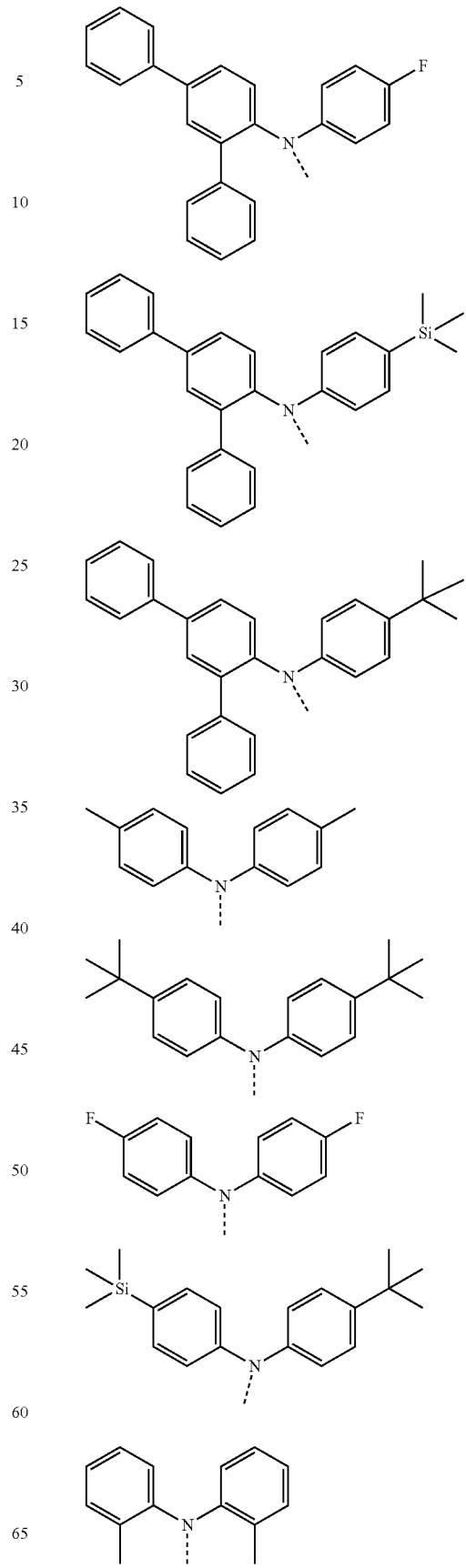

355
-continued
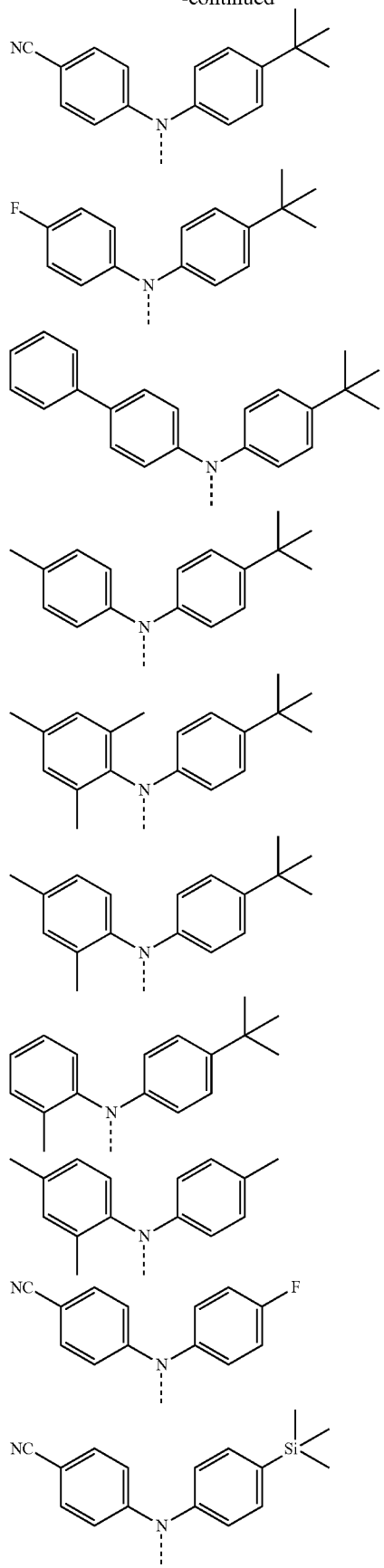
356
-continued
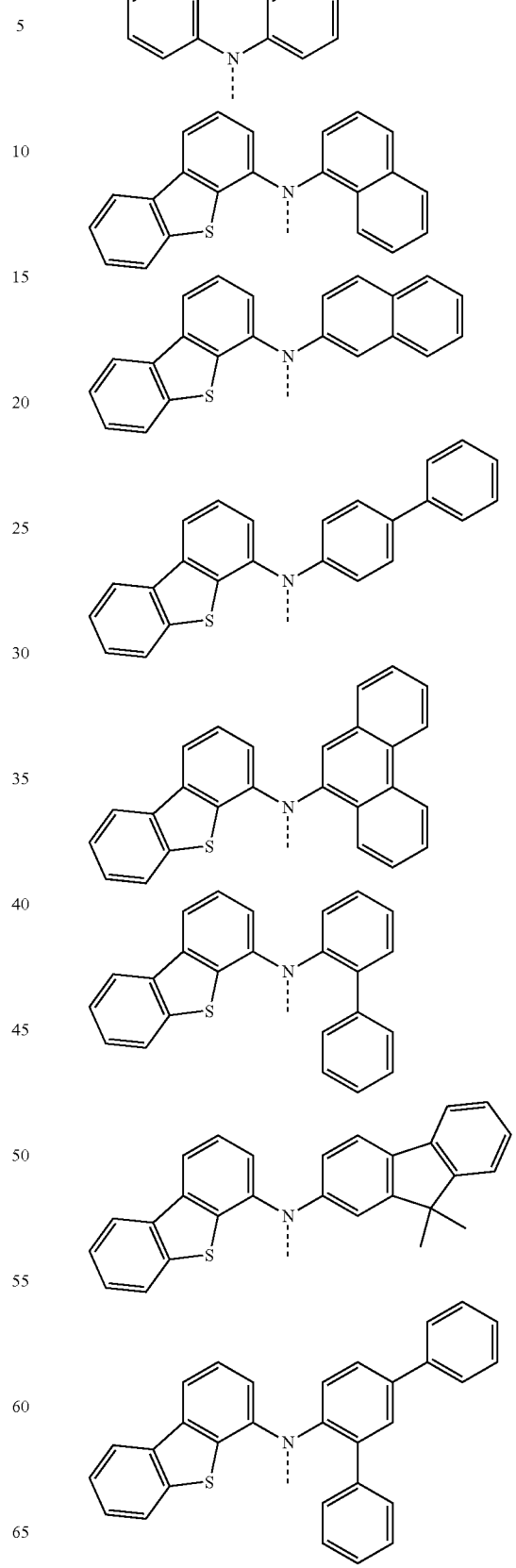

357
-continued
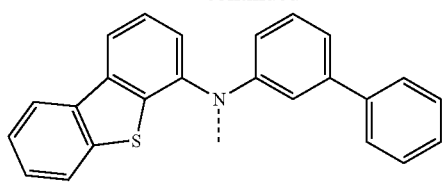
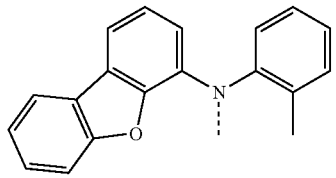
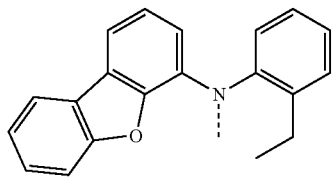
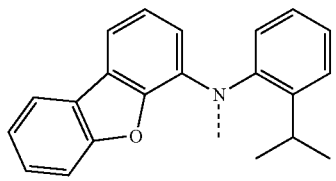
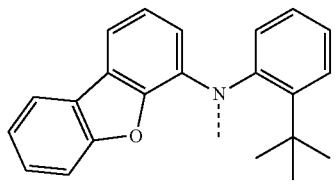
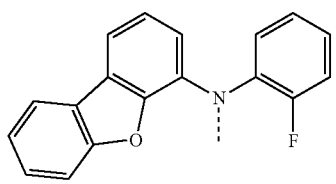
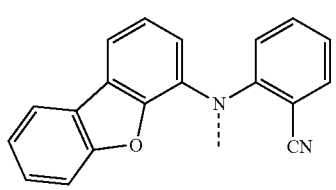
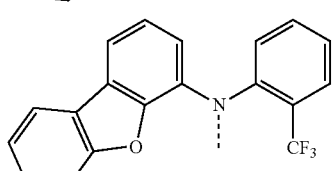
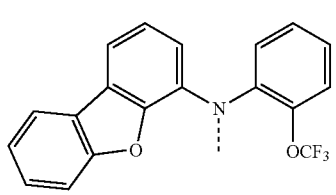
358
-continued
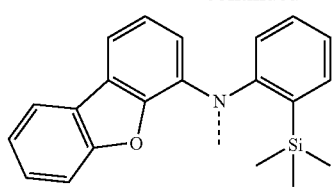
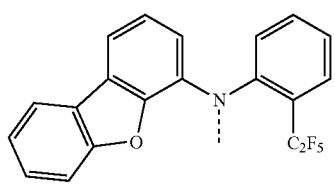
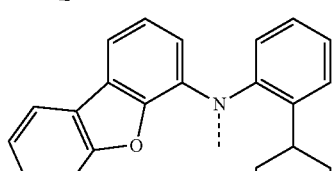
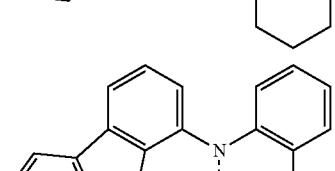
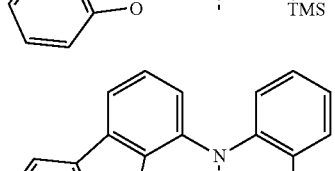
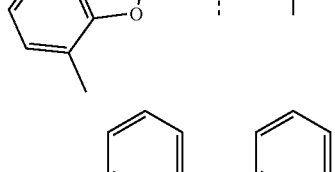
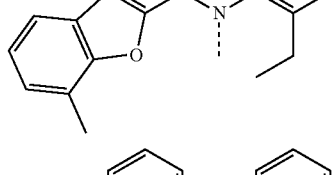
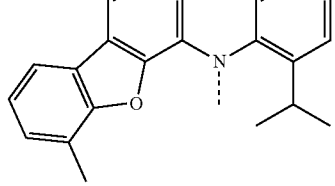
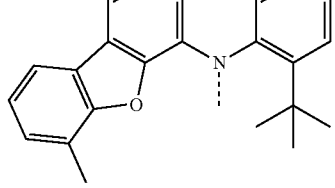

359
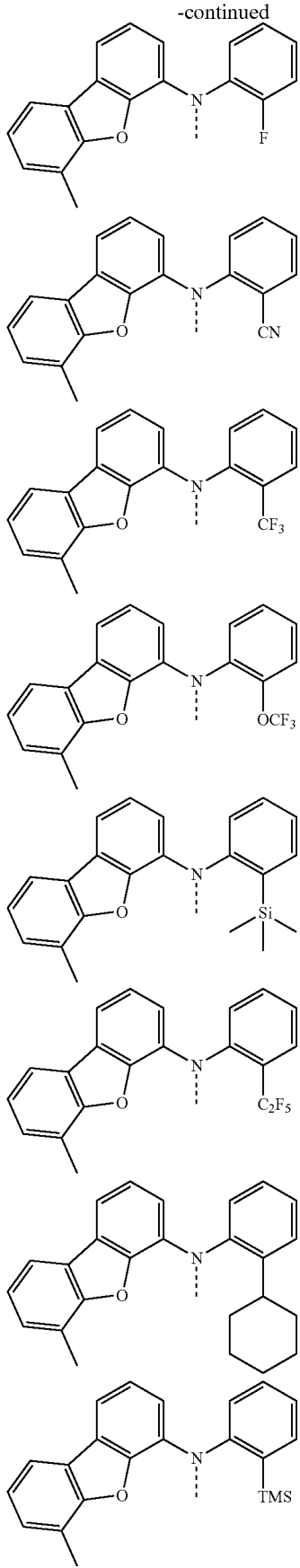
360
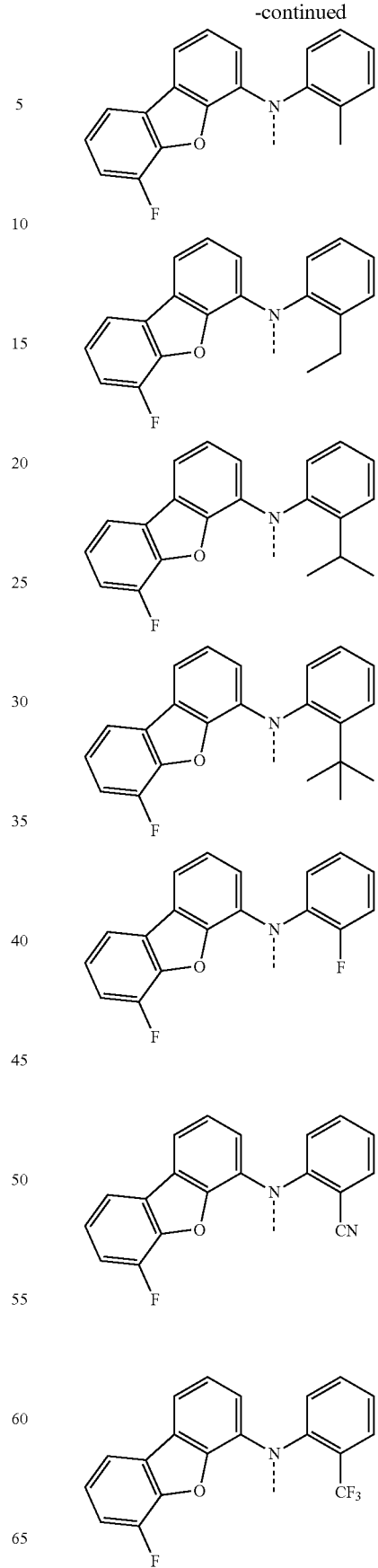

-continued
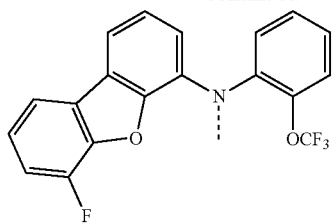
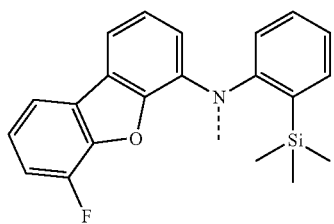
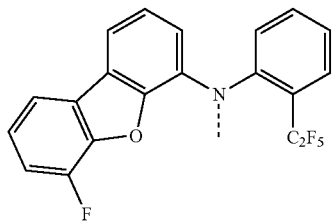
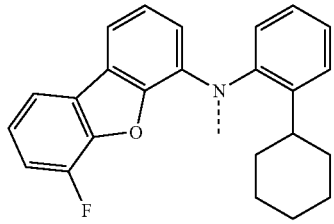
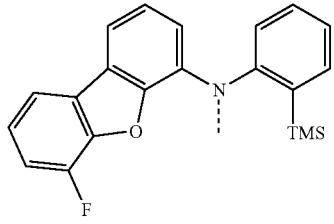
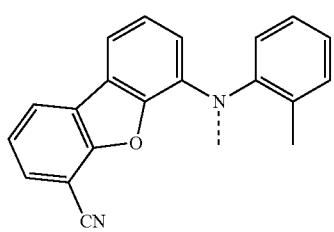
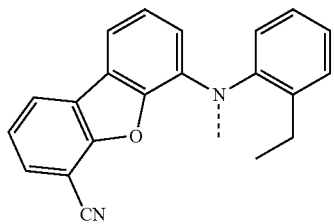
-continued
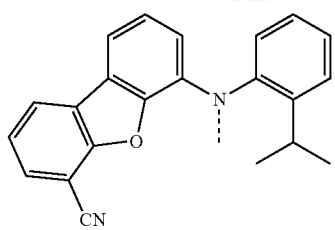
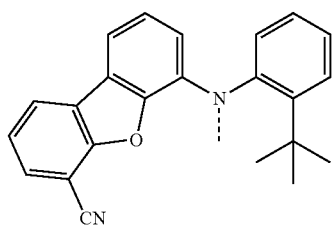
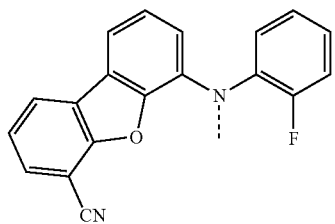
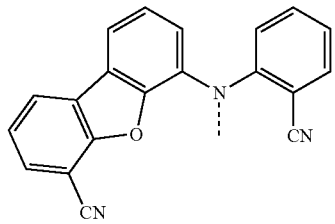
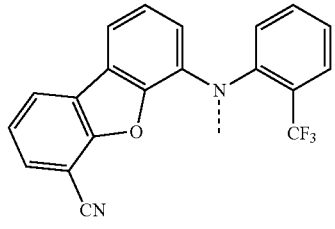
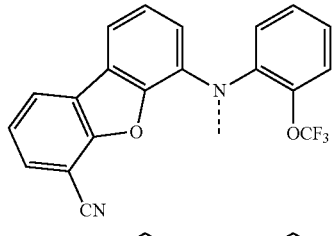
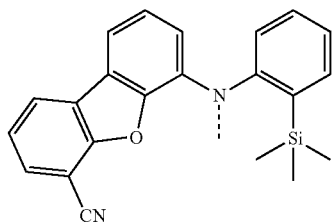

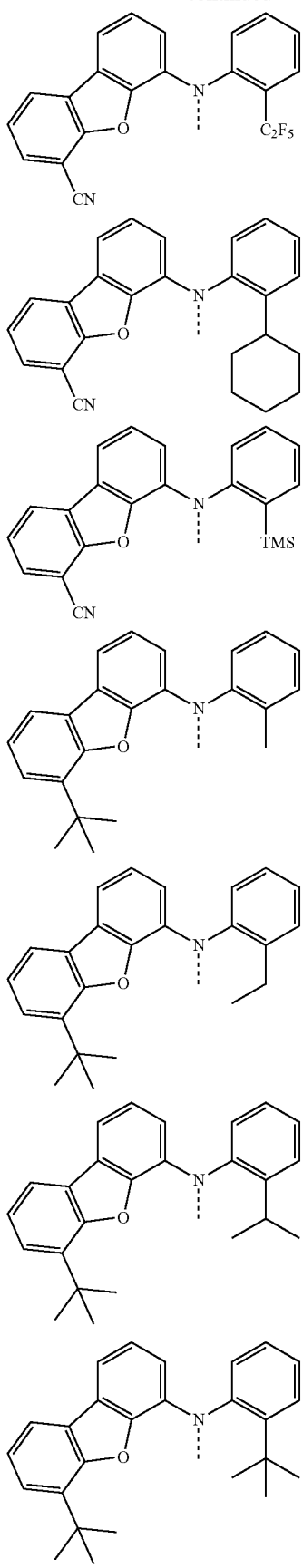
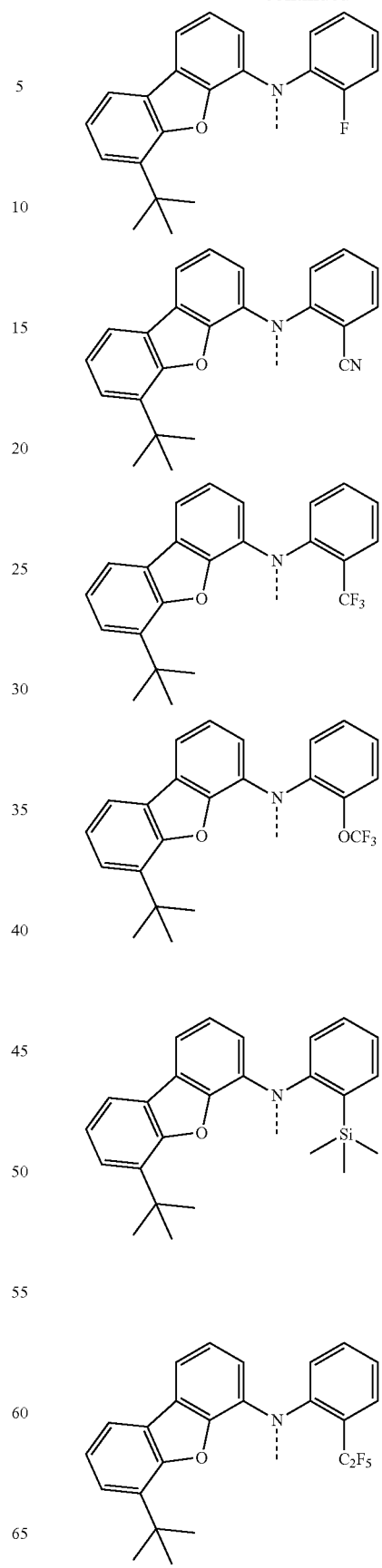

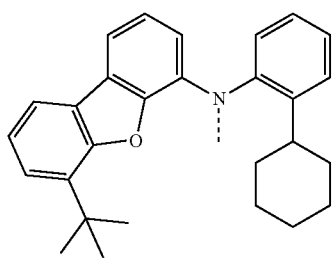
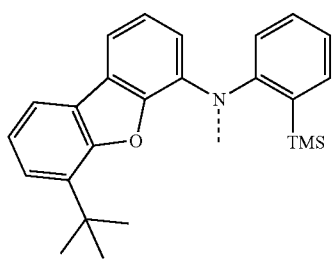
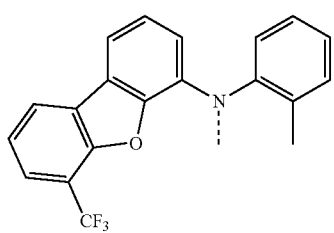
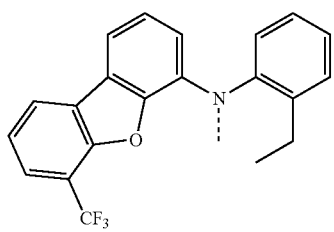
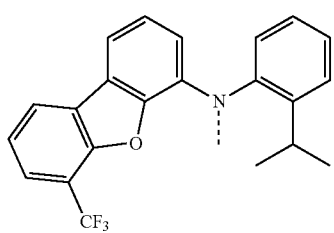
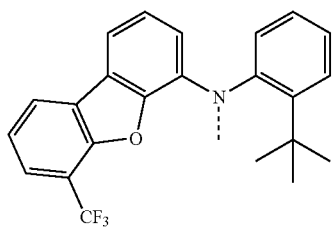
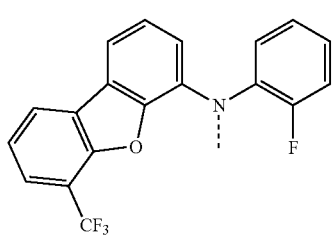
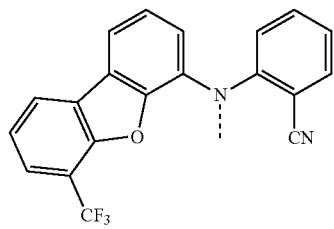
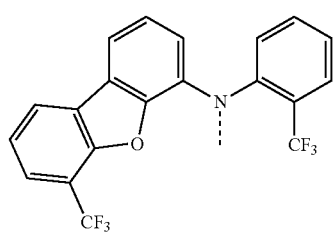
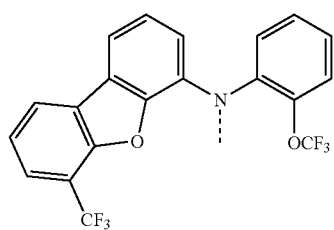
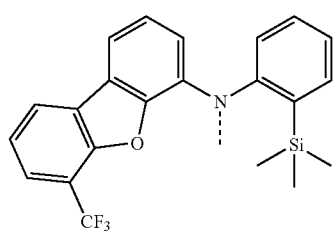
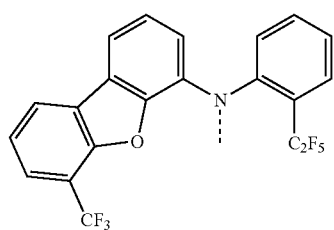
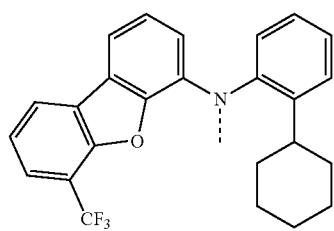
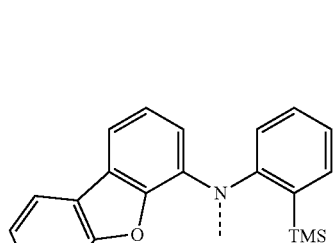

367
-continued
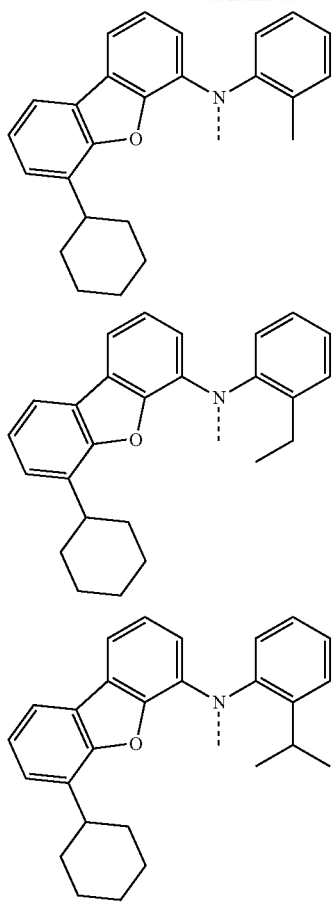
368
-continued
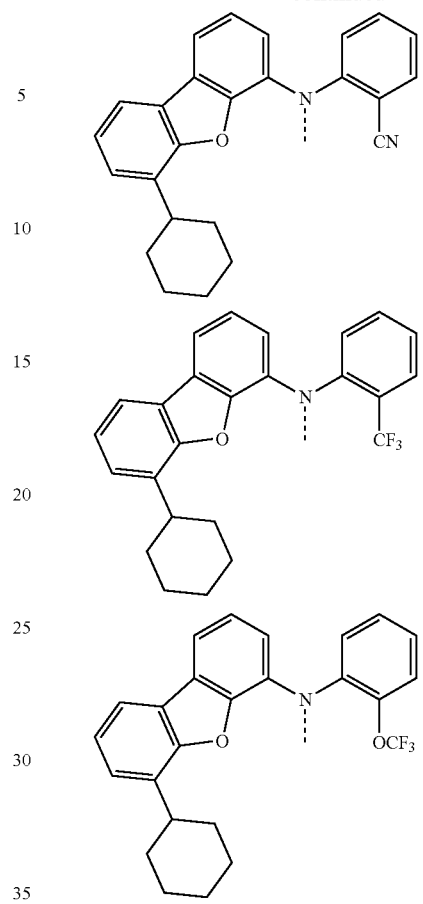
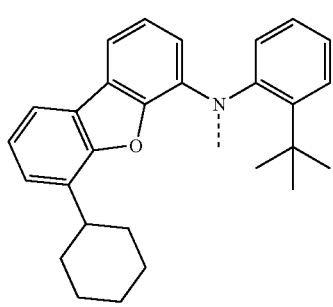
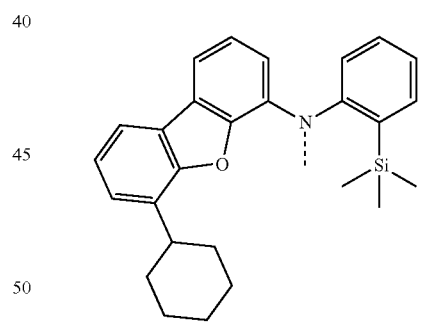
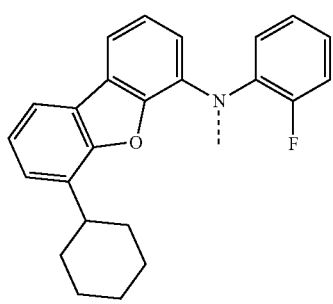

369
-continued
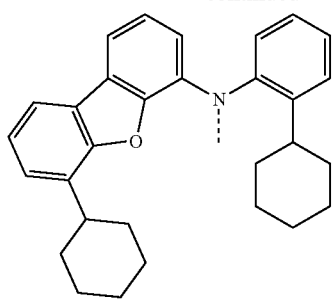
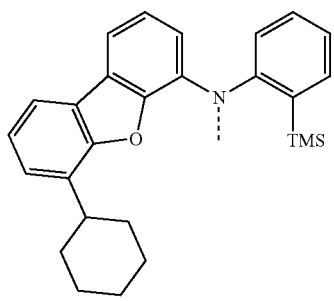
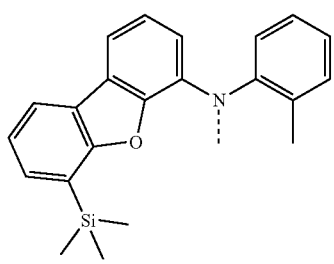
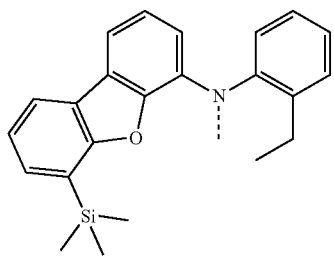
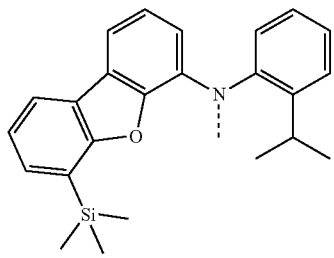
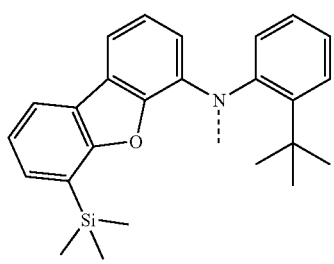
370
-continued
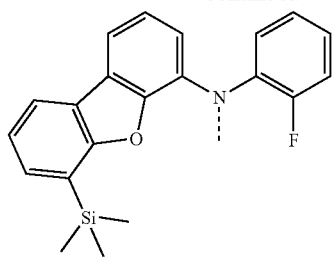
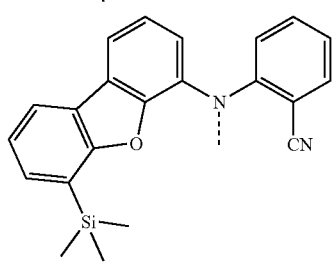
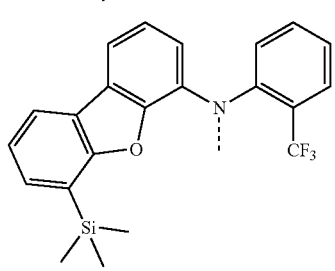
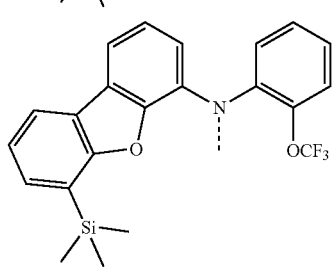
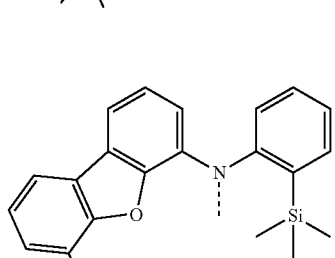
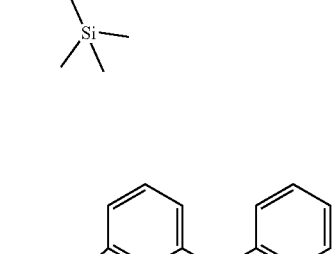
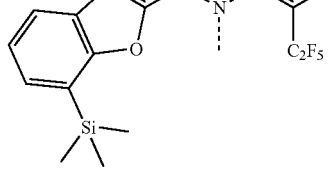

371
-continued
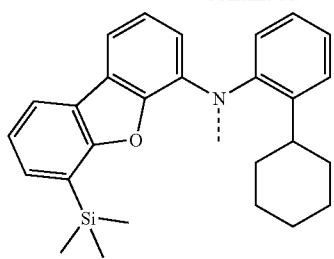
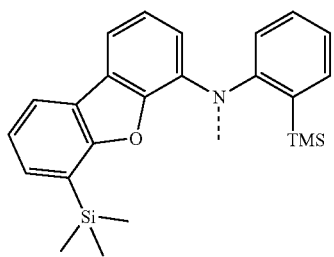
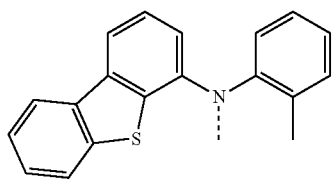
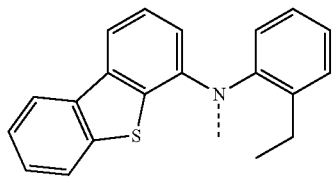
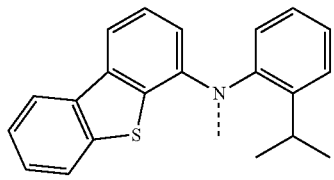
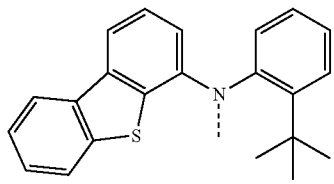
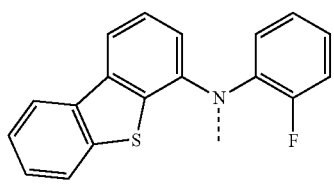
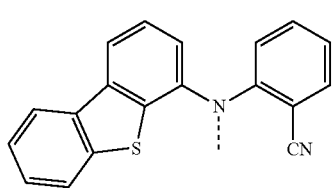
372
-continued
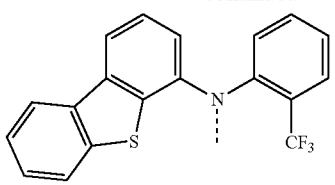
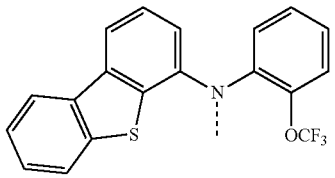
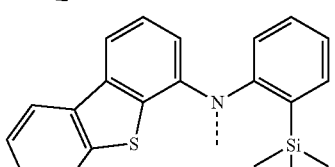
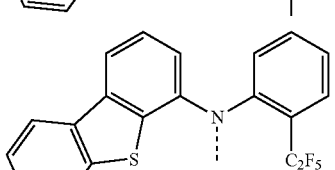
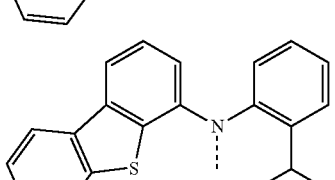
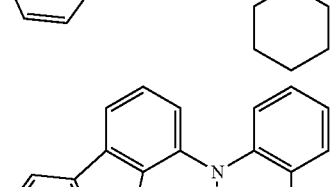
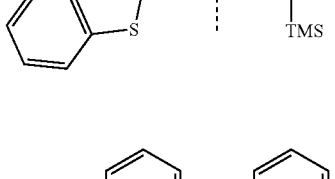
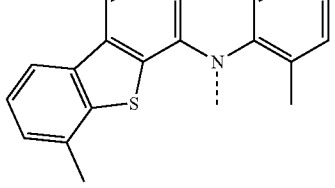

373
-continued
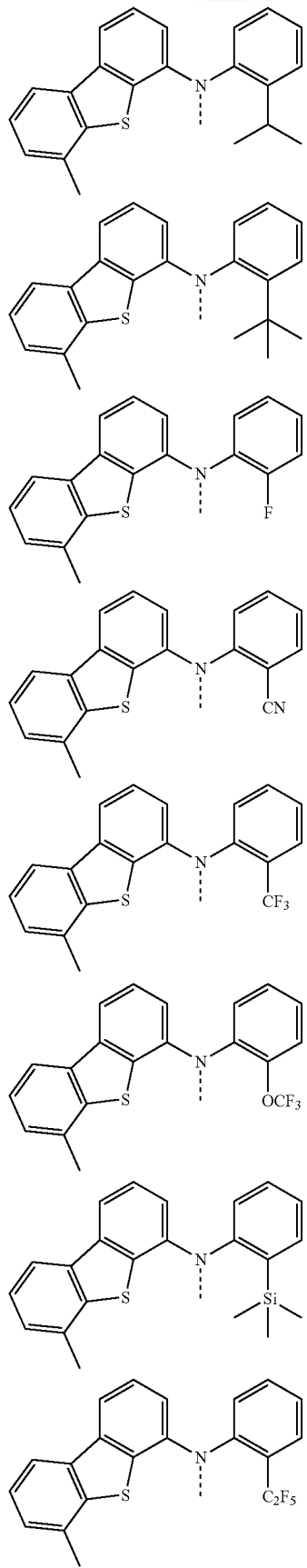
374
-continued
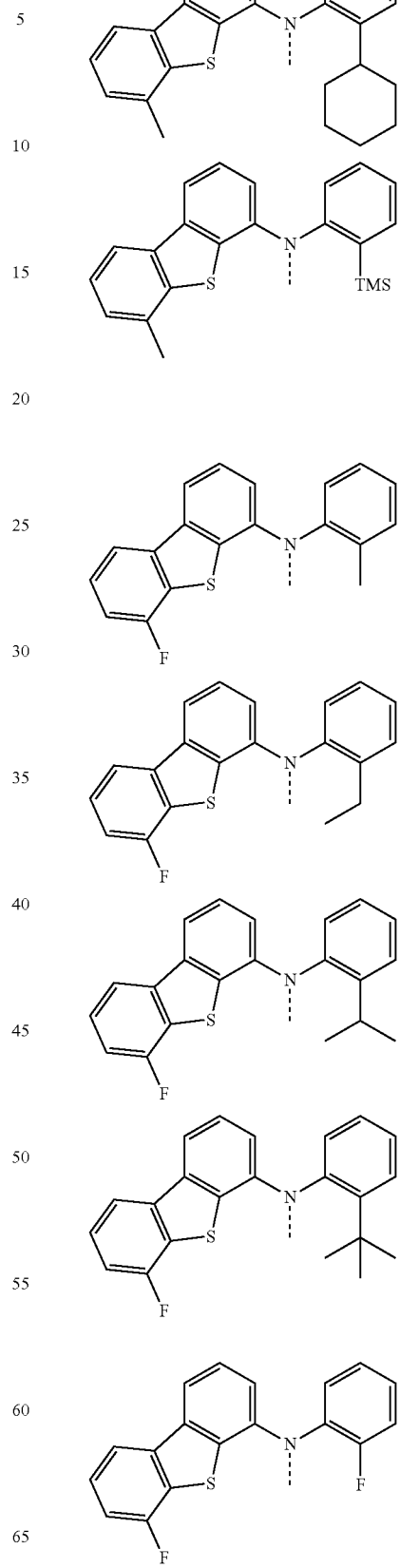

375
-continued
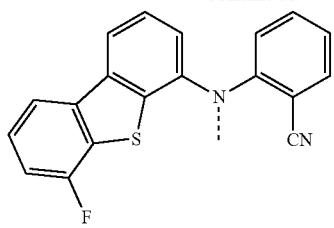
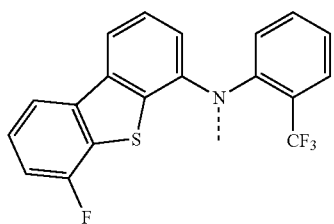
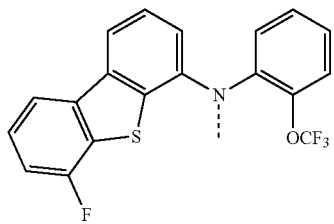
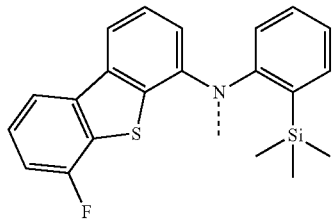
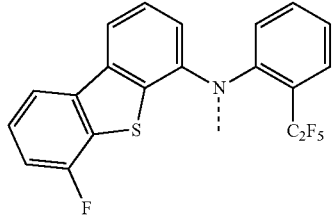
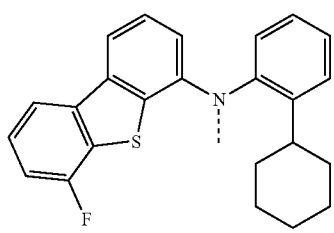
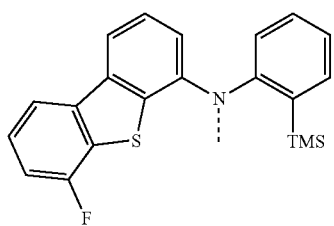
376
-continued
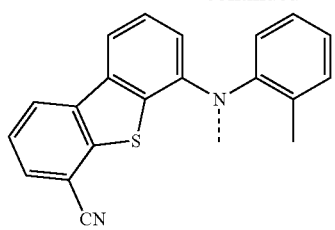
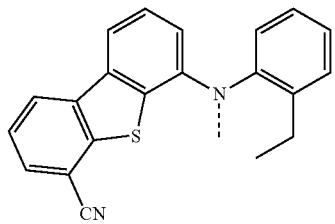
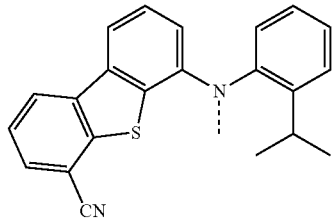
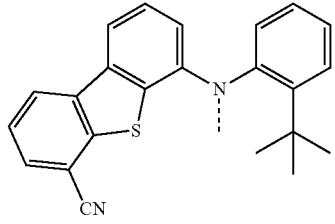
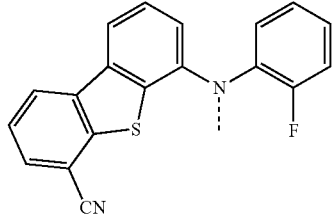
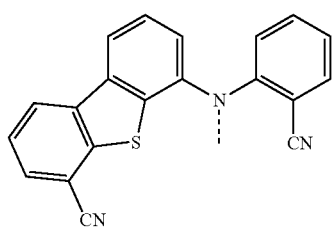
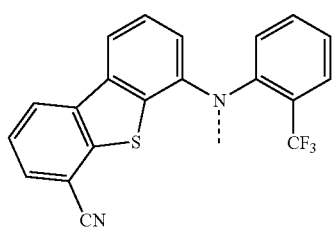

-continued
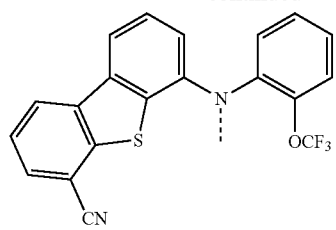
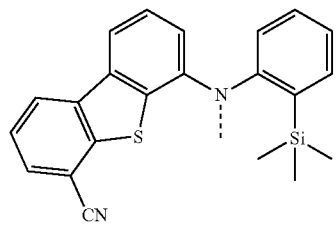
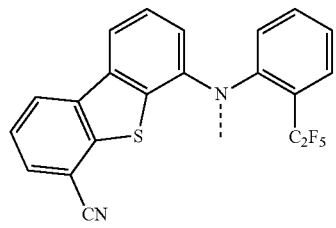
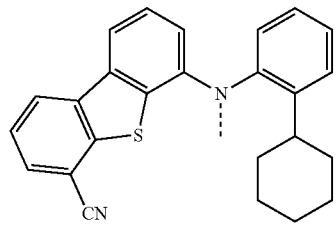
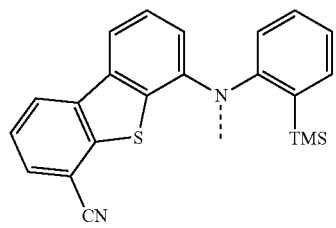
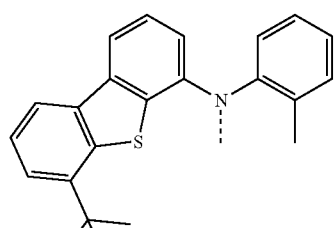
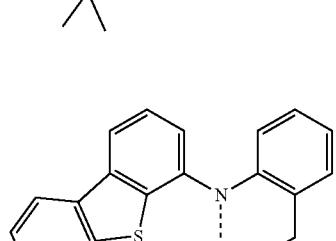
-continued
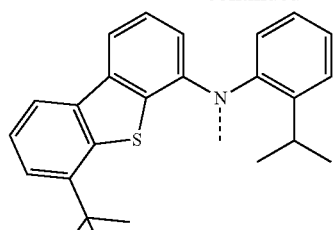
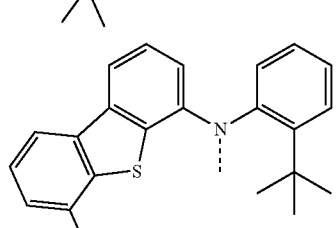
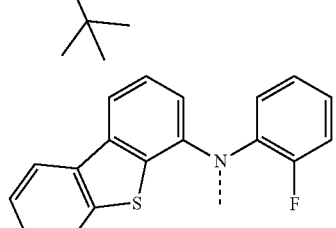
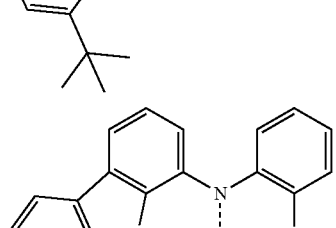
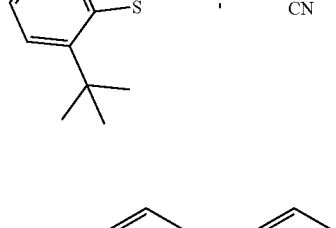
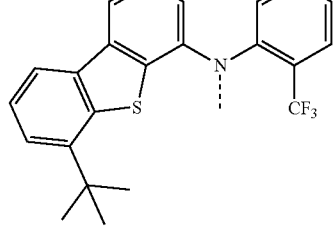
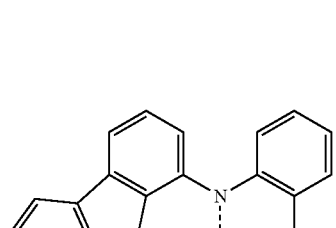

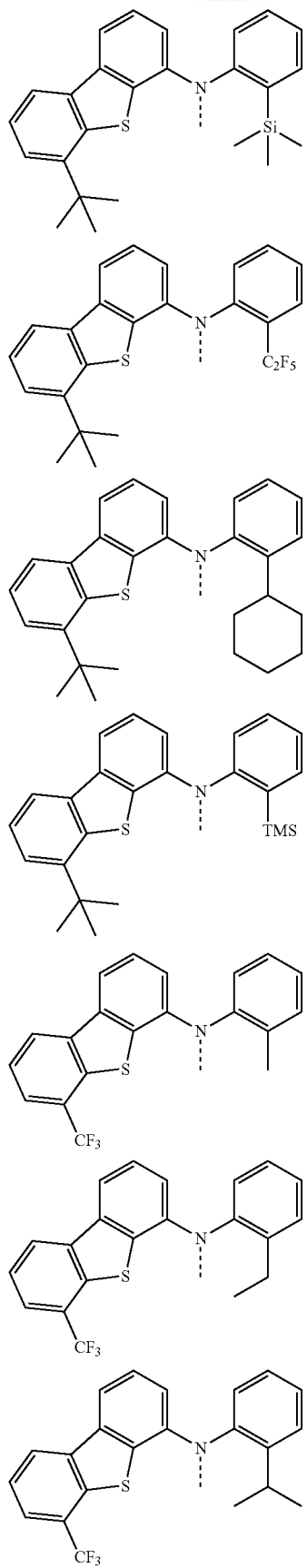
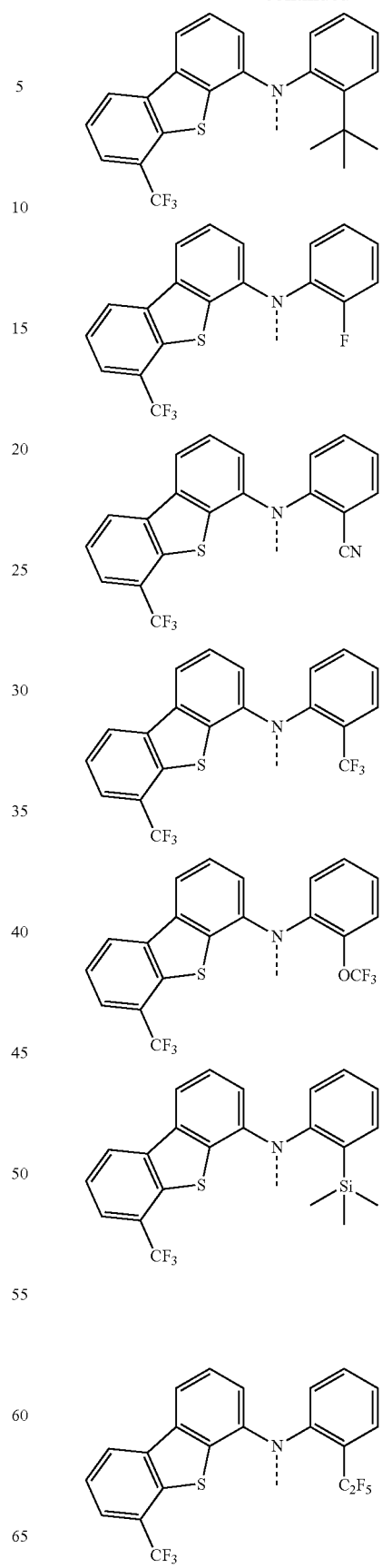

381
-continued
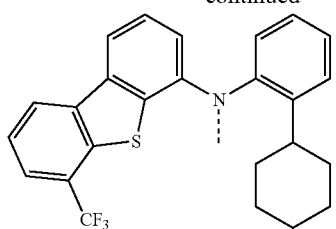
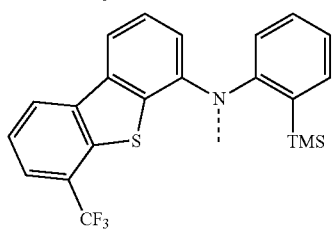
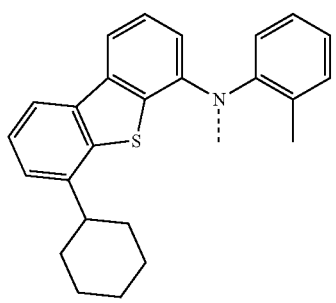
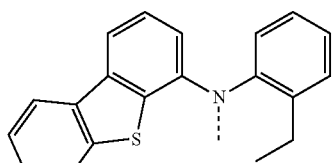
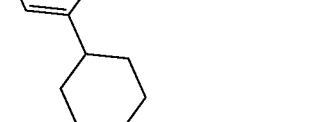
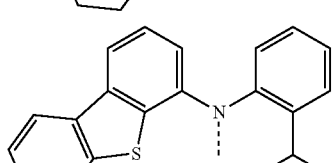
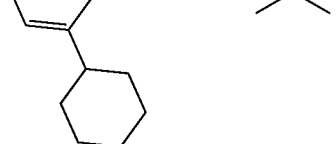
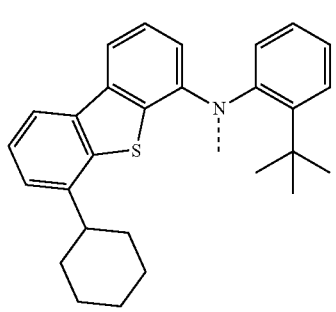
382
-continued
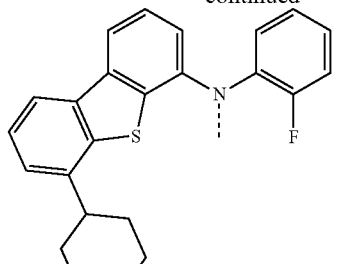
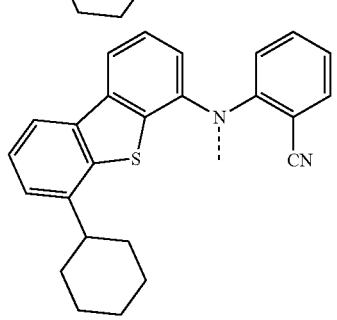
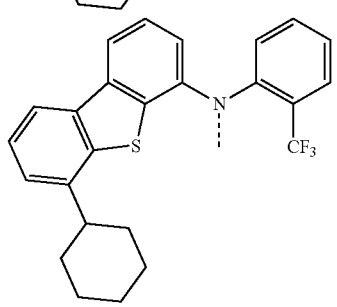
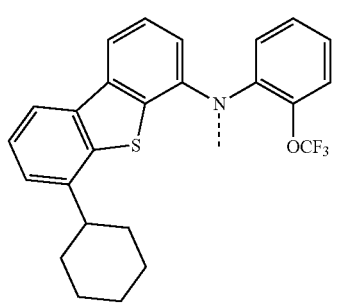
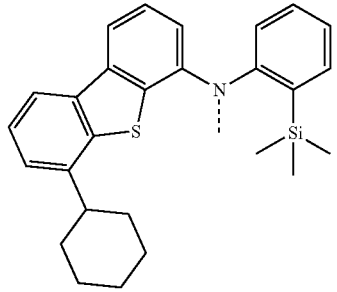

383
-continued
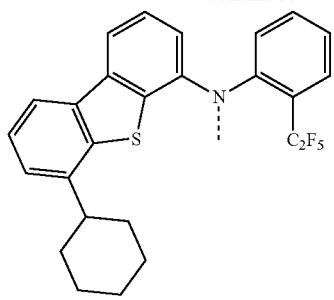
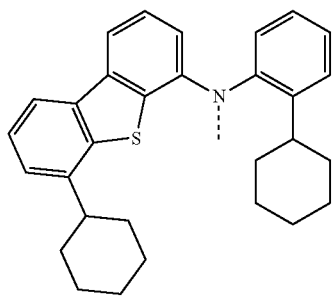
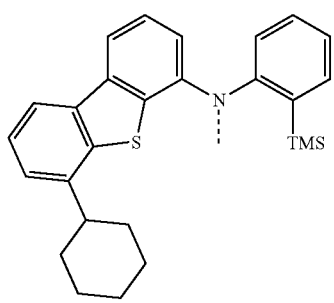
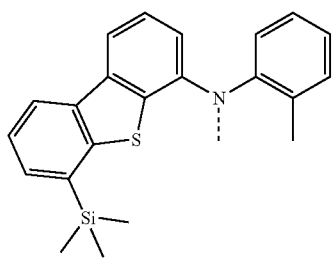
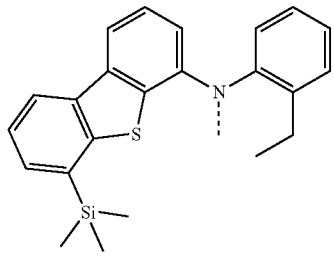
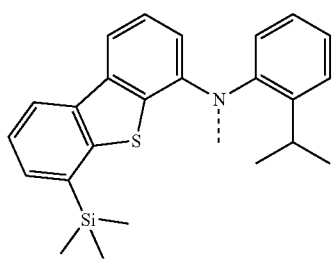
384
-continued
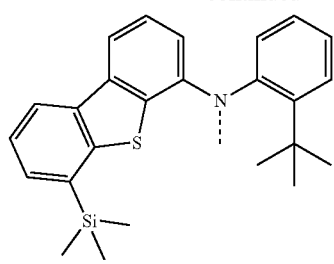
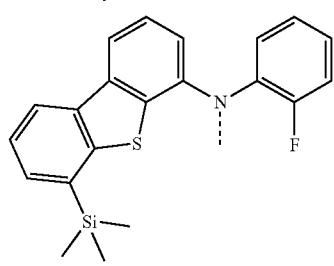
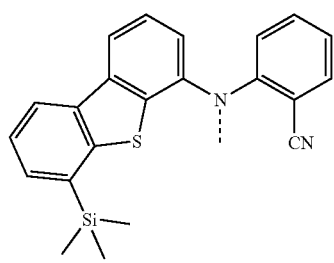
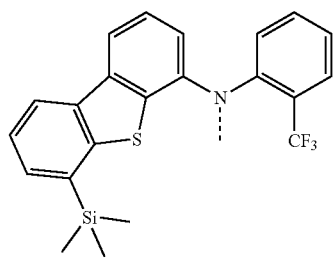
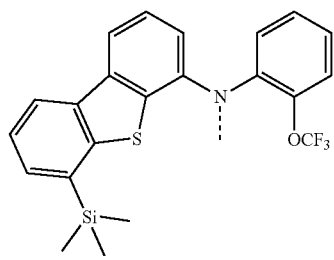
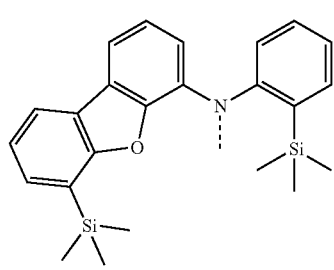

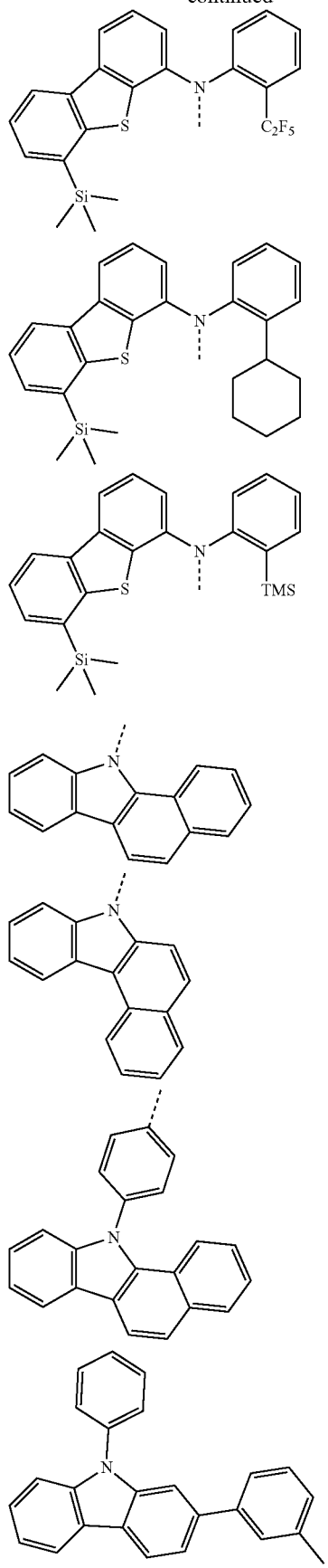
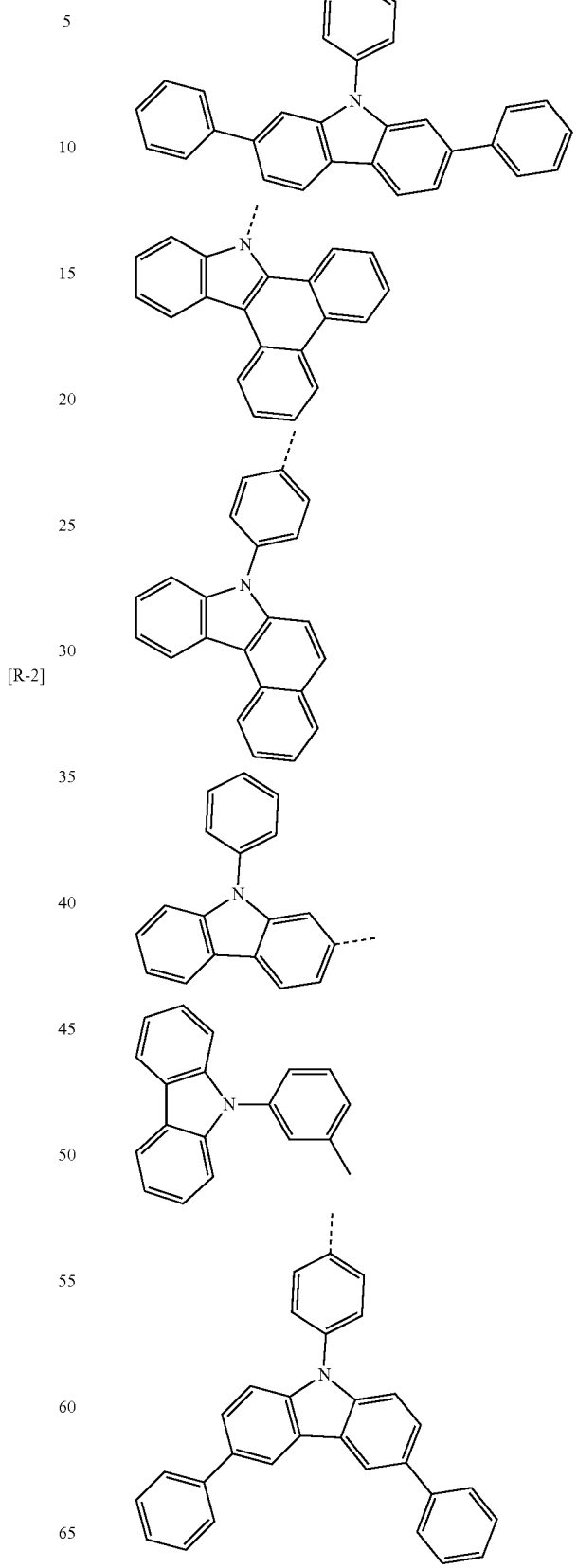
[R-2]

387
-continued
388
-continued
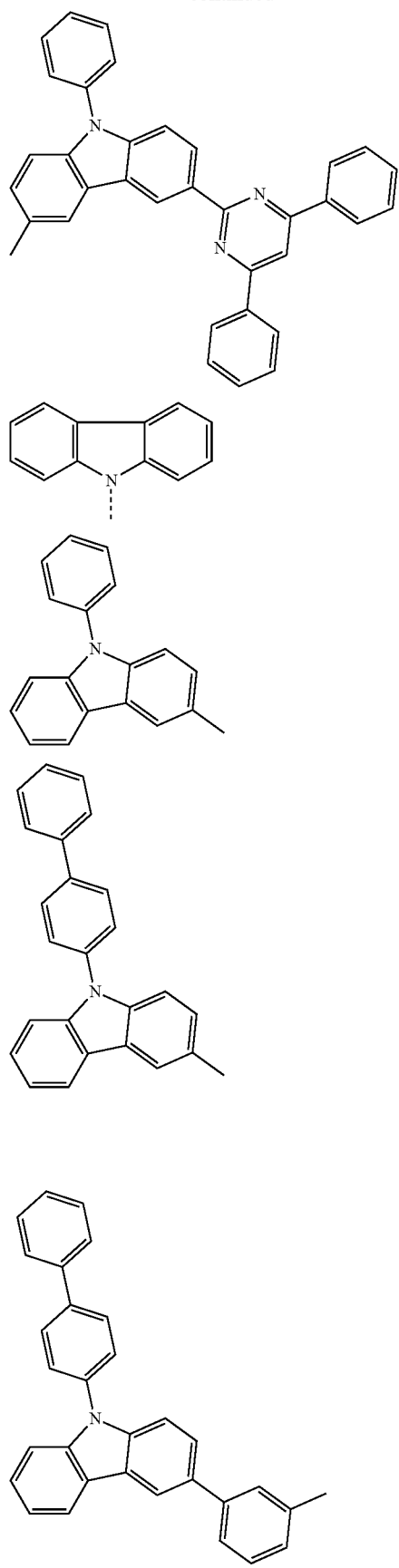
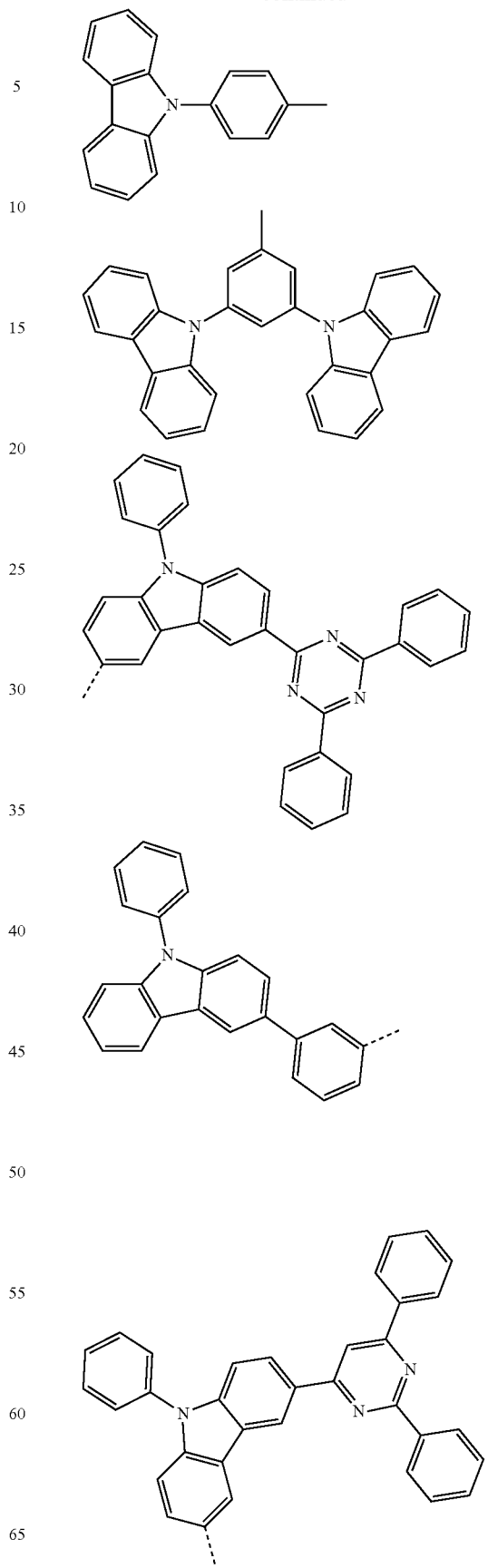

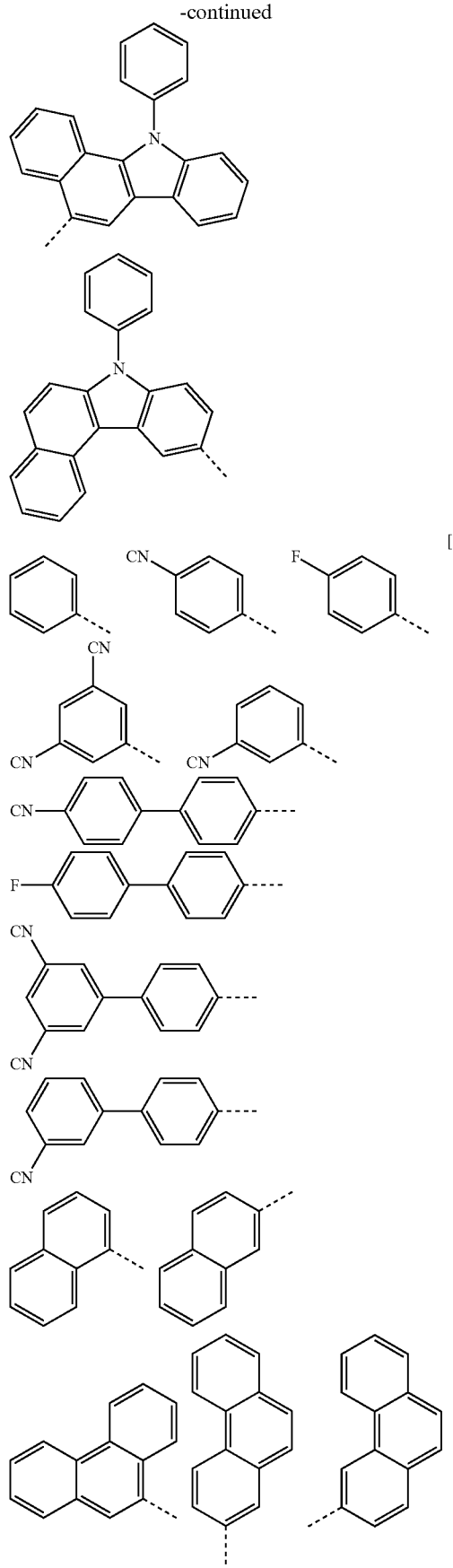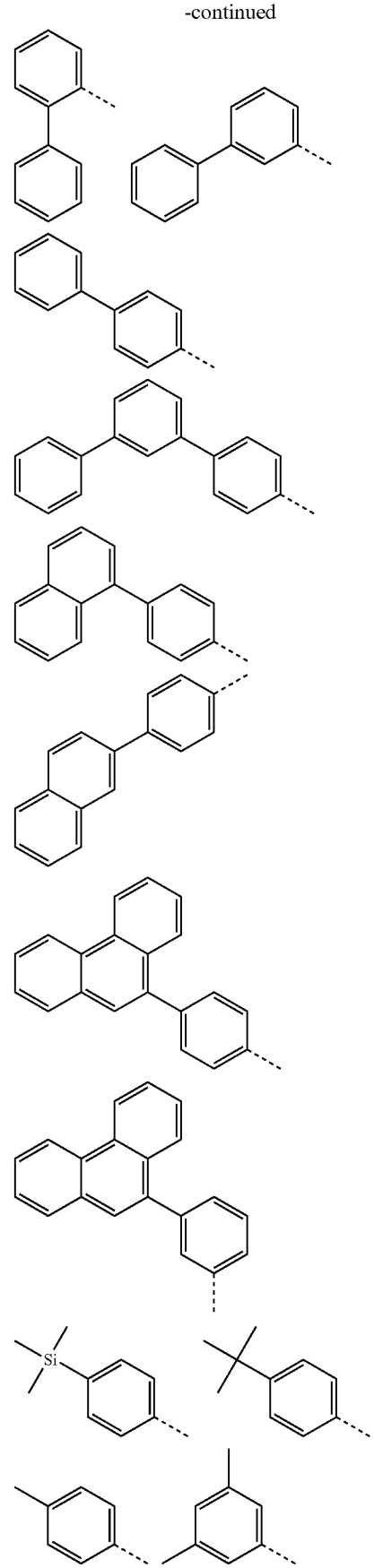

391
-continued
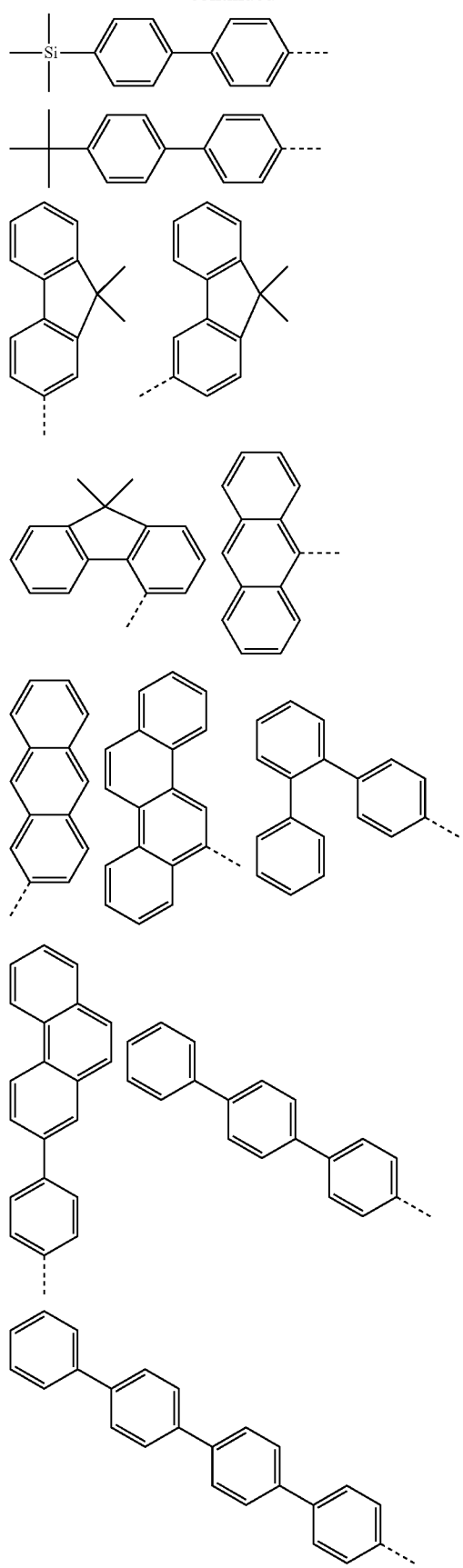
392
-continued
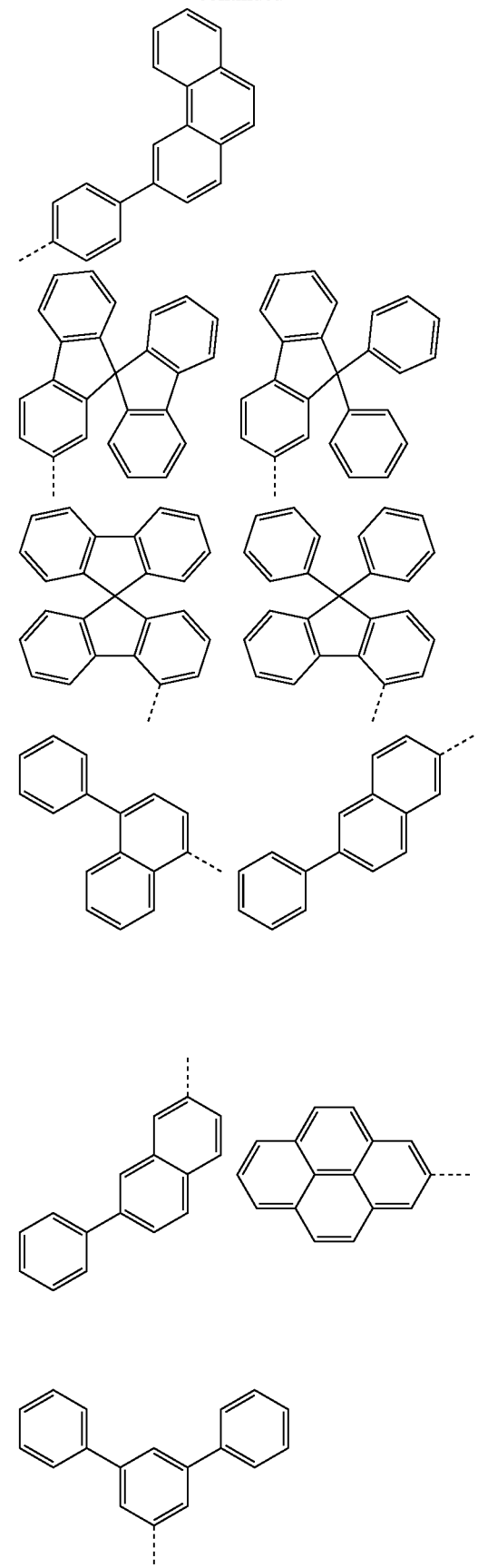

393
-continued
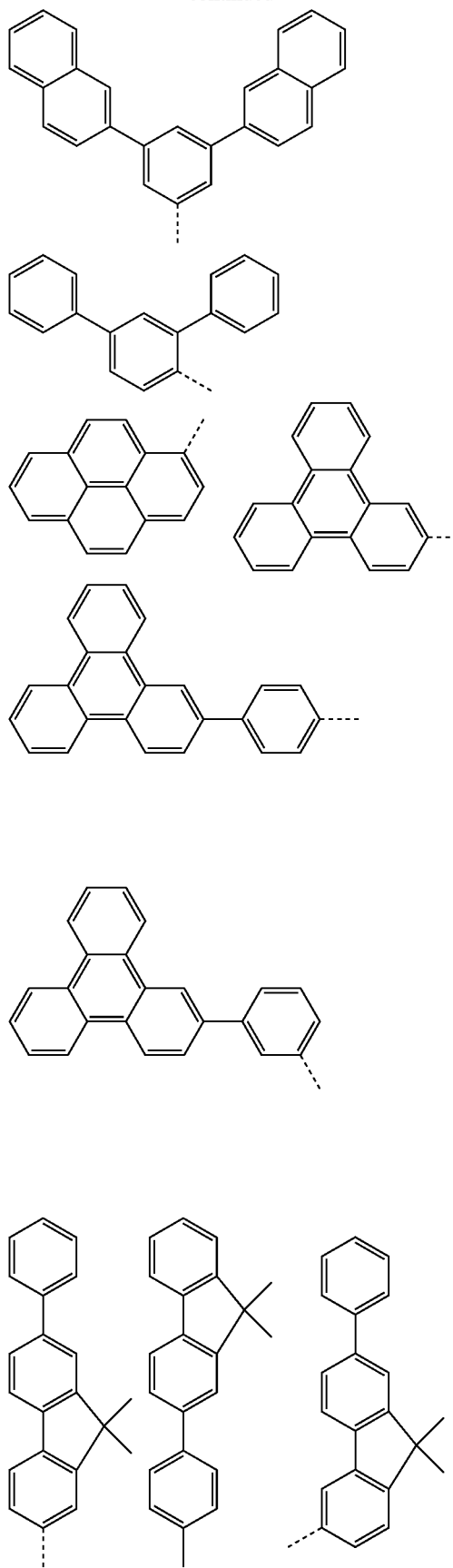
394
-continued
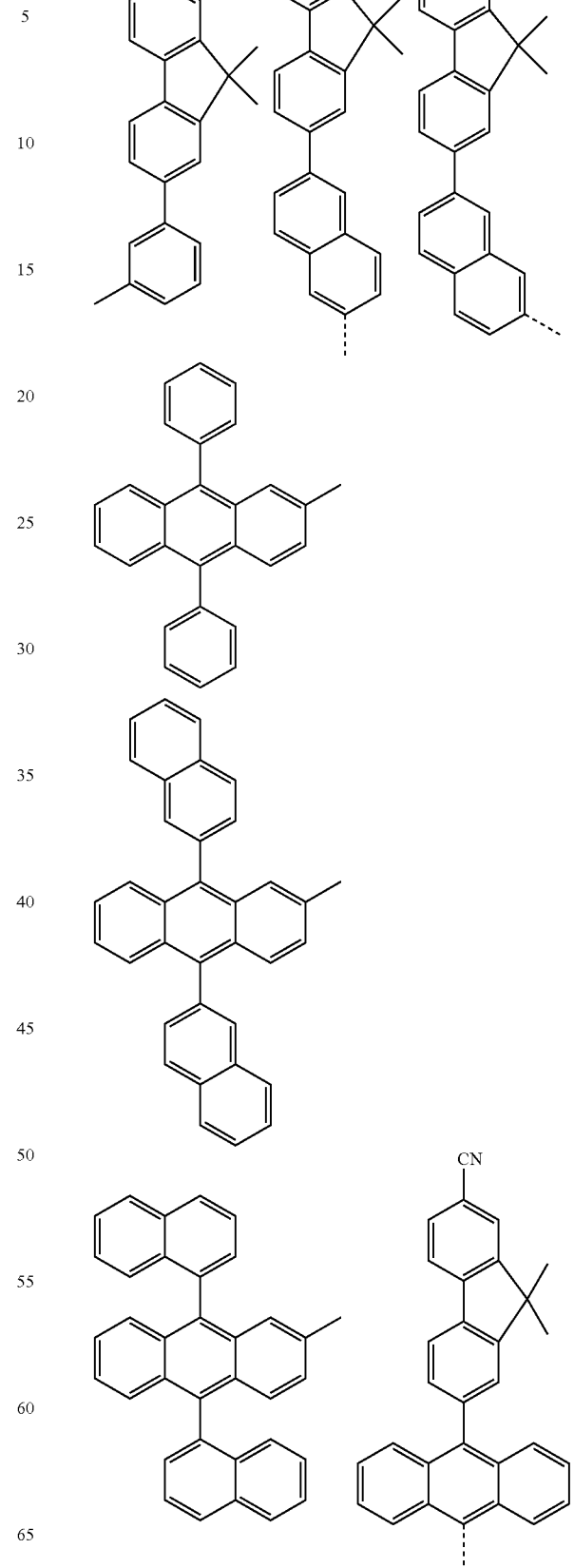

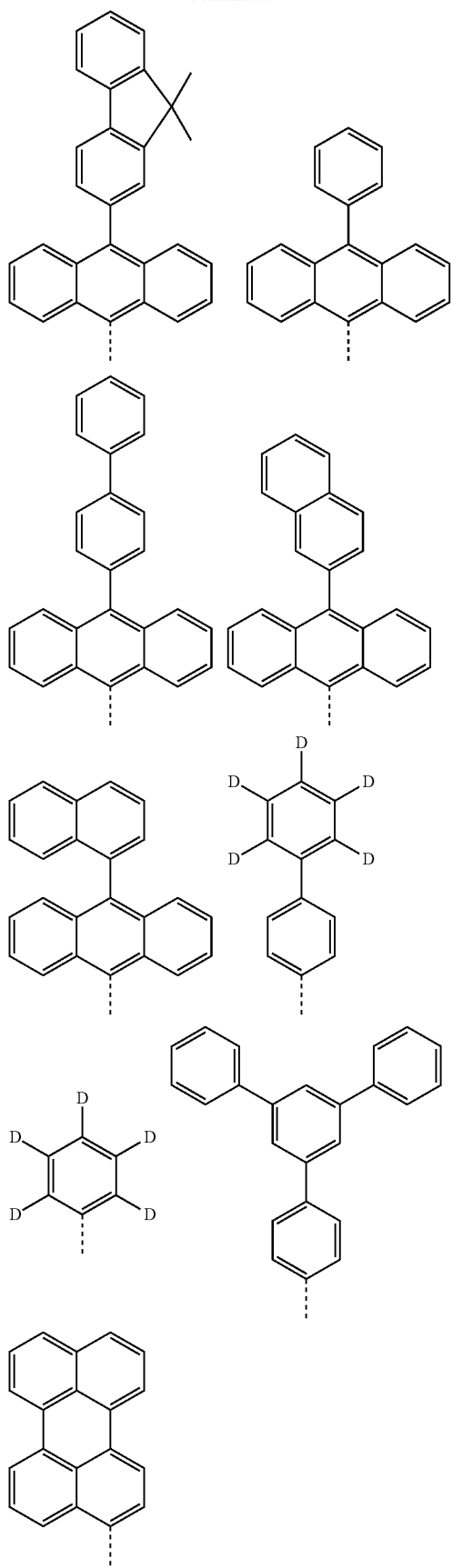
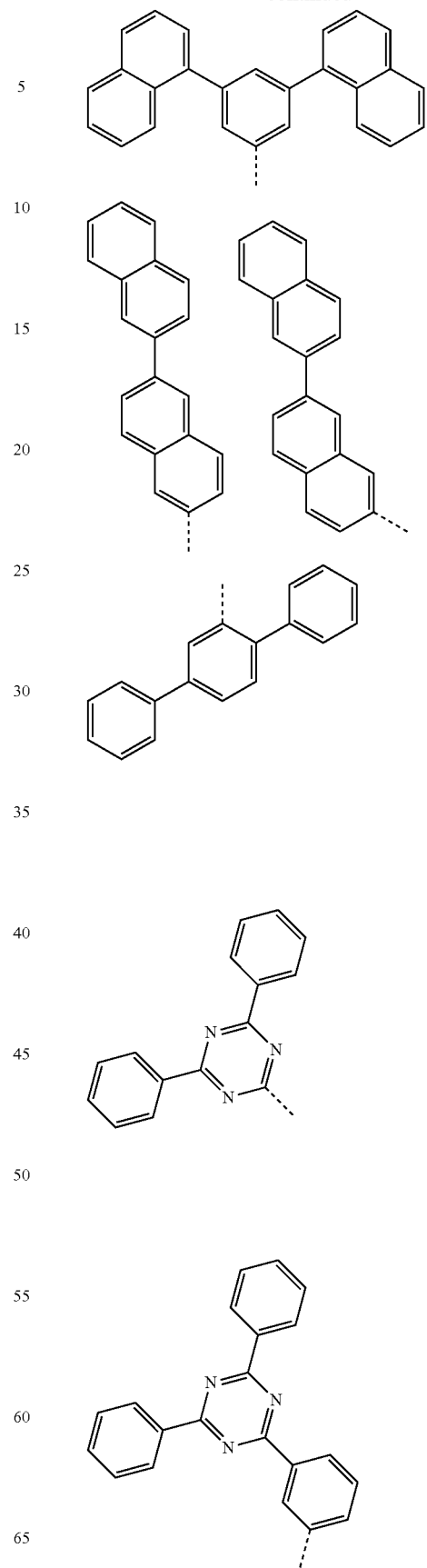
[R-4]

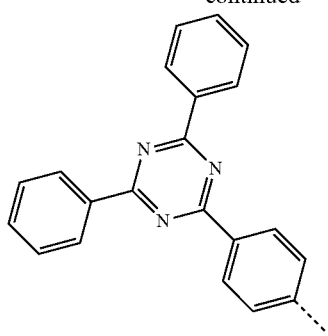
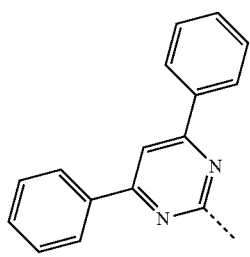
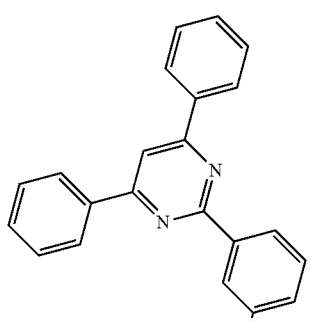
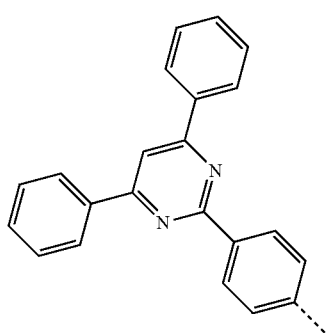
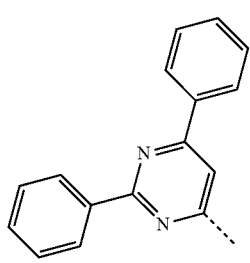
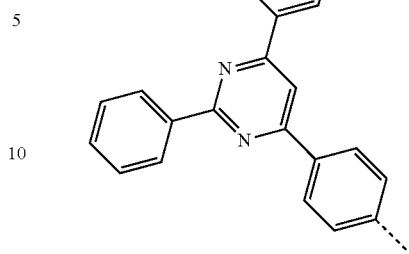
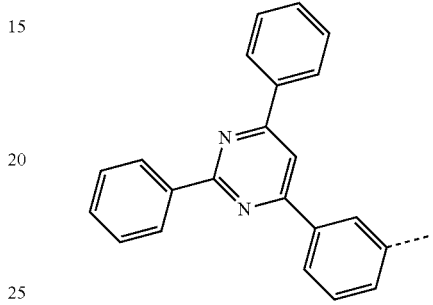
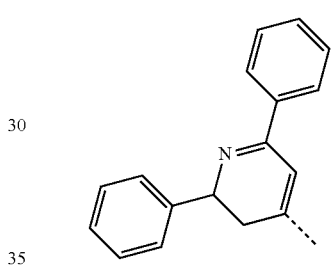
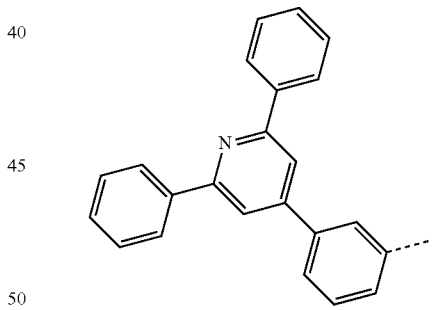
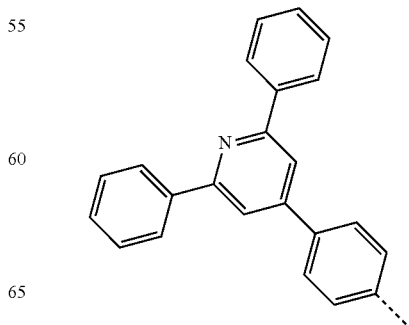

399
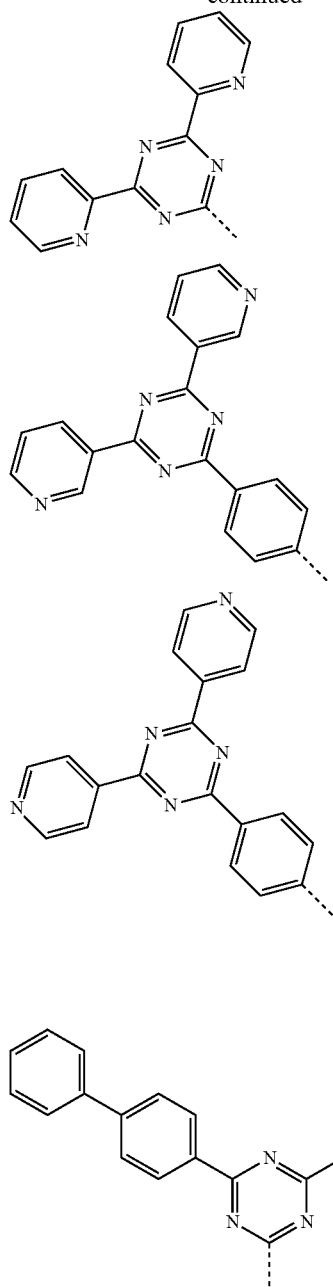
400
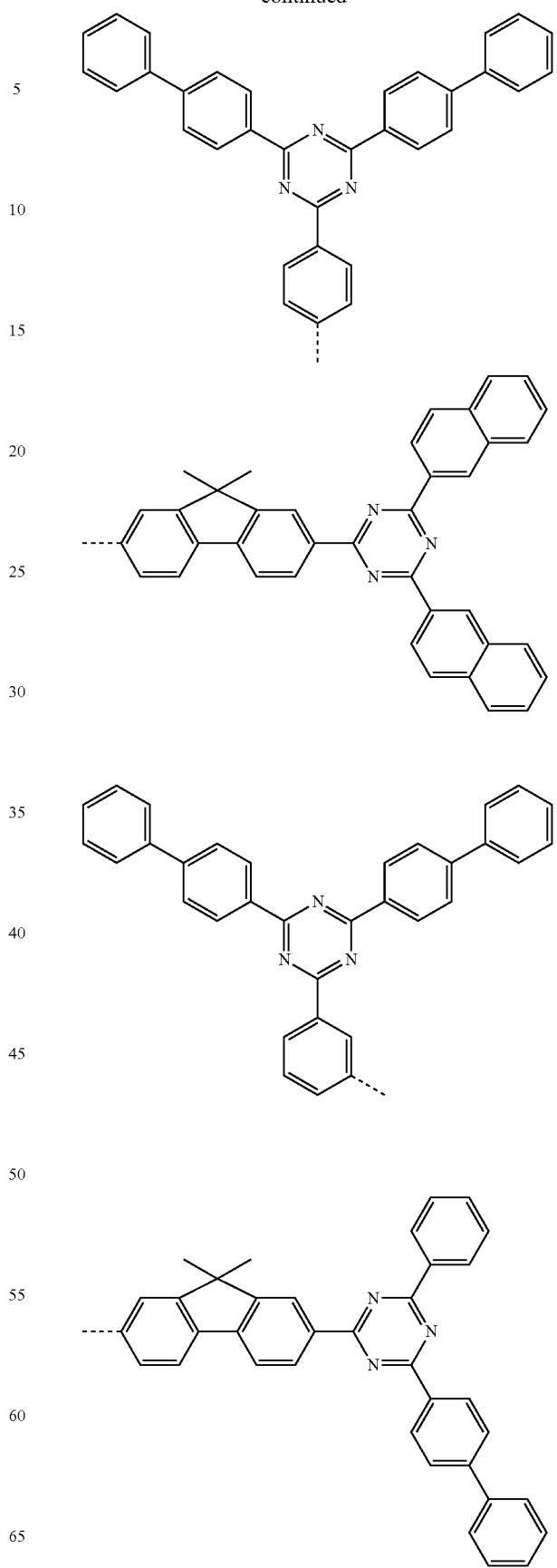

401
-continued
402
-continued
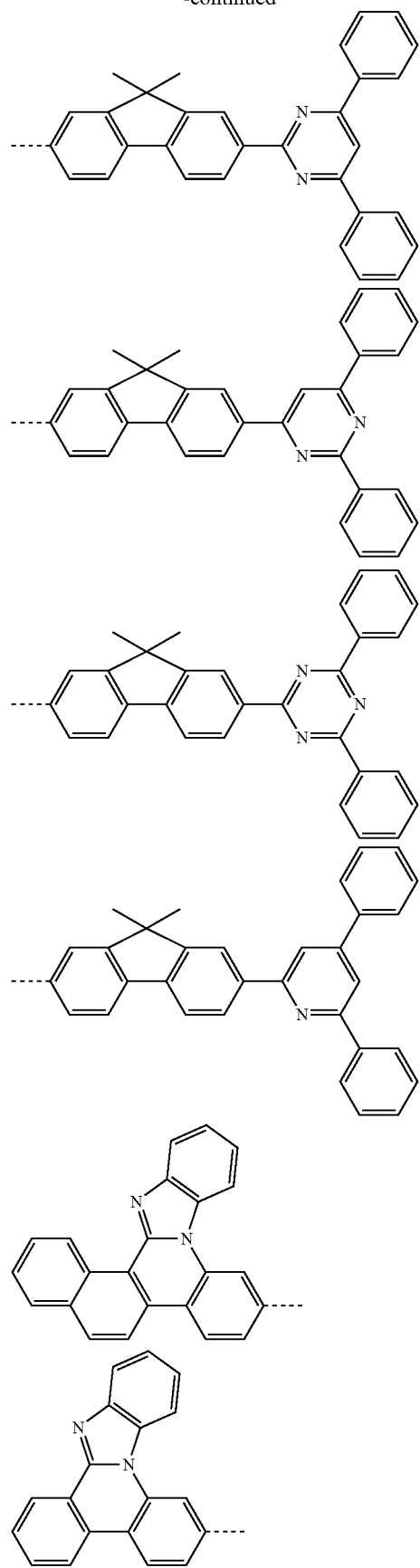
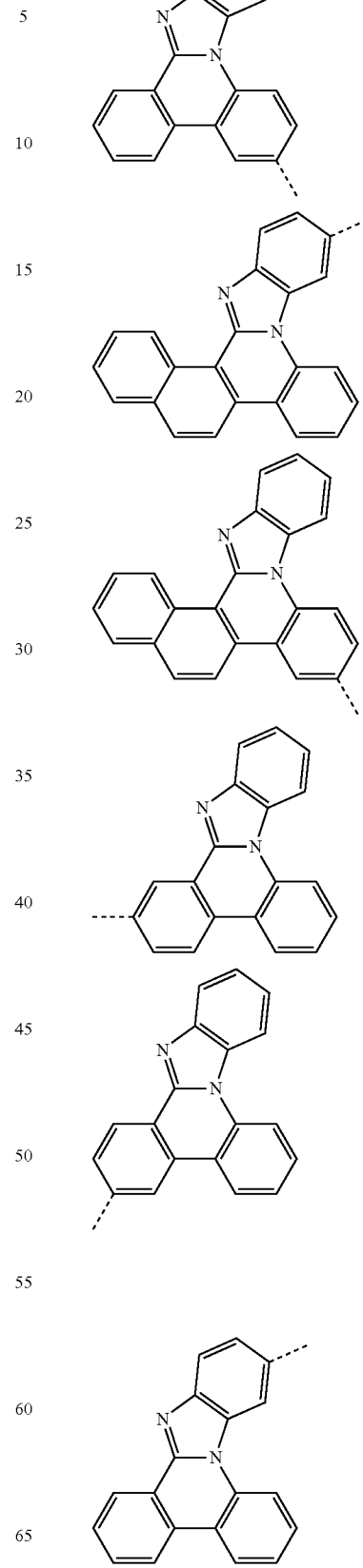

403
-continued
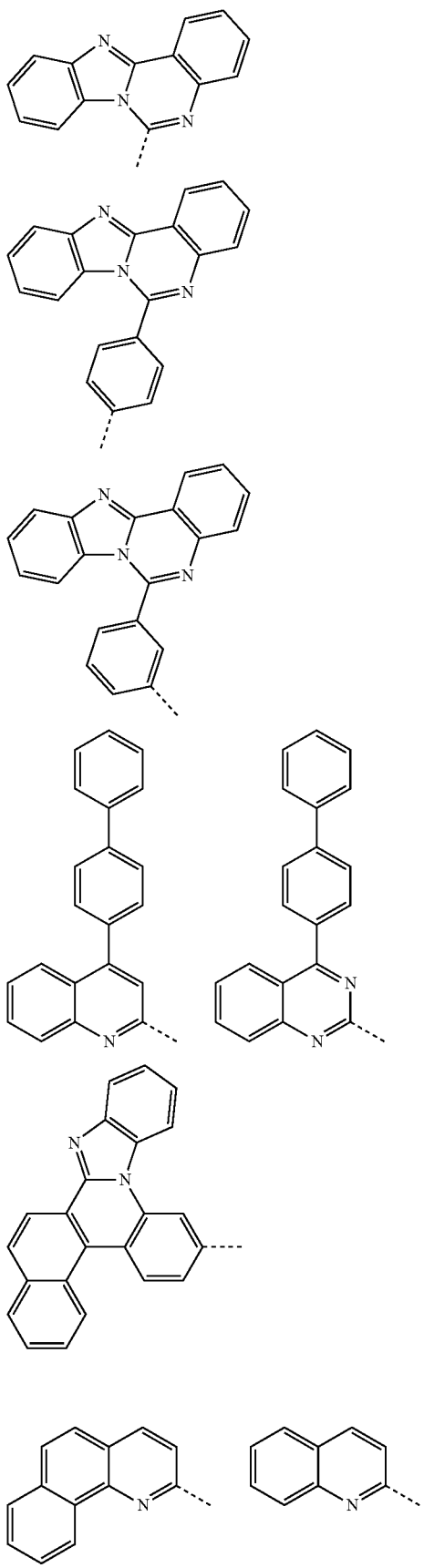
404
-continued
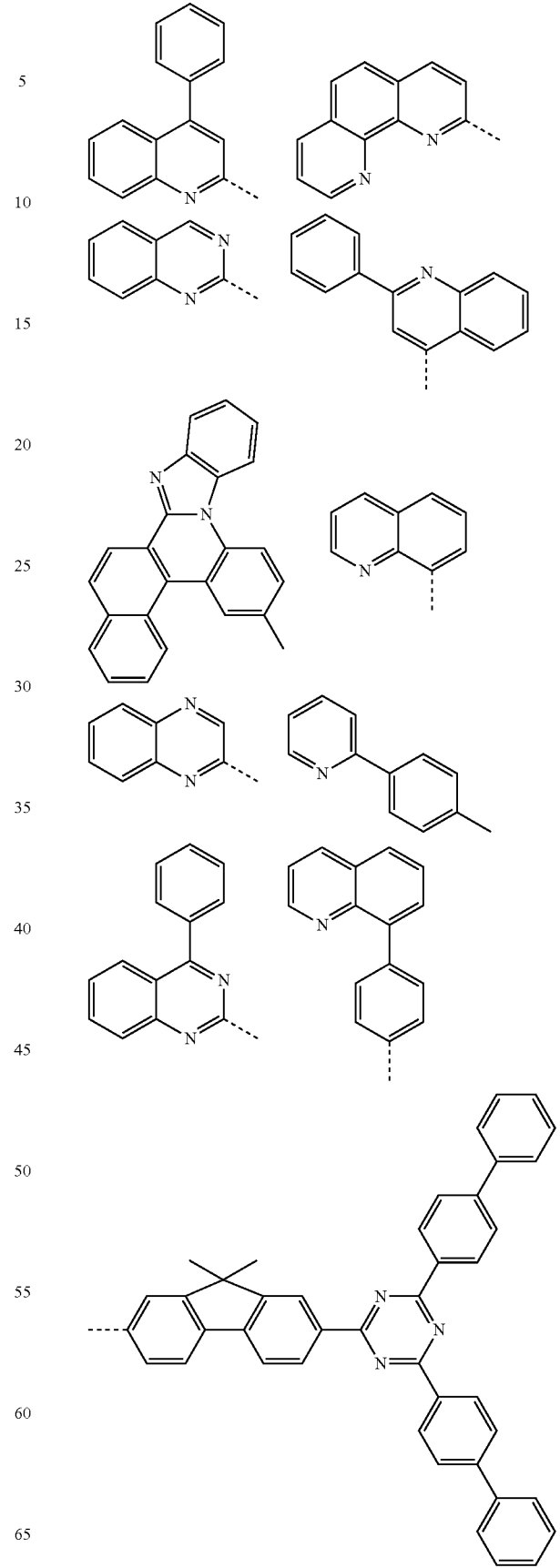

405
-continued
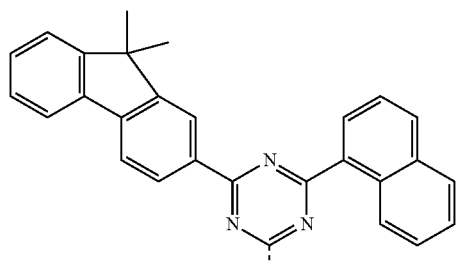
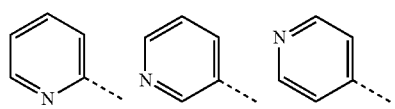
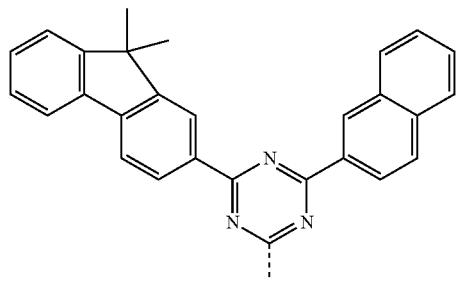
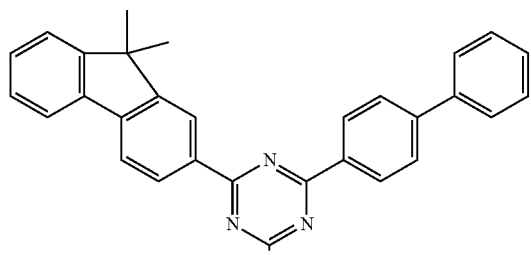
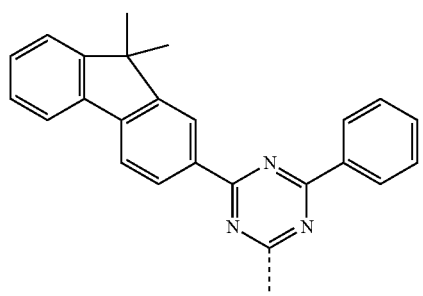
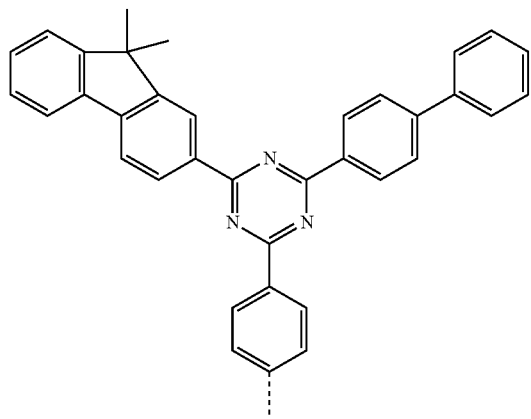
406
-continued
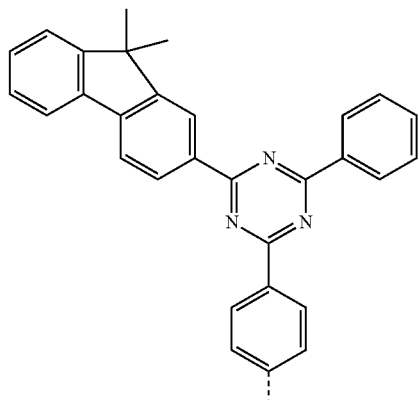
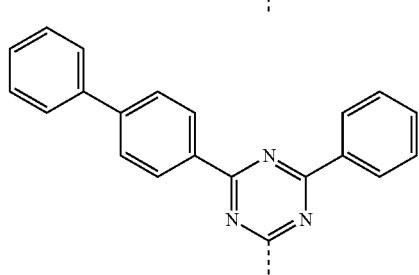
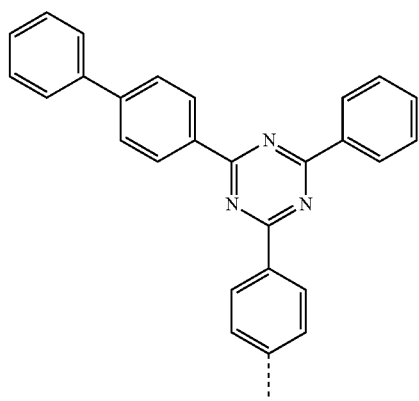
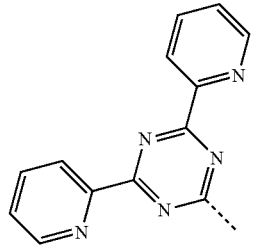
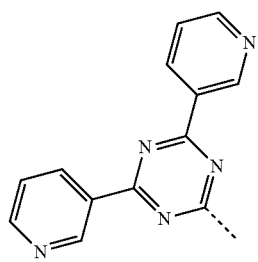

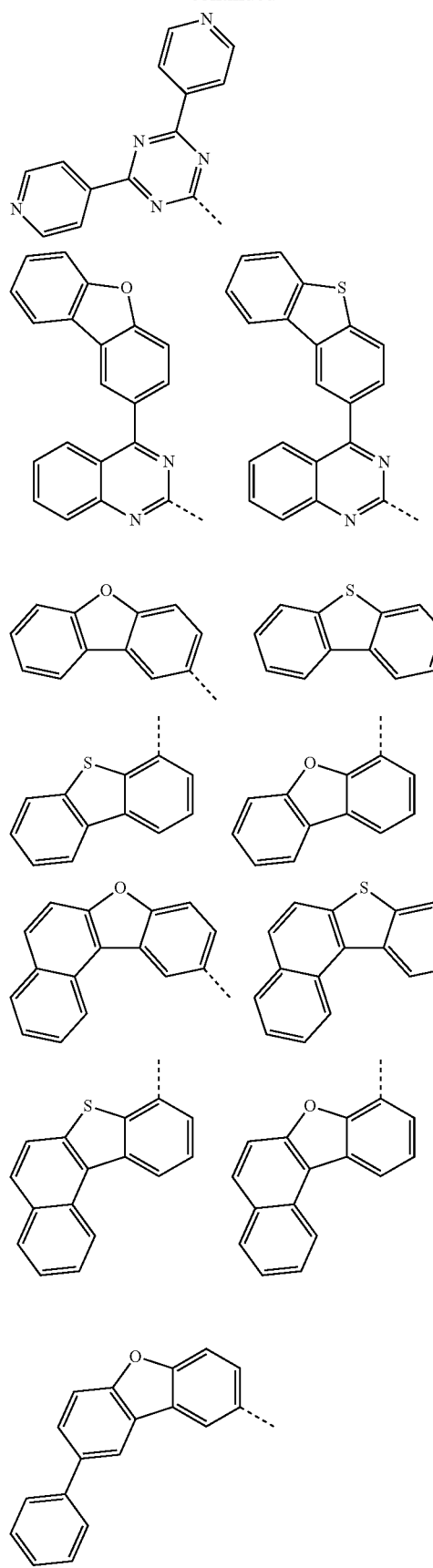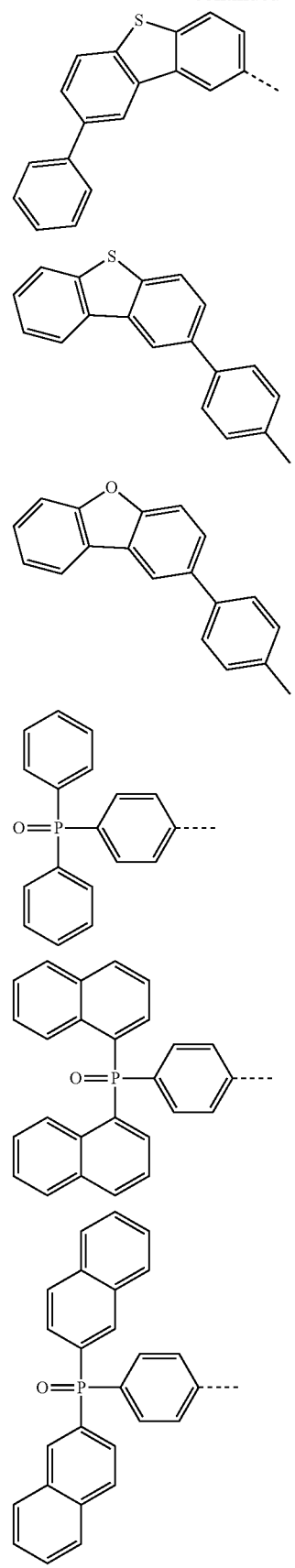

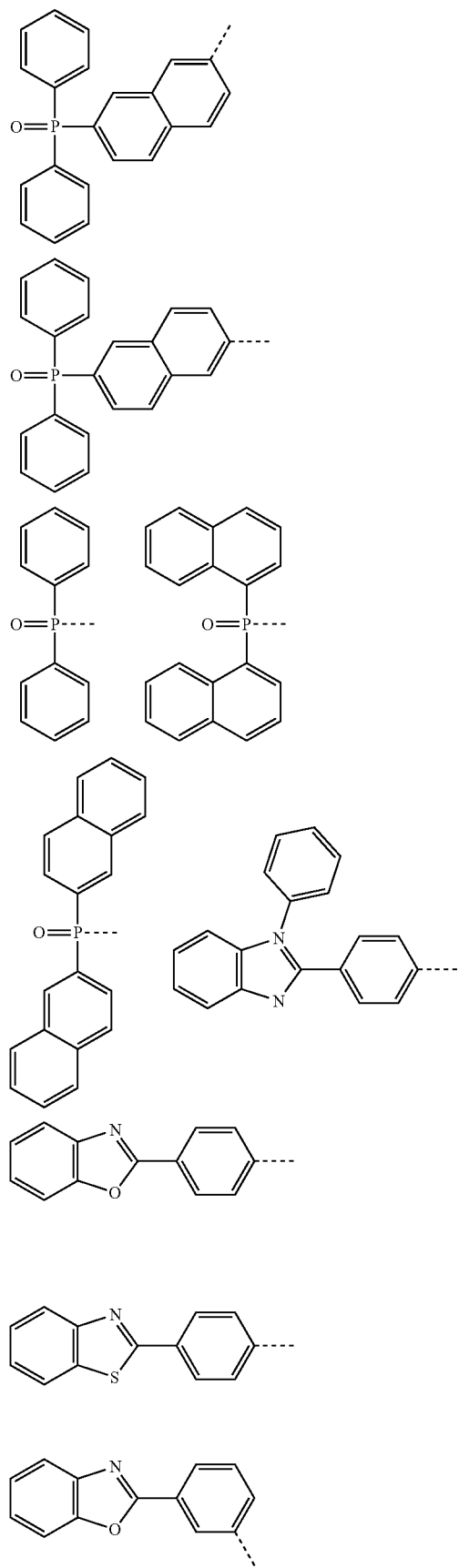

| 411 -continued | 412 -continued |
|---|---|
| 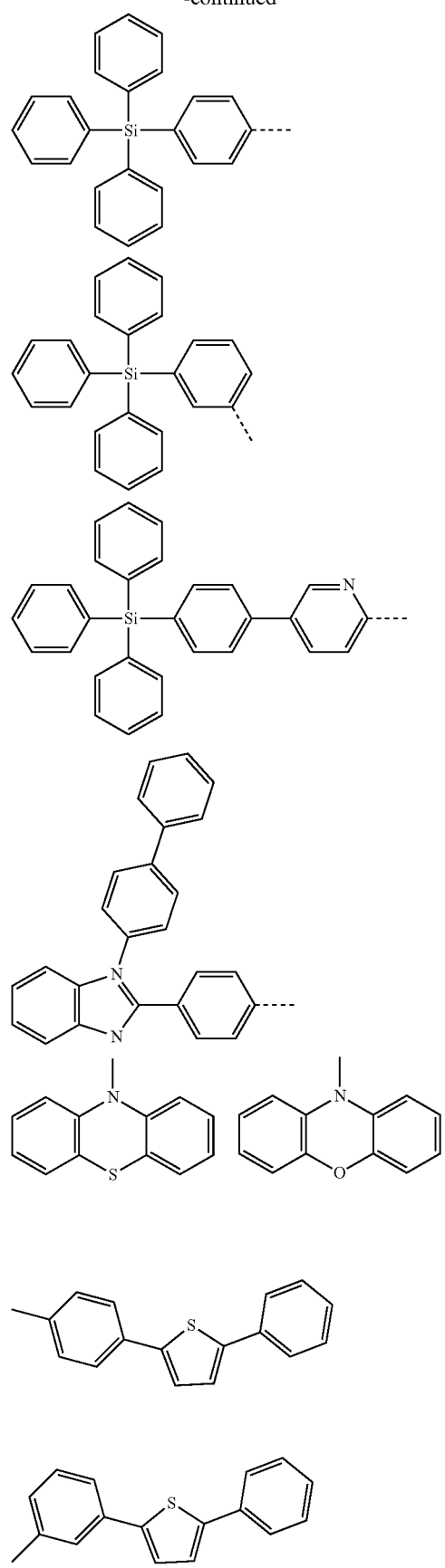 | 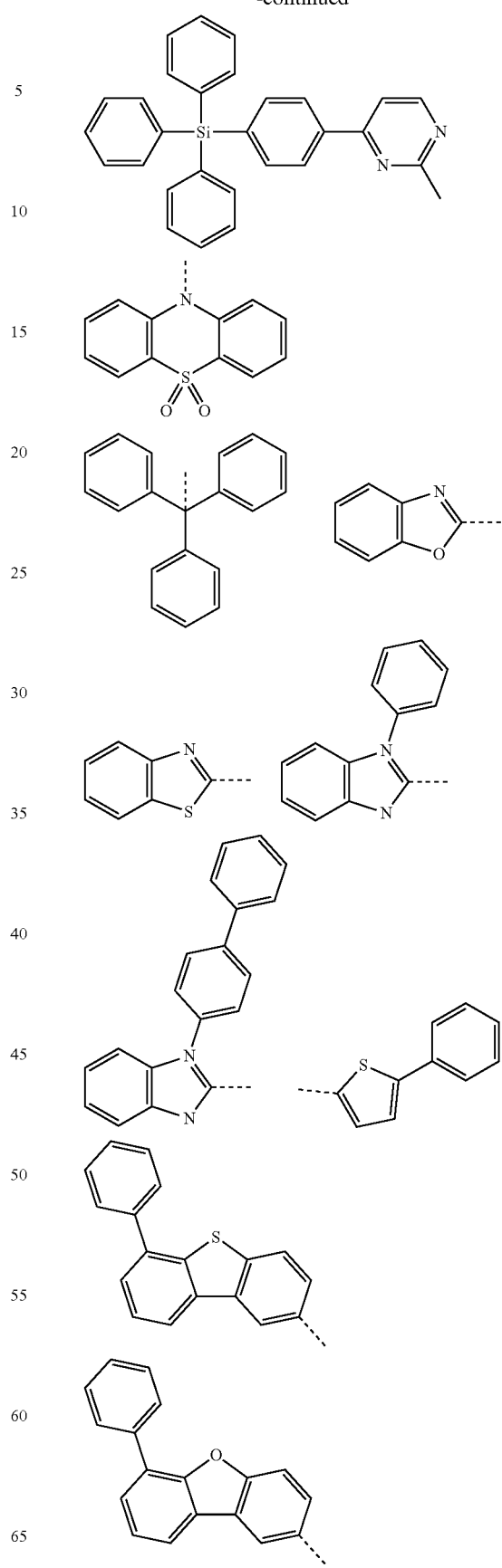 |

413
-continued
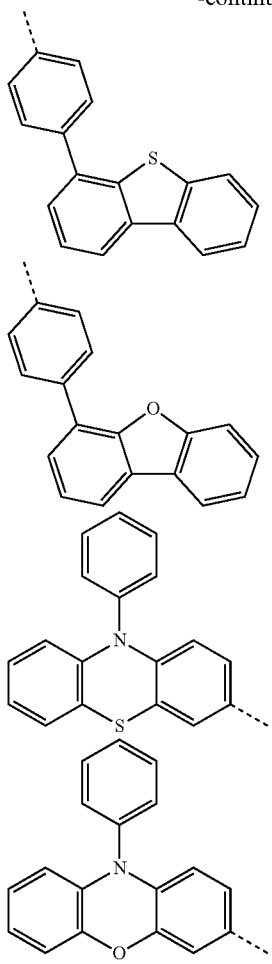
in the structural formulae, --- means a moiety bonded to Chemical Formula 1.
7. The compound of claim 1, wherein Chemical Formula 1 is represented by any one of the following compounds:
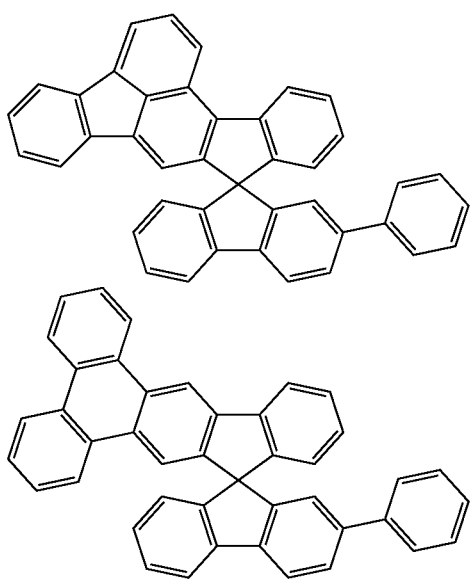
414
-continued
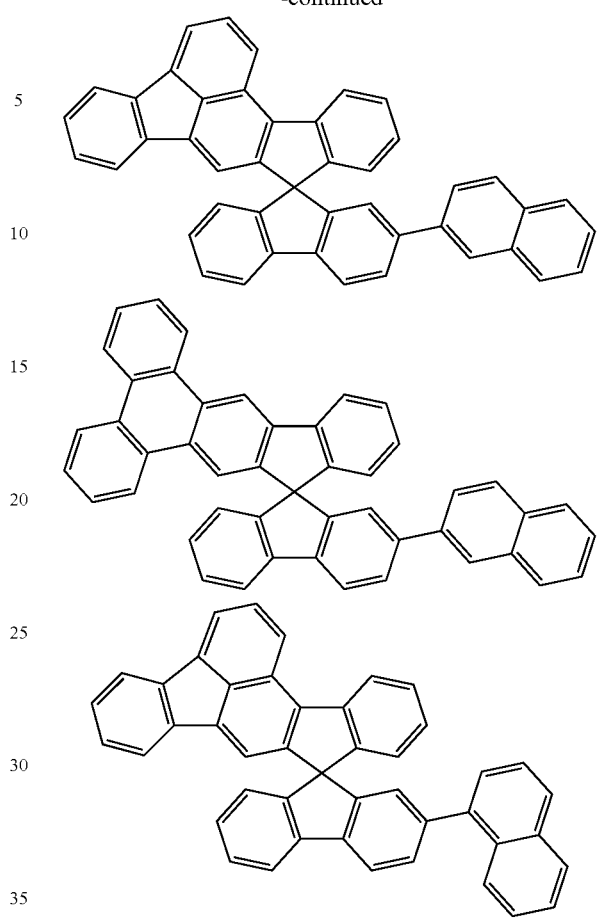
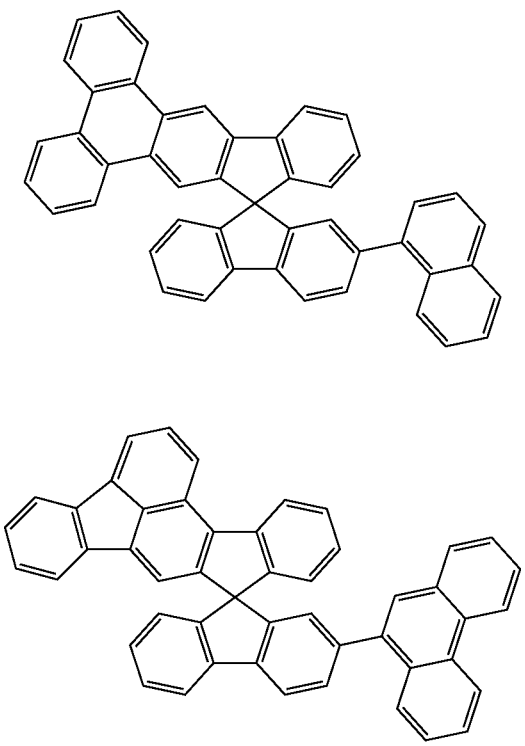

415
-continued
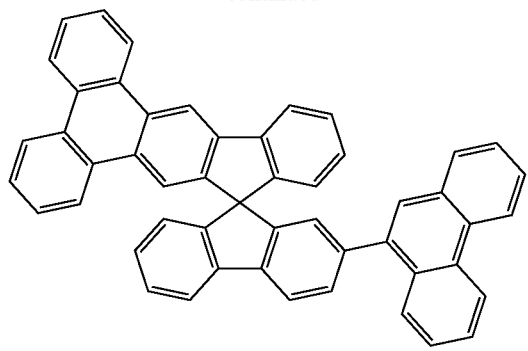
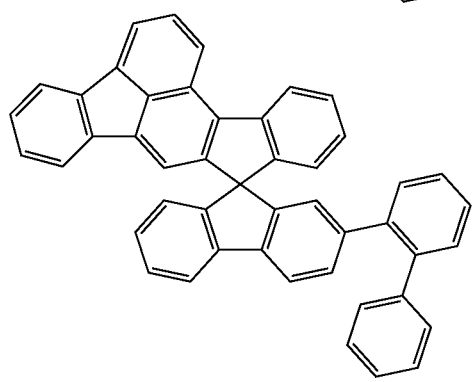
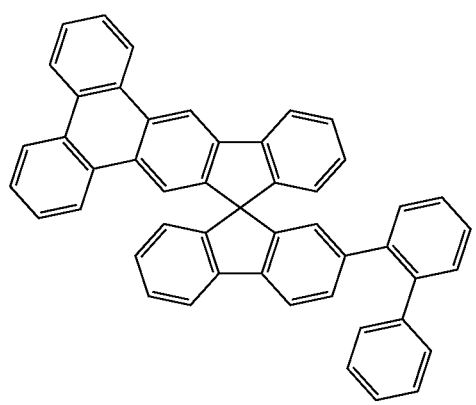
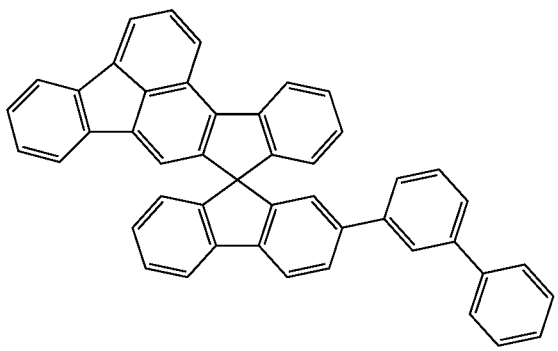
416
-continued
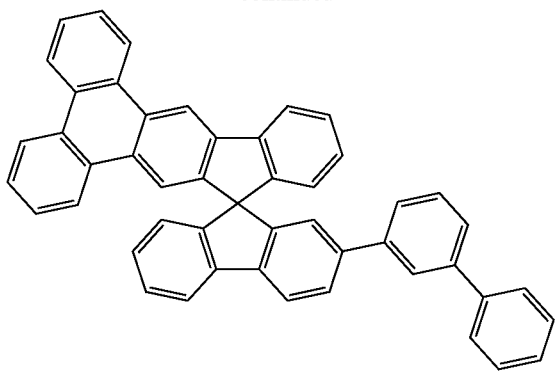
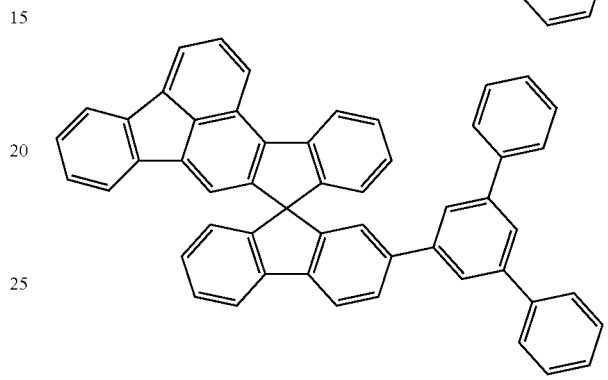
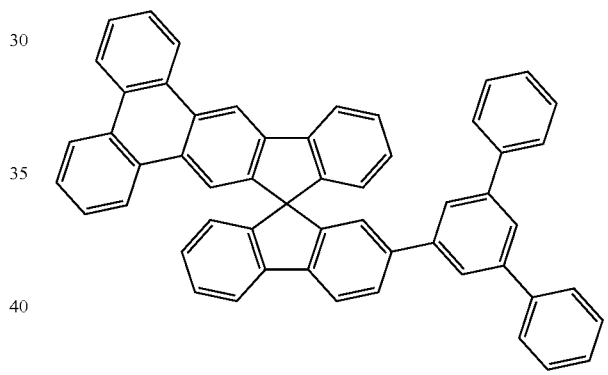
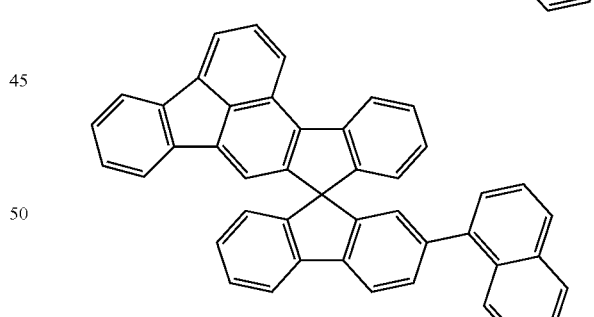
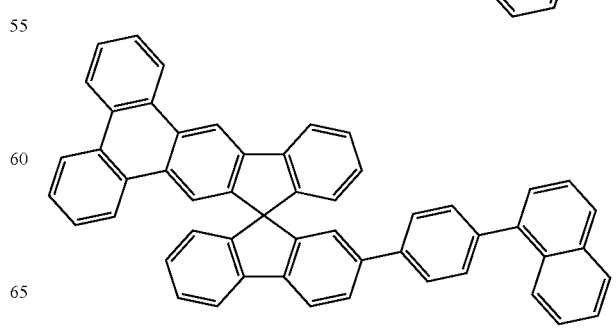

417
-continued
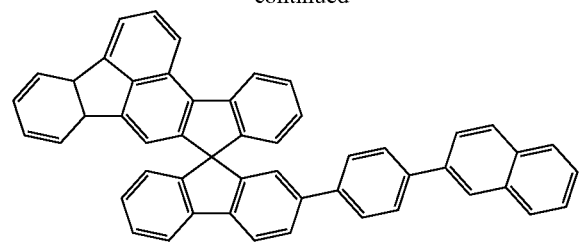
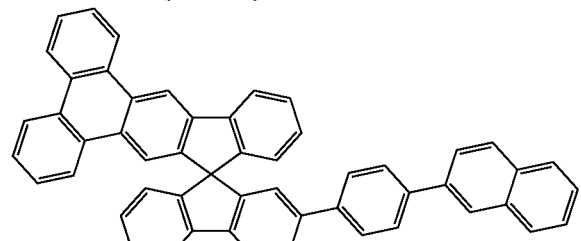
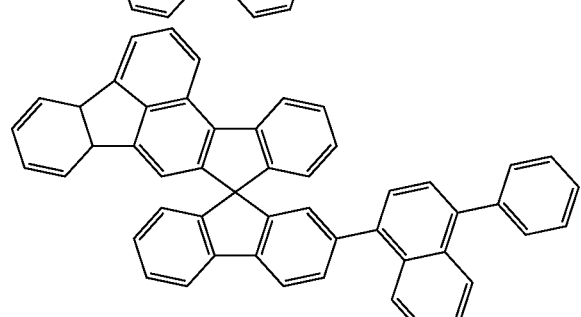
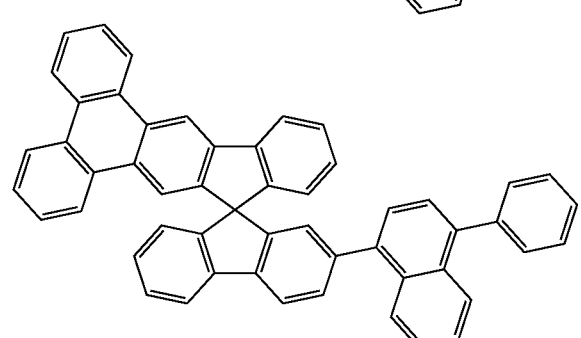
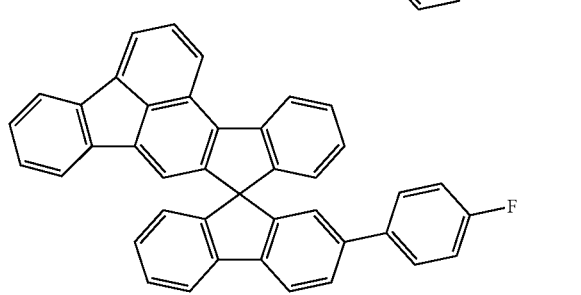
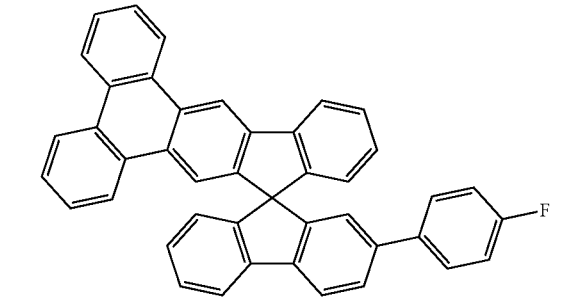
418
-continued
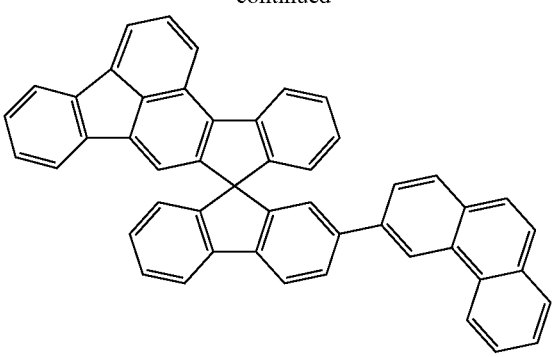
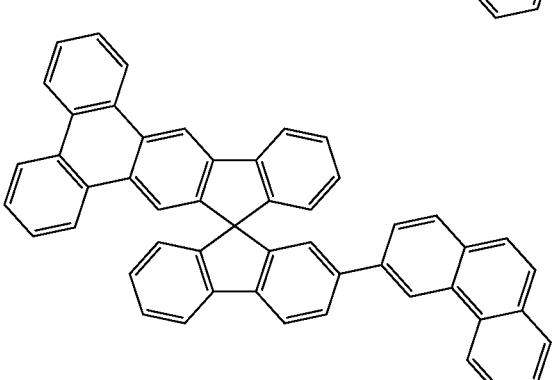
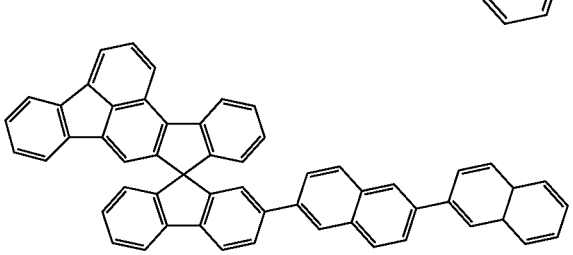
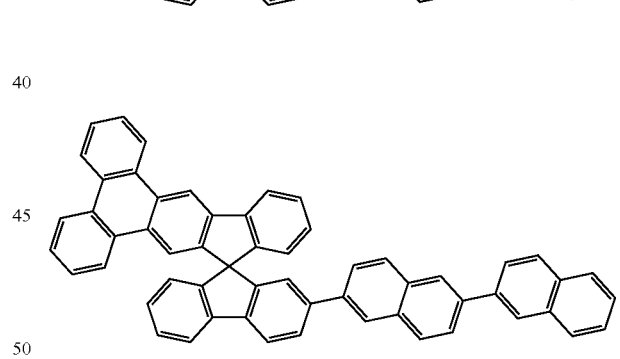
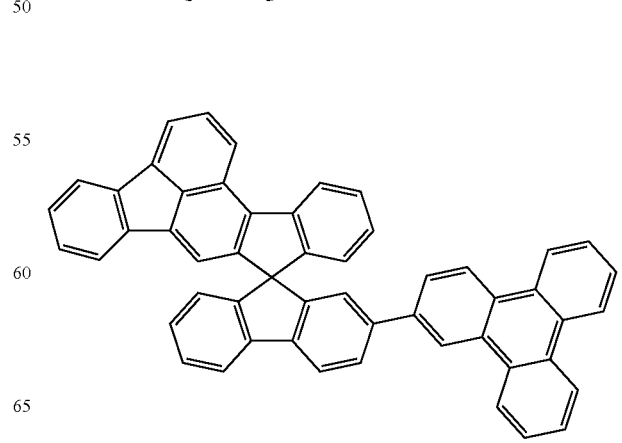

| 419 -continued | 420 -continued |
|---|---|
| 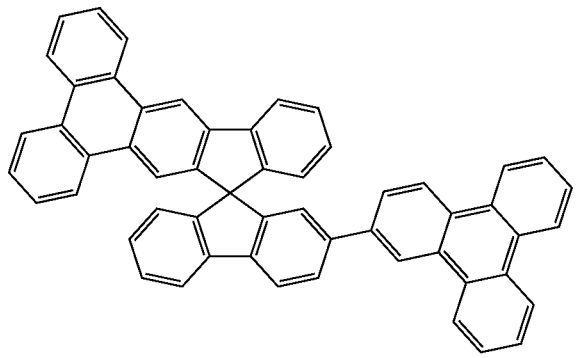 | 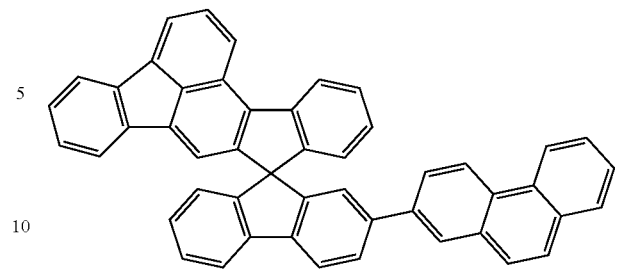 |
| 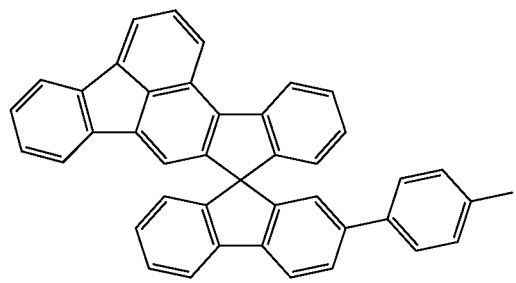 | 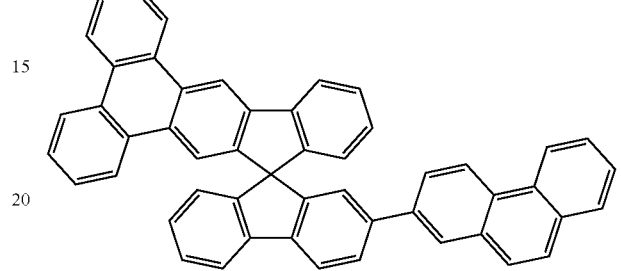 |
| 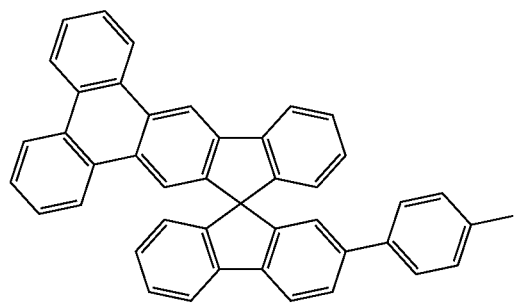 | 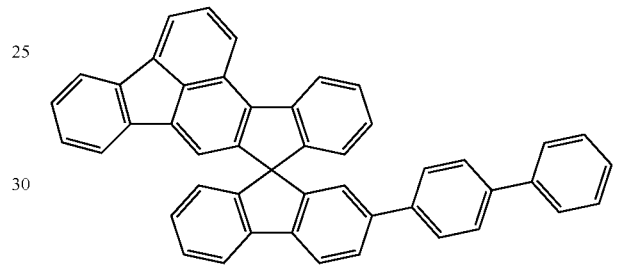 |
| 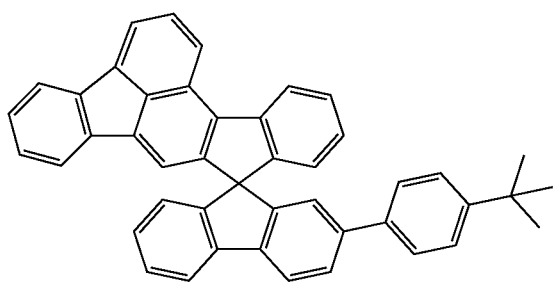 | 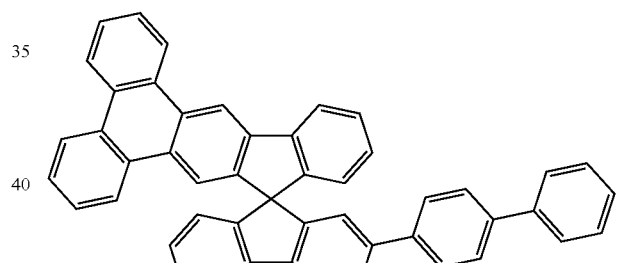 |
| 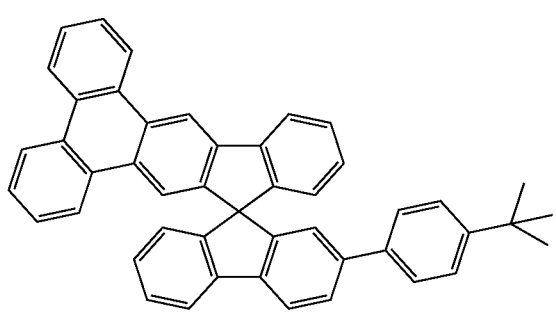 | 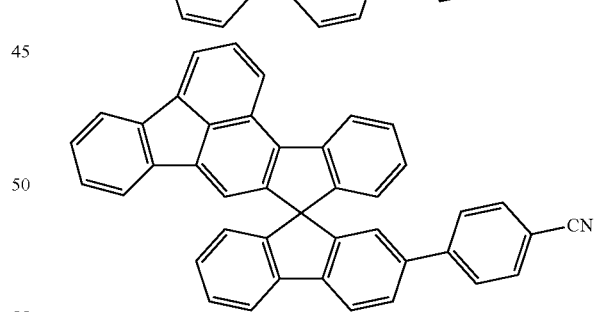 |
| | 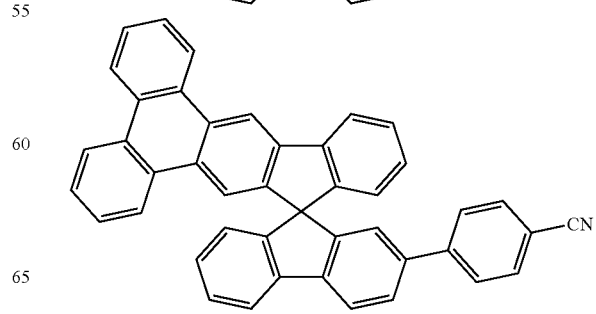 |

421
-continued
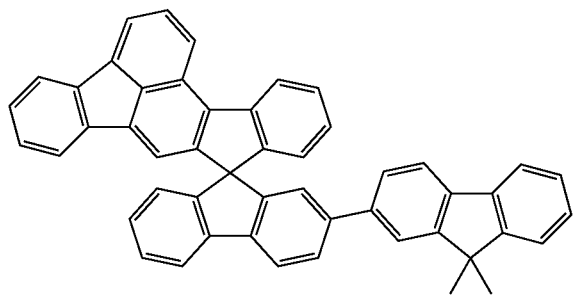
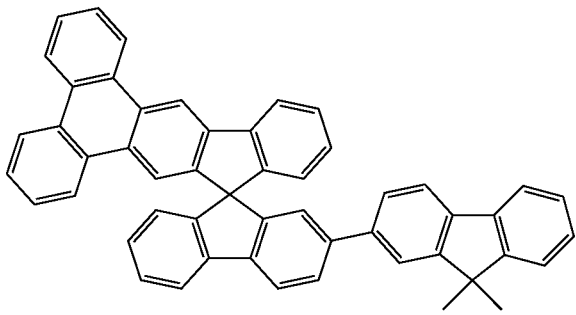
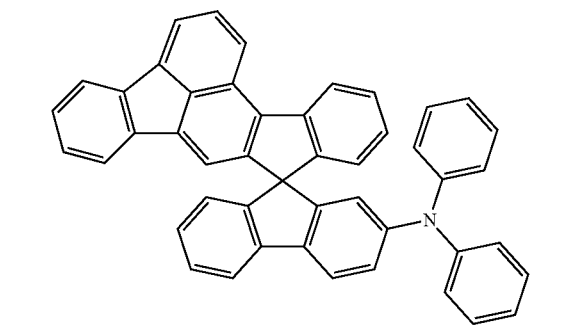
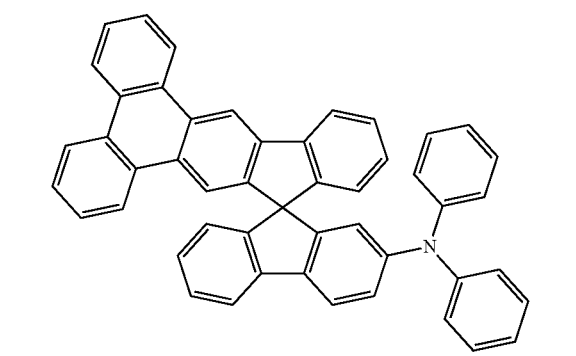
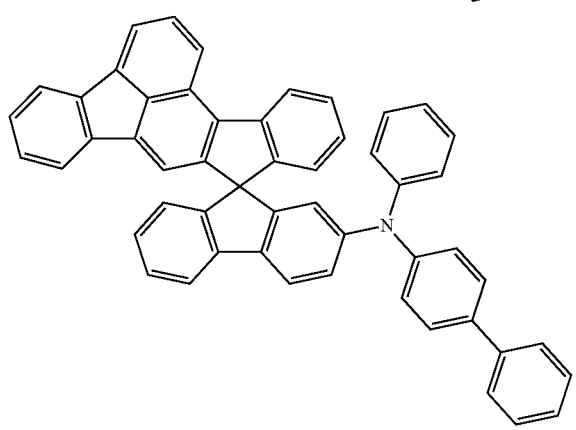
422
-continued
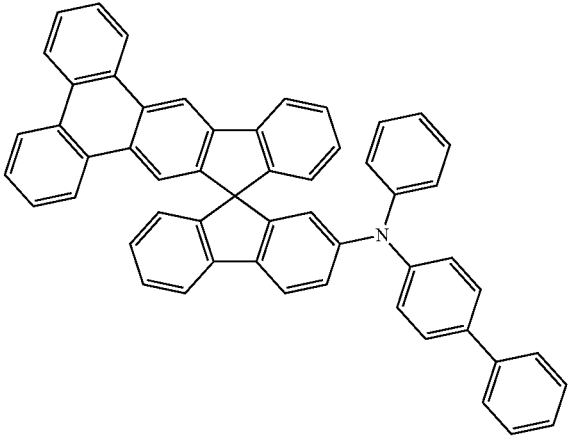
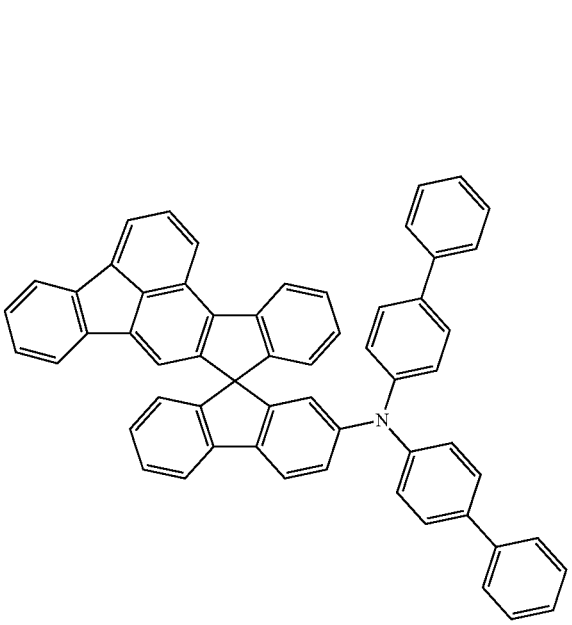
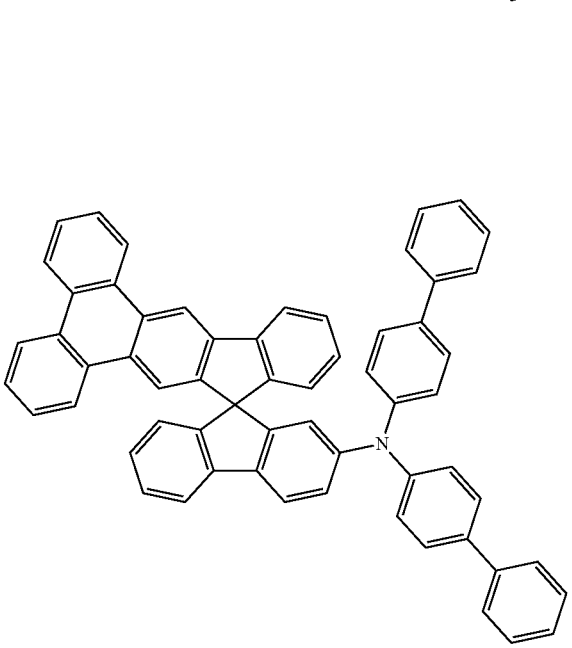

| 423 -continued | 424 -continued |
|---|---|
| 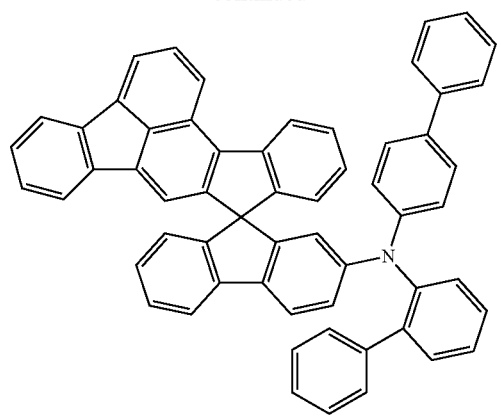 | 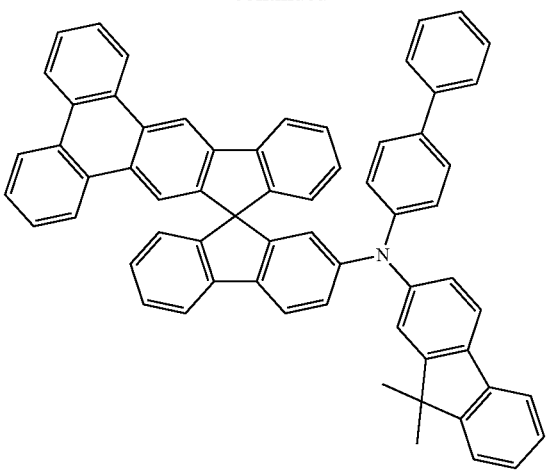 |
| 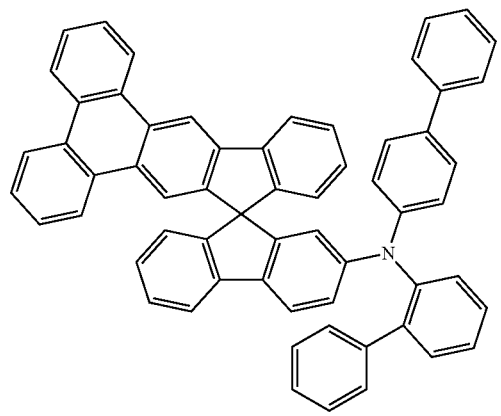 | 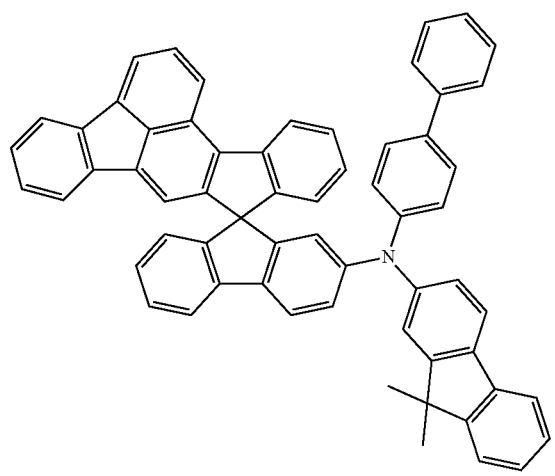 |
| 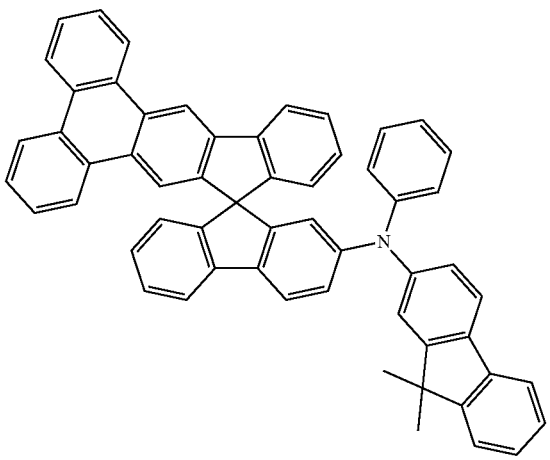 | |

425
-continued
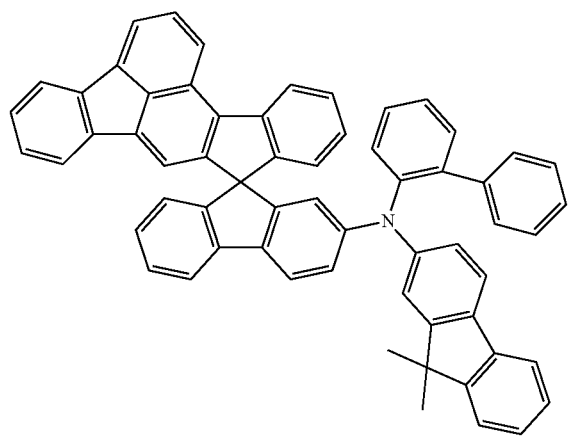
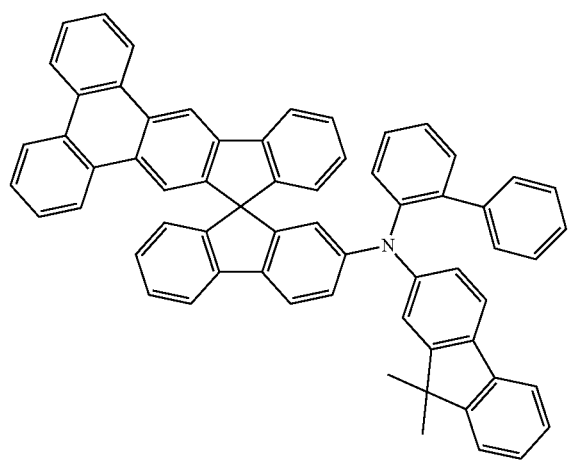
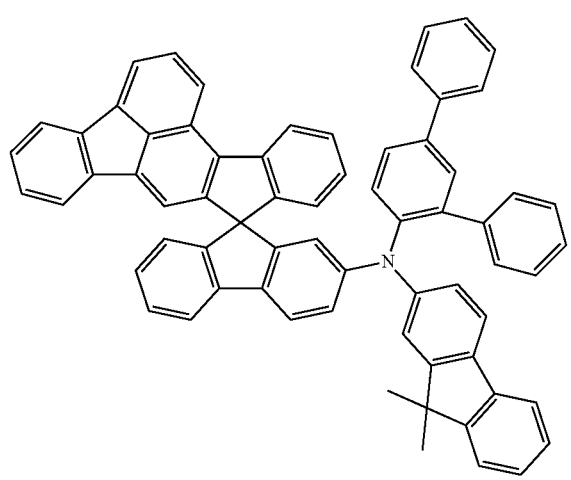
426
-continued
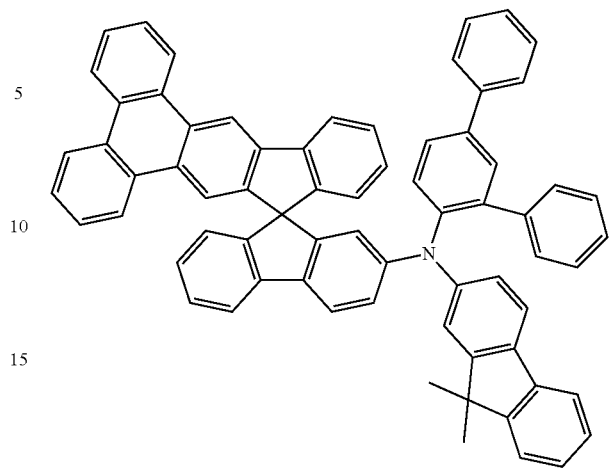
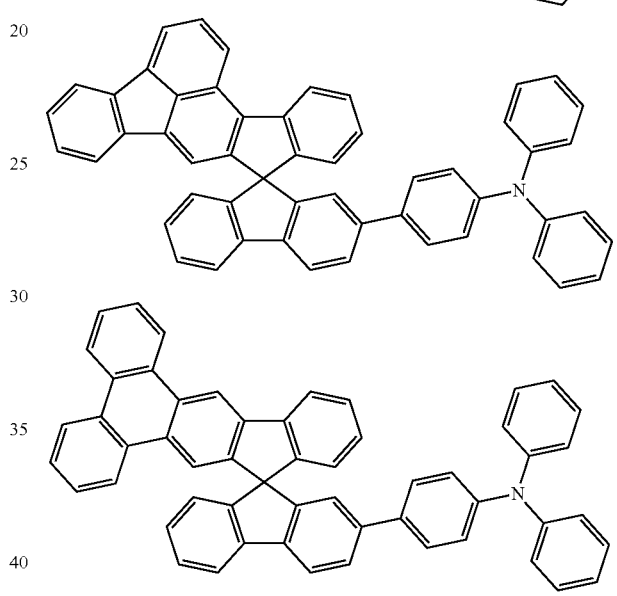
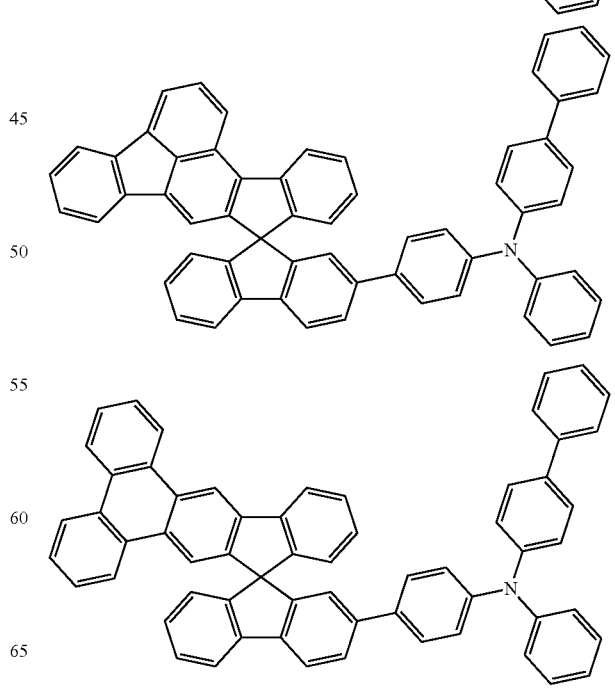

427
-continued
428
-continued
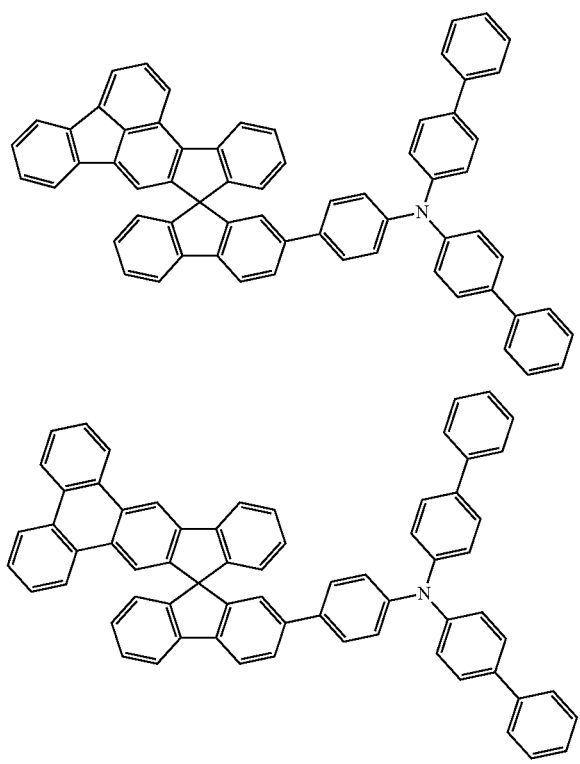
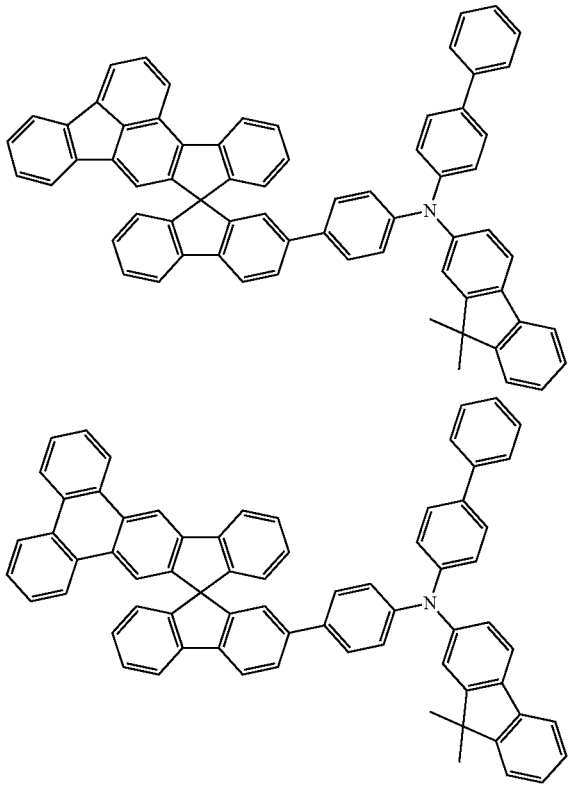
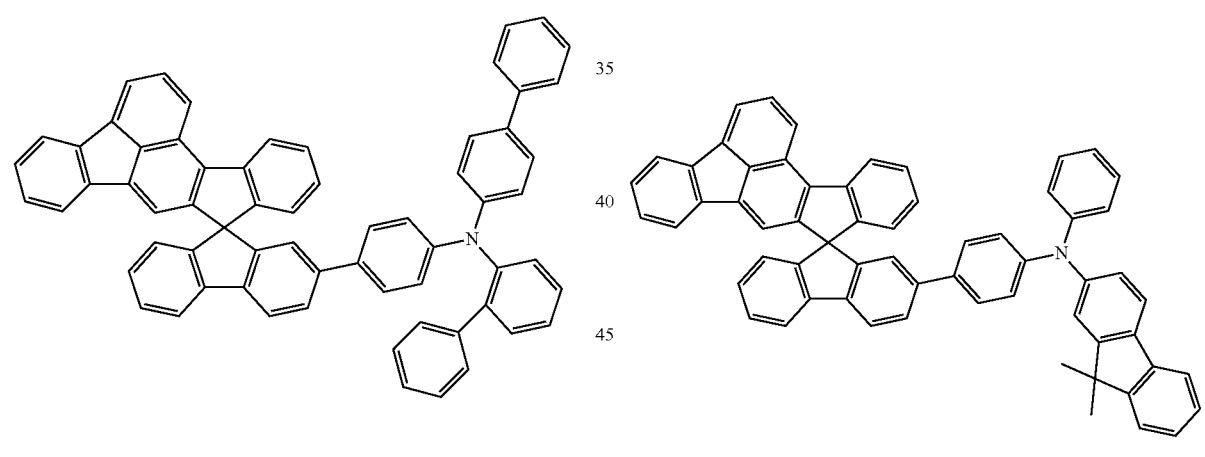
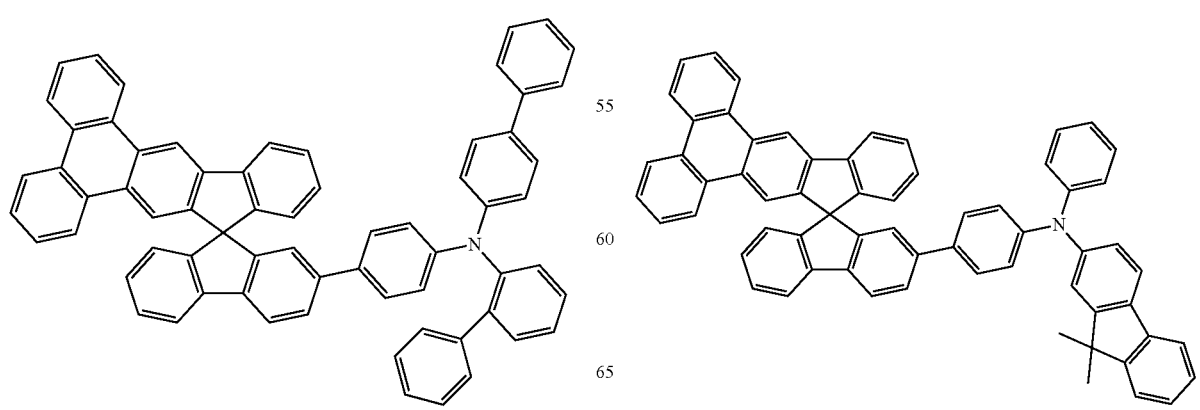

429
-continued
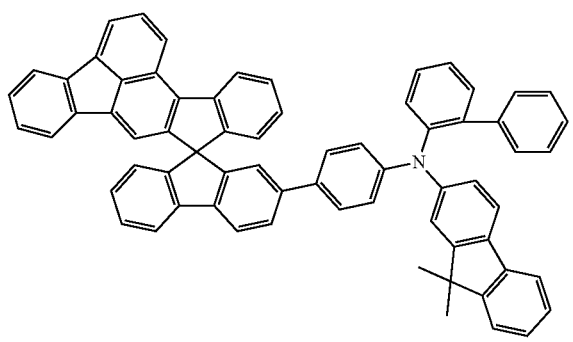
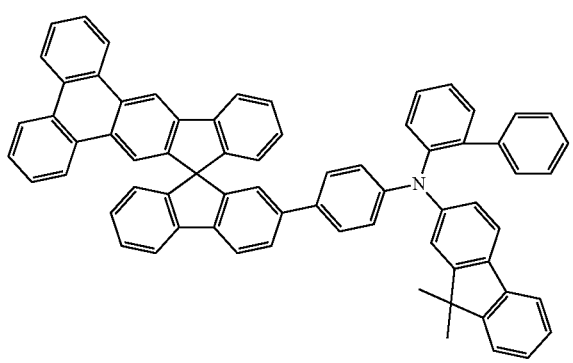
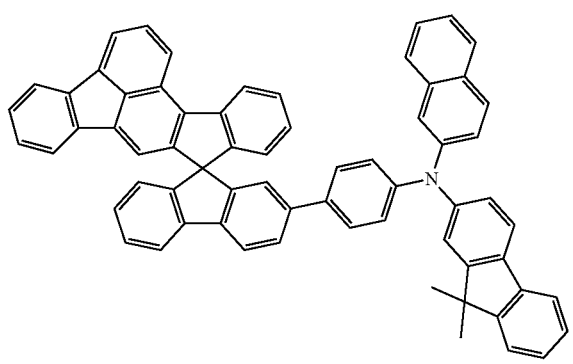
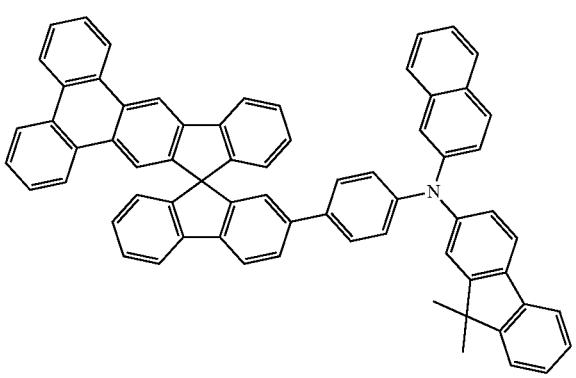
430
-continued
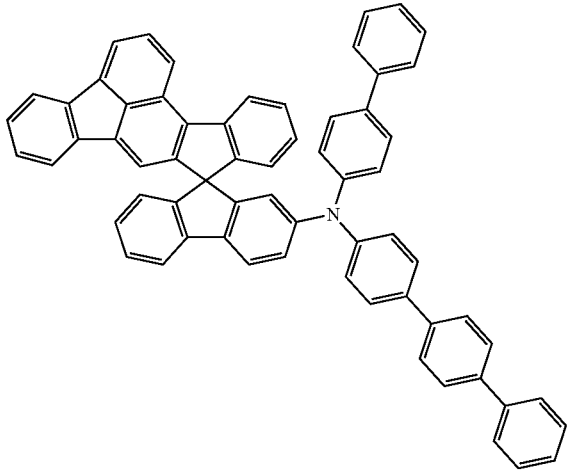
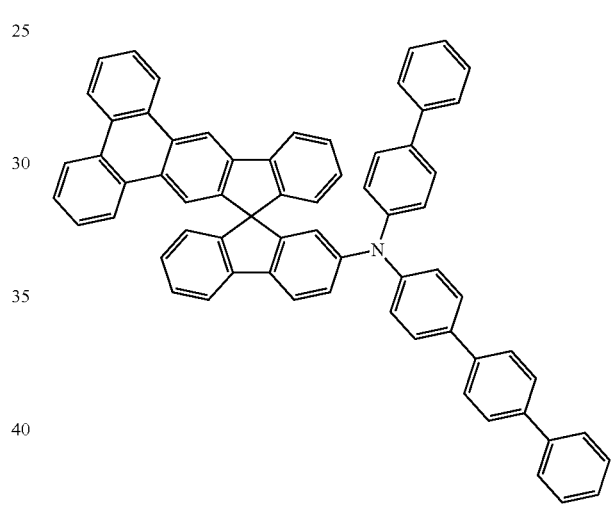
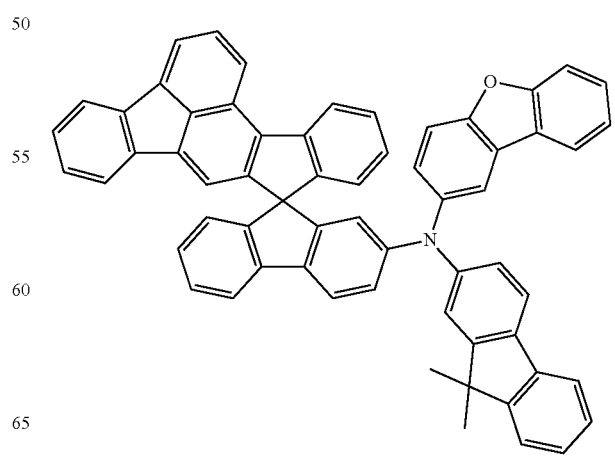

431
-continued
432
-continued
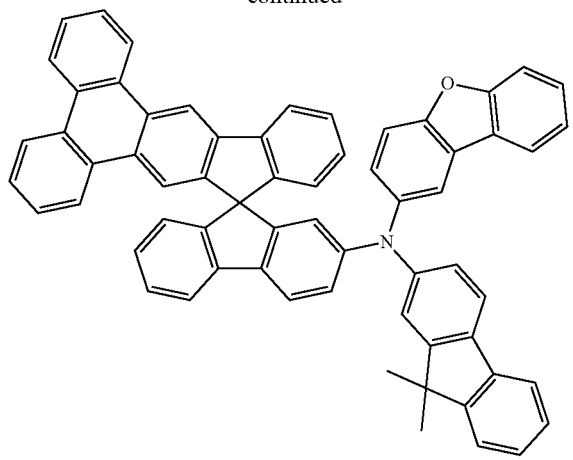
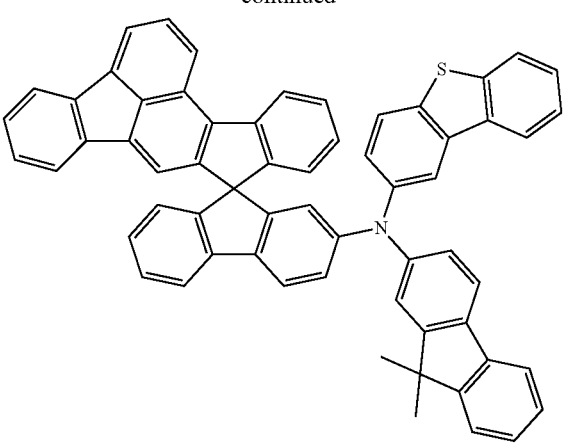
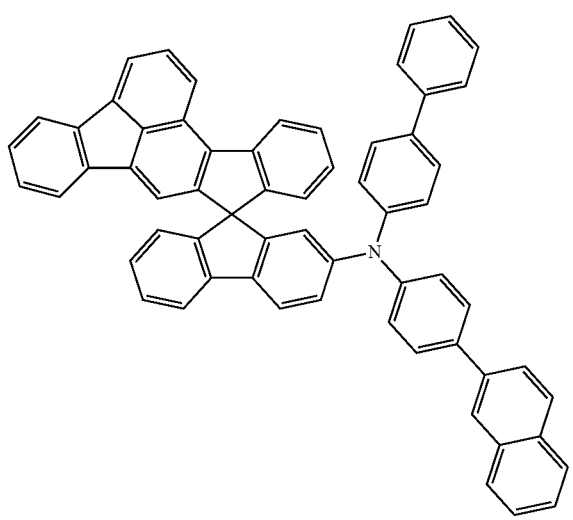
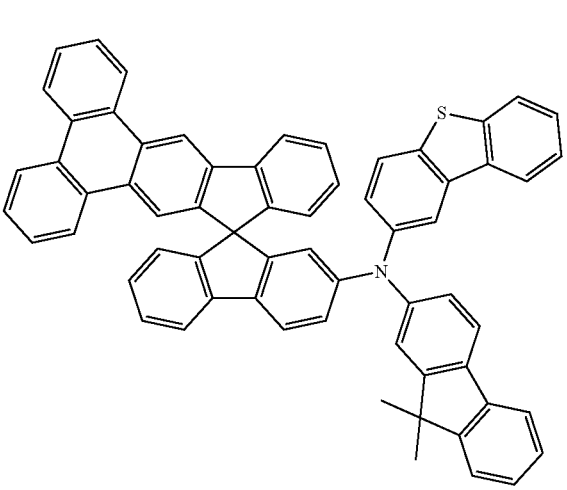
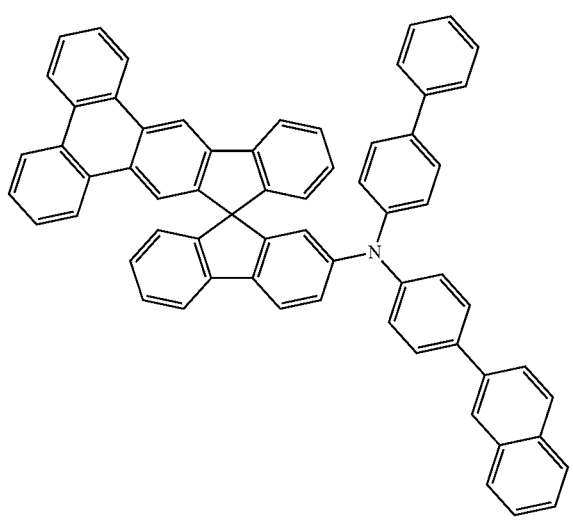
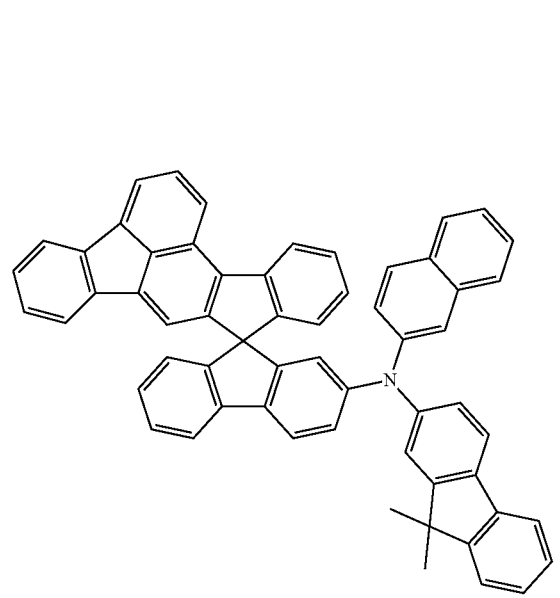

433
-continued
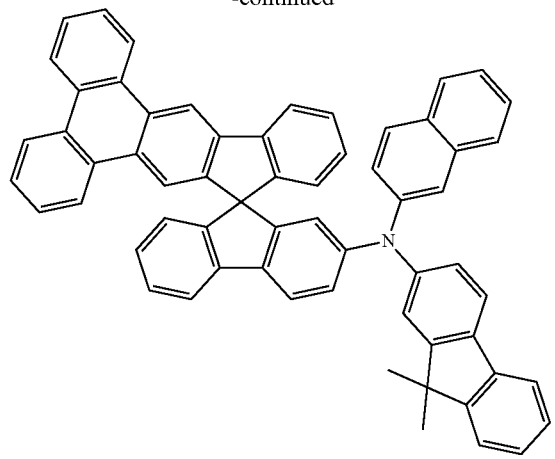
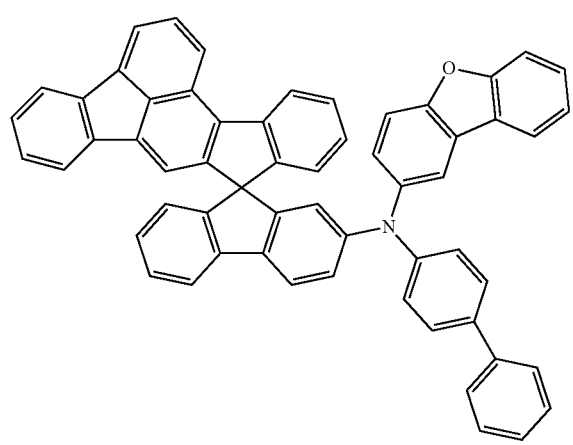
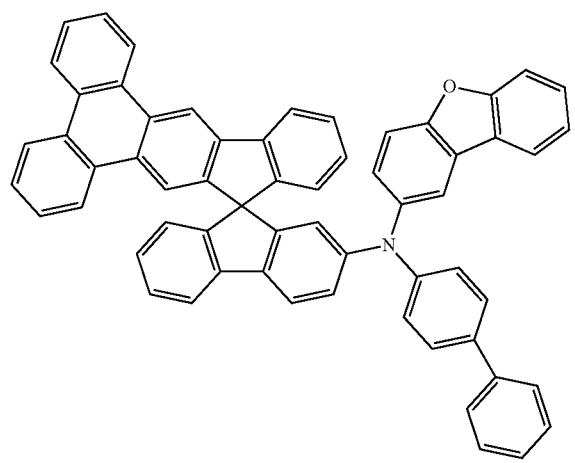
434
-continued
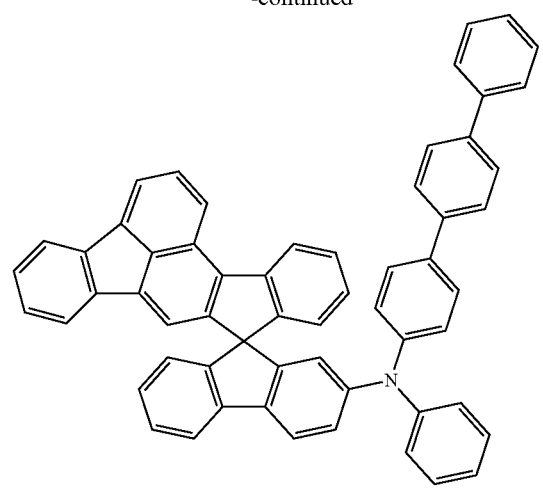
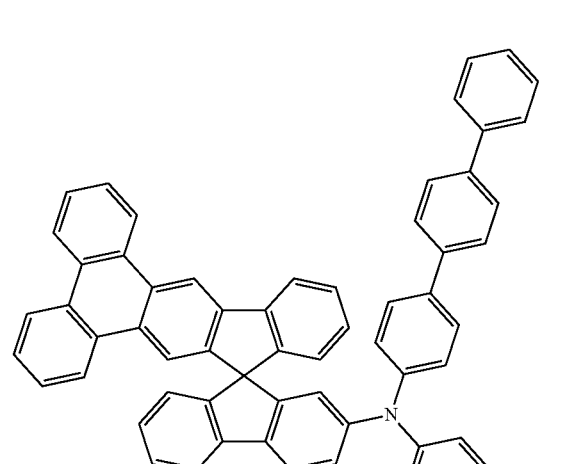
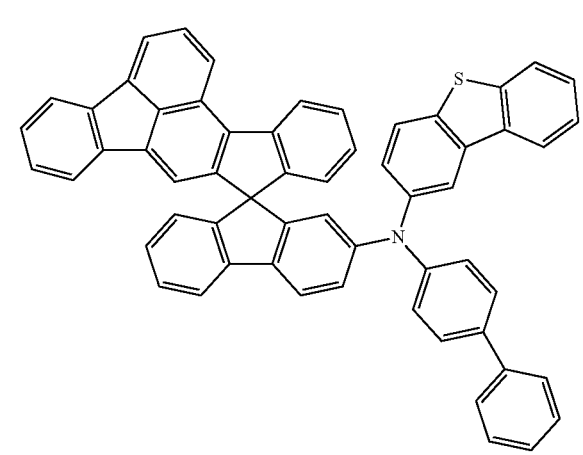

435
-continued
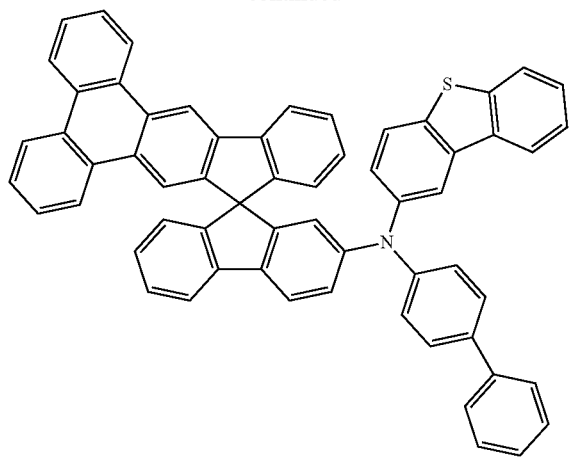
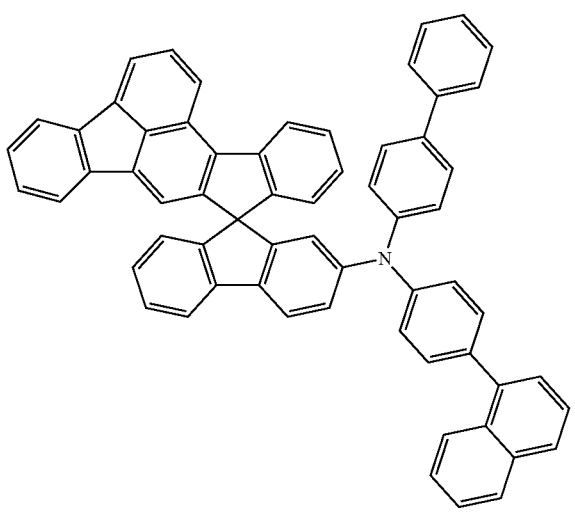
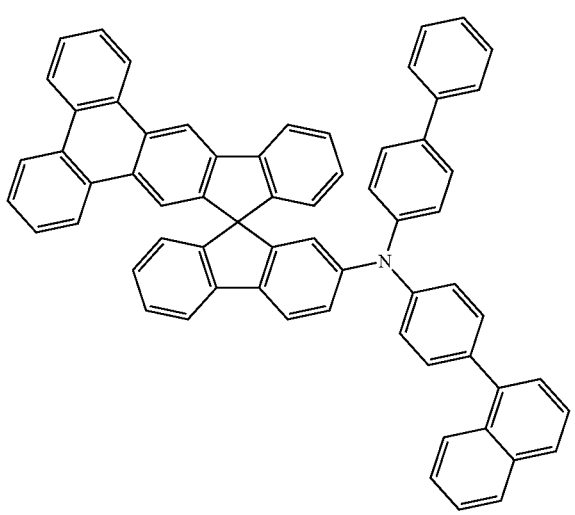
436
-continued
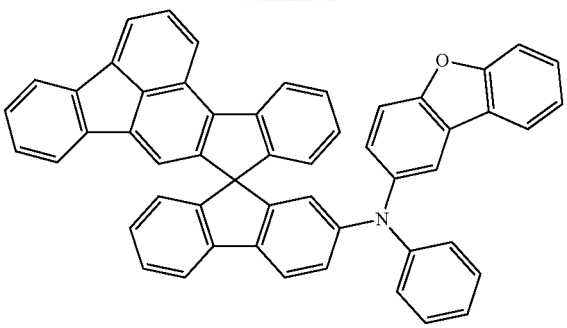
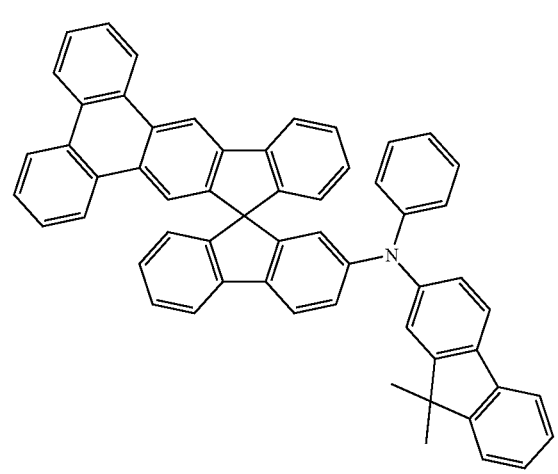

437
-continued
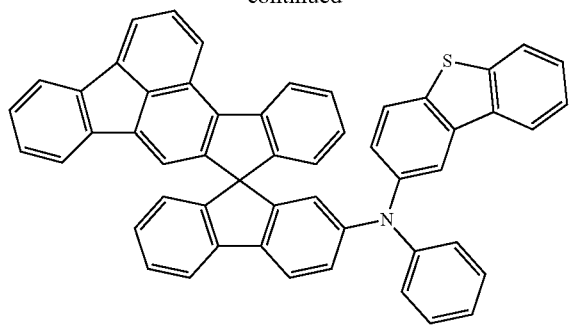
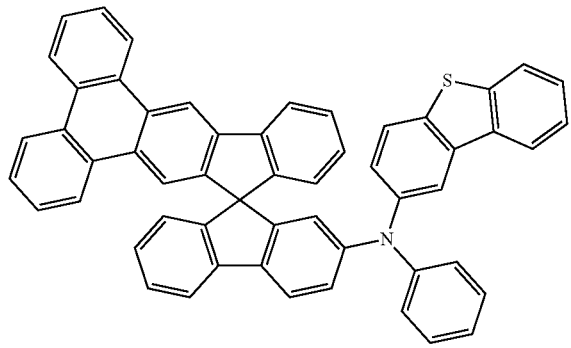
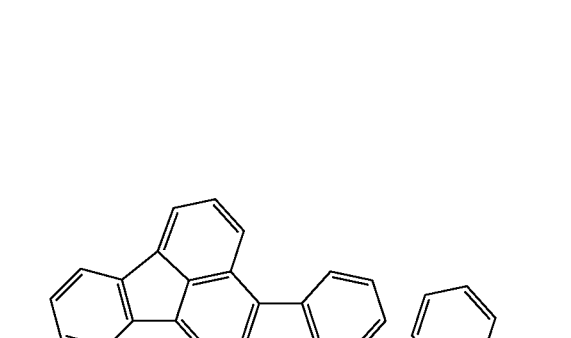
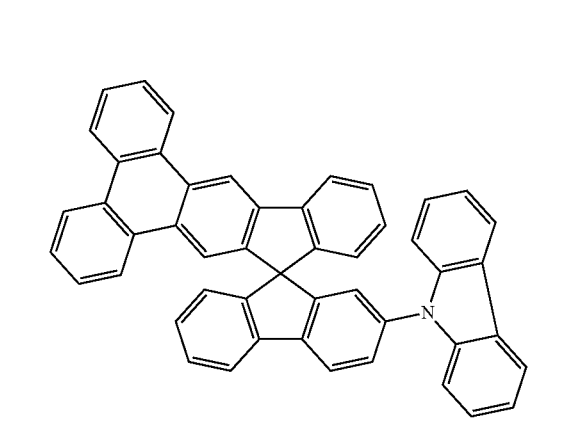
438
-continued
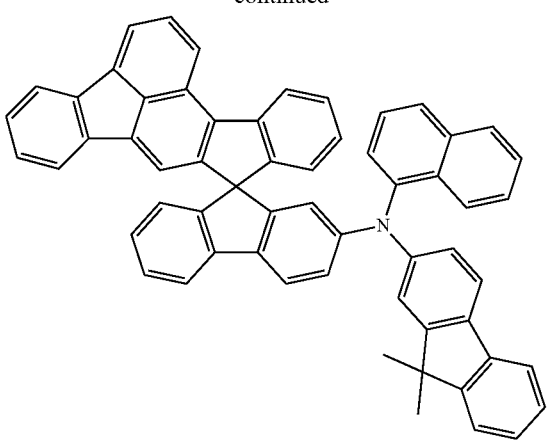
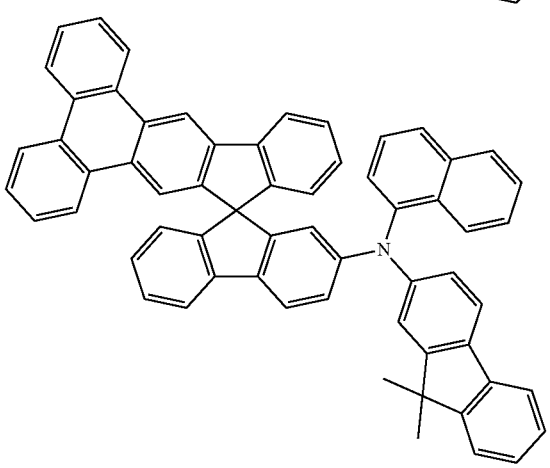
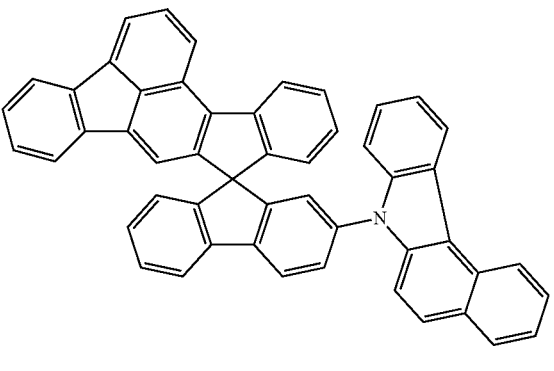
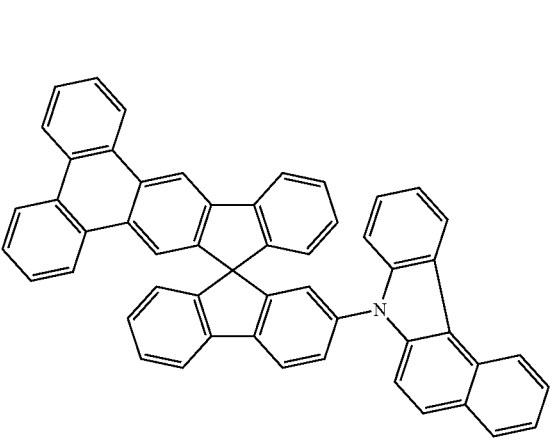

439
-continued
440
-continued
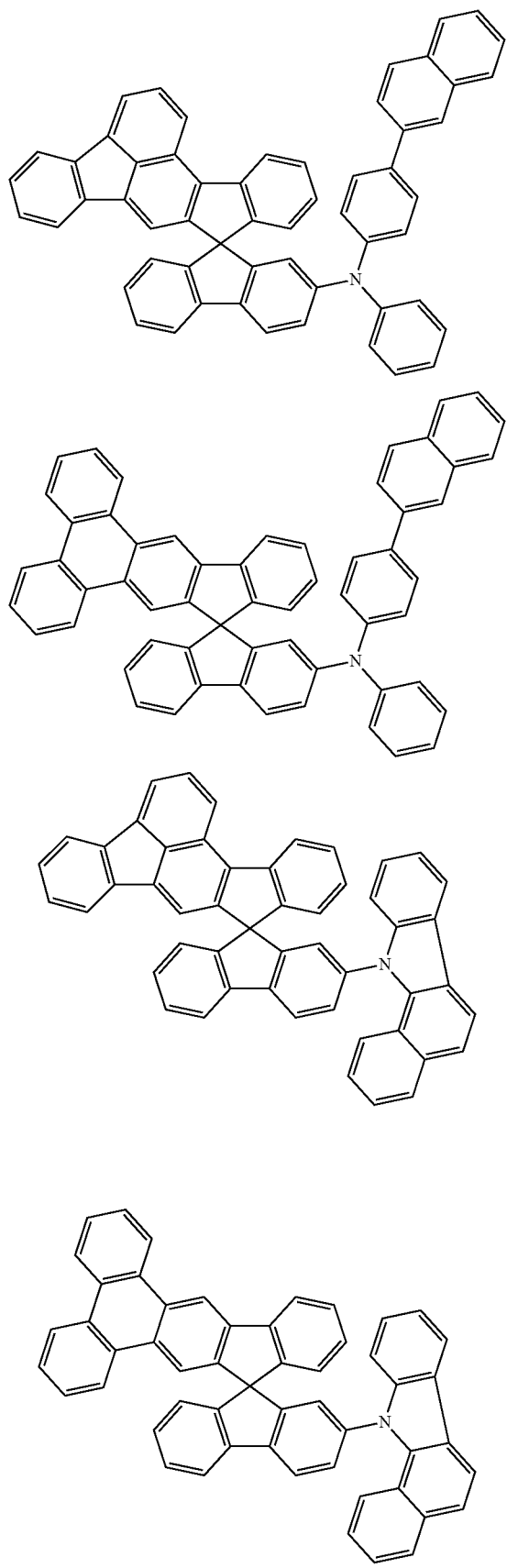
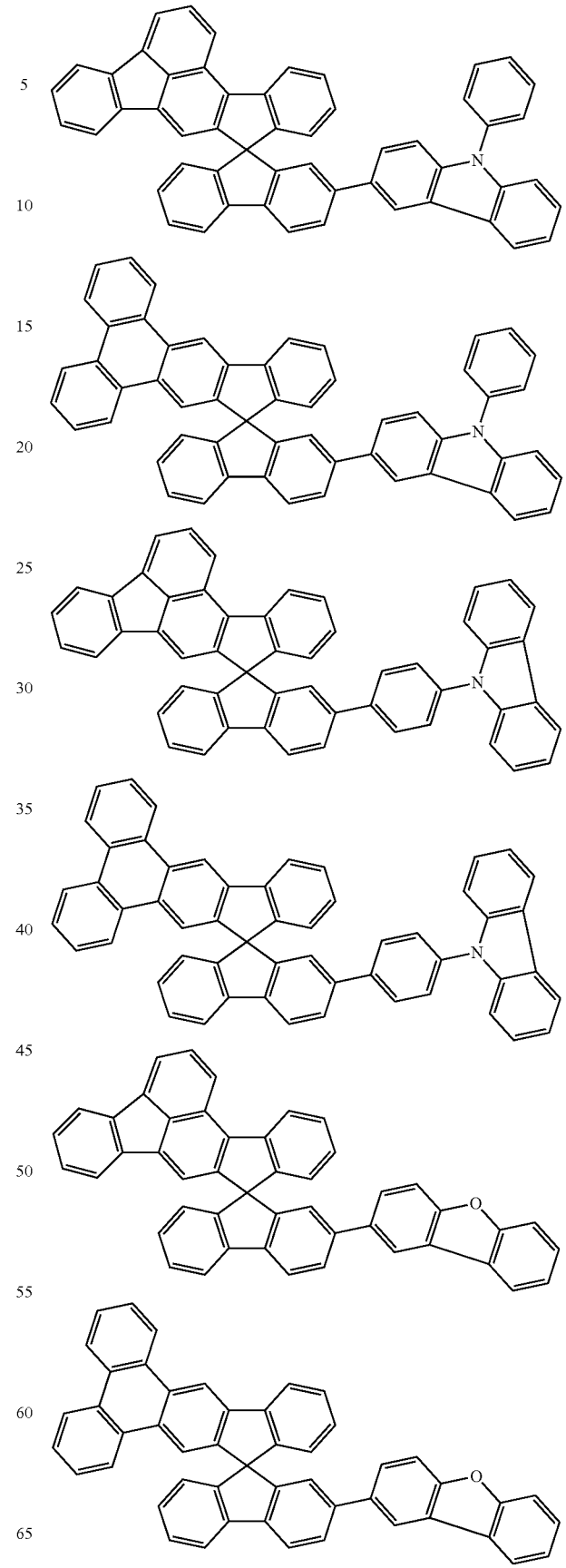

441
-continued
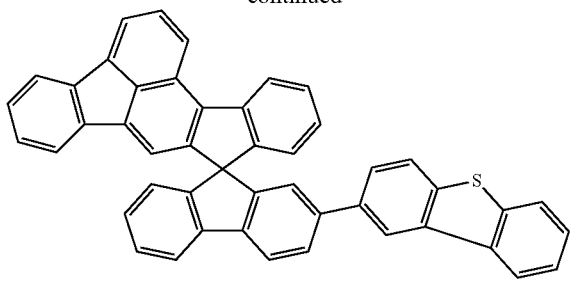
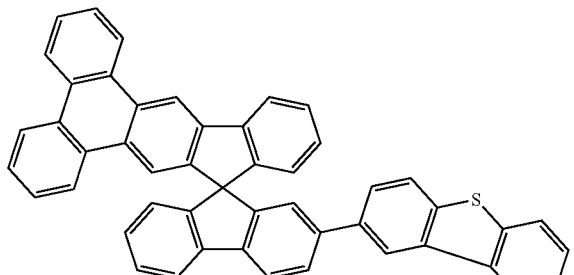
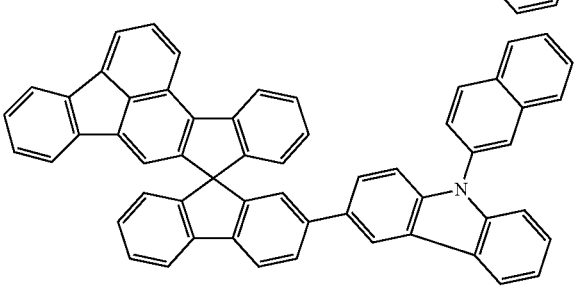
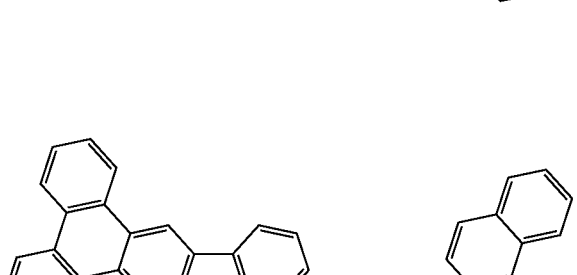
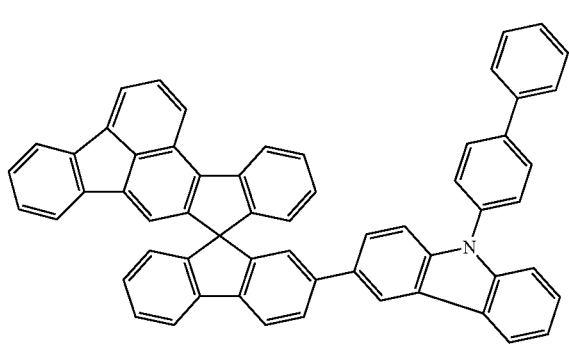
442
-continued
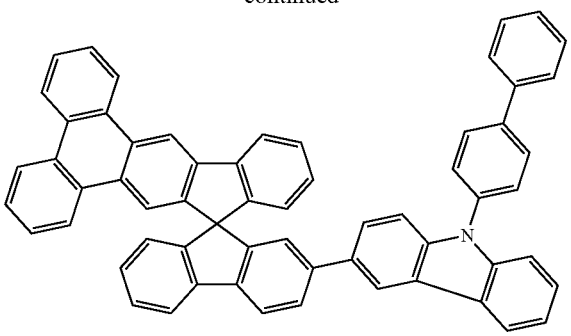
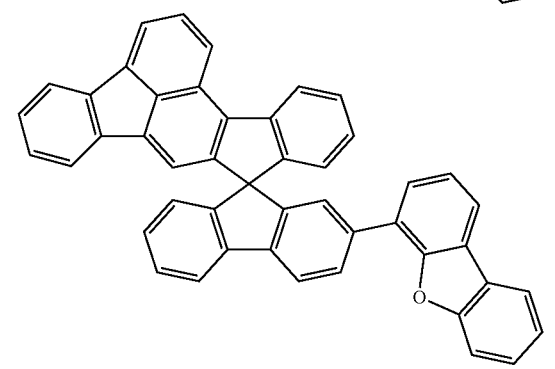
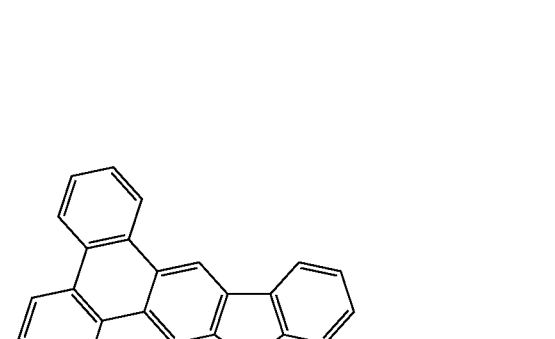
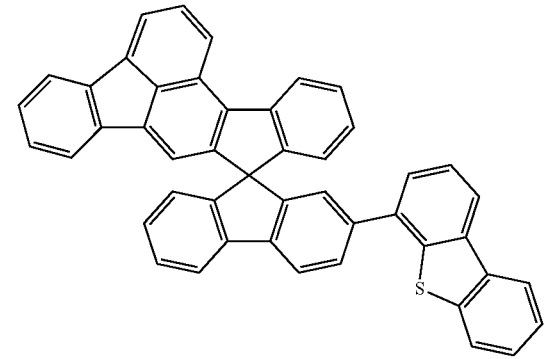

443
-continued
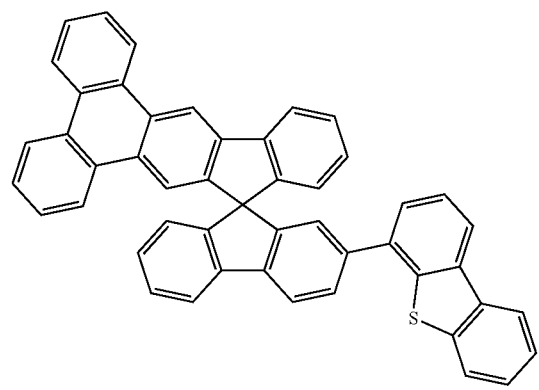
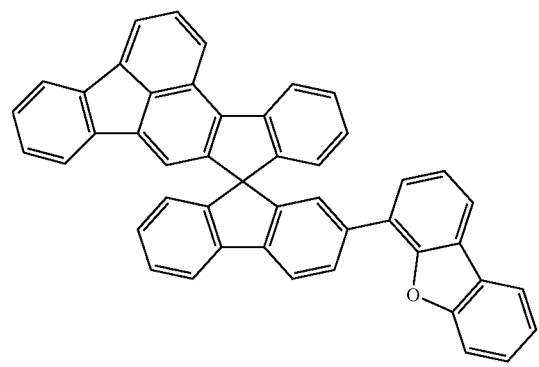
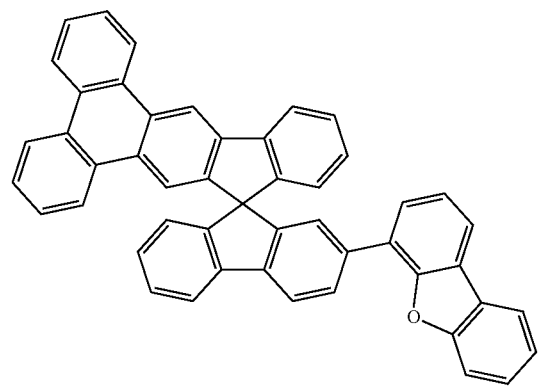
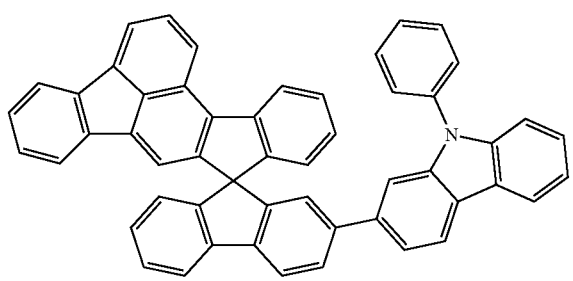
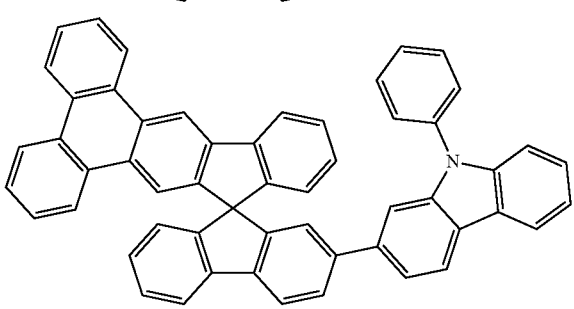
444
-continued
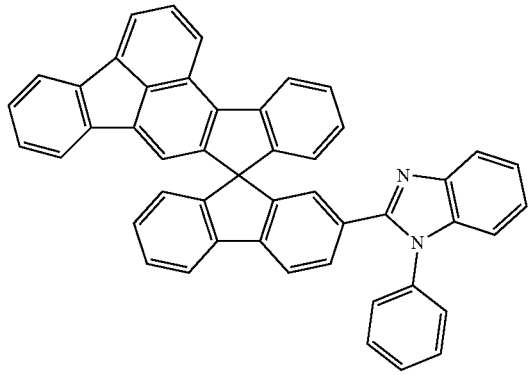
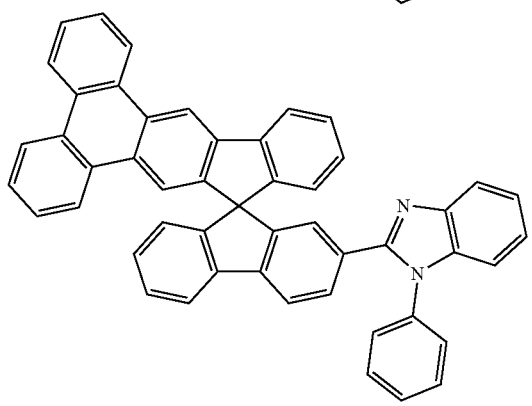
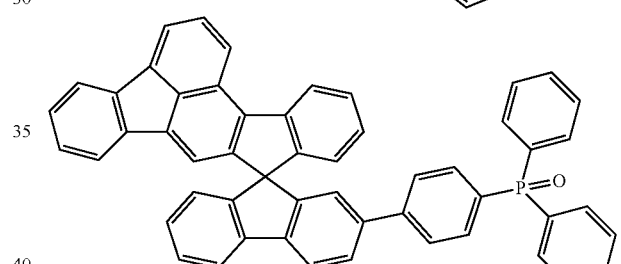
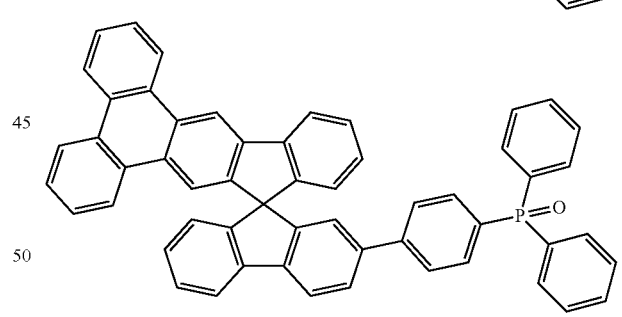
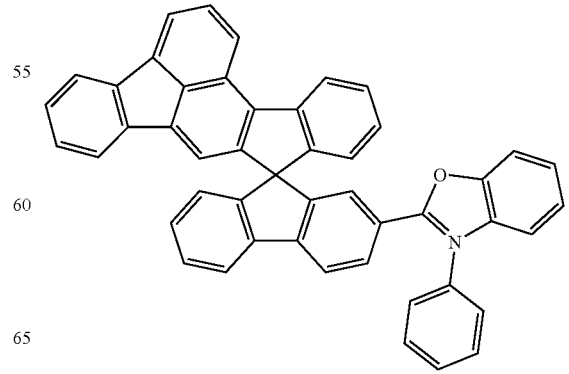

445
-continued
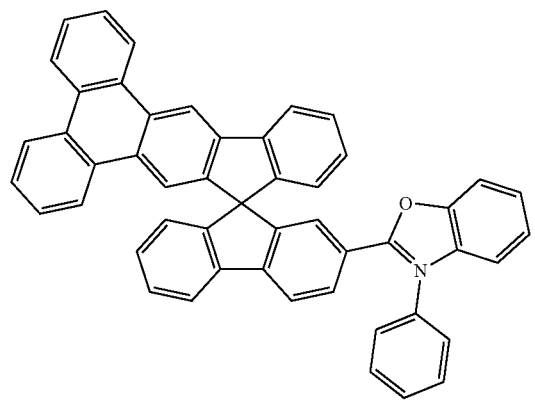
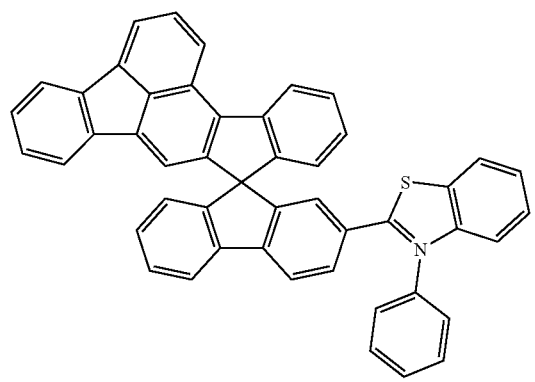
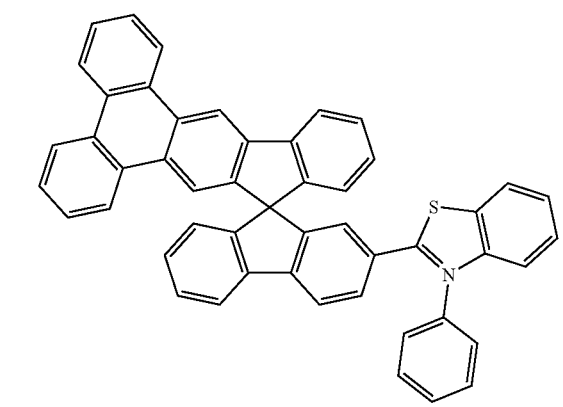
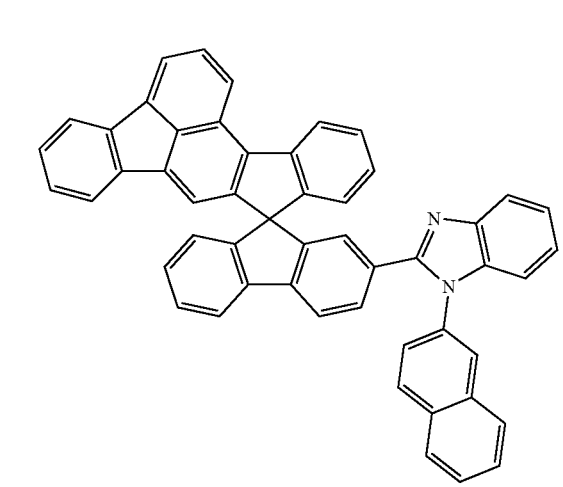
446
-continued
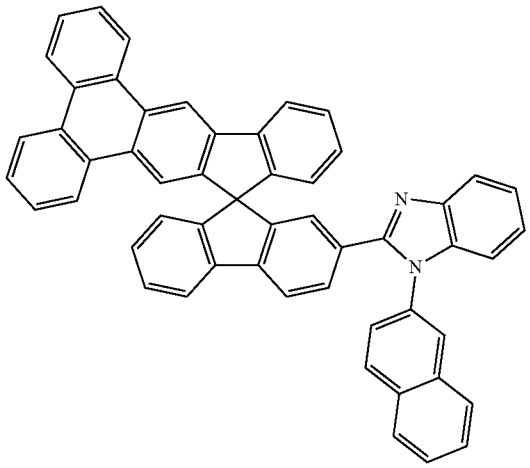
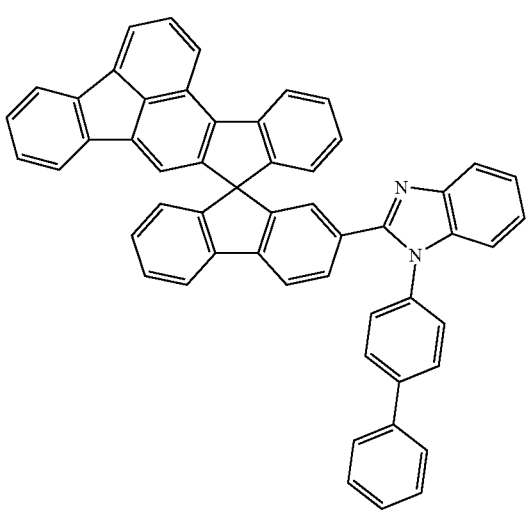
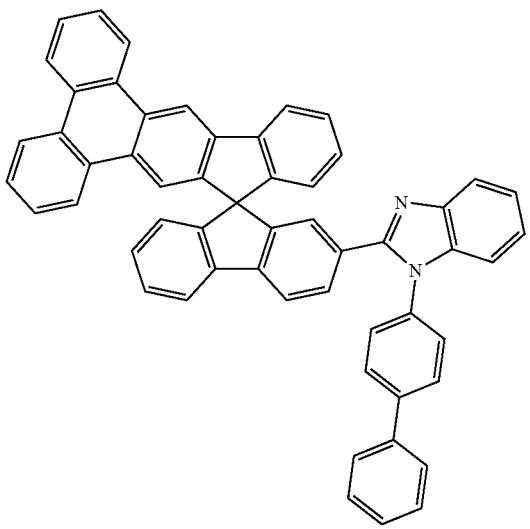

447
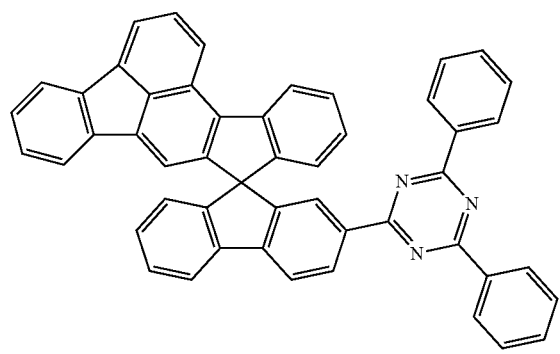
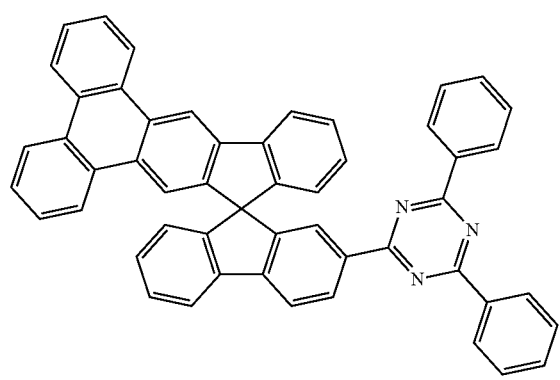
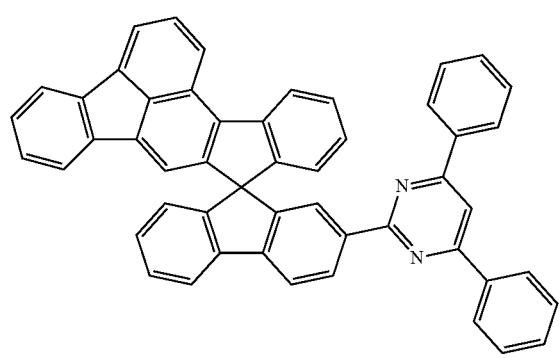
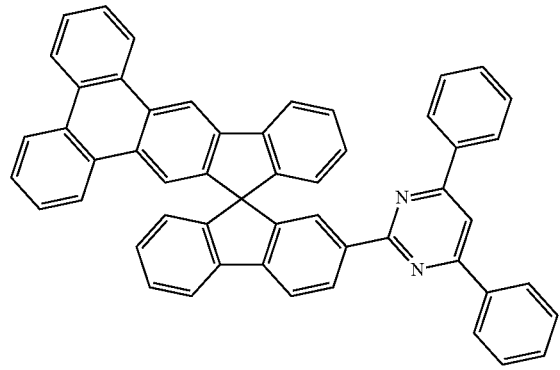
448
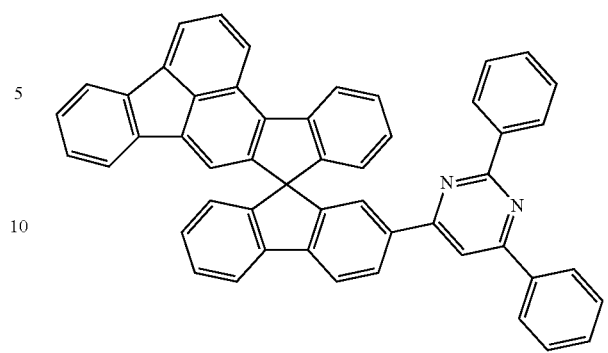
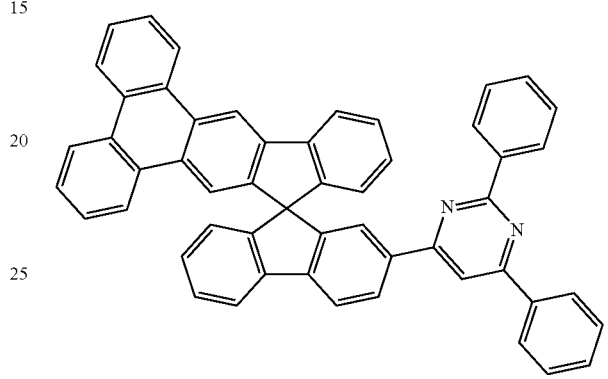
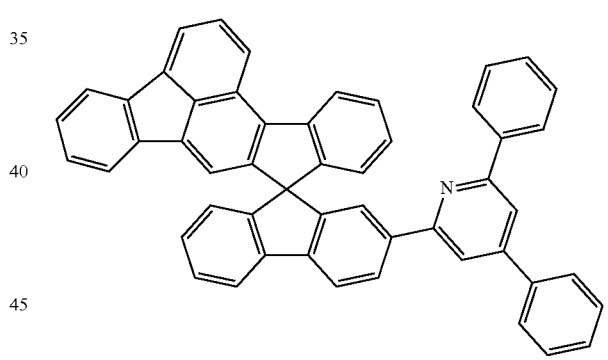
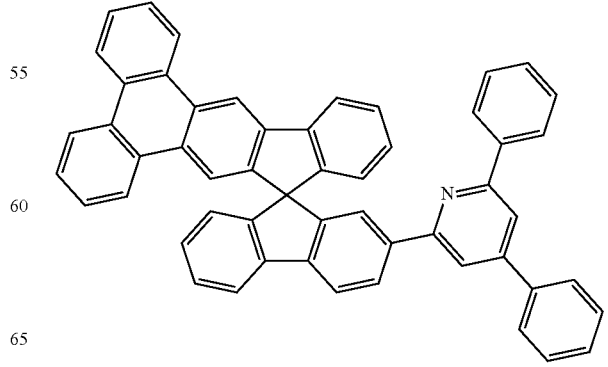

449
-continued
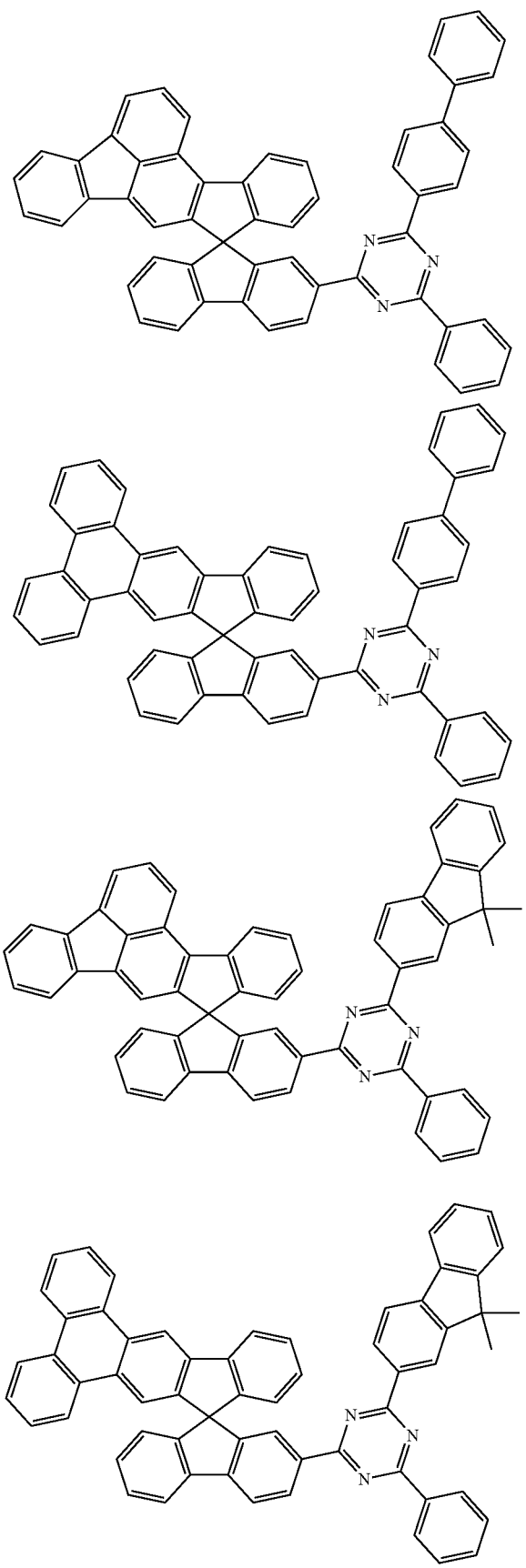
450
-continued
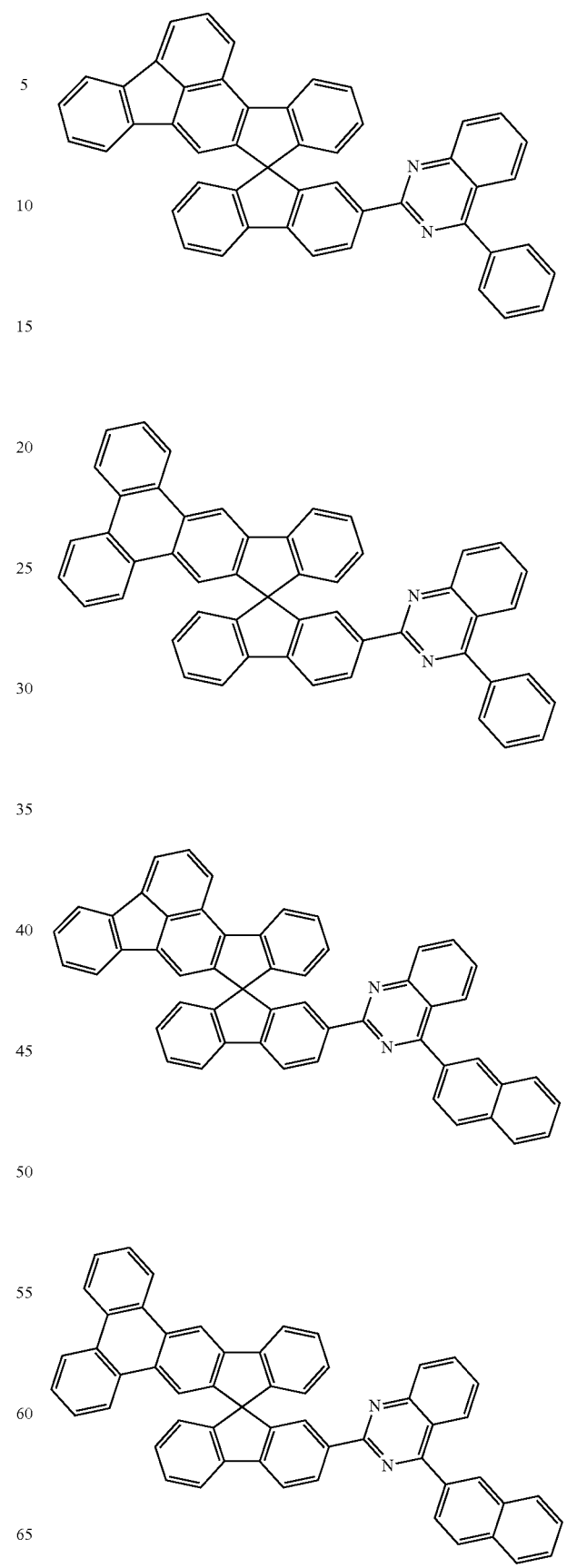

451
-continued
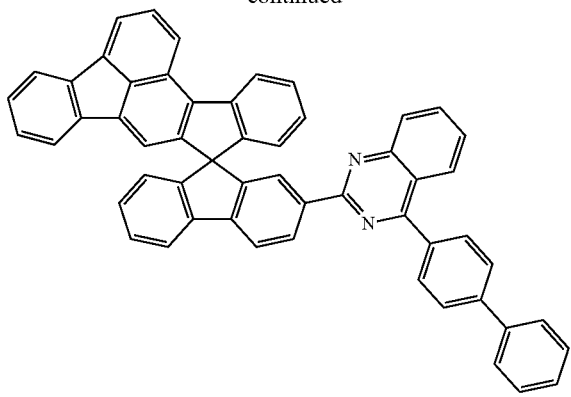
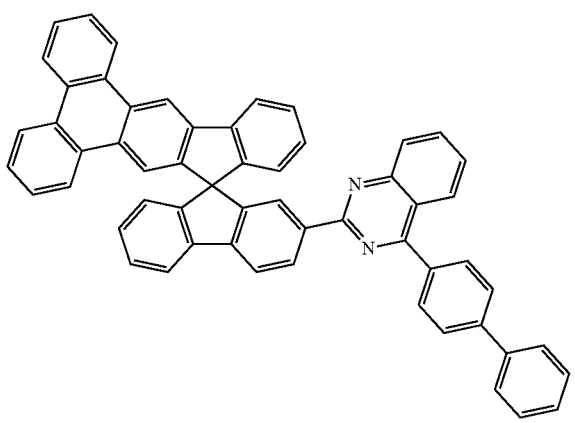
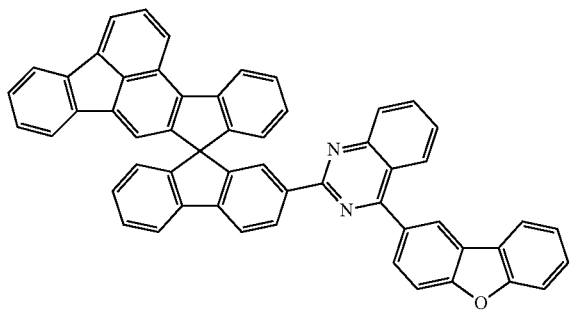
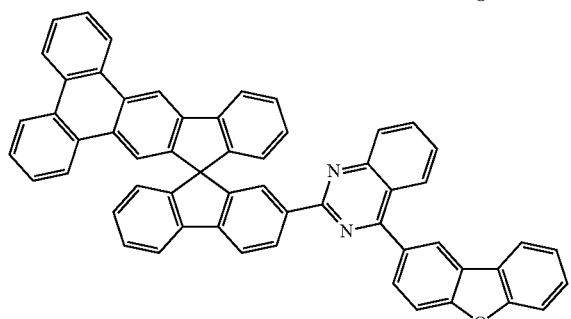
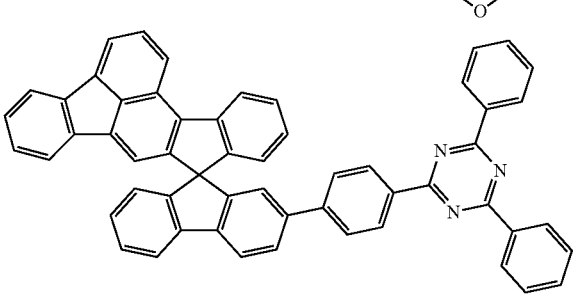
452
-continued
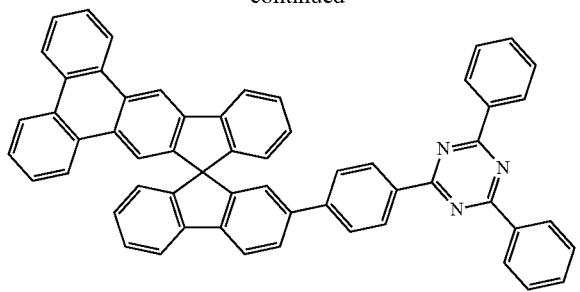
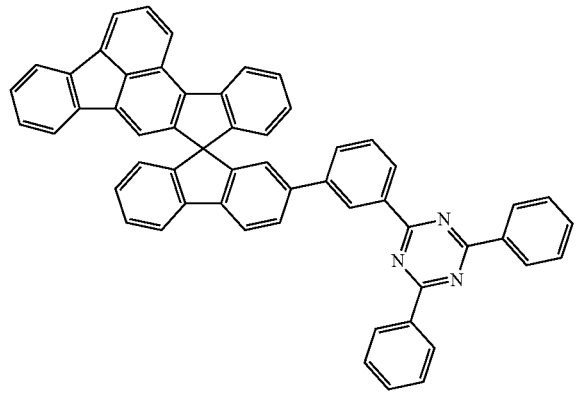
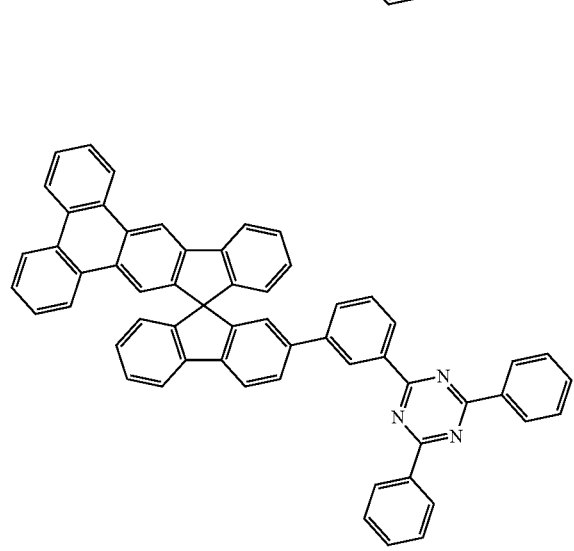

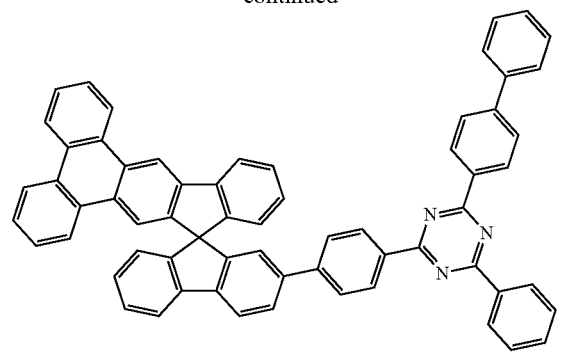
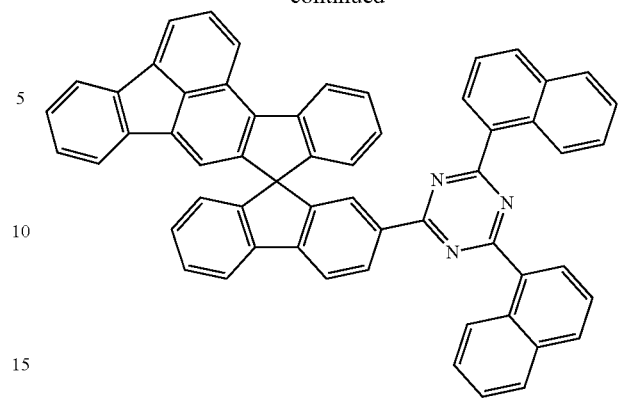
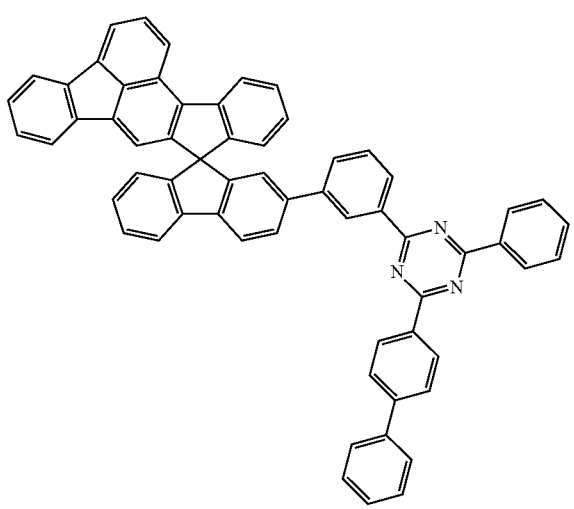
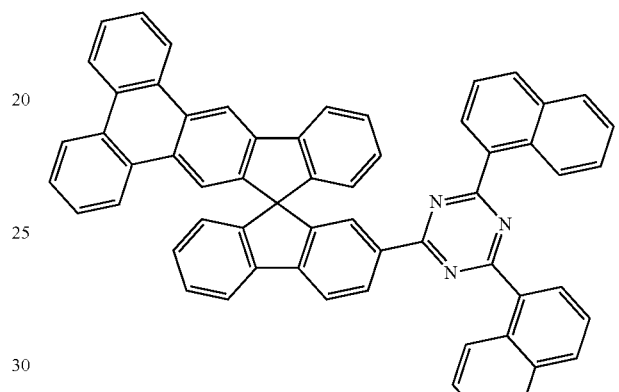
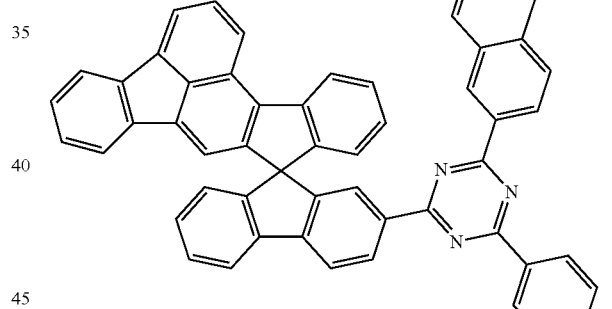
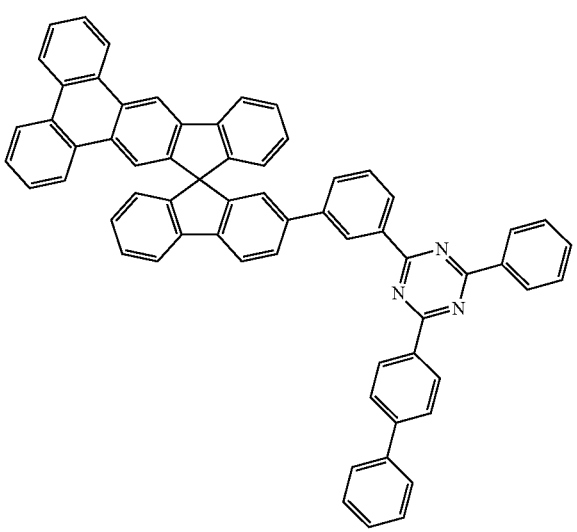
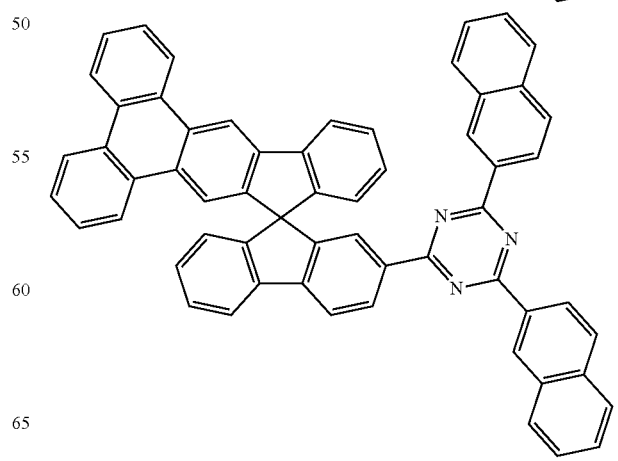

455
-continued
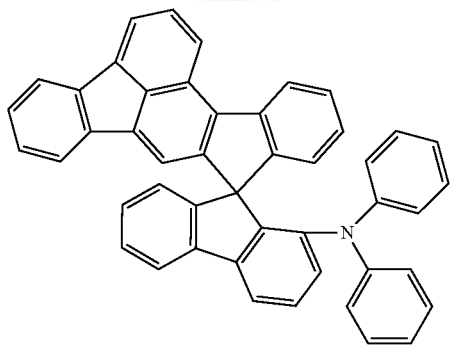
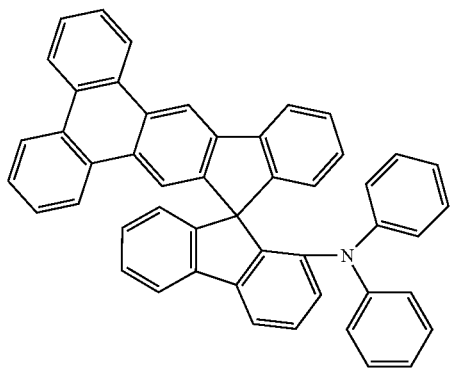
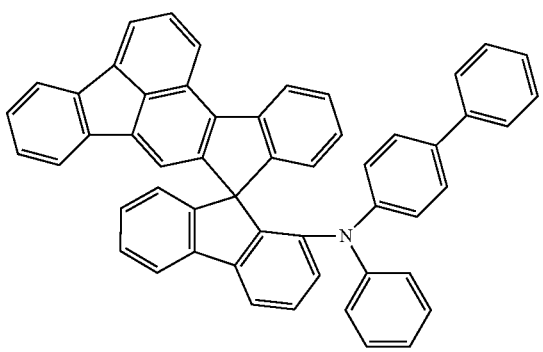
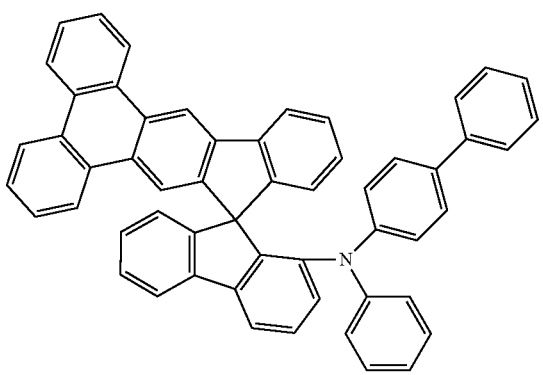
456
-continued
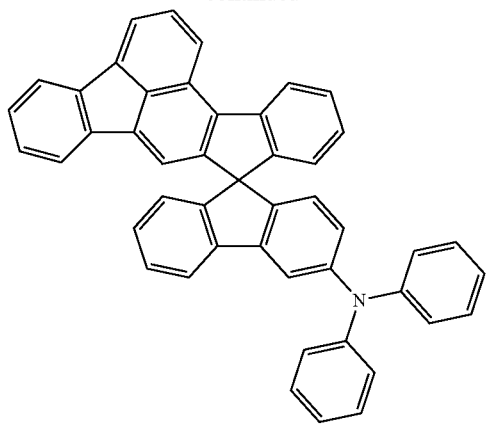
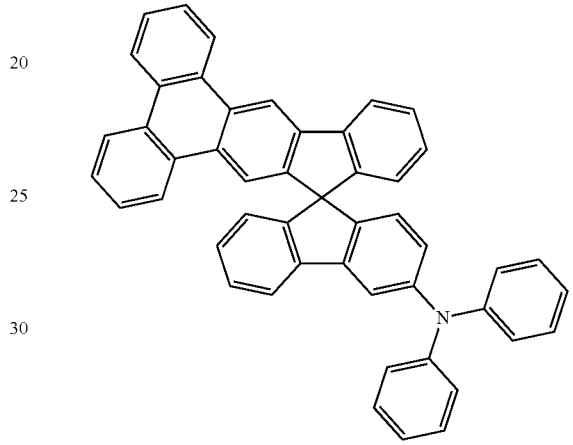
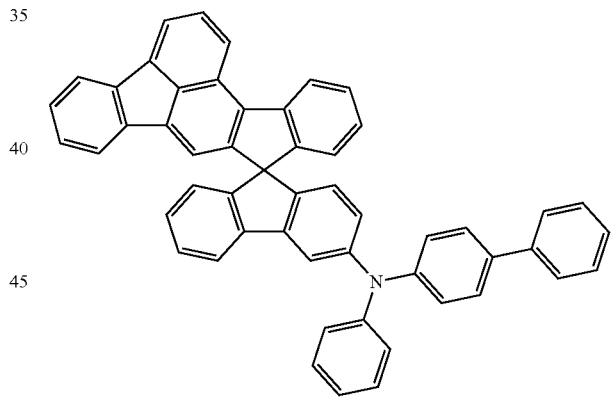
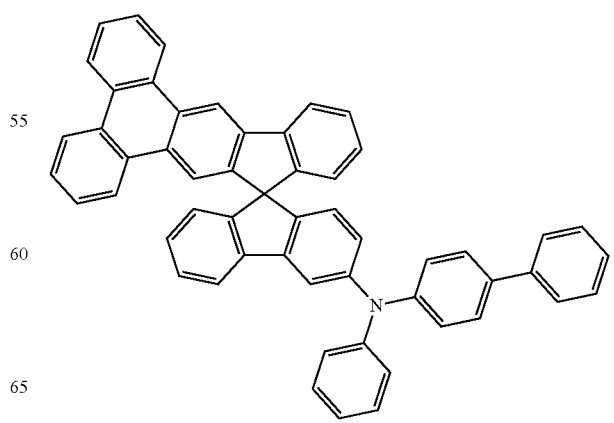

457
-continued
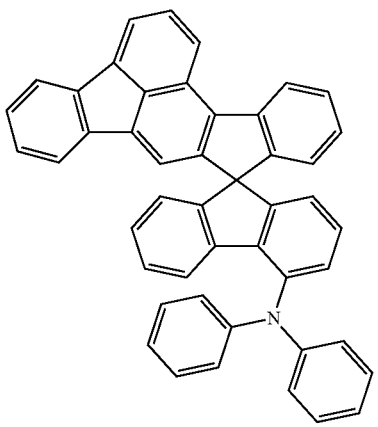
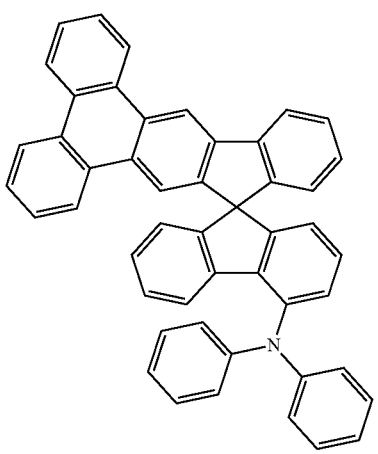
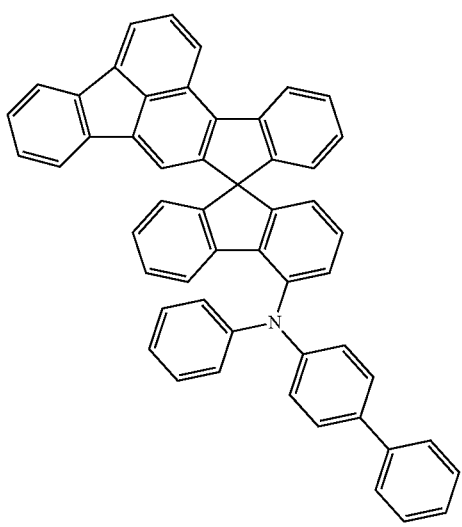
458
-continued
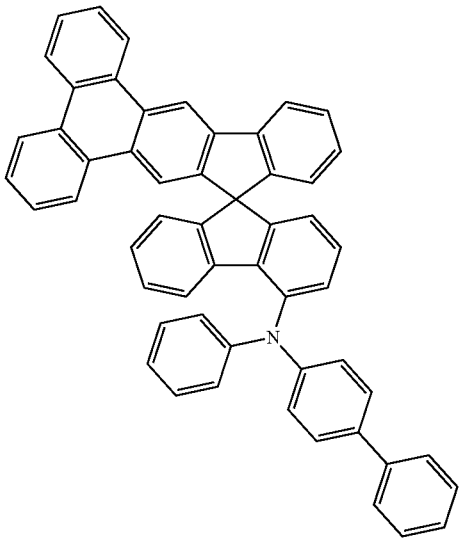
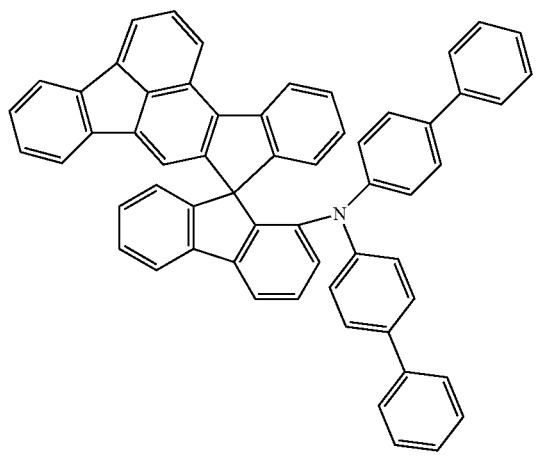
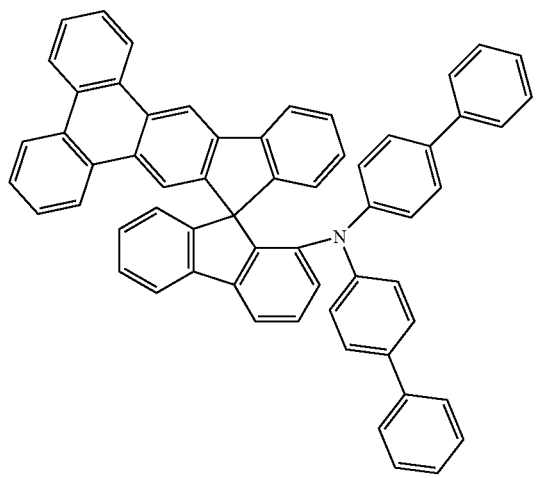

| 459 -continued | 460 -continued |
|---|---|
| 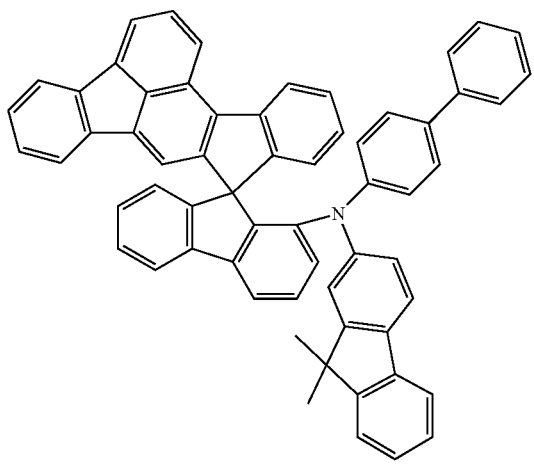 | 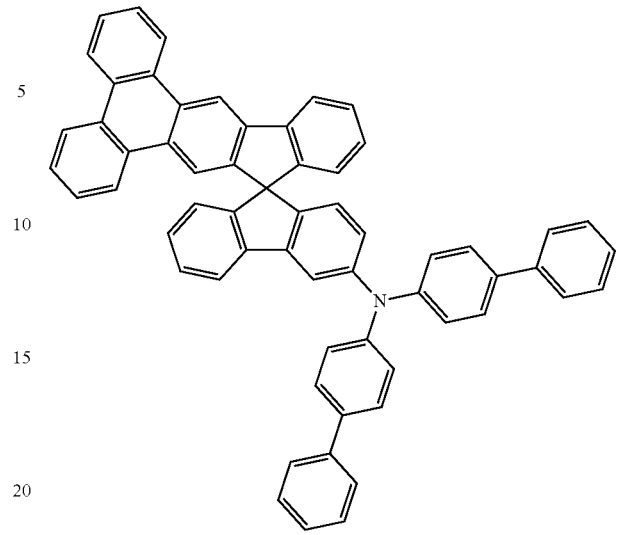 |
| 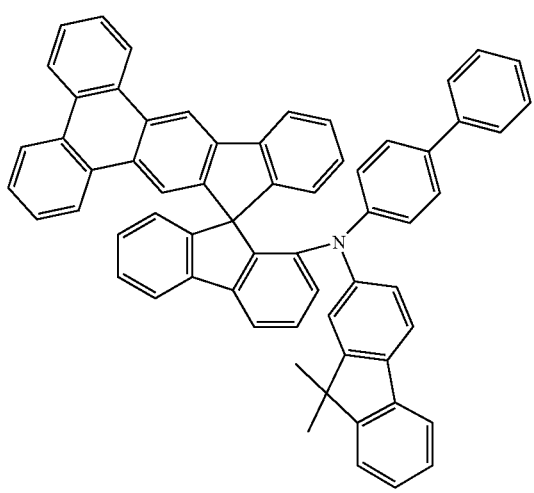 | 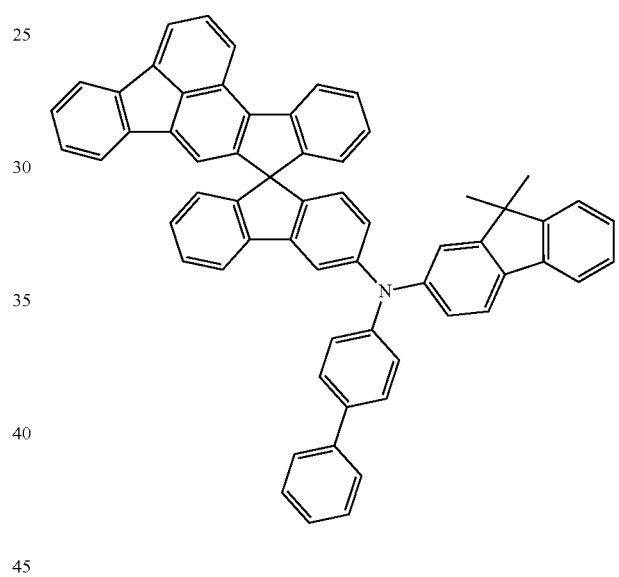 |
| 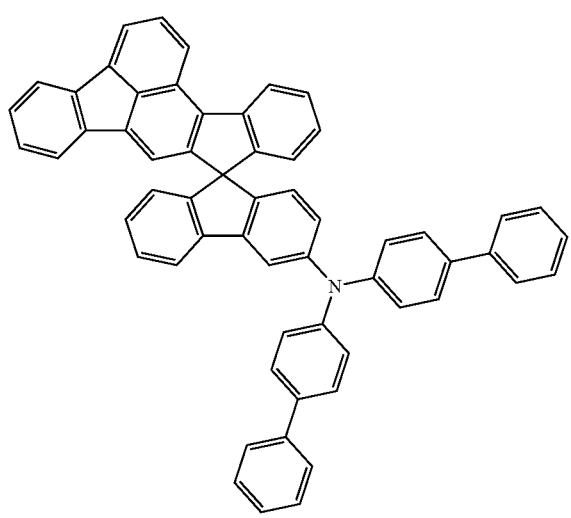 | 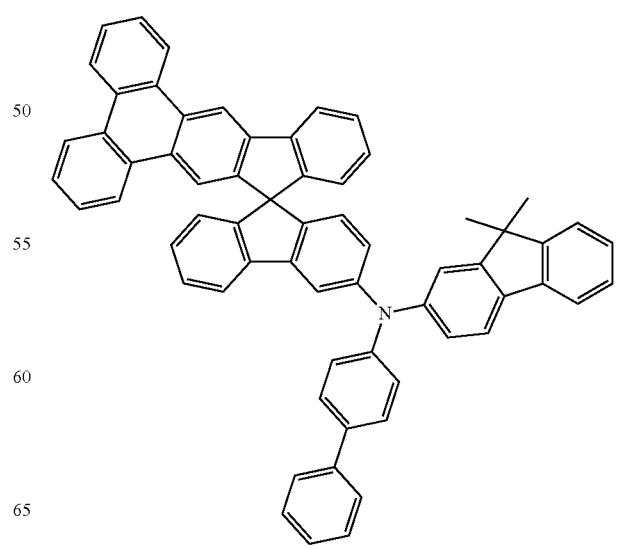 |

461
-continued
462
-continued
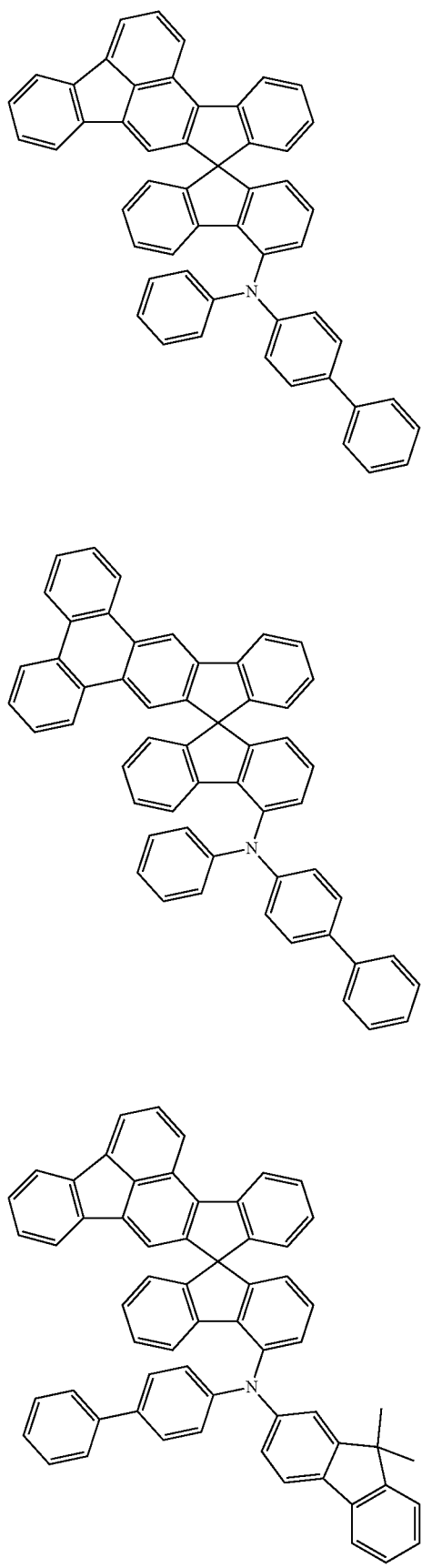
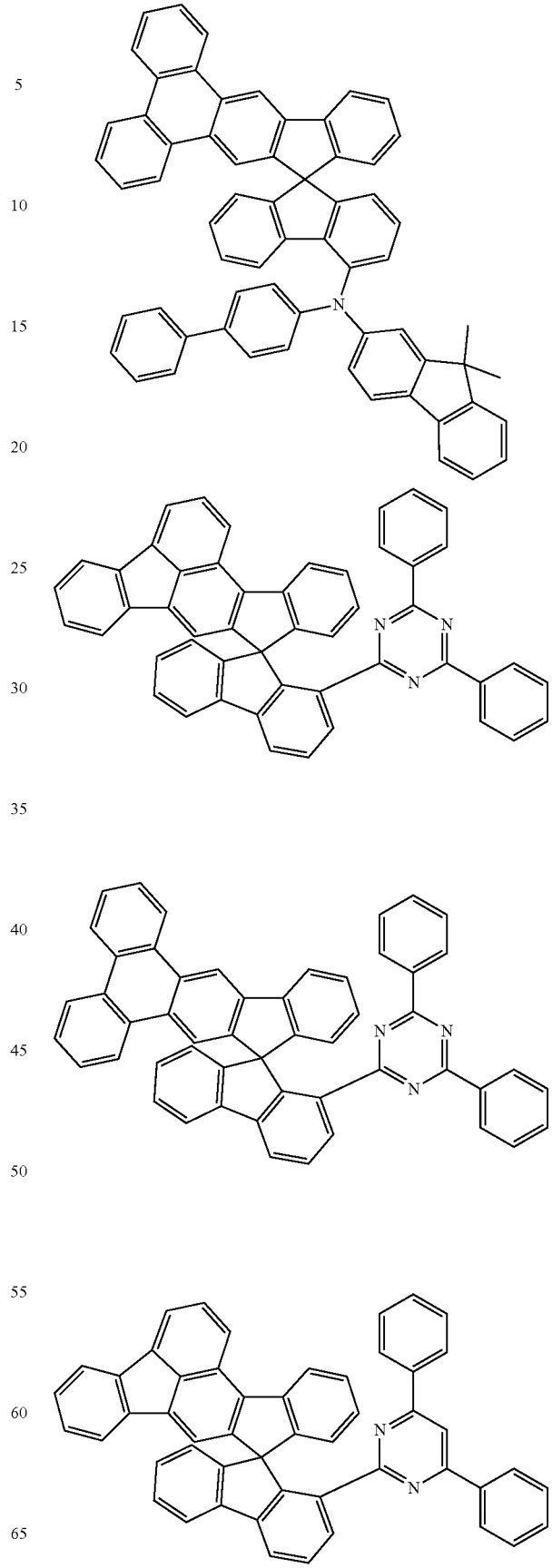

463
-continued
464
-continued
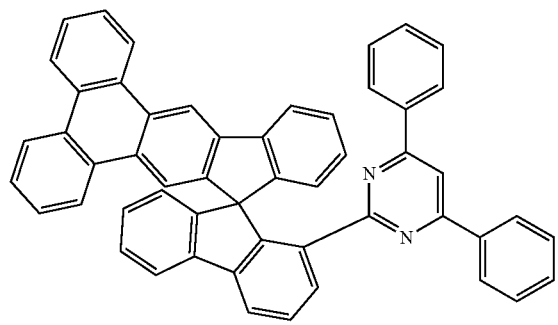
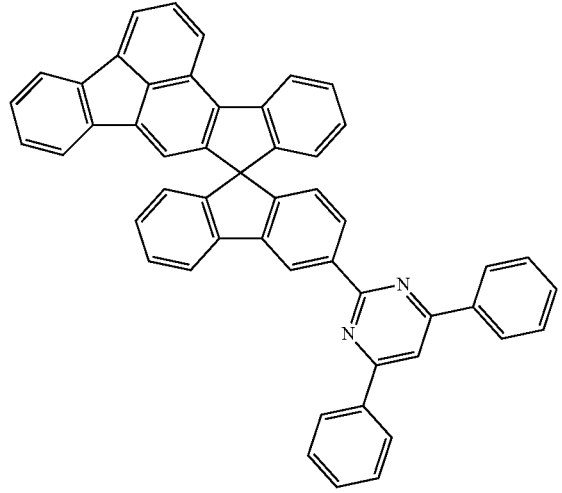
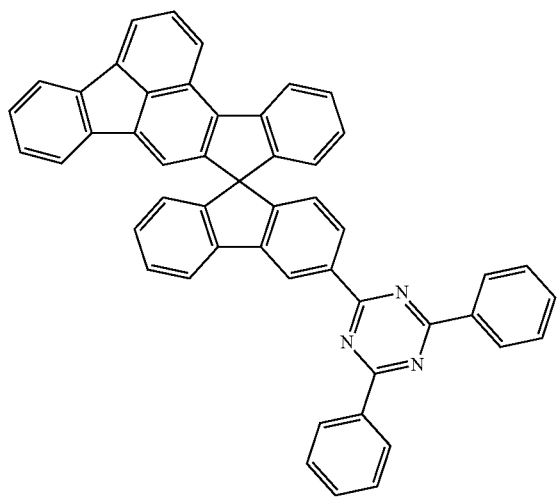
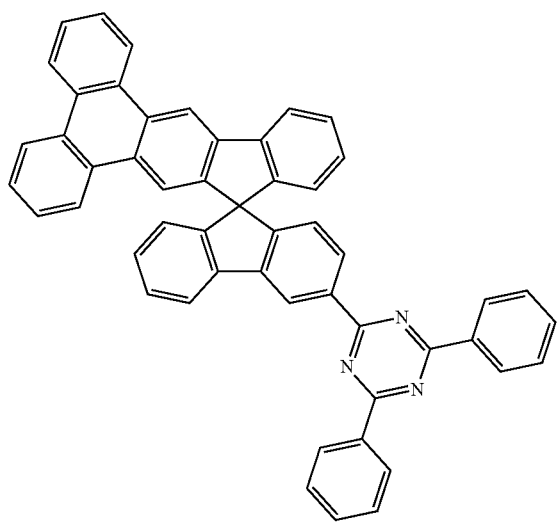
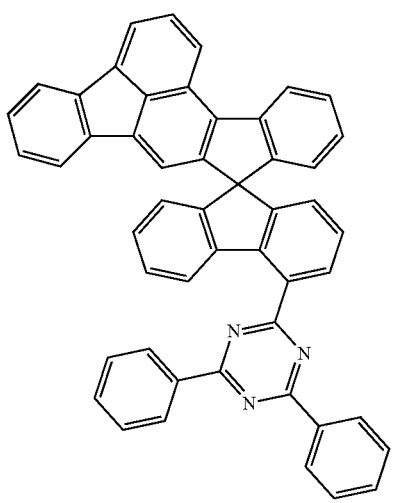

465
-continued
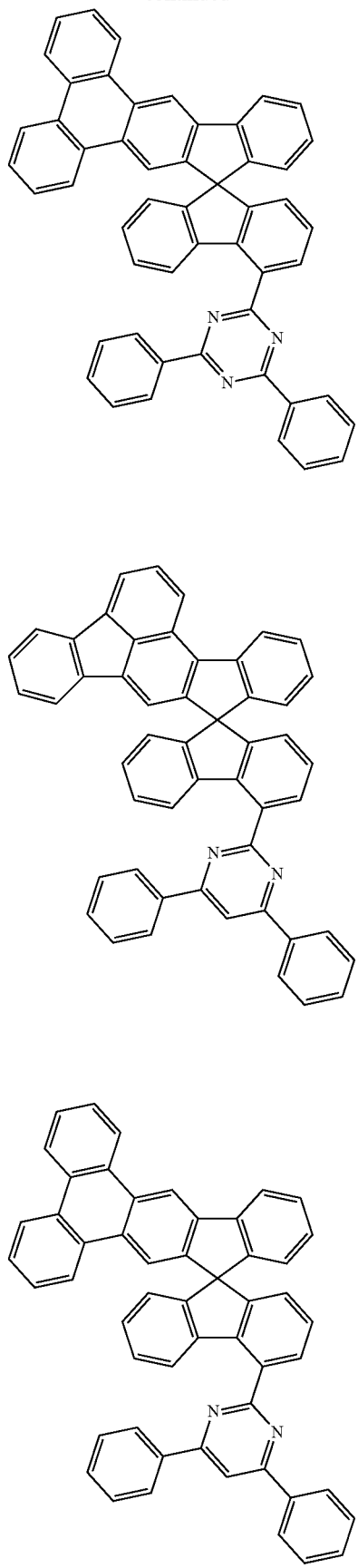
466
-continued
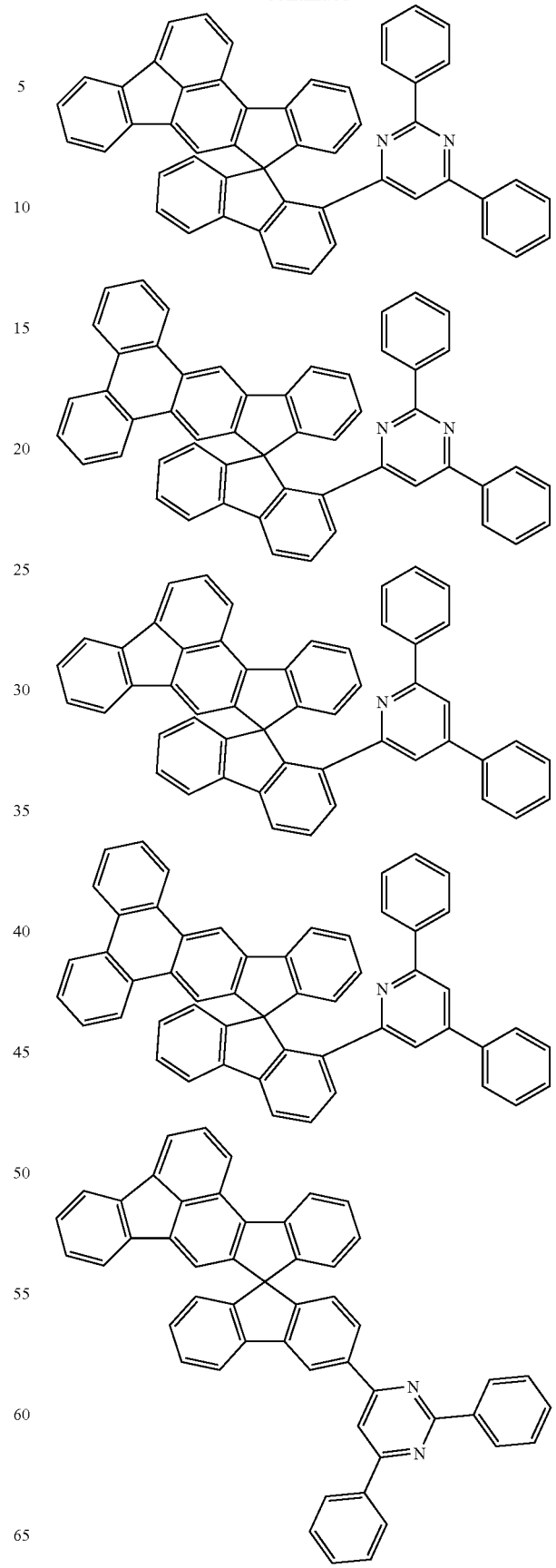

467
-continued
468
-continued
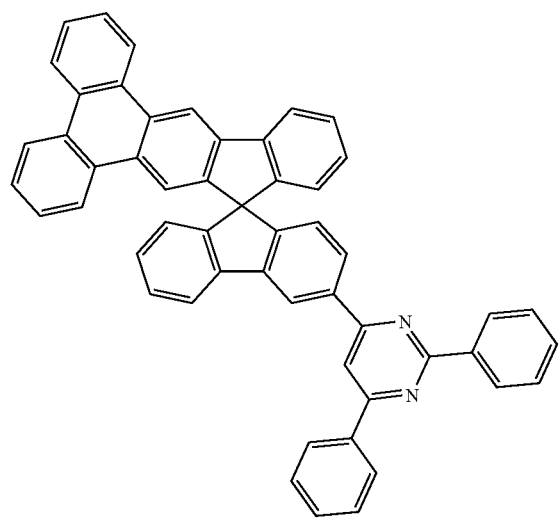
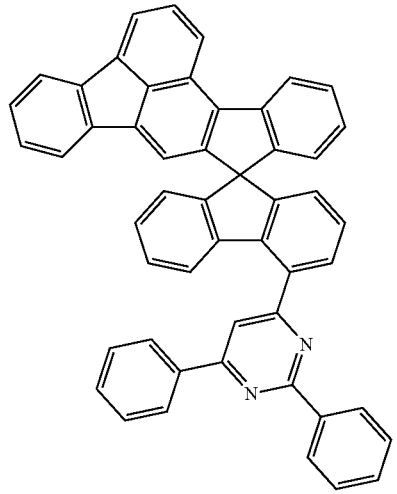
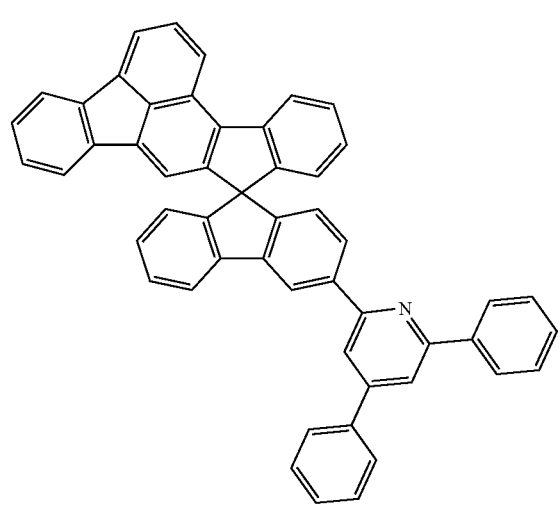
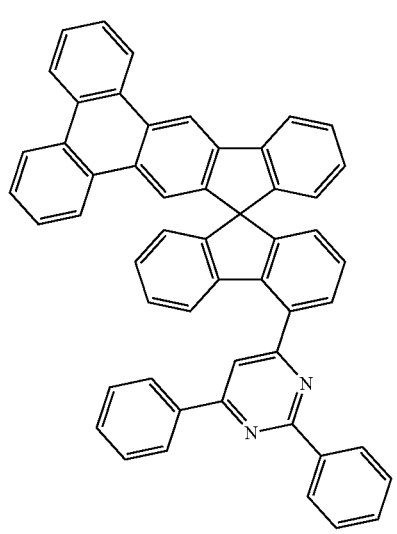
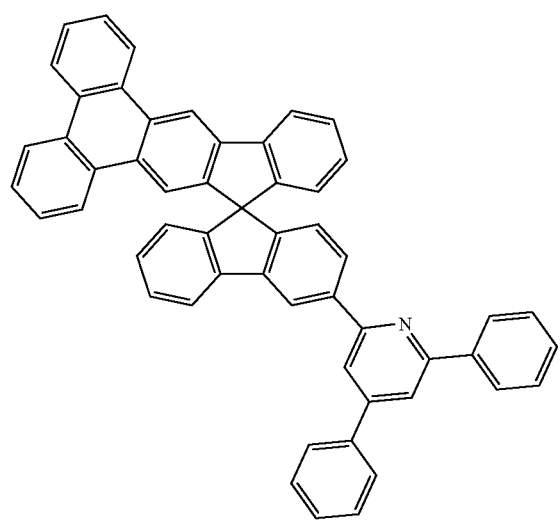
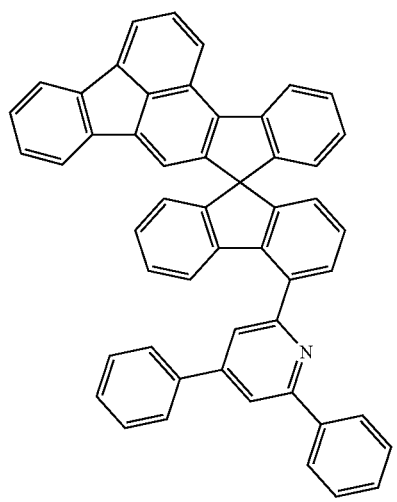

469
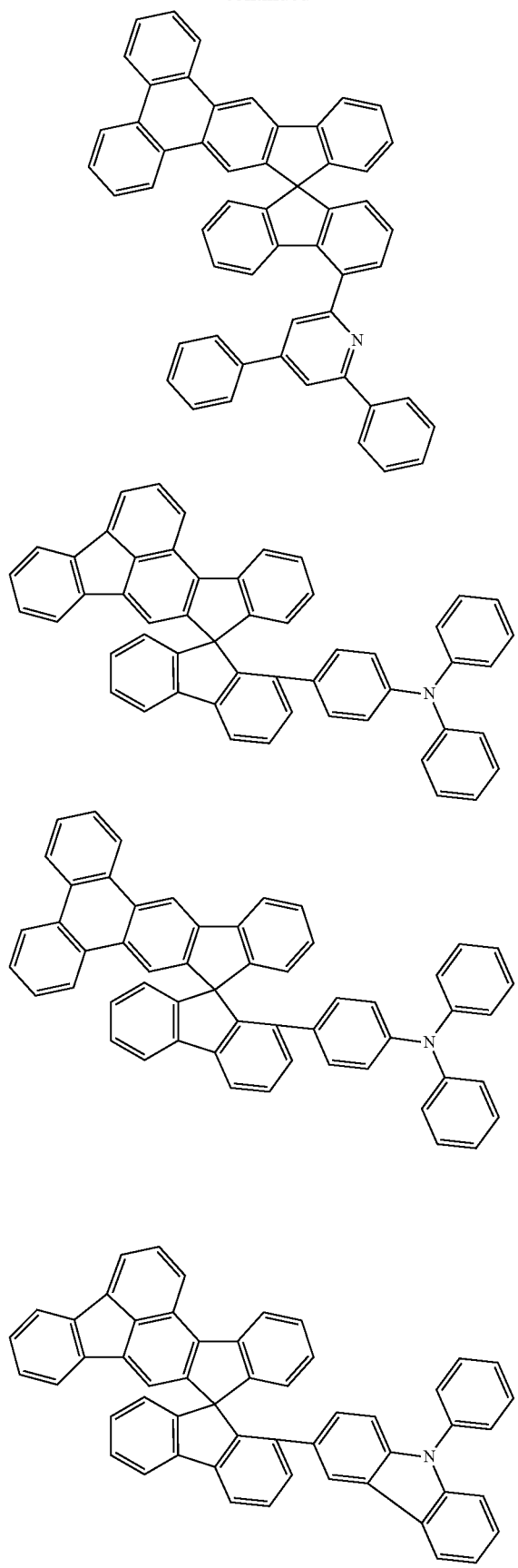
470
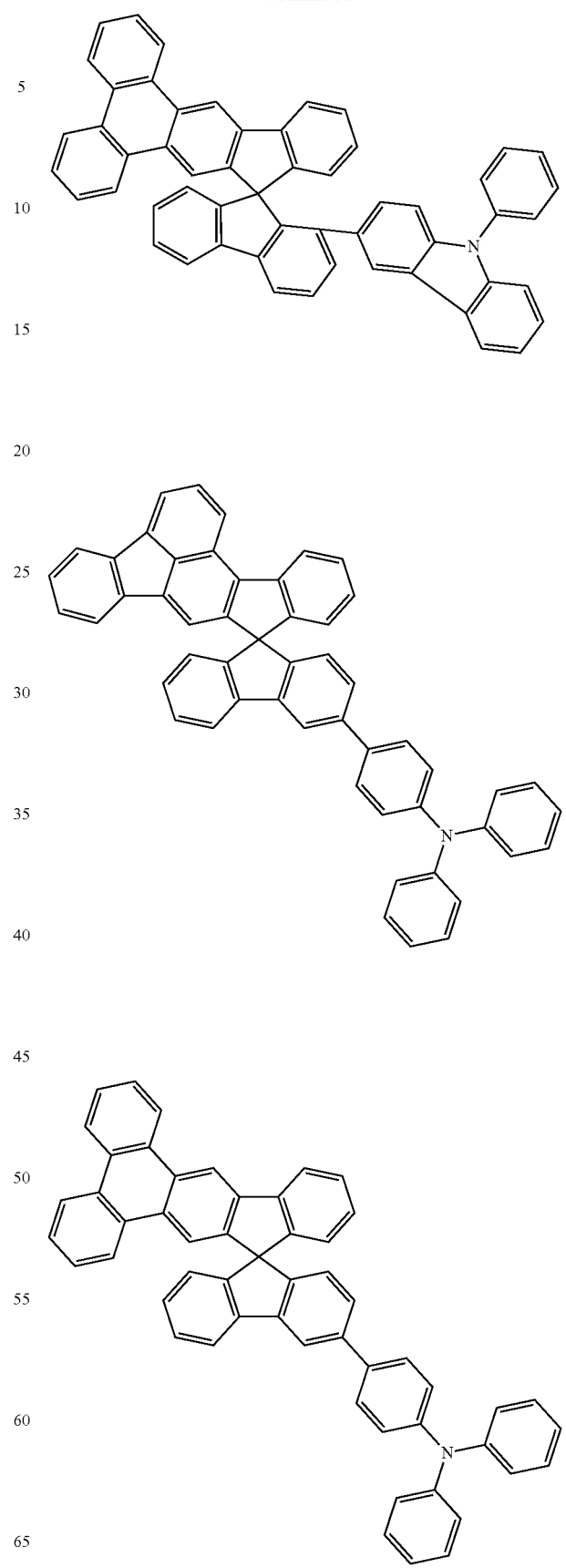

471
-continued
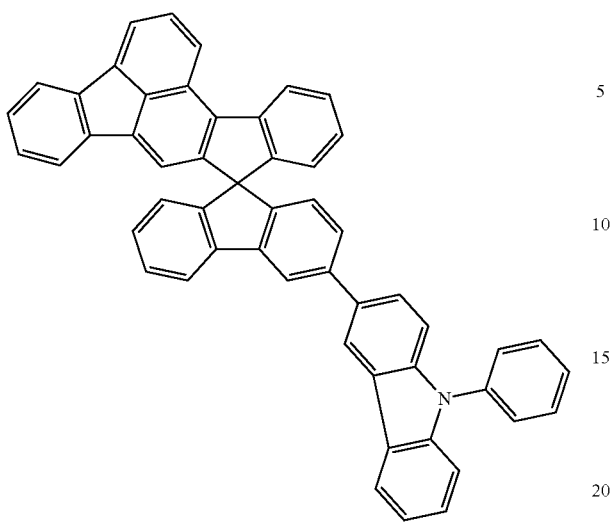
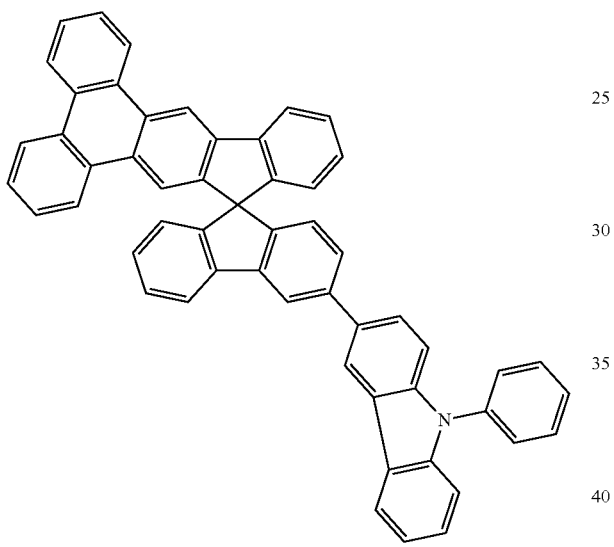
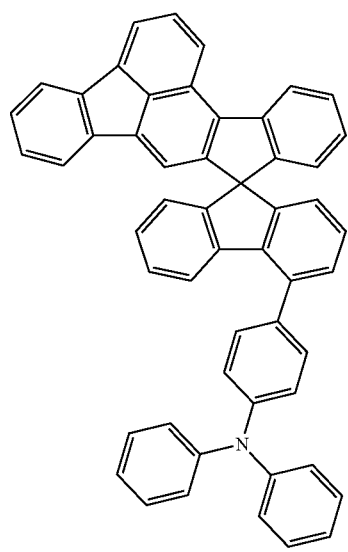
472
-continued
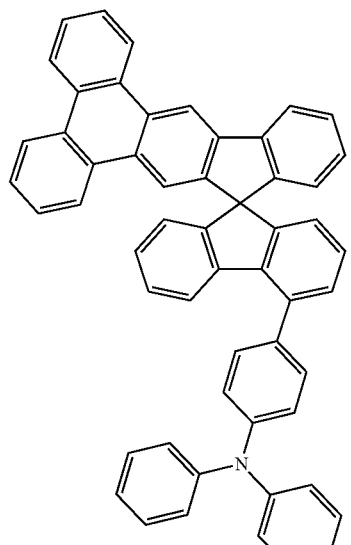
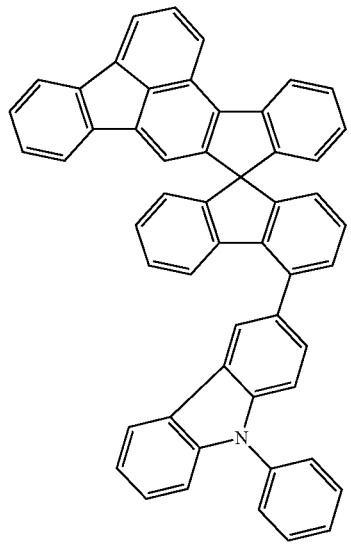
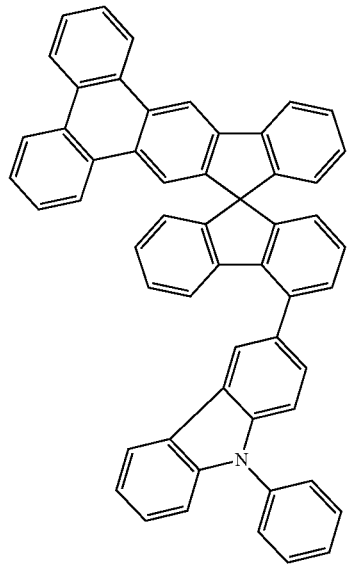

473
-continued
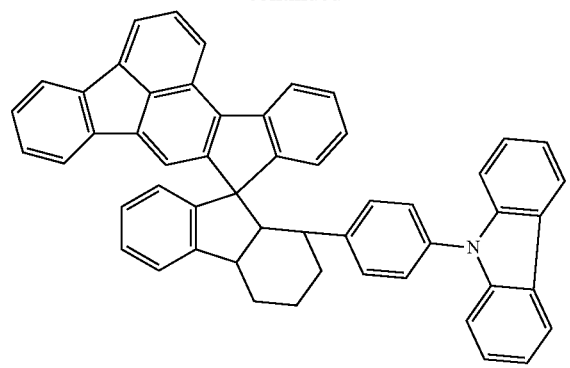
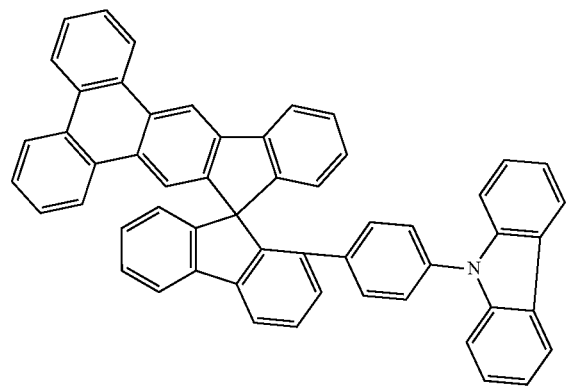
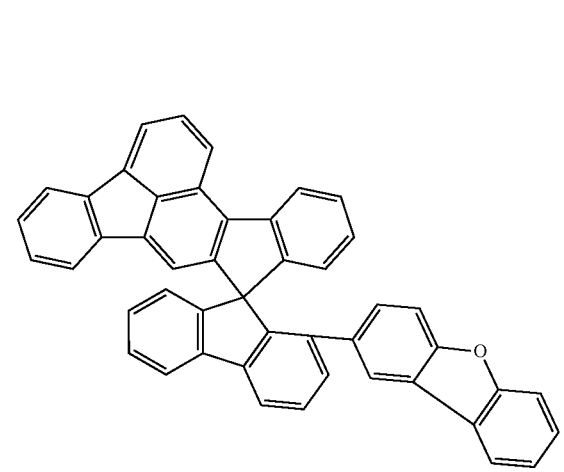
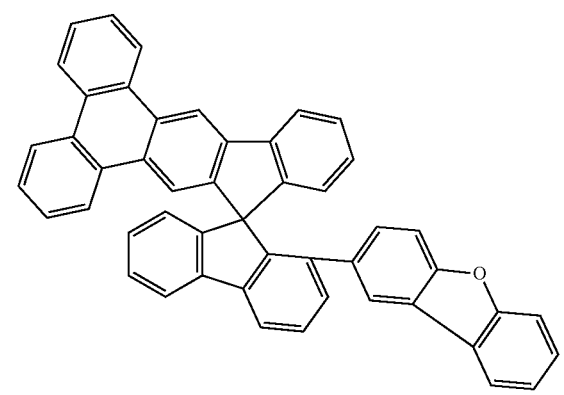
474
-continued
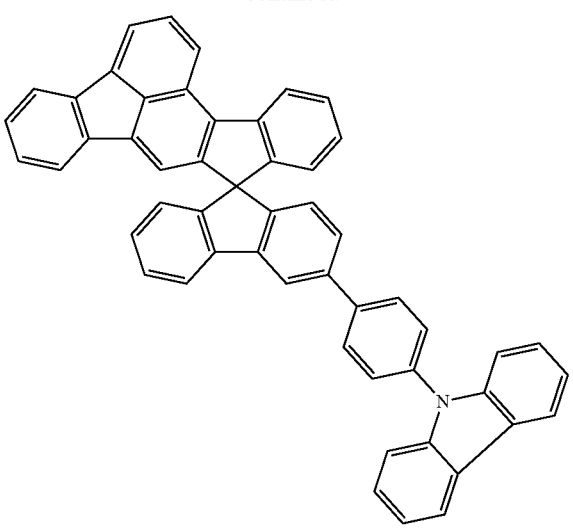
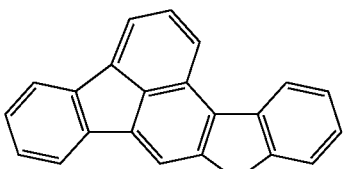
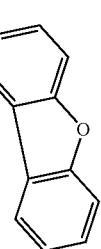

475
-continued
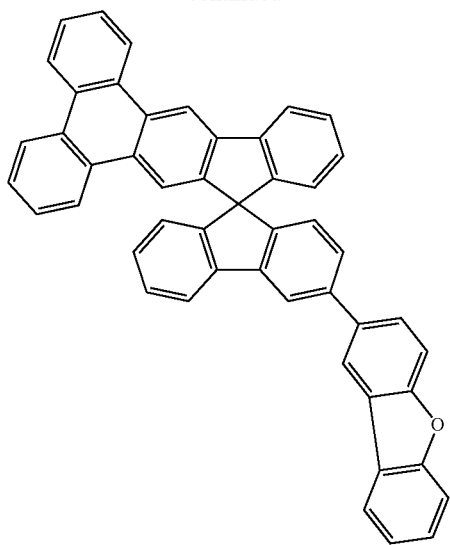
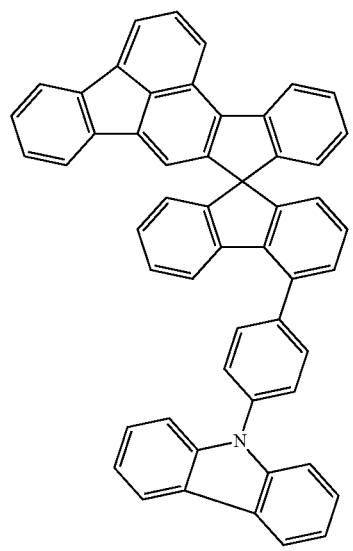
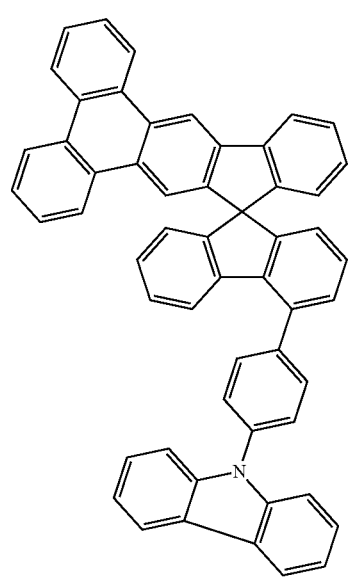
476
-continued
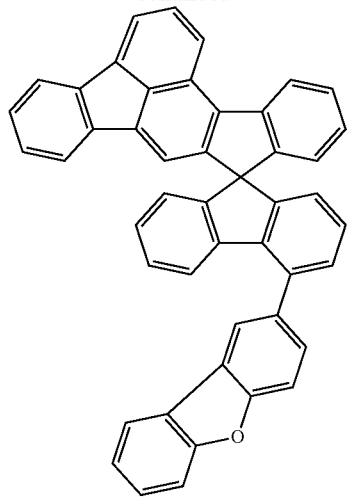
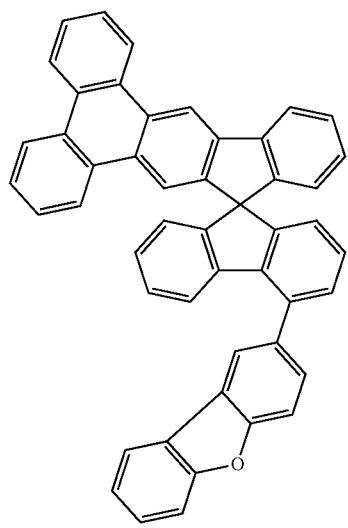
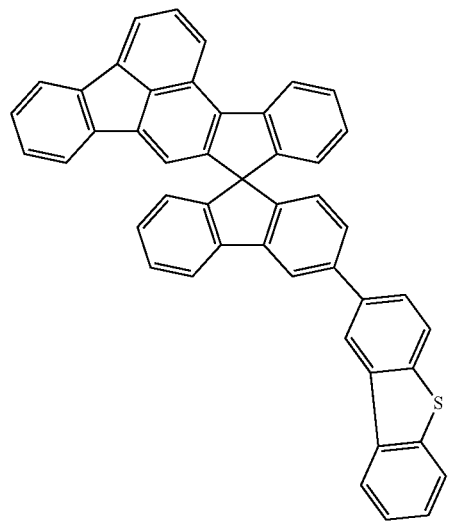

477
-continued
478
-continued
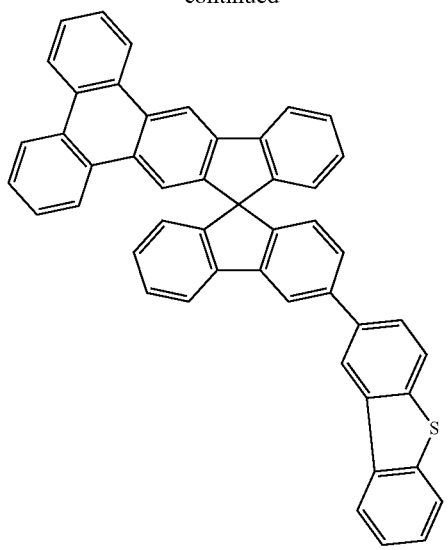
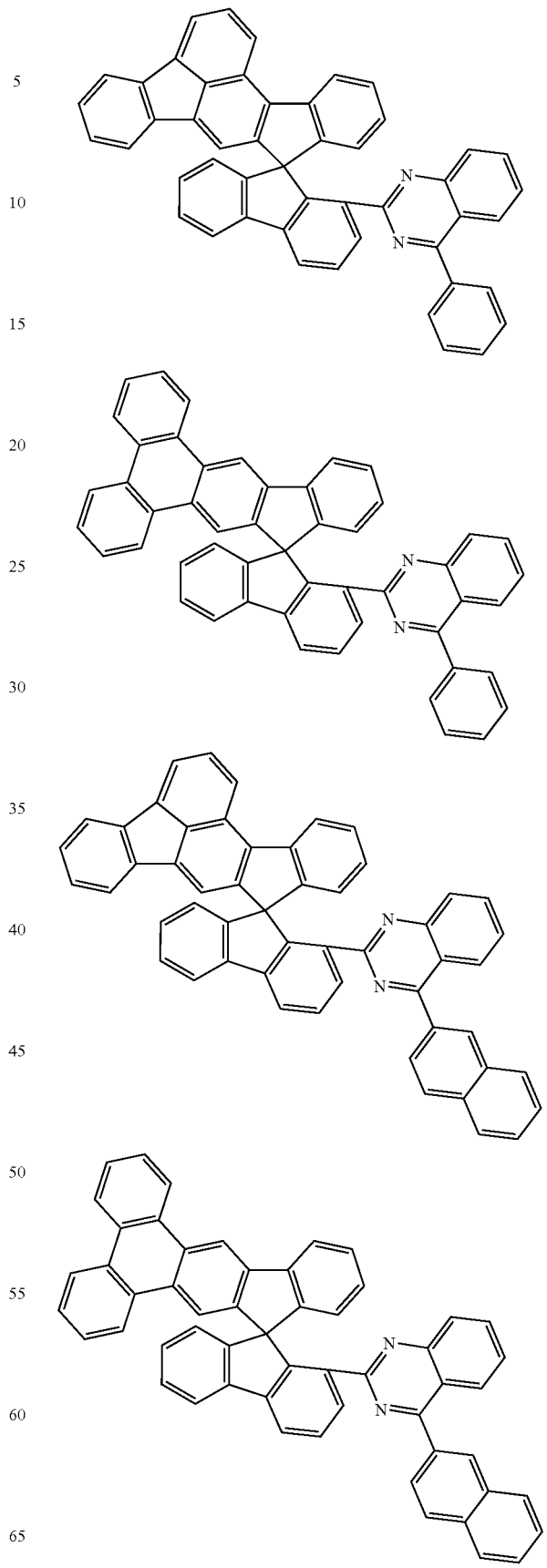

479
-continued
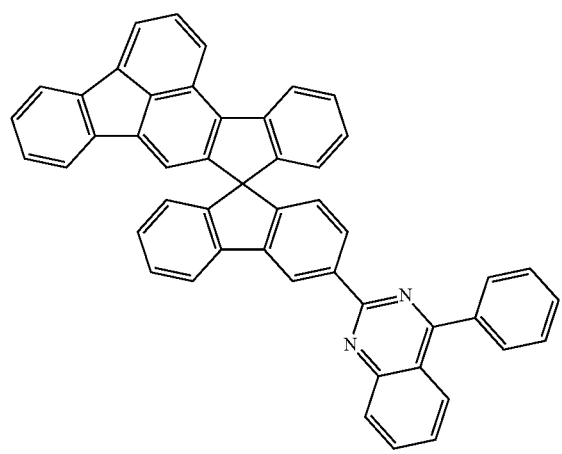
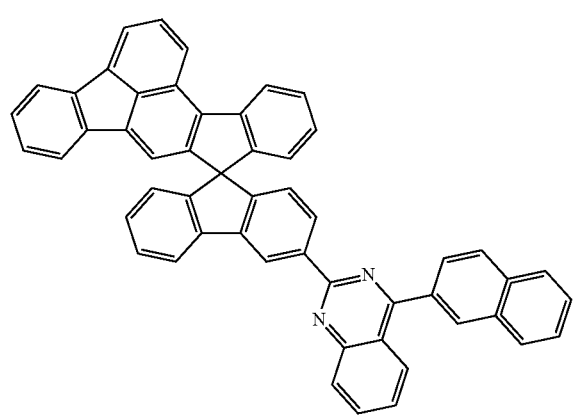
480
-continued
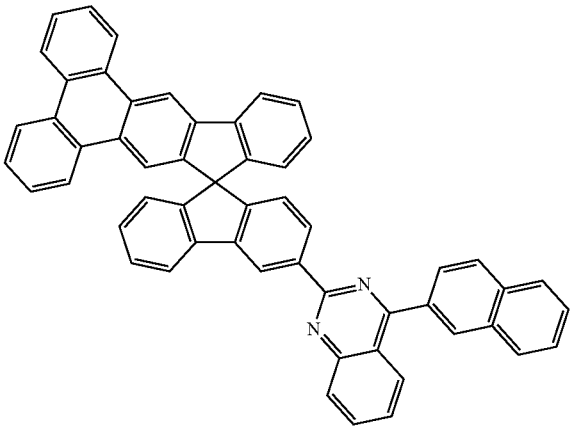
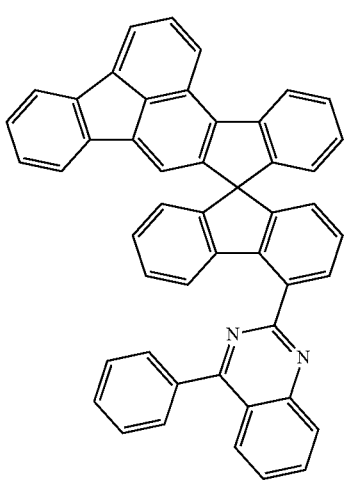
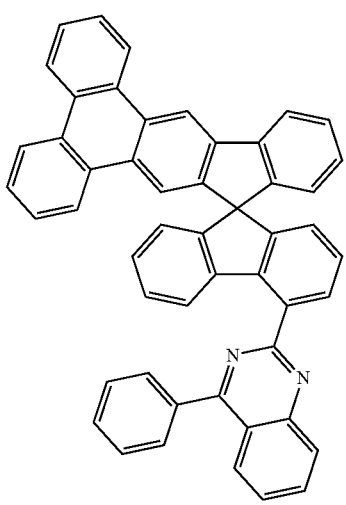

481
-continued
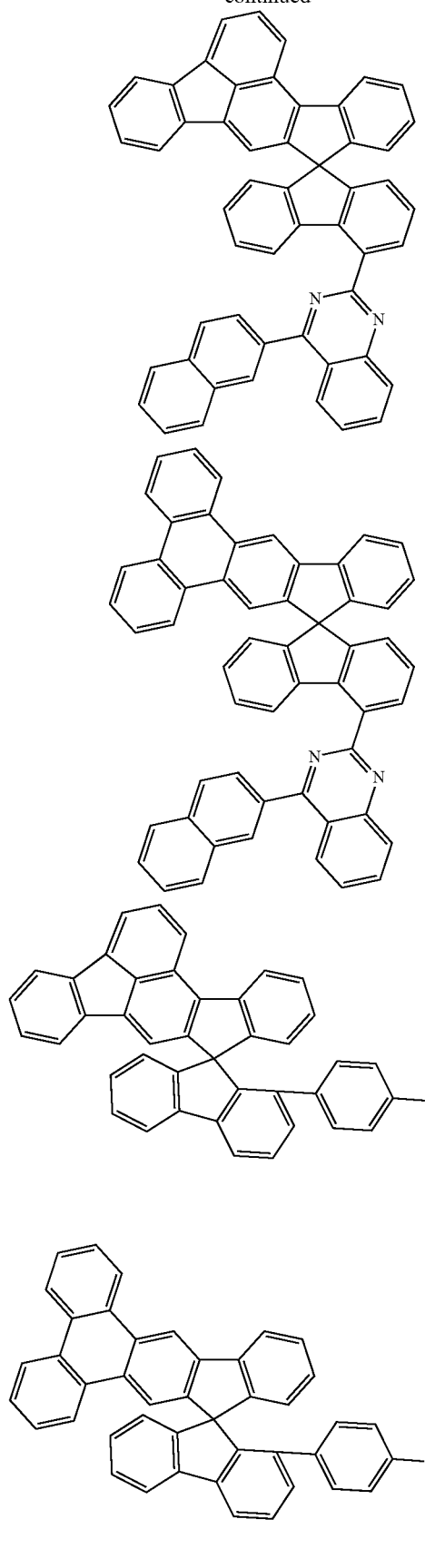
482
-continued
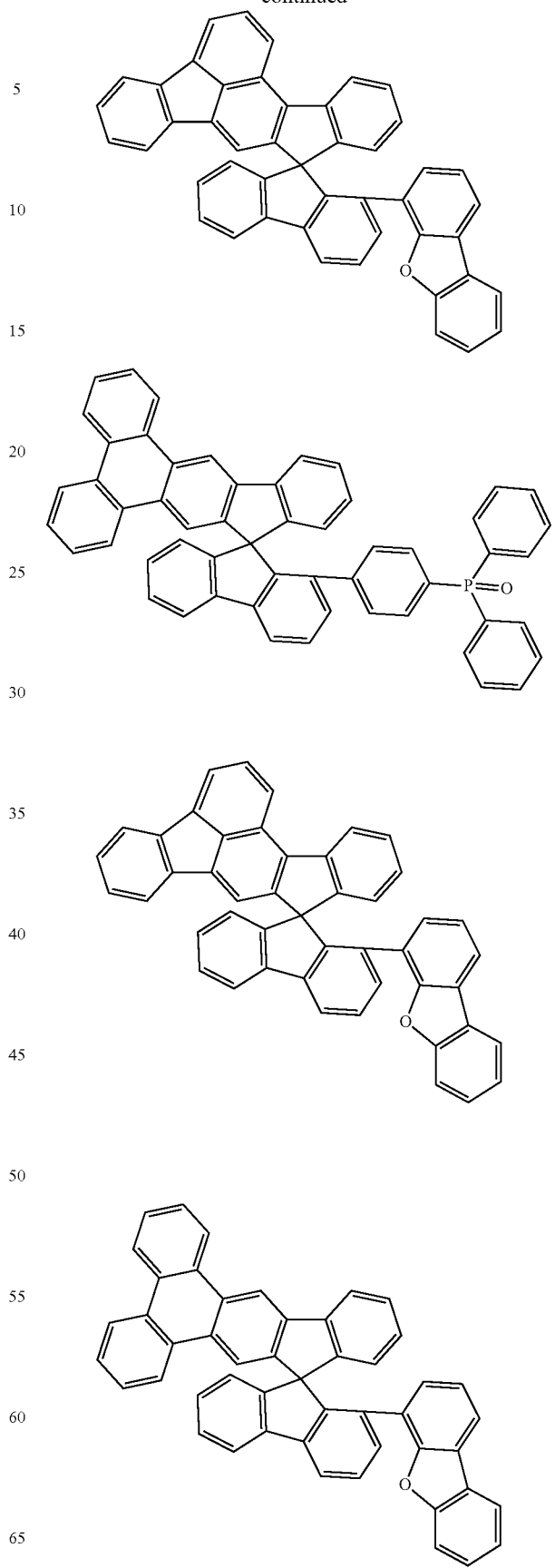

483
-continued
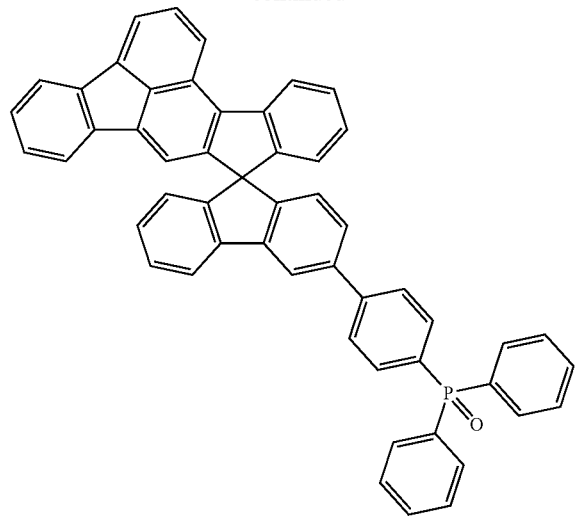
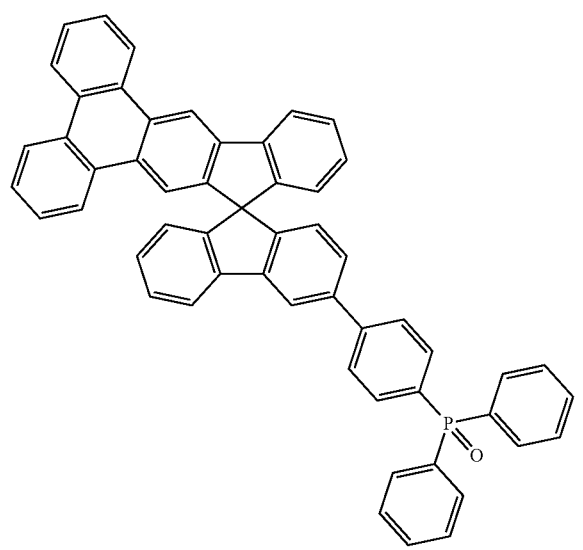
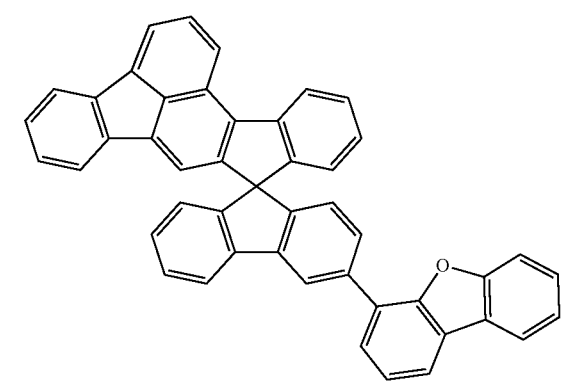
484
-continued
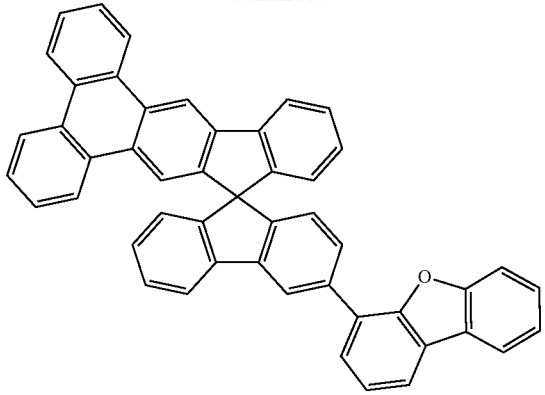
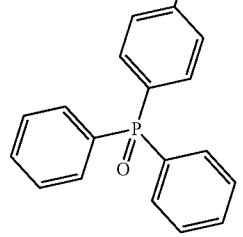
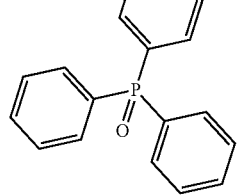

485
-continued
486
-continued
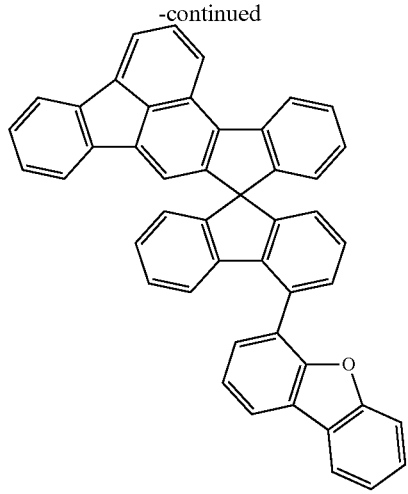
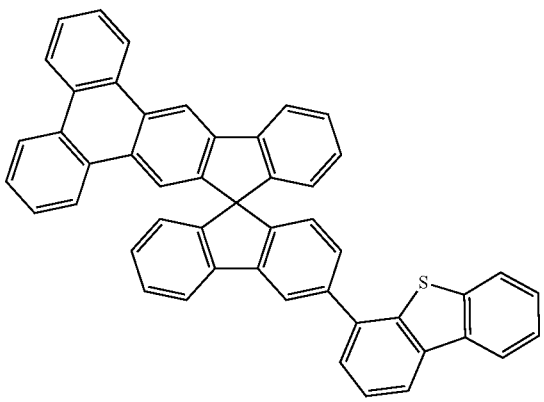
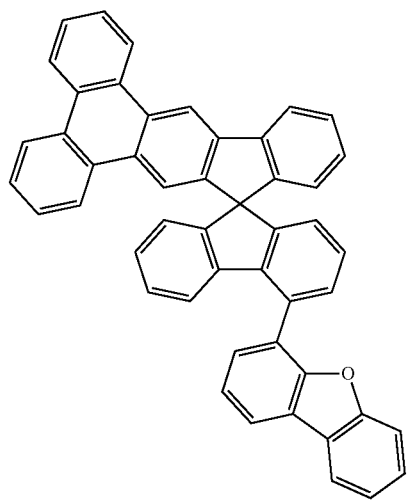
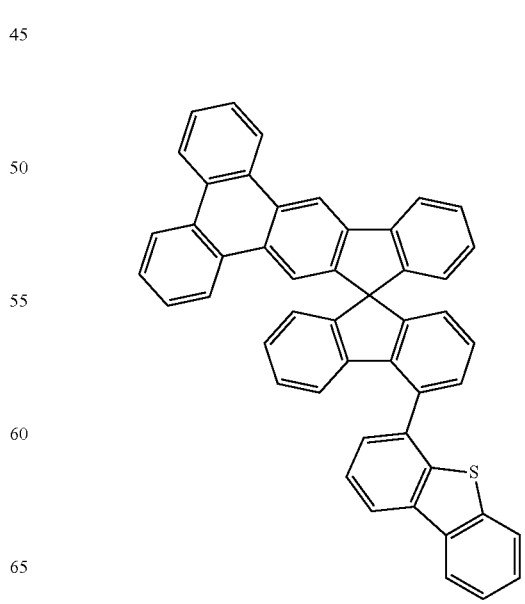
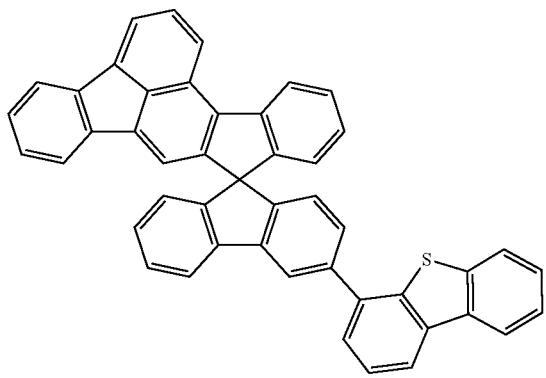

487
-continued
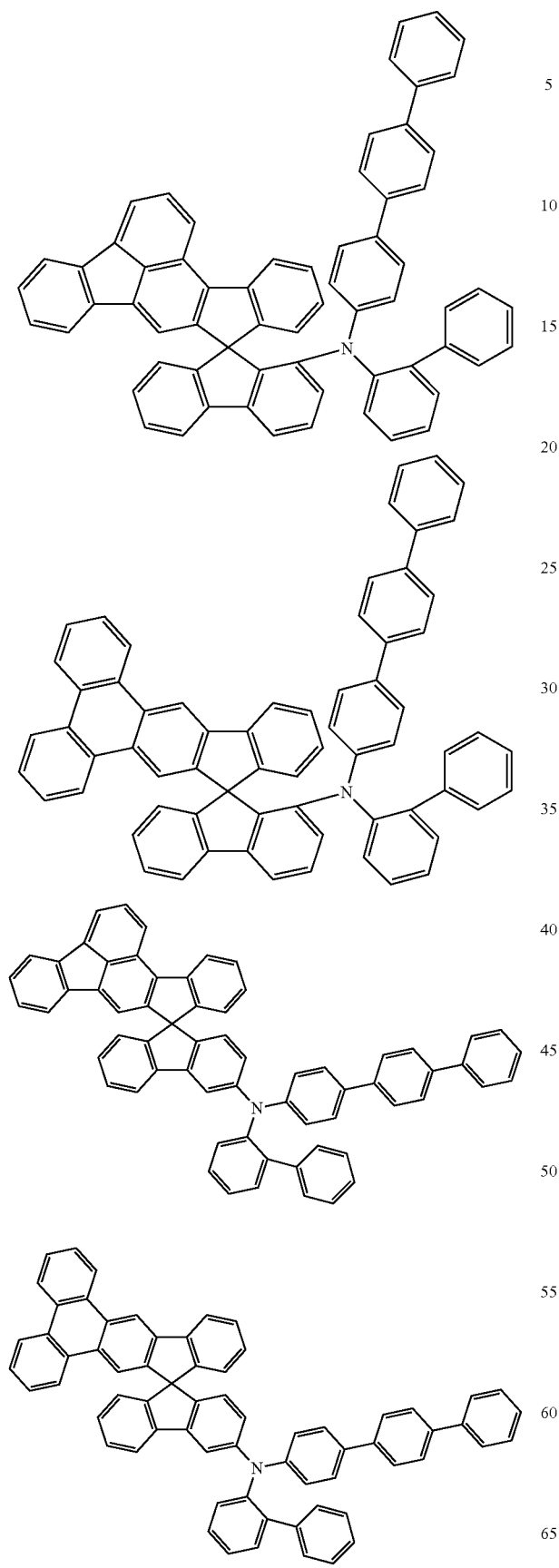
488
-continued
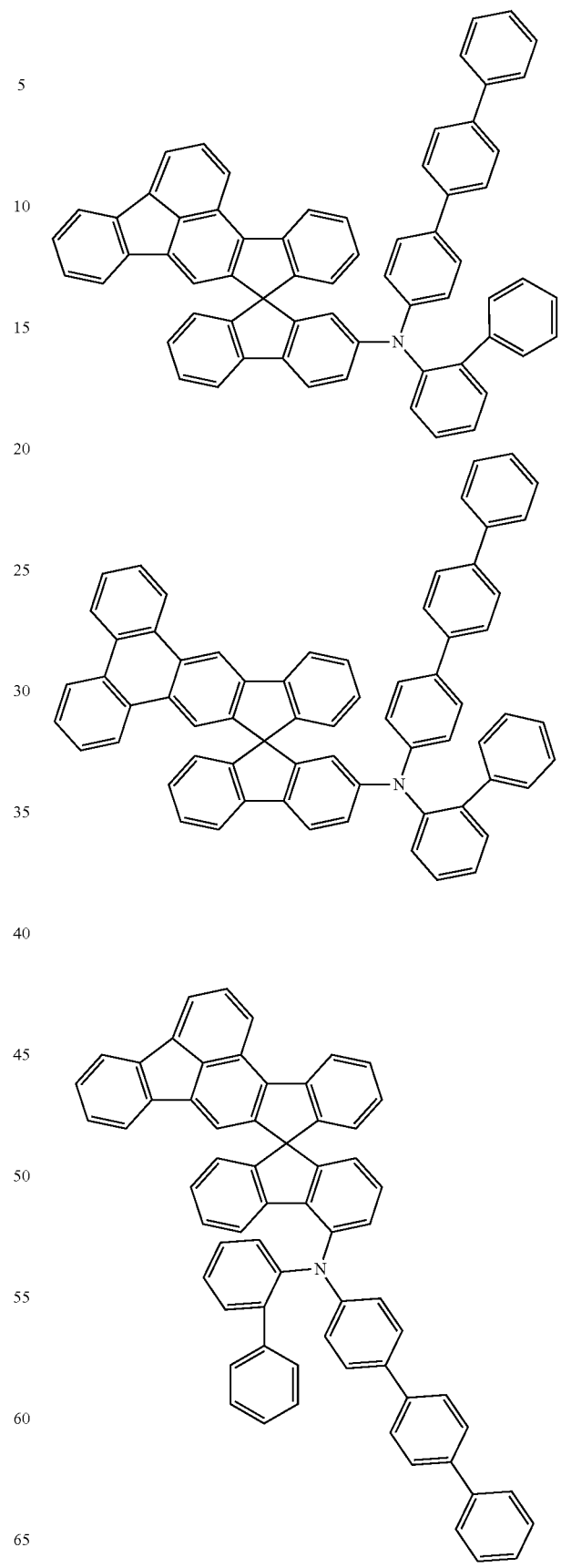

489
-continued
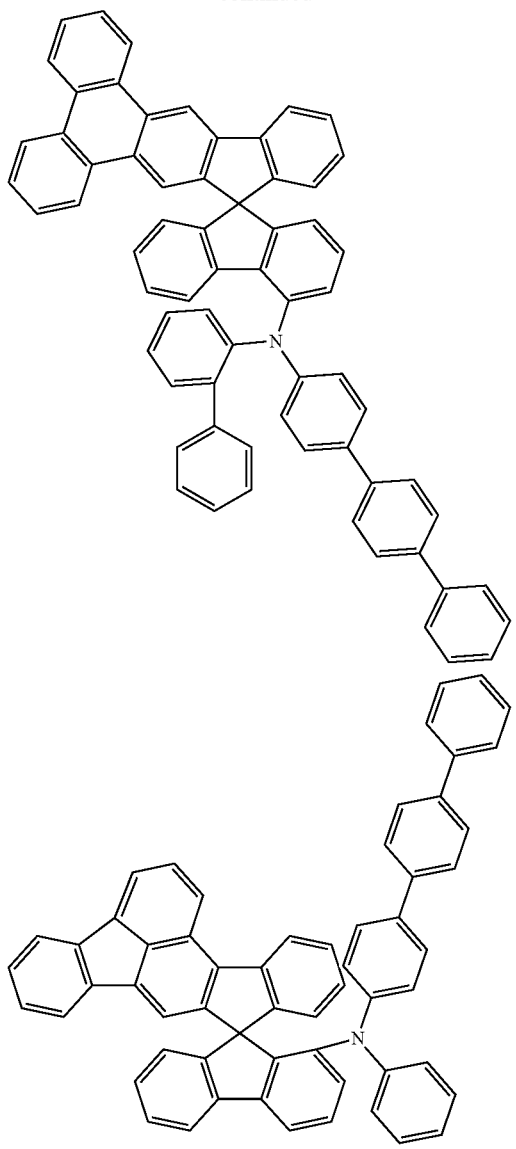
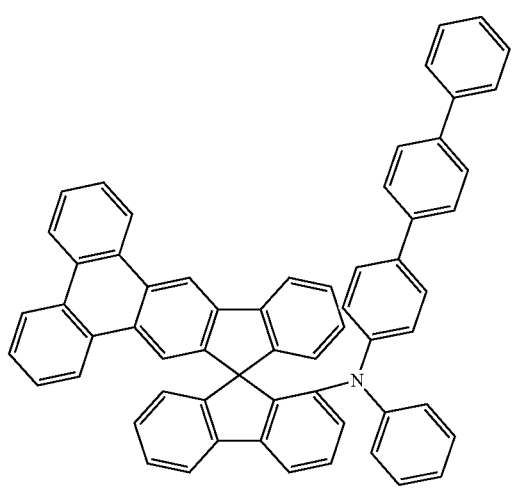
490
-continued
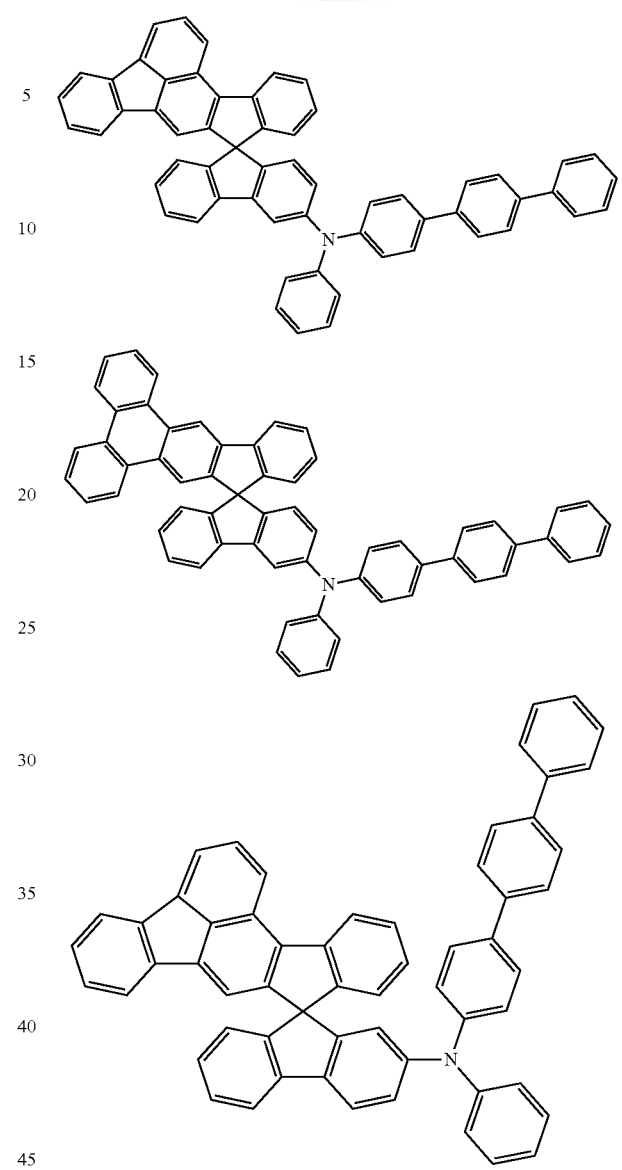

491
-continued
492
-continued
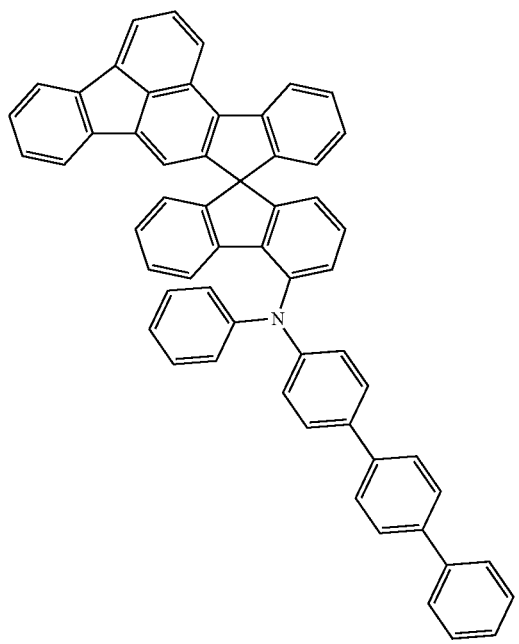
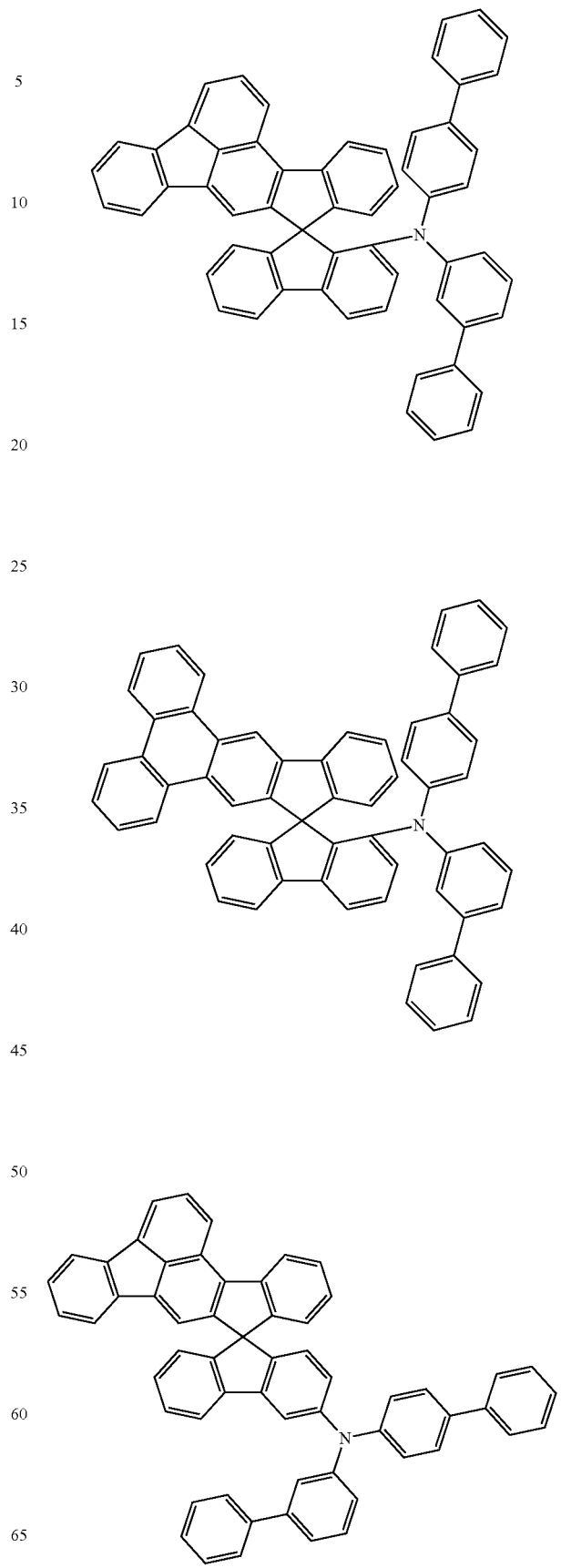

493
-continued
494
-continued
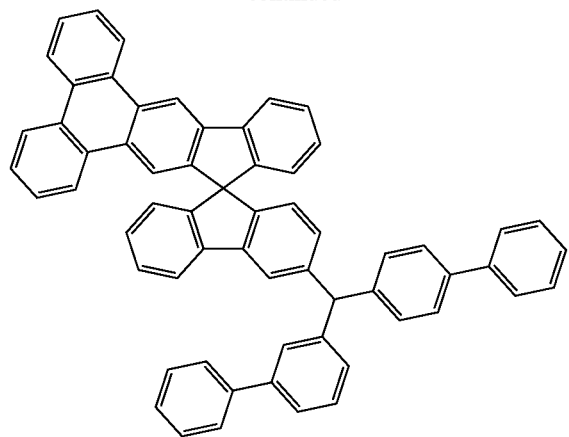
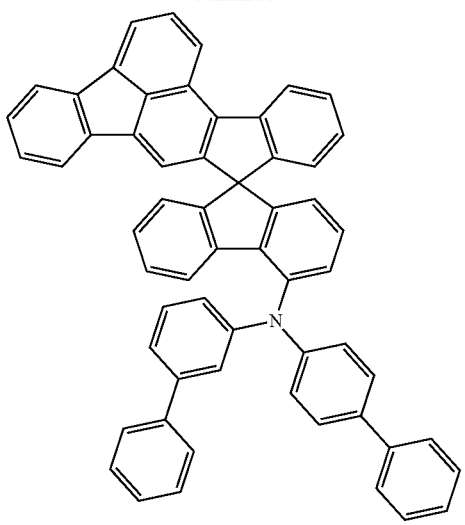
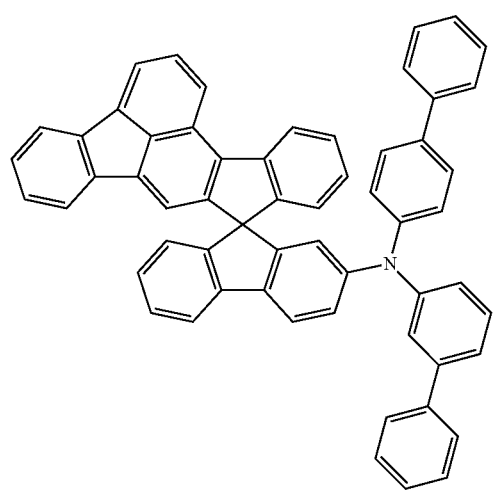
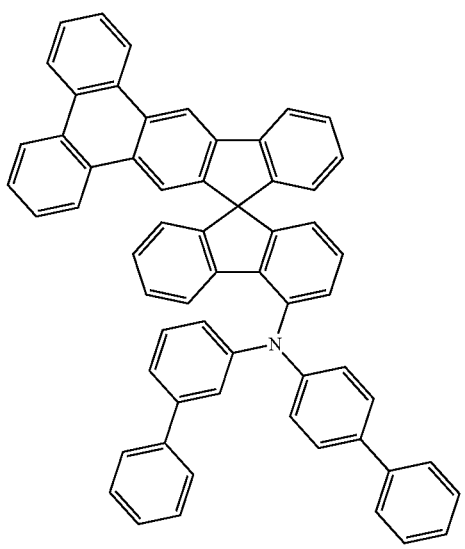
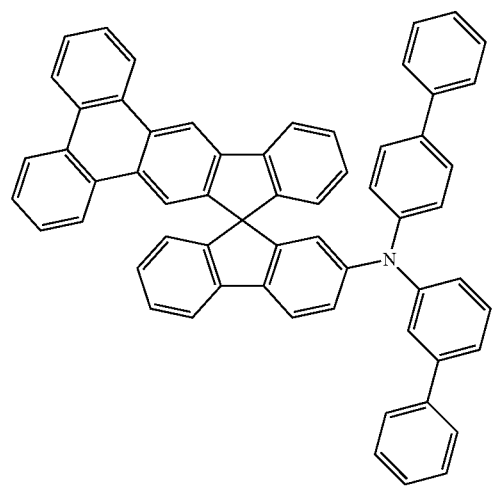
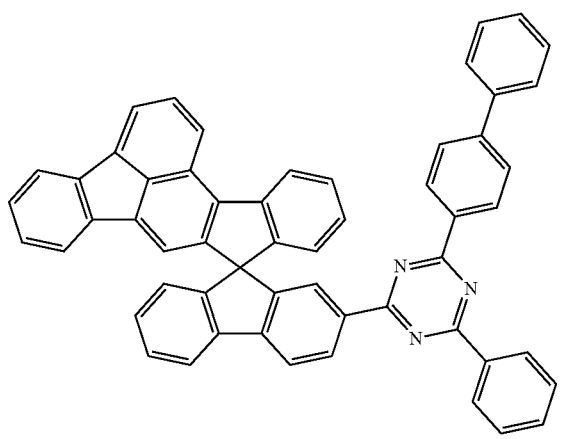

495
-continued
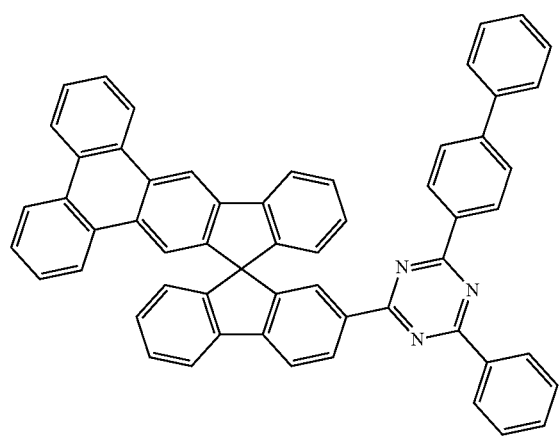
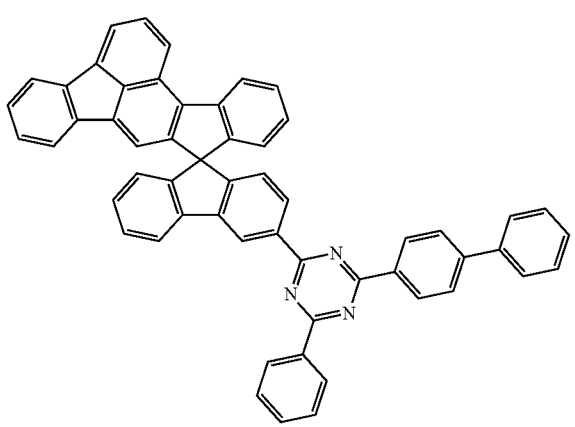
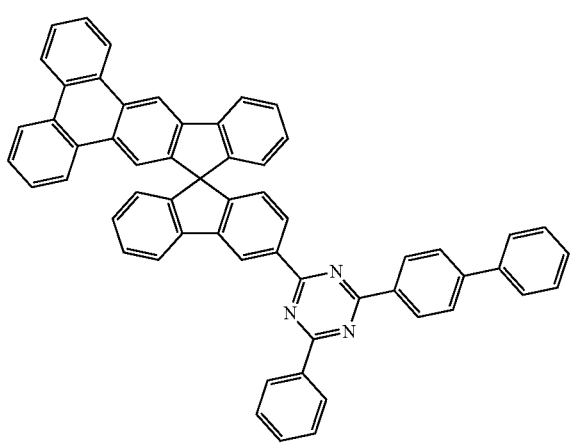
496
-continued
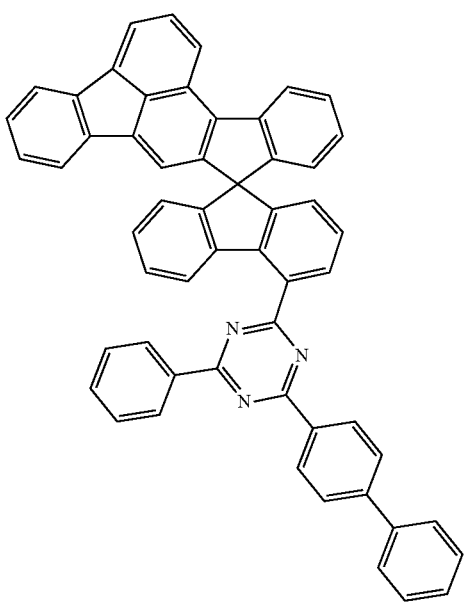
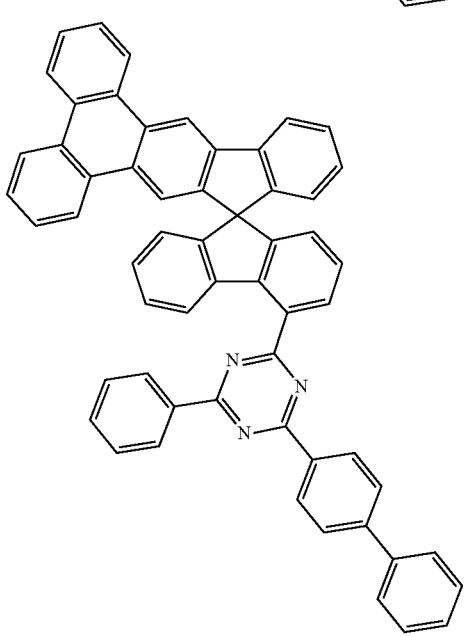
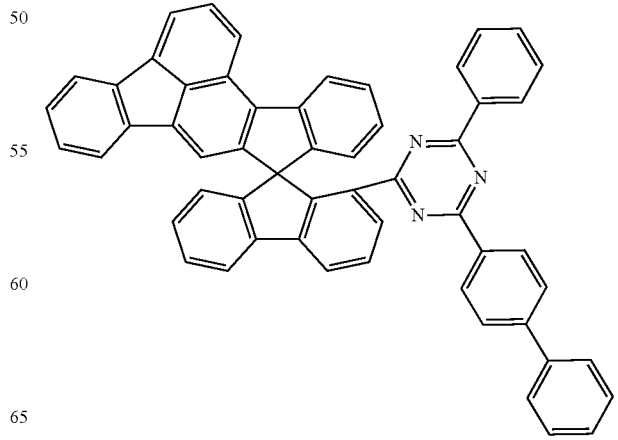

497
-continued
498
-continued
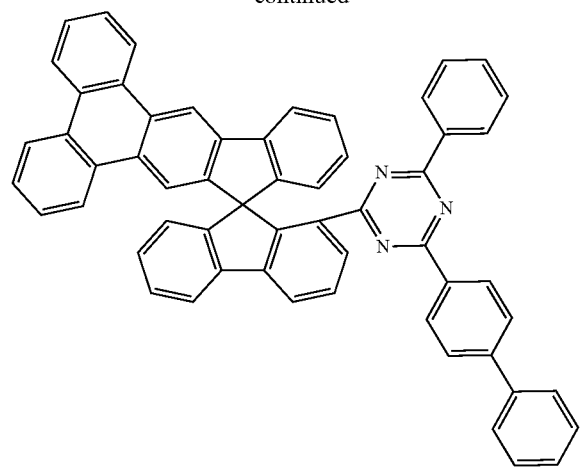
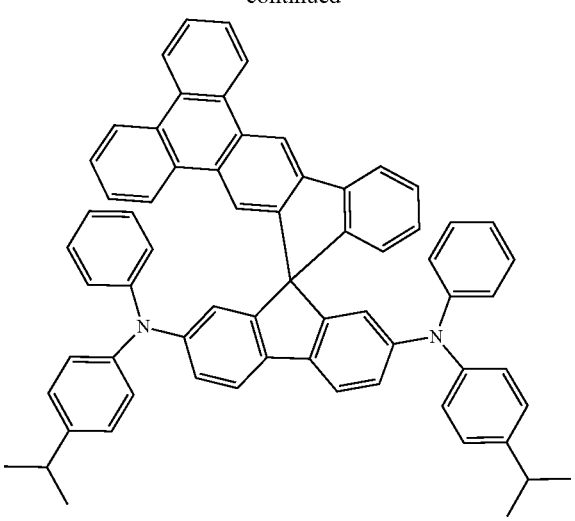
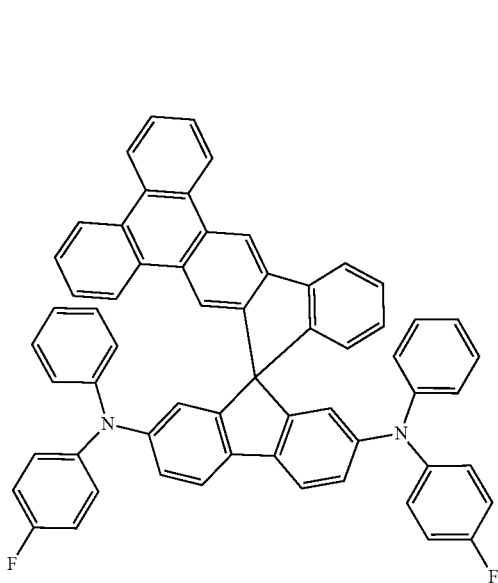

499
-continued
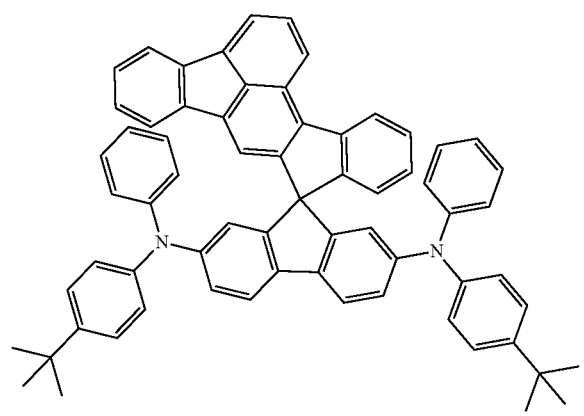
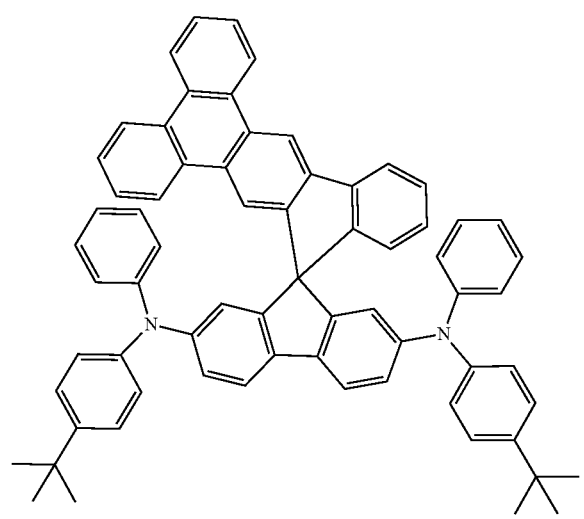
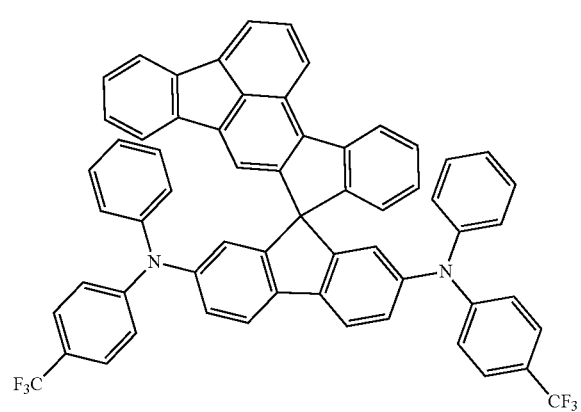
500
-continued
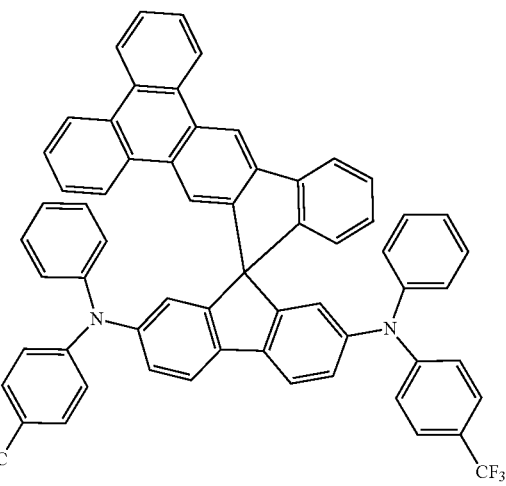
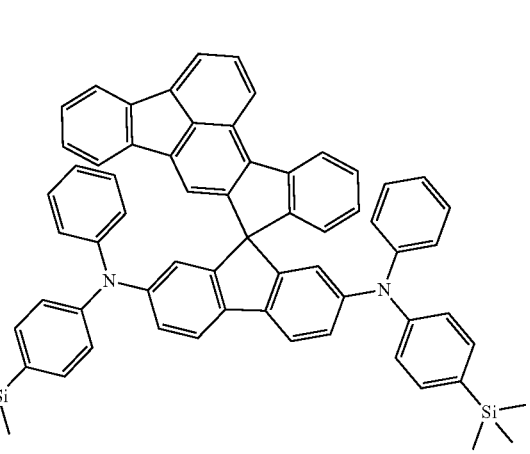
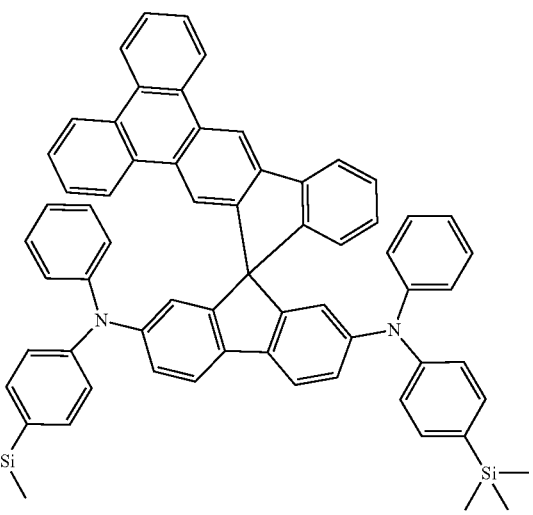

501
-continued
502
-continued
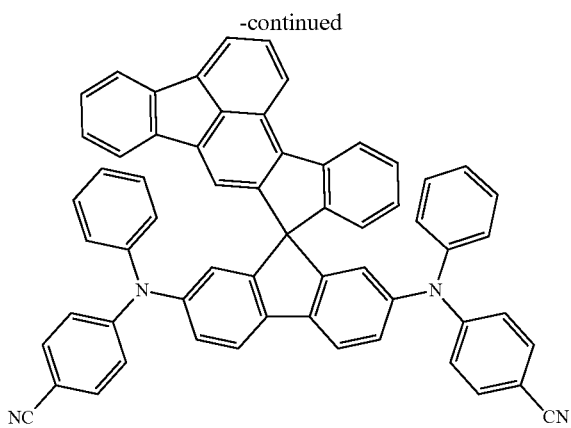
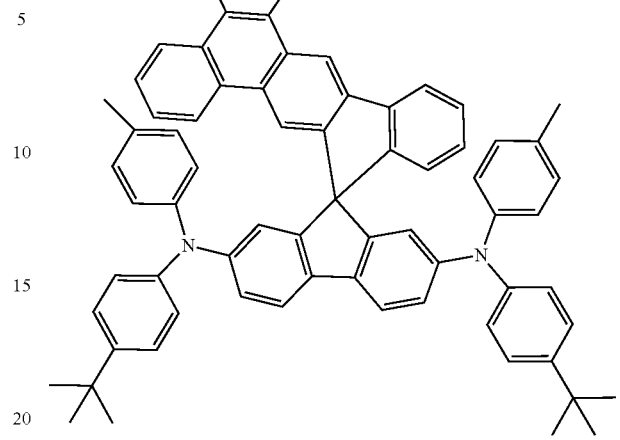
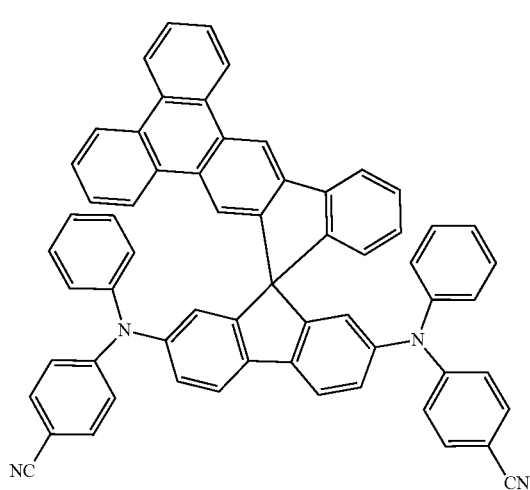
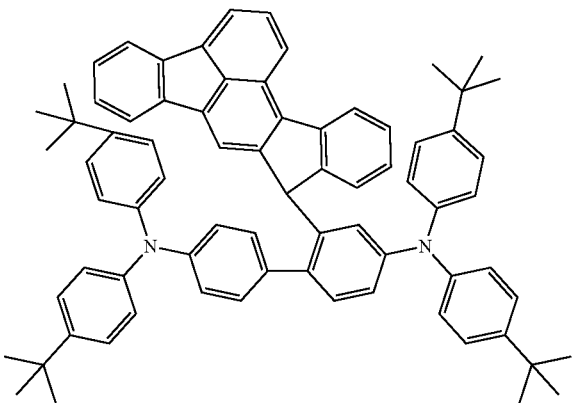
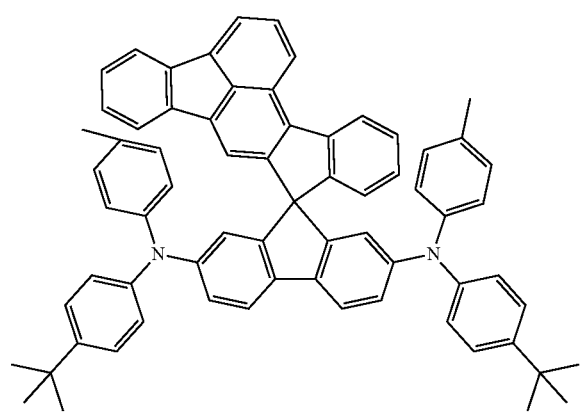
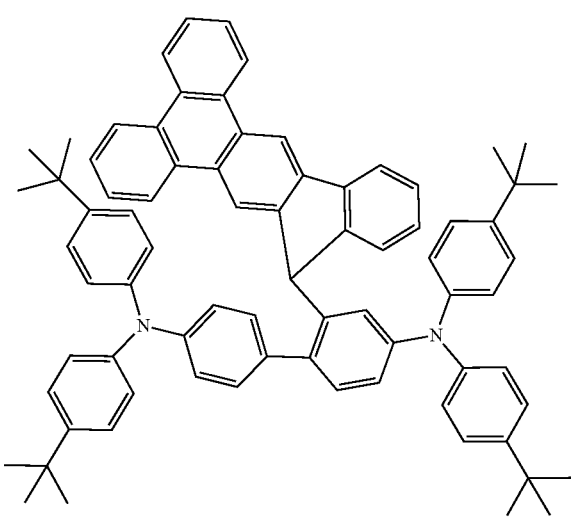

503
-continued
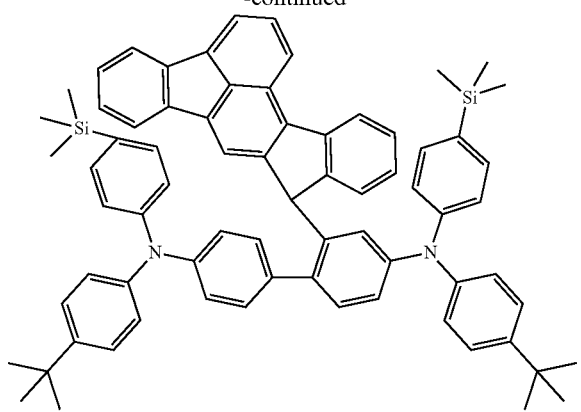
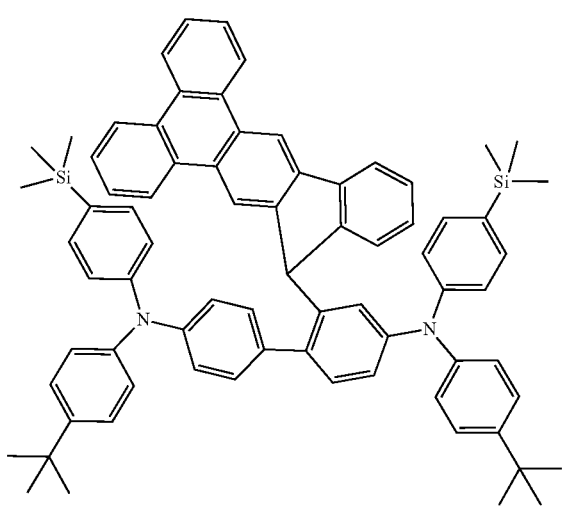
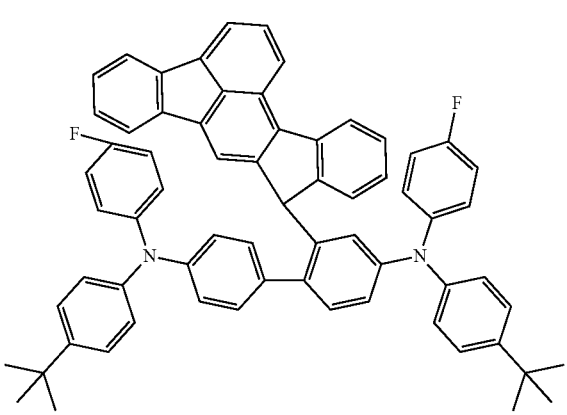
504
-continued
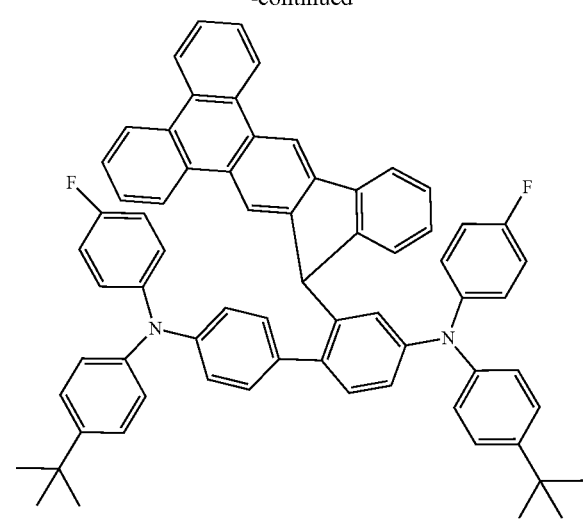
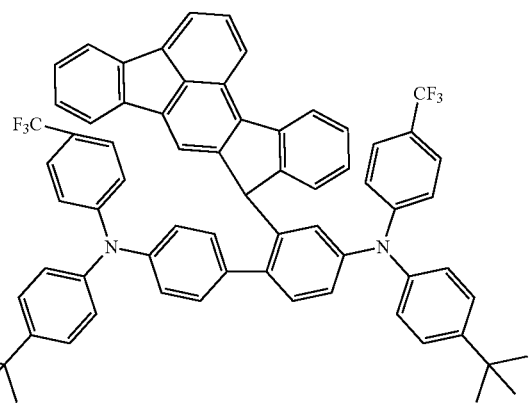
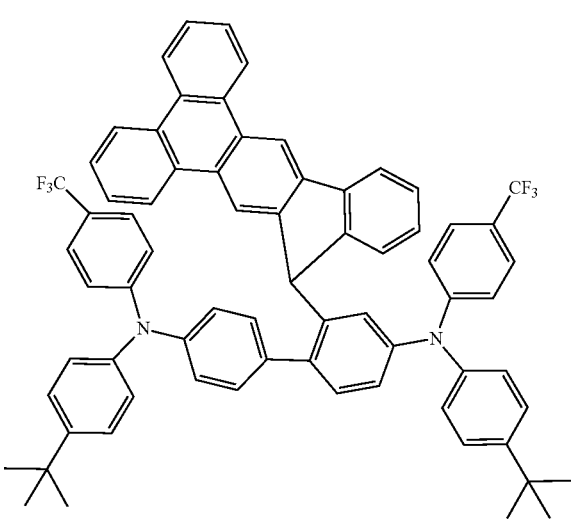

505
-continued
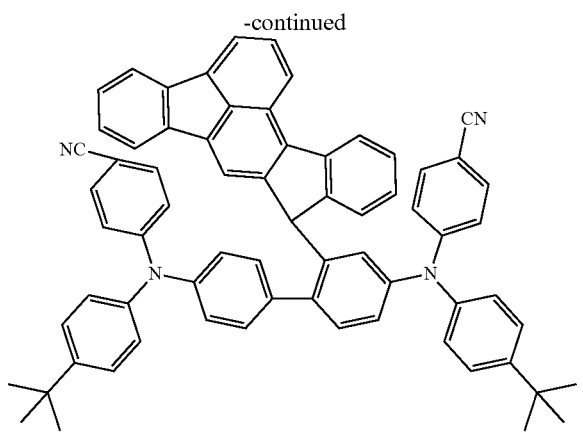
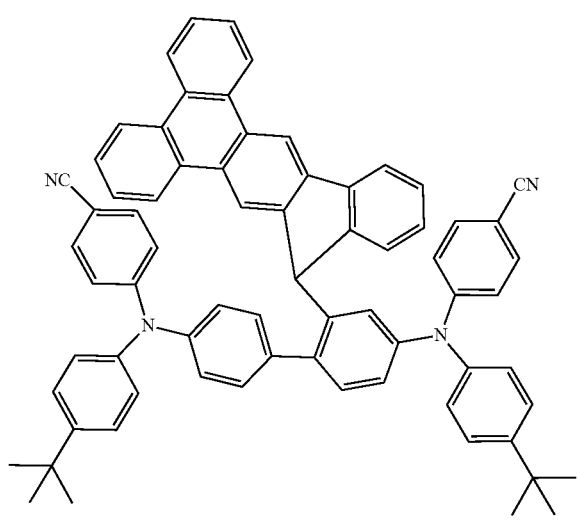
506
-continued
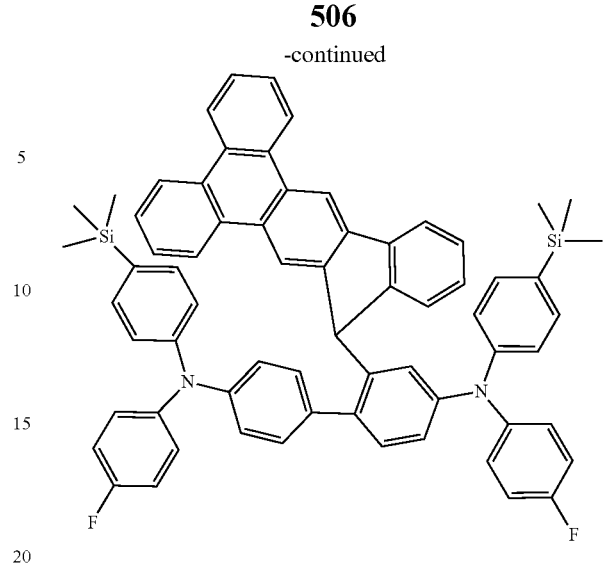
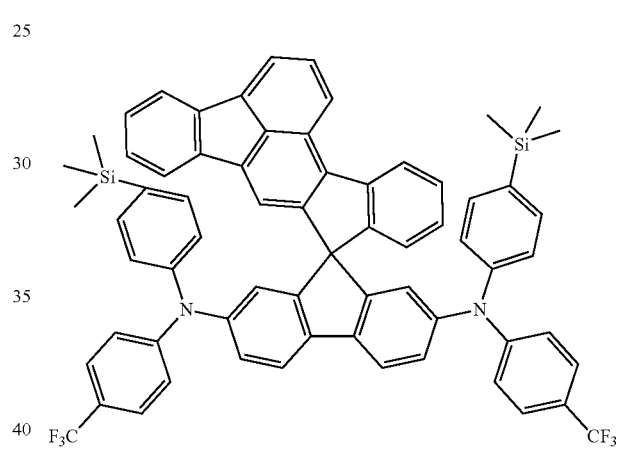
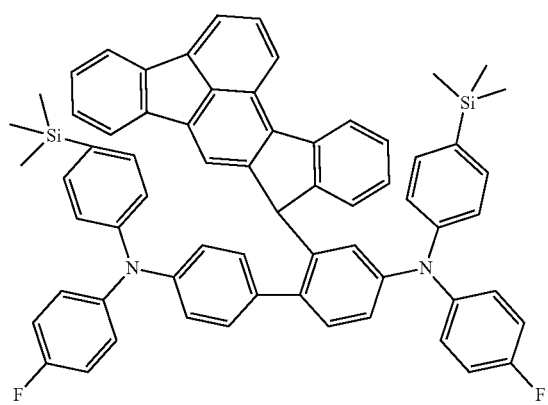
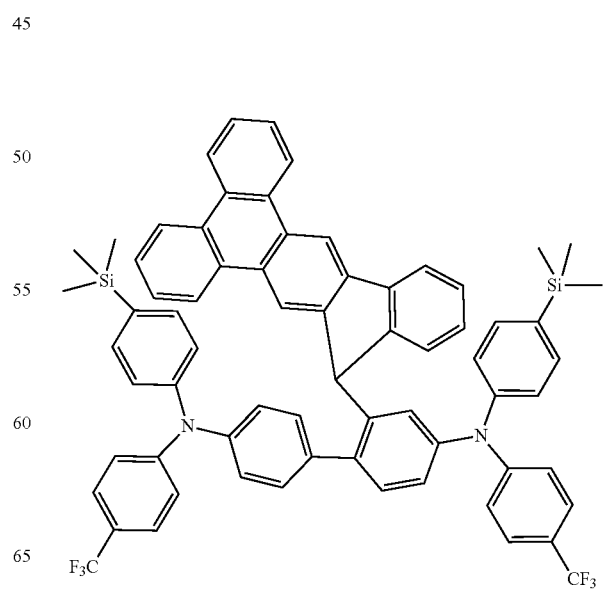

507
-continued
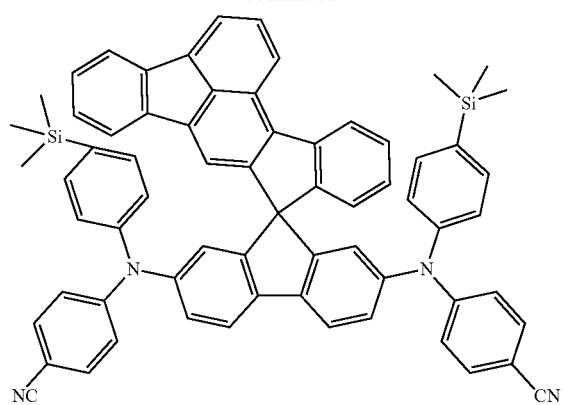
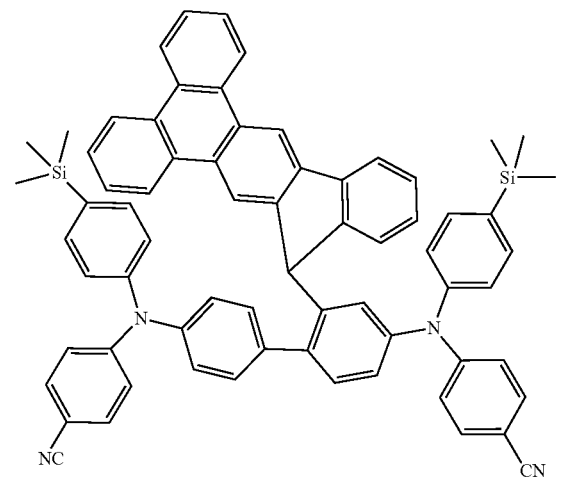
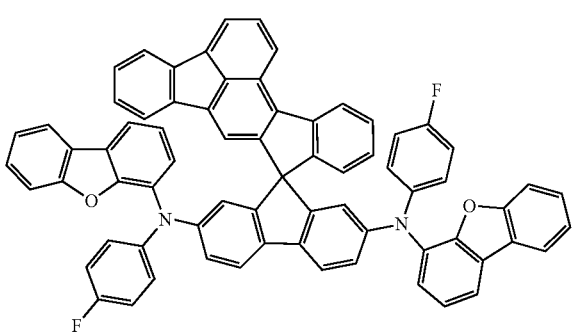
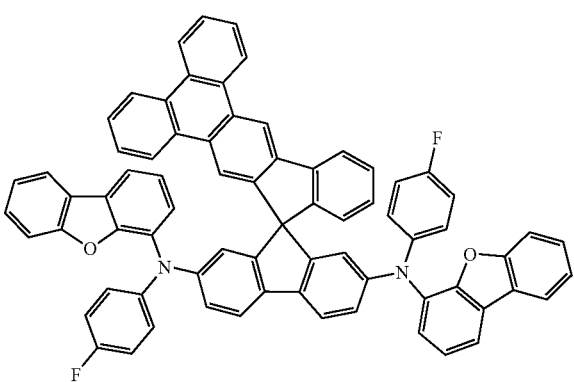
508
-continued
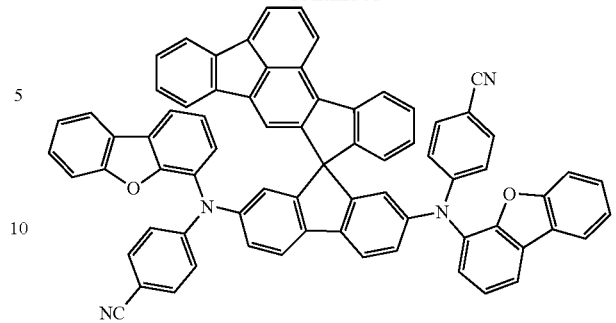
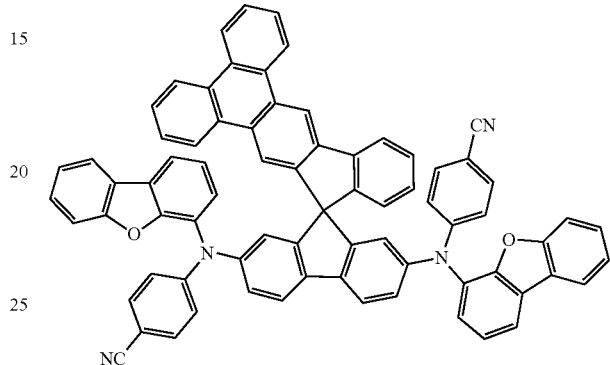
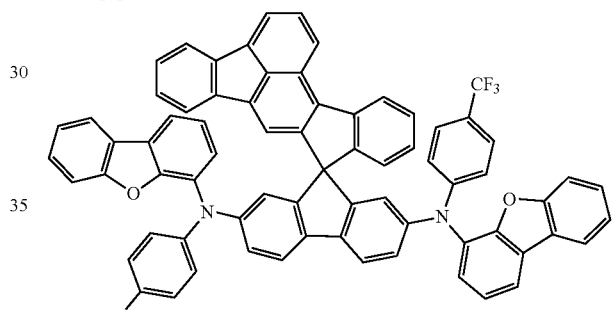
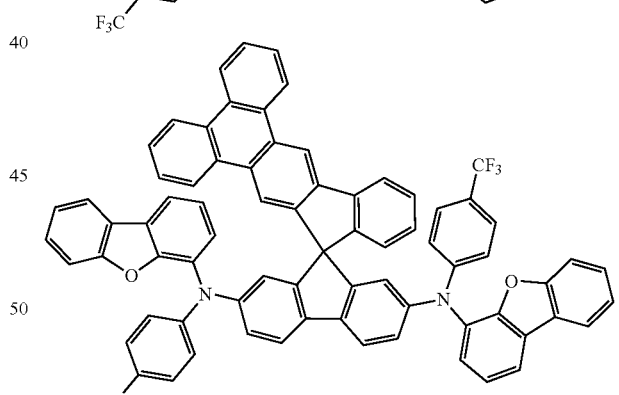
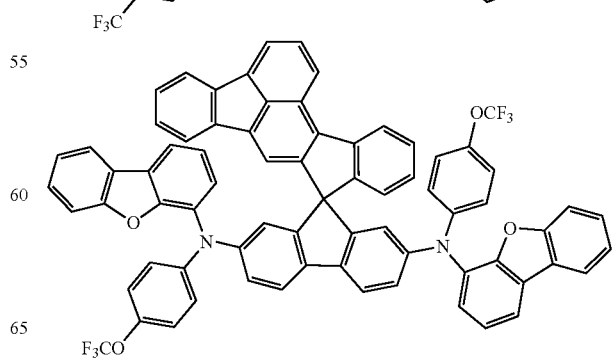

509
-continued
510
-continued
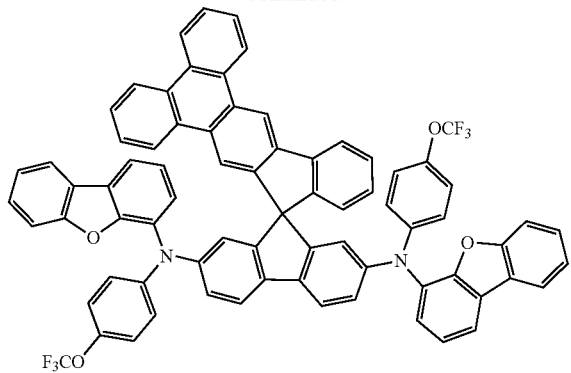
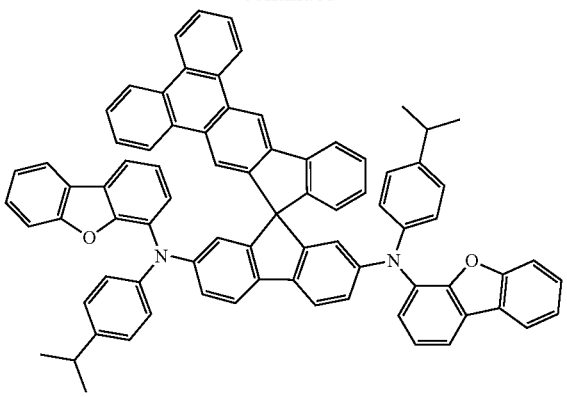
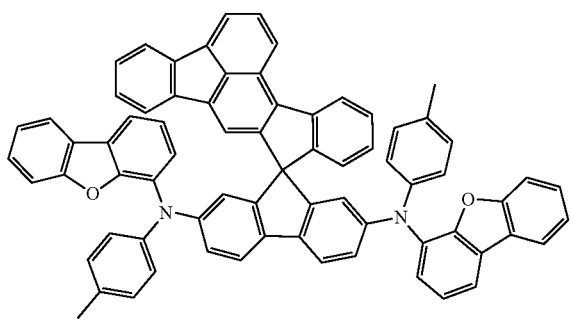
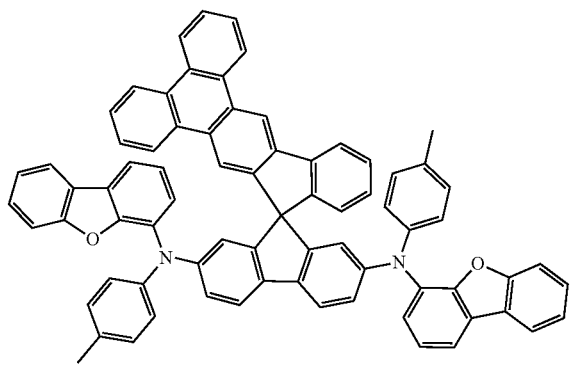
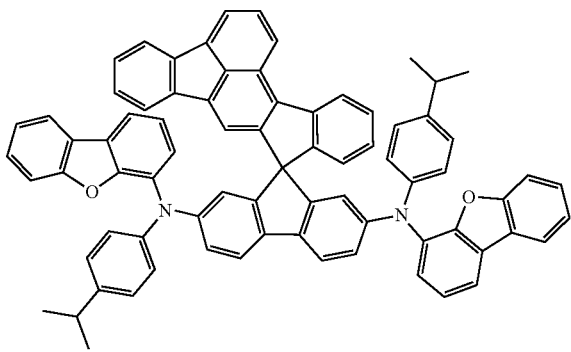
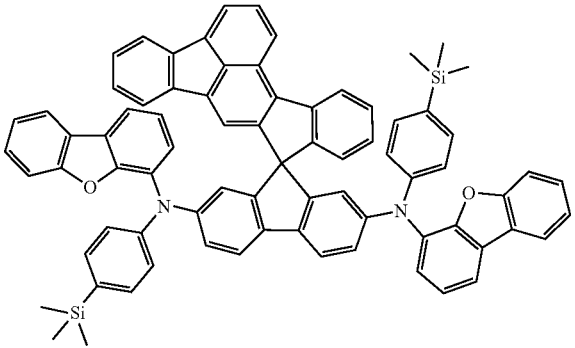

511
-continued
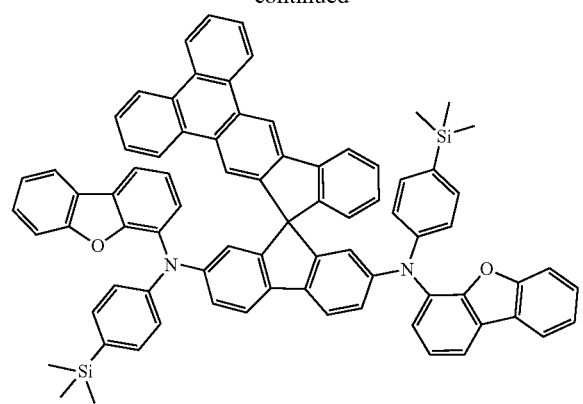
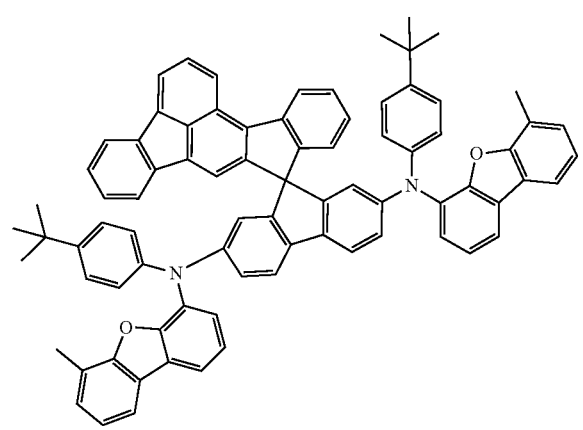
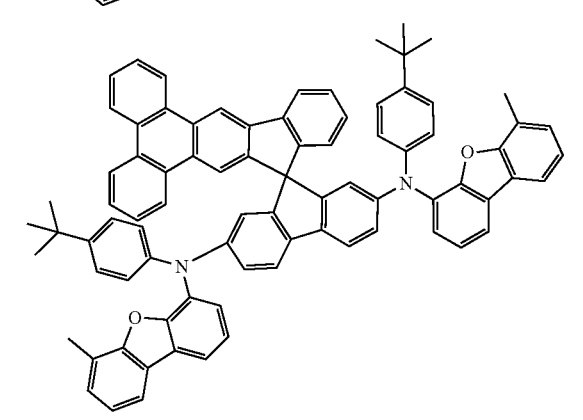
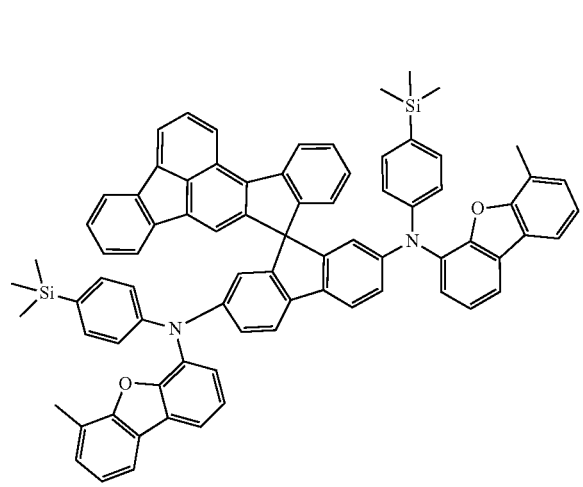
512
-continued
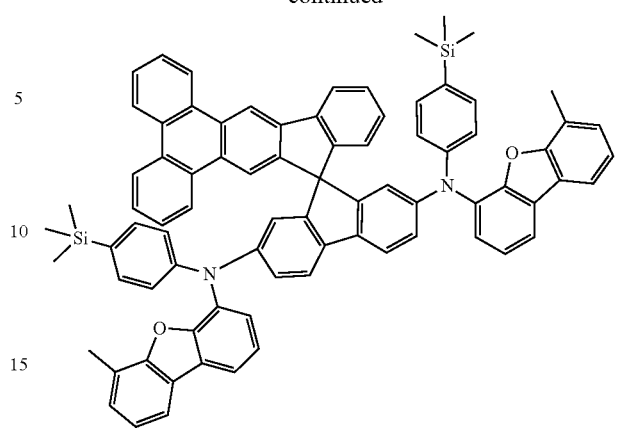
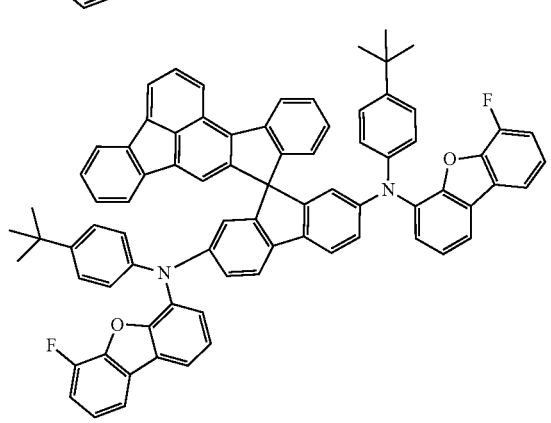
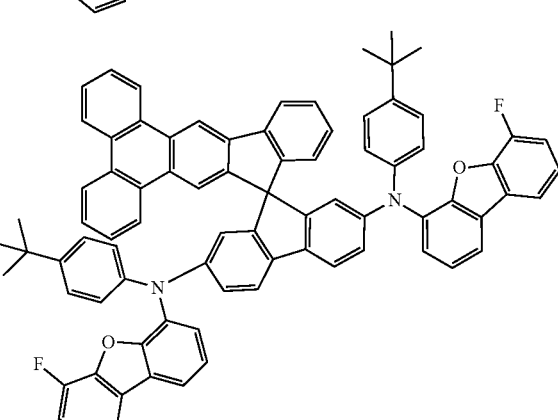
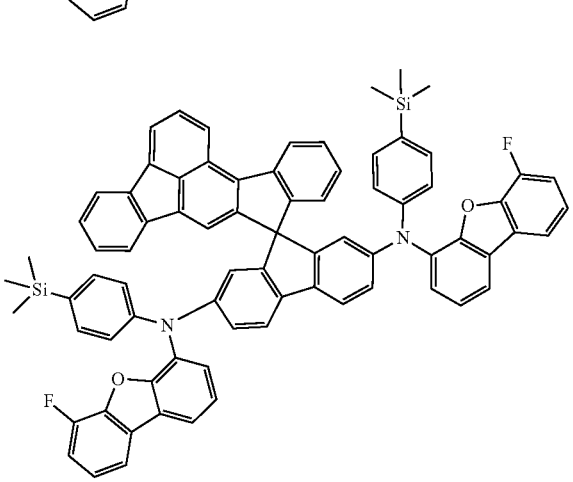

| 513 -continued | 514 -continued |
|---|---|
| 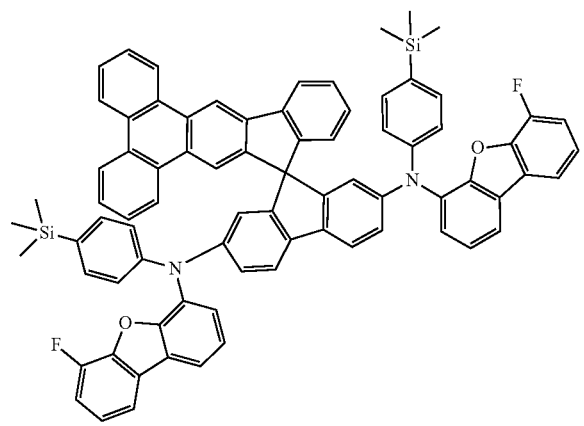 | 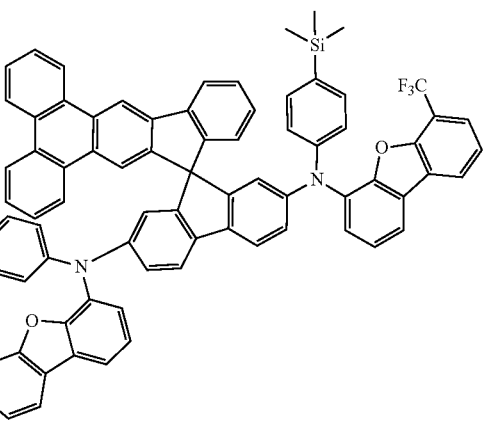 |
| 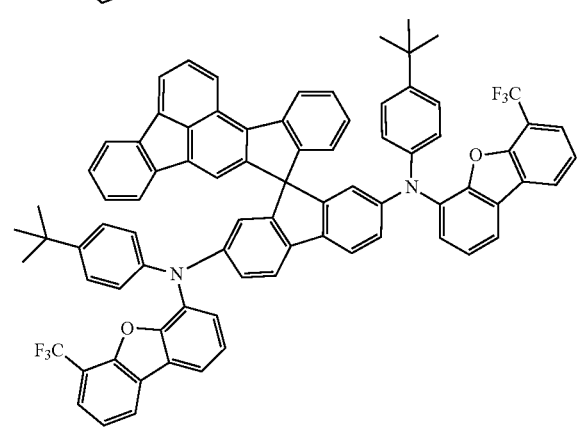 | 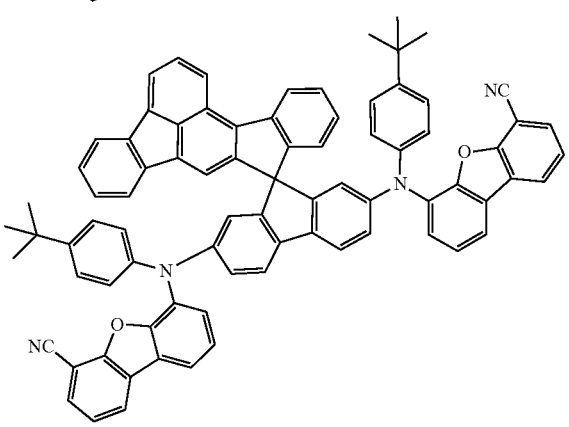 |
| 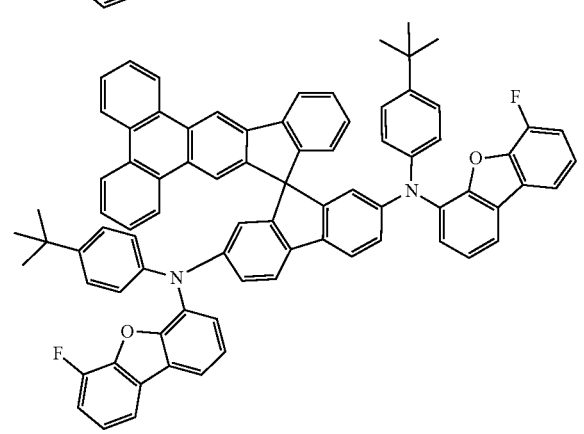 | 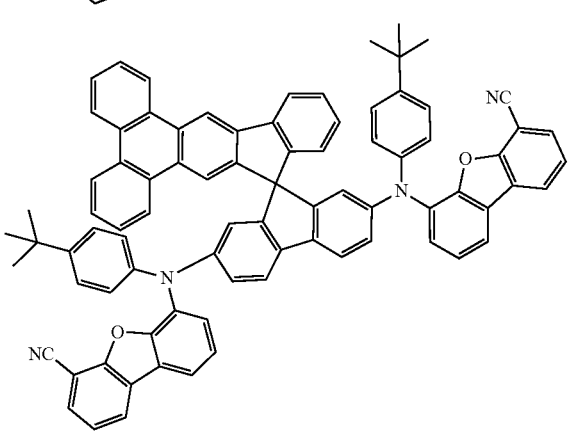 |
| 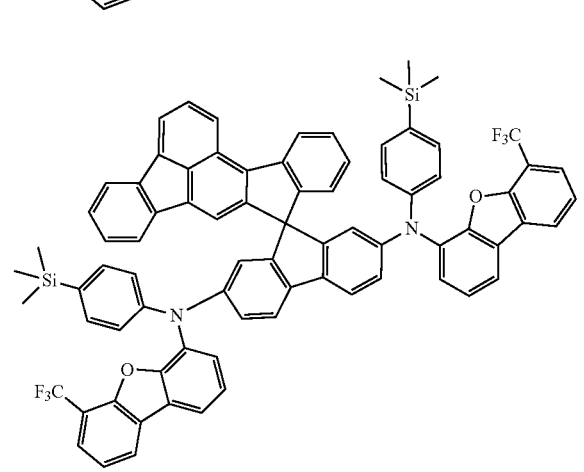 | 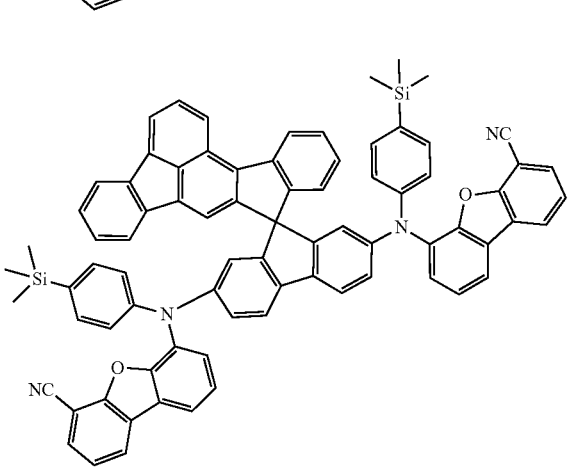 |

515
-continued
516
-continued
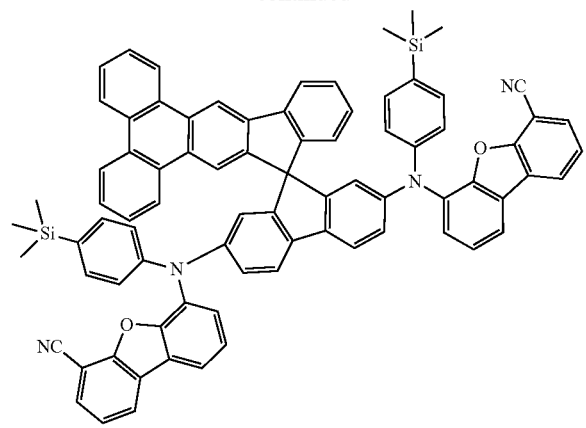
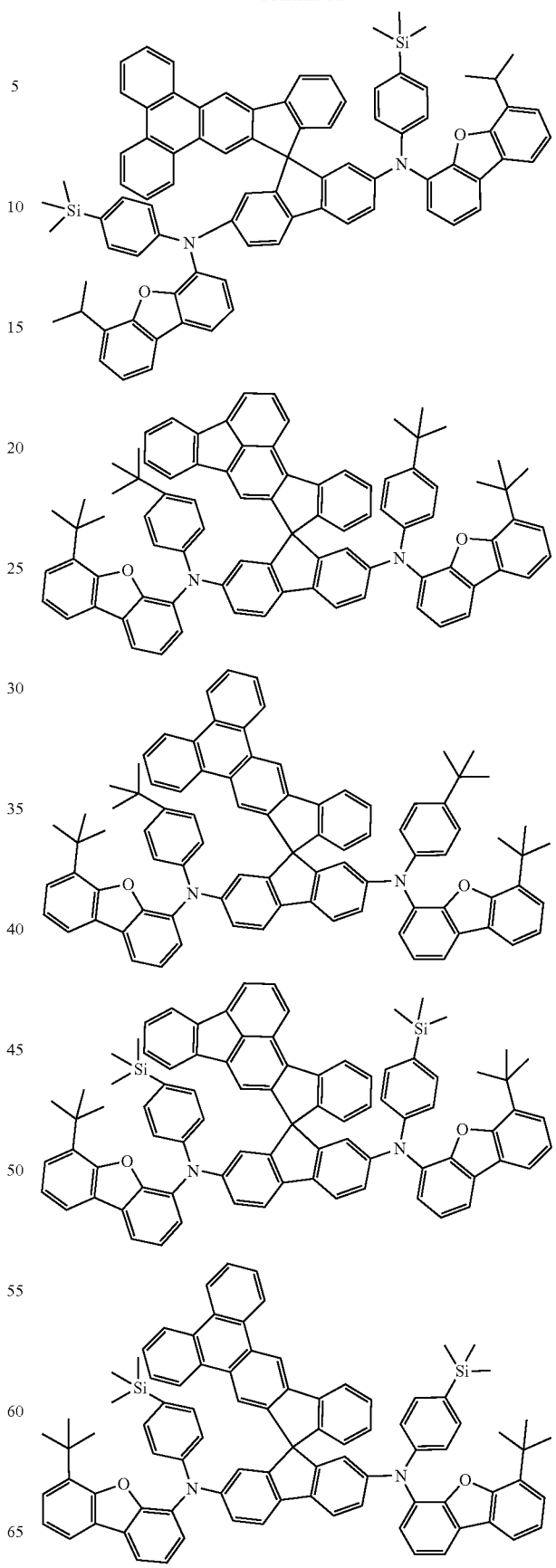

-continued

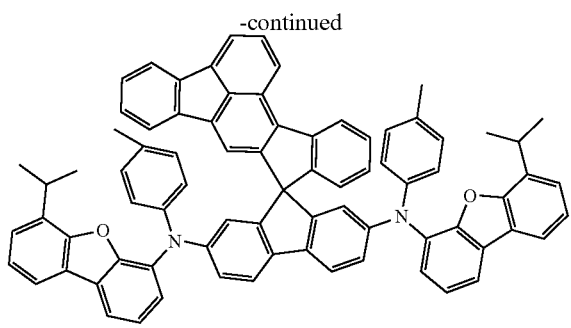

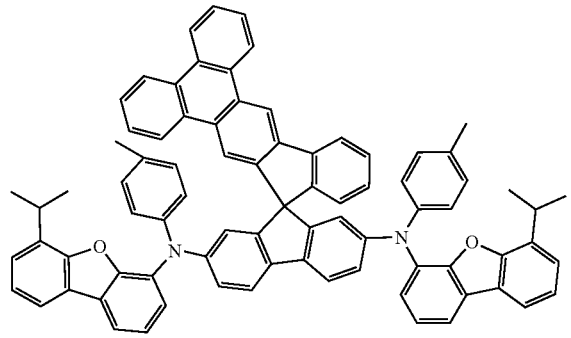

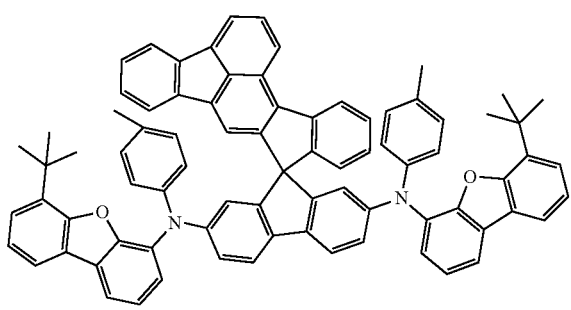

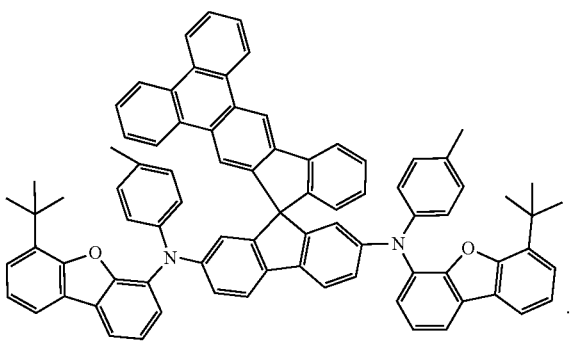 [SMILES: Cc1ccc(N(c2ccc3c(c2)C2(c4ccccc4-c4cc5c6ccccc6c6ccccc6c5cc42)c2cc(N(c4ccc(C)cc4)c4cccc5c4oc4c(C(C)(C)C)cccc45)ccc2-3)c2cccc3c2oc2c(C(C)(C)C)cccc23)cc1]

8. An organic light emitting device comprising:
a first electrode;
a second electrode provided to face the first electrode; and
one or more organic material layers provided between the first electrode and the second electrode,
wherein one or more layers of the organic material layers comprise the compound of claim 1.

9. The organic light emitting device of claim 8, wherein the organic material layer comprises a hole injection layer or a hole transport layer, and the hole injection layer or the hole transport layer comprises the compound.

10. The organic light emitting device of claim 8, wherein the organic material layer comprises an electron blocking layer, and the electron blocking layer comprises the compound.

11. The organic light emitting device of claim 8, wherein the organic material layer comprises a light emitting layer, and the light emitting layer comprises the compound.

12. The organic light emitting device of claim 8, wherein the organic material layer comprises an electron transport layer, an electron injection layer, or a layer which transports and injects electrons simultaneously, and the electron transport layer, the electron injection layer, or the layer which transports and injects electrons simultaneously comprises the compound.

13. The organic light emitting device of claim 8, wherein the organic material layer comprises a light emitting layer, and the light emitting layer comprises a compound represented by the following Chemical Formula 1-A:

[Chemical Formula 1-A]

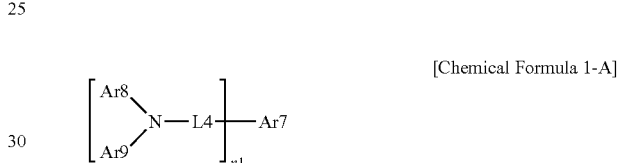

in Chemical Formula 1-A, n1 is an integer of 1 or more,

Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L4 is a direct bond; a substituted or unsubstituted arylene group; or a substituted or unsubstituted heteroarylene group, Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and when n1 is 2 or more, two or more structures in the parenthesis are the same as or different from each other.

14. The organic light emitting device of claim 13, wherein L4 is a direct bond, Ar7 is a divalent pyrene group, Ar8 and Ar9 are the same as or different from each other, and are each independently an aryl group which is unsubstituted or substituted with a germanium group substituted with an alkyl group, and n1 is 2.

15. The organic light emitting device of claim 8, wherein the organic material layer comprises a light emitting layer, and the light emitting layer comprises a compound represented by the following Chemical Formula 2-A:

[Chemical Formula 2-A]

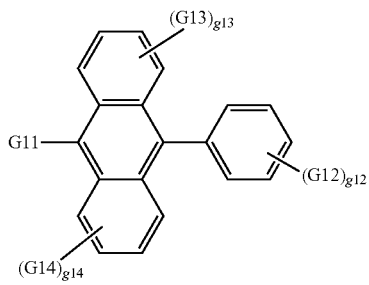

in Chemical Formula 2-A,

G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

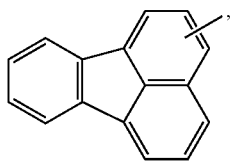

G12 is a phenyl group, a 1-naphtyl group, a 2-naphtyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

16. The organic light emitting device of claim 15, wherein G11 is a 1-naphthyl group, and G12 is a 2-naphthyl group.

17. The organic light emitting device of claim 13, wherein the light emitting layer comprises a compound represented by the following Chemical Formula 2-A:

[Chemical Formula 2-A]

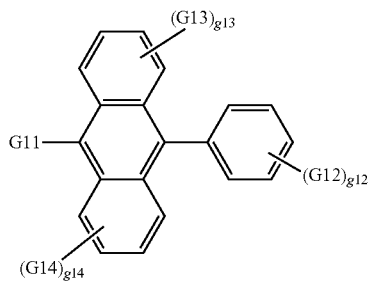

in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

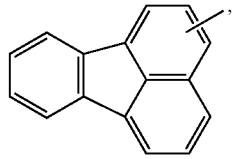

G12 is a phenyl group, a 1-naphtyl group, a 2-naphtyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

* * * * *